US012459920B2

(12) United States Patent
Liardo et al.

(10) Patent No.: US 12,459,920 B2
(45) Date of Patent: Nov. 4, 2025

(54) TARGETED PROTEIN DEGRADATION

(71) Applicant: Monte Rosa Therapeutics AG, Basel (CH)

(72) Inventors: Elisa Liardo, Basel (CH); Laura Ann McAllister, Basel (CH); Bernhard Fasching, Basel (CH)

(73) Assignee: Monte Rosa Therapeutics AG, Basel (CH)

( * ) Notice: Subject to any disclaimer, the term of this patent is extended or adjusted under 35 U.S.C. 154(b) by 0 days.

(21) Appl. No.: 19/183,531

(22) Filed: Apr. 18, 2025

(65) Prior Publication Data

US 2025/0243180 A1 Jul. 31, 2025

Related U.S. Application Data

(63) Continuation of application No. PCT/US2024/039292, filed on Jul. 24, 2024.

(60) Provisional application No. 63/528,823, filed on Jul. 25, 2023.

(51) Int. Cl.
*C07D 401/12* (2006.01)
*A61K 31/506* (2006.01)
*A61P 29/00* (2006.01)

(52) U.S. Cl.
CPC .......... *C07D 401/12* (2013.01); *A61K 31/506* (2013.01); *A61P 29/00* (2018.01); *C07B 2200/09* (2013.01)

(58) Field of Classification Search
CPC .................................................... C07D 401/12
See application file for complete search history.

(56) References Cited

U.S. PATENT DOCUMENTS

| | | | |
|---|---|---|---|
| 2022/0313827 A1 | 10/2022 | Phillips et al. |
| 2024/0374738 A1 | 11/2024 | Su et al. |
| 2025/0041429 A1 | 2/2025 | Lee et al. |
| 2025/0059162 A1 | 2/2025 | Yang et al. |

FOREIGN PATENT DOCUMENTS

| | | | |
|---|---|---|---|
| EP | 2308838 | A1 | 4/2011 |
| EP | 3455219 | A1 | 3/2019 |
| EP | 3641762 | A1 | 4/2020 |
| EP | 3684366 | A1 | 7/2020 |
| EP | 3817822 | A1 | 5/2021 |
| EP | 3897631 | A1 | 10/2021 |
| EP | 4031243 | A1 | 7/2022 |
| EP | 4039688 | A2 | 8/2022 |
| EP | 4114392 | A1 | 1/2023 |
| EP | 4334302 | A1 | 3/2024 |
| JP | 2011157349 | A | 8/2011 |
| WO | 2022161414 | A1 | 8/2022 |
| WO | 2022235698 | A1 | 11/2022 |
| WO | 2022268052 | A1 | 12/2022 |
| WO | 2022272074 | A1 | 12/2022 |
| WO | 2023072270 | A1 | 5/2023 |
| WO | 2023080732 | A1 | 5/2023 |
| WO | 2023098656 | A1 | 6/2023 |
| WO | 2023116835 | A1 | 6/2023 |
| WO | 2023125907 | A1 | 7/2023 |
| WO | 2023143249 | A1 | 8/2023 |
| WO | 2023177451 | A1 | 9/2023 |
| WO | 2023192578 | A1 | 10/2023 |
| WO | 2023227080 | A1 | 11/2023 |
| WO | 2023245327 | A1 | 12/2023 |
| WO | 2024073871 | A1 | 4/2024 |
| WO | 2024188209 | A1 | 9/2024 |
| WO | 2025016457 | A1 | 1/2025 |
| WO | 2025024521 | A1 | 1/2025 |

OTHER PUBLICATIONS

Devant, P., et al., "Molecular mechanisms of gasdermin D pore-forming activity", Nature Immunology, 24:1064-1075 (2023).
Fu, J., et al., "Structural Mechanisms of NLRP3 Inflammasome Assembly and Activation", Annual Review of Immunology, 41:301-16 (2023).
International Search Report and Written Opinion for International Patent Application No. PCT/US2024/039292, mailed Nov. 27, 2024.
Mangan, M. S. J., et al. "Targeting the NLRP3 inflammasome in inflammatory diseases", Nat. Rev. Drug Discov., 17:588-606 (2018).
McKee, C. M., et al., "NLRP3 inflammasome priming: A riddle wrapped in amystery inside an enigma", J. Leuk. Biol., 108:937-952 (2020).
Mullard, A., "NLRP3 inhibitors stoke anti-inflammatory ambitions", Nat. Rev. Drug Discov., 18:405-407 (2019).
Sharif, H., et al., "Structural mechanism for NEK7-licensed activation of NLRP3 inflammasome", Nature, 570(7761):338-343 (2019).
Taldo, S., et al., "Targeting The NLRP3 Inflammasome In Cardiovascular Diseases", Pharmacology & Therapeutics, 236(108053):1-20 (2022).

*Primary Examiner* — Brian E McDowell
(74) *Attorney, Agent, or Firm* — Goodwin Procter LLP

(57) ABSTRACT

This disclosure features chemical entities (e.g., a compound or a pharmaceutically acceptable salt thereof) that degrade and/or otherwise modulate (e.g., inhibit) NIMA Related Kinase 7 (NEK7). Said chemical entities are useful, e.g., for treating a subject (e.g., a human subject) having one or more disorders or diseases associated with NLRP3 inflammasome activation. Said disorders or diseases include but are not limited to, autoinflammatory and autoimmune disorders (e.g., gout, inflammatory bowel disease, rheumatoid arthritis, multiple sclerosis), neurodegenerative diseases (e.g., Alzheimer's disease, Parkinson's disease), cardiovascular and metabolic disorders (eg. pericarditis, atherosclerosis, Type 2 diabetes, obesity, and metabolic syndrome), fibrotic disorders (e.g. interstitial lung disease, chronic kidney disease), hematology (eg, anemia of inflammation) and eye disorders (eg. macular degeneration). In embodiments, and while not wishing to be bound by theory, it is believed that the chemical entities described herein directly target (e.g., directly bind to) NEK7, thereby altering (e.g., attenuating) the inflammatory response modulated by the NLRP3 inflammasome. This disclosure also features compositions containing the same as well as methods of using and making the same.

5 Claims, 2 Drawing Sheets

TARGETED PROTEIN DEGRADATION

CROSS-REFERENCE TO RELATED APPLICATIONS

This application is a continuation of International Patent Application No. PCT/US2024/039292, filed Jul. 24, 2024, which claims priority to U.S. Provisional Patent Application No. 63/528,823, filed Jul. 25, 2023. The entire contents of which are hereby incorporated by reference for all purposes.

TECHNICAL FIELD

This disclosure features chemical entities (e.g., a compound or a pharmaceutically acceptable salt thereof) that degrade and/or otherwise inhibit NIMA Related Kinase 7 (NEK7). Said chemical entities are useful, e.g., for treating a subject (e.g., a human subject) having a disorder or disease associated with NLRP3 inflammasome activation. This disclosure also features compositions containing the same as well as methods of using and making the same.

BACKGROUND

The ubiquitin proteasome system can be manipulated with different small molecules to trigger targeted degradation of specific proteins of interest. Promoting the targeted degradation of pathogenic proteins using small molecule degraders is emerging as a new modality in the treatment of diseases. One such modality relies on redirecting the activity of E3 ligases such as cereblon (a phenomenon known as E3 reprogramming) using low molecular weight compounds, which have been termed molecular glues to promote the poly-ubiquitination and ultimately proteasomal degradation of new protein substrates involved in the development of diseases. The molecular glues bind to both the E3 ligase and the target protein, thereby mediating an alteration of the ligase surface and enabling an interaction with the target protein. Particularly relevant compounds for the E3 ligase cereblon are the IMiD (immunomodulatory imide drugs) class including Thalidomide, Lenalidomide and Pomalidomide. These IMiDs have been approved by the FDA for use in hematological cancers. However, compounds for efficiently targeting other diseases are still required.

Inflammasomes are multi-protein complexes whose activation plays a central role in innate immunity and inflammation. NLRP3 inflammasome activation occurs in response to infectious or cell damage-related stress, and acts to initiate or amplify inflammation. The NLRP3 inflammasome is composed of NLRP3, ASC, and caspase-I, which, when activated forms an intracellular complex that cleaves gasdermin D and the cytokines IL-1β and IL-18 to release their active forms[1,2]. Cleaved gasdermin D then forms pores in the cell membrane, which allows the release of active IL-1B and IL-18 and, in most cases, the rupture of the cell membrane in a highly inflammatory process known as pyroptosis[3]. NLRP3 activation is known to contribe to many settings of inappropriate or unwanted inflammation that is associated with autoinflammatory and autoimmune disease[4,5]. NEK7 is a serine/threonine kinase and a member of the family of NIMA-related kinases (NEKs) that are associated with mitotic entry, cell cycle progression, cell division, and mitotic progression. NEK7 is expressed in a variety of tissues and acts as an NLRP3-binding protein to facilitate its oligomerization and activation[6].

REFERENCES

1. Fu J & Wu H. Structural mechanisms of NLRP3 inflammasome assembly and activation. Ann Rev Immunol. 2023; 41:301-316
2. McKee C M & Coll R$^{C}$. NLRP3 inflammasome priming: A riddle wrapped in a mystery inside an enigma. J Leuk Biol. 2020; 108:937-952
3. Devant P & Kagan J C. Molecular mechanisms of gasdermin D pore-forming activity. Nat Immunol. 2023; 24:1064-1075
4. Mangan M S J, Olhava E J, Roush W R, Seidl H M, Glick G D, Latz E. Targeting the NLRP3 inflammasome in inflammatory diseases. Nat Rev Drug Discov. 2018; 17:588-606
5. Mullard A. NLRP3 inhibitors stoke anti-inflammatory ambitions. Nat Rev Drug Discov. 2019; 18:405-407
6. Sharif H, Wang L, Wang W L, Magupalli V G, Andreeva L, Qiao Q, Hauenstein A V, Wu Z, Núñez G, Mao Y, Wu H. Structural mechanism for NEK7-licensed activation of NLRP3 inflammasome. Nature 2019; 570 (7761): 338-343

SUMMARY

This disclosure features chemical entities (e.g., a compound or a pharmaceutically acceptable salt thereof) that degrade and/or otherwise modulate (e.g., inhibit) NIMA Related Kinase 7 (NEK7). Said chemical entities are useful, e.g., for treating a subject (e.g., a human subject) having one or more disorders or diseases associated with NLRP3 inflammasome activation. Said disorders or diseases include but are not limited to, autoinflammatory and autoimmune disorders (e.g., gout, inflammatory bowel disease, rheumatoid arthritis, multiple sclerosis), neurodegenerative diseases (e.g., Alzheimer's disease, Parkinson's disease), cardiovascular and metabolic disorders (eg. pericarditis, atherosclerosis, Type 2 diabetes, obesity and metabolic syndrome), fibrotic disorders (e.g. interstitial lung disease, chronic kidney disease), hematology (eg, anemia of inflammation) and eye disorders (eg. macular degeneration). In embodiments, and while not wishing to be bound by theory, it is believed that the chemical entities described herein directly target (e.g., directly bind to) NEK7, thereby altering (e.g., attenuating) the inflammatory response modulated by the NLRP3 inflammasome. This disclosure also features compositions containing the same as well as methods of using and making the same.

In one aspect, this disclosure features compounds of Formula (I):

(I)

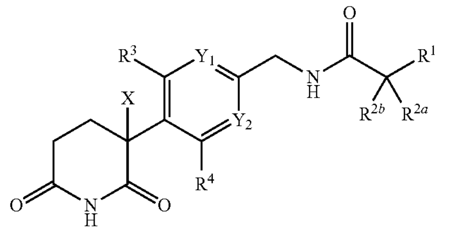

or a pharmaceutically acceptable salt thereof; wherein $R^1$, $R^{2a}$, $R^{2b}$, $R^3$, $R^4$, $Y_1$, $Y_2$, and X can be as defined anywhere herein. In another aspect, the disclosure features compounds of Formula (II):

(II)

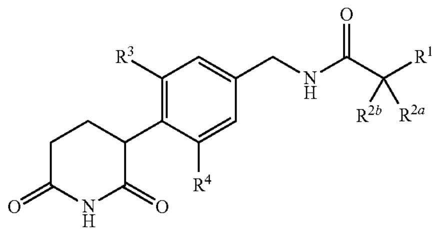

or a pharmaceutically acceptable salt thereof; wherein $R^1$, $R^{2a}$, $R^{2b}$, $R^3$, and $R^4$ can be as defined anywhere herein.

In another aspect, this disclosure features pharmaceutical compositions that include one or more of the compounds described herein, or pharmaceutically acceptable salts thereof, and a pharmaceutically acceptable carrier.

In a further aspect, this disclosure features methods of modulating (e.g., inhibiting) NIMA Related Kinase 7 (NEK7) in a subject, which include administering to the subject an effective amount of a compound described herein, or a pharmaceutically acceptable salt thereof.

In still another aspect, this disclosure features methods of altering (e.g., attenuating) the inflammatory response modulated by the NLRP3 inflammasome in a subject, which include administering to the subject an effective amount of a compound described herein, or a pharmaceutically acceptable salt thereof.

In one aspect, this disclosure features methods of degrading NIMA Related Kinase 7 (NEK7) in a subject, which include administering to the subject an effective amount of a compound described herein, or a pharmaceutically acceptable salt thereof.

In another aspect, this disclosure features methods of degrading NIMA Related Kinase 7 (NEK7), which include one or both of the following: (i) contacting a compound described herein or a pharmaceutically acceptable salt thereof with an E3 ligase; and (ii) interacting the contacted E3 ligase with NEK7, thereby degrading NEK7.

In a further aspect, this disclosure features methods of treating a disorder associated with NLRP3 inflammasome activation in a subject in need thereof, which includes administering to the subject a therapeutically effective amount of a compound described herein or a pharmaceutically acceptable salt thereof.

Compounds and pharmaceutical compositions described herein can be used in the treatment of disorders in subjects in need thereof. Said disorders include, but are not limited to, those disorders caused by or associated with increased (e.g., excessive) NLRP3 inflammasome activation.

Accordingly, in one embodiment, described herein is a method of treating a disorder caused by or associated with NLRP3 inflammasome activation in a subject in need thereof, comprising administering to the subject a therapeutically effective amount of a compound described herein or a pharmaceutically acceptable salt thereof.

In some embodiments, the disorder is a disorder of the immune system, hematopeoitic system, joints, renal system, gastro-intestinal tract, skin, eye, respiratory system, central nervous system, cardiovascular system, hepatic system, and/or endocrine system.

In some embodiments, the disorder is selected from the group consisting of: (i) inflammatory reactions in the joints; (ii) hyperactive inflammation with underlying genetic mutations; (iii) autoimmune diseases; (iv) respiratory diseases; (v) kidney diseases; (vi) central nervous system diseases; (vii) ocular diseases; (viii) cardiovascular diseases; (ix) viral infections and subsequent immune hyperactivation; (x) diseases of the hematopoietic system; (xi) liver disease; (xii) inflammatory reactions in the skin; (xiii) metabolic diseases; (xiv) cancers; (xv) infectious diseases; and (xvi) allergic disease.

In certain embodiments, the disorder is inflammatory reactions in the joints.

In certain of these embodiments, the disorder is gout, for instance acute or chronic gout.

In certain of these embodiments, the disorder is tophaceous gout.

In certain of these embodiments, the disorder is pseudogout.

In certain of these embodiments, the disorder is osteoarthritis.

In certain of these embodiments, the disorder is psoriatic arthritis.

In certain of these embodiments, the disorder is systemic juvenile idiopathic arthritis.

In certain of these embodiments, the disorder is adult-onset Still's disease.

In certain of these embodiments, the disorder is relapsing polychondritis.

In certain of these embodiments, the disorder is tendonitis.

In certain of these embodiments, the disorder is frozen shoulder.

In certain of these embodiments, the disorder is pyogenic arthritis.

In some embodiments, the disorder is selected from the group consisting of: (ii) hyperactive inflammation with underlying genetic mutations; (iii) autoimmune diseases; (iv) respiratory diseases; (v) kidney diseases; (vi) central nervous system diseases; (vii) ocular diseases; (viii) cardiovascular diseases; and (ix) metabolic diseases.

In certain embodiments, the hyperactive inflammation with underlying genetic mutations is selected from the group consisting of cryopyrin-associated periodic syndrome (CAPS): Muckle-Wells syndrome (MWS), familial cold autoinflammatory syndrome (FCAS) and neonatal-onset multisystem inflammatory disease (NOMID); familial Mediterranean fever (FMF), TNF receptor associated periodic syndrome (TRAPS), mevalonate kinase deficiency (MVK), hyperimmunoglobuliemia D and periodic fever syndrome (HIDS), deficiency of interleukin 1 receptor (DIRA) antagonist), VEXAS syndrome, Majeed syndrome, pyoderma gangrenosum, acne and hidradenitis suppurative syndrome, haploinsufficency of A20, pediatric granulomatous arthritis (PGA), PLCG2-associated antibody deficiency and immune dysregulation (PLAID), sideroblastic anemia with B-cell immunodeficiency, periodic fevers, and developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO) and any disease where an individual has been determined to carry a germline or somatic non-silent mutation in NLRP3 or NEK7.

In certain embodiments, the autoimmune disease is selected from the group consisting of multiple sclerosis (MS), rheumatoid arthritis, Behçet's disease, Sjögren's syndrome, systemic sclerosis, mixed connective tissue disease, myositis, vasculitis, lupus, including systemic and cutaneous forms, lupus nephritis, type-1 diabetes, psoriasis and Schnitzler's syndrome, Grave's disease, thrombotic thrombocytopenia purpura, idiopathic thrombocytopeniarpura, microscopic polyangiitis, inflammatory bowel disease, colitis, and Crohn's disease.

In certain embodiments, the respiratory disease is selected from the group consisting of chronic obstructive pulmonary disorder (COPD), acute respiratory distress syndrome (ARDS), steroid-resistant asthma, asbestosis, silicosis, sarcoidosis, cystic fibrosis and interstitial lung disease (ILD), including, but not limited to idiopathic pulmonary fibrosis (IPF), fibrotic hypersensitivity pneumonitis, rheumatoid arthritis-associated ILD, autoimmune myositis-associated ILD, systemic sclerosis-associated ILD, idiopathic interstitial pneumonia and progressive fibrosing ILD.

In certain embodiments, the kidney disease is selected from the group consisting of chronic kidney disease (CKD), including CKD associated with high uric acid, APOLI mutations, complement-mediated kidney diseases such as C3 glomerulopathy, IgA nephropathy, atypical hemalytic uremic syndrome and membranous nepropathy, idiopathic nephrotic syndrome, oxalate nephropathy and diabetic nephropathy.

In certain embodiments, the central nervous system disease is selected from the group consisting of Parkinson's disease, Alzheimer's disease, motor neuron disease, Huntington's disease, cerebral malaria, post-traumatic brain injury, sub-arachnoid hemorrhage and brain injury from pneumococcal meningitis, cerebral amyloid angiopathy, migraine, depression, and psychological stress.

In certain embodiments, the ocular disease is selected from the group consisting of those of the ocular epithelium, age-related macular degeneration (AMD), corneal infection, uveitis and dry eye.

In certain embodiments, the cardiovascular disease is selected from the group consisting of myocarditis, inflammatory cardiomyopathy, atherosclerosis, stroke, myocardial infarction, hypertension, abdominal aortic aneurism, pericarditis including Dressler's syndrome, thromboembolism, ischemia reperfusion injury, transthyretin amyloidosis, and vasculitis.

In certain embodiments, the metabolic disease is selected from the group consisting of obesity, metabolic syndrome, and Type 2 diabetes and related morbidities including diabetic foot ulcers, atherosclerosis, diabetic cardiomyopathy, and diabetic retinopathy.

In some embodiments, the disorder is a cancer, tumour or other malignancy.

In some embodiments, the disorder is pericarditis or gout.

In one aspect, this disclosure features methods of degrading NIMA Related Kinase 7 (NEK7) in a subject suffering from any one or more of the disorders described herein, comprising administering to the subject an effective amount of a compound of described herein or a pharmaceutically acceptable salt thereof.

Embodiments can include one or more of the following features. The compounds described herein can include any one of more of the structural features delineated throughout this specification and/or the claims. The compounds described herein can mediate the interaction of a NEK7 protein with an E3 ligase, e.g., thereby increasing degradation of the NEK7 protein. NEK7 can be an activator of an NLRP3 inflammasome. The compounds described herein can interact with the E3 ligase prior to the interaction of NEK7 with the E3 ligase. The E3 ligase can include cereblon. The methods described herein can further include identifying a subject in need thereof. Additional details of one or more embodiments of the invention are set forth in the description below. Other features and advantages of the compounds, compositions, and methods featured herein will be apparent from the description and the claims.

DETAILED DESCRIPTION

Figure 1A:
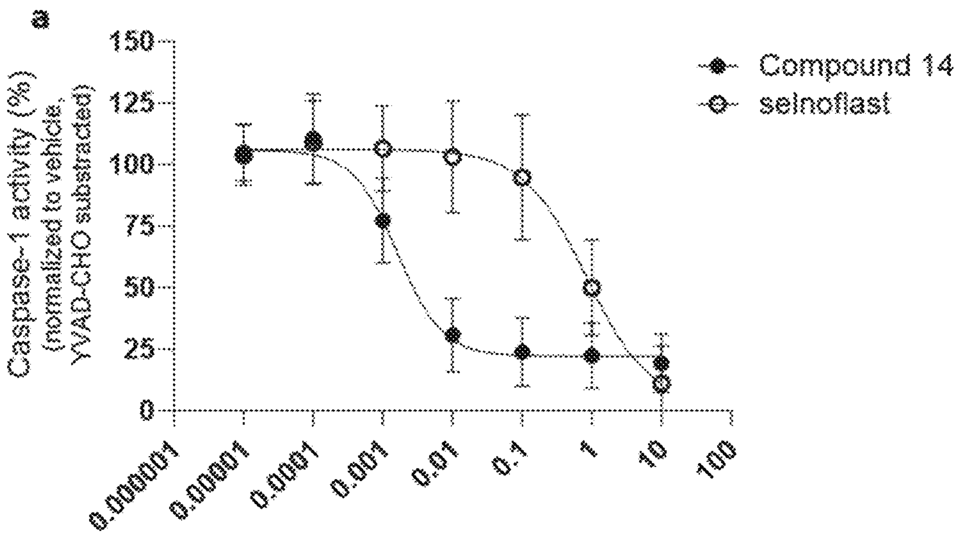
FIG. 1A depicts caspase-1 activity in the supernatant following treatment of human monocyte-derived macrophages with different doses of Compound 14 or selnoflast measured as a percentage relative to mean values in DMSO.

This disclosure features chemical entities (e.g., a compound or a pharmaceutically acceptable salt thereof) that degrade and/or otherwise modulate (e.g., inhibit) NIMA Related Kinase 7 (NEK7). Said chemical entities are useful, e.g., for treating a subject (e.g., a human subject) having one or more disorders or diseases associated with NLRP3 inflammasome activation. Said disorders or diseases include but are not limited to, autoinflammatory and autoimmune disorders (e.g., gout, inflammatory bowel disease, rheumatoid arthritis, multiple sclerosis), neurodegenerative diseases (e.g., Alzheimer's disease, Parkinson's disease), cardiovascular and metabolic disorders (eg. pericarditis, atherosclerosis, Type 2 diabetes, obesity, and metabolic syndrome), fibrotic disorders (e.g. interstitial lung disease, chronic kidney disease), hematology disorders (eg, anemia of inflammation) and eye disorders (eg. macular degeneration).

In embodiments, and while not wishing to be bound by theory, it is believed that the chemical entities described herein directly target (e.g., directly bind to) NEK7, thereby altering (e.g., attenuating) the inflammatory response modulated by the NLRP3 inflammasome. This disclosure also features compositions containing the same as well as methods of using and making the same.

Compounds

In one aspect, this disclosure features compounds having the following formula:

(I)

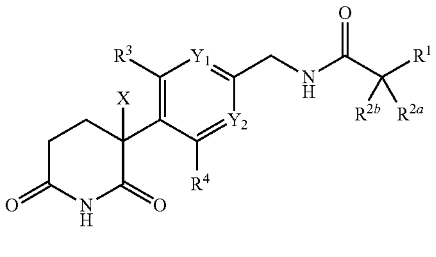

or a pharmaceutically acceptable salt thereof; wherein:

$R^1$, $R^{2a}$, and $R^{2b}$ are defined according to (A) and (B) below:

A $R^1$ is:

heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$;

heterocyclyl including 4-6 ring atoms, wherein 1-4 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo, $R^b$ and $R^c$;

$C_{3-7}$ cycloalkyl optionally substituted with 1-4 substituents independently selected from the group consisting of oxo, $R^b$, and $R^c$;

heterocycloalkenyl including 3-10 ring atoms, wherein 1-3 ring atoms are heteroatoms, each independently selected from the group consisting of N, N(H), N($R^d$), O, and $S(O)_{0-2}$, and wherein the heterocycloalkenyl is optionally substituted with 1-4 substituents independently selected from the group consisting of oxo, $R^b$, and $R^e$; or $C_{6-10}$ aryl optionally substituted with 1-4 substituents independently selected from the group consisting of oxo, $R^b$, and $R^c$; and each of $R^{2a}$ and $R^{2b}$ is independently selected from the group consisting of:

H;

$C_{1-2}$ alkyl optionally substituted with from 1-5 $R^a$;

$C_{3-5}$ cycloalkyl, which is optionally substituted with 1-4 substituents independently selected from the group consisting of oxo and $R^b$;

$C_{1-4}$ alkoxy;

$C_{1-4}$ haloalkoxy; or cyano; or $R^{2a}$ and $R^{2b}$ taken together with the carbon atom to which each is attached forms:

$C_{3-7}$ cycloalkyl, which is optionally substituted with 1-4 substituents independently selected from the group consisting of oxo and $R^b$;

heterocyclyl including 4-7 ring atoms, wherein 1-2 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^b$;

B $R^1$ taken together with (i) the carbon atom to which it is attached and (ii) and one of $R^{2a}$ and $R^{2b}$ forms:

$C_{8-10}$ aryl optionally substituted with 1-4 substituents independently selected from the group consisting of oxo, $R^b$, and $R^c$; or heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$;

and the other of $R^{2a}$ and $R^{2b}$ is H or $C_{1-2}$ alkyl optionally substituted with from 1-5 $R^a$;

X is H; or halo;

$Y_1$ and $Y_2$ are CH or N, wherein at least one of $Y_1$ and $Y_2$ is CH;

$R^3$ is H; $C_{1-2}$ alkyl, which is optionally substituted with 1-5 fluoro; fluoro; chloro; or cyano;

$R^4$ is chloro; bromo; or fluoro; optionally wherein it is provided that $R^4$ is fluoro when $R^3$ is chloro;

each occurrence of $R^a$ is independently selected from the group consisting of: —OH; -halo; —$NR^eR^f$; $C_{1-4}$ alkoxy; $C_{1-4}$ haloalkoxy,; —C(═O)O($C_{1-4}$ alkyl); —C(═O) ($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ is independently selected from the group consisting of: halo; cyano; $C_{1-10}$ alkyl which is optionally substituted with from 1-6 independently selected $R^a$; $C_{2-6}$ alkenyl; $C_{2-6}$ alkynyl; $C_{1-4}$ alkoxy; —O($C_{1-3}$ alkylene)-($C_{3-6}$ cycloalkyl); $C_{1-4}$ haloalkoxy; —$S(O)_{0-2}$($C_{1-4}$ alkyl); —$NR^eR^f$; —OH; —$S(O)_{1-2}$NR'R"; —$NO_2$; —C(═O) ($C_{1-10}$ alkyl); —C(═O)O($C_{1-4}$ alkyl); —C(═O)OH; and —C(═O)NR'R";

each occurrence of $R^e$ is independently selected from the group consisting of:

$C_{3-10}$ cycloalkyl or $C_{3-10}$ cycloalkenyl, each of which is optionally substituted with from 1-4 substituents independently selected from the group consisting of oxo and $R^b$;

heterocyclyl or heterocycloalkenyl including 3-10 ring atoms, wherein from 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with from 1-4 substituents independently selected from the group consisting of oxo and $R^b$;

heteroaryl including 5-10 ring atoms, wherein from 1-4 ring atoms are heteroatoms, each independently selected from the group consisting of N, N(H), N($R^d$), O, and $S(O)_{0-2}$, and wherein the heteroaryl is optionally substituted with from 1-4 $R^b$; and $C_{6-10}$ aryl optionally substituted with from 1-4 $R^b$;

each occurrence of $R^d$ is independently selected from the group consisting of: $C_{1-6}$ alkyl optionally substituted with from 1-3 independently selected $R^a$; —C(O) ($C_{1-4}$ alkyl); —C(O)O($C_{1-4}$ alkyl); —CONR'R"; —$S(O)_{1-2}$ NR'R"; —$S(O)_{1-2}$($C_{1-4}$ alkyl); —OH; and $C_{1-4}$ alkoxy; and each occurrence of $R^e$ and $R^f$ is independently selected from the group consisting of: H; $C_{1-6}$ alkyl; —C(O) ($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy, and each occurrence of R' and R" is independently selected from the group consisting of: H; and $C_{1-4}$ alkyl.

In some embodiments, the compound has the formula:

(I-A)

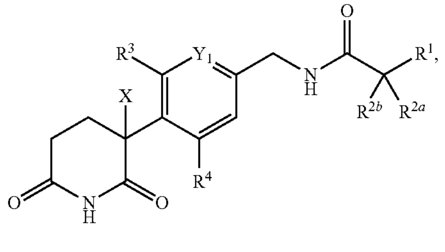

wherein $Y_1$ is CH or N.

In some embodiments, the compound has the formula:

(I-B)

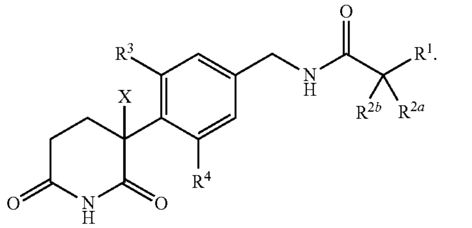

In some embodiments, X is H.

In another aspect, this disclosure features compounds having the following formula:

(II)

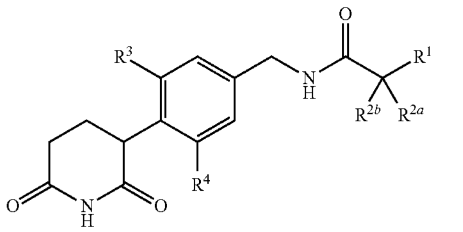

or a pharmaceutically acceptable salt thereof; wherein:

$R^1$, $R^{2a}$, and $R^{2b}$ are defined according to (A) and (B) below:

A $R^1$ is:

heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$;

heterocycloalkenyl including 3-10 ring atoms, wherein 1-3 ring atoms are heteroatoms, each independently selected from the group consisting of N, N(H), N($R^d$), O, and $S(O)_{0-2}$, and wherein the heterocycloalkenyl is optionally substituted with 1-4 substituents independently selected from the group consisting of oxo, $R^b$, and $R^e$; or $C_{6-10}$ aryl optionally substituted with 1-4 substituents independently selected from the group consisting of oxo, $R^b$, and $R^c$; and each of $R^{2a}$ and $R^{2b}$ is independently selected from the group consisting of:

H;

$C_{1-2}$ alkyl optionally substituted with from 1-5 $R^a$;

$C_{3-5}$ cycloalkyl, which is optionally substituted with 1-4 substituents independently selected from the group consisting of oxo and $R^b$;

$C_{1-4}$ alkoxy;

$C_{1-4}$ haloalkoxy; or cyano; or $R^{2a}$ and $R^{2b}$ taken together with the carbon atom to which each is attached forms:

$C_{3-7}$ cycloalkyl, which is optionally substituted with 1-4 substituents independently selected from the group consisting of oxo and $R^b$;

heterocyclyl including 4-7 ring atoms, wherein 1-2 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^b$;

B $R^1$ taken together with (i) the carbon atom to which it is attached and (ii) and one of $R^{2a}$ and $R^{2b}$ forms:

$C_{8-10}$ aryl optionally substituted with 1-4 substituents independently selected from the group consisting of oxo, $R^b$, and $R^c$; or heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$; and the other of $R^{2a}$ and $R^{2b}$ is H or $C_{1-2}$ alkyl optionally substituted with from 1-5 $R^a$;

$R^3$ is H; $C_{1-2}$ alkyl, which is optionally substituted with 1-5 fluoro; fluoro; or chloro;

$R^4$ is chloro; bromo; or fluoro; optionally wherein it is provided that $R^4$ is fluoro when $R^3$ is chloro;

each occurrence of $R^a$ is independently selected from the group consisting of: —OH; -halo; —$NR^eR^f$; $C_{1-4}$ alkoxy; $C_{1-4}$ haloalkoxy,; —C(═O)O($C_{1-4}$ alkyl); —C(═O) ($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ is independently selected from the group consisting of: halo; cyano; $C_{1-10}$ alkyl which is optionally substituted with from 1-6 independently selected $R^a$; $C_{2-6}$ alkenyl; $C_{2-6}$ alkynyl; $C_{1-4}$ alkoxy; —O($C_{1-3}$ alkylene)-($C_{3-6}$ cycloalkyl); $C_{1-4}$ haloalkoxy; —$S(O)_{0-2}$($C_{1-4}$ alkyl); —$NR^eR^f$; —OH; —$S(O)_{1-2}$ NR'R"; —$NO_2$; —C(═O) ($C_{1-10}$ alkyl); —C(═O)O ($C_{1-4}$ alkyl); —C(═O)OH; and —C(═O)NR'R";

each occurrence of $R^e$ is independently selected from the group consisting of:

$C_{3-10}$ cycloalkyl or $C_{3-10}$ cycloalkenyl, each of which is optionally substituted with from 1-4 substituents independently selected from the group consisting of oxo and $R^b$;

heterocyclyl or heterocycloalkenyl including 3-10 ring atoms, wherein from 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with from 1-4 substituents independently selected from the group consisting of oxo and $R^b$;

heteroaryl including 5-10 ring atoms, wherein from 1-4 ring atoms are heteroatoms, each independently selected from the group consisting of N, N(H), N($R^4$), O, and $S(O)_{0-2}$, and wherein the heteroaryl is optionally substituted with from 1-4 $R^b$; and $C_{6-10}$ aryl optionally substituted with from 1-4 $R^b$;

each occurrence of $R^d$ is independently selected from the group consisting of: $C_{1-6}$ alkyl optionally substituted with from 1-3 independently selected $R^a$; —C(O) ($C_{1-4}$ alkyl); —C(O)O($C_{1-4}$ alkyl); —CONR'R"; —$S(O)_{1-2}$ NR'R"; —$S(O)_{1-2}$($C_{1-4}$ alkyl); —OH; and $C_{1-4}$ alkoxy;

and each occurrence of $R^e$ and $R^f$ is independently selected from the group consisting of: H; $C_{1-6}$ alkyl; —C(O) ($C_{1-4}$ alkyl); —C(O)O($C_{1-4}$ alkyl); —CONR'R"; —$S(O)_{1-2}$NR'R"; —$S(O)_{1-2}$($C_{1-4}$ alkyl); —OH; and $C_{1-4}$ alkoxy, and each occurrence of R' and R" is independently selected from the group consisting of: H; and $C_{1-4}$ alkyl.

Embodiments can include one or more of the following features.

In some embodiments, $R^1$, $R^{2a}$, and $R^{2b}$ are defined according to (A).

In some embodiments, $R^1$ is heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments, $R^1$ is heteroaryl including 5-6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments, $R^1$ is heteroaryl including 6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments, $R^1$ is heteroaryl including 6 ring atoms, wherein 1-2 ring atoms are N, and wherein the heteroaryl is optionally substituted with 1-4 substituents independently selected from the group consisting of oxo, $R^b$ and $R^c$.

In some of the foregoing embodiments, $R^1$ is unsubstituted.

In some of the foregoing embodiments, $R^1$ is substituted with at least one substituent (e.g., $R^b$ or $R^c$ or a combination thereof).

In certain of the foregoing embodiments, $R^1$ is substituted with one substituent (e.g., $R^b$ or $R^c$)

In certain of the foregoing embodiments, $R^1$ is substituted with two substituents, each independently selected from the group consisting of $R^b$ and $R^c$.

In certain of the foregoing embodiments, $R^1$ is substituted with three substituents, each independently selected from the group consisting of $R^b$ and $R^c$.

In some of the foregoing embodiments, $R^1$ is substituted with one $R^b$ or one $R^c$.

In some of the foregoing embodiments, $R^1$ is substituted with one $R^b$.

In certain of the foregoing embodiments, $R^b$ is $C_{1-10}$ alkyl, which is optionally substituted with 1-6 independently selected $R^a$.

In certain of the foregoing embodiments, $R^b$ is $C_{1-6}$ alkyl, which is optionally substituted with 1-6 independently selected $R^a$.

In certain of the foregoing embodiments, $R^b$ is $C_{1-3}$ alkyl, which is optionally substituted with 1-6 independently selected $R^a$.

In certain of the foregoing embodiments, $R^b$ is unsubstituted $C_{1-3}$ alkyl. For example, $R^b$ can be —$CH_3$.

In other embodiments, $R^b$ is $C_{1-3}$ alkyl, which is substituted with 1-6 (e.g., 1-4, 1-3, 1-2, or 1) independently selected $R^a$.

By way of example, $R^a$, or each occurrence of $R^a$, can be an independently selected halo; e.g., $R^a$, or each occurrence of $R^a$, can be fluoro. A representative $R^b$ group is —$CF_3$. Another representative $R^b$ group is —$CHF_2$.

As another example, $R^a$, or each occurrence of $R^a$, can be an independently selected $C_{1-4}$ alkoxy; e.g., $R^a$, or each occurrence of $R^a$, is —$OCH_3$. A representative $R^b$ group is $CH_2OCH_3$.

As a further example, $R^a$ can be —OH. A representative $R^b$ group is $CH_2OH$.

In certain of the foregoing embodiments, $R^b$ is $C_{1-4}$ alkoxy. For example, $R^b$ can be —$OCH_3$.

In certain of the foregoing embodiments, $R^b$ is $C_{1-4}$ haloalkoxy. For example, $R^b$ can be —$OCHF_2$.

In certain of the foregoing embodiments, $R^b$ is halo. For example, $R^b$ can be fluoro. As another example, $R^b$ can be chloro.

In certain of the foregoing embodiments, $R^b$ is cyano.

In some of the foregoing embodiments, $R^1$ is substituted with 1 $R^c$.

In certain of the foregoing embodiments, $R^e$ is $C_{3-10}$ cycloalkyl or $C_{3-10}$ cycloalkenyl, each of which is optionally substituted with from 1-4 substituents independently selected from the group consisting of oxo and $R^b$.

In certain of the foregoing embodiments, $R^e$ is $C_{3-10}$ cycloalkyl which is optionally substituted with from 1-4 substituents independently selected from the group consisting of oxo and $R^b$.

In certain of the foregoing embodiments, $R^e$ is $C_{3-6}$ cycloalkyl which is optionally substituted with from 1-4 substituents independently selected from the group consisting of oxo and $R^b$.

In certain of the foregoing embodiments, $R^e$ is cyclopropyl, which is optionally substituted with from 1-4 substituents independently selected from the group consisting of oxo and $R^b$; e.g., unsubstituted cyclopropyl.

In certain of the foregoing embodiments, wherein $R^1$ has the formula:

(III-A)

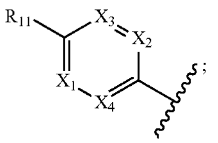

wherein each of $X_1$, $X_2$, $X_3$, and $X_4$ is, independently, CH or N; and $R^{11}$ is H, $R^b$, or $R^c$.

In certain of the foregoing embodiments, wherein $R^1$ has the formula:

(IV-A)

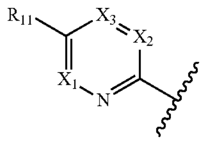

or (IV-B)

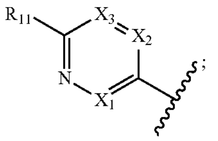

in which each of $X_1$, $X_1$, and $X_3$ is, independently, CH or N; and $R^{11}$ is H, $R^b$, or $R^c$.

In certain embodiments of formula (IV-A), not more than two of $X_1$, $X_1$, and $X_3$ are N.

In certain embodiments of formula (IV-A) or (IV-B), $X_2$ is N. In certain of these embodiments, $X_2$ is CH. In certain of these embodiments, $X_3$ is CH. For example, $R^1$ can have the formula:

(V-A)

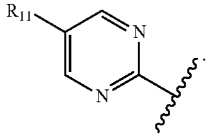

In certain embodiments of formula (IV-A) or (IV-B), $X_1$ is N. In certain of these embodiments, $X_2$ is CH. In certain of these embodiments, $X_3$ is CH. For example, $R^1$ can have the formula:

(V-B)

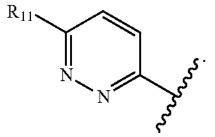

In certain embodiments of formula (IV-A) or (IV-B), $X_3$ is N. In certain of these embodiments, $X_2$ is CH. In certain of these embodiments, $X_1$ is CH. For example, $R^1$ can have the formula:

(V-C)

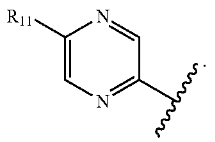

In certain embodiments of formula (IV-A), $R^1$ has the formula:

(V-D)

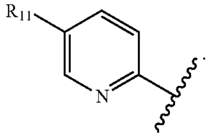

In certain embodiments of formula (IV-A) or (IV-B), $R^{11}$ is H.

In certain embodiments of formula (IV-A), (IV-B), (V-A), (V-B), (V-C), or (V-D), $R^{11}$ is $R^b$.

In certain of these embodiments of formula (IV-A), (IV-B), (V-A), (V-B), (V-C), or (V-D), $R^{11}$ is unsubstituted $C_{1-3}$ alkyl. For example, $R^{11}$ can be $CH_3$.

In certain embodiments of formula (IV-A), (IV-B), (V-A), (V-B), (V-C), or (V-D), or (II-A-4), $R^{11}$ is $C_1$-3 alkyl, which is substituted with from 1-6 (e.g., 1-4, 1-3, 1-2, or 1) independently selected $R^a$.

By way of example, $R^a$, or each occurrence of $R^a$, can be an independently selected halo; e.g., $R^a$, or each occurrence of $R^a$, can be fluoro. A representative $R^{11}$ group is —$CF_3$. Another representative $R^{11}$ group is —$CHF_2$.

As another example, $R^a$, or each occurrence of $R^a$, can be an independently selected $C_{1-4}$ alkoxy; e.g., $R^a$, or each occurrence of $R^a$, is —$OCH_3$. A representative $R^{11}$ group is $CH_2OCH_3$.

As a further example, $R^a$ can be —OH. A representative $R^{11}$ group is $CH_2OH$.

In certain embodiments of formula (IV-A), (IV-B), (V-A), (V-B), (V-C), or (V-D), $R^{11}$ is $C_{1-4}$ alkoxy. For example, $R^{11}$ can be —$OCH_3$.

In certain embodiments of formula (IV-A), (IV-B), (V-A), (V-B), (V-C), or (V-D), $R^{11}$ is $C_{1-4}$ haloalkoxy. For example, $R^{11}$ can be —$OCHF_2$.

In certain embodiments of formula (IV-A), (IV-B), (V-A), (V-B), (V-C), or (V-D), $R^{11}$ is halo. For example, $R^{11}$ can be fluoro. As another example, $R^{11}$ can be chloro.

In certain embodiments of formula (IV-A), (IV-B), (V-A), (V-B), (V-C), or (V-D), $R^b$ is cyano.

In certain embodiments of formula (IV-A), (IV-B), (V-A), (V-B), (V-C), or (V-D), $R^{11}$ is $R^c$.

In certain embodiments of formula (IV-A), (IV-B), (V-A), (V-B), (V-C), or (V-D), $R^{11}$ is cyclopropyl, which is optionally substituted with from 1-4 substituents independently selected from the group consisting of oxo and $R^e$; e.g., unsubstituted cyclopropyl.

In certain embodiments, $R^1$ is heteroaryl including 8-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments, $R^1$ is heteroaryl including 8-10 ring atoms, wherein 1-4 ring atoms are heteroatoms, each independently selected from the group consisting of N, N(H), N($R^d$), O, and S, and wherein the heteroaryl is optionally substituted with 1-4 substituents independently selected from the group consisting of oxo, $R^b$ and $R^c$.

In certain embodiments, $R^1$ is heteroaryl including 10 ring atoms, wherein 1-4 ring atoms are N, and wherein the heteroaryl is optionally substituted with 1-4 substituents independently selected from the group consisting of oxo, $R^b$ and $R^c$.

In certain embodiments, $R^1$ is

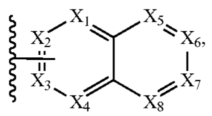

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, and each of $X_5$ to $X_8$ is independently selected from CH, $CR^{13}$ or N; wherein $R^{13}$ is $R^b$ or $R^c$; and provided that no more than four of $X_1$ to $X_8$ are heteroatoms and no more than four of $X_1$ to $X_8$ are $CR^{13}$; preferably wherein none of $X_1$ to $X_8$ are $CR^{13}$.

In certain embodiments, $R^1$ is:

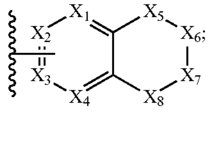

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, and each of $X_5$ to $X_8$ is independently selected from $CH_2$, $CHR^{13}$, NH, $NR^{13}$, O or $SO_2$; wherein $R^{13}$ is $R^b$ or $R^c$; and provided that no more than four of $X_1$ to $X_8$ are heteroatoms and no more than four of $X_1$ to $X_8$ include an $R^{13}$ group; preferably wherein none of $X_1$ to $X_8$ include an $R^{13}$ group.

In certain embodiments, $R^1$ is:

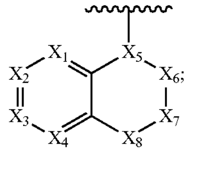

wherein $X_1$ to $X_4$ are each independently selected from CH, $CR^{13}$ or N, $X_5$ is CH, $CR^{13}$ or N, and each of $X_6$ to $X_8$ is independently selected from $CH_2$, $CR^{13}$, NH, $NR^{13}$, O or $SO_2$; wherein $R^{13}$ is $R^b$ or $R^c$; and provided that no more than four of $X_1$ to $X_8$ are heteroatoms and no more than four of $X_1$ to $X_8$ include an $R^{13}$ group; preferably wherein none of $X_1$ to $X_8$ include an $R^{13}$ group.

In certain embodiments, $R^1$ is:

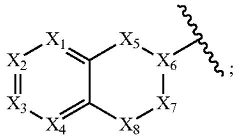

wherein $X_1$ to $X_4$ are each independently selected from CH or N, $X_6$ is CH, $CR^{13}$ or N, and each of $X_5$, $X_7$ and $X_8$ is independently selected from $CH_2$, $CHR^{13}$, NH, $NR^{13}$, O or $SO_2$; wherein $R^{13}$ is $R^b$ or $R^c$; and provided that no more than four of $X_1$ to $X_8$ are heteroatoms and and no more than four of $X_1$ to $X_8$ include an $R^{13}$ group; preferably wherein none of $X_1$ to $X_8$ include an $R^{13}$ group.

For example, $R^1$ can be:

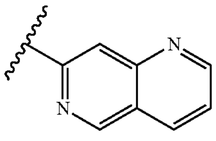
,
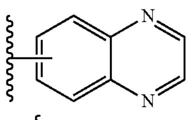
,
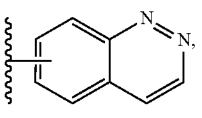
or
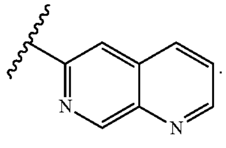
.

In certain embodiments, $R^1$ is heteroaryl including 8 ring atoms, wherein 1-4 ring atoms are heteroatoms, each independently selected from the group consisting of N, N(H), $N(R^d)$, O, and S, and wherein the heteroaryl is optionally substituted with 1-4 substituents independently selected from the group consisting of oxo, $R^b$ and $R^c$.

In certain embodiments, $R^1$ is heteroaryl including 9 ring atoms, wherein 1-4 ring atoms are heteroatoms, each independently selected from the group consisting of N, N(H), $N(R^d)$, O, and S, and wherein the heteroaryl is optionally substituted with 1-4 substituents independently selected from the group consisting of oxo, $R^b$ and $R^c$.

In certain embodiments, $R^1$ is:

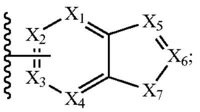

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, $X_5$ and $X_6$ are independently selected from CH, $CR^{13}$ or N, and $X_7$ is selected from $CH_2$, $CHR^{13}$, NH, $NR^{13}$, O or S wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

In certain embodiments, $R^1$ is

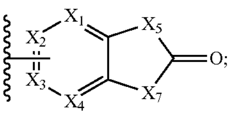

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, $X_5$ and $X_7$ are independently selected from $CH_2$, $CHR^{13}$, NH, $NR^{13}$ or O; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

In certain embodiments, $R^1$ is:

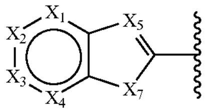
or
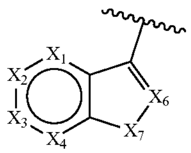
;

wherein $X_1$ to $X_4$ are each independently selected from CH, $CR^{13}$ or N; $X_5$ and $X_6$ are selected from CH, $CR^{13}$ or N, and $X_7$ is selected from NH, $NR^{13}$ or O; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

In certain embodiments, $R^1$ is:

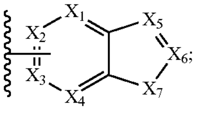

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, and $X_5$ to $X_7$ are each independently selected from $CH_2$, $CHR^{13}$, NH, $NR^{13}$, O or $SO_2$; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group.

In certain embodiments, $R^1$ is:

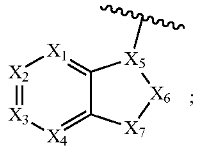
;

wherein $X_1$ to $X_4$ are each independently selected from CH, $CR^{13}$ or N, $X_5$ is CH or N and $X_6$ and $X_7$ are each independently selected from $CH_2$, $CHR^{13}$, NH, $NR^{13}$, O or $SO_2$; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group.

In certain embodiments, $R^1$ is:

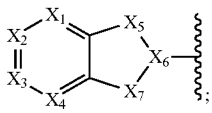
;

wherein $X_1$ to $X_4$ are each independently selected from CH, $CR^{13}$ or N, $X_6$ is CH or N and $X_5$ and $X_7$ are each independently selected from $CH_2$, $CHR^{13}$, NH, $NR^{13}$, O or $SO_2$; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group.

In certain embodiments, $R^1$ has the formula:

(VI-A)

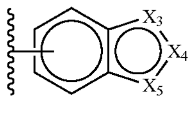
or (VI-B)

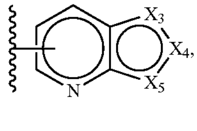
, wherein:

$X_3$ is NH, O, or S;

$X_4$ is N, O, or CH; and $X_5$ is N or CH.

In certain embodiments of formula (VI-A) or (VI-B), $X_5$ is CH.

In certain embodiments of formula (VI-A) or (VI-B), $X_4$ is CH.

In certain embodiments of formula (VI-A) or (VI-B), $X_4$ and $X_5$ are CH.

In certain embodiments of formula (VI-A) or (VI-B), $X_3$ is NH, and $X_4$ and $X_5$ are CH.

In certain embodiments of formula (VI-A) or (VI-B), $X_3$ is O, and $X_4$ and $X_5$ are CH.

In certain embodiments of formula (VI-A) or (VI-B), $X_3$ is S, and $X_4$ and $X_5$ are CH.

In certain embodiments of formula (VI-A) or (VI-B), one of $X_4$ and $X_5$ is CH, and the other of $X_4$ and $X_5$ is N. In embodiments, $X_4$ is CH; and $X_5$ is N. In embodiments, $X_4$ is N; and $X_5$ is CH.

In certain of these embodiments, $X_3$ is O or S. In other embodiments, $X_3$ is NH For example, $X_3$ can be O or S; $X_4$ can be CH; and $X_5$ can be N.

As another example, $X_3$ can be NH, $X_4$ can be N; and $X_5$ can be CH.

In certain embodiments of formula (VI-A) or (VI-B), each of $X_3$ and $X_4$ is other than CH.

For example, $X_3$ can be N, $X_4$ can be O; and $X_5$ can be N.

In certain embodiments, $R^1$ is heteroaryl including 5 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-4 substituents independently selected from the group consisting of $R^b$ and $R^c$.

In certain embodiments, $R^1$ has the formula:

(VI-C)

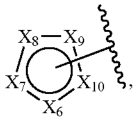
, wherein:

$X_6$ is NH, $NCH_3$, O, or S;

$X_7$ is N, C, CH, $CCF_3$, $CCHF_2$, C(cyclopropyl), or $CCH_3$;

$X_8$ is N, C, CH, $CCH_3$, $CCF_3$, or $COCH_3$;

$X_9$ is N, C, CH, $CCH_3$, $CCF_3$, or $COCH_3$; and $X_{10}$ is N, C, CH, $CCF_3$, $CCHF_2$, C(cyclopropyl), or $CCH_3$.

In certain embodiments, $R^1$ has the formula:

(VI-C-1)

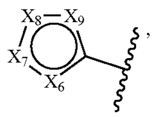
, wherein:

$X_6$ is NH, $NCH_3$, O, or S;

$X_7$ is N, CH, $CCF_3$, $CCHF_2$, C(cyclopropyl), or $CCH_3$;

$X_8$ is N, CH, or $CCH_3$; and $X_9$ is N, CH, or $CCH_3$.

In certain embodiments of formula (VI-C) or (VI-C-1), $X_8$ is N.

In certain embodiments of formula (VI-C) or (VI-C-1), $X_9$ is N.

In certain embodiments of formula (VI-C) or (VI-C-1), $X_6$ is O.

In certain embodiments of formula (VI-C) or (VI-C-1), $X_7$ is CH, $CCF_3$, $CCHF_2$, C(cyclopropyl), or $CCH_3$.

In certain embodiments of formula (VI-C) or (VI-C-1), $X_7$ is $CCH_3$.

For example, $R^1$ can have the formula:

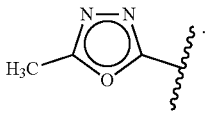

In certain embodiments of formula (VI-C) or (VI-C-1), $X_6$ is O or S.

In certain embodiments of formula (VI-C) or (VI-C-1), $X_7$ is N.

In certain embodiments of formula (VI-C) or (VI-C-1), $X_6$ is O; and $X_7$ is N.

In certain embodiments of formula (VI-C) or (VI-C-1), $X_6$ is S; and $X_7$ is N.

In certain embodiments of formula (VI-C) or (VI-C-1), $X_8$ is CH or $CCH_3$.

In certain embodiments of formula (VI-C) or (VI-C-1), $X_9$ is CH or $CCH_3$.

In certain embodiments of formula (VI-C) or (VI-C-1), $X_8$ is CH or $CCH_3$; and $X_9$ is CH or $CCH_3$.

In certain embodiments of formula (VI-C) or (VI-C-1), $X_6$ is O; $X_7$ is N; $X_8$ is CH or $CCH_3$; and $X_9$ is CH or $CCH_3$.

In certain embodiments of formula (VI-C) or (VI-C-1), $X_6$ is S; $X_7$ is N; $X_8$ is CH or $CCH_3$; and $X_9$ is CH or $CCH_3$.

In certain embodiments of formula (VI-C) or (VI-C-1):

$X_6$ is NH, $NCH_3$, or O;

$X_7$ is CH or $CCH_3$;

$X_8$ is N; and $X_9$ is CH or $CCH_3$.

In certain embodiments of formula (VI-C) or (VI-C-1), $X_8$ is N; and $X_6$ is O.

In certain embodiments of formula (VI-C) or (VI-C-1):

$X_6$ is $NCH_3$;

$X_7$ is CH or $CCH_3$;

$X_8$ is N; and $X_9$ is N.

In some embodiments, $R^1$ is $C_{6-10}$ aryl optionally substituted with 1-4 substituents independently selected from the group consisting of $R^b$, and $R^c$.

In certain embodiments, $R^1$ is phenyl optionally substituted with 1-4 substituents independently selected from the group consisting of $R^b$, and $R^c$.

In certain embodiments, $R^1$ has the formula:

(VI-D)

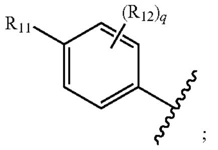

;

wherein each $R^{11}$ is independently selected from the group consisting of H, $R^b$, and $R^c$; each $R^{12}$ is independently selected from the group consisting of $R^b$ and $R^e$; and q is 0, 1, or 2.

In certain embodiments of formula (VI-D), $R^{11}$ is H, fluoro, CN, $CH_3$, $CHF_2$, —$SO_2NH_2$, $SO_2CH_3$, —C(O)$NH_2$, or cyclopropyl.

In certain embodiments of formula (VI-D), $R^{11}$ is H.

In certain embodiments of formula (VI-D), $R^{11}$ is $CH_3$.

In certain embodiments of formula (VI-D), $R^{11}$ is CN.

In certain embodiments of formula (VI-D), q is 1.

In certain embodiments of formula (VI-D), $R^{12}$ is F.

In some embodiments, each of $R^{2a}$ and $R^{2b}$ is independently selected from the group consisting of H and $C_{1-2}$ alkyl optionally substituted with from 1-5 $R^a$.

In certain embodiments, each of $R^{2a}$ and $R^{2b}$ is an independently selected $C_{1-2}$ alkyl optionally substituted with from 1-5 $R^a$.

In certain embodiments, each of $R^{2a}$ and $R^{2b}$ is an independently selected unsubstituted $C_{1-2}$alkyl. For example, each of $R^{2a}$ and $R^{2b}$ can be $CH_3$.

In some embodiments, $R^{2a}$ and $R^{2b}$ taken together with the carbon atom to which each is attached forms:

$C_{3-7}$ cycloalkyl, which is optionally substituted with 1-4 substituents independently selected from the group consisting of oxo and $R^b$;

heterocyclyl including 4-7 ring atoms, wherein 1-2 ring atoms are heteroatoms, each independently selected from the group consisting of N, N(H), $N(R^4)$, O, and $S(O)_{0-2}$, and wherein the heterocyclyl is optionally substituted with 1-4 substituents independently selected from the group consisting of oxo and $R^b$.

In certain embodiments, $R^{2a}$ and $R^{2b}$ taken together with the carbon atom to which each is attached forms $C_{3-7}$ cycloalkyl, which is optionally substituted with 1-4 substituents independently selected from the group consisting of oxo and $R^b$.

In certain embodiments, $R^{2a}$ and $R^{2b}$ taken together with the carbon atom to which each is attached forms:

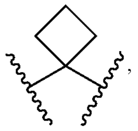

,

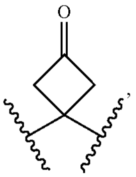

, or

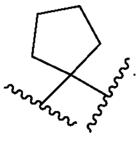

.

In some embodiments, $R^{2a}$ and $R^{2b}$ taken together with the carbon atom to which each is attached forms heterocyclyl including 4-7 ring atoms, wherein 1-2 ring atoms are heteroatoms, each independently selected from the group consisting of N, N(H), $N(R^d)$, O, and $S(O)_{0-2}$, and wherein the heterocyclyl is optionally substituted with 1-4 substituents independently selected from the group consisting of oxo and $R^b$.

In certain embodiments, $R^{2a}$ and $R^{2b}$ taken together with the carbon atom to which each is attached forms:

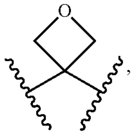

,

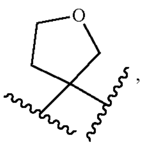

, or

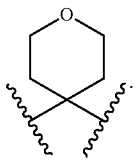

.

In some embodiments, $R^1$, $R^{2a}$, and $R^{2b}$ are defined according to (B).

In certain embodiments, wherein $R^1$ taken together with (i) the carbon atom to which it is attached and (ii) and one of $R^{2a}$ and $R^{2b}$ forms:

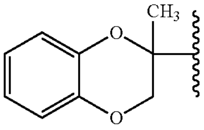 [SMILES: *C1(C)COc2ccccc2O1]

wherein as indicated in the formula above, the other of $R^{2a}$ and $R^{2b}$ is $CH_3$.

In some embodiments, $R^1$ is heterocycloalkenyl including 3-10 ring atoms, wherein 1-3 ring atoms are heteroatoms, each independently selected from the group consisting of N, N(H), N($R^d$), O, and $S(O)_{0-2}$, and wherein the heterocycloalkenyl is optionally substituted with 1-4 substituents independently selected from the group consisting of oxo, $R^b$, and $R^c$.

In some embodiments, $R^1$ is heterocycloalkenyl including 6 ring atoms.

In some embodiments, $R^1$ is heterocyclyl including 4-6 ring atoms, wherein 1-4 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo, $R^b$ and $R^c$.

In some embodiments, $R^1$ is heterocyclyl including 6 ring atoms.

In some embodiments, $R^1$ is $C_{3-7}$ cycloalkyl optionally substituted with 1-4 substituents independently selected from the group consisting of oxo, $R^b$, and $R^c$.

In some embodiments, $R^1$ is $C_{5-6}$ cycloalkyl.

In some embodiments, $R^1$ is:

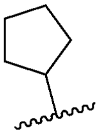 or 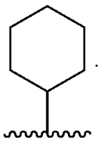.

In some embodiments, $R^1$ is:

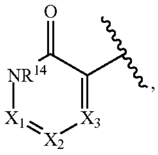, 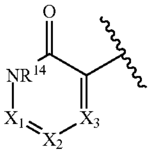 or 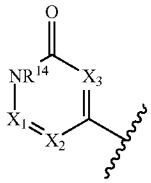

wherein $X_1$, $X_2$ and $X_3$ are each independently CH, $CR^{15}$ or N; wherein $R^{14}$ and $R^{15}$ are each independently $R^b$ or $R^c$.

In some embodiments, $R^{14}$ is $C_{1-2}$ alkyl or $C_{1-2}$ fluoroalkyl, and/or only one of $X_1$, $X_2$ and $X_3$ is $CR^{15}$ and $R^{15}$ is methyl or F.

In some embodiments, $R^1$ is:

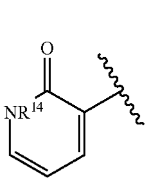, 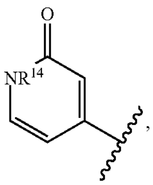, 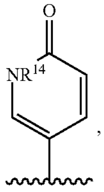,

-continued

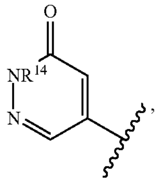, or 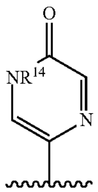

wherein $R^{14}$ is $R^b$ or $R^c$.

In some embodiments, $R^{14}$ is $C_{1-2}$ alkyl or $C_{1-2}$ fluoroalkyl.

In some embodiments, $R^1$ is:

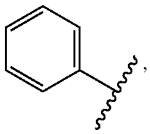, 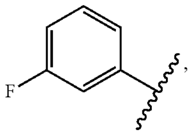, 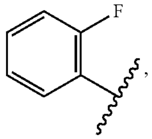,

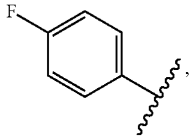, 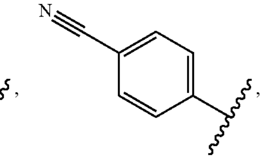,

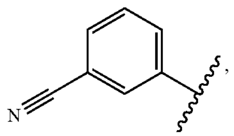, 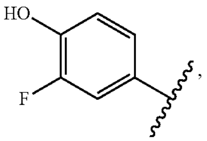,

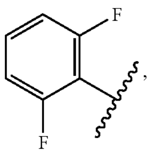, 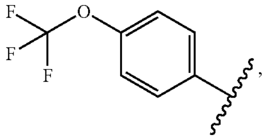,

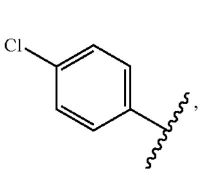, 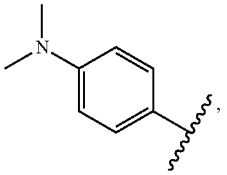,

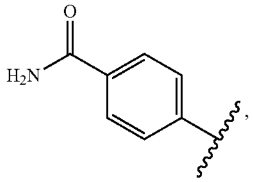, 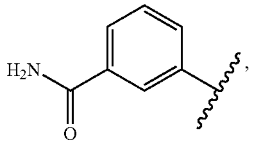,

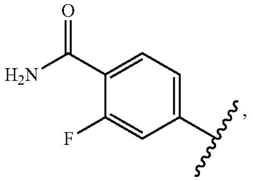, 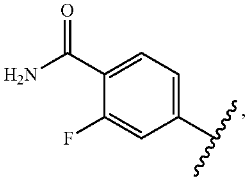,

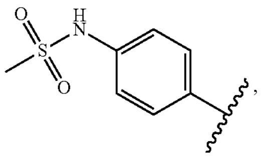, 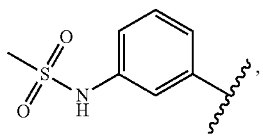,

-continued
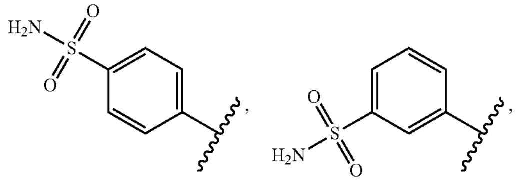
, ,
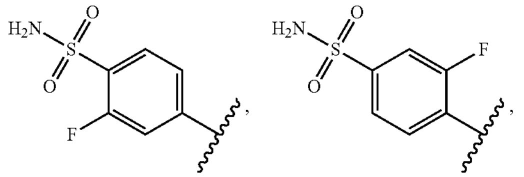
, ,
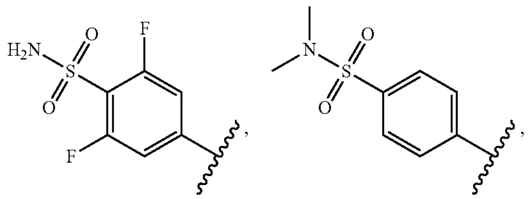
, ,
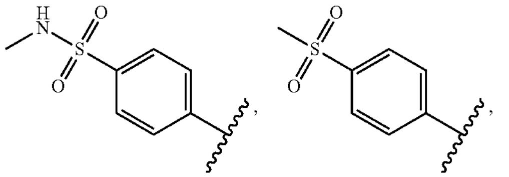
, ,
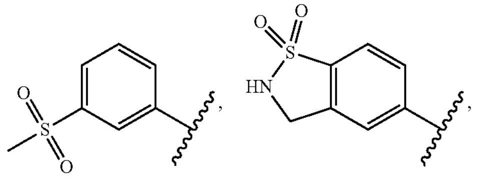
, ,
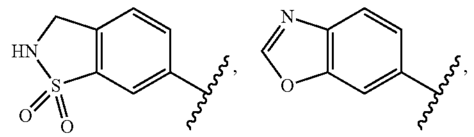
, ,
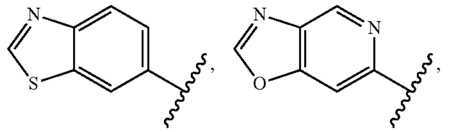
, ,
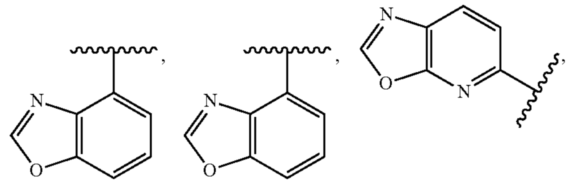
, , ,
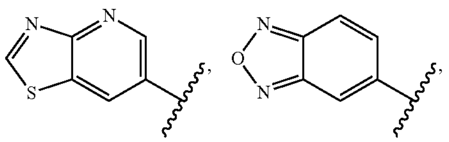
, ,
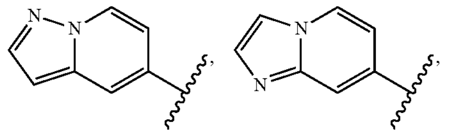
, ,
-continued
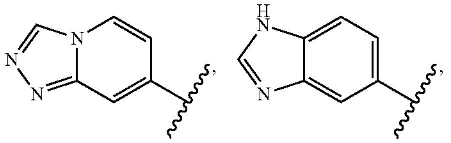
, ,
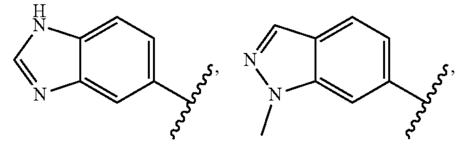
, ,
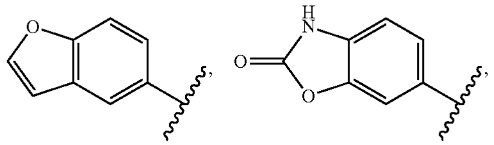
, ,
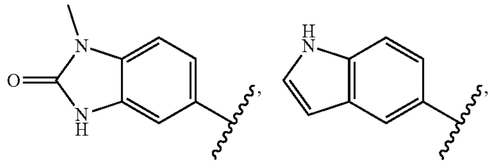
, ,
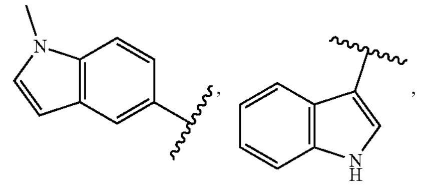
, ,
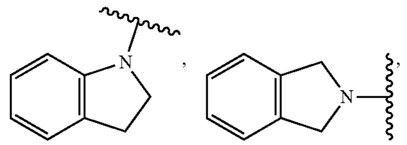
, ,
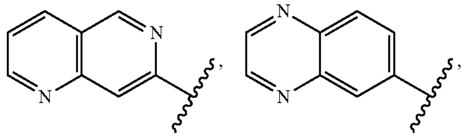
, ,
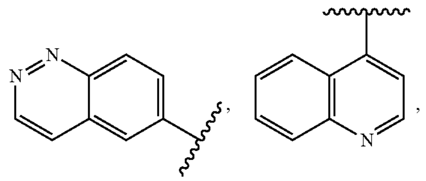
, ,
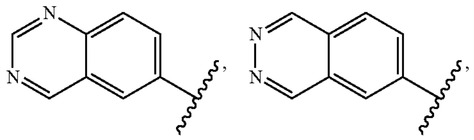
, ,
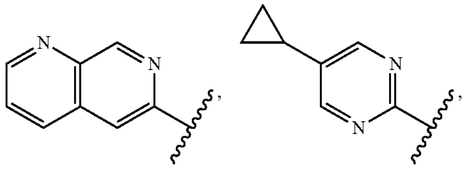
, ,
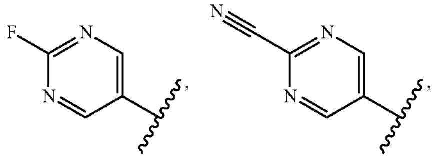
, , -continued
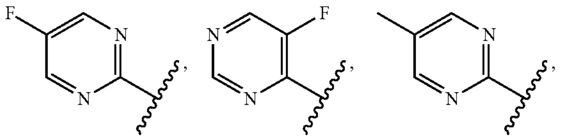
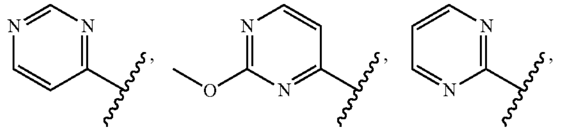
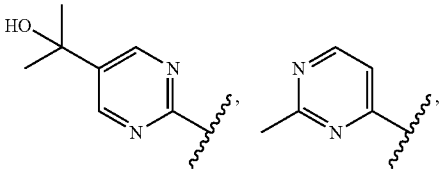
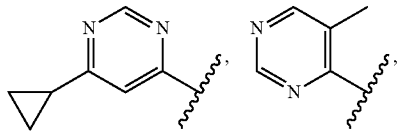
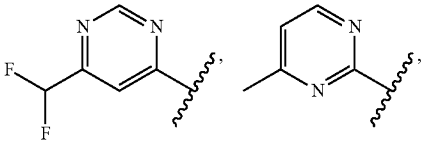
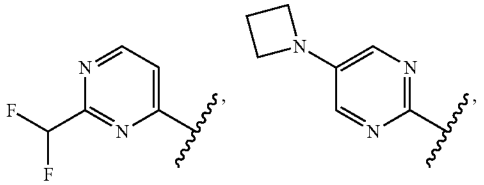
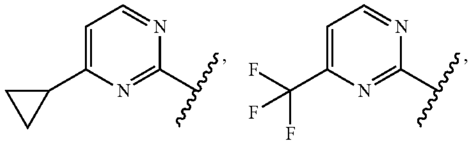
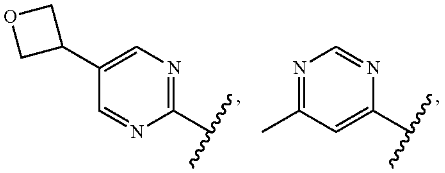
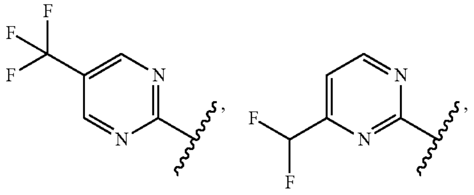
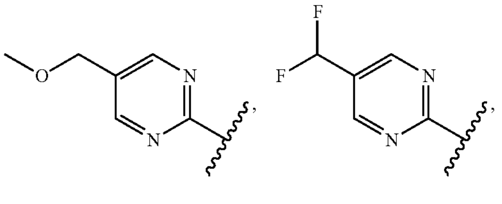
-continued
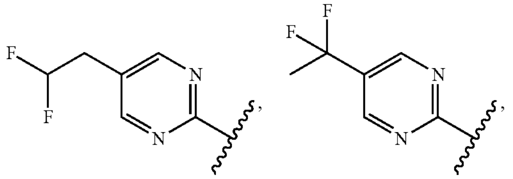
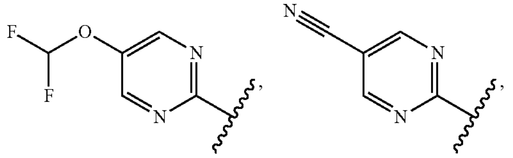
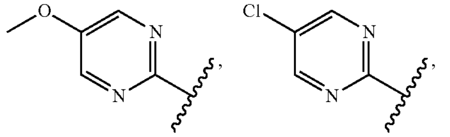
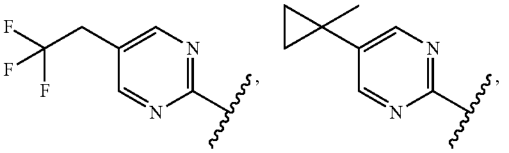
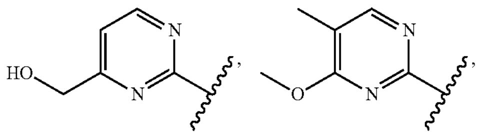
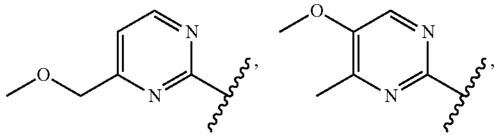
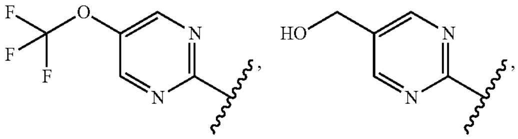
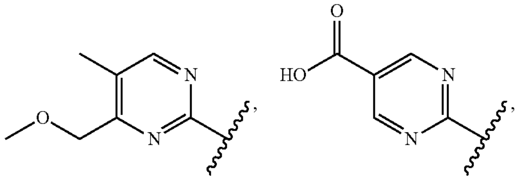
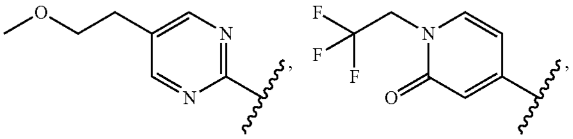
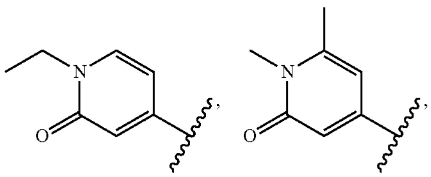
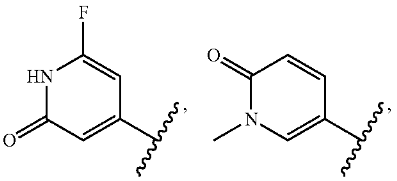

-continued
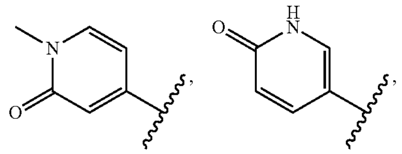
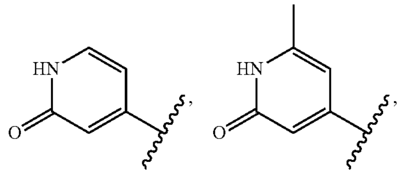
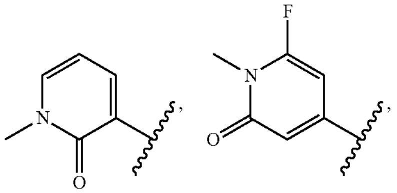
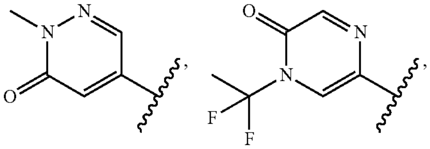
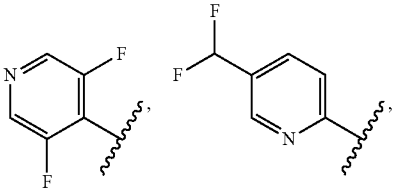
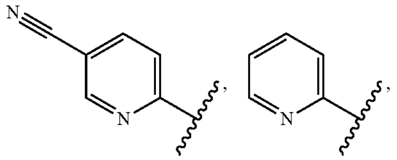
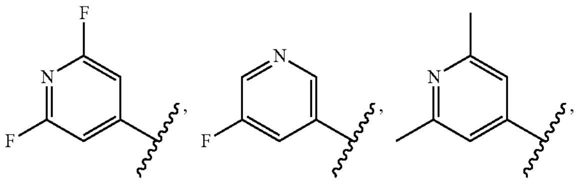
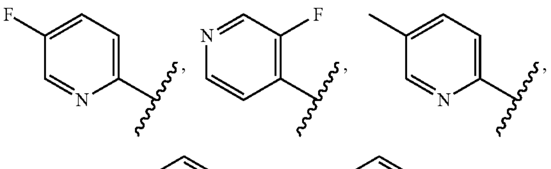
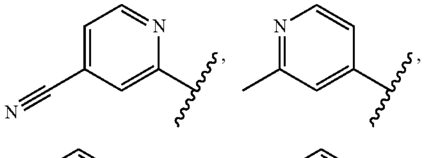
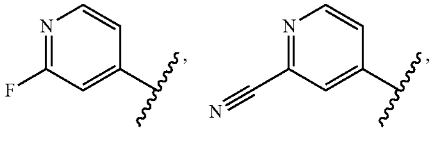
-continued
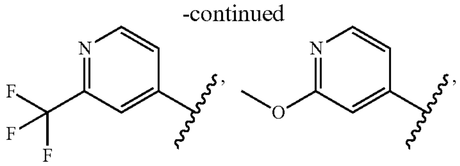
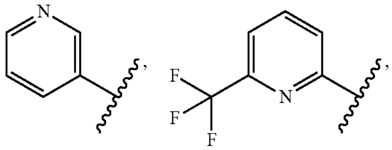
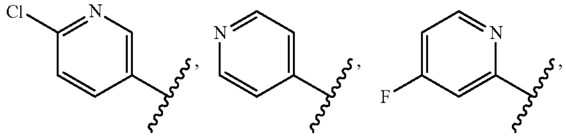
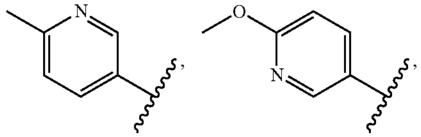
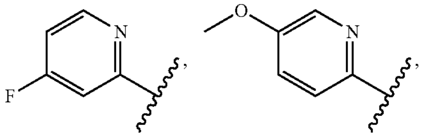
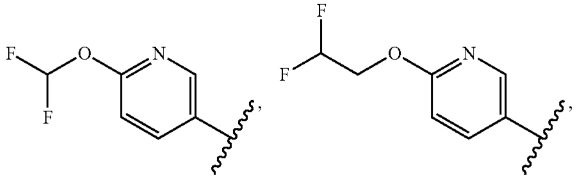
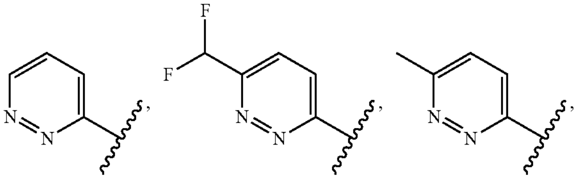
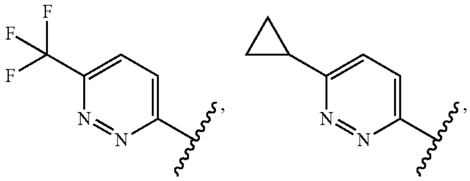
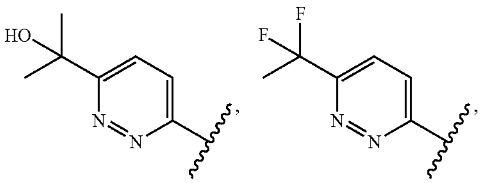
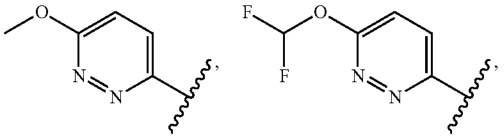
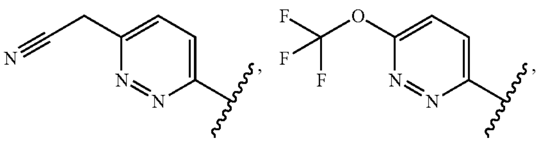

-continued
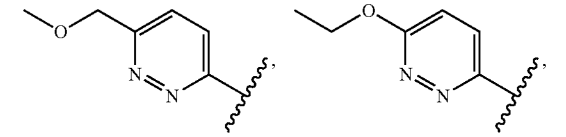
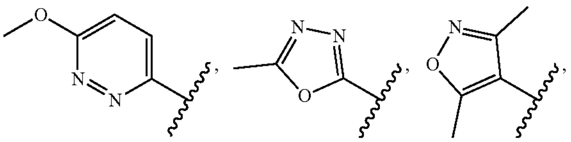
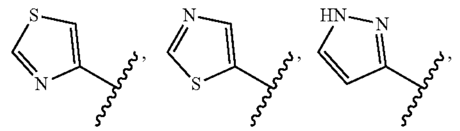
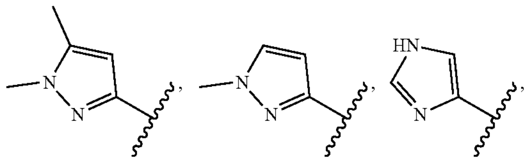
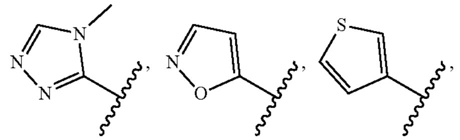
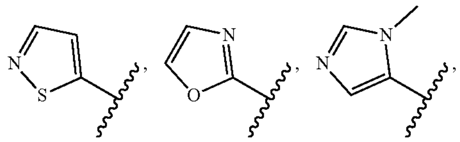
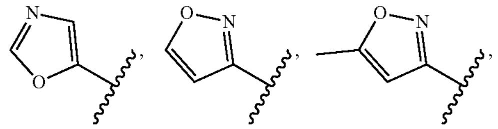
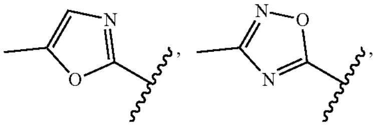
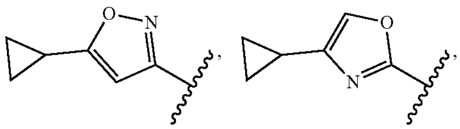
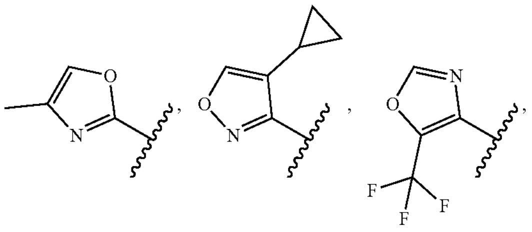
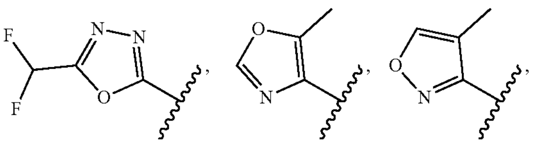
-continued
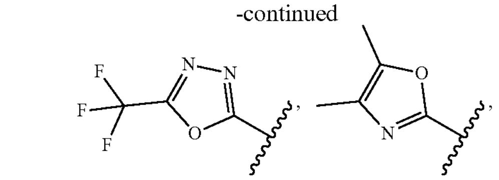
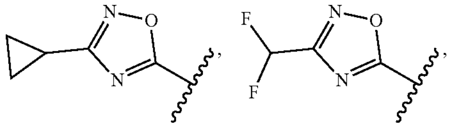
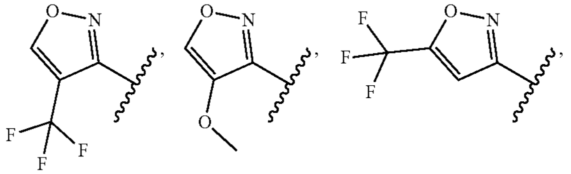
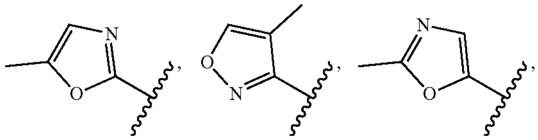
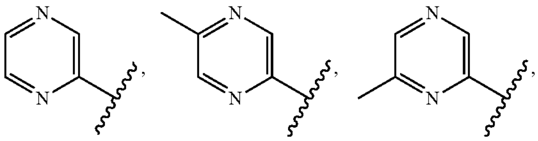
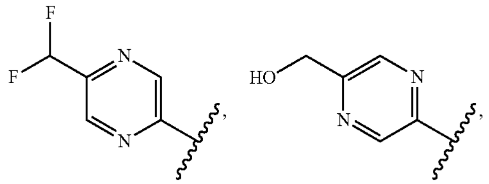
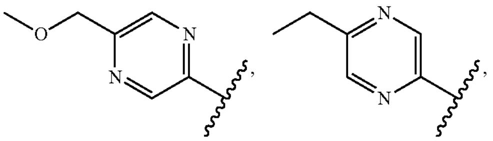
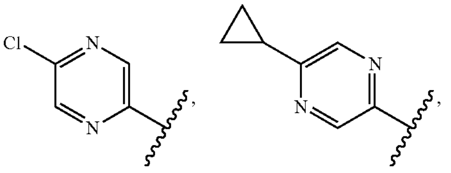
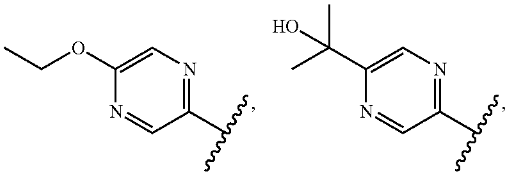
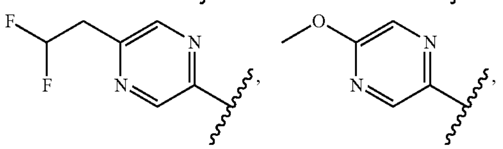
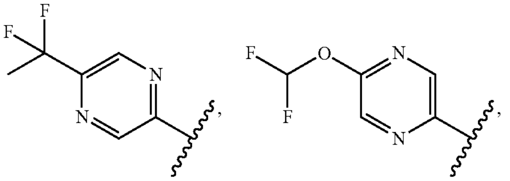

-continued

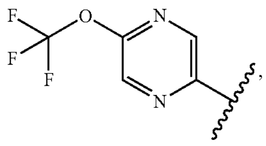,
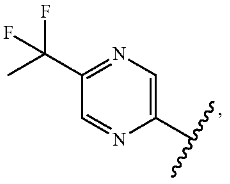,
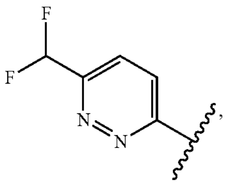,
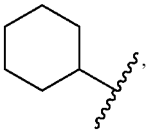,
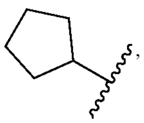, or
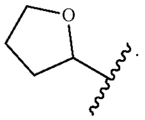.

In some embodiments, $R^3$ is Cl.

In some embodiments, $R^3$ is F.

In some embodiments, $R^3$ is H.

In some embodiments, $R^4$ is Cl.

In some embodiments, $R^4$ is Br.

In some embodiments, $R^4$ is F.

In some embodiments, $R^3$ is Cl, and $R^4$ is Cl.

In some embodiments, $R^3$ is H, and $R^4$ is Cl.

In some embodiments, $R^3$ is H, and $R^4$ is Br.

In some embodiments, $R^3$ is $CH_3$, and $R^4$ is Cl.

In some embodiments, $R^3$ is Cl, and $R^4$ is F.

In some embodiments, the compound has the formula:

(VIII-A)

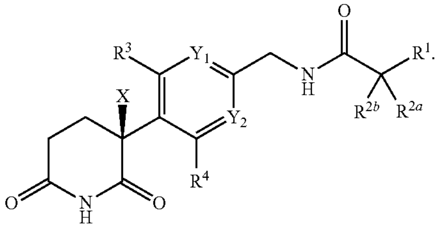

In some embodiments, the compound has the formula:

(VIII-B)

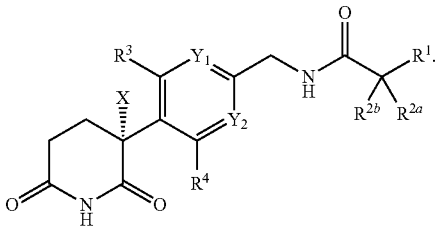

In some embodiments, the compound has the formula:

(VIII-C)

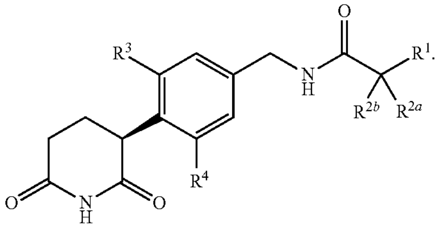

In some embodiments, the compound has the formula:

(VIII-D)

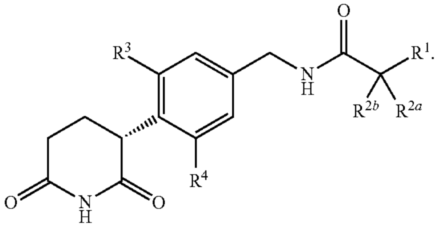

In some embodiments, the compound has the formula:

(VIII-E)

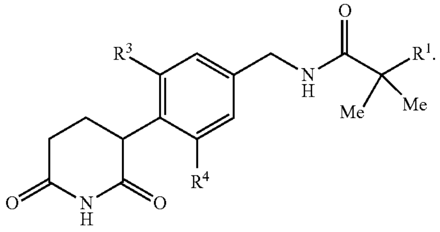

In some embodiments, the compound has the formula:

(VIII-F)

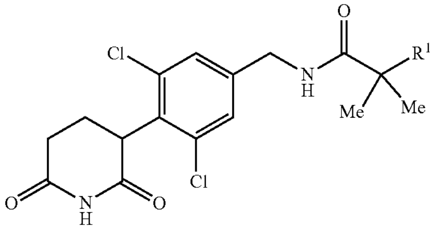

or (VIII-G)

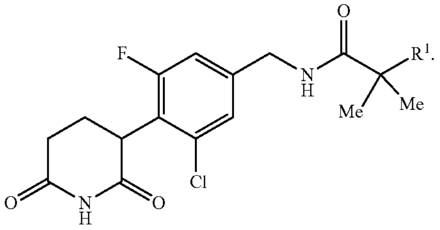

In some embodiments, wherein the compound has the formula:

(VIII-H)

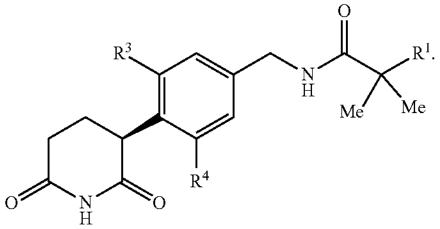

In some embodiments, wherein the compound has the formula:

(VIII-I)

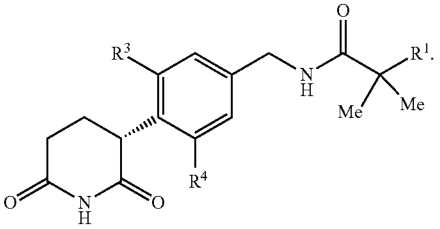

In formula (VIII-A), (VIII-B), (VIII-C), (VIII-D), (VIII-E), (VIII-F), (VIII-G), (VIII-H), or (VIII-I), $R^1$, $R^{2a}$, $R^{2b}$, $R^3$, $R^4$, $Y_1$, $Y_2$, and X are as defined herein.

In some embodiments of formula (VIII-A), (VIII-B), (VIII-C), (VIII-D), (VIII-E), (VIII-F), (VIII-G), (VIII-H), or (VIII-I), $R^1$ is heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments of formula (VIII-A), (VIII-B), (VIII-C), (VIII-D), (VIII-E), (VIII-F), (VIII-G), (VIII-H), or (VIII-I), $R^1$ is heteroaryl including 5-6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments of formula (VIII-A), (VIII-B), (VIII-C), (VIII-D), (VIII-E), (VIII-F), (VIII-G), (VIII-H), or (VIII-I), $R^1$ is heteroaryl including 6 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

In certain embodiments of formula (VIII-A), (VIII-B), (VIII-C), (VIII-D), (VIII-E), (VIII-F), (VIII-G), (VIII-H), or (VIII-I), $R^1$ is heteroaryl including 6 ring atoms, wherein 1-2 ring atoms are N, and wherein the heteroaryl is optionally substituted with 1-4 substituents independently selected from the group consisting of oxo, $R^b$ and $R^c$.

In certain embodiments of formula (VIII-A), (VIII-B), (VIII-C), (VIII-D), (VIII-E), (VIII-F), (VIII-G), (VIII-H), or (VIII-I), $R^1$ is unsubstituted.

In certain embodiments of formula (VIII-A), (VIII-B), (VIII-C), (VIII-D), (VIII-E), (VIII-F), (VIII-G), (VIII-H), or (VIII-I), $R^1$ is substituted with at least one substituent (e.g., $R^b$ or $R^e$ or a combination thereof).

In certain embodiments formula (VIII-A), (VIII-B), (VIII-C), (VIII-D), (VIII-E), (VIII-F), (VIII-G), (VIII-H), or (VIII-I), $R^1$ is substituted with one substituent (e.g., $R^b$ or $R^c$).

In certain embodiments of formula (VIII-A), (VIII-B), (VIII-C), (VIII-D), (VIII-E), (VIII-F), (VIII-G), (VIII-H), or (VIII-I), $R^1$ is substituted with two substituents, each independently selected from the group consisting of $R^b$ and $R^c$.

In certain embodiments of formula (VIII-A), (VIII-B), (VIII-C), (VIII-D), (VIII-E), (VIII-F), (VIII-G), (VIII-H), or (VIII-I), $R^1$ is substituted with three substituents, each independently selected from the group consisting of $R^b$ and $R^c$.

In certain embodiments formula (VIII-A), (VIII-B), (VIII-C), (VIII-D), (VIII-E), (VIII-F), (VIII-G), (VIII-H), or (VIII-I), $R^1$ is substituted with one $R^b$ or one $R^e$.

In certain embodiments of formula (VIII-A), (VIII-B), (VIII-C), (VIII-D), (VIII-E), (VIII-F), (VIII-G), (VIII-H), or (VIII-I), $R^1$ is substituted with one $R^b$.

In certain of these embodiments of formula (VIII-A), (VIII-B), (VIII-C), (VIII-D), (VIII-E), (VIII-F), (VIII-G), (VIII-H), or (VIII-I), $R^b$ is $C_{1-10}$ alkyl, which is optionally substituted with 1-6 independently selected $R^a$.

In certain embodiments of formula (VIII-A), (VIII-B), (VIII-C), (VIII-D), (VIII-E), (VIII-F), (VIII-G), (VIII-H), or (VIII-I), $R^b$ is $C_{1-6}$ alkyl, which is optionally substituted with 1-6 independently selected $R^a$.

In certain of these embodiments of formula (VIII-A), (VIII-B), (VIII-C), (VIII-D), (VIII-E), (VIII-F), (VIII-G), (VIII-H), or (VIII-I), $R^b$ is $C_{1-3}$ alkyl, which is optionally substituted with 1-6 independently selected $R^a$.

In certain of these embodiments of formula (VIII-A), (VIII-B), (VIII-C), (VIII-D), (VIII-E), (VIII-F), (VIII-G), (VIII-H), or (VIII-I), $R^b$ is unsubstituted $C_{1-3}$ alkyl. For example, $R^b$ can be —$CH_3$.

In certain of these embodiments of formula (VIII-A), (VIII-B), (VIII-C), (VIII-D), (VIII-E), (VIII-F), (VIII-G), (VIII-H), or (VIII-I), $R^b$ is $C_{1-3}$ alkyl, which is substituted with 1-6 (e.g., 1-4, 1-3, 1-2, or 1) independently selected $R^a$.

By way of example, $R^a$, or each occurrence of $R^a$, can be an independently selected halo; e.g., $R^a$, or each occurrence of $R^a$, can be fluoro. A representative $R^b$ group is —$CF_3$. Another representative $R^b$ group is —$CHF_2$.

As another example, $R^a$, or each occurrence of $R^a$, can be an independently selected $C_{1-4}$ alkoxy; e.g., $R^a$, or each occurrence of $R^a$, is —$OCH_3$. A representative $R^b$ group is $CH_2OCH_3$. As a further example, $R^a$ can be —OH. A representative $R^b$ group is $CH_2OH$.

In certain of these embodiments of formula (VIII-A), (VIII-B), (VIII-C), (VIII-D), (VIII-E), (VIII-F), (VIII-G), (VIII-H), or (VIII-I), $R^b$ is $C_{1-4}$ alkoxy. For example, $R^b$ can be —$OCH_3$. In certain of these embodiments of formula (VIII-A), (VIII-B), (VIII-C), (VIII-D), (VIII-E), (VIII-F), (VIII-G), (VIII-H), or (VIII-I), $R^b$ is $C_{1-4}$ haloalkoxy. For example, $R^b$ can be —$OCHF_2$.

In certain of these embodiments of formula (VIII-A), (VIII-B), (VIII-C), (VIII-D), (VIII-E), (VIII-F), (VIII-G), (VIII-H), or (VIII-I), $R^b$ is halo. For example, $R^b$ can be fluoro. As another example, $R^b$ can be chloro.

In certain of these embodiments of formula (VIII-A), (VIII-B), (VIII-C), (VIII-D), (VIII-E), (VIII-F), (VIII-G), (VIII-H), or (VIII-I), $R^b$ is cyano.

In certain embodiments of formula (VIII-A), (VIII-B), (VIII-C), (VIII-D), (VIII-E), (VIII-F), (VIII-G), (VIII-H), or (VIII-I), $R^1$ is substituted with 1 $R^e$.

In certain of these embodiments of formula (VIII-A), (VIII-B), (VIII-C), (VIII-D), (VIII-E), (VIII-F), (VIII-G), (VIII-H), or (VIII-I), $R^e$ is $C_{3-10}$ cycloalkyl or $C_{3-10}$ cycloalkenyl, each of which is optionally substituted with from 1-4 substituents independently selected from the group consisting of oxo and $R^b$.

In certain of these embodiments of formula (VIII-A), (VIII-B), (VIII-C), (VIII-D), (VIII-E), (VIII-F), (VIII-G), (VIII-H), or (VIII-I), $R^e$ is $C_{3-10}$ cycloalkyl which is optionally substituted with from 1-4 substituents independently selected from the group consisting of oxo and $R^b$.

In certain of these embodiments of formula (VIII-A), (VIII-B), (VIII-C), (VIII-D), (VIII-E), (VIII-F), (VIII-G), (VIII-H), or (VIII-I), $R^e$ is $C_{3-6}$ cycloalkyl which is optionally substituted with from 1-4 substituents independently selected from the group consisting of oxo and $R^b$.

In certain of these embodiments of formula (VIII-A), (VIII-B), (VIII-C), (VIII-D), (VIII-E), (VIII-F), (VIII-G), (VIII-H), or (VIII-I), $R^e$ is cyclopropyl, which is optionally substituted with from 1-4 substituents independently selected from the group consisting of oxo and $R^b$; e.g., unsubstituted cyclopropyl.

In certain embodiments of formula (VIII-A), (VIII-B), (VIII-C), (VIII-D), (VIII-E), (VIII-F), (VIII-G), (VIII-H), or (VIII-I), $R^3$ is $C_1$.

In certain embodiments of formula (VIII-A), (VIII-B), (VIII-C), (VIII-D), (VIII-E), (VIII-F), (VIII-G), (VIII-H), or (VIII-I), $R^3$ is H.

In certain embodiments of formula (VIII-A), (VIII-B), (VIII-C), (VIII-D), (VIII-E), (VIII-F), (VIII-G), (VIII-H), or (VIII-I), $R^3$ is $CH_3$.

In certain embodiments of formula (VIII-A), (VIII-B), (VIII-C), (VIII-D), (VIII-E), (VIII-F), (VIII-G), (VIII-H), or (VIII-I), $R^4$ is Cl.

In certain embodiments of formula (VIII-A), (VIII-B), (VIII-C), (VIII-D), (VIII-E), (VIII-F), (VIII-G), (VIII-H), or (VIII-I), $R^4$ is Br.

In certain embodiments of formula (VIII-A), (VIII-B), (VIII-C), (VIII-D), (VIII-E), (VIII-F), (VIII-G), (VIII-H), or (VIII-I), $R^4$ is F (e.g., when $R^3$ is Cl).

In certain embodiments of formula (VIII-A), (VIII-B), (VIII-C), (VIII-D), (VIII-E), (VIII-F), (VIII-G), (VIII-H), or (VIII-I), $R^3$ is Cl, and $R^4$ is Cl.

In certain embodiments of formula (VIII-A), (VIII-B), (VIII-C), (VIII-D), (VIII-E), (VIII-F), (VIII-G), (VIII-H), or (VIII-I), $R^3$ is H, and $R^4$ is Cl.

In certain embodiments of formula (VIII-A), (VIII-B), (VIII-C), (VIII-D), (VIII-E), (VIII-F), (VIII-G), (VIII-H), or (VIII-I), $R^3$ is H, and $R^4$ is Br.

In certain embodiments of formula (VIII-A), (VIII-B), (VIII-C), (VIII-D), (VIII-E), (VIII-F), (VIII-G), (VIII-H), or (VIII-I), $R^3$ is $CH_3$, and $R^4$ is Cl.

In certain embodiments of formula (VIII-A), (VIII-B), (VIII-C), (VIII-D), (VIII-E), (VIII-F), (VIII-G), (VIII-H), or (VIII-I), $R^3$ is Cl, and $R^4$ is F.

In some embodiments, the compound has the formula:

(VIII-J)

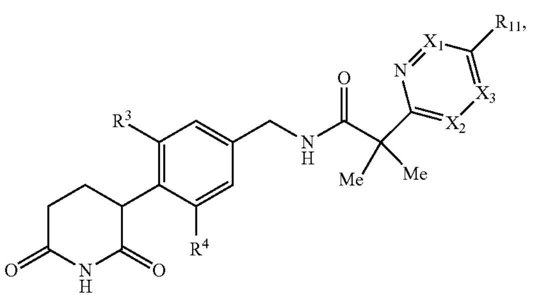

in which each of $X_1$, $X_1$, and $X_3$ is, independently, CH or N; and $R^{11}$ is H, $R^b$, or $R^c$.

In some embodiments, the compound has the formula:

(VIII-K)

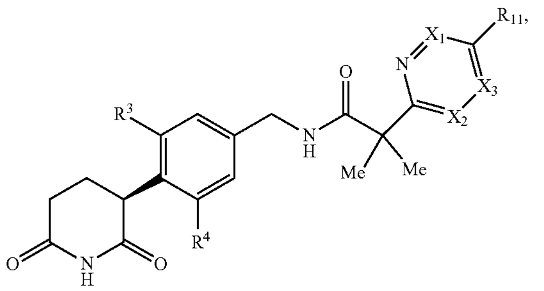

in which each of $X_1$, $X_1$, and $X_3$ is, independently, CH or N; and $R^{11}$ is H, $R^b$, or $R^c$. In some embodiments, wherein the compound has the formula:

(VIII-L)

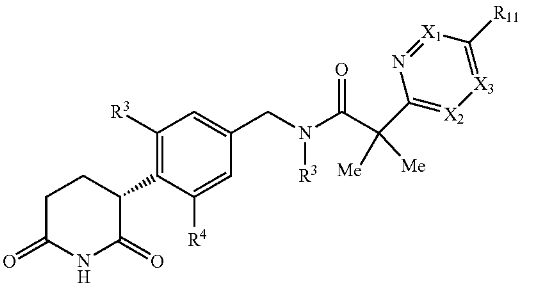

or (VIII-M)

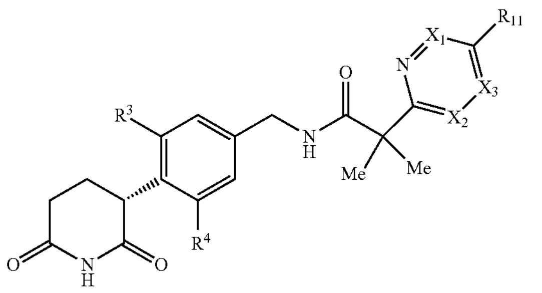

in which each of $X_1$, $X_1$, and $X_3$ is, independently, CH or N; and $R^{11}$ is H, $R^b$, or $R^c$.

In some embodiments of formula (VIII-J), (VIII-K), (VIII-L), or (VIII-M), not more than two of $X_1$, $X_1$, and $X_3$ are N.

In certain embodiments of formula (VIII-J), (VIII-K), (VIII-L), or (VIII-M), $X_2$ is N. In certain of these embodiments, $X_2$ is CH. In certain of these embodiments, $X_3$ is CH. For example, the compound can include:

(V-A)

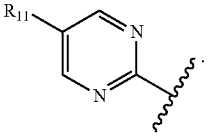

In certain embodiments of formula (VIII-J), (VIII-K), (VIII-L), or (VIII-M), $X_1$ is N. In certain of these embodiments, $X_2$ is CH. In certain of these embodiments, $X_3$ is CH. For example, the compound can include:

(V-B)

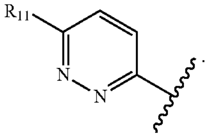

In certain embodiments of formula (VIII-J), (VIII-K), (VIII-L), or (VIII-M), $X_3$ is N. In certain of these embodiments, $X_2$ is CH. In certain of these embodiments, $X_1$ is CH. For example, the compound can include:

(V-C)

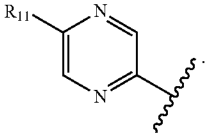

In certain embodiments of formula (VIII-J), (VIII-K), (VIII-L), or (VIII-M), the compound can include:

(V-D)

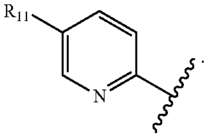

In some embodiments, the compound has the formula:

(VIII-N)

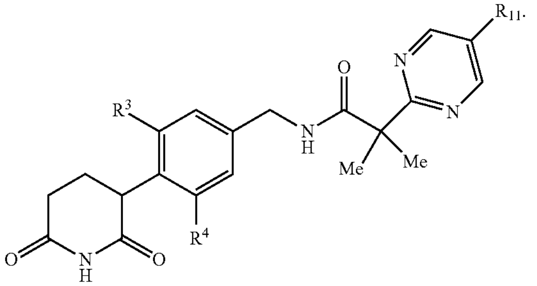

In some embodiments, the compound has the formula:

(VIII-O)

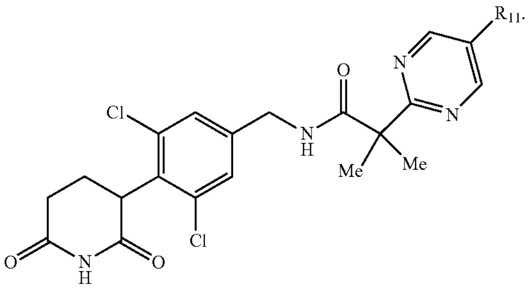

In some embodiments, each of $R^{2a}$ and $R^{2b}$ is CD3.

In some embodiments, the compound has the structure:

(VIII-P)

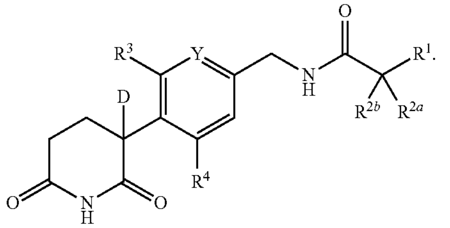

In some embodiments, the compound has the structure:

(VIII-Q)

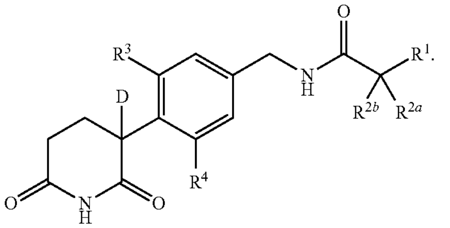

In certain embodiments of formula (VIII-J), (VIII-K), (VIII-L), (VIII-M), (VIII-N), (VIII-O), (V-A), (V-B), (V-C), or (V-D), $R^{11}$ is H.

In certain embodiments of formula (VIII-J), (VIII-K), or (VIII-L), (VIII-M), (VIII-N), (VIII-O), (V-A), (V-B), (V-C), or (V-D), $R^{11}$ is $R^b$.

In certain of these embodiments of formula (VIII-J), (VIII-K), (VIII-L), (VIII-M), (VIII-N), (VIII-O), (V-A), (V-B), (V-C), or (V-D), $R^{11}$ is unsubstituted $C_{1-3}$ alkyl. For example, $R^{11}$ can be $CH_3$.

In certain embodiments of formula (VIII-J), (VIII-K), (VIII-L), (VIII-M), (VIII-N), (VIII-O), (V-A), (V-B), (V-C), or (V-D), $R^{11}$ is $C_{1-3}$ alkyl, which is substituted with from 1-6 (e.g., 1-4, 1-3, 1-2, or 1) independently selected $R^a$.

By way of example, $R^a$, or each occurrence of $R^a$, can be an independently selected halo; e.g., $R^a$, or each occurrence of $R^a$, can be fluoro. A representative $R^{11}$ group is $—CF_3$. Another representative $R^{11}$ group is $—CHF_2$.

As another example, $R^a$, or each occurrence of $R^a$, can be an independently selected $C_{1-4}$ alkoxy; e.g., $R^a$, or each occurrence of $R^a$, is $—OCH_3$. A representative $R^{11}$ group is $CH_2OCH_3$. As a further example, $R^a$ can be —OH. A representative $R^{11}$ group is $CH_2OH$.

In certain embodiments of formula (VIII-J), (VIII-K), (VIII-L), (VIII-M), (VIII-N), (VIII-O), (V-A), (V-B), (V-C), or (V-D), $R^{11}$ is $C_{1-4}$ alkoxy. For example, $R^{11}$ can be $—OCH_3$. In certain embodiments of formula (VIII-J), (VIII-K), (VIII-L), (VIII-M), (VIII-N), (VIII-O), (V-A), (V-B), (V-C), or (V-D), $R^{11}$ is $C_{1-4}$ haloalkoxy. For example, $R^{11}$ can be $—OCHF_2$.

In certain embodiments of formula (VIII-J), (VIII-K), (VIII-L), (VIII-M), (VIII-N), (VIII-O), (V-A), (V-B), (V-C), or (V-D), $R^{11}$ is halo. For example, $R^{11}$ can be fluoro. As another example, $R^{11}$ can be chloro.

In certain embodiments of formula (VIII-J), (VIII-K), (VIII-L), (VIII-M), (VIII-N), (VIII-O), (V-A), (V-B), (V-C), or (V-D), $R^b$ is cyano.

In certain embodiments of formula (VIII-J), (VIII-K), (VIII-L), (VIII-M), (VIII-N), (VIII-O), (V-A), (V-B), (V-C), or (V-D), $R^{11}$ is $R^e$ In certain embodiments of formula (VIII-J), (VIII-K), (VIII-L), (VIII-M), (VIII-N), (VIII-O), (V-A), (V-B), (V-C), or (V-D), $R^{11}$ is cyclopropyl, which is optionally substituted with from 1-4 substituents independently selected from the group consisting of oxo and $R^e$; e.g., unsubstituted cyclopropyl.

In certain embodiments of formula (VIII-J), (VIII-K), (VIII-L), (VIII-M), (VIII-N), (VIII-P), or (VIII-Q), $R^3$ is Cl.

In certain embodiments of formula (VIII-J), (VIII-K), (VIII-L), (VIII-M), (VIII-N), (VIII-P), or (VIII-Q), $R^3$ is H.

In certain embodiments of formula (VIII-J), (VIII-K), (VIII-L), (VIII-M), (VIII-N), (VIII-P), or (VIII-Q), $R^3$ is $CH_3$.

In certain embodiments of formula (VIII-J), (VIII-K), (VIII-L), (VIII-M), (VIII-N), (VIII-P), or (VIII-Q), $R^4$ is Cl.

In certain embodiments of formula (VIII-J), (VIII-K), (VIII-L), (VIII-M), (VIII-N), (VIII-P), or (VIII-Q), $R^4$ is Br.

In certain embodiments of formula (VIII-J), (VIII-K), (VIII-L), (VIII-M), (VIII-N), (VIII-P), or (VIII-Q), $R^4$ is F (e.g., when $R^3$ is Cl).

In certain embodiments of formula (VIII-J), (VIII-K), (VIII-L), (VIII-M), (VIII-N), (VIII-P), or (VIII-Q), $R^3$ is Cl, and $R^4$ is Cl.

In certain embodiments of formula (VIII-J), (VIII-K), (VIII-L), (VIII-M), (VIII-N), (VIII-P), or (VIII-Q), $R^3$ is H, and $R^4$ is Cl.

In certain embodiments of formula (VIII-J), (VIII-K), (VIII-L), (VIII-M), (VIII-N), (VIII-P), or (VIII-Q), $R^3$ is H, and $R^4$ is Br.

In certain embodiments of formula (VIII-J), (VIII-K), (VIII-L), (VIII-M), (VIII-N), (VIII-P), or (VIII-Q), $R^3$ is $CH_3$, and $R^4$ is Cl.

In certain embodiments of formula (VIII-J), (VIII-K), (VIII-L), (VIII-M), (VIII-N), (VIII-P), or (VIII-Q), $R^3$ is Cl, and $R^4$ is F.

In some embodiments, the compound has the formula:

(IX-I)

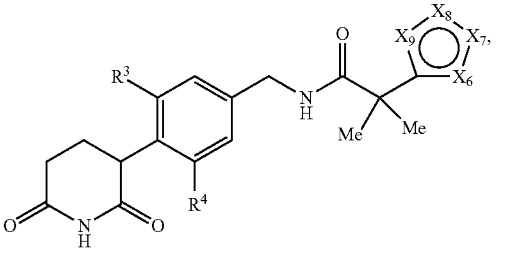

wherein:

$X_6$ is NH, $NCH_3$, O, or S;

$X_7$ is N, CH, $CCF_3$, $CCHF_2$, C(cyclopropyl), or $CCH_3$;

$X_8$ is N, CH, or $CCH_3$; and $X_9$ is N, CH, or $CCH_3$.

In some embodiments, the compound has the formula:

(IX-J)

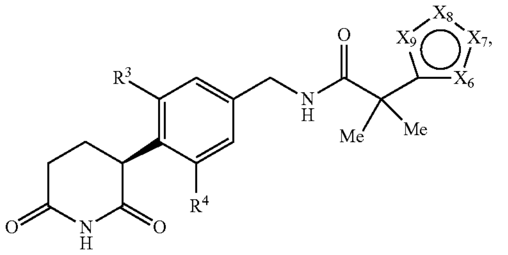

wherein:

$X_6$ is NH, $NCH_3$, O, or S;

$X_7$ is N, CH, $CCF_3$, $CCHF_2$, C(cyclopropyl), or $CCH_3$;

$X_8$ is N, CH, or $CCH_3$; and $X_9$ is N, CH, or $CCH_3$.

In some embodiments, the compound has the formula:

(IX-K)

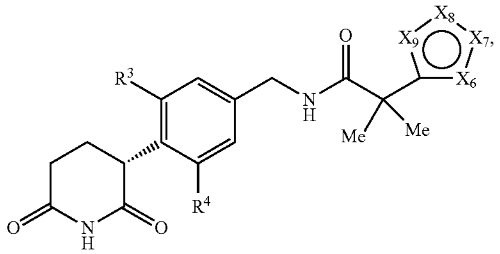

wherein:

$X_6$ is NH, $NCH_3$, O, or S;

$X_7$ is N, CH, $CCF_3$, $CCHF_2$, C(cyclopropyl), or $CCH_3$;

$X_8$ is N, CH, or $CCH_3$; and $X_9$ is N, CH, or $CCH_3$.

In certain embodiments of formula (IX-I), (IX-J), or (IX—K), $X_8$ is N.

In certain embodiments of formula (IX-I), (IX-J), or (IX—K), $X_9$ is N.

In certain embodiments of formula (IX-I), (IX-J), or (IX—K), $X_6$ is O.

In certain embodiments of formula (IX-I), (IX-J), or (IX—K), $X_7$ is CH, $CCF_3$, $CCHF_2$, C(cyclopropyl), or $CCH_3$.

In certain embodiments of formula (IX-I), (IX-J), or (IX—K), $X_7$ is $CCH_3$.

For example, the compound can include:

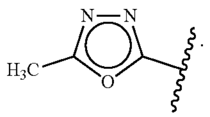

In certain embodiments of formula (IX-I), (IX-J), or (IX—K), $X_6$ is O or S.

In certain embodiments of formula (IX-I), (IX-J), or (IX—K), $X_7$ is N.

In certain embodiments of formula (IX-I), (IX-J), or (IX—K), $X_6$ is O; and $X_7$ is N.

In certain embodiments of formula (IX-I), (IX-J), or (IX—K), $X_6$ is S; and $X_7$ is N.

In certain embodiments of formula (IX-I), (IX-J), or (IX—K), $X_8$ is CH or $CCH_3$.

In certain embodiments of formula (IX-I), (IX-J), or (IX—K), $X_9$ is CH or $CCH_3$.

In certain embodiments of formula (IX-I), (IX-J), or (IX—K), $X_8$ is CH or $CCH_3$; and $X_9$ is CH or $CCH_3$.

In certain embodiments of formula (IX-I), (IX-J), or (IX—K), $X_6$ is O; $X_7$ is N; $X_8$ is CH or $CCH_3$; and $X_9$ is CH or $CCH_3$.

In certain embodiments of formula (IX-I), (IX-J), or (IX—K), $X_6$ is S; $X_7$ is N; $X_8$ is CH or $CCH_3$; and $X_9$ is CH or $CCH_3$.

In certain embodiments of formula (IX-I), (IX-J), or (IX—K):

$X_6$ is NH, $NCH_3$, or O;

$X_7$ is CH or $CCH_3$;

$X_8$ is N; and $X_9$ is CH or $CCH_3$.

In certain embodiments of formula (IX-I), (IX-J), or (IX—K), $X_8$ is N; and $X_6$ is O.

In certain embodiments of formula (IX-I), (IX-J), or (IX—K):

$X_6$ is $NCH_3$;

$X_7$ is CH or $CCH_3$;

$X_8$ is N; and $X_9$ is N.

In certain embodiments of formula (IX-I), (IX-J), or (IX—K), $R^3$ is Cl.

In certain embodiments of formula (IX-I), (IX-J), or (IX—K), $R^3$ is Cl.

In certain embodiments of formula (IX-I), (IX-J), or (IX—K), $R^3$ is H.

In certain embodiments of formula (IX-I), (IX-J), or (IX—K), $R^3$ is $CH_3$.

In certain embodiments of formula (IX-I), (IX-J), or (IX—K), $R^4$ is Cl.

In certain embodiments of formula (IX-I), (IX-J), or (IX—K), $R^4$ is Br.

In certain embodiments of formula (IX-I), (IX-J), or (IX—K), $R^4$ is F (e.g., when $R^3$ is Cl). In certain embodiments of formula (IX-I), (IX-J), or (IX—K), $R^3$ is Cl, and $R^4$ is Cl. In certain embodiments of formula (IX-I), (IX-J), or (IX—K), $R^3$ is H, and $R^4$ is Cl. In certain embodiments of formula (IX-I), (IX-J), or (IX—K), $R^3$ is H, and $R^4$ is Br. In certain embodiments of formula (IX-I), (IX-J), or (IX—K), $R^3$ is $CH_3$, and $R^4$ is Cl.

In certain embodiments of formula (IX-I), (IX-J), or (IX—K), $R^3$ is Cl, and $R^4$ is F.

Pharmaceutical Compositions

In another aspect, the present disclosure provides a pharmaceutical composition comprising a compound described herein, or pharmaceutically acceptable salt thereof, and a pharmaceutically acceptable excipient. In certain embodiments, the pharmaceutical composition comprises an effective amount of the compound. In certain embodiments, the pharmaceutical composition comprises a therapeutically effective amount of the compound.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Compositions for oral administration can take the form of bulk liquid solutions or suspensions, or bulk powders. In some embodiments, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component with the remainder being various vehicles or excipients and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component with the remainder being the injectable excipient and the like.

Transdermal compositions are typically formulated as a topical ointment or cream containing the active ingredient (s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope of the disclosure provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

Methods of Use

Compounds and pharmaceutical compositions described herein can be used in the treatment of disorders in subjects in need thereof. Said disorders include, but are not limited to, those disorders caused by or associated with NLRP3 inflammasome activation.

Accordingly, in one embodiment, described herein is a method of treating a disorder caused by or associated with NLRP3 inflammasome activation in a subject in need thereof, comprising administering to the subject a therapeutically effective amount of a compound described herein or a pharmaceutically acceptable salt thereof.

In some embodiments, the disorder is gout.

In some embodiments, the disorder is pericarditis.

In some embodiments, the disorder is a disorder of the immune system, hematopeoitic system, joints, renal system, gastro-intestinal tract, skin, eye, respiratory system, central nervous system, cardiovascular system, hepatic system, and/or endocrine system.

In some embodiments, the disorder is an autoinflammatory or autoimmune disorder.

In certain of these embodiments, the disorder is gout (e.g., acute and chronic gout, tophaceous gout, or pseudo-gout).

In certain of these embodiments, the disorder is inflammatory bowel disease.

In certain of these embodiments, the disorder is rheumatoid arthritis.

In certain of these embodiments, the disorder is multiple sclerosis.

In some embodiments, the disorder is a neurodegenerative disorder (e.g., Alzheimer's disease).

In some embodiments, the disorder is a cardiovascular or metabolic disorder (e.g., pericarditis, atherosclerosis, Type 2 diabetes, obesity or metabolic syndrome).

In some embodiments, the disorder is a fibrotic disorder (e.g., interstitial lung disease or chronic kidney disease).

In some embodiments, the disorder is a disorder associated with hematology (e.g., anemia of inflammation).

In some embodiments, the disorder is an eye disorder (e.g., macular degeneration).

In some embodiments, the disorder is a disorder of the immune system, hematopeoitic system, joints, renal system, gastro-intestinal tract, skin, eye, respiratory system, central nervous system, cardiovascular system, hepatic system, and/or endocrine system.

In some embodiments, the disorder is a cancer, tumour or other malignancy.

In some embodiments, the disorder is selected from the group consisting of (i) inflammatory reactions in the joints including acute and chronic gout, tophaceous gout, pseudo-gout, osteoarthritis, psoriatic arthritis, systemic juvenile idiopathic arthritis, adult-onset Still's disease, relapsing polychondritis, tendonitis, frozen shoulder and pyogenic arthritis;

(ii) hyperactive inflammation with underlying genetic mutations, including auto-inflammatory diseases such as cryopyrin-associated periodic syndrome (CAPS): Muckle-Wells syndrome (MWS), familial cold autoinflammatory syndrome (FCAS) and neonatal-onset multisystem inflammatory disease (NOMID); familial Mediterranean fever (FMF), TNF receptor associated periodic syndrome (TRAPS), mevalonate kinase deficiency (MVK), hyperimmunoglobuliemia D and periodic fever syndrome (HIDS), deficiency of interleukin 1 receptor (DIRA) antagonist), VEXAS syndrome, Majeed syndrome, pyoderma gangrenosum, acne and hidradenitis suppurative syndrome, haploinsufficency of A20, pediatric granulomatous arthritis (PGA), PLCG2-associated antibody deficiency and immune dysregulation (PLAID), sideroblastic anemia with B-cell immunodeficiency, periodic fevers, and developmental delay (SIFD), Sweet's syndrome, chronic non-bacterial osteomyelitis (CNO), chronic recurrent multifocal osteomyelitis (CRMO) and synovitis, acne, pustulosis, hyperostosis, osteitis syndrome (SAPHO) and any disease where an individual has been determined to carry a germline or somatic non-silent mutation in NLRP3 or NEK7

(iii) autoimmune diseases including multiple sclerosis (MS), rheumatoid arthritis, Behçet's disease, Sjögren's syndrome, systemic sclerosis, mixed connective tissue disease, myositis, vasculitis, lupus, including systemic and cutaneous forms, lupus nephritis, type-1 diabetes, psoriasis and Schnitzler's syndrome, Grave's disease, thrombotic thrombocytopeniarpura, idiopathic thrombocytopenia purpura, microscopic polyangiitis, inflammatory bowel disease, colitis, Crohn's disease;

(iv) respiratory diseases including chronic obstructive pulmonary disorder (COPD), acute respiratory distress syndrome (ARDS), steroid-resistant asthma, asbestosis, silicosis, sarcoidosis, cystic fibrosis and interstitial lung disease (ILD), including, but not limited to idiopathic pulmonary fibrosis (IPF), fibrotic hypersensitivity pneumonitis, rheumatoid arthritis-associated ILD, autoimmune myositis-associated ILD, systemic sclerosis-associated ILD, idiopathic interstitial pneumonia and progressive fibrosing ILD;

(v) kidney disease including chronic kidney disease (CKD), including CKD associated with high uric acid, APOLI mutations, complement-mediated kidney diseases such as C3 glomerulopathy, IgA nephropathy, atypical hemalytic uremic syndrome and membranous nepropathy, idiopathic nephrotic syndrome, oxalate nephropathy and diabetic nephropathy;

(vi) central nervous system diseases including Parkinson's disease, Alzheimer's disease, motor neuron disease, Huntington's disease, cerebral malaria, post-traumatic brain injury, sub-arachnoid hemorrhage and brain injury from pneumococcal meningitis, cerebral amyloid angiopathy, migraine, depression, psychological stress;

(vii) ocular diseases including those of the ocular epithelium, age-related macular degeneration (AMD), corneal infection, uveitis and dry eye;

(viii) cardiovascular diseases including myocarditis, inflammatory cardiomyopathy, atherosclerosis, stroke, myocardial infarction, hypertension, abdominal aortic aneurism, pericarditis including Dressler's syndrome, thromboembolism, ischemia reperfusion injury, transthyretin amyloidosis, vasculitis;

(ix) viral infections and subsequent immune hyperactivation including alphavirus including Chikungunya and Ross River virus, and flavivirus including Dengue and Zika viruses, COVID-19/SARS-COV-2, influenza, HIV;;

(x) diseases of the hematopoietic system including anemia of inflammation (anemia of chronic disease), paroxysmal nocturnal hemaglobinuria (PNH), sickle cell disease;

(xi) liver disease including non-alcoholic steatohepatitis, alcoholic liver disease and drug-induced liver injury;

(xii) inflammatory reactions in the skin including contact hypersensitivity and sunburn, psoriasis, hidradenitis suppurativa (HS) and other cyst-causing skin diseases, dermatomyositis, pemphigus, pyoderma gangrenosum;

(xiii) metabolic diseases including obesity, metabolic syndrome, and Type 2 diabetes and related morbidities including diabetic foot ulcers, atherosclerosis, obesity, diabetic cardiomyopathy and diabetic retinopathy;

(xiv) cancers including lung cancer and lung cancer metastasis, pancreatic cancers, gastric cancers, myelodysplastic syndrome, leukemia and melanoma; polymyositis; graft-versus-host disease and transplant rejection;

(xv) infectious diseases including bacterial infections, including *Clostridium* species, viral infections, helminth infections; wound healing; sepsis; gangrene; and (xvi) allergic diseases and Type 2 inflammation-associated diseases including asthma, atopic dermatitis, eosinophilic esophagitis, chronic obstructive pulmonary disease, chronic sinusitis, nasal polyps.

In another embodiment, described herein is a method of degrading NIMA Related Kinase 7 (NEK7) in a subject suffering from any one or more of the disorders described herein, comprising administering to the subject an effective amount of a compound of described herein or a pharmaceutically acceptable salt thereof.

In an aspect, the disclosure provides a compound or pharmaceutically acceptable salt as described herein for use in any of the above-recited methods of treatment. In a further aspect, the disclosure provides the use of a compound or pharmaceutically acceptable salt as described herein for the manufacture of a medicament for any of the above-recited methods of treatment. In an aspect, the disclosure provides a degrader conjugate as described herein for use in any of the above-recited methods of treatment.

NEK7 Degradation

The compounds described herein can act as degraders of NIMA-Related Kinase 7 (NEK7). NEK7 is an activator of the NLRP3 inflammasome, a central regulator of cellular inflammatory responses to pathogens, damage and stress. The NLRP3 inflammasome is a multiprotein complex that serves as a central node to integrate cellular signals generated by pathogens, damage and stress, and triggers the generation of pro-inflammatory cytokines. The assembly of NLRP3/NEK7 with ASC and pro-caspase 1 in a multiprotein complex induces cleavage of pro-caspase 1, which then activates multiple inflammatory responses including secretion or release of the cytokines interleukin-1β and interleukin-18 and induction of pyroptosis. Additionally, multiple activating NLRP3 mutations have been shown to be associated with Cryopyrin-associated periodic syndromes.

NEK7, a serine/threonine-protein kinase, activates the NLRP3 inflammasome in a kinase independent manner. Increased (e.g., excessive) NLRP3 inflammasome activation has been implicated in the pathogenesis of several of the disorders described herein (e.g., disorders of the immune system, hematopeoitic system, joints, renal system, gastrointestinal tract, skin, eye, respiratory system, central nervous system, cardiovascular system, hepatic system, and/or endocrine system). In certain embodiments, the increased (e.g., excessive) NLRP3 inflammasome activation is chronically increased (e.g., excessive) NLRP3 inflammasome activation. In certain embodiments, the NLRP3/NEK7 inflammasome activation is occurring in the brain or central nervous system (CNS), thereby requiring CNS penetration and exposure of any therapeutic agent targeting this inflammasome. NEK7 binding to NLRP3 has been shown to be involved in promoting the assembly of the NLRP3 inflammasome. While not wishing to be bound by theory, by being able to degrade NEK7, the compounds described herein may be used to treat disorders caused by or associated with increased (e.g., excessive) NLRP3 inflammasome activation.

In an embodiment, described herein is a method of degrading NIMA Related Kinase 7 (NEK7) in a subject, comprising administering to the subject an effective amount of a compound described herein (e.g., Compound 1), or pharmaceutically acceptable salt thereof. In some embodiments, the compound mediates the interaction of a NEK7 protein with an E3 ligase, thereby increasing degradation of the NEK7 protein. In some embodiments, NEK7 is an activator of an NLRP3 inflammasome. In an embodiment, the compound interacts with the E3 ligase prior to the interaction of NEK7 with the E3 ligase. In some embodiments, the E3 ligase comprises cereblon.

In another embodiment, described herein is a method of degrading NIMA Related Kinase 7 (NEK7), comprising: (i) contacting a compound described herein (e.g., Compound 1) or a pharmaceutically acceptable salt thereof with an E3 ligase; and (ii) interacting the contacted E3 ligase with NEK7, thereby degrading NEK7.

In other embodiments, the compounds described herein (e.g., Compound 1) are capable of selectively binding to a specific amino acid sequence of NEK7, thereby causing degradation of NEK7. In other embodiments, such degradation of NEK7 is mediated by the compound interacting with both the specific amino acid sequence of NEK7 and an E3 ligase. In other embodiments, the E3 ligase comprises cereblon.

Degrader Conjugates

In an aspect is a conjugate comprising a compound of Formula (I). For instance, in an aspect is an antibody-degrader conjugate or pharmaceutically acceptable salt thereof comprising a compound of Formula (I). The conjugate includes a compound of Formula (I) or pharmaceutically acceptable salt thereof which is conjugated to an antibody via a linker structure moiety.

In some embodiments, the conjugate has a structure according to Formula (A) below:

$$Bm—(—M-I)_a \qquad \text{Formula (A)}$$

in which I is a compound of Formula (I) or any subformula defined herein, or a pharmaceutically acceptable salt thereof, M is a linker moiety, Bm is a binding moiety that is capable of specifically binding to an antigen, and a is from 1 to 10. In some embodiments, a is 1, 2, 3, 4, 5, 6, 7, 8, 9 or 10, for example 2, 3, 4, 5, 6, 7, or 8. The binding moiety may be an antibody, antibody fragment or an antibody-binding fragment.

In some embodiments, I is one of Compounds 1-282.

Thus, in some embodiments of Formula (A), the disclosure provides an antibody-drug conjugate or pharmaceutically acceptable salt thereof according to formula (A1):

Formula (A1)

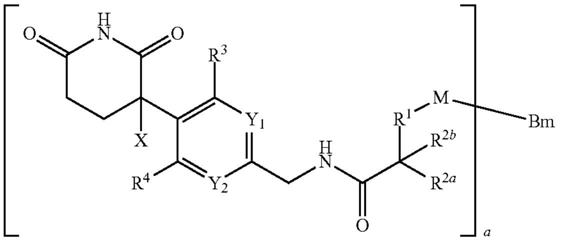

in which X, $Y_1$, $Y_2$, $R^1$, $R^{2a}$, $R^{2b}$, $R^3$ and $R^4$ can be as defined anywhere herein, M is a linker moiety, Bm is a binding moiety that is capable of specifically binding to a protein, as defined above, and a is from 1 to 10. In some embodiments, X, $L_1$, $L_2$, $R^1$, $R^{2a}$, $R^{2b}$, $R^3$ and $R^4$ are defined to provide a compound selected from any one of Compounds 1-282.

In some embodiments, the disclosure provides an antibody-drug conjugate or pharmaceutically acceptable salt thereof according to Formula (A4):

Formula (A4)

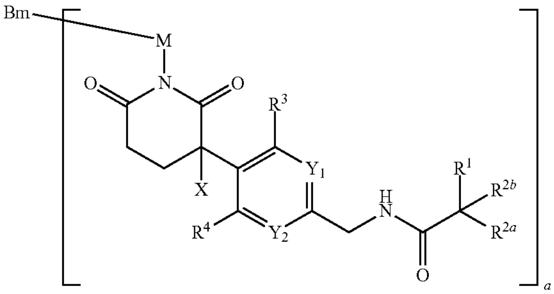

in which X, $Y_1$, $Y_2$, $R^1$, $R^{2a}$, $R^{2b}$, $R^3$ and $R^4$ can be as defined anywhere here, M is a linker moiety, Bm is a binding moiety that is capable of specifically binding to a protein, as defined above and a is from 1 to 10. In some embodiments, X, $Y_1$, $Y_2$, $R^1$, $R^{2a}$, $R^{2b}$, $R^3$ and $R^4$ are defined to provide a compound selected from any one of Compounds 1-282.

In some embodiments, M is a linker as defined in WO 2021/198966, which is incorporated by reference in its entirety. The linker may be a cleavable linker or non-cleavable linker. In certain aspects, the linker can contain a heterobifunctional group. In the present disclosure, the term "heterobifunctional group" refers to a chemical moiety that connects the linker of which it is a part to the binding moiety. Heterobifunctional groups are characterized as having different reactive groups at either end of the chemical moiety. Attachment to Bm, can be accomplished through chemical or enzymatic conjugation, or a combination of both. Chemical conjugation involves the controlled reaction of accessible amino acid residues on the surface of the binding moiety with a reaction handle on the heterobifunctional group. Examples of chemical conjugation include, but are not limited to, lysine amide coupling, cysteine mediated coupling, and coupling via a non-natural amino acid incorporated by genetic engineering, wherein non-natural amino acid residues with a desired reaction handle are installed onto Bm. In enzymatic conjugation, an enzyme mediates the coupling of the linker with an accessible amino residue on the binding moiety. Examples of enzymatic conjugation include, but are not limited to, transpeptidation using sortase, transpeptidation using microbial transglutaminase, and N-glycan engineering. Chemical conjugation and enzymatic conjugation may also be used sequentially. For example, enzymatic conjugation can also be used for installing unique reaction handles on Bm to be utilized in subsequent chemical conjugation.

In some embodiments, M is a linker as defined in WO 2023/037268, which is incorporated by reference in its entirety. M may have the structure:

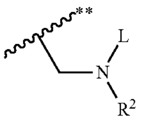

wherein:

indicates the point of attachment of M to I (preferably attached as shown in formula (A4) above);

$R^2$ is selected from the group consisting of hydrogen, $-(CH_2CH_2O)_v-CH_3$, $C_2$-$C_6$alkenyl, $C_1$-$C_6$alkyl; $C_2$-$C_6$alkynyl, benzyl, $C_3$-$C_6$cycloalkyl, and $C_3$-$C_6$cycloalkyl($C_1$-$C_3$alkyl), wherein v is from 1 to 24;

and L is selected from the group consisting of:

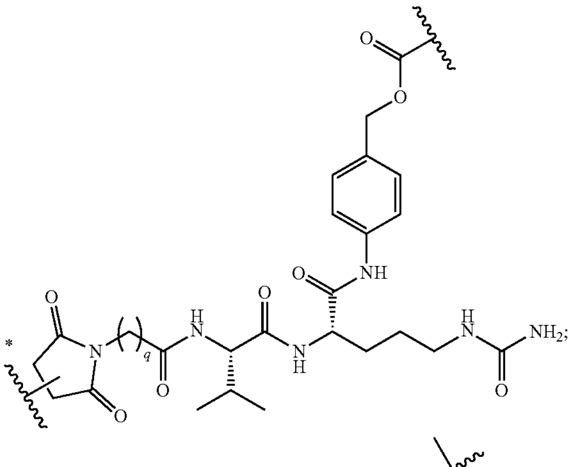

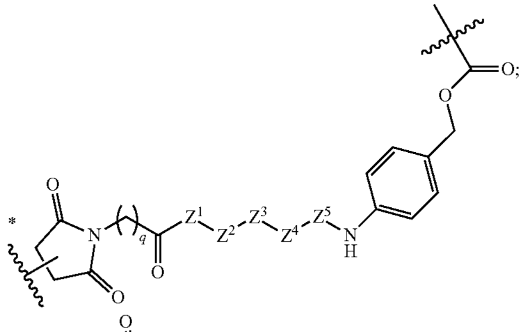

and

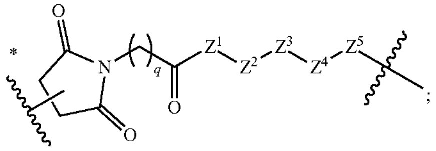

wherein:

q is from 2 to 10;

$Z^1$, $Z^2$, $Z^3$, $Z^4$, and $Z^5$ are each independently absent or a naturally occurring amino acid residue in the L- or D-configuration, provided that at least two of $Z^1$, $Z^2$, $Z^3$, $Z^4$, and $Z^5$ are amino acid residues;

is the point of attachment of L to $NR^2$—$CH_2$—I; and

is the point of attachment to the binding moiety Bm.

In some embodiments, $Z^1$, $Z^2$, $Z^3$, $Z^4$, and $Z^5$ are independently absent or selected from the group consisting of L-valine, D-valine, L-citrulline, D-citrulline, L-alanine, D-alanine, L-glutamine, D-glutamine, L-glutamic acid, D-glutamic acid, L-aspartic acid, D-aspartic acid, L-asparagine, D-asparagine, L-phenylalanine, D-phenylalanine, L-lysine, D-lysine, and glycine; provided that at least two of $Z^1$, $Z^2$, $Z^3$, $Z^4$, and $Z^5$ are amino acid residues.

The term "binding moiety" as used herein refers to any molecule that recognizes and binds to a cell surface marker or receptor. The binding moiety may be an antibody, antibody fragment, or an antigen-binding fragment. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. The term "antibody" herein is used in the broadest sense and specifically covers monoclonal antibodies, single domain antibodies, polyclonal antibodies, multispecific antibodies (e.g., bispecific antibodies), and antibody fragments, so long as they exhibit the desired biological activity. Antibodies may be murine, human, humanized, chimeric, or derived from other species. A monoclonal antibody (mAb) to an antigen-of-interest can be prepared by using any technique known in the art which provides for the production of antibody molecules by continuous cell lines in culture. These include, but are not limited to, the hybridoma technique, the human B cell hybridoma technique, and the EBV-hybridoma technique. Such antibodies may be of any immunoglobulin class including IgG, IgM, IgE, IgA, and IgD and any subclass thereof. The hybridoma producing the mAbs of use in this disclosure may be cultivated in vitro or in vivo.

The skilled person would understand how to provide an appropriate binding moiety for use in a conjugate depending on the intended therapeutic use. This is described, for example, in Nature Reviews Drug Discovery volume 22, pages 641-661 (2023), which is incorporated by reference in its entirety. In particular, an antibody, antibody fragment or an antibody-binding fragment used as a binding moiety must be capable of targeting a particular cell surface marker or receptor associated with the disorder to be treated. For example, the antibody trastuzumab can be employed if the desired target is HER2.

In some embodiments, the binding moiety is capable of binding to an antigen selected from CD11b, CD68, CD14, CD1a, CD141, CD1c, CD15, CD66b, CD49d, CSF1R, CD64, CX3CR[1], CD206, CD33, CD20, CD19, BAFFR, CD38, a4B7 integrin, IL6R, TSLPR, CD40, IFNAR1, or combinations thereof. In preferred embodiments, the binding moiety is capable of binding to an antigen selected from CD11b, CD68, CD14 and CD15.

In some embodiments, the binding moiety comprises an antibody selected from Vedolizumab, Etrolizumab, Gemtuzumab, Rituximab, Ublituximab, Ofatumumab, Ocrelizumab, Inebilizumab, Tafasitamab, Loncastuximab, Isatuximab, Daratumumab, Tocilizumab, Iscalimab, Bleselumab, Anifrolumab.

In some embodiments, the binding moiety is capable of binding to CD19 and is preferably Tafasitamab, Loncastuximab or Inebilizumab. In some embodiments, the binding moiety is capable of binding to CD20 and is preferably Rituximab, Ublituximab, Ofatumumab, Ocrelizumab or Inebilizumab. In some embodiments, the binding moiety is capable of binding to CD33 and is preferably Gemtuzumab. In some embodiments, the binding moiety is capable of binding to CD38 and is preferably Isatuximab or Daratumumab.

Exemplary combinations of antibodies, target antigens, and associated therapeutic indications are listed in the table below. In some embodiments, the binding moiety of the antibody-drug conjugate comprises an antibody listed in the table below and targets an antigen listed in the table below. In some aspects, the disclosure provides a method of treating a disorder listed in the table below comprising administering to a subject in need thereof an antibody-drug conjugate comprising an antibody listed in the table below.

| Target | Indication | Antibody |
|---|---|---|
| α4β7 | Ulcerative colitis (UC), Crohn's disease (CD), | Vedolizumab, Etrolizumab |
| CD20, CD19, CD38 | Autoimmune diseases with a B cell component, eg. pemphigus vulgaris, cutaneous lupus erythematosus (CLE), systemic sclerosis (SSc), Grave's disease, relapse-remitting/primary-progressive multiple sclerosis (RR/PP MS), lupus nephritis, systemic lupus erythematosus (SLE), rheumatoid arthritis (RA), thrombotic thrombocytopenic purpura, nephrotic syndrome; idiopathic thrombocytopenic purpura, microscopic polyangiitis | Rituximab, Ublituximab, Ofatumumab, Ocrelizumab, Inebilizumab, Tafasitamab, Loncastuximab, Isatuximab or Daratumumab |
| CD11b, CD68, CD14, CD1A, IFNAR1, CD40, CD64, CD206, CSF1R, CD33, CD1a, CD1c, CX3CR1, CD141 | Myeloid cell-driven diseases such as gout, cardiovascular diseases, Alzheimer's disease, Parkinson's disease, obesity | Bleselumab, Iscalimab, Anifrolimab |

-continued

| Target | Indication | Antibody |
|---|---|---|
| CD15 | Neutrophil-driven diseases such as gout, pericarditis and asthma | |
| CD66b, CD49d | Eosinophil-driven diseases such as eosinophilic esophagitis, asthma, COPD | |
| CD19, CD20, BAFFR | B-cell mediated autoimmune diseases such as SLE | Tafasitamab, Loncastuximab, Rituximab, Ublituximab, Ofatumumab, Ocrelizumab or Inebilizumab |
| CD33 | FcR-driven diseases, such as Chronic Urticaria; cancer | Gemtuzumab |
| IL-6R | Diseases of chronic hepatocyte inflammation, injury, such as non-alcoholic steatohepatitis | Tocilizumab |
| CD38 | Inflammatory bowel diseases, such as Ulcerative Colitis (UC), cancer | Isatuximab or Daratumumab |

Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+$ ($C_{1-4}$alkyl) 4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein. Preferably, the subject is a human.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the present disclosure may vary depending on such factors as the desired biological endpoint, the pharmacokinetics of the compound, the disease being treated, the mode of administration, and the age, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

The present disclosure, in an alternative embodiment, also embraces isotopically labeled compounds which are identical to those recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium (see for instance, compound 237, and the compounds of Formula VIII-P, or VIII-Q).

The term "halo" refers to fluoro (F), chloro (Cl), bromo (Br), or iodo (I).

The term "alkyl" refers to a saturated acyclic hydrocarbon radical that may be a straight chain or branched chain, containing the indicated number of carbon atoms. For example, $C_{1-10}$ indicates that the group may have from 1 to 10 (inclusive) carbon atoms in it. Alkyl groups can either be unsubstituted or substituted with one or more substituents. Non-limiting examples include methyl, ethyl, iso-propyl, tert-butyl, n-hexyl. The term "saturated" as used in this context means only single bonds present between constituent carbon atoms and other available valences occupied by hydrogen and/or other substituents as defined herein.

The term "haloalkyl" refers to an alkyl, in which one or more hydrogen atoms is/are replaced with an independently selected halo.

The term "alkoxy" refers to an—O-alkyl radical (e.g., $—OCH_3$).

The term "alkylene" refers to a divalent alkyl (e.g., $—CH_2—$).

The term "alkenyl" refers to an acyclic hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it. Alkenyl groups can either be unsubstituted or substituted with one or more substituents.

The term "alkynyl" refers to an acyclic hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it. Alkynyl groups can either be unsubstituted or substituted with one or more substituents.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system, or more specifically 6-carbon monocyclic, or 10-carbon bicyclic); and wherein 0, 1, 2, 3, or 4 atoms of each ring may be substituted by a substituent. Examples of aryl groups include phenyl, naphthyl, tetrahydronaphthyl, dihydro-1H-indenyl and the like.

The term "cycloalkyl" as used herein refers to cyclic saturated hydrocarbon groups having, e.g., 3 to 20 ring carbons, preferably 3 to 16 ring carbons, and more preferably 3 to 12 ring carbons or 3-10 ring carbons, most preferably 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butanyl, bicyclo[2.1.0]pentanyl, bicyclo[1.1.1]pentanyl, bicyclo[3.1.0]hexanyl, bicyclo [2.1.1]hexanyl, bicyclo[3.2.0]heptanyl, bicyclo[4.1.0]heptanyl, bicyclo[2.2.1]heptanyl, bicyclo[3.1.1]heptanyl, bicyclo [4.2.0]octanyl, bicyclo[3.2.1]octanyl, bicyclo[2.2.2]octanyl, and the like. Cycloalkyl also includes spirocyclic rings (e.g., spirocyclic bicycle wherein two rings are connected through just one atom). Non-limiting examples of spirocyclic cycloalkyls include spiro[2.2]pentanyl, spiro[2.5]octanyl, spiro[3.5]nonanyl, spiro[3.5]nonanyl, spiro[3.5]nonanyl, spiro[4.4]nonanyl, spiro[2.6]nonanyl, spiro[4.5]decanyl, spiro[3.6]decanyl, spiro[5.5]undecanyl, and the like. The term "saturated" as used in this context means only single bonds present between constituent carbon atoms.

The term "cycloalkenyl" as used herein means partially unsaturated cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkenyl group may be optionally substituted. Examples of cycloalkenyl groups include, without limitation, cyclopentenyl, cyclohexenyl, cycloheptenyl, and cyclooctenyl. As partially unsaturated cyclic hydrocarbon groups, cycloalkenyl groups may have any degree of unsaturation provided that one or more double bonds is present in the ring, none of the rings in the ring system are aromatic, and the cycloalkenyl group is not fully saturated overall. Cycloalkenyl may include multiple fused and/or bridged and/or spirocyclic rings.

The term "heteroaryl", as used herein, means a mono-, bi-, tri- or polycyclic group having to 20 ring atoms, alternatively 5, 6, 9, 10, or 14 ring atoms, preferably 5 to 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S (but does not have to be a ring which contains a heteroatom, e.g. tetrahydroisoquinolinyl, e.g., tetrahydroquinolinyl). Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridinyl, pyrazolo[4,3-b]pyridinyl, tetrazolyl, chromanyl, 2,3-dihydrobenzo[b][1,4]dioxinyl, benzo[d][1,3]dioxolyl, 2,3-dihydrobenzofuranyl, tetrahydroquinolinyl, 2,3-dihydrobenzo[b][1,4]oxathiinyl, isoindolinyl, and others. In some embodiments, the heteroaryl is selected from thienyl, pyridinyl, furyl, pyrazolyl, imidazolyl, isoindolinyl, pyranyl, pyrazinyl, and pyrimidinyl.

The term "heterocyclyl" refers to a mon-, bi-, tri-, or polycyclic saturated ring system with 3-16 ring atoms (e.g., 5-8 membered monocyclic, 8-12 membered bicyclic, or 11-14 membered tricyclic ring system, preferably 5 or 6-membered monocyclic) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heteorocyclyl includes: 2-azabicyclo[1.1.0]butanyl, 2-azabicyclo[2.1.0]pentanyl, 2-azabicyclo[1.1.1]pentanyl, 3-azabicyclo[3.1.0]hexanyl, 5-azabicyclo[2.1.1]hexanyl, 3-azabicyclo[3.2.0]heptanyl, octahydrocyclopenta[c]pyrrolyl, 3-azabicyclo[4.1.0]heptanyl, 7-azabicyclo[2.2.1]heptanyl, 6-azabicyclo[3.1.1]heptanyl, 2-azabicyclo[2.2.2]octanyl, 3-azabicyclo[3.2.1]octanyl, 2-oxabicyclo[2.1.0]pentanyl, 2-2-oxabicyclo[1.1.0]butanyl, oxabicyclo[1.1.1]pentanyl, 3-oxabicyclo[3.1.0]hexanyl, 5-oxabicyclo[2.1.1]hexanyl, 3-oxabicyclo[3.2.0]heptanyl, 3-oxabicyclo[4.1.0]heptanyl, 6-7-oxabicyclo[2.2.1]heptanyl, oxabicyclo[3.1.1]heptanyl, 7-oxabicyclo[4.2.0]octanyl, 2-oxabicyclo[2.2.2]octanyl, 3-oxabicyclo[3.2.1]octanyl, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentanyl, 4-azaspiro[2.5]octanyl, 1-azaspiro[3.5]nonanyl, 2-azaspiro[3.5]nonanyl, 7-azaspiro[3.5]nonanyl, 2-azaspiro[4.4]nonanyl, 6-7-azabicyclo[4.2.0]octanyl, azaspiro[2.6]nonanyl, 1,7-diazaspiro[4.5]decanyl, 7-azaspiro[4.5]decanyl 2,5-diazaspiro[3.6]decanyl, 3-azaspiro[5.5]undecanyl, 2-oxaspiro[2.2]pentanyl, 4-oxaspiro[2.5]octanyl, 1-oxaspiro[3.5]nonanyl, 2-oxaspiro[3.5]nonanyl, 7-oxaspiro[3.5]nonanyl, 2-oxaspiro[4.4]nonanyl, 6-oxaspiro[2.6]nonane, 1,7-dioxaspiro[4.5]decanyl, 2,5-dioxaspiro[3.6]decanyl, 1-oxaspiro[5.5]undecanyl, 3-oxaspiro[5.5]undecanyl, 3-oxa-9-azaspiro[5.5]undecanyl and the like. The term "saturated" as used in this context means only single bonds present between constituent ring atoms and other available valences occupied by hydrogen and/or other substituents as defined herein.

The term "heterocycloalkenyl" as used herein means partially unsaturated cyclic ring system with 3-16 ring atoms (e.g., 5-8 membered monocyclic, 8-12 membered bicyclic, or 11-14 membered tricyclic ring system, preferably 6-membered monocyclic) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkenyl groups include, without limitation, tetrahydropyridyl, dihydropyrazinyl, dihydropyridyl, dihydropyrrolyl, dihydrofuranyl, dihydrothiophenyl. As partially unsaturated cyclic groups, heterocycloalkenyl groups may have any degree of unsaturation provided that one or more double bonds is present in the ring, none of the rings in the ring system are aromatic, and the heterocycloalkenyl group is not fully saturated overall. Heterocycloalkenyl may include multiple fused and/or bridged and/or spirocyclic rings.

Certain groups, such as

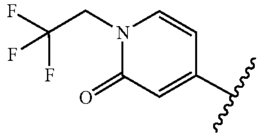,
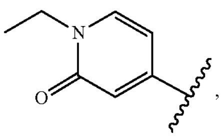,
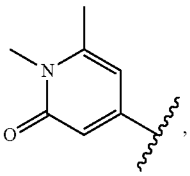,
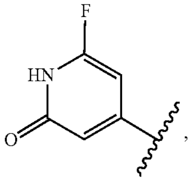,

-continued

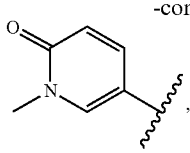,
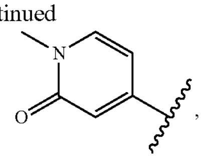,
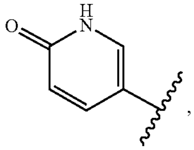,
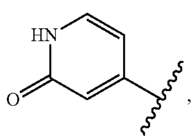,
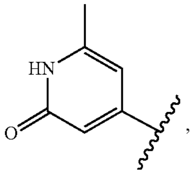,
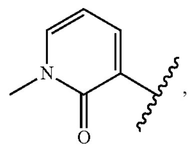,
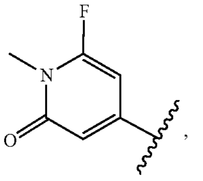,
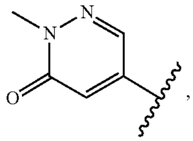, or
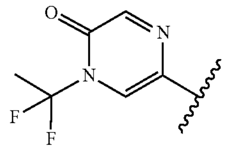, can be considered as either: (i) a heterocycloalkenyl which is substituted with an oxo group; or (ii) a heteroaryl group.

As used herein, when a ring is described as being "aromatic", it means said ring has a continuous, delocalized x-electron system. Typically, the number of out of plane x-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like.

As used herein, when a ring is described as being "partially unsaturated", it means said ring has one or more additional degrees of unsaturation (in addition to the degree of unsaturation attributed to the ring itself; e.g., one or more double or triple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

For the avoidance of doubt, and unless otherwise specified, for rings and cyclic groups (e.g., aryl, heteroaryl, heterocyclyl, heterocycloalkenyl, cycloalkenyl, cycloalkyl, and the like described herein) containing a sufficient number of ring atoms to form bicyclic or higher order ring systems (e.g., tricyclic, polycyclic ring systems), it is understood that such rings and cyclic groups encompass those having fused rings, including those in which the points of fusion are located (i) on adjacent ring atoms (e.g., [x.x.0] ring systems, in which 0 represents a zero atom bridge (e.g., 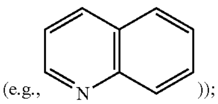));

(ii) a single ring atom (spiro-fused ring systems)

(e.g., 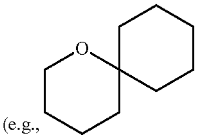, 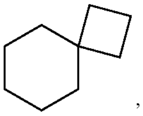, or 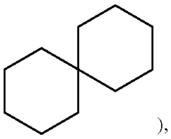), or (iii) a contiguous array of ring atoms (bridged ring systems having all bridge lengths >0)

(e.g., , 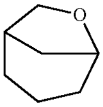, or 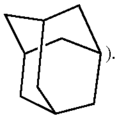).

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In addition, the compounds generically or specifically disclosed herein are intended to include all tautomeric forms. Thus, by way of example, a compound containing the moiety:

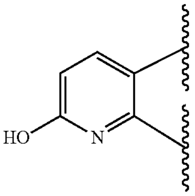 [SMILES: *c1ccc(O)nc1*]

encompasses the tautomeric form containing the moiety:

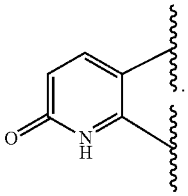.

Similarly, a pyridinyl or pyrimidinyl moiety that is described to be optionally substituted with hydroxyl encompasses pyridone or pyrimidone tautomeric forms.

Further, compounds described herein may exist in one or more stereoisomeric forms. In some cases, such forms may be described through an assignment of absolute configuration, whereas other cases, stereochemistry is unknown and may be assigned arbitrarily to isolated stereoisomers. Isolation of stereoisomers may be conducted using chiral separation.

Compounds described herein having one enantiomeric form may epimerise into the other enantiomeric form if the chiral center is in a position susceptible to epimerization (for instance on the 3-position of the piperidine-2,6-dione ring). Thus, unless it is specifically stated or the context indicates otherwise, disclosure of one stereoisomer with a chiral centre encompasses the isolated stereoisomer and a mixture, such as a racemic mixture, of the (R) and(S) stereoisomers if the stereoisomers epimerise. For example, a disclosure of a compound

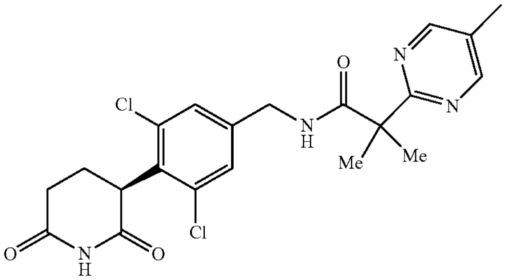 [SMILES: Cc1cnc(C(C)(C)C(=O)NCc2cc(Cl)c([C@@H]3CCC(=O)NC3=O)c(Cl)c2)nc1]

encompasses both isolated

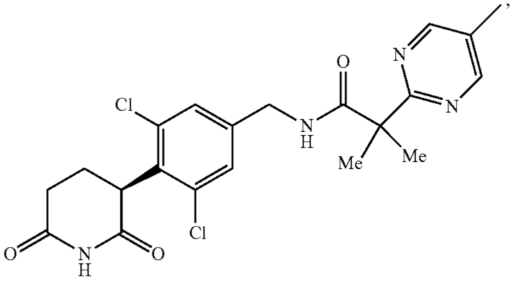 [SMILES: Cc1cnc(C(C)(C)C(=O)NCc2cc(Cl)c([C@@H]3CCC(=O)NC3=O)c(Cl)c2)nc1], and a mixture of

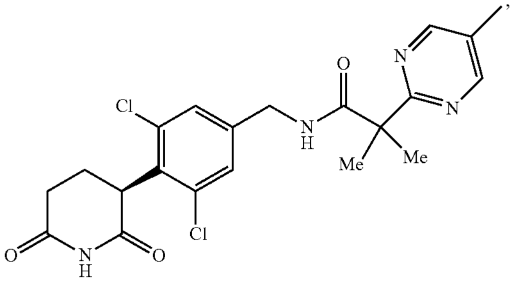, and

-continued

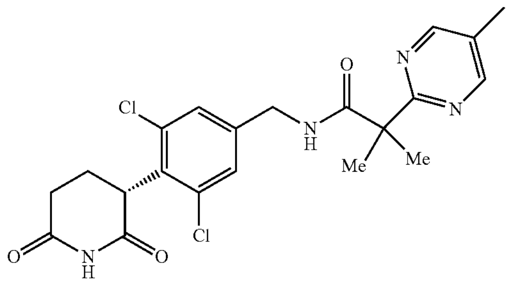

including a racemic mixture of the two stereoisomers.

Similarly, a compound comprising an epimerisable chiral center on the glutarimide ring disclosed herein without its stereoisomeric form indicated encompasses the isolated enantiomer and a mixture, such as a racemic mixture. For example, a disclosure of a compound

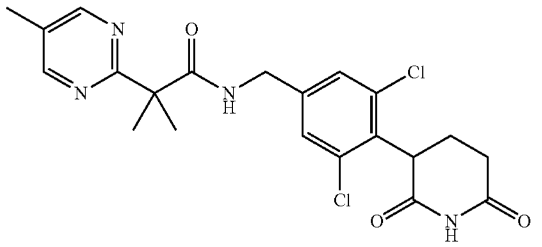

encompasses both isolated

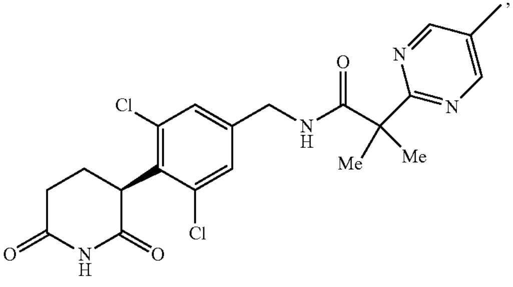 [SMILES: Cc1cnc(C(C)(C)C(=O)NCc2cc(Cl)c([C@@H]3CCC(=O)NC3=O)c(Cl)c2)nc1]

, isolated

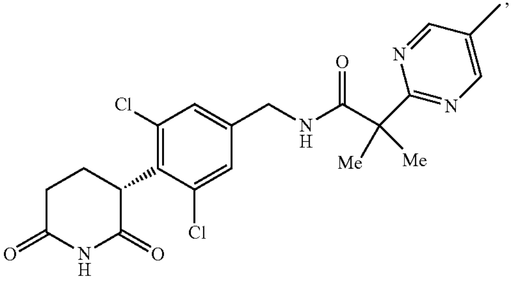 [SMILES: Cc1cnc(C(C)(C)C(=O)NCc2cc(Cl)c([C@H]3CCC(=O)NC3=O)c(Cl)c2)nc1]

, and a mixture of

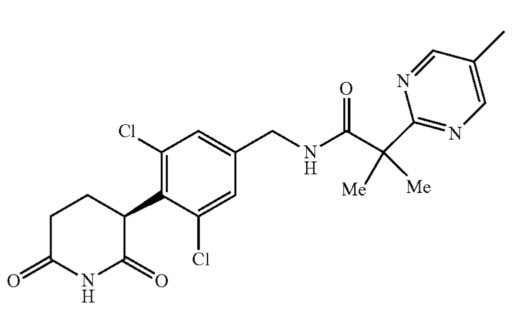

and

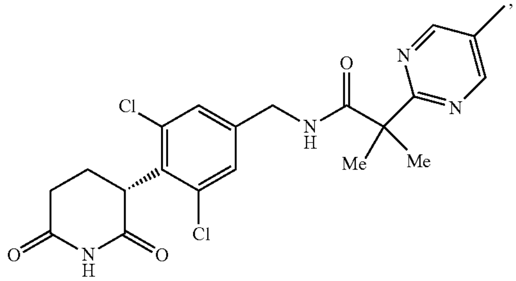

, including a racemic mixture of the two stereoisomers.

As used herein, the phrase "optionally substituted" when used in conjunction with a structural moiety (e.g., alkyl) is intended to encompass both the unsubstituted structural moiety (i.e., none of the substitutable hydrogen atoms are replaced with one or more non-hydrogen substituents) and substituted structural moieties substituted with the indicated range of non-hydrogen substituents. For example, "$C_1$-$C_4$ alkyl optionally substituted with 1-4 Ra" is intended to encompass both unsubstituted $C_1$-$C_4$ alkyl and $C_1$-$C_4$ alkyl substituted with 1-4 $R^a$.

As used herein, the term "antibody" encompasses an immunoglobulin, whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv) 2, Fab, Fab', and F(ab')$_2$, F(abl)$_2$, Fv, dAb, and Fd fragments, diabodies, and antibody-related polypeptides. Antibody includes bispecific antibodies and multispecific antibodies so long as they exhibit the desired biological activity or function.

As used herein, an "antibody fragment" comprises a portion of an intact antibody, generally the antigen binding or variable region thereof. Examples of antibody fragments include Fab, Fab', F(ab').sub.2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

As used herein, the term "antibody-drug conjugate" refers to an antibody or antibody fragment linked, e.g., covalently, to a compound of the disclosure.

The details of one or more embodiments of the invention are set forth in the accompanying drawings and the description below. Other features and advantages of the invention will be apparent from the description and drawings, and from the claims.

Non-Limiting Exemplary Compounds

In some embodiments, the compound is selected from the group consisting of the compounds delineated in Table 1 or a pharmaceutically acceptable salt thereof.

TABLE 1

| Compounds Table | |
|---|---|
| 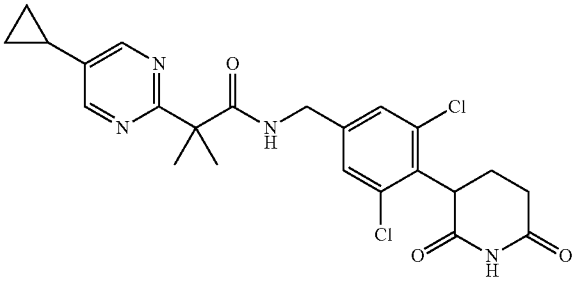 [SMILES: CC(C)(C(=O)NCc1cc(Cl)c(C2CCC(=O)NC2=O)c(Cl)c1)c1ncc(C2CC2)cn1] | Compound 1 |
| 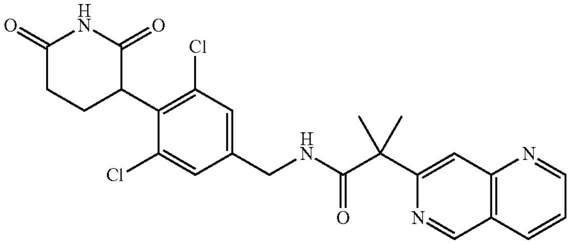 [SMILES: CC(C)(C(=O)NCc1cc(Cl)c(C2CCC(=O)NC2=O)c(Cl)c1)c1cc2ncccc2cn1] | Compound 2 |
| 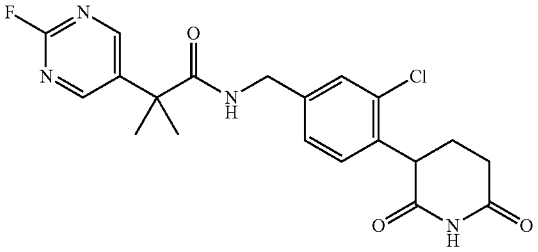 [SMILES: CC(C)(C(=O)NCc1ccc(C2CCC(=O)NC2=O)c(Cl)c1)c1cnc(F)nc1] | Compound 3 |
| 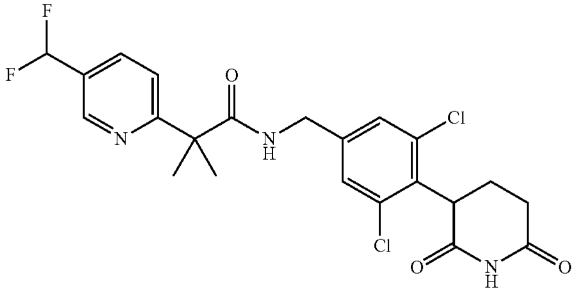 | Compound 4 |
| 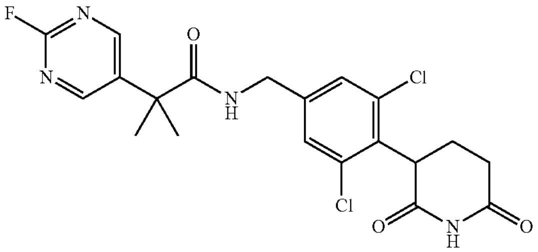 [SMILES: CC(C)(C(=O)NCc1cc(Cl)c(C2CCC(=O)NC2=O)c(Cl)c1)c1cnc(F)nc1] | Compound 5 |

TABLE 1-continued
Compounds Table
Compound 6
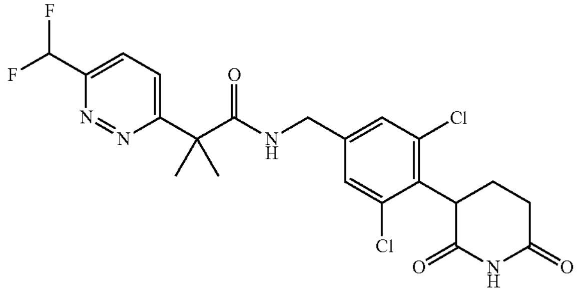 [SMILES: CC(C)(C(=O)NCc1cc(Cl)c(C2CCC(=O)NC2=O)c(Cl)c1)c1ccc(C(F)F)nn1]
Compound 7
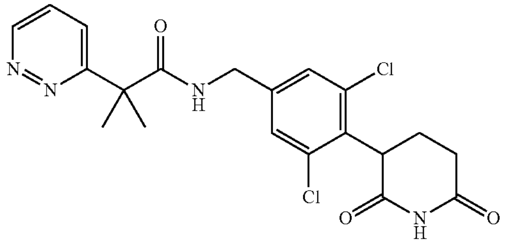 [SMILES: CC(C)(C(=O)NCc1cc(Cl)c(C2CCC(=O)NC2=O)c(Cl)c1)c1cccnn1]
Compound 8
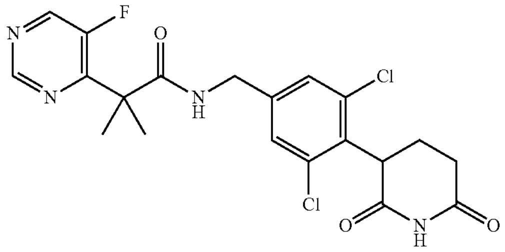
Compound 9
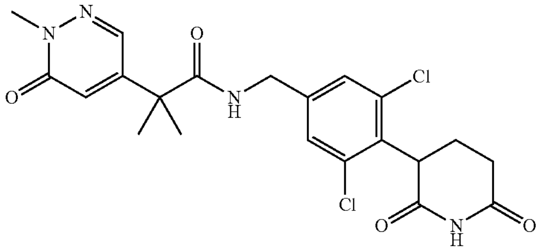 [SMILES: Cn1ncc(C(C)(C)C(=O)NCc2cc(Cl)c(C3CCC(=O)NC3=O)c(Cl)c2)cc1=O]
Compound 10
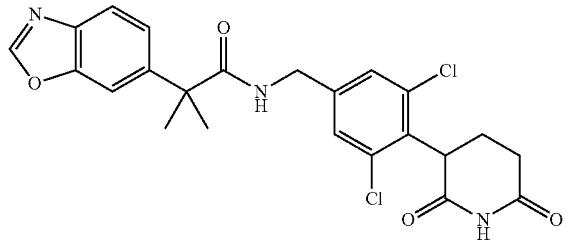 [SMILES: CC(C)(C(=O)NCc1cc(Cl)c(C2CCC(=O)NC2=O)c(Cl)c1)c1ccc2ncoc2c1]
Compound 11
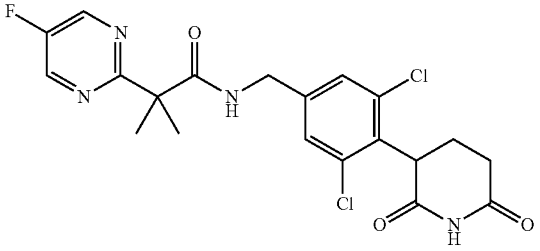 [SMILES: CC(C)(C(=O)NCc1cc(Cl)c(C2CCC(=O)NC2=O)c(Cl)c1)c1ncc(F)cn1]

TABLE 1-continued
| Compounds Table |
| --- |
| 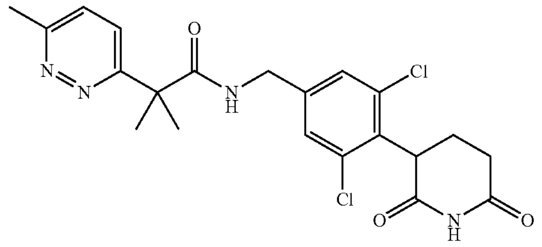 [SMILES: Cc1ccc(C(C)(C)C(=O)NCc2cc(Cl)c(C3CCC(=O)NC3=O)c(Cl)c2)nn1] Compound 12 |
| 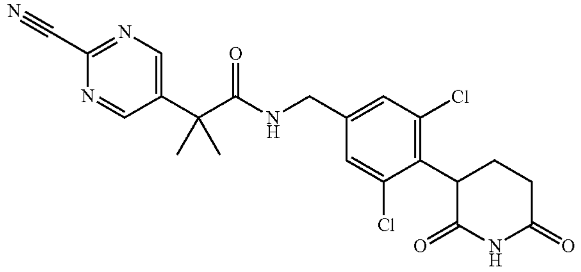 [SMILES: CC(C)(C(=O)NCc1cc(Cl)c(C2CCC(=O)NC2=O)c(Cl)c1)c1cnc(C#N)nc1] Compound 13 |
| 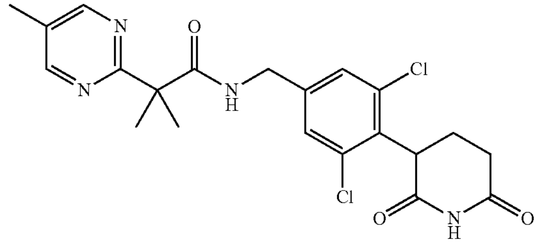 [SMILES: Cc1cnc(C(C)(C)C(=O)NCc2cc(Cl)c(C3CCC(=O)NC3=O)c(Cl)c2)nc1] Compound 14 |
| 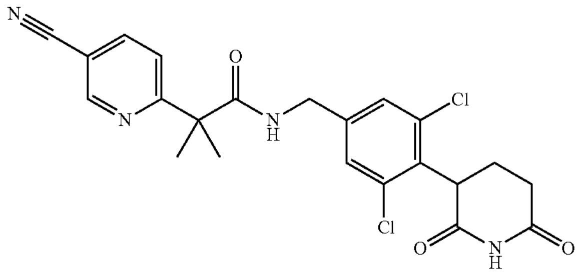 [SMILES: CC(C)(C(=O)NCc1cc(Cl)c(C2CCC(=O)NC2=O)c(Cl)c1)c1ccc(C#N)cn1] Compound 15 |
| 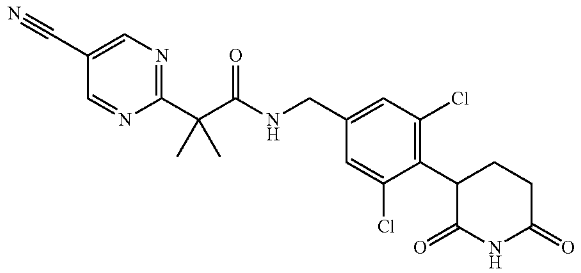 [SMILES: CC(C)(C(=O)NCc1cc(Cl)c(C2CCC(=O)NC2=O)c(Cl)c1)c1ncc(C#N)cn1] Compound 16 |
| 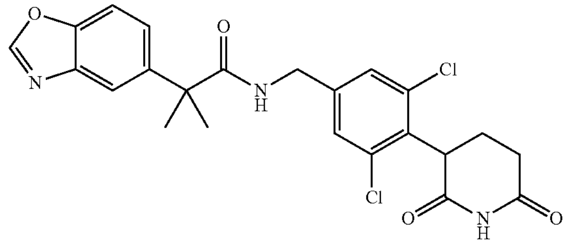 [SMILES: CC(C)(C(=O)NCc1cc(Cl)c(C2CCC(=O)NC2=O)c(Cl)c1)c1ccc2ocnc2c1] Compound 17 |

TABLE 1-continued
Compounds Table
Compound 18
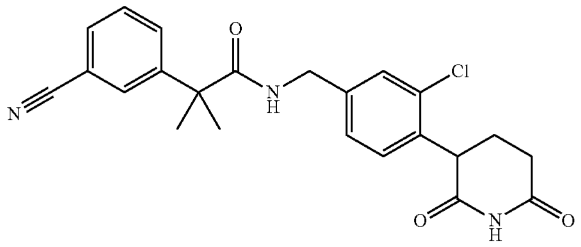 [SMILES: CC(C)(C(=O)NCc1ccc(C2CCC(=O)NC2=O)c(Cl)c1)c1cccc(C#N)c1]
Compound 19
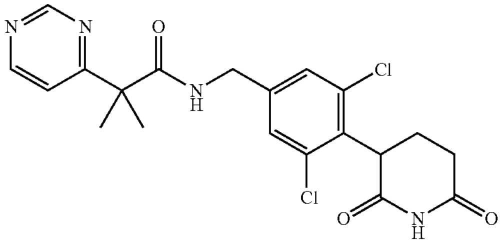
Compound 20
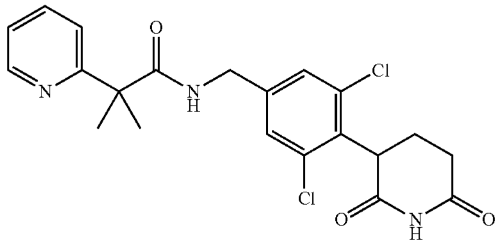 [SMILES: CC(C)(C(=O)NCc1cc(Cl)c(C2CCC(=O)NC2=O)c(Cl)c1)c1ccccn1]
Compound 21
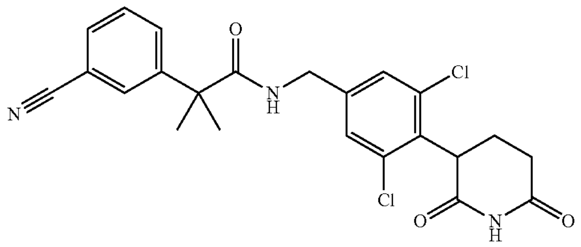 [SMILES: CC(C)(C(=O)NCc1cc(Cl)c(C2CCC(=O)NC2=O)c(Cl)c1)c1cccc(C#N)c1]
Compound 22
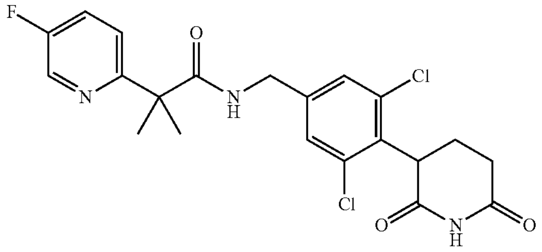 [SMILES: CC(C)(C(=O)NCc1cc(Cl)c(C2CCC(=O)NC2=O)c(Cl)c1)c1ccc(F)cn1]
Compound 23
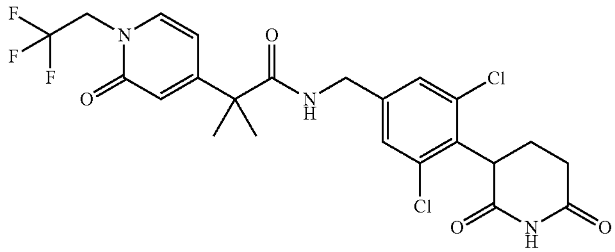 [SMILES: CC(C)(C(=O)NCc1cc(Cl)c(C2CCC(=O)NC2=O)c(Cl)c1)c1ccn(CC(F)(F)F)c(=O)c1]

TABLE 1-continued
| Compounds Table |
| --- |
| 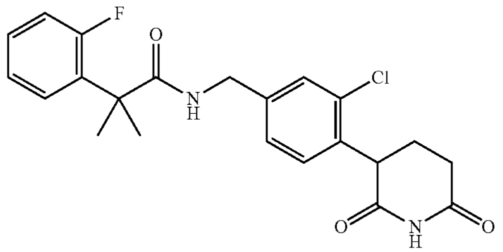 [SMILES: CC(C)(C(=O)NCc1ccc(C2CCC(=O)NC2=O)c(Cl)c1)c1ccccc1F] Compound 24 |
| 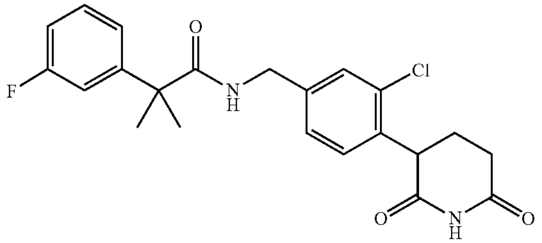 [SMILES: CC(C)(C(=O)NCc1ccc(C2CCC(=O)NC2=O)c(Cl)c1)c1cccc(F)c1] Compound 25 |
| 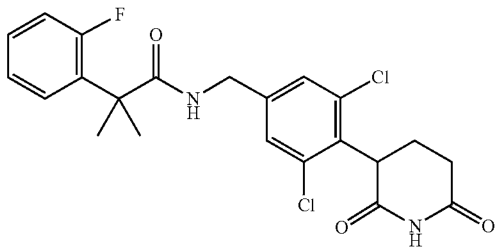 [SMILES: CC(C)(C(=O)NCc1cc(Cl)c(C2CCC(=O)NC2=O)c(Cl)c1)c1ccccc1F] Compound 26 |
| 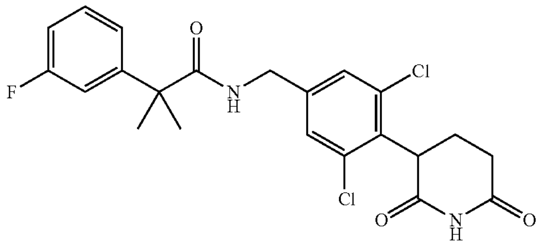 [SMILES: CC(C)(C(=O)NCc1cc(Cl)c(C2CCC(=O)NC2=O)c(Cl)c1)c1cccc(F)c1] Compound 27 |
| 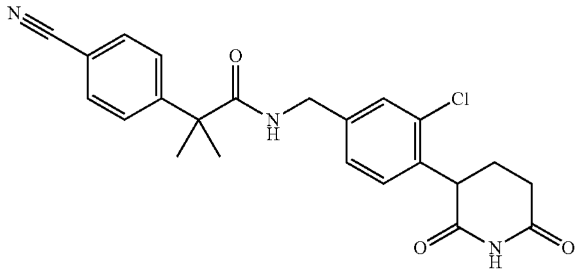 [SMILES: CC(C)(C(=O)NCc1ccc(C2CCC(=O)NC2=O)c(Cl)c1)c1ccc(C#N)cc1] Compound 28 |
| 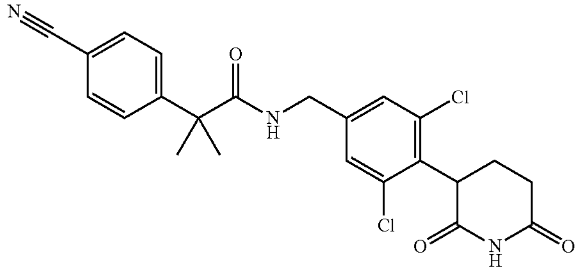 [SMILES: CC(C)(C(=O)NCc1cc(Cl)c(C2CCC(=O)NC2=O)c(Cl)c1)c1ccc(C#N)cc1] Compound 29 |

TABLE 1-continued
| Compounds Table |
| --- |
| 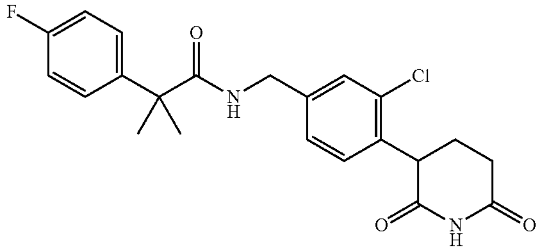 [SMILES: CC(C)(C(=O)NCc1ccc(C2CCC(=O)NC2=O)c(Cl)c1)c1ccc(F)cc1] Compound 30 |
| 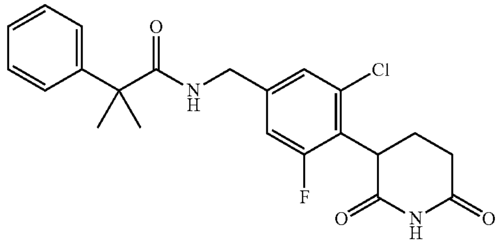 [SMILES: CC(C)(C(=O)NCc1cc(F)c(C2CCC(=O)NC2=O)c(Cl)c1)c1ccccc1] Compound 31 |
| 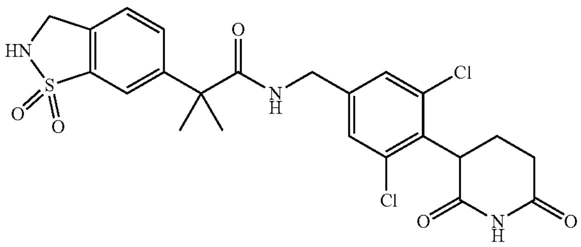 [SMILES: CC(C)(C(=O)NCc1cc(Cl)c(C2CCC(=O)NC2=O)c(Cl)c1)c1ccc2c(c1)S(=O)(=O)NC2] Compound 32 |
| 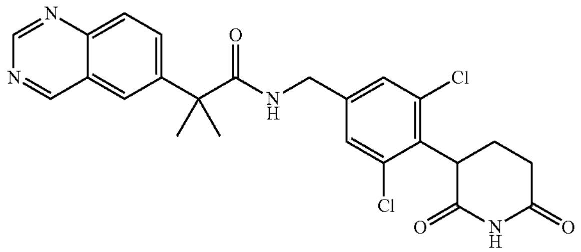 [SMILES: CC(C)(C(=O)NCc1cc(Cl)c(C2CCC(=O)NC2=O)c(Cl)c1)c1ccc2ncncc2c1] Compound 33 |
| 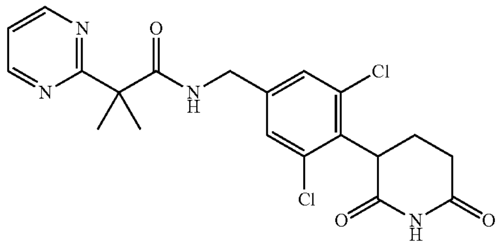 [SMILES: CC(C)(C(=O)NCc1cc(Cl)c(C2CCC(=O)NC2=O)c(Cl)c1)c1ncccn1] Compound 34 |
| 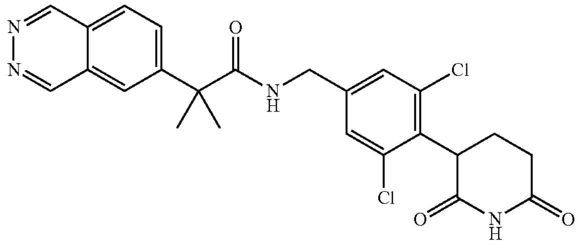 [SMILES: CC(C)(C(=O)NCc1cc(Cl)c(C2CCC(=O)NC2=O)c(Cl)c1)c1ccc2cnncc2c1] Compound 35 |

TABLE 1-continued
| Compounds Table |
| --- |
| 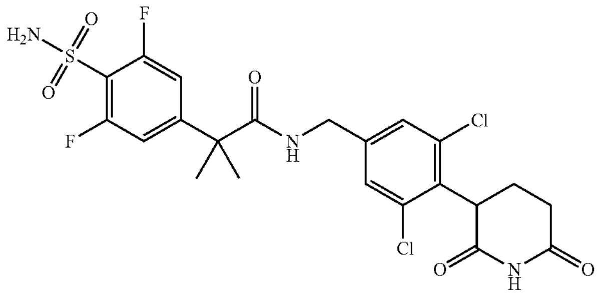 [SMILES: CC(C)(C(=O)NCc1cc(Cl)c(C2CCC(=O)NC2=O)c(Cl)c1)c1cc(F)c(S(N)(=O)=O)c(F)c1] Compound 36 |
| 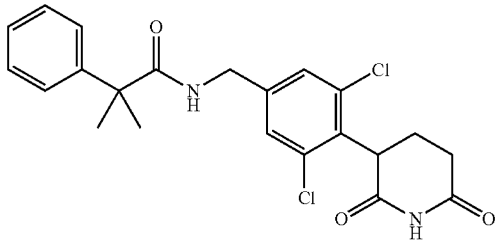 [SMILES: CC(C)(C(=O)NCc1cc(Cl)c(C2CCC(=O)NC2=O)c(Cl)c1)c1ccccc1] Compound 37 |
| 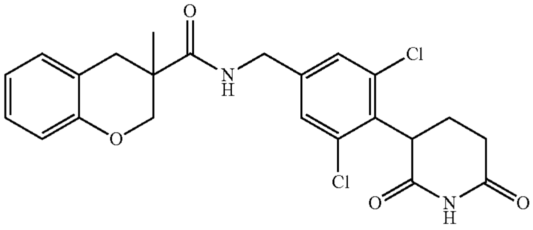 [SMILES: CC1(C(=O)NCc2cc(Cl)c(C3CCC(=O)NC3=O)c(Cl)c2)COc2ccccc2C1] Compound 38 |
| 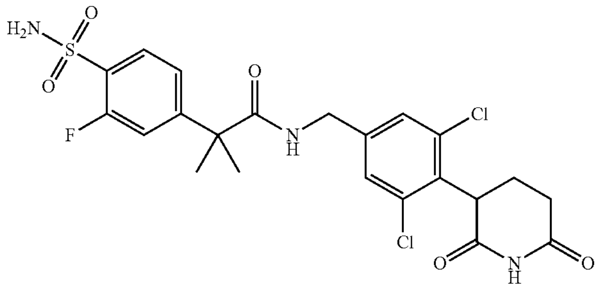 [SMILES: CC(C)(C(=O)NCc1cc(Cl)c(C2CCC(=O)NC2=O)c(Cl)c1)c1ccc(S(N)(=O)=O)c(F)c1] Compound 39 |
| 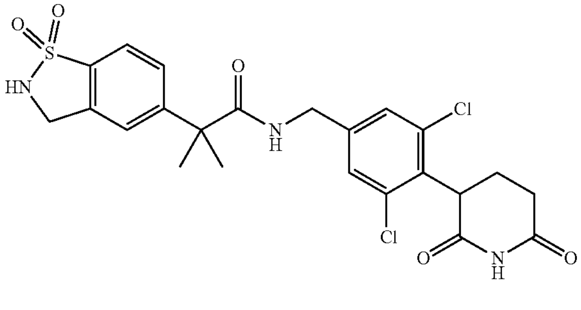 [SMILES: CC(C)(C(=O)NCc1cc(Cl)c(C2CCC(=O)NC2=O)c(Cl)c1)c1ccc2c(c1)CNS2(=O)=O] Compound 40 |

TABLE 1-continued
| Compounds Table | |
|---|---|
| 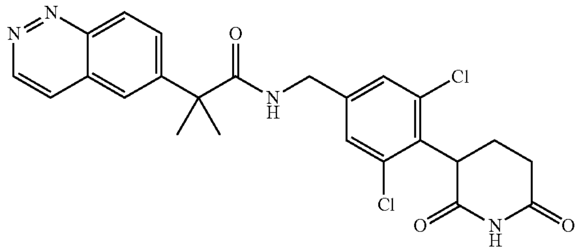 [SMILES: CC(C)(C(=O)NCc1cc(Cl)c(C2CCC(=O)NC2=O)c(Cl)c1)c1ccc2nnccc2c1] | Compound 41 |
| 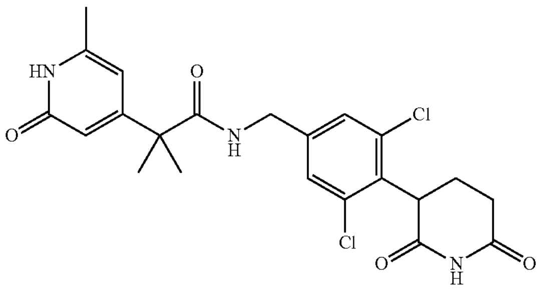 [SMILES: Cc1cc(C(C)(C)C(=O)NCc2cc(Cl)c(C3CCC(=O)NC3=O)c(Cl)c2)cc(=O)[nH]1] | Compound 42 |
| 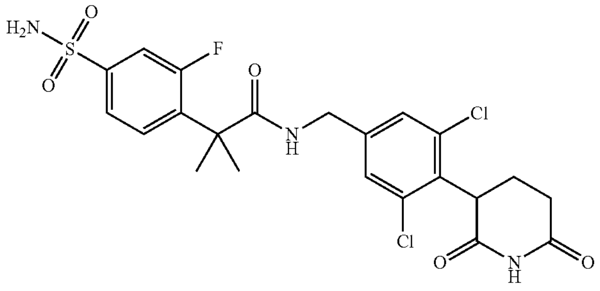 [SMILES: CC(C)(C(=O)NCc1cc(Cl)c(C2CCC(=O)NC2=O)c(Cl)c1)c1ccc(S(N)(=O)=O)cc1F] | Compound 43 |
| 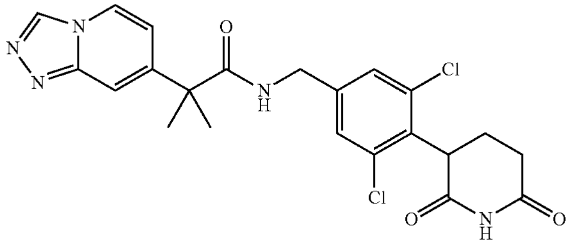 [SMILES: CC(C)(C(=O)NCc1cc(Cl)c(C2CCC(=O)NC2=O)c(Cl)c1)c1ccn2cnnc2c1] | Compound 44 |
| 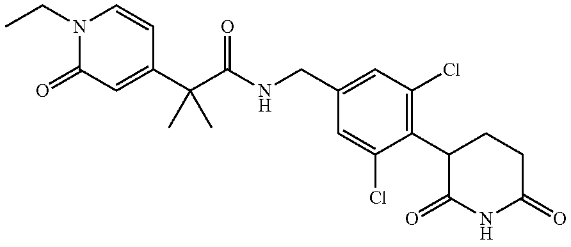 [SMILES: CCn1ccc(C(C)(C)C(=O)NCc2cc(Cl)c(C3CCC(=O)NC3=O)c(Cl)c2)cc1=O] | Compound 45 |
| 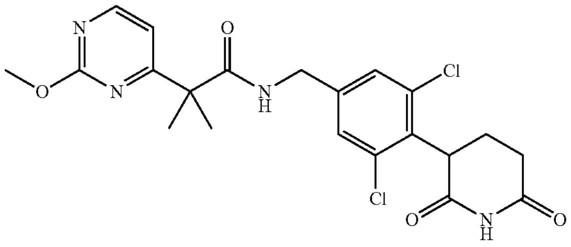 [SMILES: COc1nccc(C(C)(C)C(=O)NCc2cc(Cl)c(C3CCC(=O)NC3=O)c(Cl)c2)n1] | Compound 46 |

TABLE 1-continued
| Compounds Table |
| --- |
| 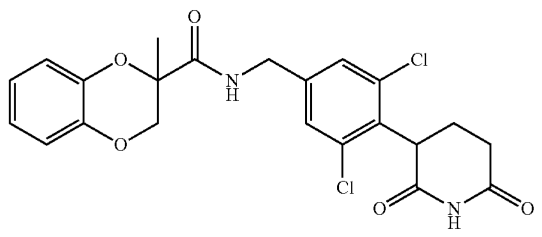 [SMILES: CC1(C(=O)NCc2cc(Cl)c(C3CCC(=O)NC3=O)c(Cl)c2)COc2ccccc2O1] Compound 47 |
| 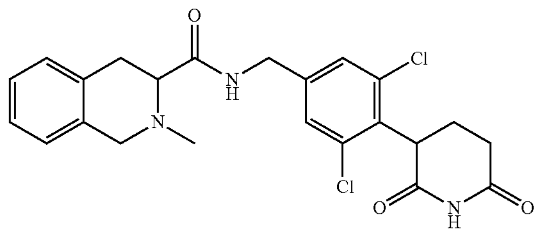 [SMILES: CN1Cc2ccccc2CC1C(=O)NCc1cc(Cl)c(C2CCC(=O)NC2=O)c(Cl)c1] Compound 48 |
| 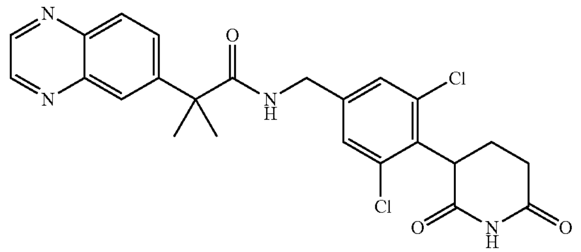 [SMILES: CC(C)(C(=O)NCc1cc(Cl)c(C2CCC(=O)NC2=O)c(Cl)c1)c1ccc2nccnc2c1] Compound 49 |
| 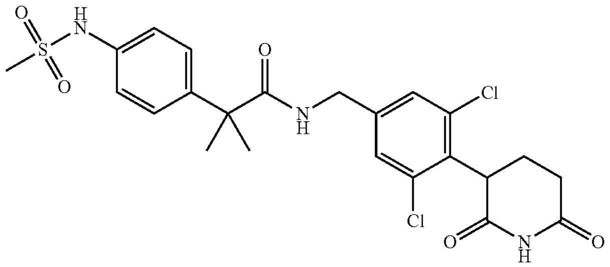 [SMILES: CC(C)(C(=O)NCc1cc(Cl)c(C2CCC(=O)NC2=O)c(Cl)c1)c1ccc(NS(C)(=O)=O)cc1] Compound 50 |
| 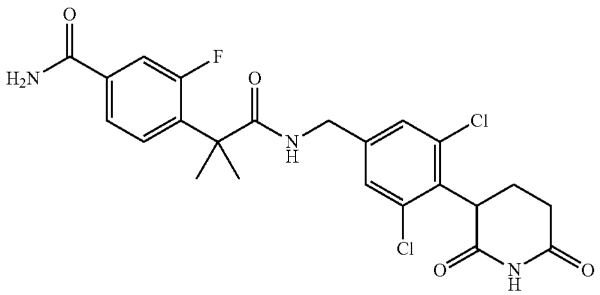 [SMILES: CC(C)(C(=O)NCc1cc(Cl)c(C2CCC(=O)NC2=O)c(Cl)c1)c1ccc(C(N)=O)cc1F] Compound 51 |
| 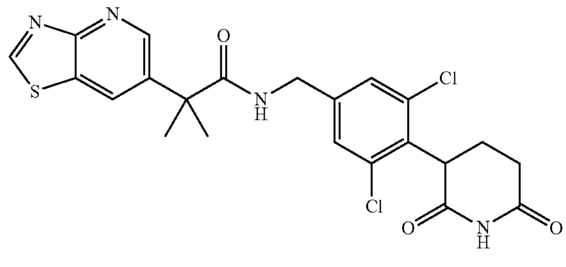 [SMILES: CC(C)(C(=O)NCc1cc(Cl)c(C2CCC(=O)NC2=O)c(Cl)c1)c1cnc2ncsc2c1] Compound 52 |

TABLE 1-continued
| Compounds Table |
| --- |
| Compound 53<br>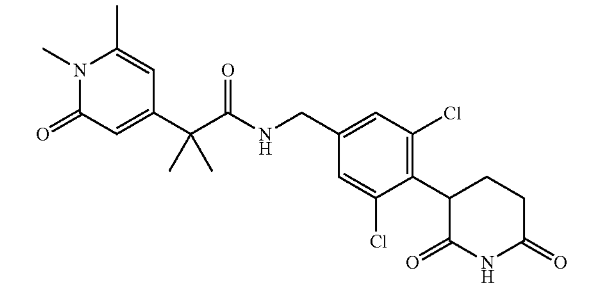 [SMILES: Cc1cc(C(C)(C)C(=O)NCc2cc(Cl)c(C3CCC(=O)NC3=O)c(Cl)c2)cc(=O)n1C] |
| Compound 54<br>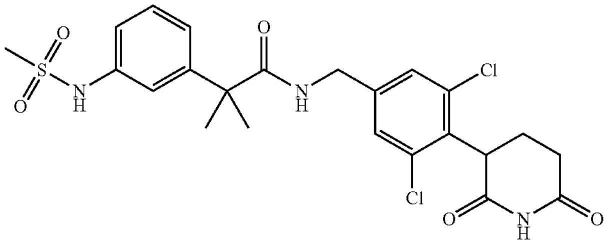 [SMILES: CC(C)(C(=O)NCc1cc(Cl)c(C2CCC(=O)NC2=O)c(Cl)c1)c1cccc(NS(C)(=O)=O)c1] |
| Compound 55<br>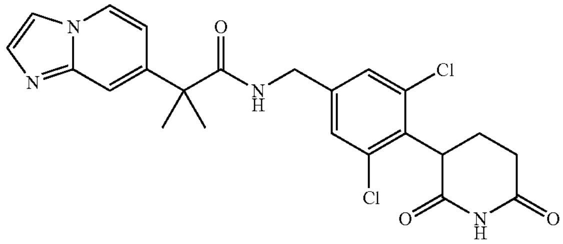 [SMILES: CC(C)(C(=O)NCc1cc(Cl)c(C2CCC(=O)NC2=O)c(Cl)c1)c1ccn2ccnc2c1] |
| Compound 56<br>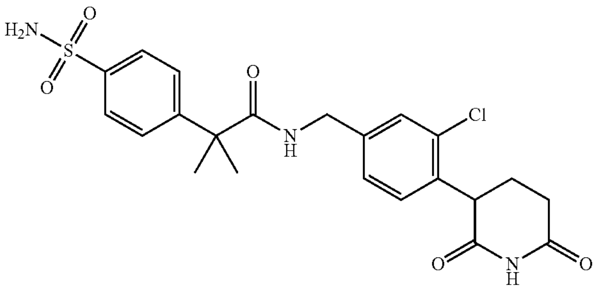 [SMILES: CC(C)(C(=O)NCc1ccc(C2CCC(=O)NC2=O)c(Cl)c1)c1ccc(S(N)(=O)=O)cc1] |
| Compound 57<br>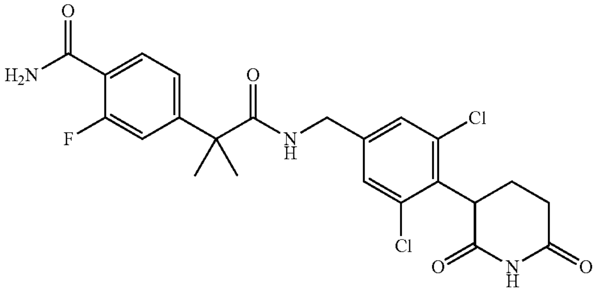 [SMILES: CC(C)(C(=O)NCc1cc(Cl)c(C2CCC(=O)NC2=O)c(Cl)c1)c1ccc(C(N)=O)c(F)c1] |

TABLE 1-continued
| Compounds Table |
| --- |
| 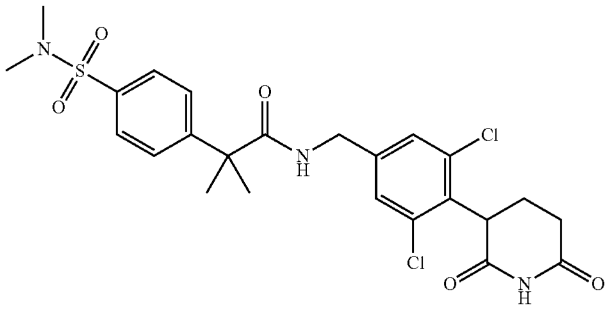 [SMILES: CN(C)S(=O)(=O)c1ccc(C(C)(C)C(=O)NCc2cc(Cl)c(C3CCC(=O)NC3=O)c(Cl)c2)cc1] Compound 58 |
| 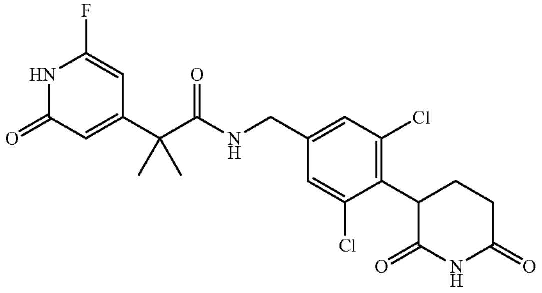 [SMILES: CC(C)(C(=O)NCc1cc(Cl)c(C2CCC(=O)NC2=O)c(Cl)c1)c1cc(F)[nH]c(=O)c1] Compound 59 |
| 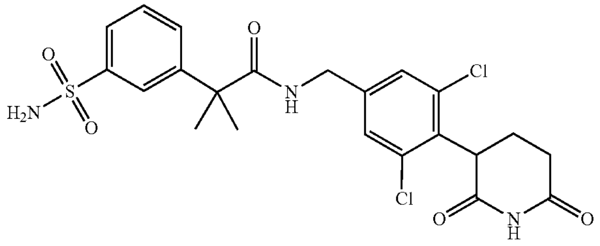 [SMILES: CC(C)(C(=O)NCc1cc(Cl)c(C2CCC(=O)NC2=O)c(Cl)c1)c1cccc(S(N)(=O)=O)c1] Compound 60 |
| 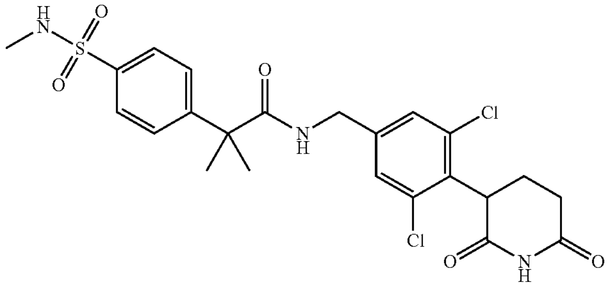 [SMILES: CNS(=O)(=O)c1ccc(C(C)(C)C(=O)NCc2cc(Cl)c(C3CCC(=O)NC3=O)c(Cl)c2)cc1] Compound 61 |
| 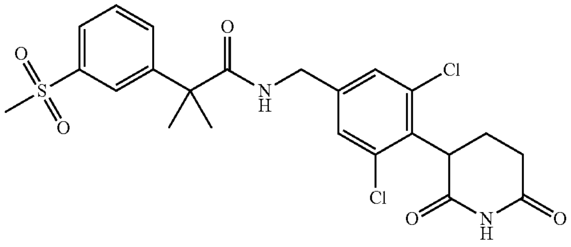 [SMILES: CC(C)(C(=O)NCc1cc(Cl)c(C2CCC(=O)NC2=O)c(Cl)c1)c1cccc(S(C)(=O)=O)c1] Compound 62 |

TABLE 1-continued
| Compounds Table | |
| --- | --- |
| 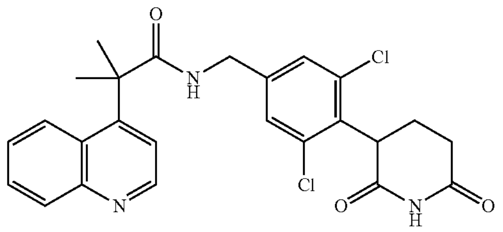 [SMILES: CC(C)(C(=O)NCc1cc(Cl)c(C2CCC(=O)NC2=O)c(Cl)c1)c1ccnc2ccccc12] | Compound 63 |
| 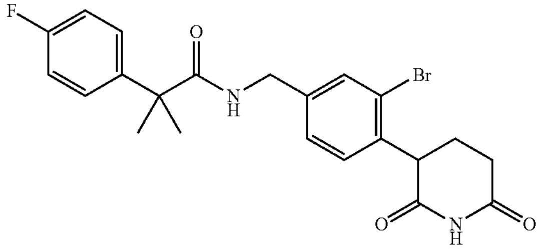 [SMILES: CC(C)(C(=O)NCc1ccc(C2CCC(=O)NC2=O)c(Br)c1)c1ccc(F)cc1] | Compound 64 |
| 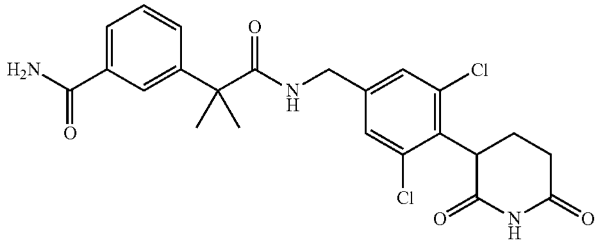 [SMILES: CC(C)(C(=O)NCc1cc(Cl)c(C2CCC(=O)NC2=O)c(Cl)c1)c1cccc(C(N)=O)c1] | Compound 65 |
| 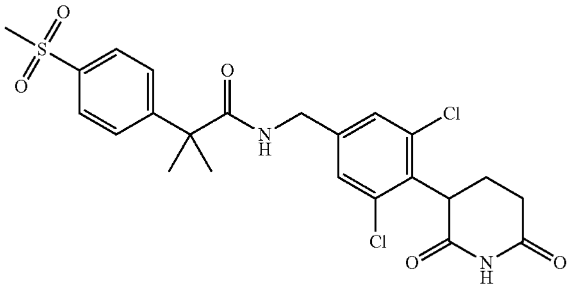 [SMILES: CC(C)(C(=O)NCc1cc(Cl)c(C2CCC(=O)NC2=O)c(Cl)c1)c1ccc(S(C)(=O)=O)cc1] | Compound 66 |
| 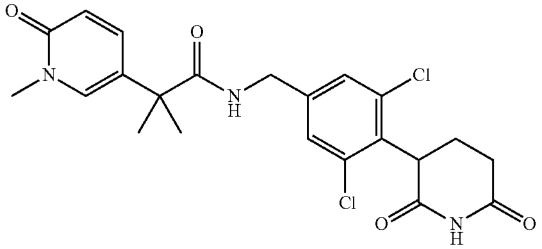 [SMILES: Cn1cc(C(C)(C)C(=O)NCc2cc(Cl)c(C3CCC(=O)NC3=O)c(Cl)c2)ccc1=O] | Compound 67 |
| 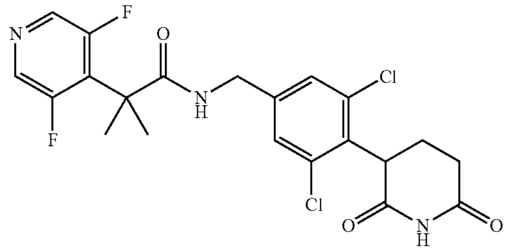 | Compound 68 |

TABLE 1-continued
| Compounds Table | |
|---|---|
| 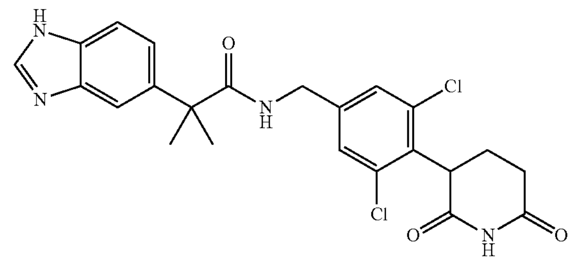 [SMILES: CC(C)(C(=O)NCc1cc(Cl)c(C2CCC(=O)NC2=O)c(Cl)c1)c1ccc2[nH]cnc2c1] | Compound 69 |
| 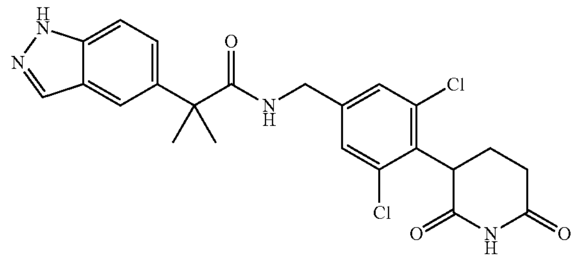 [SMILES: CC(C)(C(=O)NCc1cc(Cl)c(C2CCC(=O)NC2=O)c(Cl)c1)c1ccc2[nH]ncc2c1] | Compound 70 |
| 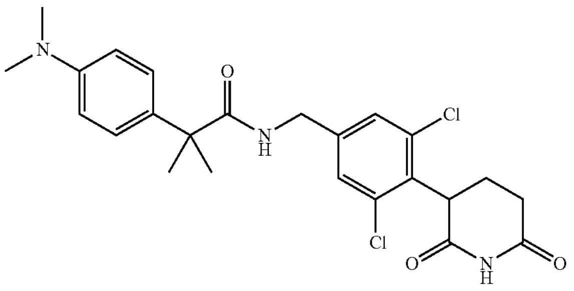 [SMILES: CN(C)c1ccc(C(C)(C)C(=O)NCc2cc(Cl)c(C3CCC(=O)NC3=O)c(Cl)c2)cc1] | Compound 71 |
| 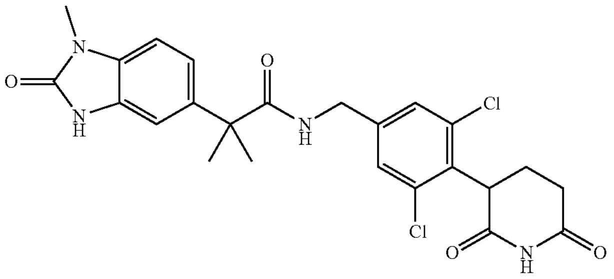 [SMILES: Cn1c(=O)[nH]c2cc(C(C)(C)C(=O)NCc3cc(Cl)c(C4CCC(=O)NC4=O)c(Cl)c3)ccc21] | Compound 72 |
| 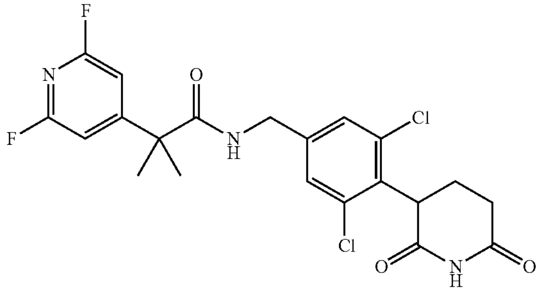 [SMILES: CC(C)(C(=O)NCc1cc(Cl)c(C2CCC(=O)NC2=O)c(Cl)c1)c1cc(F)nc(F)c1] | Compound 73 |

TABLE 1-continued
Compounds Table
Compound 74
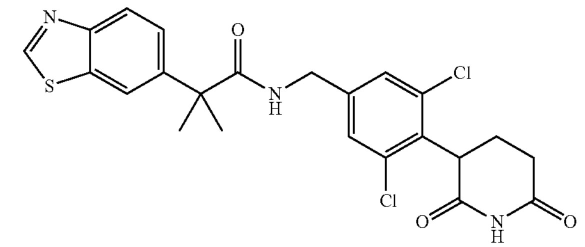 [SMILES: CC(C)(C(=O)NCc1cc(Cl)c(C2CCC(=O)NC2=O)c(Cl)c1)c1ccc2ncsc2c1]
Compound 75
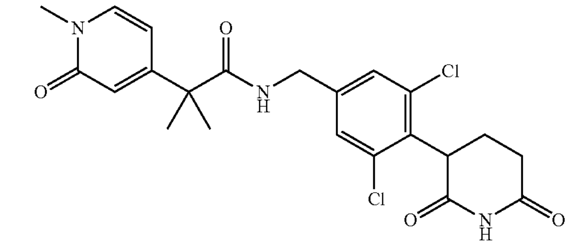 [SMILES: Cn1ccc(C(C)(C)C(=O)NCc2cc(Cl)c(C3CCC(=O)NC3=O)c(Cl)c2)cc1=O]
Compound 76
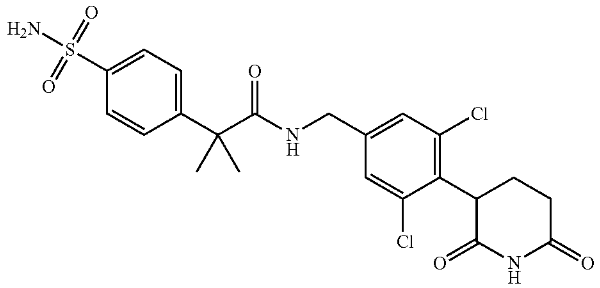 [SMILES: CC(C)(C(=O)NCc1cc(Cl)c(C2CCC(=O)NC2=O)c(Cl)c1)c1ccc(S(N)(=O)=O)cc1]
Compound 77
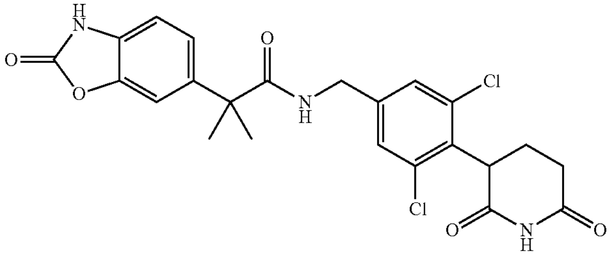 [SMILES: CC(C)(C(=O)NCc1cc(Cl)c(C2CCC(=O)NC2=O)c(Cl)c1)c1ccc2[nH]c(=O)oc2c1]
Compound 78
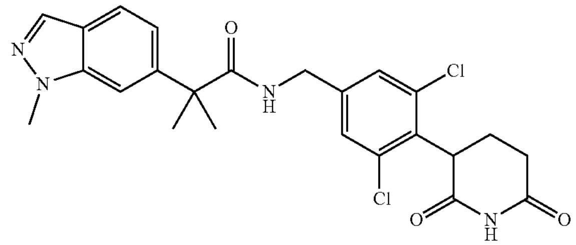 [SMILES: Cn1ncc2ccc(C(C)(C)C(=O)NCc3cc(Cl)c(C4CCC(=O)NC4=O)c(Cl)c3)cc21]
Compound 79
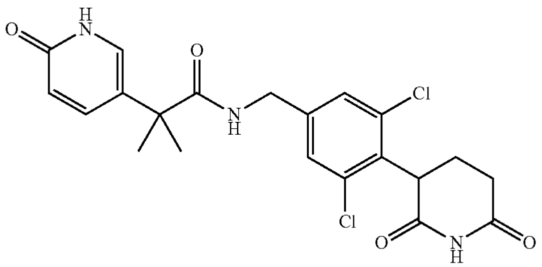 [SMILES: CC(C)(C(=O)NCc1cc(Cl)c(C2CCC(=O)NC2=O)c(Cl)c1)c1ccc(=O)[nH]c1]

TABLE 1-continued
| Compounds Table |
| --- |
| 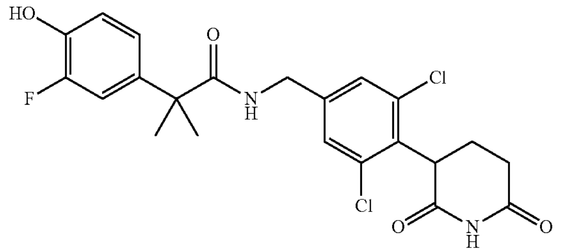 [SMILES: CC(C)(C(=O)NCc1cc(Cl)c(C2CCC(=O)NC2=O)c(Cl)c1)c1ccc(O)c(F)c1] Compound 80 |
| 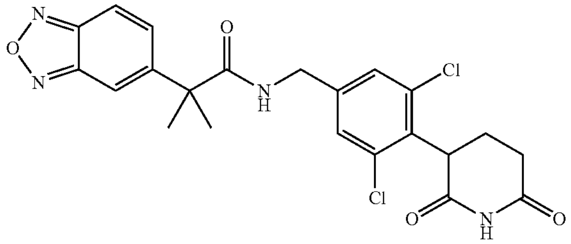 [SMILES: CC(C)(C(=O)NCc1cc(Cl)c(C2CCC(=O)NC2=O)c(Cl)c1)c1ccc2nonc2c1] Compound 81 |
| 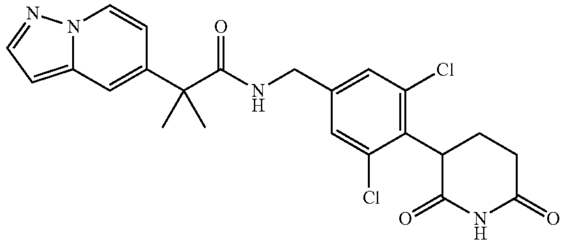 [SMILES: CC(C)(C(=O)NCc1cc(Cl)c(C2CCC(=O)NC2=O)c(Cl)c1)c1ccn2nccc2c1] Compound 82 |
| 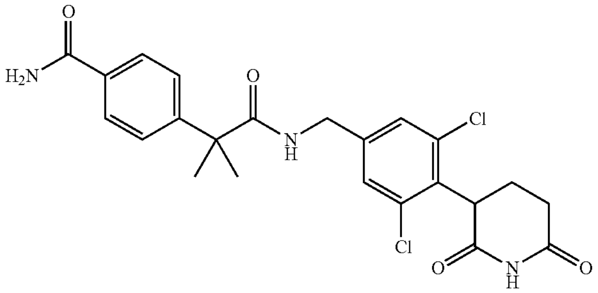 [SMILES: CC(C)(C(=O)NCc1cc(Cl)c(C2CCC(=O)NC2=O)c(Cl)c1)c1ccc(C(N)=O)cc1] Compound 83 |
| 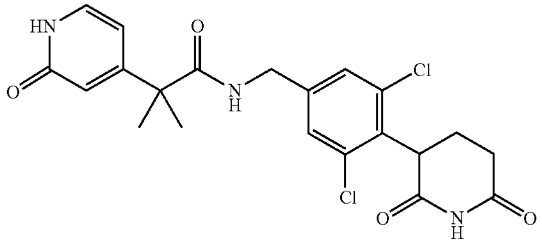 [SMILES: CC(C)(C(=O)NCc1cc(Cl)c(C2CCC(=O)NC2=O)c(Cl)c1)c1cc[nH]c(=O)c1] Compound 84 |
| 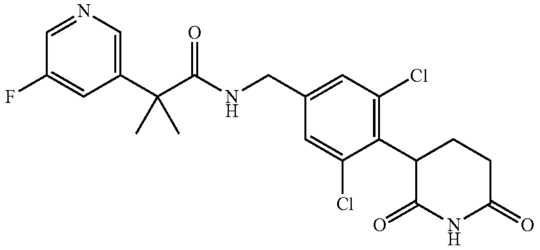 [SMILES: CC(C)(C(=O)NCc1cc(Cl)c(C2CCC(=O)NC2=O)c(Cl)c1)c1cncc(F)c1] Compound 85 |

TABLE 1-continued
Compounds Table
Compound 86
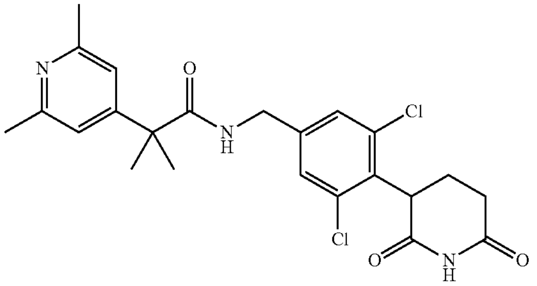 [SMILES: Cc1cc(C(C)(C)C(=O)NCc2cc(Cl)c(C3CCC(=O)NC3=O)c(Cl)c2)cc(C)n1]
Compound 87
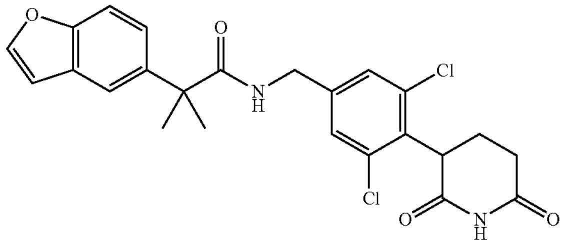 [SMILES: CC(C)(C(=O)NCc1cc(Cl)c(C2CCC(=O)NC2=O)c(Cl)c1)c1ccc2occc2c1]
Compound 88
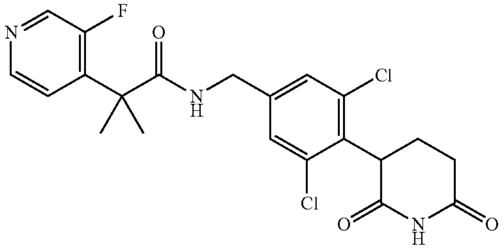 [SMILES: CC(C)(C(=O)NCc1cc(Cl)c(C2CCC(=O)NC2=O)c(Cl)c1)c1ccncc1F]
Compound 89
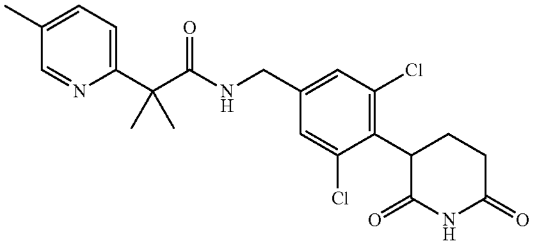
Compound 90
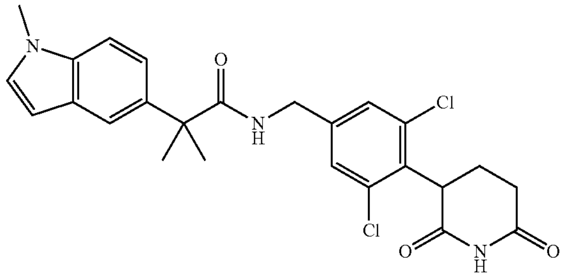 [SMILES: Cn1ccc2cc(C(C)(C)C(=O)NCc3cc(Cl)c(C4CCC(=O)NC4=O)c(Cl)c3)ccc21]
Compound 91
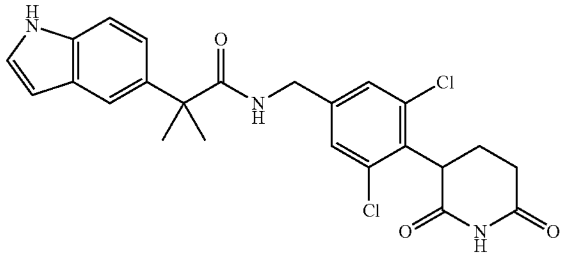 [SMILES: CC(C)(C(=O)NCc1cc(Cl)c(C2CCC(=O)NC2=O)c(Cl)c1)c1ccc2[nH]ccc2c1]

TABLE 1-continued
| Compounds Table | |
|---|---|
| 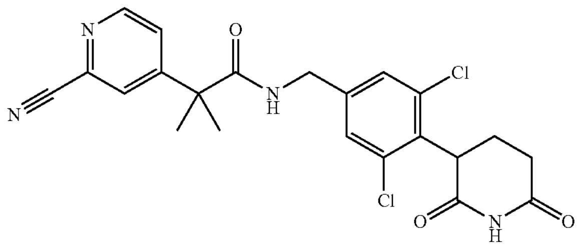 [SMILES: CC(C)(C(=O)NCc1cc(Cl)c(C2CCC(=O)NC2=O)c(Cl)c1)c1ccnc(C#N)c1] | Compound 92 |
| 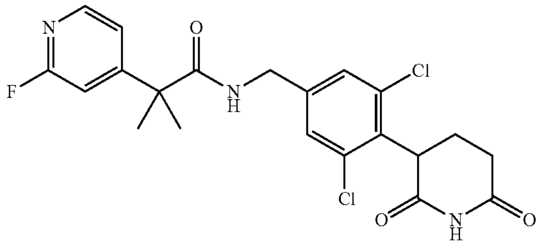 | Compound 93 |
| 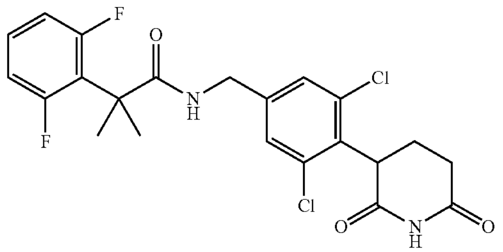 [SMILES: CC(C)(C(=O)NCc1cc(Cl)c(C2CCC(=O)NC2=O)c(Cl)c1)c1c(F)cccc1F] | Compound 94 |
| 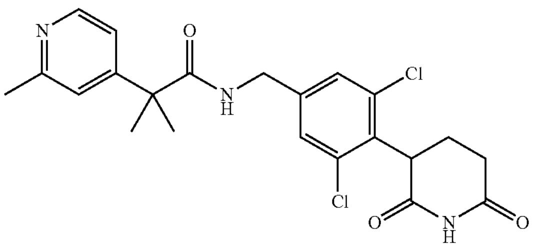 [SMILES: Cc1cc(C(C)(C)C(=O)NCc2cc(Cl)c(C3CCC(=O)NC3=O)c(Cl)c2)ccn1] | Compound 95 |
| 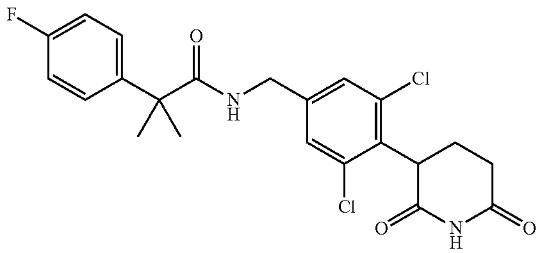 | Compound 96 |
| 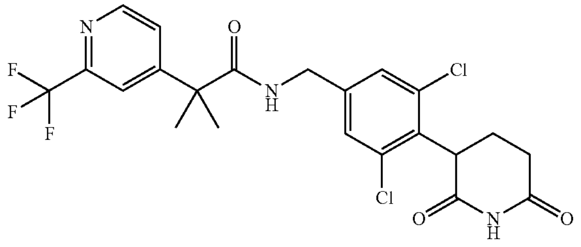 [SMILES: CC(C)(C(=O)NCc1cc(Cl)c(C2CCC(=O)NC2=O)c(Cl)c1)c1ccnc(C(F)(F)F)c1] | Compound 97 |

TABLE 1-continued
| Compounds Table |
| --- |
| Compound 98<br>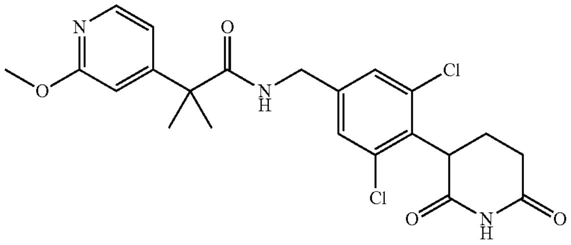 [SMILES: COc1cc(C(C)(C)C(=O)NCc2cc(Cl)c(C3CCC(=O)NC3=O)c(Cl)c2)ccn1] |
| Compound 99<br>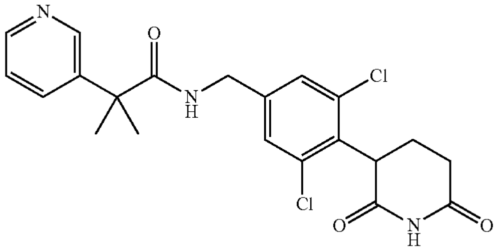 [SMILES: CC(C)(C(=O)NCc1cc(Cl)c(C2CCC(=O)NC2=O)c(Cl)c1)c1cccnc1] |
| Compound 100<br>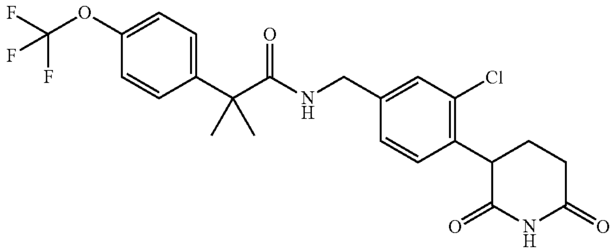 [SMILES: CC(C)(C(=O)NCc1ccc(C2CCC(=O)NC2=O)c(Cl)c1)c1ccc(OC(F)(F)F)cc1] |
| Compound 101<br>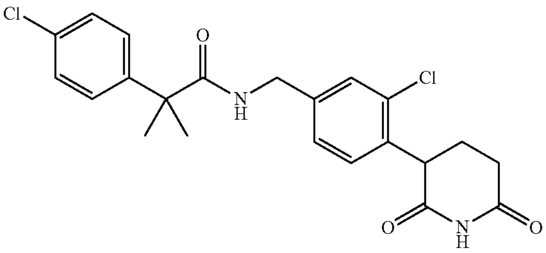 [SMILES: CC(C)(C(=O)NCc1ccc(C2CCC(=O)NC2=O)c(Cl)c1)c1ccc(Cl)cc1] |
| Compound 102<br>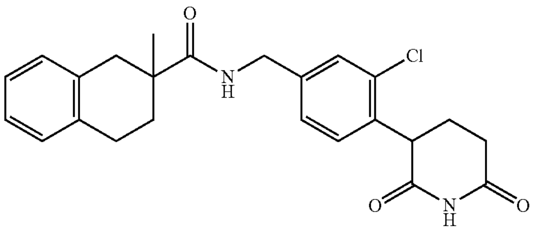 [SMILES: CC1(C(=O)NCc2ccc(C3CCC(=O)NC3=O)c(Cl)c2)CCc2ccccc2C1] |
| Compound 103<br>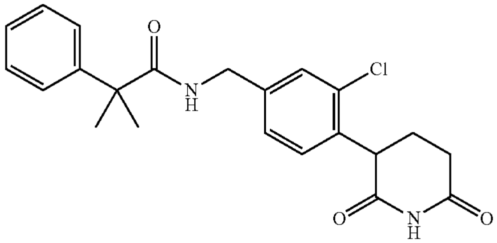 [SMILES: CC(C)(C(=O)NCc1ccc(C2CCC(=O)NC2=O)c(Cl)c1)c1ccccc1] |

TABLE 1-continued
| Compounds Table |
| --- |
| 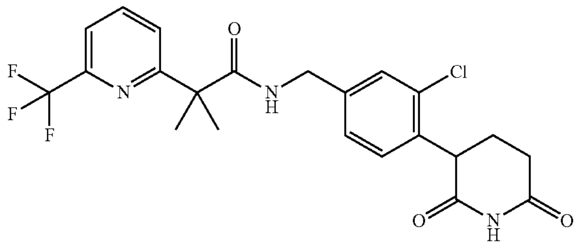 [SMILES: CC(C)(C(=O)NCc1ccc(C2CCC(=O)NC2=O)c(Cl)c1)c1cccc(C(F)(F)F)n1] Compound 104 |
| 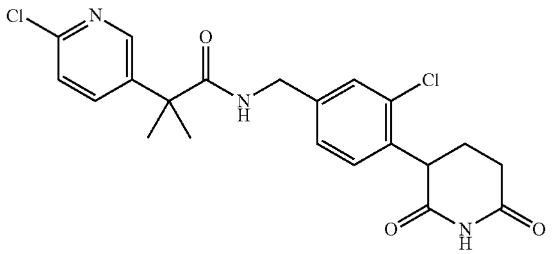 [SMILES: CC(C)(C(=O)NCc1ccc(C2CCC(=O)NC2=O)c(Cl)c1)c1ccc(Cl)nc1] Compound 105 |
| 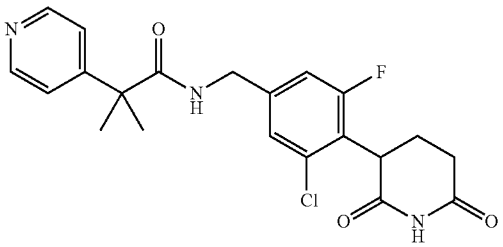 [SMILES: CC(C)(C(=O)NCc1cc(F)c(C2CCC(=O)NC2=O)c(Cl)c1)c1ccncc1] Compound 106 |
| 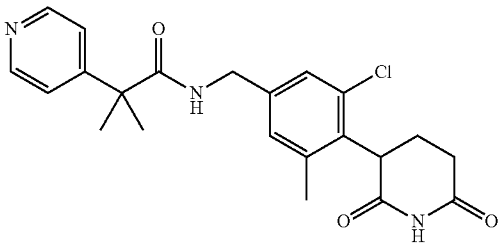 Compound 107 |
| 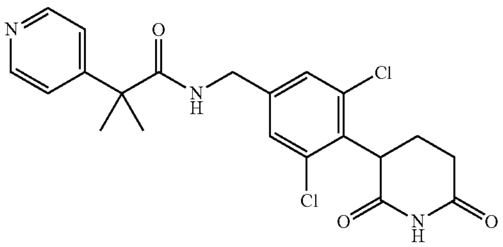 [SMILES: CC(C)(C(=O)NCc1cc(Cl)c(C2CCC(=O)NC2=O)c(Cl)c1)c1ccncc1] Compound 108 |
| 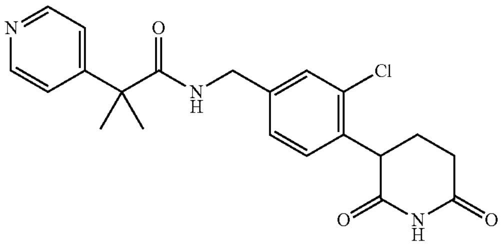 [SMILES: CC(C)(C(=O)NCc1ccc(C2CCC(=O)NC2=O)c(Cl)c1)c1ccncc1] Compound 109 |

TABLE 1-continued
| Compounds Table | |
|---|---|
| 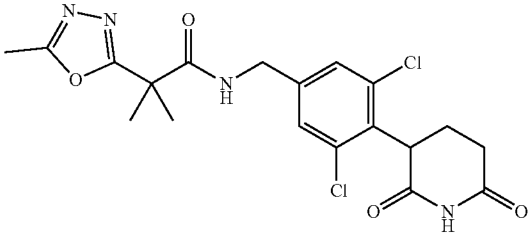 | Compound 110 |
| 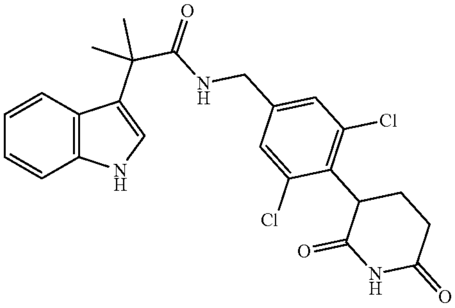 [SMILES: CC(C)(C(=O)NCc1cc(Cl)c(C2CCC(=O)NC2=O)c(Cl)c1)c1c[nH]c2ccccc12] | Compound 111 |
| 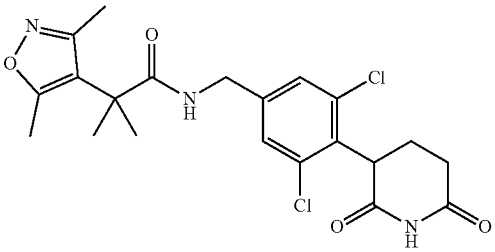 [SMILES: Cc1noc(C)c1C(C)(C)C(=O)NCc1cc(Cl)c(C2CCC(=O)NC2=O)c(Cl)c1] | Compound 112 |
| 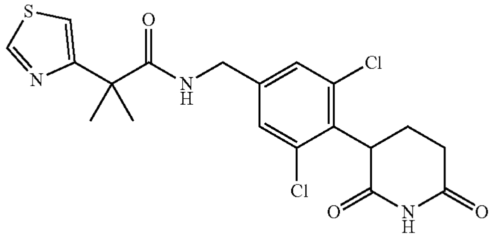 [SMILES: CC(C)(C(=O)NCc1cc(Cl)c(C2CCC(=O)NC2=O)c(Cl)c1)c1cscn1] | Compound 113 |
| 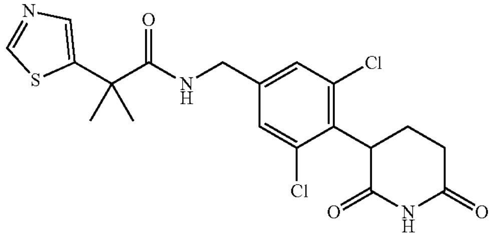 [SMILES: CC(C)(C(=O)NCc1cc(Cl)c(C2CCC(=O)NC2=O)c(Cl)c1)c1cncs1] | Compound 114 |
| 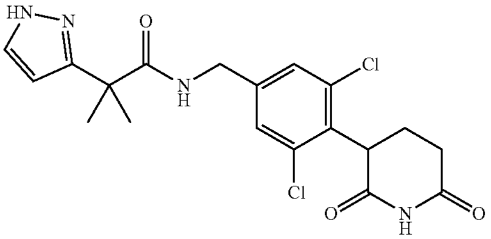 [SMILES: CC(C)(C(=O)NCc1cc(Cl)c(C2CCC(=O)NC2=O)c(Cl)c1)c1cc[nH]n1] | Compound 115 |

TABLE 1-continued
| Compounds Table |
| --- |
| 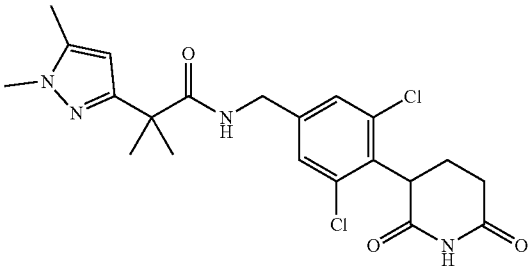 [SMILES: Cc1cc(C(C)(C)C(=O)NCc2cc(Cl)c(C3CCC(=O)NC3=O)c(Cl)c2)nn1C] Compound 116 |
| 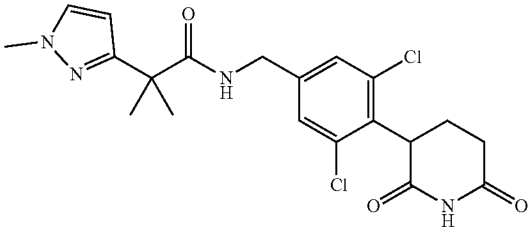 [SMILES: Cn1ccc(C(C)(C)C(=O)NCc2cc(Cl)c(C3CCC(=O)NC3=O)c(Cl)c2)n1] Compound 117 |
| 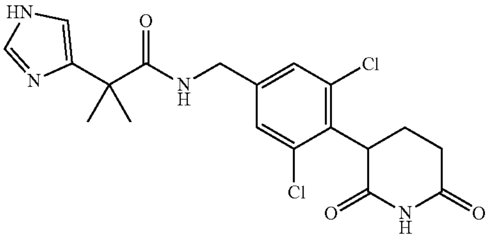 [SMILES: CC(C)(C(=O)NCc1cc(Cl)c(C2CCC(=O)NC2=O)c(Cl)c1)c1c[nH]cn1] Compound 118 |
| 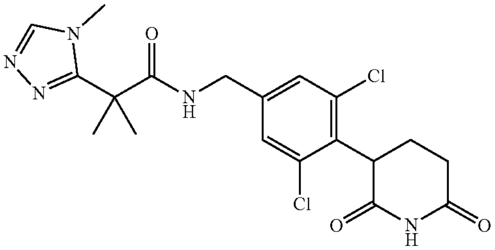 [SMILES: Cn1cnnc1C(C)(C)C(=O)NCc1cc(Cl)c(C2CCC(=O)NC2=O)c(Cl)c1] Compound 119 |
| 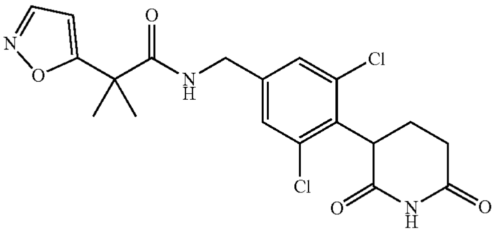 [SMILES: CC(C)(C(=O)NCc1cc(Cl)c(C2CCC(=O)NC2=O)c(Cl)c1)c1ccno1] Compound 120 |
| 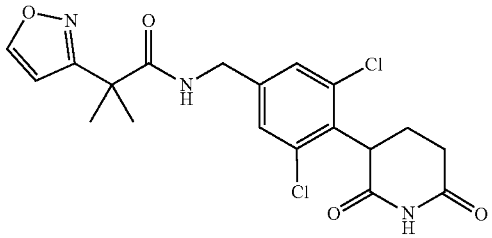 [SMILES: CC(C)(C(=O)NCc1cc(Cl)c(C2CCC(=O)NC2=O)c(Cl)c1)c1ccon1] Compound 121 |

TABLE 1-continued
| Compounds Table | |
|---|---|
| 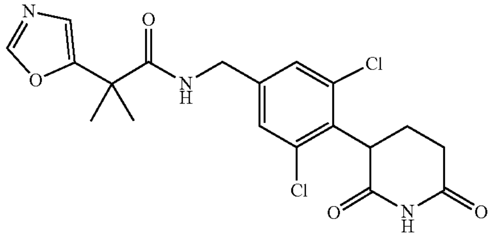 [SMILES: CC(C)(C(=O)NCc1cc(Cl)c(C2CCC(=O)NC2=O)c(Cl)c1)c1cnco1] | Compound 122 |
| 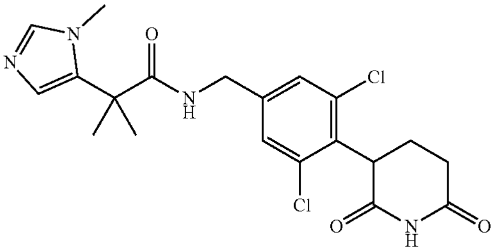 [SMILES: Cn1cncc1C(C)(C)C(=O)NCc1cc(Cl)c(C2CCC(=O)NC2=O)c(Cl)c1] | Compound 123 |
| 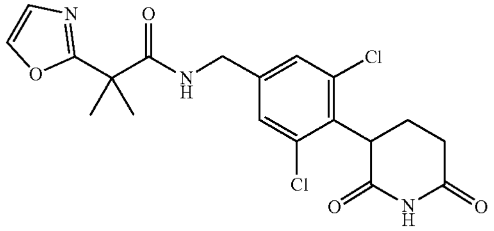 [SMILES: CC(C)(C(=O)NCc1cc(Cl)c(C2CCC(=O)NC2=O)c(Cl)c1)c1ncco1] | Compound 124 |
| 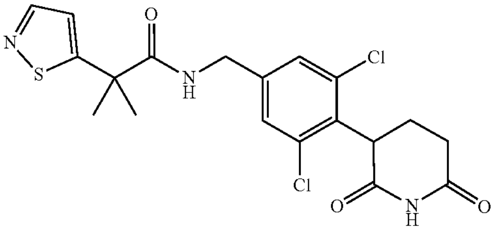 [SMILES: CC(C)(C(=O)NCc1cc(Cl)c(C2CCC(=O)NC2=O)c(Cl)c1)c1ccns1] | Compound 125 |
| 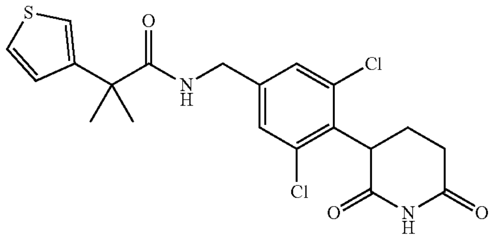 [SMILES: CC(C)(C(=O)NCc1cc(Cl)c(C2CCC(=O)NC2=O)c(Cl)c1)c1ccsc1] | Compound 126 |
| 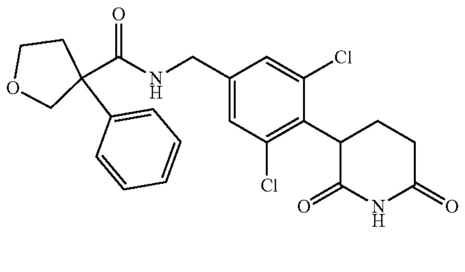 [SMILES: O=C1CCC(c2c(Cl)cc(CNC(=O)C3(c4ccccc4)CCOC3)cc2Cl)C(=O)N1] | Compound 127 |

TABLE 1-continued
| Compounds Table | |
|---|---|
| 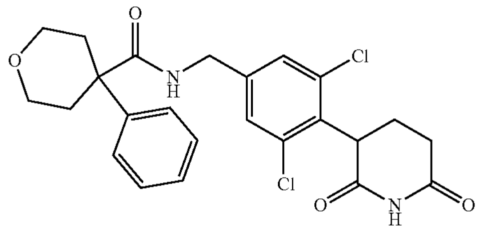 [SMILES: O=C1CCC(c2c(Cl)cc(CNC(=O)C3(c4ccccc4)CCOCC3)cc2Cl)C(=O)N1] | Compound 128 |
| 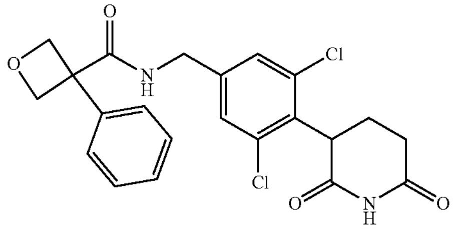 [SMILES: O=C1CCC(c2c(Cl)cc(CNC(=O)C3(c4ccccc4)COC3)cc2Cl)C(=O)N1] | Compound 129 |
| 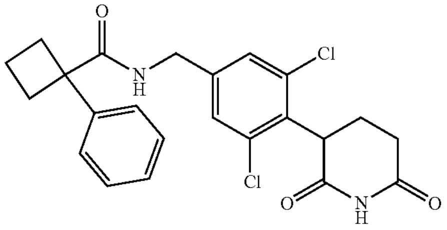 [SMILES: O=C1CCC(c2c(Cl)cc(CNC(=O)C3(c4ccccc4)CCC3)cc2Cl)C(=O)N1] | Compound 130 |
| 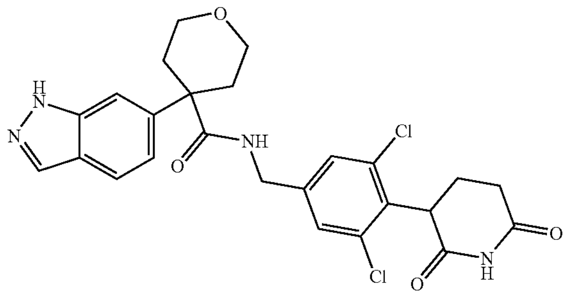 [SMILES: O=C1CCC(c2c(Cl)cc(CNC(=O)C3(c4ccc5cn[nH]c5c4)CCOCC3)cc2Cl)C(=O)N1] | Compound 131 |
| 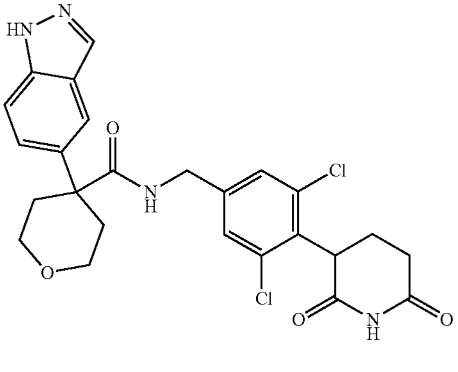 [SMILES: O=C1CCC(c2c(Cl)cc(CNC(=O)C3(c4ccc5[nH]ncc5c4)CCOCC3)cc2Cl)C(=O)N1] | Compound 132 |

TABLE 1-continued
| Compounds Table | |
| --- | --- |
| 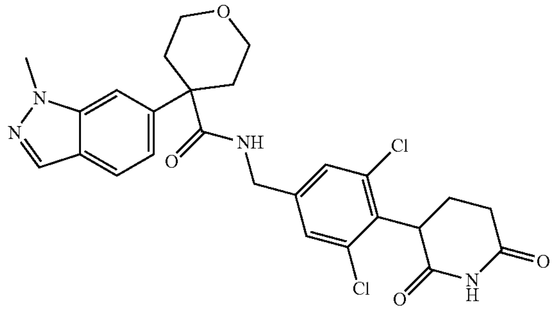 [SMILES: Cn1ncc2ccc(C3(C(=O)NCc4cc(Cl)c(C5CCC(=O)NC5=O)c(Cl)c4)CCOCC3)cc21] | Compound 133 |
| 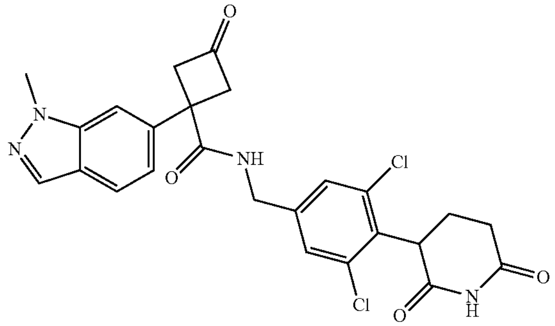 [SMILES: Cn1ncc2ccc(C3(C(=O)NCc4cc(Cl)c(C5CCC(=O)NC5=O)c(Cl)c4)CC(=O)C3)cc21] | Compound 134 |
| 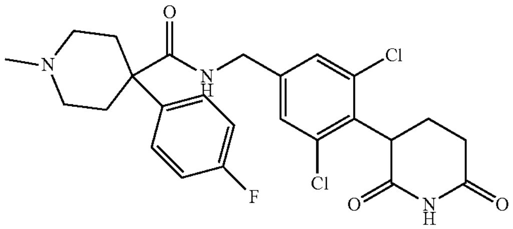 [SMILES: CN1CCC(C(=O)NCc2cc(Cl)c(C3CCC(=O)NC3=O)c(Cl)c2)(c2ccc(F)cc2)CC1] | Compound 135 |
| 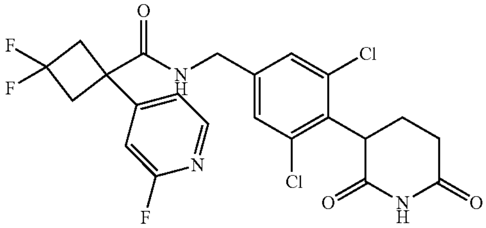 [SMILES: O=C1CCC(c2c(Cl)cc(CNC(=O)C3(c4ccnc(F)c4)CC(F)(F)C3)cc2Cl)C(=O)N1] | Compound 136 |
| 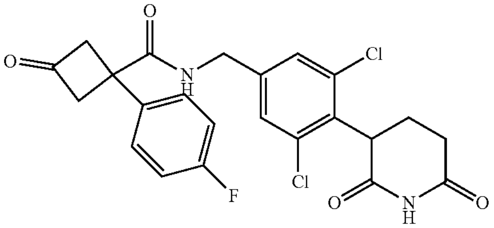 [SMILES: O=C1CC(C(=O)NCc2cc(Cl)c(C3CCC(=O)NC3=O)c(Cl)c2)(c2ccc(F)cc2)C1] | Compound 137 |
| 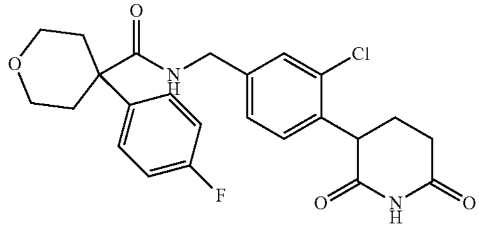 [SMILES: O=C1CCC(c2ccc(CNC(=O)C3(c4ccc(F)cc4)CCOCC3)cc2Cl)C(=O)N1] | Compound 138 |

TABLE 1-continued
| Compounds Table | |
|---|---|
| 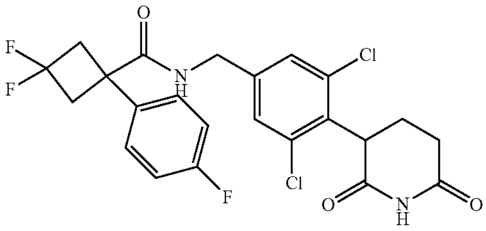 [SMILES: O=C1CCC(c2c(Cl)cc(CNC(=O)C3(c4ccc(F)cc4)CC(F)(F)C3)cc2Cl)C(=O)N1] | Compound 139 |
| 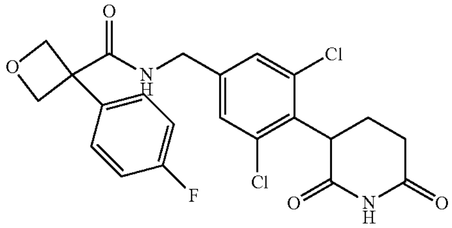 [SMILES: O=C1CCC(c2c(Cl)cc(CNC(=O)C3(c4ccc(F)cc4)COC3)cc2Cl)C(=O)N1] | Compound 140 |
| 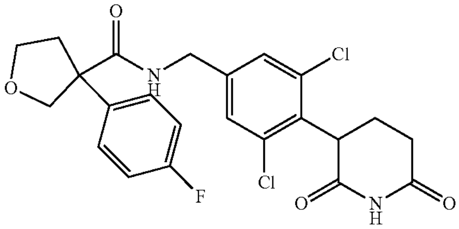 [SMILES: O=C1CCC(c2c(Cl)cc(CNC(=O)C3(c4ccc(F)cc4)CCOC3)cc2Cl)C(=O)N1] | Compound 141 |
| 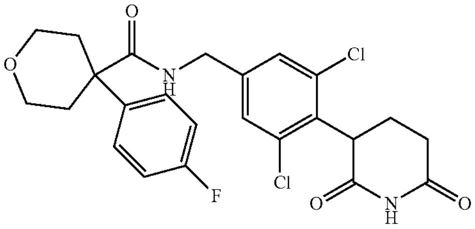 [SMILES: O=C1CCC(c2c(Cl)cc(CNC(=O)C3(c4ccc(F)cc4)CCOCC3)cc2Cl)C(=O)N1] | Compound 142 |
| 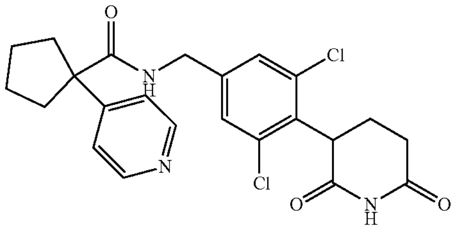 [SMILES: O=C1CCC(c2c(Cl)cc(CNC(=O)C3(c4ccncc4)CCCC3)cc2Cl)C(=O)N1] | Compound 143 |
| 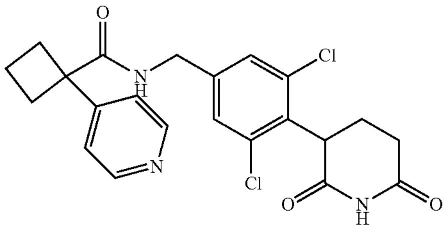 [SMILES: O=C1CCC(c2c(Cl)cc(CNC(=O)C3(c4ccncc4)CCC3)cc2Cl)C(=O)N1] | Compound 144 |

TABLE 1-continued
| Compounds Table |
| --- |
| 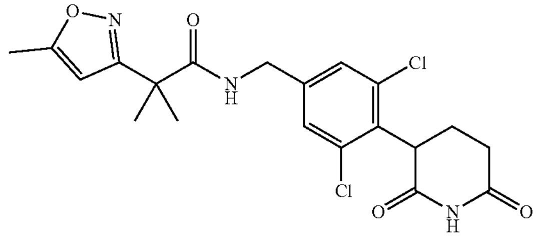 [SMILES: Cc1cc(C(C)(C)C(=O)NCc2cc(Cl)c(C3CCC(=O)NC3=O)c(Cl)c2)no1] Compound 145 |
| 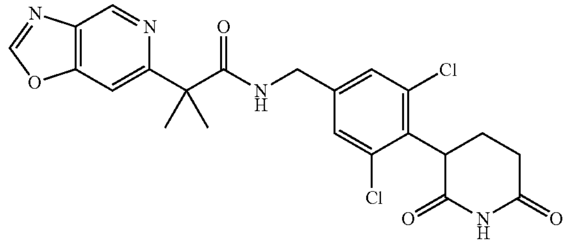 [SMILES: CC(C)(C(=O)NCc1cc(Cl)c(C2CCC(=O)NC2=O)c(Cl)c1)c1cc2ocnc2cn1] Compound 146 |
| 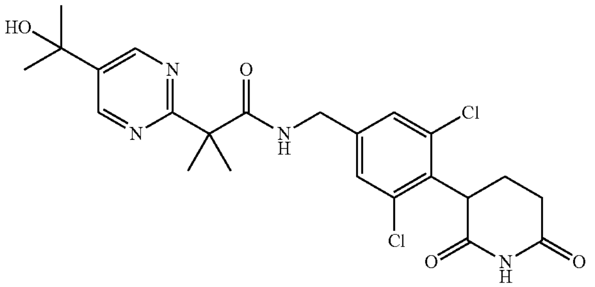 [SMILES: CC(C)(O)c1cnc(C(C)(C)C(=O)NCc2cc(Cl)c(C3CCC(=O)NC3=O)c(Cl)c2)nc1] Compound 147 |
| 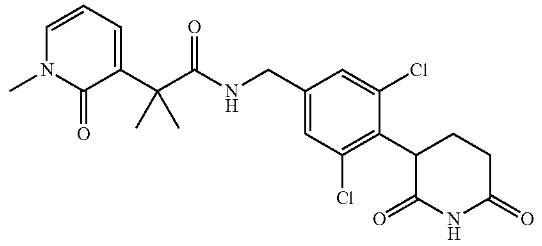 [SMILES: Cn1cccc(C(C)(C)C(=O)NCc2cc(Cl)c(C3CCC(=O)NC3=O)c(Cl)c2)c1=O] Compound 148 |
| 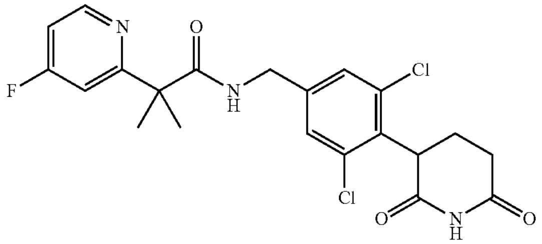 [SMILES: CC(C)(C(=O)NCc1cc(Cl)c(C2CCC(=O)NC2=O)c(Cl)c1)c1cc(F)ccn1] Compound 149 |
| 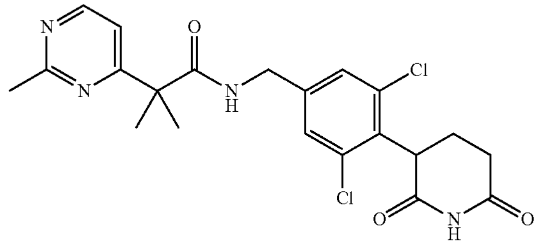 [SMILES: Cc1nccc(C(C)(C)C(=O)NCc2cc(Cl)c(C3CCC(=O)NC3=O)c(Cl)c2)n1] Compound 150 |

TABLE 1-continued
| Compounds Table |
| --- |
| 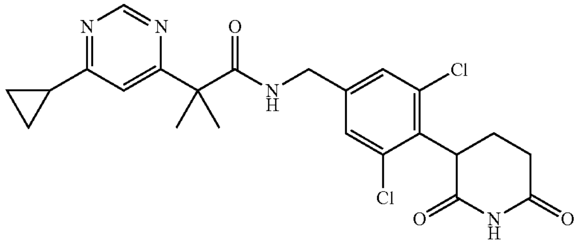 [SMILES: CC(C)(C(=O)NCc1cc(Cl)c(C2CCC(=O)NC2=O)c(Cl)c1)c1cc(C2CC2)ncn1] Compound 151 |
| 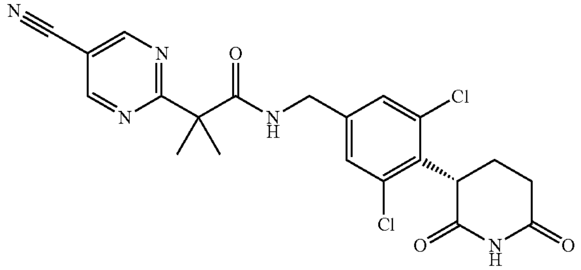 [SMILES: CC(C)(C(=O)NCc1cc(Cl)c([C@@H]2CCC(=O)NC2=O)c(Cl)c1)c1ncc(C#N)cn1] Compound 152<br>*first eluting isomer |
| 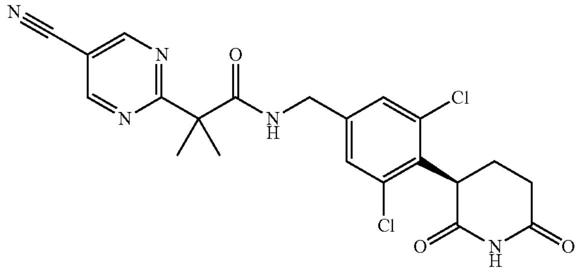 [SMILES: CC(C)(C(=O)NCc1cc(Cl)c([C@H]2CCC(=O)NC2=O)c(Cl)c1)c1ncc(C#N)cn1] Compound 153<br>*second eluting isomer |
| 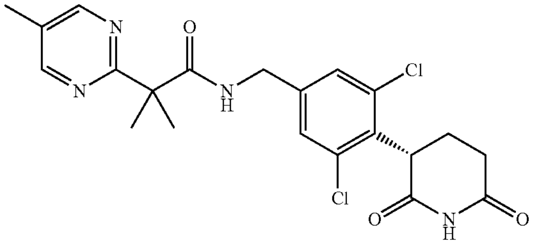 [SMILES: Cc1cnc(C(C)(C)C(=O)NCc2cc(Cl)c([C@@H]3CCC(=O)NC3=O)c(Cl)c2)nc1] Compound 154<br>*first eluting isomer |
| 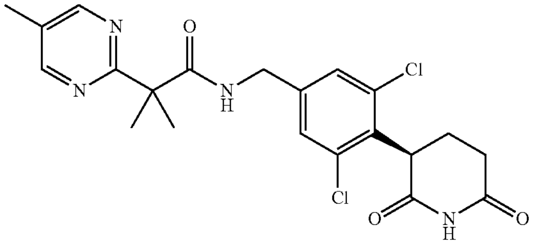 [SMILES: Cc1cnc(C(C)(C)C(=O)NCc2cc(Cl)c([C@H]3CCC(=O)NC3=O)c(Cl)c2)nc1] Compound 155<br>*second eluting isomer |

TABLE 1-continued
| Compounds Table |
| --- |
| 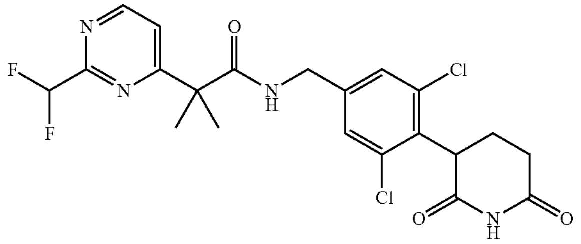 [SMILES: CC(C)(C(=O)NCc1cc(Cl)c(C2CCC(=O)NC2=O)c(Cl)c1)c1ccnc(C(F)F)n1] Compound 156 |
| 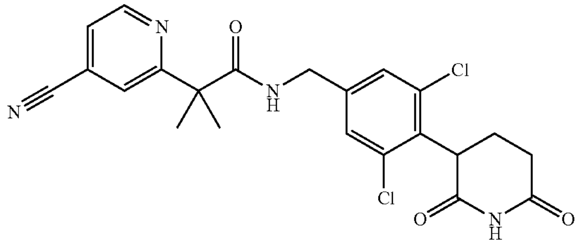 [SMILES: CC(C)(C(=O)NCc1cc(Cl)c(C2CCC(=O)NC2=O)c(Cl)c1)c1cc(C#N)ccn1] Compound 157 |
| 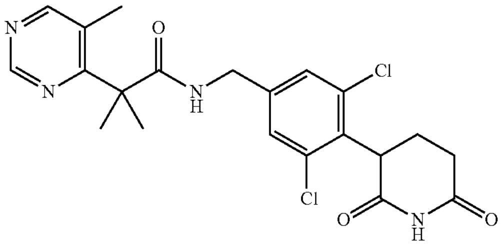 [SMILES: Cc1cncnc1C(C)(C)C(=O)NCc1cc(Cl)c(C2CCC(=O)NC2=O)c(Cl)c1] Compound 158 |
| 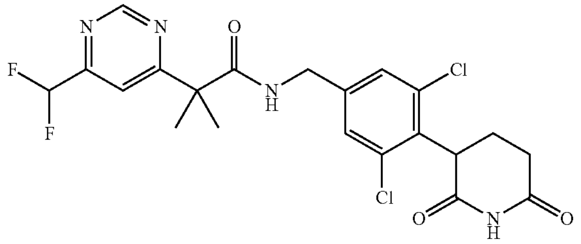 [SMILES: CC(C)(C(=O)NCc1cc(Cl)c(C2CCC(=O)NC2=O)c(Cl)c1)c1cc(C(F)F)ncn1] Compound 159 |
| 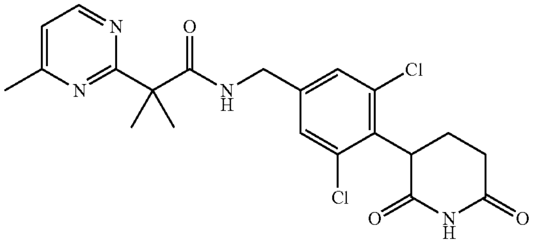 [SMILES: Cc1ccnc(C(C)(C)C(=O)NCc2cc(Cl)c(C3CCC(=O)NC3=O)c(Cl)c2)n1] Compound 160 |
| 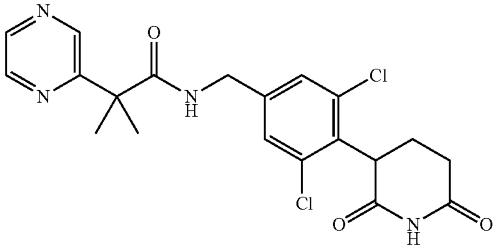 [SMILES: CC(C)(C(=O)NCc1cc(Cl)c(C2CCC(=O)NC2=O)c(Cl)c1)c1cnccn1] Compound 161 |

TABLE 1-continued
| Compounds Table |
| --- |
| 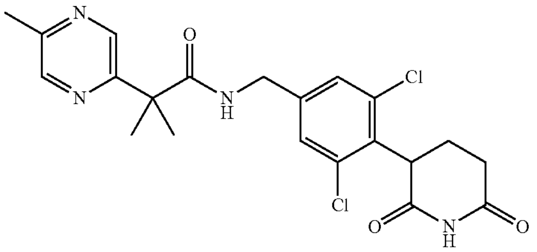 [SMILES: Cc1cnc(C(C)(C)C(=O)NCc2cc(Cl)c(C3CCC(=O)NC3=O)c(Cl)c2)cn1] Compound 162 |
| 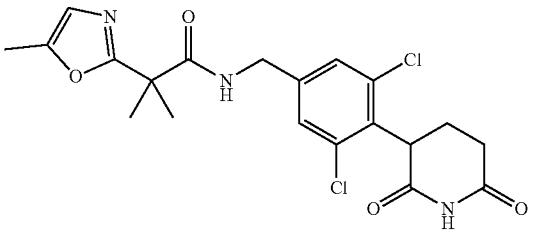 [SMILES: Cc1cnc(C(C)(C)C(=O)NCc2cc(Cl)c(C3CCC(=O)NC3=O)c(Cl)c2)o1] Compound 163 |
| 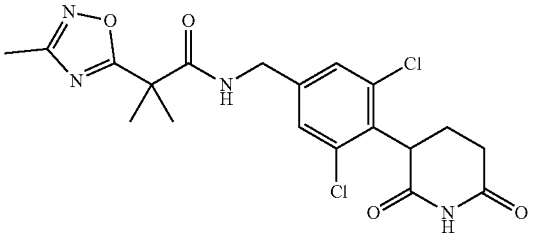 [SMILES: Cc1noc(C(C)(C)C(=O)NCc2cc(Cl)c(C3CCC(=O)NC3=O)c(Cl)c2)n1] Compound 164 |
| 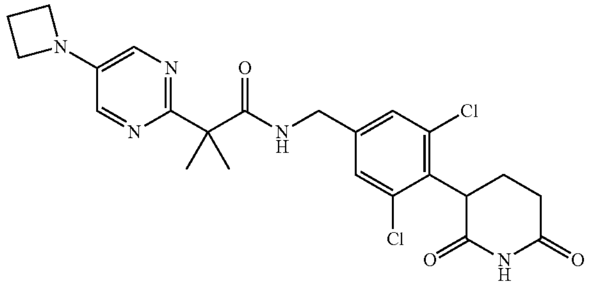 [SMILES: CC(C)(C(=O)NCc1cc(Cl)c(C2CCC(=O)NC2=O)c(Cl)c1)c1ncc(N2CCC2)cn1] Compound 165 |
| 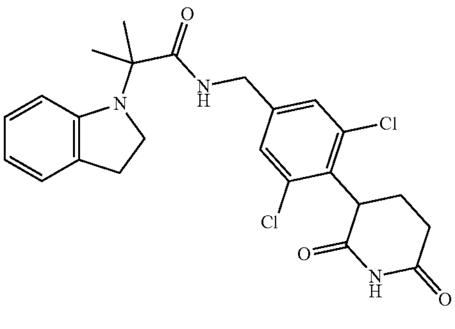 [SMILES: CC(C)(C(=O)NCc1cc(Cl)c(C2CCC(=O)NC2=O)c(Cl)c1)N1CCc2ccccc21] Compound 166 |
| 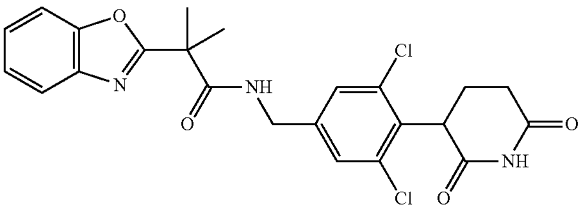 Compound 167 |

TABLE 1-continued
| Compounds Table | |
|---|---|
| 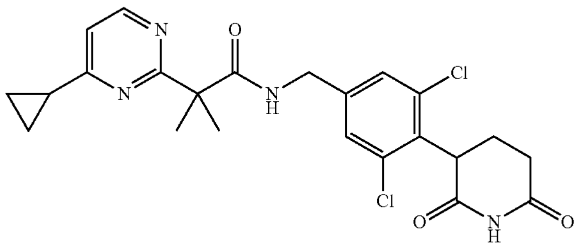 [SMILES: CC(C)(C(=O)NCc1cc(Cl)c(C2CCC(=O)NC2=O)c(Cl)c1)c1nccc(C2CC2)n1] | Compound 168 |
| 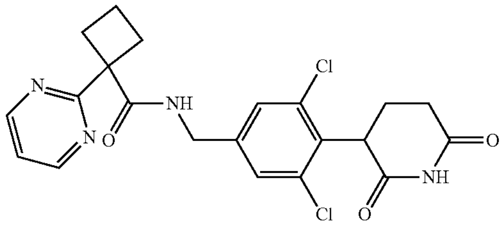 [SMILES: O=C1CCC(c2c(Cl)cc(CNC(=O)C3(c4ncccn4)CCC3)cc2Cl)C(=O)N1] | Compound 169 |
| 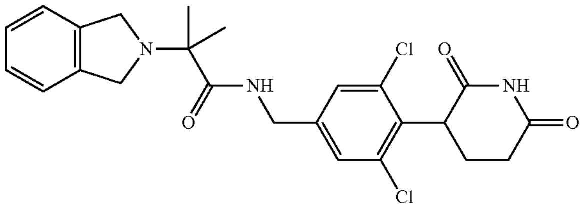 [SMILES: CC(C)(C(=O)NCc1cc(Cl)c(C2CCC(=O)NC2=O)c(Cl)c1)N1Cc2ccccc2C1] | Compound 170 |
| 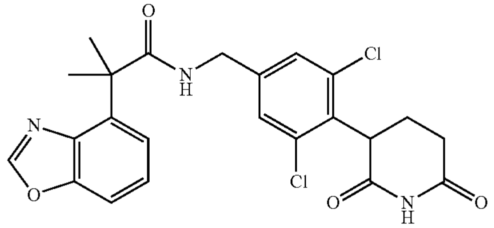 [SMILES: CC(C)(C(=O)NCc1cc(Cl)c(C2CCC(=O)NC2=O)c(Cl)c1)c1cccc2ocnc12] | Compound 171 |
| 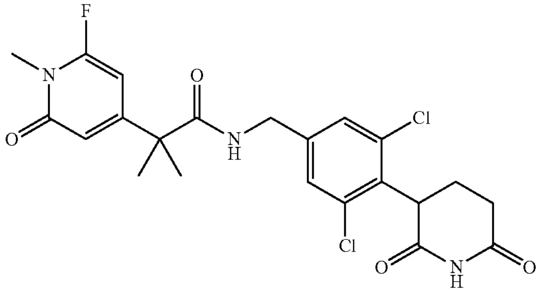 [SMILES: Cn1c(F)cc(C(C)(C)C(=O)NCc2cc(Cl)c(C3CCC(=O)NC3=O)c(Cl)c2)cc1=O] | Compound 172 |
| 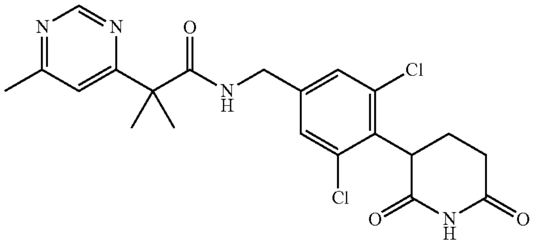 [SMILES: Cc1cc(C(C)(C)C(=O)NCc2cc(Cl)c(C3CCC(=O)NC3=O)c(Cl)c2)ncn1] | Compound 173 |

TABLE 1-continued
Compounds Table
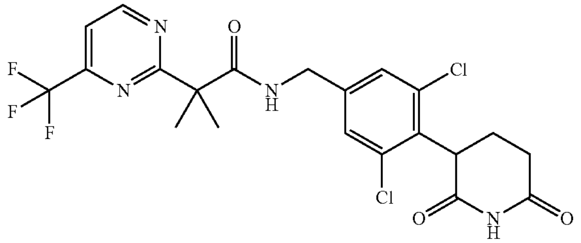 [SMILES: CC(C)(C(=O)NCc1cc(Cl)c(C2CCC(=O)NC2=O)c(Cl)c1)c1nccc(C(F)(F)F)n1]
Compound 174
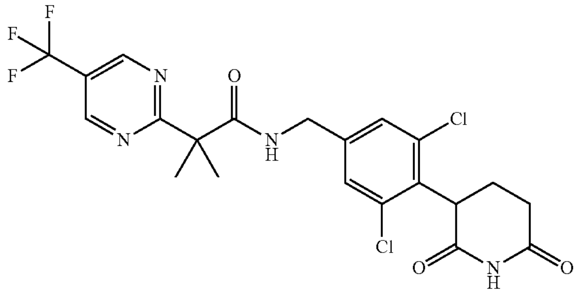 [SMILES: CC(C)(C(=O)NCc1cc(Cl)c(C2CCC(=O)NC2=O)c(Cl)c1)c1ncc(C(F)(F)F)cn1]
Compound 175
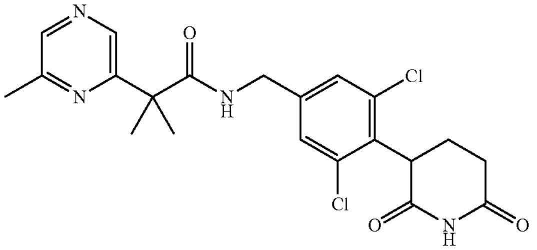 [SMILES: Cc1cncc(C(C)(C)C(=O)NCc2cc(Cl)c(C3CCC(=O)NC3=O)c(Cl)c2)n1]
Compound 176
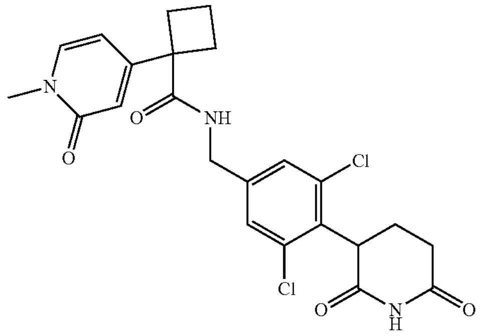 [SMILES: Cn1ccc(C2(C(=O)NCc3cc(Cl)c(C4CCC(=O)NC4=O)c(Cl)c3)CCC2)cc1=O]
Compound 177
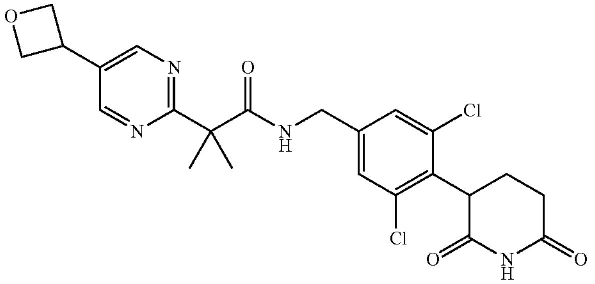 [SMILES: CC(C)(C(=O)NCc1cc(Cl)c(C2CCC(=O)NC2=O)c(Cl)c1)c1ncc(C2COC2)cn1]
Compound 178

TABLE 1-continued
Compounds Table
Compound 179
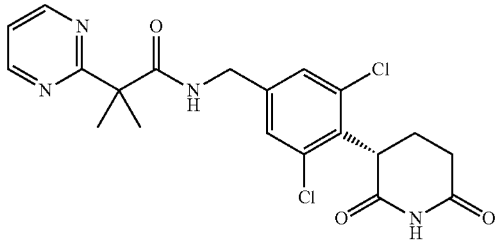 [SMILES: CC(C)(C(=O)NCc1cc(Cl)c([C@@H]2CCC(=O)NC2=O)c(Cl)c1)c1ncccn1]
*second eluting isomer
Compound 180
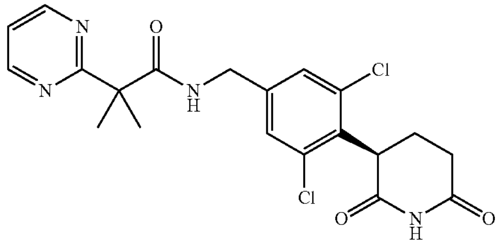 [SMILES: CC(C)(C(=O)NCc1cc(Cl)c([C@H]2CCC(=O)NC2=O)c(Cl)c1)c1ncccn1]
*first eluting isomer
Compound 181
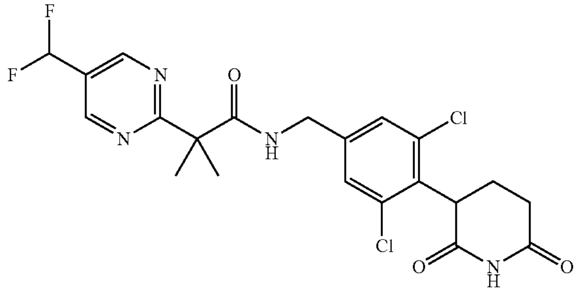
Compound 182
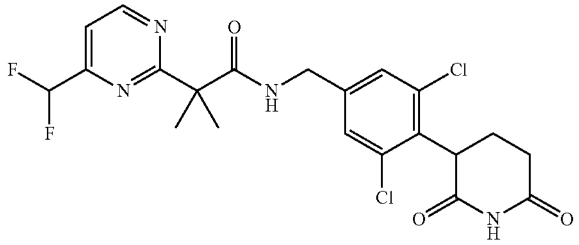
Compound 183
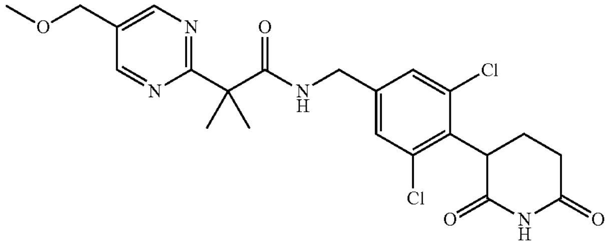 [SMILES: COCc1cnc(C(C)(C)C(=O)NCc2cc(Cl)c(C3CCC(=O)NC3=O)c(Cl)c2)nc1]

TABLE 1-continued
Compounds Table
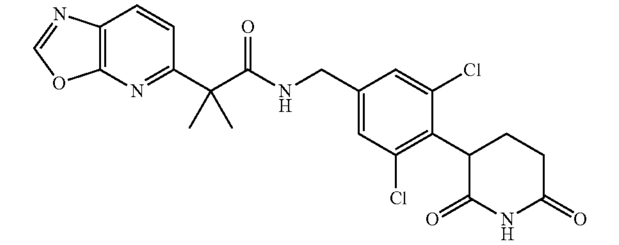 [SMILES: CC(C)(C(=O)NCc1cc(Cl)c(C2CCC(=O)NC2=O)c(Cl)c1)c1ccc2ncoc2n1]
Compound 184
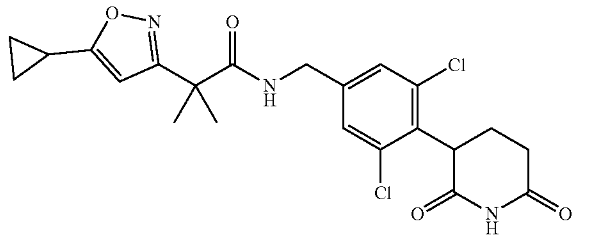 [SMILES: CC(C)(C(=O)NCc1cc(Cl)c(C2CCC(=O)NC2=O)c(Cl)c1)c1cc(C2CC2)on1]
Compound 185
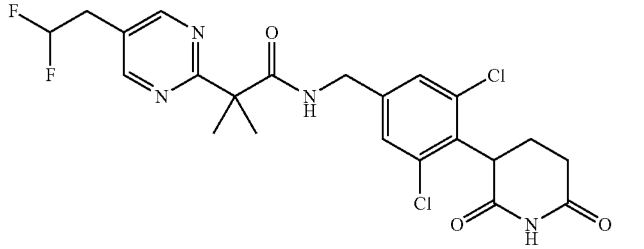
Compound 186
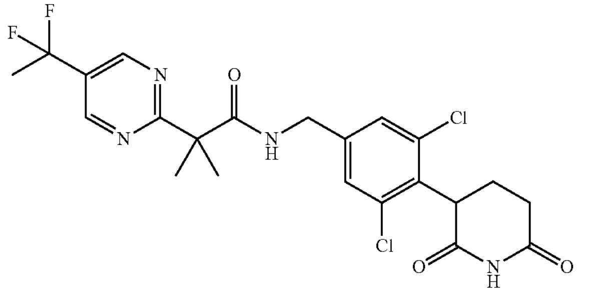
Compound 187
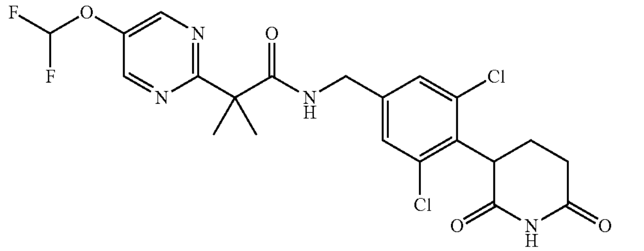 [SMILES: CC(C)(C(=O)NCc1cc(Cl)c(C2CCC(=O)NC2=O)c(Cl)c1)c1ncc(CC(F)F)cn1]
Compound 188
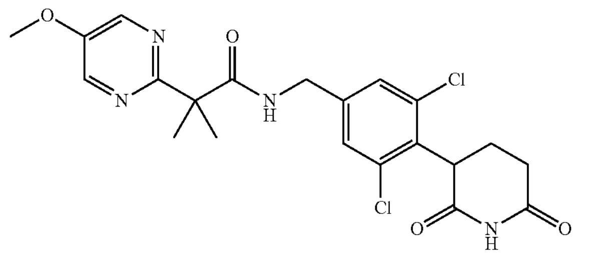 [SMILES: COc1cnc(C(C)(C)C(=O)NCc2cc(Cl)c(C3CCC(=O)NC3=O)c(Cl)c2)nc1]
Compound 189

TABLE 1-continued
Compounds Table
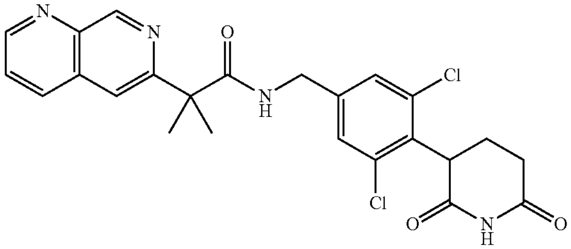 [SMILES: CC(C)(C(=O)NCc1cc(Cl)c(C2CCC(=O)NC2=O)c(Cl)c1)c1cc2cccnc2cn1]
Compound 190
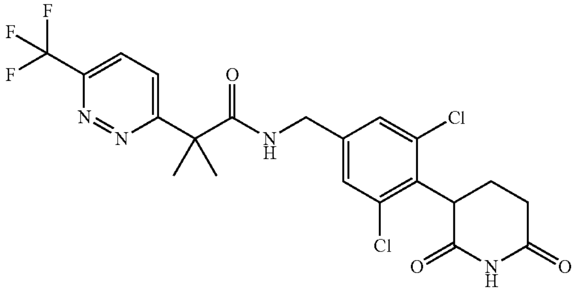
Compound 191
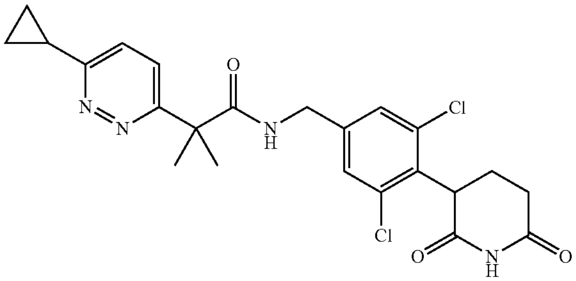 [SMILES: CC(C)(C(=O)NCc1cc(Cl)c(C2CCC(=O)NC2=O)c(Cl)c1)c1ccc(C2CC2)nn1]
Compound 192
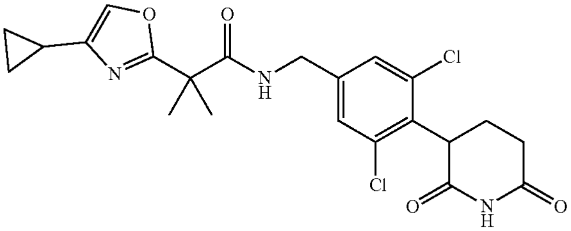 [SMILES: CC(C)(C(=O)NCc1cc(Cl)c(C2CCC(=O)NC2=O)c(Cl)c1)c1nc(C2CC2)co1]
Compound 193
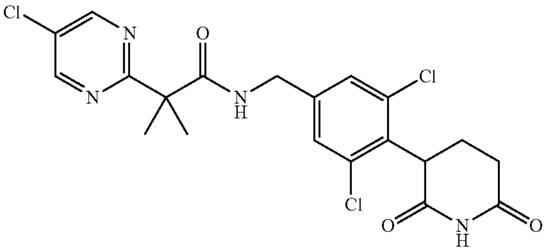 [SMILES: CC(C)(C(=O)NCc1cc(Cl)c(C2CCC(=O)NC2=O)c(Cl)c1)c1ncc(Cl)cn1]
Compound 194
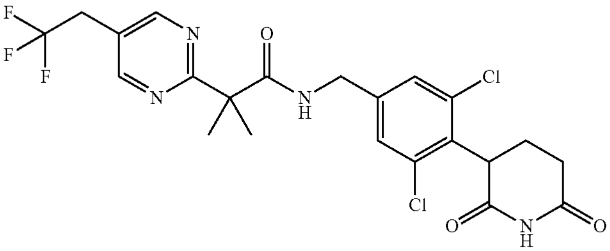 [SMILES: CC(C)(C(=O)NCc1cc(Cl)c(C2CCC(=O)NC2=O)c(Cl)c1)c1ncc(CC(F)(F)F)cn1]
Compound 195

TABLE 1-continued
Compounds Table
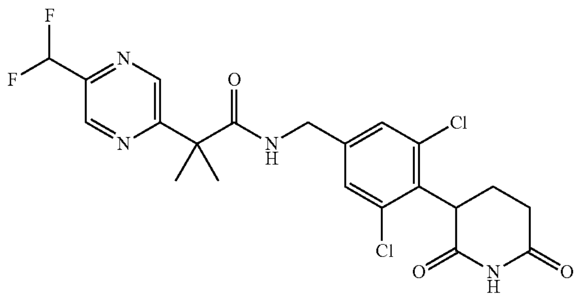
Compound 196
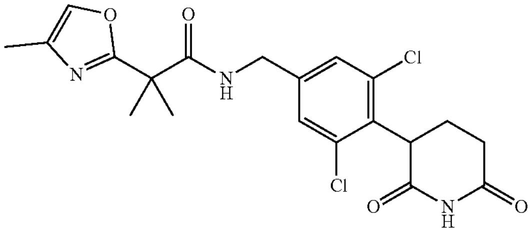 [SMILES: Cc1coc(C(C)(C)C(=O)NCc2cc(Cl)c(C3CCC(=O)NC3=O)c(Cl)c2)n1]
Compound 197
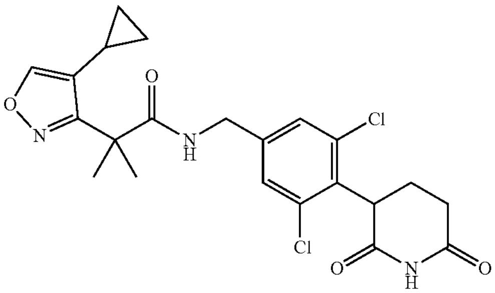 [SMILES: CC(C)(C(=O)NCc1cc(Cl)c(C2CCC(=O)NC2=O)c(Cl)c1)c1nocc1C1CC1]
Compound 198
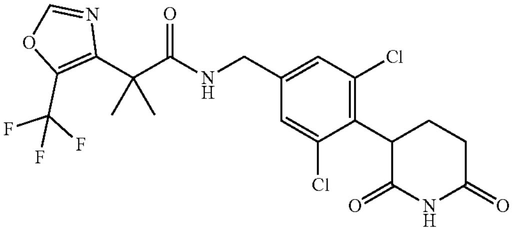 [SMILES: CC(C)(C(=O)NCc1cc(Cl)c(C2CCC(=O)NC2=O)c(Cl)c1)c1ncoc1C(F)(F)F]
Compound 199
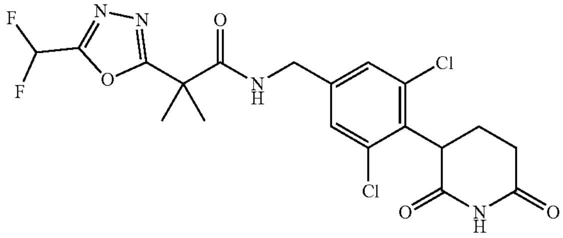 [SMILES: CC(C)(C(=O)NCc1cc(Cl)c(C2CCC(=O)NC2=O)c(Cl)c1)c1nnc(C(F)F)o1]
Compound 200
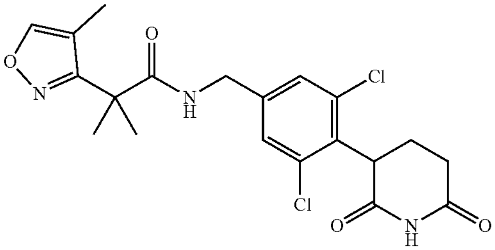 [SMILES: Cc1conc1C(C)(C)C(=O)NCc1cc(Cl)c(C2CCC(=O)NC2=O)c(Cl)c1]
Compound 201

TABLE 1-continued
| Compounds Table |
|---|
| 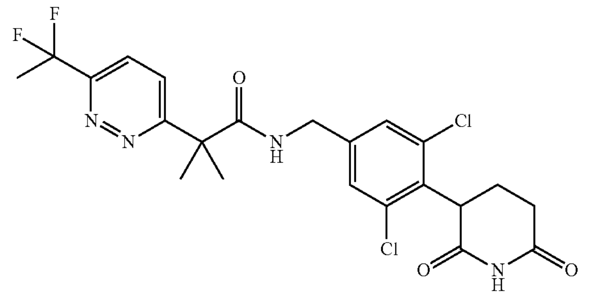 Compound 202 |
| 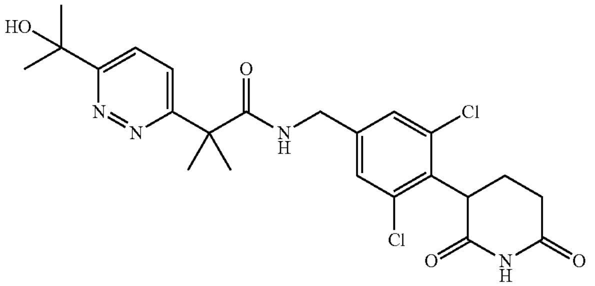 [SMILES: CC(C)(O)c1ccc(C(C)(C)C(=O)NCc2cc(Cl)c(C3CCC(=O)NC3=O)c(Cl)c2)nn1] Compound 203 |
| 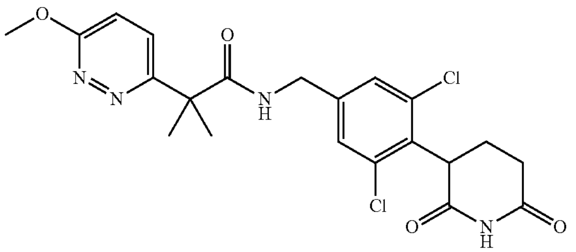 [SMILES: COc1ccc(C(C)(C)C(=O)NCc2cc(Cl)c(C3CCC(=O)NC3=O)c(Cl)c2)nn1] Compound 204 |
| 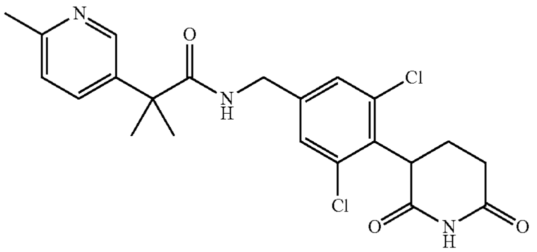 [SMILES: Cc1ccc(C(C)(C)C(=O)NCc2cc(Cl)c(C3CCC(=O)NC3=O)c(Cl)c2)cn1] Compound 205 |
| 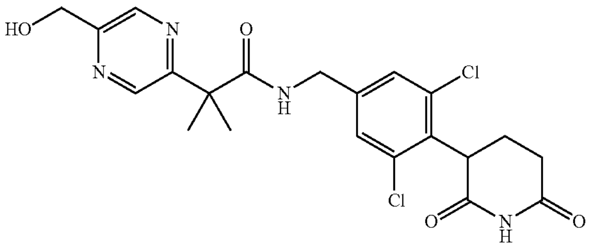 [SMILES: CC(C)(C(=O)NCc1cc(Cl)c(C2CCC(=O)NC2=O)c(Cl)c1)c1cnc(CO)cn1] Compound 206 |

TABLE 1-continued
| Compounds Table |
|---|
| 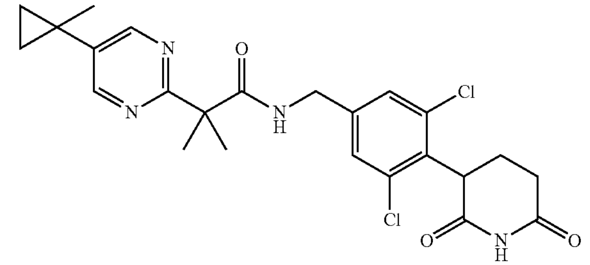 [SMILES: CC1(c2cnc(C(C)(C)C(=O)NCc3cc(Cl)c(C4CCC(=O)NC4=O)c(Cl)c3)nc2)CC1] Compound 207 |
| 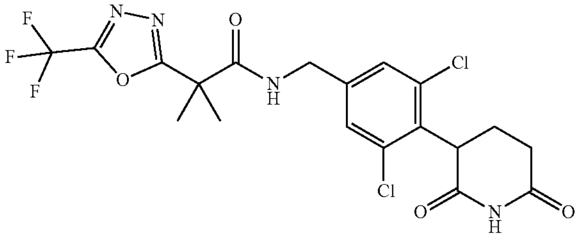 [SMILES: CC(C)(C(=O)NCc1cc(Cl)c(C2CCC(=O)NC2=O)c(Cl)c1)c1nnc(C(F)(F)F)o1] Compound 208 |
| 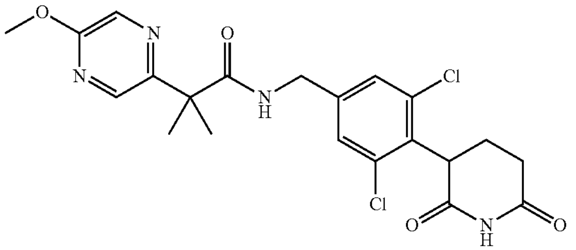 [SMILES: COc1cnc(C(C)(C)C(=O)NCc2cc(Cl)c(C3CCC(=O)NC3=O)c(Cl)c2)cn1] Compound 209 |
| 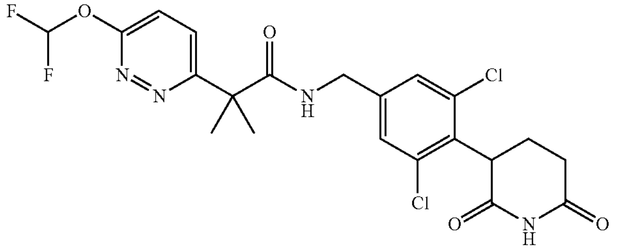 Compound 210 |
| 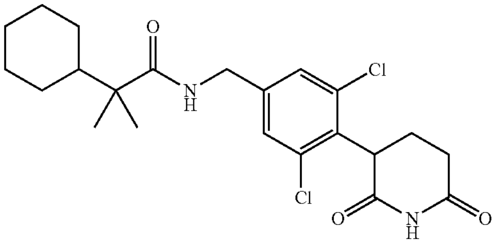 [SMILES: CC(C)(C(=O)NCc1cc(Cl)c(C2CCC(=O)NC2=O)c(Cl)c1)C1CCCCC1] Compound 211 |
| 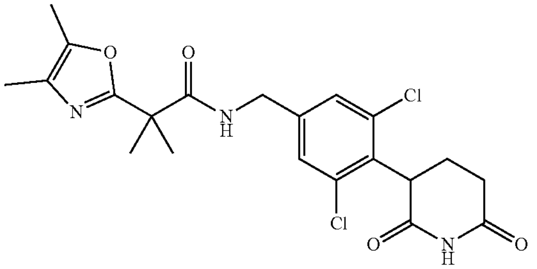 [SMILES: Cc1nc(C(C)(C)C(=O)NCc2cc(Cl)c(C3CCC(=O)NC3=O)c(Cl)c2)oc1C] Compound 212 |

TABLE 1-continued
| Compounds Table | |
|---|---|
| 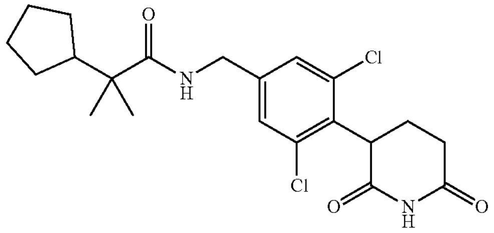 [SMILES: CC(C)(C(=O)NCc1cc(Cl)c(C2CCC(=O)NC2=O)c(Cl)c1)C1CCCC1] | Compound 213 |
| 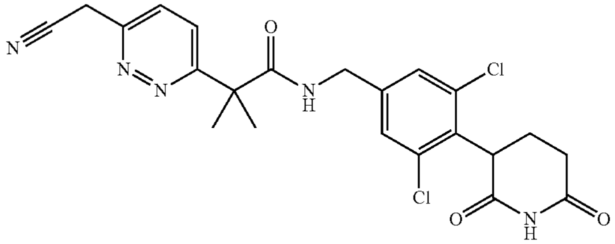 [SMILES: CC(C)(C(=O)NCc1cc(Cl)c(C2CCC(=O)NC2=O)c(Cl)c1)c1ccc(CC#N)nn1] | Compound 214 |
| 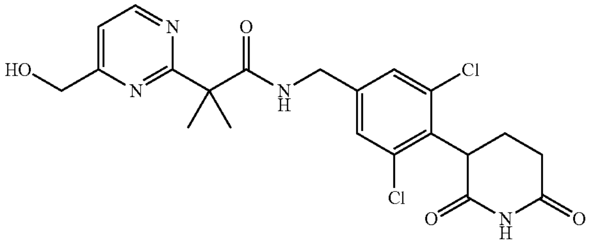 [SMILES: CC(C)(C(=O)NCc1cc(Cl)c(C2CCC(=O)NC2=O)c(Cl)c1)c1nccc(CO)n1] | Compound 215 |
| 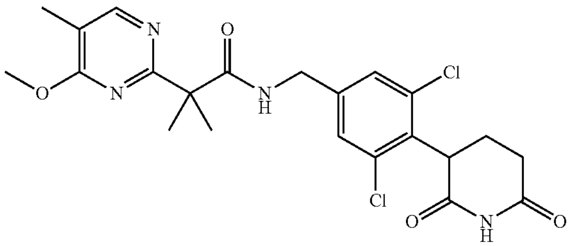 [SMILES: COc1nc(C(C)(C)C(=O)NCc2cc(Cl)c(C3CCC(=O)NC3=O)c(Cl)c2)ncc1C] | Compound 216 |
| 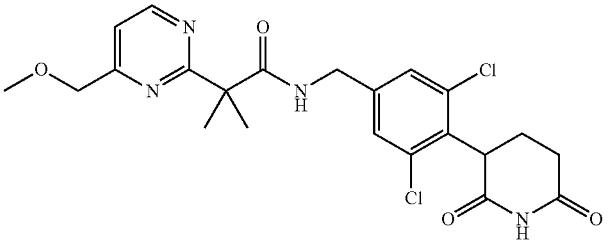 [SMILES: COCc1ccnc(C(C)(C)C(=O)NCc2cc(Cl)c(C3CCC(=O)NC3=O)c(Cl)c2)n1] | Compound 217 |
| 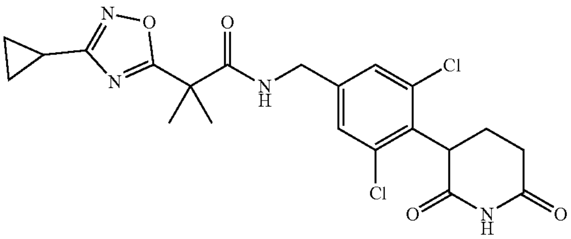 [SMILES: CC(C)(C(=O)NCc1cc(Cl)c(C2CCC(=O)NC2=O)c(Cl)c1)c1nc(C2CC2)no1] | Compound 218 |

TABLE 1-continued
Compounds Table
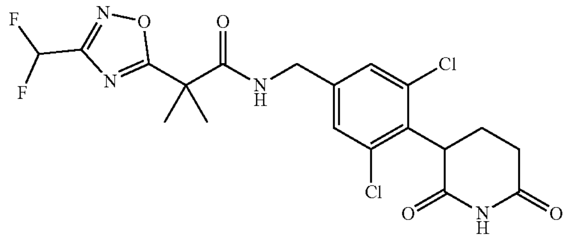 [SMILES: CC(C)(C(=O)NCc1cc(Cl)c(C2CCC(=O)NC2=O)c(Cl)c1)c1nc(C(F)F)no1]
Compound 219
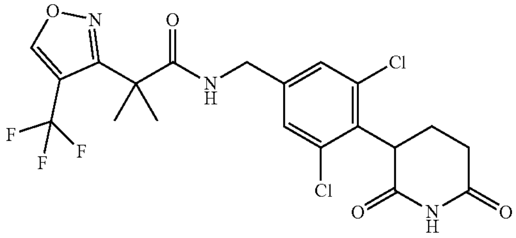 [SMILES: CC(C)(C(=O)NCc1cc(Cl)c(C2CCC(=O)NC2=O)c(Cl)c1)c1nocc1C(F)(F)F]
Compound 220
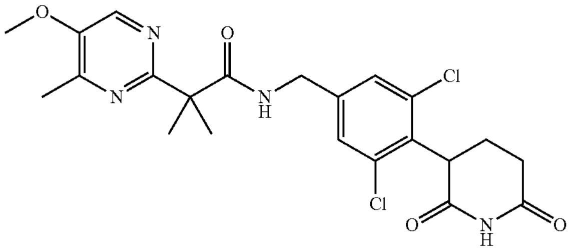 [SMILES: COc1cnc(C(C)(C)C(=O)NCc2cc(Cl)c(C3CCC(=O)NC3=O)c(Cl)c2)nc1C]
Compound 221
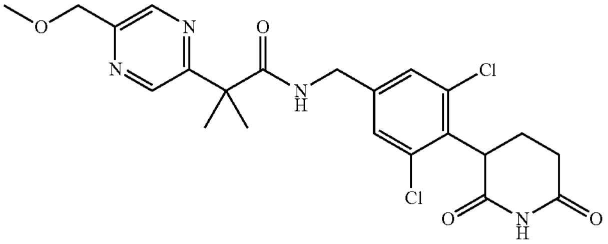 [SMILES: COCc1cnc(C(C)(C)C(=O)NCc2cc(Cl)c(C3CCC(=O)NC3=O)c(Cl)c2)cn1]
Compound 222
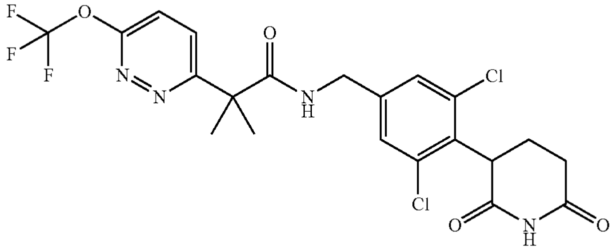
Compound 223
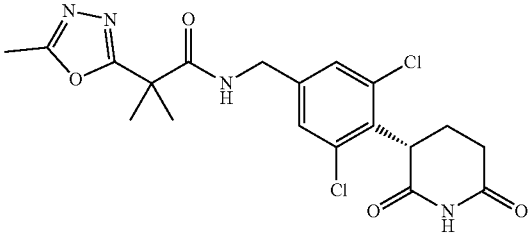 [SMILES: Cc1nnc(C(C)(C)C(=O)NCc2cc(Cl)c([C@@H]3CCC(=O)NC3=O)c(Cl)c2)o1]
Compound 224
*first eluting isomer TABLE 1-continued
| Compounds Table |
|---|
| 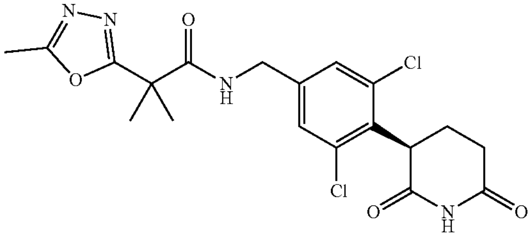 [SMILES: Cc1nnc(C(C)(C)C(=O)NCc2cc(Cl)c([C@H]3CCC(=O)NC3=O)c(Cl)c2)o1] Compound 225<br>*second eluting isomer |
| 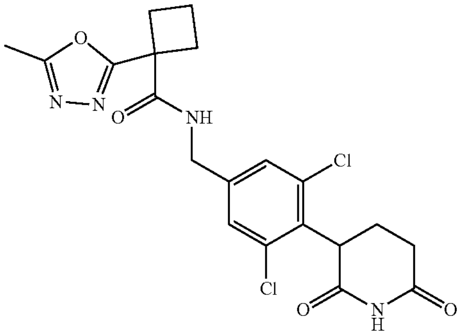 [SMILES: Cc1nnc(C2(C(=O)NCc3cc(Cl)c(C4CCC(=O)NC4=O)c(Cl)c3)CCC2)o1] Compound 226 |
| 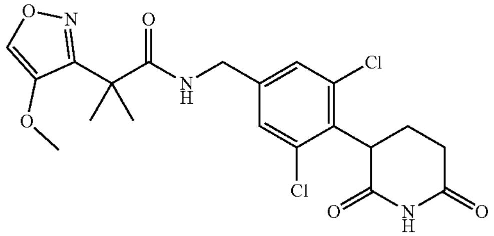 [SMILES: COc1conc1C(C)(C)C(=O)NCc1cc(Cl)c(C2CCC(=O)NC2=O)c(Cl)c1] Compound 227 |
| 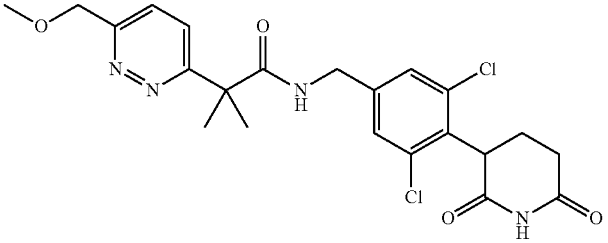 [SMILES: COCc1ccc(C(C)(C)C(=O)NCc2cc(Cl)c(C3CCC(=O)NC3=O)c(Cl)c2)nn1] Compound 228 |
| 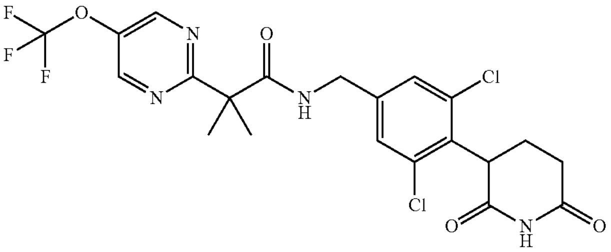 Compound 229 |

TABLE 1-continued
Compounds Table
Compound 230
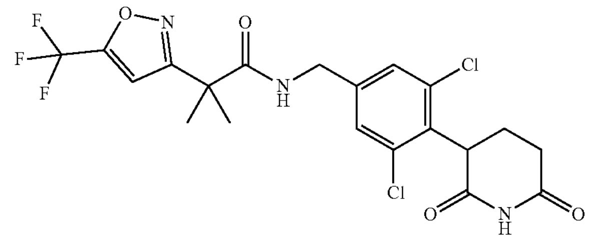 [SMILES: CC(C)(C(=O)NCc1cc(Cl)c(C2CCC(=O)NC2=O)c(Cl)c1)c1cc(C(F)(F)F)on1]
Compound 231
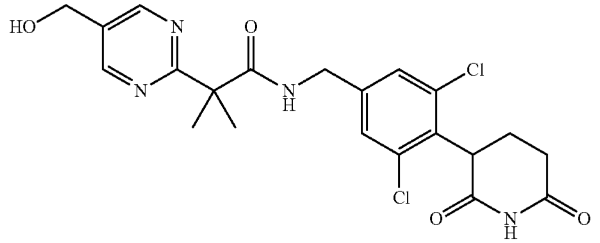 [SMILES: CC(C)(C(=O)NCc1cc(Cl)c(C2CCC(=O)NC2=O)c(Cl)c1)c1ncc(CO)cn1]
Compound 232
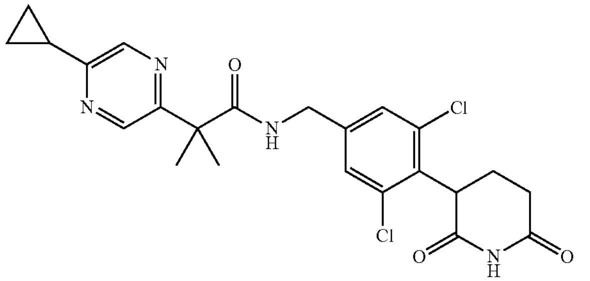 [SMILES: CC(C)(C(=O)NCc1cc(Cl)c(C2CCC(=O)NC2=O)c(Cl)c1)c1cnc(C2CC2)cn1]
Compound 233
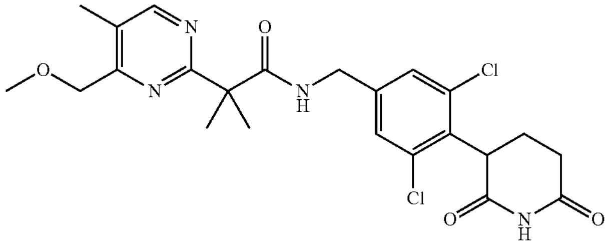 [SMILES: COCc1nc(C(C)(C)C(=O)NCc2cc(Cl)c(C3CCC(=O)NC3=O)c(Cl)c2)ncc1C]
Compound 234
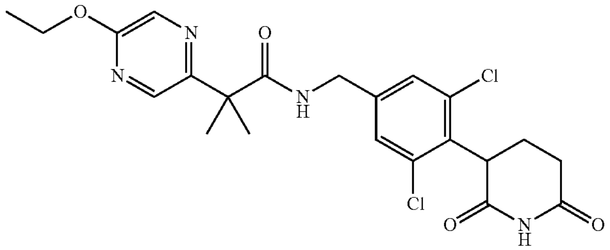
Compound 235
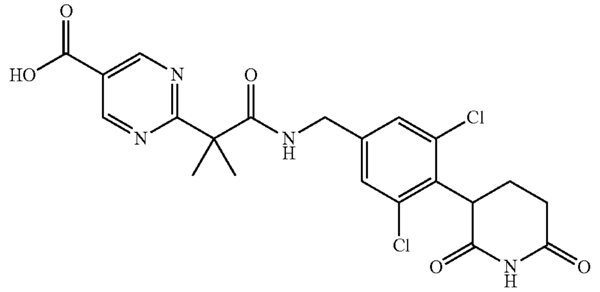 [SMILES: CC(C)(C(=O)NCc1cc(Cl)c(C2CCC(=O)NC2=O)c(Cl)c1)c1ncc(C(=O)O)cn1]

TABLE 1-continued
| Compounds Table |
| --- |
| 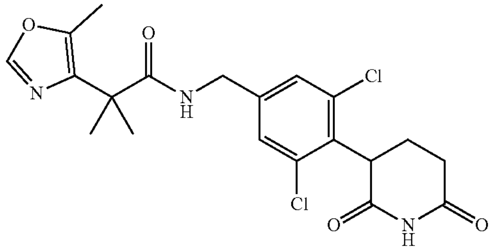 [SMILES: Cc1ocnc1C(C)(C)C(=O)NCc1cc(Cl)c(C2CCC(=O)NC2=O)c(Cl)c1] Compound 236 |
| 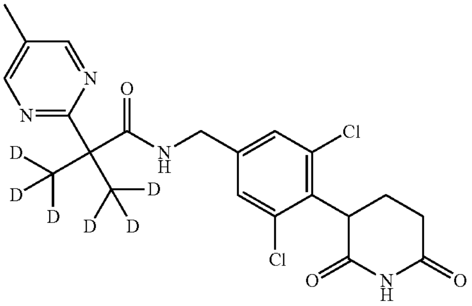 [SMILES: [2H]C([2H])([2H])C(C(=O)NCc1cc(Cl)c(C2CCC(=O)NC2=O)c(Cl)c1)(c1ncc(C)cn1)C([2H])([2H])[2H]] Compound 237 |
| 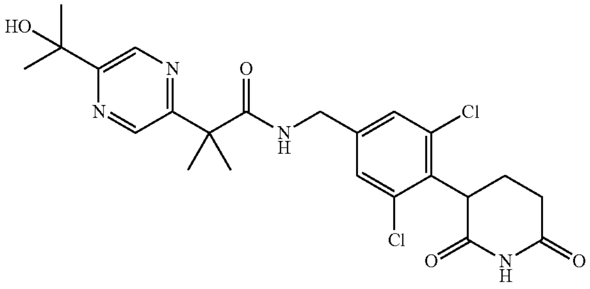 [SMILES: CC(C)(O)c1cnc(C(C)(C)C(=O)NCc2cc(Cl)c(C3CCC(=O)NC3=O)c(Cl)c2)cn1] Compound 238 |
| 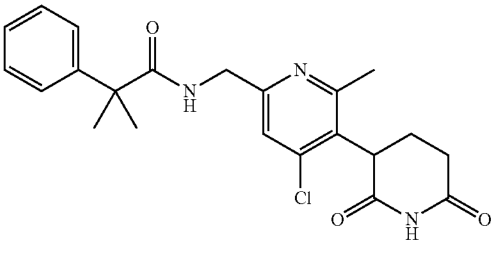 [SMILES: Cc1nc(CNC(=O)C(C)(C)c2ccccc2)cc(Cl)c1C1CCC(=O)NC1=O] Compound 239 |
| 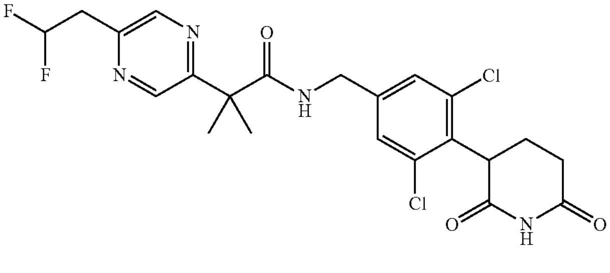 [SMILES: CC(C)(C(=O)NCc1cc(Cl)c(C2CCC(=O)NC2=O)c(Cl)c1)c1cnc(CC(F)F)cn1] Compound 240 |

TABLE 1-continued
Compounds Table
Compound 241
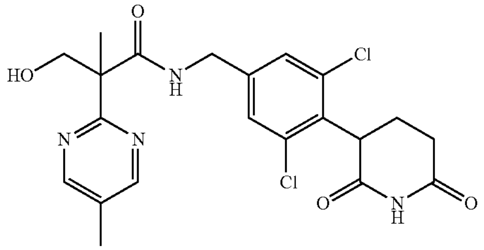 [SMILES: Cc1cnc(C(C)(CO)C(=O)NCc2cc(Cl)c(C3CCC(=O)NC3=O)c(Cl)c2)nc1]
Compound 242
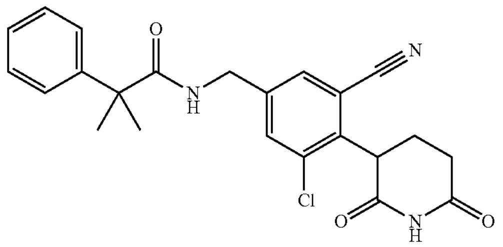 [SMILES: CC(C)(C(=O)NCc1cc(Cl)c(C2CCC(=O)NC2=O)c(C#N)c1)c1ccccc1]
Compound 243
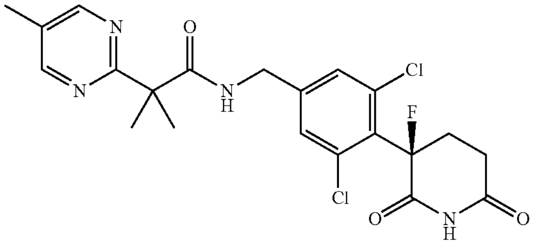 [SMILES: Cc1cnc(C(C)(C)C(=O)NCc2cc(Cl)c([C@]3(F)CCC(=O)NC3=O)c(Cl)c2)nc1]
*first eluting isomer
Compound 244
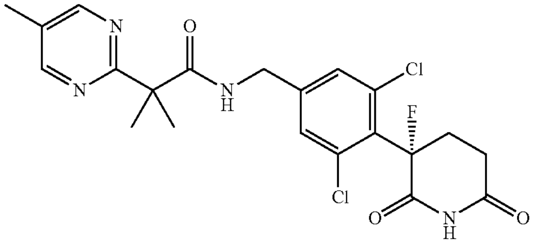 [SMILES: Cc1cnc(C(C)(C)C(=O)NCc2cc(Cl)c([C@@]3(F)CCC(=O)NC3=O)c(Cl)c2)nc1]
*second eluting isomer
Compound 245
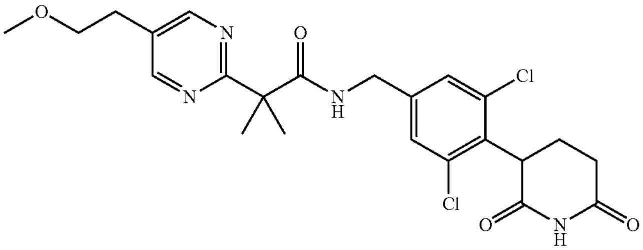 [SMILES: COCCc1cnc(C(C)(C)C(=O)NCc2cc(Cl)c(C3CCC(=O)NC3=O)c(Cl)c2)nc1]
Compound 246
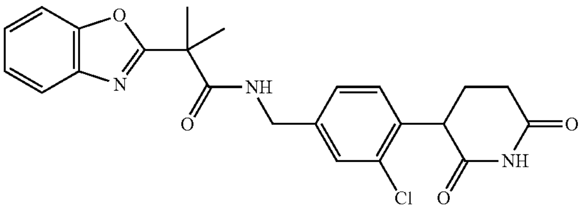 [SMILES: CC(C)(C(=O)NCc1ccc(C2CCC(=O)NC2=O)c(Cl)c1)c1nc2ccccc2o1]

TABLE 1-continued
Compounds Table
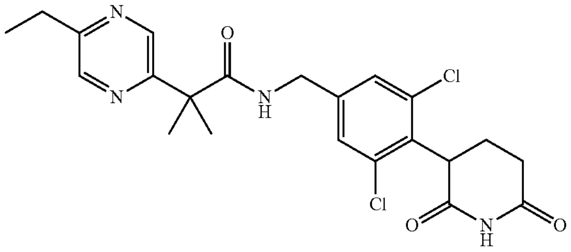 [SMILES: CCc1cnc(C(C)(C)C(=O)NCc2cc(Cl)c(C3CCC(=O)NC3=O)c(Cl)c2)cn1]
Compound 247
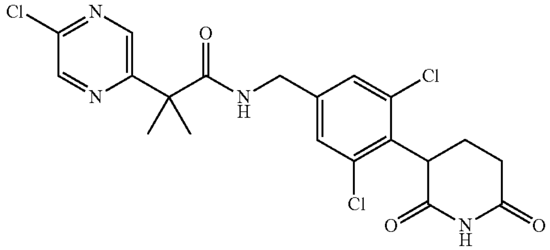 [SMILES: CC(C)(C(=O)NCc1cc(Cl)c(C2CCC(=O)NC2=O)c(Cl)c1)c1cnc(Cl)cn1]
Compound 248
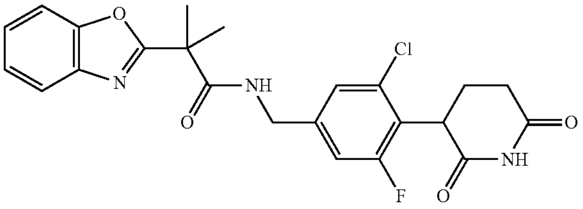
Compound 249
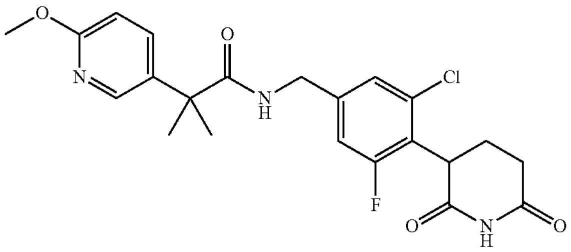 [SMILES: COc1ccc(C(C)(C)C(=O)NCc2cc(F)c(C3CCC(=O)NC3=O)c(Cl)c2)cn1]
Compound 250
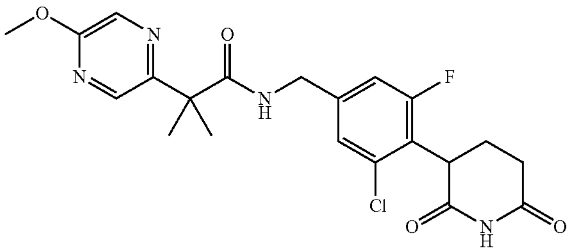 [SMILES: COc1cnc(C(C)(C)C(=O)NCc2cc(F)c(C3CCC(=O)NC3=O)c(Cl)c2)cn1]
Compound 251
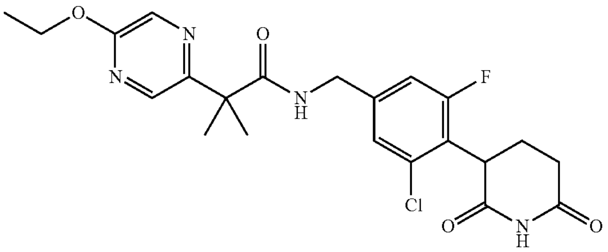 [SMILES: CCOc1cnc(C(C)(C)C(=O)NCc2cc(F)c(C3CCC(=O)NC3=O)c(Cl)c2)cn1]
Compound 252

TABLE 1-continued
| Compounds Table | |
|---|---|
| 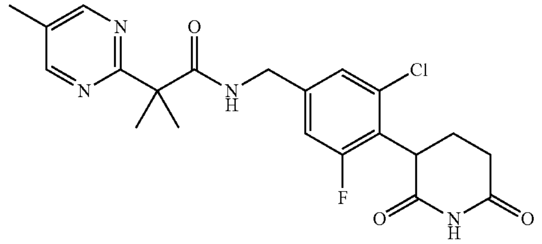 [SMILES: Cc1cnc(C(C)(C)C(=O)NCc2cc(F)c(C3CCC(=O)NC3=O)c(Cl)c2)nc1] | Compound 253 |
| 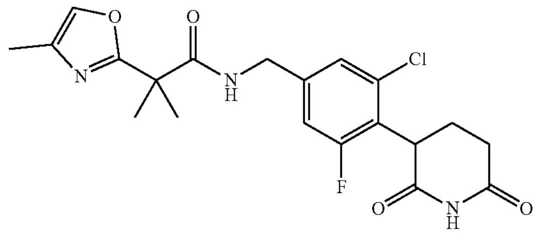 [SMILES: Cc1coc(C(C)(C)C(=O)NCc2cc(F)c(C3CCC(=O)NC3=O)c(Cl)c2)n1] | Compound 254 |
| 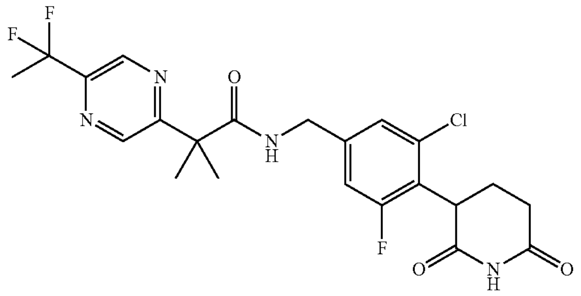 [SMILES: CC(F)(F)c1cnc(C(C)(C)C(=O)NCc2cc(F)c(C3CCC(=O)NC3=O)c(Cl)c2)cn1] | Compound 255 |
| 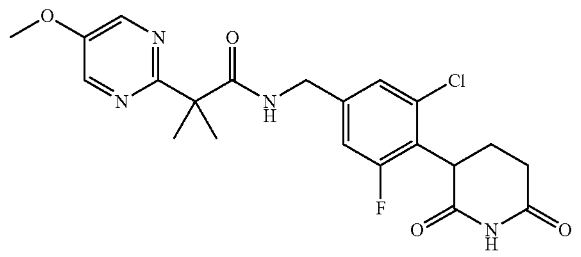 [SMILES: COc1cnc(C(C)(C)C(=O)NCc2cc(F)c(C3CCC(=O)NC3=O)c(Cl)c2)nc1] | Compound 256 |
| 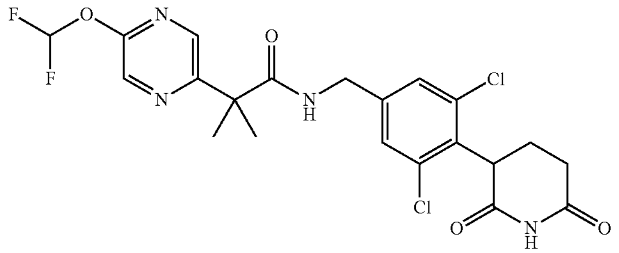 [SMILES: CC(C)(C(=O)NCc1cc(Cl)c(C2CCC(=O)NC2=O)c(Cl)c1)c1cnc(OC(F)F)cn1] | Compound 257 |
| 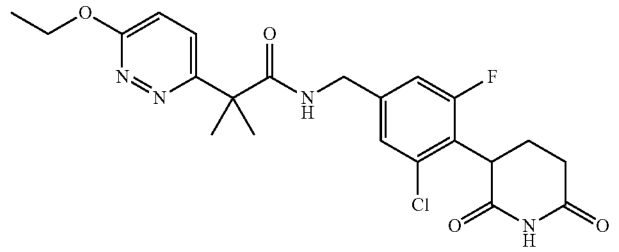 [SMILES: CCOc1ccc(C(C)(C)C(=O)NCc2cc(F)c(C3CCC(=O)NC3=O)c(Cl)c2)nn1] | Compound 258 |

TABLE 1-continued
| Compounds Table |
| --- |
| 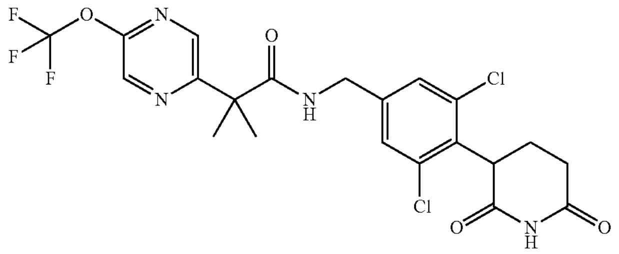 [SMILES: CC(C)(C(=O)NCc1cc(Cl)c(C2CCC(=O)NC2=O)c(Cl)c1)c1cnc(OC(F)(F)F)cn1] Compound 259 |
| 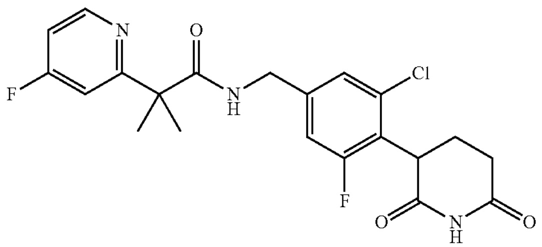 [SMILES: CC(C)(C(=O)NCc1cc(F)c(C2CCC(=O)NC2=O)c(Cl)c1)c1cc(F)ccn1] Compound 260 |
| 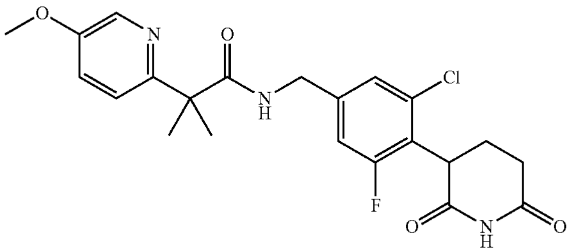 [SMILES: COc1ccc(C(C)(C)C(=O)NCc2cc(F)c(C3CCC(=O)NC3=O)c(Cl)c2)nc1] Compound 261 |
| 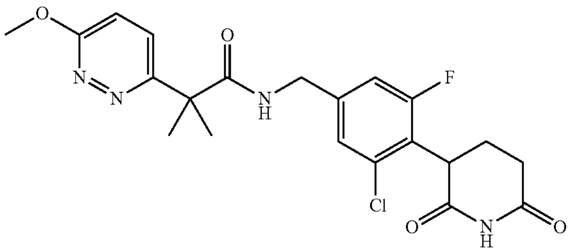 Compound 262 |
| 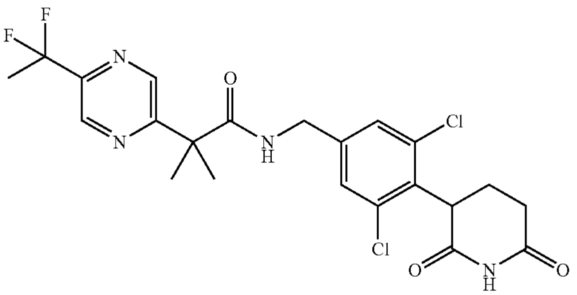 [SMILES: CC(F)(F)c1cnc(C(C)(C)C(=O)NCc2cc(Cl)c(C3CCC(=O)NC3=O)c(Cl)c2)cn1] Compound 263 |
| 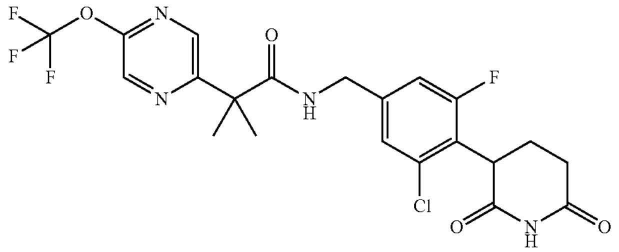 [SMILES: CC(C)(C(=O)NCc1cc(F)c(C2CCC(=O)NC2=O)c(Cl)c1)c1cnc(OC(F)(F)F)cn1] Compound 264 |

TABLE 1-continued
| Compounds Table | |
|---|---|
| 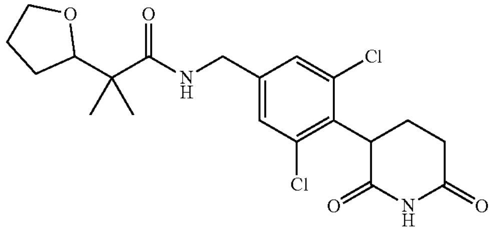 [SMILES: CC(C)(C(=O)NCc1cc(Cl)c(C2CCC(=O)NC2=O)c(Cl)c1)C1CCCO1] | Compound 265 |
| 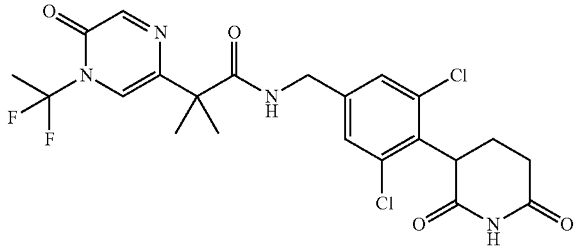 [SMILES: CC(C)(C(=O)NCc1cc(Cl)c(C2CCC(=O)NC2=O)c(Cl)c1)c1cn(C(C)(F)F)c(=O)cn1] | Compound 266 |
| 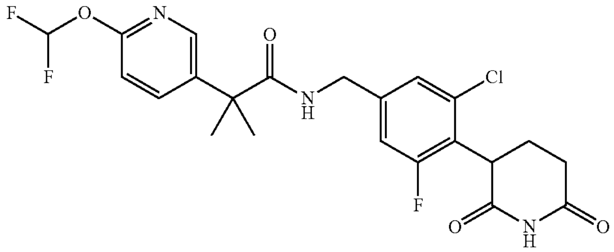 [SMILES: CC(C)(C(=O)NCc1cc(F)c(C2CCC(=O)NC2=O)c(Cl)c1)c1ccc(OC(F)F)nc1] | Compound 267 |
| 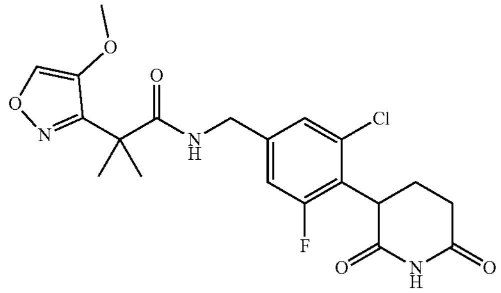 [SMILES: COc1conc1C(C)(C)C(=O)NCc1cc(F)c(C2CCC(=O)NC2=O)c(Cl)c1] | Compound 268 |
| 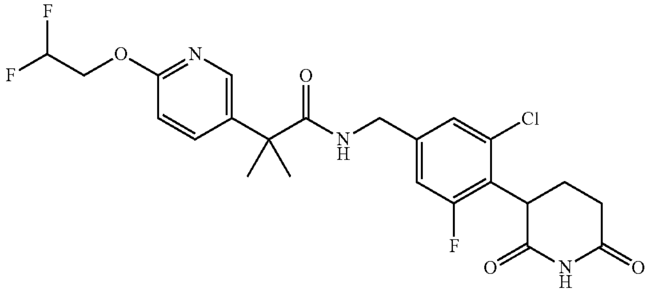 [SMILES: CC(C)(C(=O)NCc1cc(F)c(C2CCC(=O)NC2=O)c(Cl)c1)c1ccc(OCC(F)F)nc1] | Compound 269 |
| 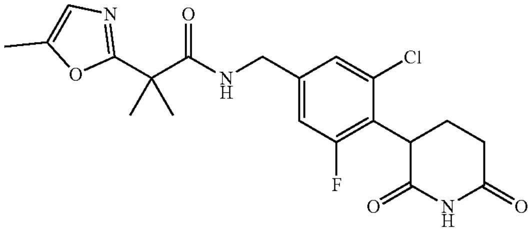 [SMILES: Cc1cnc(C(C)(C)C(=O)NCc2cc(F)c(C3CCC(=O)NC3=O)c(Cl)c2)o1] | Compound 270 |

TABLE 1-continued
Compounds Table
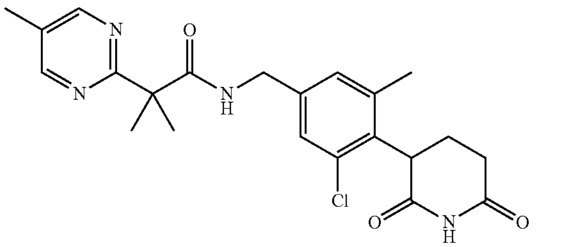 [SMILES: Cc1cnc(C(C)(C)C(=O)NCc2cc(C)c(C3CCC(=O)NC3=O)c(Cl)c2)nc1]
Compound 271
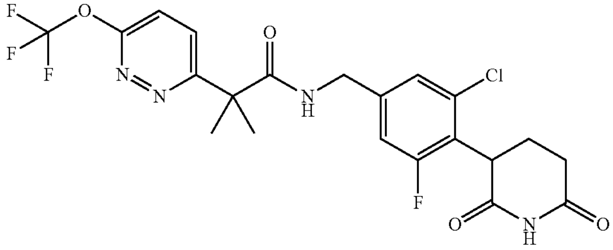 [SMILES: CC(C)(C(=O)NCc1cc(F)c(C2CCC(=O)NC2=O)c(Cl)c1)c1ccc(OC(F)(F)F)nn1]
Compound 272
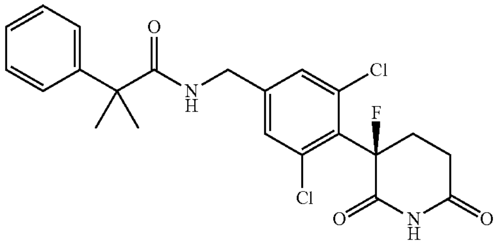 [SMILES: CC(C)(C(=O)NCc1cc(Cl)c([C@]2(F)CCC(=O)NC2=O)c(Cl)c1)c1ccccc1]
Compound 273
*first eluting isomer
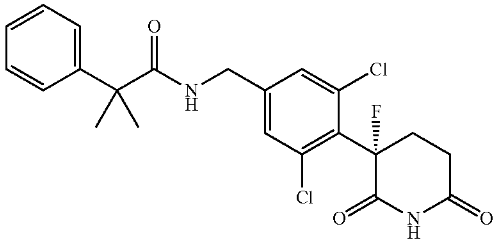 [SMILES: CC(C)(C(=O)NCc1cc(Cl)c([C@@]2(F)CCC(=O)NC2=O)c(Cl)c1)c1ccccc1]
Compound 274
*second eluting isomer
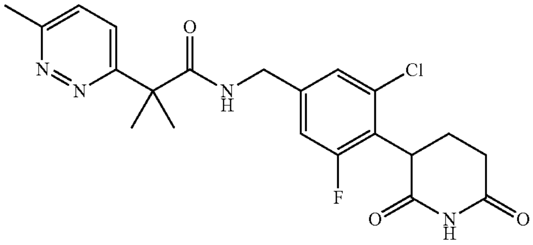 [SMILES: Cc1ccc(C(C)(C)C(=O)NCc2cc(F)c(C3CCC(=O)NC3=O)c(Cl)c2)nn1]
Compound 275
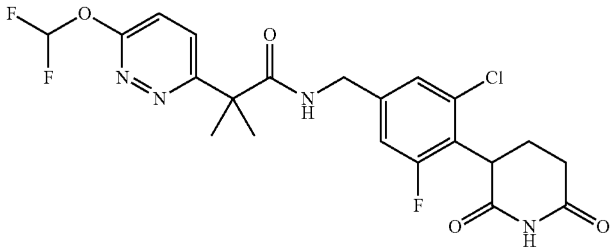 [SMILES: CC(C)(C(=O)NCc1cc(F)c(C2CCC(=O)NC2=O)c(Cl)c1)c1ccc(OC(F)F)nn1]
Compound 276

TABLE 1-continued
| Compounds Table |
| --- |
| 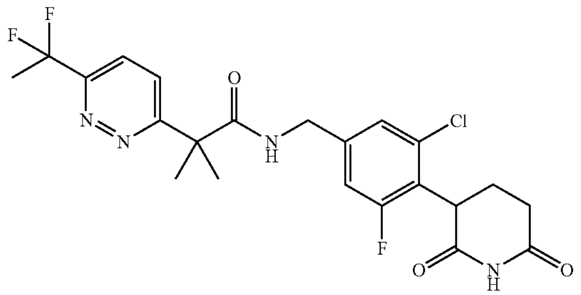 [SMILES: CC(F)(F)c1ccc(C(C)(C)C(=O)NCc2cc(F)c(C3CCC(=O)NC3=O)c(Cl)c2)nn1] Compound 277 |
| 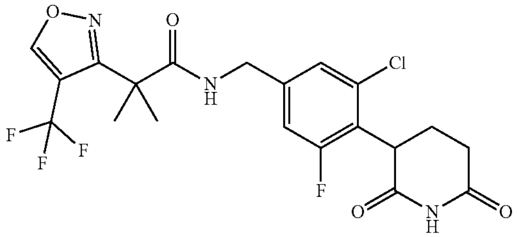 [SMILES: CC(C)(C(=O)NCc1cc(F)c(C2CCC(=O)NC2=O)c(Cl)c1)c1nocc1C(F)(F)F] Compound 278 |
| 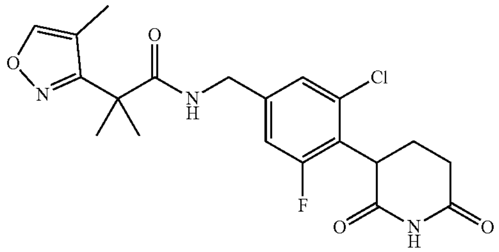 [SMILES: Cc1conc1C(C)(C)C(=O)NCc1cc(F)c(C2CCC(=O)NC2=O)c(Cl)c1] Compound 279 |
| 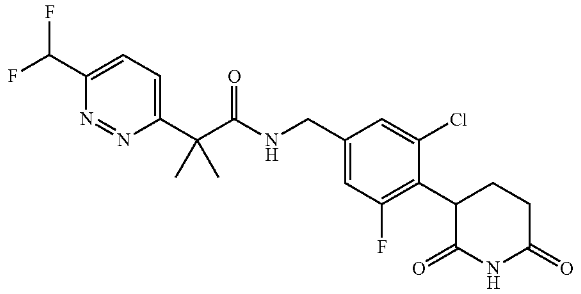 [SMILES: CC(C)(C(=O)NCc1cc(F)c(C2CCC(=O)NC2=O)c(Cl)c1)c1ccc(C(F)F)nn1] Compound 280 |
| 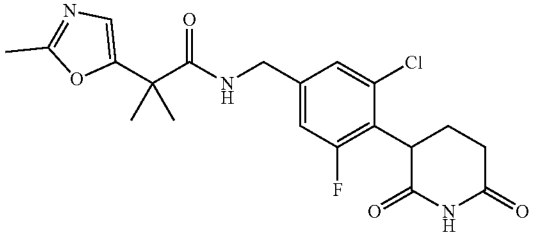 [SMILES: Cc1ncc(C(C)(C)C(=O)NCc2cc(F)c(C3CCC(=O)NC3=O)c(Cl)c2)o1] Compound 281 |

TABLE 1-continued

| Compounds Table | |
|---|---|
| 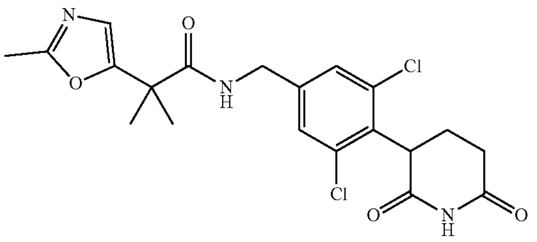 | Compound 282 |

Non-Limiting Numbered Embodiments

1. A compound having formula (I):

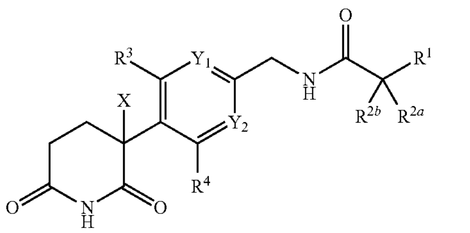

(I)

or a pharmaceutically acceptable salt thereof; wherein:

$R^1$, $R^{2a}$, and $R^{2b}$ are defined according to (A) and (B) below:

A $R^1$ is:

heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$;

heterocyclyl including 4-6 ring atoms, wherein 1-4 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo, $R^b$ and $R^c$;

$C_{3-7}$ cycloalkyl optionally substituted with 1-4 substituents independently selected from the group consisting of oxo, $R^b$, and $R^c$;

heterocycloalkenyl including 3-10 ring atoms, wherein 1-3 ring atoms are heteroatoms, each independently selected from the group consisting of N, N(H), N($R^d$), O, and $S(O)_{0-2}$, and wherein the heterocycloalkenyl is optionally substituted with 1-4 substituents independently selected from the group consisting of oxo, $R^b$, and $R^e$; or $C_{6-10}$ aryl optionally substituted with 1-4 substituents independently selected from the group consisting of oxo, $R^b$, and $R^c$; and each of $R^{2a}$ and $R^{2b}$ is independently selected from the group consisting of:

H;

$C_{1-2}$ alkyl optionally substituted with from 1-5 $R^a$;

$C_{3-5}$ cycloalkyl, which is optionally substituted with 1-4 substituents independently selected from the group consisting of oxo and $R^b$;

$C_{1-4}$ alkoxy;

$C_{1-4}$ haloalkoxy; or cyano; or $R^{2a}$ and $R^{2b}$ taken together with the carbon atom to which each is attached forms:

$C_{3-7}$ cycloalkyl, which is optionally substituted with 1-4 substituents independently selected from the group consisting of oxo and $R^b$;

heterocyclyl including 4-7 ring atoms, wherein 1-2 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^b$;

B $R^1$ taken together with (i) the carbon atom to which it is attached and (ii) and one of $R^{2a}$ and $R^{2b}$ forms:

$C_{8-10}$ aryl optionally substituted with 1-4 substituents independently selected from the group consisting of oxo, $R^b$, and $R^c$; or heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$; and the other of $R^{2a}$ and $R^{2b}$ is H or $C_{1-2}$ alkyl optionally substituted with from 1-5 $R^a$;

X is H; or halo;

$Y_1$ and $Y_2$ are CH or N, wherein at least one of $Y_1$ and $Y_2$ is CH;

$R^3$ is H; $C_{1-2}$ alkyl, which is optionally substituted with 1-5 fluoro; fluoro; chloro; or cyano;

$R^4$ is chloro; bromo; or fluoro; optionally wherein it is provided that $R^4$ is fluoro when $R^3$ is chloro;

each occurrence of $R^a$ is independently selected from the group consisting of: —OH; -halo; —$NR^eR^f$; $C_{1-4}$ alkoxy; $C_{1-4}$ haloalkoxy,; —C(═O)O($C_{1-4}$ alkyl); —C(═O) ($C_{1-4}$ alkyl); —C(═O)OH; —CONR'R"; —$S(O)_{1-2}$NR'R"; —$S(O)_{1-2}$($C_{1-4}$ alkyl); and cyano;

each occurrence of $R^b$ is independently selected from the group consisting of: halo; cyano; $C_{1-10}$ alkyl which is optionally substituted with from 1-6 independently selected $R^a$; $C_{2-6}$ alkenyl; $C_{2-6}$ alkynyl; $C_{1-4}$ alkoxy; —O($C_{1-3}$ alkylene)-($C_{3-6}$ cycloalkyl); $C_{1-4}$ haloalkoxy;

—$S(O)_{0-2}(C_{1-4}$ alkyl); —$NR^eR^f$; —OH; —$S(O)_{1-2}$NR'R"; —$NO_2$; —C(═O) ($C_{1-10}$ alkyl); —C(═O)O ($C_{1-4}$ alkyl); —C(═O)OH; and —C(═O)NR'R";

each occurrence of $R^e$ is independently selected from the group consisting of:

$C_{3-10}$ cycloalkyl or $C_{3-10}$ cycloalkenyl, each of which is optionally substituted with from 1-4 substituents independently selected from the group consisting of oxo and $R^b$;

heterocyclyl or heterocycloalkenyl including 3-10 ring atoms, wherein from 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with from 1-4 substituents independently selected from the group consisting of oxo and $R^b$;

heteroaryl including 5-10 ring atoms, wherein from 1-4 ring atoms are heteroatoms, each independently selected from the group consisting of N, N(H), N($R^d$), O, and $S(O)_{0-2}$, and wherein the heteroaryl is optionally substituted with from 1-4 $R^b$; and $C_{6-10}$ aryl optionally substituted with from 1-4 $R^b$;

each occurrence of $R^d$ is independently selected from the group consisting of: $C_{1-6}$ alkyl optionally substituted with from 1-3 independently selected $R^a$; —C(O) ($C_{1-4}$ alkyl); —C(O)O($C_{1-4}$ alkyl); —CONR'R"; —$S(O)_{1-2}$NR'R"; —$S(O)_{1-2}(C_{1-4}$ alkyl); —OH; and $C_{1-4}$ alkoxy; and each occurrence of $R^e$ and $R^f$ is independently selected from the group consisting of: H; $C_{1-6}$ alkyl; —C(O) ($C_{1-4}$ alkyl); —C(O)O($C_{1-4}$ alkyl); —CONR'R"; —$S(O)_{1-2}$NR'R"; —$S(O)_{1-2}(C_{1-4}$ alkyl); —OH; and $C_{1-4}$ alkoxy, and each occurrence of R' and R" is independently selected from the group consisting of: H; and $C_{1-4}$ alkyl.

2. The compound of embodiment 1, wherein the compound has the formula:

(I-A)

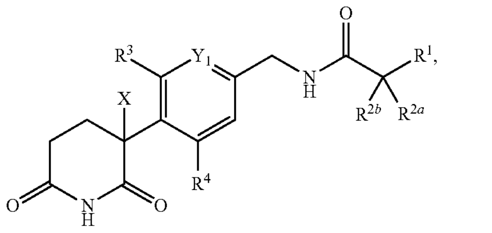

wherein $Y_1$ is CH or N.

3. The compound of embodiment 1 or 2, wherein the compound has the formula:

(I-B)

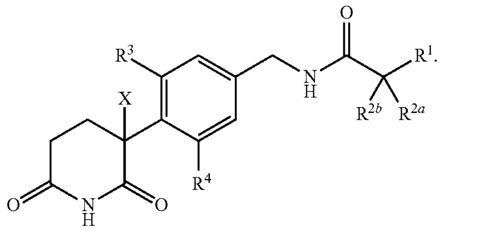

4. The compound of any one of embodiments 1-4, wherein X is H.

5. A compound having formula (II):

(II)

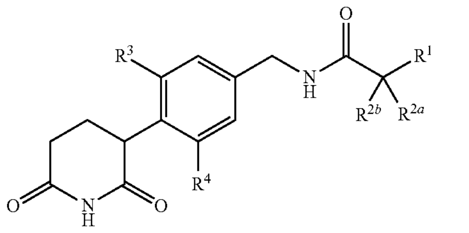

or a pharmaceutically acceptable salt thereof; wherein:

$R^1$, $R^{2a}$, and $R^{2b}$ are defined according to (A) and (B) below:

A $R^1$ is:

heteroaryl including 5-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$;

heterocycloalkenyl including 3-10 ring atoms, wherein 1-3 ring atoms are heteroatoms, each independently selected from the group consisting of N, N(H), N($R^d$), O, and $S(O)_{0-2}$, and wherein the heterocycloalkenyl is optionally substituted with 1-4 substituents independently selected from the group consisting of oxo, $R^b$, and $R^c$; or $C_{6-10}$ aryl optionally substituted with 1-4 substituents independently selected from the group consisting of oxo, $R^b$, and $R^c$; and each of $R^{2a}$ and $R^{2b}$ is independently selected from the group consisting of:

H;

$C_{1-2}$ alkyl optionally substituted with from 1-5 $R^a$;

$C_{3-5}$ cycloalkyl, which is optionally substituted with 1-4 substituents independently selected from the group consisting of oxo and $R^b$;

$C_{1-4}$ alkoxy;

$C_{1-4}$ haloalkoxy; or cyano; or $R^{2a}$ and $R^{2b}$ taken together with the carbon atom to which each is attached forms:

$C_{3-7}$ cycloalkyl, which is optionally substituted with 1-4 substituents independently selected from the group consisting of oxo and $R^b$;

heterocyclyl including 4-7 ring atoms, wherein 1-2 ring atoms are heteroatoms, each independently selected from the group consisting of N, N(H), N($R^4$), O, and $S(O)_{0-2}$, and wherein the heterocyclyl is optionally substituted with 1-4 substituents independently selected from the group consisting of oxo and $R^b$;

B $R^1$ taken together with (i) the carbon atom to which it is attached and (ii) and one of $R^{2a}$ and $R^{2b}$ forms:

$C_{8-10}$ aryl optionally substituted with 1-4 substituents independently selected from the group consisting of oxo, $R^b$, and $R^c$; or heteroaryl including 5-10 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-4 substituents independently selected from the group consisting of oxo, $R^b$ and $R^c$; and the other of $R^{2a}$ and $R^{2b}$ is H or $C_{1-2}$ alkyl optionally substituted with from 1-5 $R^a$;

$R^3$ is H; $C_{1-2}$ alkyl, which is optionally substituted with 1-5 fluoro; fluoro; or chloro;

$R^4$ is chloro; bromo; or fluoro; optionally wherein it is provided that $R^4$ is fluoro when $R^3$ is chloro;

each occurrence of $R^a$ is independently selected from the group consisting of: —OH; -halo; $NR^eR^f$; $C_{1-4}$ alkoxy; $C_{1-4}$ haloalkoxy,; —C(═O)O($C_{1-4}$ alkyl); —C(═O)($C_{1-4}$ alkyl); —C(═O)OH; —CONR'R"; $—S(O)_{1-2}$NR'R"; $—S(O)_{1-2}$($C_{1-4}$ alkyl); and cyano;

each occurrence of $R^b$ is independently selected from the group consisting of: halo; cyano; $C_{1-10}$ alkyl which is optionally substituted with from 1-6 independently selected $R^a$; $C_{2-6}$ alkenyl; $C_{2-6}$ alkynyl; $C_{1-4}$ alkoxy; —O($C_{1-3}$ alkylene)-($C_{3-6}$ cycloalkyl); $C_{1-4}$ haloalkoxy; $—S(O)_{0-2}$($C_{1-4}$ alkyl); $—NR^eR^f$; —OH; $—S(O)_{1-2}$NR'R"; $—NO_2$; —C(═O)($C_{1-10}$ alkyl); —C(═O)O($C_{1-4}$ alkyl); —C(═O)OH; and —C(═O)NR'R";

each occurrence of $R^e$ is independently selected from the group consisting of:

$C_{3-10}$ cycloalkyl or $C_{3-10}$ cycloalkenyl, each of which is optionally substituted with from 1-4 substituents independently selected from the group consisting of oxo and $R^b$;

heterocyclyl or heterocycloalkenyl including 3-10 ring atoms, wherein from 1-3 ring atoms are heteroatoms, each independently selected from the group consisting of N, N(H), $N(R^d)$, O, and $S(O)_{0-2}$, and wherein the heterocyclyl or heterocycloalkenyl is optionally substituted with from 1-4 substituents independently selected from the group consisting of oxo and $R^b$;

heteroaryl including 5-10 ring atoms, wherein from 1-4 ring atoms are heteroatoms, each independently selected from the group consisting of N, N(H), $N(R^d)$, O, and $S(O)_{0-2}$, and wherein the heteroaryl is optionally substituted with from 1-4 $R^b$; and $C_{6-10}$ aryl optionally substituted with from 1-4 $R^b$;

each occurrence of $R^d$ is independently selected from the group consisting of: $C_{1-6}$ alkyl optionally substituted with from 1-3 independently selected $R^a$; —C(O)($C_{1-4}$ alkyl); —C(O)O($C_{1-4}$ alkyl); —CONR'R"; $—S(O)_{1-2}$NR'R"; $—S(O)_{1-2}$($C_{1-4}$ alkyl); —OH; and $C_{1-4}$ alkoxy; and each occurrence of $R^e$ and $R^f$ is independently selected from the group consisting of: H; $C_{1-6}$ alkyl; —C(O)($C_{1-4}$ alkyl); —C(O)O($C_{1-4}$ alkyl); —CONR'R"; $—S(O)_{1-2}$NR'R"; $—S(O)_{1-2}$($C_{1-4}$ alkyl); —OH; and $C_{1-4}$ alkoxy, and each occurrence of R' and R" is independently selected from the group consisting of: H; and $C_{1-4}$ alkyl.

6. The compound of any one of embodiments 1-5, wherein $R^1$, $R^{2a}$, and $R^{2b}$ are defined according to (A).

7. The compound of any one of embodiments 1-6, wherein $R^1$ is heteroaryl including 5-10 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-4 substituents independently selected from the group consisting of oxo, $R^b$ and $R^c$.

8. The compound of any one of embodiments 1-7, wherein $R^1$ is heteroaryl including 5-6 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-4 substituents independently selected from the group consisting of oxo, $R^b$ and $R^c$.

9. The compound of any one of embodiments 1-8, wherein $R^1$ is heteroaryl including 6 ring atoms, wherein 1-4 ring atoms are heteroatoms, each independently selected from the group consisting of N, N(H), $N(R^d)$, O, and $S(O)_{0-2}$, and wherein the heteroaryl is optionally substituted with 1-4 substituents independently selected from the group consisting of oxo, $R^b$ and $R^c$.

10. The compound of any one of embodiments 1-9, wherein $R^1$ is heteroaryl including 6 ring atoms, wherein 1-2 ring atoms are N, and wherein the heteroaryl is optionally substituted with 1-4 substituents independently selected from the group consisting of oxo, $R^b$ and $R^c$.

11. The compound of any one of embodiments 1-10, wherein $R^1$ is unsubstituted.

12. The compound of any one of embodiments 1-10, wherein $R^1$ is substituted with one $R^b$ or one $R^c$.

13. The compound of any one of embodiments 1-10 and 12, wherein $R^1$ is substituted with one $R^b$.

14. The compound of embodiment 12 or 13, wherein $R^b$ is $C_{1-10}$ alkyl, which is optionally substituted with 1-6 independently selected $R^a$.

15. The compound of any one of embodiments 12-14, wherein $R^b$ is $C_{1-6}$ alkyl, which is optionally substituted with 1-6 independently selected $R^a$.

16. The compound of any one of embodiments 12-15, wherein $R^b$ is $C_{1-3}$ alkyl, which is optionally substituted with 1-6 independently selected $R^a$.

17. The compound of any one of embodiments 12-16, wherein $R^b$ is unsubstituted $C_1$-3 alkyl.

18. The compound of any one of embodiments 12-17, wherein $R^b$ is $—CH_3$.

19. The compound of any one of embodiments 12-16, wherein $R^b$ is $C_{1-3}$ alkyl, which is substituted with 1-6 independently selected $R^a$.

20. The compound of any one of embodiments 14-16 and 19, wherein $R^a$, or each occurrence of $R^a$, is an independently selected halo; optionally wherein $R^a$, or each occurrence of $R^a$, is fluoro.

21. The compound of any one of embodiments 14-16 and 19-20, wherein $R^b$ is $—CF_3$.

22. The compound of any one of embodiments 14-16 and 19-20, wherein $R^b$ is $—CHF_2$.

23. The compound of any one of embodiments 14-16 and 19, wherein $R^a$, or each occurrence of $R^a$, is an independently selected $C_{1-4}$ alkoxy.

24. The compound of any one of embodiments 14-16, 19, and 23, wherein $R^a$, or each occurrence of $R^a$, is $—OCH_3$.

25. The compound of any one of embodiments 14-16 and 19, and 23-24, wherein $R^b$ is $CH_2OCH_3$.

26. The compound of embodiment 12 or 13, wherein $R^b$ is $C_{1-4}$ alkoxy.

27. The compound of embodiment 12, 13, or 26, wherein $R^b$ is $—OCH_3$.

28 The compound of embodiment 12 or 13, wherein $R^b$ is $C_{1-4}$ haloalkoxy.

29 The compound of embodiment 12, 13, or 26, wherein $R^b$ is $—OCHF_2$.

The compound of embodiment 12 or 13, wherein $R^b$ is halo.

31. The compound of embodiment 12, 13, or 30, wherein $R^b$ is fluoro.

32. The compound of embodiment 12, 13, or 30, wherein $R^b$ is chloro.

33. The compound of embodiment 12 or 13, wherein $R^b$ is cyano.

34 The compound of any one of embodiments 1-10 and 12, wherein $R^1$ is substituted with 1 $R^c$.

35. The compound of embodiment 12 or 34, wherein $R^e$ is $C_{3-10}$ cycloalkyl or $C_{3-10}$ cycloalkenyl, each of which is optionally substituted with from 1-4 substituents independently selected from the group consisting of oxo and $R^c$.

36. The compound of embodiment 12, 34, or 35 wherein $R^e$ is $C_{3-10}$ cycloalkyl which is optionally substituted with from 1-4 substituents independently selected from the group consisting of oxo and $R^b$.

37. The compound of any one of embodiments 12 and 34-36, wherein $R^e$ is $C_{3-6}$ cycloalkyl which is optionally substituted with from 1-4 substituents independently selected from the group consisting of oxo and $R^b$.

38. The compound of any one of embodiments 12 and 34-37, wherein $R^e$ is cyclopropyl, which is optionally substituted with from 1-4 substituents independently selected from the group consisting of oxo and $R^b$.

39. The compound of any one of embodiments 1-38, wherein $R^1$ has the formula:

(III-A)

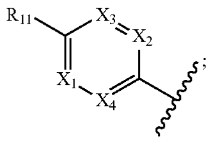

wherein each of $X_1$, $X_2$, $X_3$, and $X_4$ is, independently, CH or N; and $R^{11}$ is H, $R^b$, or $R^c$, preferably wherein $R^1$ has the formula:

(IV-A)

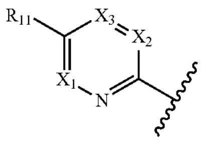

or (IV-B)

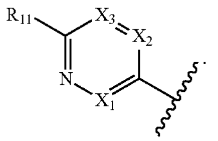

40. The compound of embodiment 39, wherein not more than two of $X_1$, $X_1$, and $X_3$ are N.

41. The compound of embodiment 39 or 40, wherein $X_2$ is N.

42. The compound of any one of embodiments 39-41, wherein $X_1$ is CH.

43 The compound of any one of embodiments 39-42, wherein $X_3$ is CH.

44. The compound of any one of embodiments 39-43, wherein $R^1$ has the formula:

(V-A)

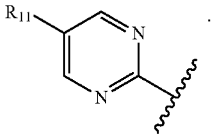

45. The compound of embodiment 39 or 40, wherein $X_1$ is N.

46 The compound of any one of embodiments 39, 40, and 45, wherein $X_2$ is CH.

47. The compound of any one of embodiments 39, 40, 45, and 46 wherein $X_3$ is CH.

48. The compound of any one of embodiments 39-40 and 45-47, wherein $R^1$ has the formula:

(V-B)

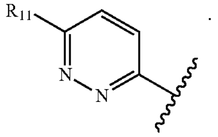

49. The compound of embodiment 39 or 40, wherein $X_3$ is N.

50. The compound of any one of embodiments 39, 40, and 49, wherein $X_2$ is CH.

51. The compound of any one of embodiments 39, 40, 49, and 50, wherein $X_1$ is CH.

52. The compound of any one of embodiments 39-40 and 49-51, wherein $R^1$ has the formula:

(V-C)

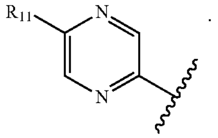

53. The compound of embodiment 39 or 40, wherein $R^1$ has the formula:

(V-D)

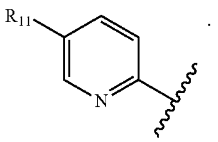

54. The compound of any one of embodiments 39-53, wherein $R^{11}$ is H.

55. The compound of any one of embodiments 39-53, wherein $R^{11}$ is $R^b$.

56. The compound of any one of embodiments 39-53 and 55, wherein $R^{11}$ is unsubstituted $C_{1-3}$ alkyl.

57. The compound of any one of embodiments 39-53 and 55-56, wherein $R^{11}$ is $CH_3$.

58. The compound of any one of embodiments 39-53 and 55, wherein $R^{11}$ is $C_{1-3}$ alkyl, which is substituted with from 1-6 independently selected $R^a$.

59 The compound of embodiment 58, wherein $R^a$, or each occurrence of $R^a$, is an independently selected halo.

60. The compound of embodiment 58 or 59, wherein $R^a$, or each occurrence of $R^a$, is fluoro.

61. The compound of any one of embodiments 58-60, wherein $R^{11}$ is $-CF_3$.

62. The compound of any one of embodiments 58-60, wherein $R^{11}$ is $-CHF_2$.

63. The compound of embodiment 58, wherein $R^a$, or each occurrence of $R^a$, is an independently selected $C_{1-4}$ alkoxy.

64. The compound of embodiment 58 and 63, wherein $R^a$, or each occurrence of $R^a$, is $-OCH_3$.

65. The compound of any one of embodiments 58 and 63-64, wherein $R^{11}$ is $CH_2OCH_3$.

66. The compound of any one of embodiments 39-53 and 55, wherein $R^{11}$ is $C_{1-4}$ alkoxy.

67. The compound of any one of embodiments 39-53, 55, and 66, wherein $R^{11}$ is $-OCH_3$.

68. The compound of any one of embodiments 39-53 and 55, wherein $R^{11}$ is $C_{1-4}$ haloalkoxy.

69. The compound of any one of embodiments 39-53, 55, and 68, wherein $R^{11}$ is $-OCHF_2$.

70 The compound of any one of embodiments 39-53 and 55, wherein $R^{11}$ is halo.

71. The compound of any one of embodiments 39-53, 55, and 70, wherein $R^{11}$ is fluoro.

72. The compound of any one of embodiments 39-53, 55, and 70, wherein $R^{11}$ is chloro.

73. The compound of any one of embodiments 39-53 and 55, wherein $R^{11}$ is cyano.

74. The compound of any one of embodiments 39-53, wherein $R^{11}$ is cyclopropyl, which is optionally substituted with from 1-4 substituents independently selected from the group consisting of oxo and $R^c$.

75 The compound of any one of embodiments 1-7, or 11-38, wherein $R^1$ is heteroaryl including 8-10 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of oxo, $R^b$ and $R^c$.

76. The compound of embodiment 75, wherein $R^1$ is heteroaryl including 10 ring atoms, wherein 1-4 ring atoms are heteroatoms, each independently selected from the group consisting of N, N(H), N($R^4$), O, and S, and wherein the heteroaryl is optionally substituted with 1-4 substituents independently selected from the group consisting of oxo, $R^b$ and $R^c$.

77. The compound of embodiment 76, wherein $R^1$ is:

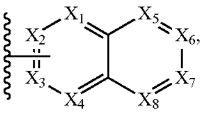

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, and each of $X_5$ to $X_8$ is independently selected from CH, $CR^{13}$ or N; wherein $R^{13}$ is $R^b$ or $R^c$; and provided that no more than four of $X_1$ to $X_8$ are heteroatoms and no more than four of $X_1$ to $X_8$ are $CR^{13}$; preferably wherein none of $X_1$ to $X_8$ are $CR^{13}$.

78. The compound of embodiment 76, wherein $R^1$ is:

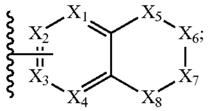

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, and each of $X_5$ to $X_8$ is independently selected from $CH_2$, $CHR^{13}$, NH, $NR^{13}$, O or $SO_2$; wherein $R^{13}$ is $R^b$ or $R^c$; and provided that no more than four of $X_1$ to $X_8$ are heteroatoms and no more than four of $X_1$ to $X_8$ include an $R^{13}$ group; preferably wherein none of $X_1$ to $X_8$ include an $R^{13}$ group.

79. The compound of embodiment 76, wherein $R^1$ is:

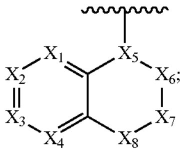

wherein $X_1$ to $X_4$ are each independently selected from CH, $CR^{13}$ or N, $X_5$ is CH, $CR^{13}$ or N, and each of $X_6$ to $X_8$ is independently selected from $CH_2$, $CR^{13}$, NH, $NR^{13}$, O or $SO_2$; wherein $R^{13}$ is $R^b$ or $R^c$; and provided that no more than four of $X_1$ to $X_8$ are heteroatoms and no more than four of $X_1$ to $X_8$ include an $R^{13}$ group; preferably wherein none of $X_1$ to $X_8$ include an $R^{13}$ group.

80. The compound of embodiment 76, wherein $R^1$ is:

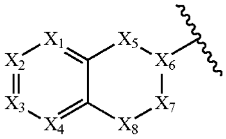

wherein $X_1$ to $X_4$ are each independently selected from CH or N, $X_6$ is CH, $CR^{13}$ or N, and each of $X_5$, $X_7$ and $X_8$ is independently selected from $CH_2$, $CHR^{13}$, NH, $NR^{13}$, O or $SO_2$; wherein $R^{13}$ is $R^b$ or $R^c$; and provided that no more than four of $X_1$ to $X_8$ are heteroatoms and and no more than four of $X_1$ to $X_8$ include an $R^{13}$ group; preferably wherein none of $X_1$ to $X_8$ include an $R^{13}$ group.

81. The compound of embodiment 75 or 76, wherein $R^1$ is:

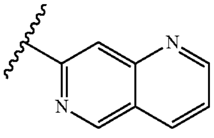
,
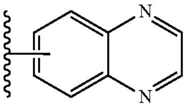
,
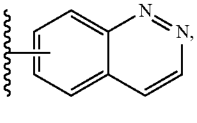
, or
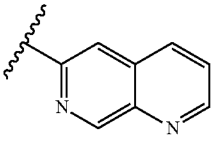
.

82. The compound of embodiment 75, wherein $R^1$ is heteroaryl including 9 ring atoms, wherein 1-4 ring atoms are heteroatoms, each independently selected from the group consisting of N, N(H), $N(R^d)$, O, and S, and wherein the heteroaryl is optionally substituted with 1-4 substituents independently selected from the group consisting of oxo, $R^b$ and $R^c$.

83. The compound of embodiment 82, wherein $R^1$ is:

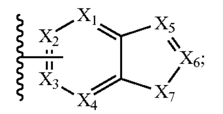

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, $X_5$ and $X_6$ are independently selected from CH, $CR^{13}$ or N, and $X_7$ is selected from $CH_2$, $CHR^{13}$, NH, $NR^{13}$, O or S; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

84. The compound of embodiment 82, wherein $R^1$ is

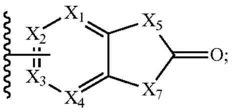

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, $X_5$ and $X_7$ are independently selected from $CH_2$, $CHR^{13}$, NH, $NR^{13}$ or O; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

85. The compound of embodiment 82, wherein $R^1$ is:

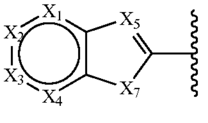
or
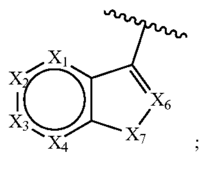
;

wherein $X_1$ to $X_4$ are each independently selected from CH, $CR^{13}$ or N; $X_5$ and $X_6$ are selected from CH, $CR^{13}$ or N, and $X_7$ is selected from NH, $NR^{13}$ or O; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

86. The compound of embodiment 82, wherein $R^1$ is:

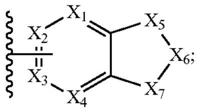

wherein whichever of $X_1$ to $X_4$ provides the position of attachment of the $R^1$ group to the rest of the molecule is carbon, the rest of $X_1$ to $X_4$ are each independently selected from CH, $CR^{13}$ or N, and $X_5$ to $X_7$ are each independently selected from $CH_2$, $CHR^{13}$, NH, $NR^{13}$, O or $SO_2$; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group or wherein only one of $X_1$ to $X_7$ includes an $R^{13}$ group and the $R^{13}$ group is $CH_3$.

87. The compound of embodiment 82, wherein $R^1$ is:

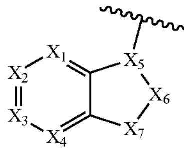
;

wherein $X_1$ to $X_4$ are each independently selected from CH, $CR^{13}$ or N, $X_5$ is CH or N and $X_6$ and $X_7$ are each independently selected from $CH_2$, $CHR^{13}$, NH, $NR^{13}$, O or $SO_2$; wherein $R^{13}$ is $R^b$ or $R^c$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group.

88. The compound of embodiment 82, wherein $R^1$ is:

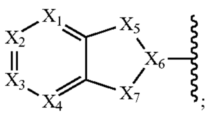

wherein $X_1$ to $X_4$ are each independently selected from CH, $CR^{13}$ or N, $X_6$ is CH or N and $X_5$ and $X_7$ are each independently selected from $CH_2$, $CHR^{13}$, NH, $NR^{13}$, O or $SO_2$; wherein $R^{13}$ is $R^b$ or $R^e$; and provided that no more than four of $X_1$ to $X_7$ are heteroatoms and no more than four of $X_1$ to $X_7$ include an $R^{13}$ group; preferably wherein none of $X_1$ to $X_7$ include an $R^{13}$ group.

89 The compound of embodiment 75 or 76, wherein $R^1$ has the formula:

(VI-A)

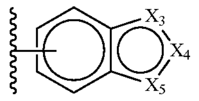
or (VI-B)

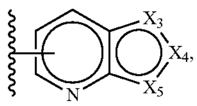

wherein:

$X_3$ is NH, O, or S;

$X_4$ is N, O, or CH; and $X_5$ is N or CH.

90. The compound of embodiment 89, wherein $X_3$ is NH, O, or S; and $X_4$ and $X_5$ are CH.

91. The compound of embodiment 89, wherein $X_3$ is O or S; $X_4$ is CH; and $X_5$ is N.

92. The compound of embodiment 89, wherein $X_3$ is NH, $X_4$ is N; and $X_5$ is CH.

93. The compound of embodiment 89, wherein $X_3$ is N, $X_4$ is O; and $X_5$ is N.

94. The compound of any one of embodiments 1-8, or 11-38, wherein $R^1$ is heteroaryl including 5 ring atoms, wherein 1-4 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of $R^b$ and $R^c$.

95. The compound of embodiment 94, wherein $R^1$ has the formula:

(VI-C)

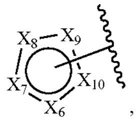

wherein:

$X_6$ is NH, $NCH_3$, O, or S;

$X_7$ is N, C, CH, $CCF_3$, $CCHF_2$, C(cyclopropyl), or $CCH_3$;

$X_8$ is N, C, CH, $CCH_3$, $CCF_3$, or $COCH_3$;

$X_9$ is N, C, CH, $CCH_3$, $CCF_3$, or $COCH_3$; and $X_{10}$ is N, C, CH, $CCF_3$, $CCHF_2$, C(cyclopropyl), or $CCH_3$.

96. The compound of embodiment 94 or 95, wherein $R^1$ has the formula:

(VI-C-1)

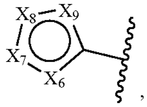

wherein:

$X_6$ is NH, $NCH_3$, O, or S;

$X_7$ is N, CH, $CCF_3$, $CCHF_2$, C(cyclopropyl), or $CCH_3$;

$X_8$ is N, CH, or $CCH_3$; and $X_9$ is N, CH, or $CCH_3$.

97. The compound of embodiment 95 or 96, wherein $X_8$ is N.

98. The compound of any one of embodiments 95-97, wherein $X_9$ is N.

99. The compound of any one of embodiments 95-98, wherein $X_6$ is O.

100. The compound of any one of embodiments 95-99, wherein $X_7$ is CH, $CCF_3$, $CCHF_2$, C(cyclopropyl), or $CCH_3$.

101. The compound of any one of embodiments 95-100, wherein $X_7$ is $CCH_3$.

102. The compound of any one of embodiments 95-101, wherein $R^1$ has the formula:

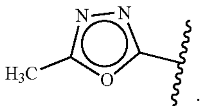

103. The compound of embodiment 95 or 96, wherein $X_6$ is O or S; and $X_7$ is N.

104. The compound of embodiment 103, wherein $X_8$ is CH or $CCH_3$; and $X_9$ is CH or $CCH_3$.

105. The compound of embodiment 95 or 96, wherein: $X_6$ is NH, $NCH_3$, or O;

$X_7$ is CH or $CCH_3$;

$X_8$ is N; and $X_9$ is CH or $CCH_3$.

106. The compound of embodiment 95 or 96, wherein: $X_6$ is $NCH_3$;

$X_7$ is CH or $CCH_3$;

$X_8$ is N; and $X_9$ is N.

107. The compound of embodiment 1-6, or 11-38, wherein $R^1$ is $C_{6-10}$ aryl optionally substituted with 1-4 substituents independently selected from the group consisting of $R^b$, and $R^c$.

108. The compound of embodiment 107, wherein $R^1$ is phenyl optionally substituted with 1-4 substituents independently selected from the group consisting of $R^b$, and $R^c$.

109. The compound of embodiment 107 or 108, wherein $R^1$ has the formula:

(VI-D)

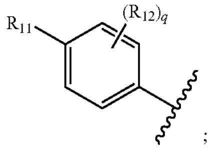

wherein each $R^{11}$ is independently selected from the group consisting of H, $R^b$, and $R^c$; each $R^{12}$ is independently selected from the group consisting of $R^b$ and $R^e$; and q is 0, 1, or 2.

110. The compound of embodiment 109, wherein $R^{11}$ is H, fluoro, CN, $CH_3$, $CHF_2$, —$SO_2NH_2$, $SO_2CH_3$, —C(O)$NH_2$, or cyclopropyl.

111. The compound of embodiment 109 or 110, wherein $R^{11}$ is H.

112. The compound of embodiment 109 or 110, wherein $R^{11}$ is $CH_3$.

113. The compound of embodiment 109 or 110, wherein $R^{11}$ is CN.

114. The compound of any one of embodiments 109-113, wherein q is 1.

115. The compound of embodiment 114, wherein $R^{12}$ is F.

116. The compound of any one of embodiments 1-115, wherein each of $R^2$a and $R^{2b}$ is independently selected from the group consisting of H and $C_{1-2}$ alkyl optionally substituted with from 1-5 $R^a$.

117. The compound of any one of embodiments 1-116, wherein each of $R^{2a}$ and $R^{2b}$ is an independently selected $C_{1-2}$ alkyl optionally substituted with from 1-5 $R^a$.

118. The compound of any one of embodiments 1-117, wherein each of $R^{2a}$ and $R^{2b}$ is an independently selected unsubstituted $C_{1-2}$ alkyl.

119. The compound of any one of embodiments 1-118, wherein each of $R^{2a}$ and $R^{2b}$ is $CH_3$.

120. The compound of any one of embodiments 1-115, wherein $R^{2a}$ and $R^{2b}$ taken together with the carbon atom to which each is attached forms:

$C_{3-7}$ cycloalkyl, which is optionally substituted with 1-4 substituents independently selected from the group consisting of oxo and $R^b$;

heterocyclyl including 4-7 ring atoms, wherein 1-2 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^b$.

121. The compound of embodiment 120, wherein $R^{2a}$ and $R^{2b}$ taken together with the carbon atom to which each is attached forms $C_{3-7}$ cycloalkyl, which is optionally substituted with 1-4 substituents independently selected from the group consisting of oxo and $R^b$.

122. The compound of embodiment 120 or 121, wherein $R^{2a}$ and $R^{2b}$ taken together with the carbon atom to which each is attached forms:

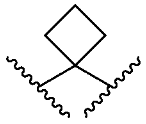
,
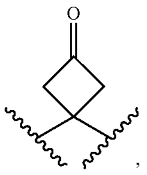
, or
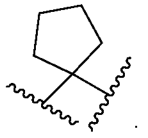
.

123. The compound of embodiment 120, wherein $R^{2a}$ and $R^{2b}$ taken together with the carbon atom to which each is attached forms heterocyclyl including 4-7 ring atoms, wherein 1-2 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^b$.

124. The compound of embodiment 120, wherein $R^{2a}$ and $R^{2b}$ taken together with the carbon atom to which each is attached forms:

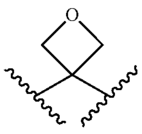
,
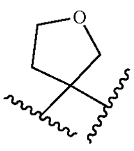
, or
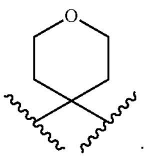
.

125. The compound of embodiments 1 or 5, wherein $R^1$, $R^{2a}$, and $R^{2b}$ are defined according to (B).

126. The compound of embodiment 125, wherein $R^1$ taken together with (i) the carbon atom to which it is attached and (ii) and one of $R^{2a}$ and $R^{2b}$ forms:

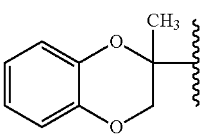 [SMILES: *C1(C)COc2ccccc2O1]

wherein as indicated in the formula above, the other of $R^{2a}$ and $R^{2b}$ is $CH_3$.

127. The compound of any one of embodiments 1-6, or 11-38, wherein $R^1$ is heterocycloalkenyl including 3-10 ring atoms, wherein 1-3 ring atoms are heteroatoms, each independently selected from the group consisting of N, N(H), N($R^d$), O, and $S(O)_{0-2}$, and wherein the heterocycloalkenyl is optionally substituted with 1-4 substituents independently selected from the group consisting of oxo, $R^b$, and $R^c$.

128. The compound of embodiment 127, wherein $R^1$ is heterocycloalkenyl including 6 ring atoms.

129. The compound of any one of embodiments 1-6, or 11-38, wherein $R^1$ is heterocyclyl including 4-6 ring atoms, wherein 1-4 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo, $R^b$ and $R^c$.

130. The compound of embodiment 129, wherein $R^1$ is heterocyclyl including 6 ring atoms.

131. The compound of any one of embodiments 1-6, or 11-38, wherein $R^1$ is $C_{3-7}$ cycloalkyl optionally substituted with 1-4 substituents independently selected from the group consisting of oxo, $R^b$, and $R^c$.

132. The compound of embodiment 131, wherein $R^1$ is $C_{5-6}$ cycloalkyl.

133. The compound of embodiment 132, wherein $R^1$ is:

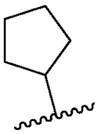
or
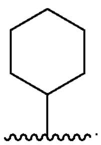
.

134. The compound of embodiment 7 or 127, wherein $R^1$ is:

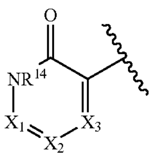
,
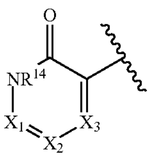
or
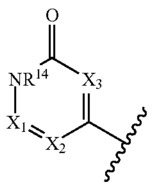
, wherein $X_1$, $X_2$ and $X_3$ are each independently CH, $CR^{15}$ or N; wherein $R^{14}$ and $R^{15}$ are each independently $R^b$ or $R^c$; optionally wherein only one of $X_1$, $X_2$ and $X_3$ is $CR^{15}$ and $R^{15}$ is methyl or F and/or wherein $R^{14}$ is $C_{1-2}$ alkyl or $C_{1-2}$ fluoroalkyl.

135. The compound of embodiment 134, wherein $R^1$ is:

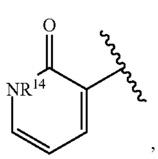
,
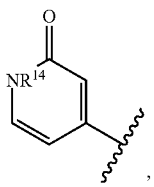
,
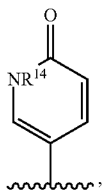
,

-continued
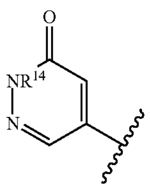
, or
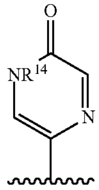
wherein $R^{14}$ is $R^b$ or $R^c$; optionally wherein $R^{14}$ is $C_{1-2}$ alkyl or $C_{1-2}$ fluoroalkyl.
136. The compound of any one of embodiments 1-5, wherein $R^1$ is:
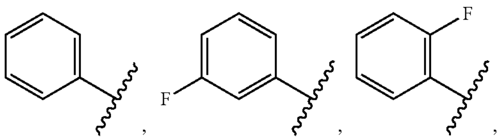
, , ,
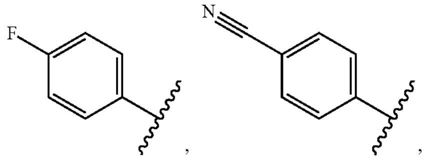
, ,
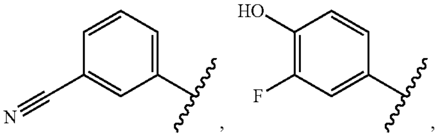
, ,
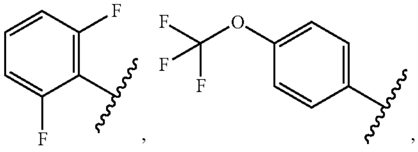
, ,
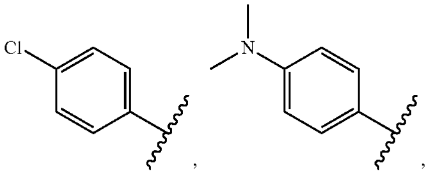
, ,
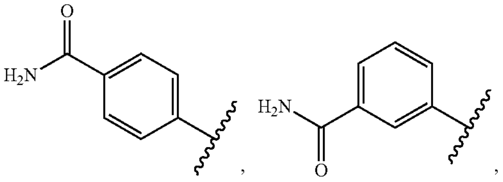
, ,
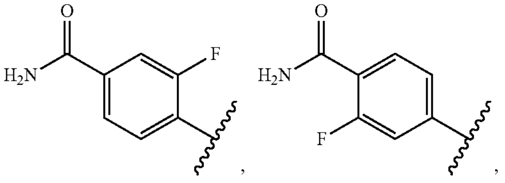
, ,
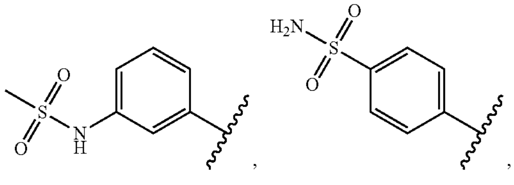
, ,
-continued
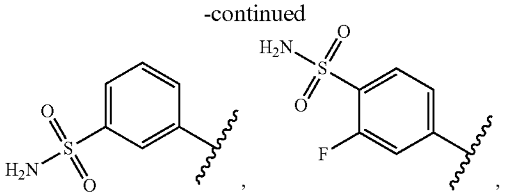
, ,
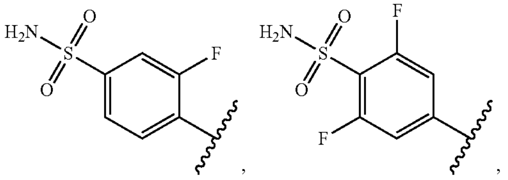
, ,
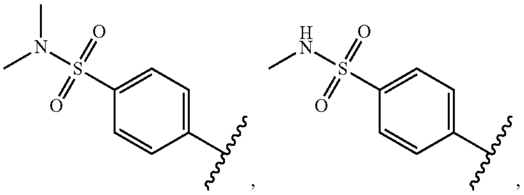
, ,
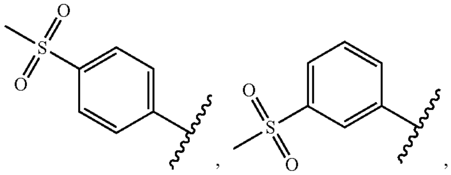
, ,
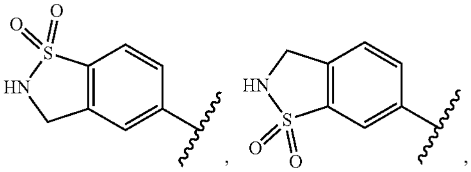
, ,
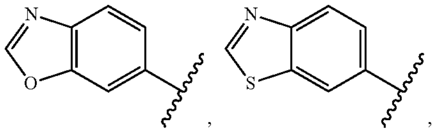
, ,
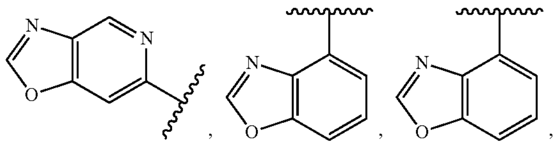
, , ,
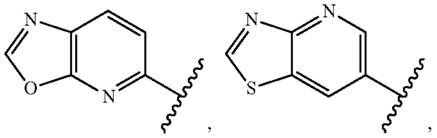
, ,
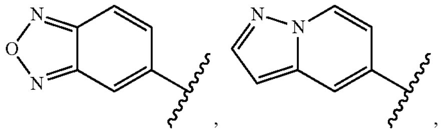
, ,
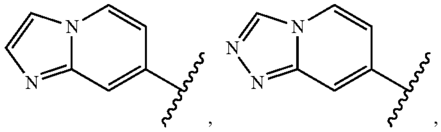
, ,
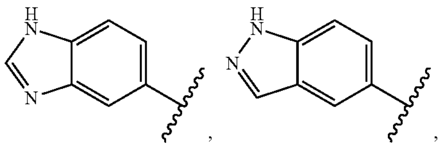
, , -continued
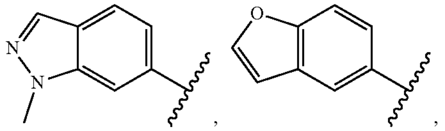
,
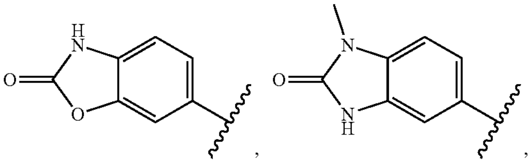
,
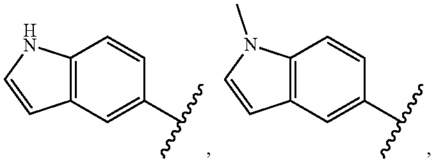
,
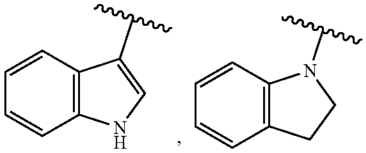
,
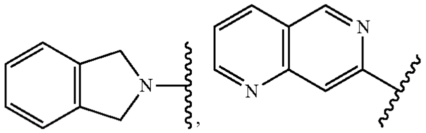
,
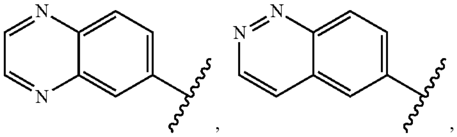
,
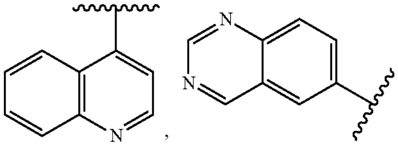
,
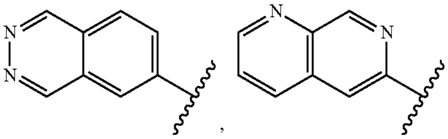
,
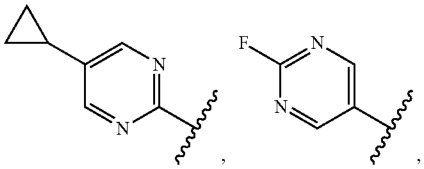
,
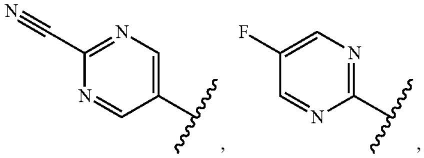
,
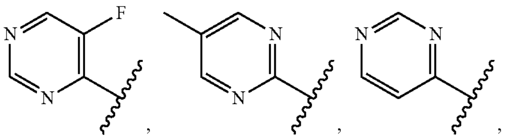
,
-continued
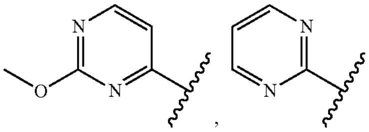
,
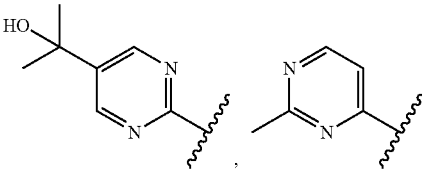
,
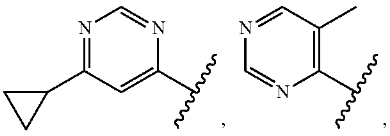
,
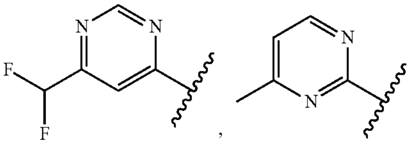
,
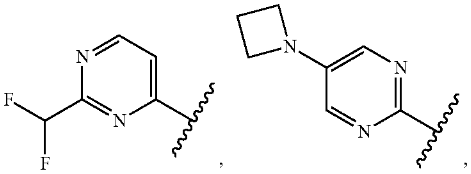
,
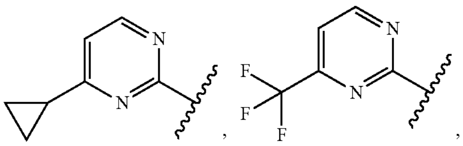
,
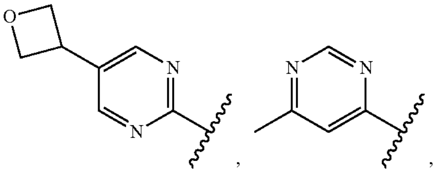
,
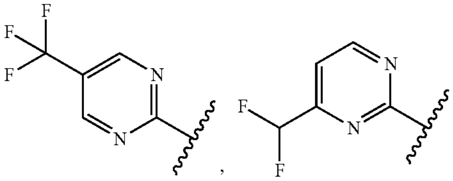
,
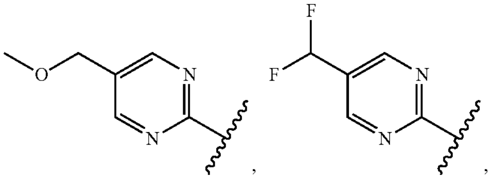
,
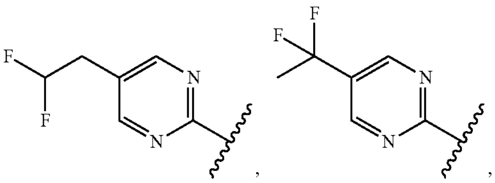
, -continued
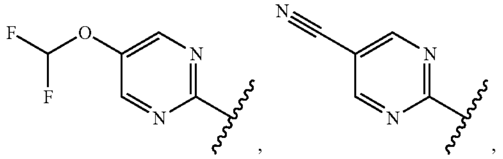
, ,
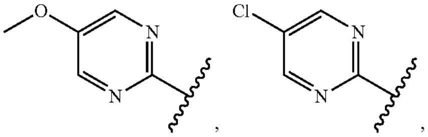
, ,
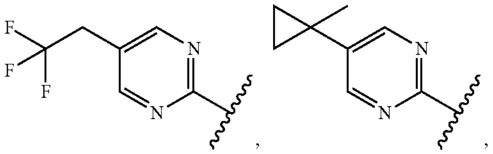
, ,
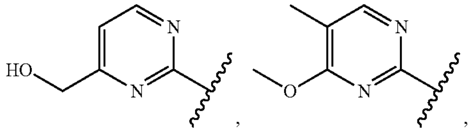
, ,
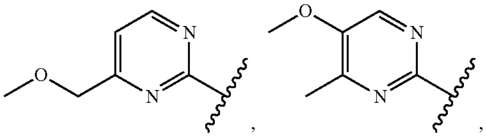
, ,
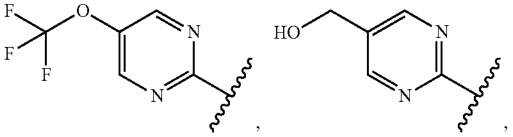
, ,
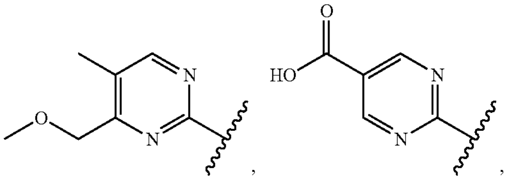
, ,
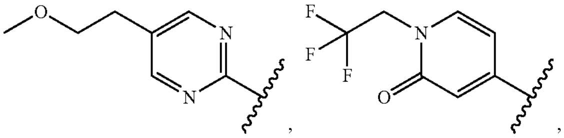
, ,
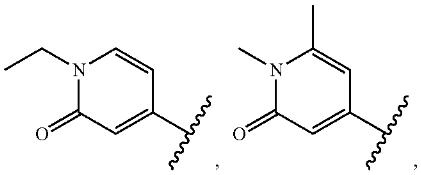
, ,
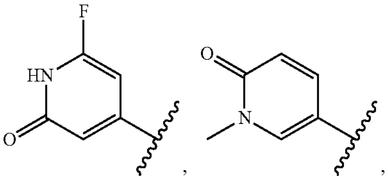
, ,
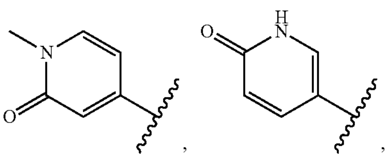
, ,
-continued
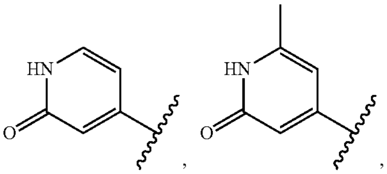
, ,
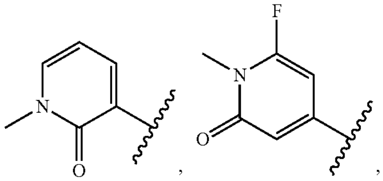
, ,
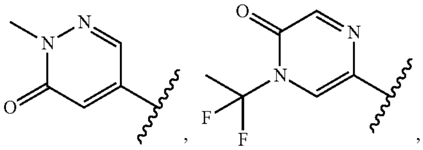
, ,
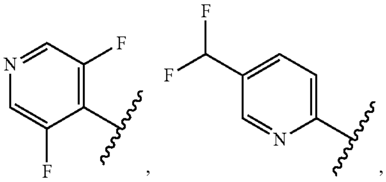
, ,
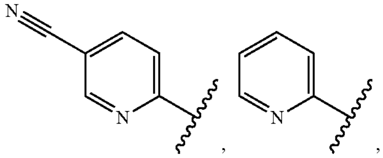
, ,
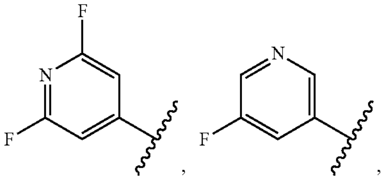
, ,
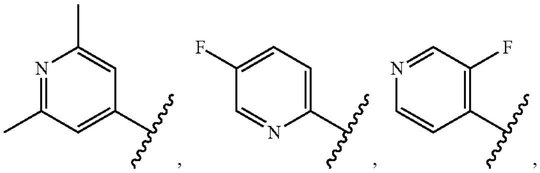
, , ,
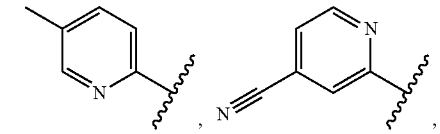
, ,
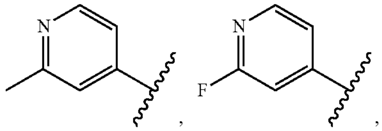
, ,
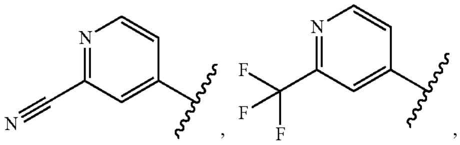
, , -continued
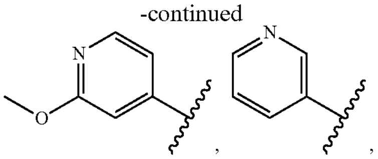
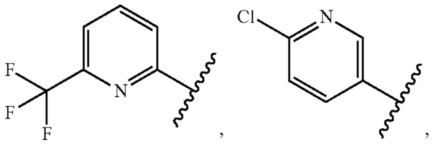
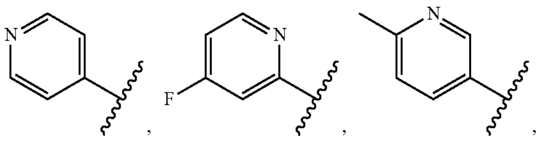
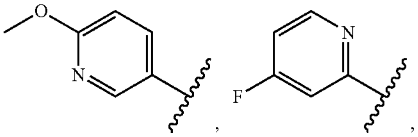
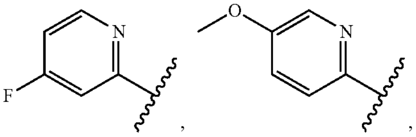
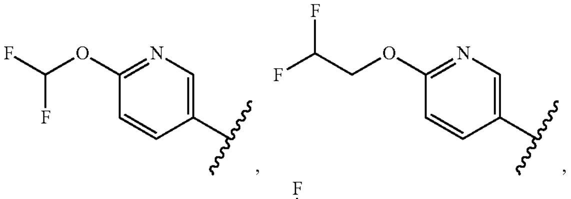
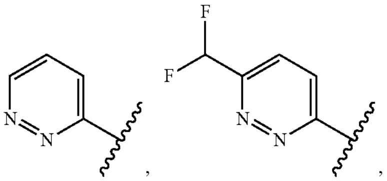
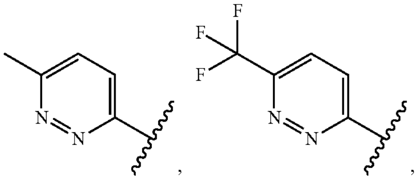
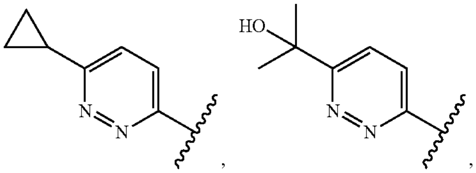
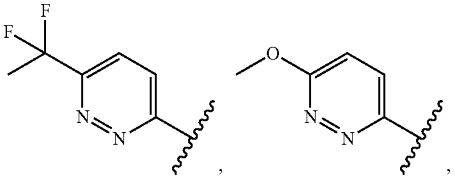
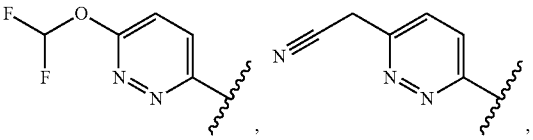
-continued
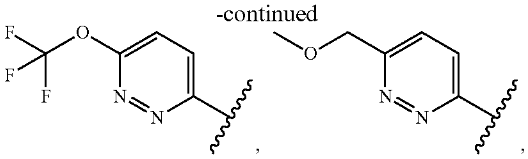
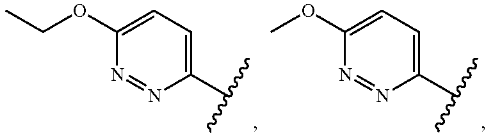
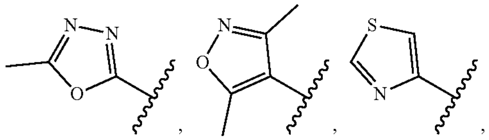
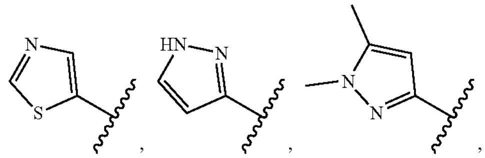
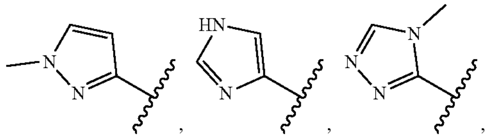
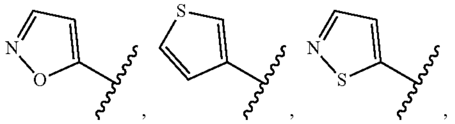
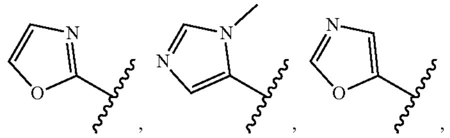
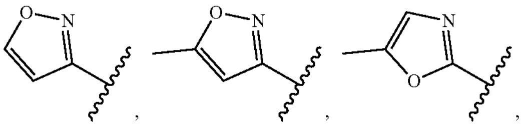
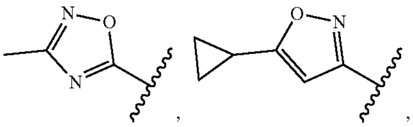
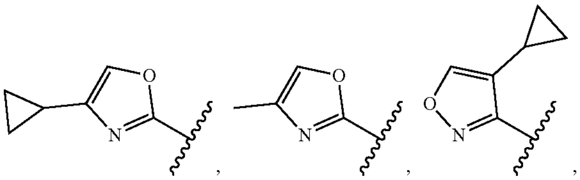
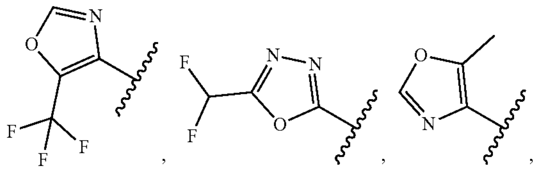
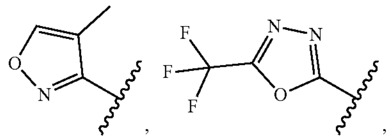

-continued
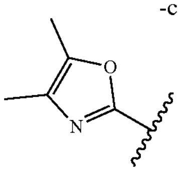
,
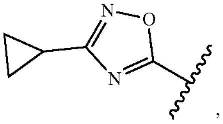
,
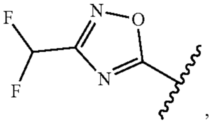
,
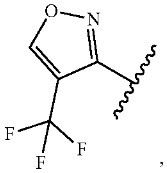
,
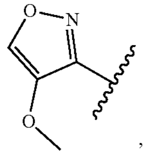
,
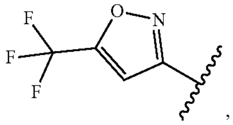
,
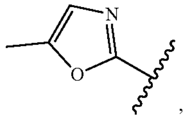
,
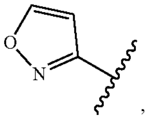
,
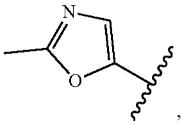
,
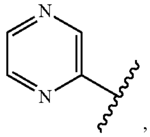
,
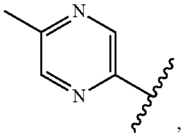
,
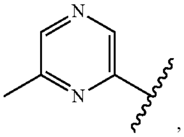
,
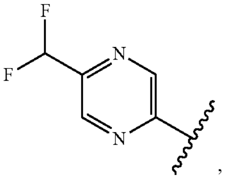
,
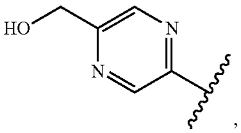
,
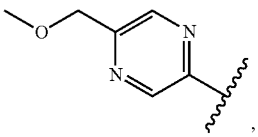
,
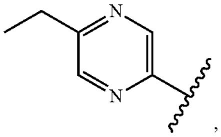
,
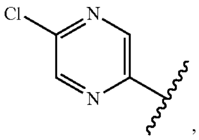
,
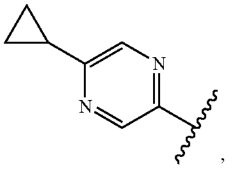
,
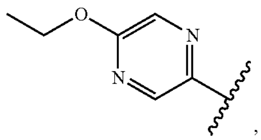
,
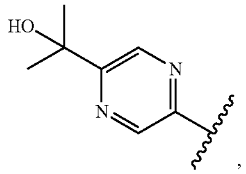
,
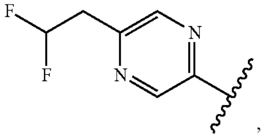
,
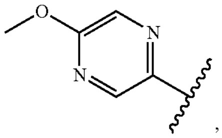
,
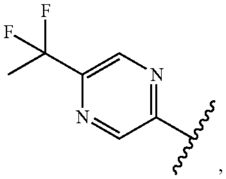
,
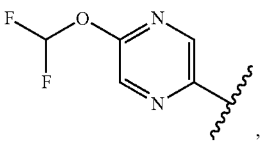
,
-continued
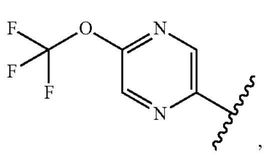
,
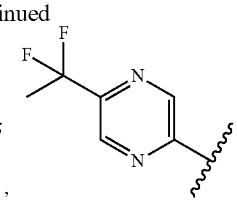
,
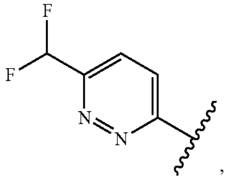
,
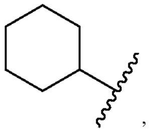
,
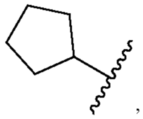
, or
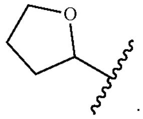
.
137. The compound of any one of embodiments 1-136, wherein $R^3$ is $C_1$.
138. The compound of embodiment 1, wherein the compound has the formula:
(VIII-A)
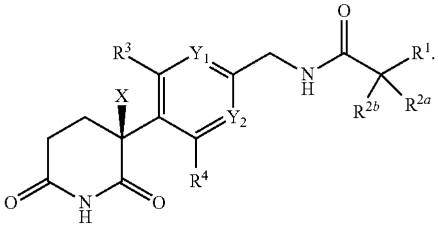
139. The compound of embodiment 1, wherein the compound has the formula:
(VIII-B)
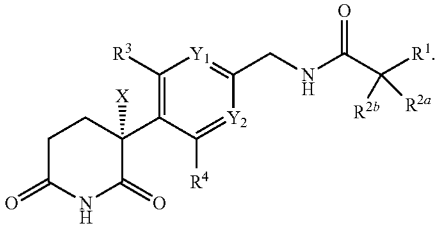
140. The compound of any one of embodiments 1-137, wherein the compound has the formula:
(VIII-C)
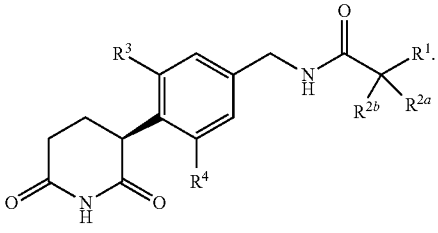

141. The compound of any one of embodiments 1-137, wherein the compound has the formula:

(VIII-D)

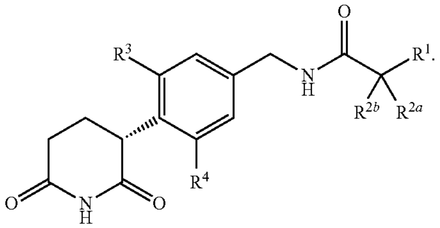

142. The compound of any one of embodiments 1-137, wherein the compound has the formula:

(VIII-E)

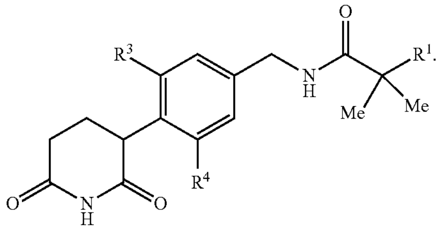

143. The compound of any one of embodiments 1-137, wherein the compound has the formula:

(VIII-F)

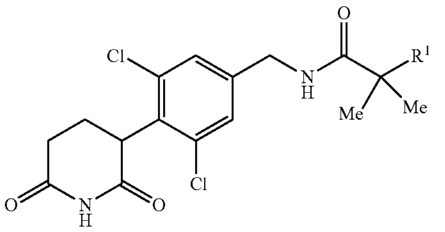

or (VIII-G)

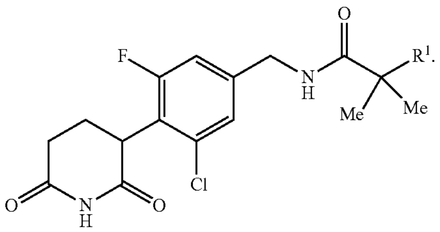

144. The compound of any one of embodiments 1-137, wherein the compound has the formula:

(VIII-H)

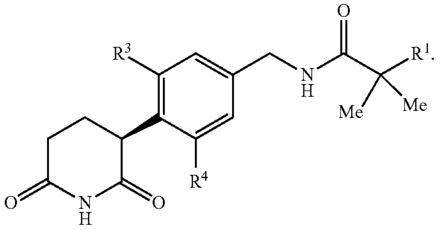

145. The compound of any one of embodiments 1-137, wherein the compound has the formula:

(VIII-I)

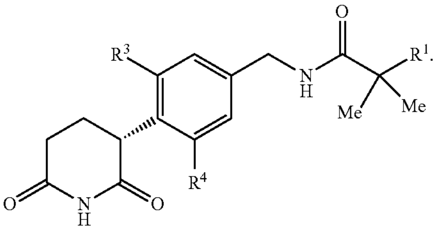

146. The compound of any one of embodiments 1-137, wherein the compound has the formula:

(VIII-J)

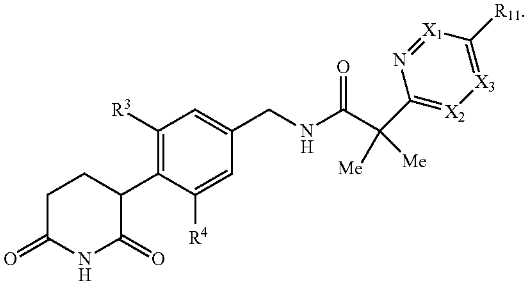

147. The compound of any one of embodiments 1-137, wherein the compound has the formula:

(VIII-K)

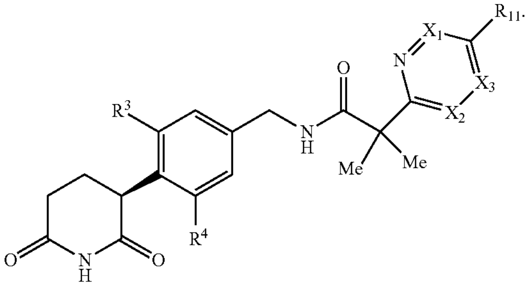

148. The compound of any one of embodiments 1-137, wherein the compound has the formula:

(VIII-L)

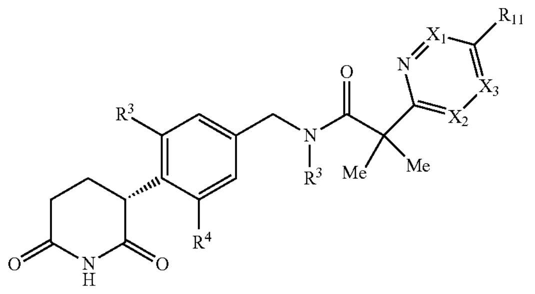

or (VIII-M)

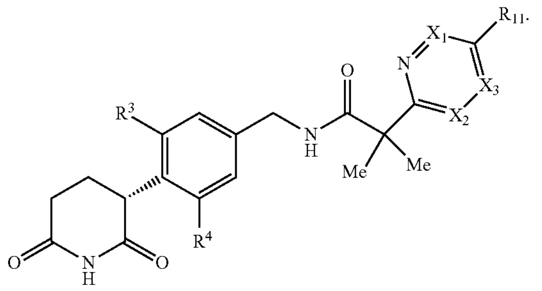

149. The compound of any one of embodiments 138-142 or 144-148, wherein $R^3$ is $C_1$.

150. The compound of any one of embodiments 1-142, or 144-148, wherein $R^4$ is $C_1$.

151. The compound of any one of embodiments 1-137, wherein the compound has the formula:

(VIII-N)

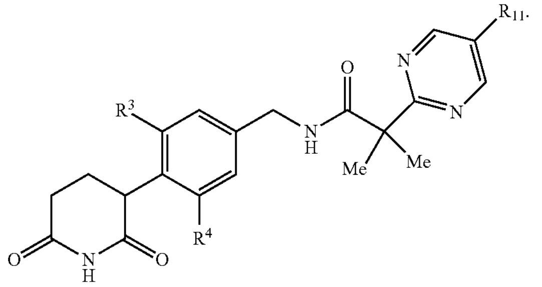

152. The compound of embodiment 151, wherein the compound has the formula:

(VIII-O)

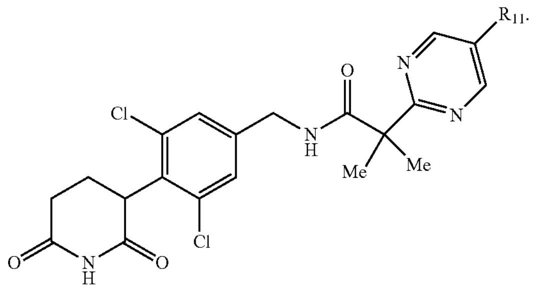

153. The compound of any one of embodiments 1-123 or 127-152, wherein each of $R^{2a}$ and $R^{2b}$ is $CD_3$.

154. The compound of embodiments 1 or 2, wherein the compound has the structure:

(VIII-P)

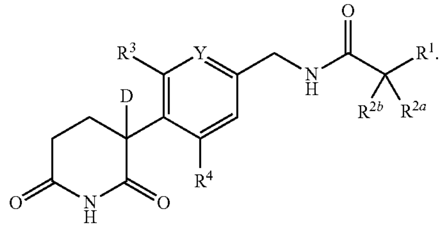

155. The compound of embodiment 154, wherein the compound has the structure:

(VIII-Q)

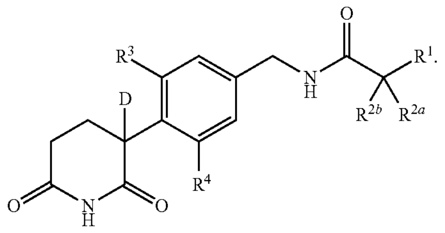

156. The compound of any one of embodiments 1-155, wherein the compound is selected from the compounds delineated in Table $C_1$.

157. A pharmaceutical composition comprising the compound of any one of embodiments 1-156, or pharmaceutically acceptable salt thereof, and a pharmaceutically acceptable excipient.

158. A method of degrading NIMA Related Kinase 7 (NEK7) in a subject, comprising administering to the subject an effective amount of a compound according to any one of embodiments 1-156, or a pharmaceutically acceptable salt thereof, or a pharmaceutical composition according to embodiment 157.

159. The method of embodiment 158, wherein the compound mediates the interaction of a NEK7 protein with an E3 ligase, thereby increasing degradation of the NEK7 protein.

160. The method of embodiment 158 or 159, wherein NEK7 is an activator of an NLRP3 inflammasome.

161. The method of embodiment 159 or 160, wherein the compound interacts with the E3 ligase prior to the interaction of NEK7 with the E3 ligase.

162. The method of any one of embodiments 159-161, wherein the E3 ligase comprises cereblon.

163. A method of degrading NIMA Related Kinase 7 (NEK7), comprising:

(i) contacting the compound of any one of embodiments 1-156 or a pharmaceutically acceptable salt thereof or the pharmaceutical composition of embodiment 157 with an E3 ligase; and (ii) interacting the contacted E3 ligase with NEK7, thereby degrading NEK7.

164. A method of treating a disorder caused by or associated with NLRP3 inflammasome activation in a subject in need thereof, comprising administering to the subject a therapeutically effective amount of the compound of any one of embodiments 1-156 or a pharmaceutically acceptable salt thereof or the pharmaceutical composition of embodiment 157.

165. The method of embodiment 164, wherein the disorder is a disorder of the immune system, hematopeoitic system, joints, renal system, gastro-intestinal tract, skin, eye, respiratory system, central nervous system, cardiovascular system, hepatic system, and/or endocrine system.

166. The method of embodiment 164 or 165, wherein the disorder is selected from the group consisting of:

(i) inflammatory reactions in the joints;
(ii) hyperactive inflammation with underlying genetic mutations;
(iii) autoimmune diseases;
(iv) respiratory diseases;
(v) kidney diseases;
(vi) central nervous system diseases;
(vii) ocular diseases;
(viii) cardiovascular diseases;
(ix) viral infections and subsequent immune hyperactivation;
(x) diseases of the hematopoietic system;
(xi) liver disease;
(xii) inflammatory reactions in the skin;
(xiii) metabolic diseases;
(xiv) cancers;
(xv) infectious diseases; and
(xvi) allergic disease.

167. The method of any one of embodiments 164-166, wherein the disorder is inflammatory reactions in the joints.

168. The method of embodiment 167, wherein the disorder is gout, optionally wherein the disorder is acute or chronic gout.

169. The method of embodiment 167, wherein the disorder is tophaceous gout.

170. The method of embodiment 167, wherein the disorder is pseudo-gout.

171. The method of embodiment 167, wherein the disorder is osteoarthritis.

172. The method of embodiment 167, wherein the disorder is psoriatic arthritis.

173. The method of embodiment 167, wherein the disorder is systemic juvenile idiopathic arthritis.

174. The method of embodiment 167, wherein the disorder is adult-onset Still's disease.

175. The method of embodiment 167, wherein the disorder is relapsing polychondritis.

176. The method of embodiment 167, wherein the disorder is tendonitis.

177. The method of embodiment 167, wherein the disorder is frozen shoulder.

178. The method of embodiment 167, wherein the disorder is pyogenic arthritis.

179. The method of any one of embodiments 164-166, wherein the disorder is selected from the group consisting of:

(ii) hyperactive inflammation with underlying genetic mutations;
(iii) autoimmune diseases;
(iv) respiratory diseases;
(v) kidney diseases;
(vi) central nervous system diseases;
(vii) ocular diseases;
(viii) cardiovascular diseases; and
(ix) metabolic diseases.

180. The method of embodiment 179, wherein the hyperactive inflammation with underlying genetic mutations is selected from the gourp consisting of cryopyrin-associated periodic syndrome (CAPS): Muckle-Wells syndrome (MWS), familial cold autoinflammatory syndrome (FCAS) and neonatal-onset multisystem inflammatory disease (NOMID); familial Mediterranean fever (FMF), TNF receptor associated periodic syndrome (TRAPS), mevalonate kinase deficiency (MVK), hyperimmunoglobuliemia D and periodic fever syndrome (HIDS), deficiency of interleukin 1 receptor (DIRA) antagonist), VEXAS syndrome, Majeed syndrome, pyoderma gangrenosum,acne and hidradenitis suppurative syndrome, haploinsufficency of A20, pediatric granulomatous arthritis (PGA), PLCG2-associated antibody deficiency and immune dysregulation (PLAID), sideroblastic anemia with B-cell immunodeficiency, periodic fevers, and developmental delay (SIFD), Sweet's syndrome, chronic non-bacterial osteomyelitis (CNO), chronic recurrent multifocal osteomyelitis (CRMO) and synovitis, acne, pustulosis, hyperostosis, osteitis syndrome (SAPHO) and any disease where an individual has been determined to carry a germline or somatic non-silent mutation in NLRP3 or NEK7.

181. The method of embodiment 179, wherein the autoimmune disease is selected from the group consisting of multiple sclerosis (MS), rheumatoid arthritis, Behçet's disease, Sjögren's syndrome, systemic sclerosis, mixed connective tissue disease, myositis, vasculitis, lupus, including systemic and cutaneous forms, lupus nephritis, type-1 diabetes, psoriasis and Schnitzler's syndrome, Grave's disease, thrombotic thrombocytopeniaurpura, idiopathic thrombocytopenia purpura, microscopic polyangiitis, inflammatory bowel disease, colitis, and Crohn's disease.

182. The method of embodiment 179, wherein the respiratory disease is selected from the group consisting of chronic obstructive pulmonary disorder (COPD), acute respiratory distress syndrome (ARDS), steroid-resistant asthma, asbestosis, silicosis,sarcoidosis, cystic fibrosis and interstitial lung disease (ILD), including, but not limited to idiopathic pulmonary fibrosis (IPF), fibrotic hypersensitivity pneumonitis, rheumatoid arthritis-associated ILD, autoimmune myositis-associated ILD, systemic sclerosis-associated ILD, idiopathic interstitial pneumonia and progressive fibrosing ILD.

183. The method of embodiment 179, wherein the kidney disease is selected from the group consisting of chronic kidney disease (CKD), including CKD associated with high uric acid, APOL1 mutations, complement-mediated kidney diseases such as C3 glomerulopathy, IgA nephropathy, atypical hemalytic uremic syndrome and membranous nepropathy, idiopathic nephrotic syndrome, oxalate nephropathy and diabetic nephropathy.

184. The method of embodiment 179, wherein the central nervous system disease is selected from the group consisting of Parkinson's disease, Alzheimer's disease, motor neuron disease, Huntington's disease, cerebral malaria, post-traumatic brain injury, sub-arachnoid hemorrhage and brain injury from pneumococcal meningitis, cerebral amyloid angiopathy, migraine, depression, and psychological stress.

185. The method of embodiment 179, wherein the ocular disease is selected from the group consisting of those of the ocular epithelium, age-related macular degeneration (AMD), corneal infection, uveitis and dry eye.

186. The method of embodiment 179, wherein the cardiovascular disease is selected from the group consisting of atherosclerosis, stroke, myocardial infarction, hypertension, abdominal aortic aneurism, pericarditis including Dressler's syndrome, myocarditis, inflammatory cardiomyopathy, transthyretin amyloidosis, thromboembolism, ischemia reperfusion injury, and vasculitis.

187. The method of embodiment 186, wherein the cardiovascular disease is pericarditis.

188. The method of embodiment 187, wherein the pericarditis is Dressler's syndrome.

189. The method of embodiment 179, wherein the metabolic disease is selected from the group consisting of obesity, metabolic disease, Type 2 diabetes and related morbidities including diabetic foot ulcers, atherosclerosis, obesity, diabetic cardiomyopathy, and diabetic retinopathy.

190. A method of degrading NIMA Related Kinase 7 (NEK7) in a subject suffering from a disorder according to any one of embodiments 164-189, comprising administering to the subject an effective amount of the compound of embodiments 1 or 5 or a pharmaceutically acceptable salt thereof.

190. The method of any one of embodiments 164-189, wherein the subject is a human.

EXAMPLES

Abbreviations: Å=Angstrom; Boc: tert-butyloxycarbonyl; $Boc_2O$: Boc anhydride; brd: broad doublet; brdd: broad doublet of doublet; brs: broad singlet; brt: broad triplet; [eq: equivalents; d: doublet; DBU: 1,8-Diazabicyclo(5.4.0)undec-7-ene; dd: doublet of doublet; ddd: doublet of doublet of doublet; DMAC: dimethylacetamide; DMAP: 4-Dimethylaminopyridine; DIPEA or DIEA: diisopropylethylamine; DMEDA: N,N'-Dimethylethylenediamine; DMF: dimethylformamide; DMSO: dimethyl sulfoxide; EDCI: 1-Ethyl-3-(3-dimethylaminopropyl) carbodiimide; ESI: electrospray ionization; EtOAc: ethyl acetate; h: hours; HATU: 1-[Bis(dimethylamino)methylene]-1H-1,2,3-triazolo[4,5-b]pyridinium 3-oxide hexafluorophosphate; HCl: hydrochloric acid; HMPA: hexamethylphosphoramide; HOBt: Hydroxybenzotriazole; HPLC: high-performance liquid chromatography; $K_2CO_3$: potassium carbonate; m: multiplet; MeCN: acetonitrile; MOM: methoxymethyl ether; MS: mass spectrometry; $NaHCO_3$: sodium bicarbonate; NaI: sodium iodide; $NH_4Cl$: ammonium chloride; NMR: nuclear magnetic resonance; $Pd(dppf)Cl_2$: [1,1'-Bis(diphenylphosphino)ferrocene]dichloropalladium (II); Pd-PEPPSI-IHeptCl: 3-chloropyridine 4,5-dichloro-1,3-bis [2,6H-di(heptan-4-yl)phenyl]-2H-imidazol-2-ide dichloropalladium; Pd-PEPPSI-IPentCl: 3-chloropyridine 4,5-dichloro-1,3-bis [2,6-di(pentan-4-yl)phenyl]-2H-imidazol-2-ide dichloropalladium; $Pd(PPh_3)_4$: tetrakis (triphenylphosphine)-palladium (0); PSI: pounds per square inch; quin: quintet; q: quartet; RuPhos Pd G3: (2-Dicyclohexylphosphino-2',6'-diisopropoxy-1,1'-biphenyl) [2-(2'-amino-1,1'-biphenyl)]palladium (II) methanesulfonate; S: singlet; sol.: sat. saturated solution; Selectfluor: 1-(Chloromethyl)-4-fluoro-1,4-diazabicyclo[2.2.2]octane-1,4-diium ditetrafluoroborate; t: triplet; TBAF: tetrabutylammonium fluoride; td: triplet of doublet; TEA: triethylamine; Tf: triflate; THF: tetrahydrofuran; tt: triplet of triplet; XPhos Pd G4: (SP-4-3)-[Dicyclohexyl[2',4',6'-tris(1-methylethyl) [1,1'-biphenyl]-2-yl]phosphine](methanesulfonato-KO) [2'-(methylamino-KN) [1,1'-biphenyl]-2-yl-KC]palladium.

Example 1-Synthesis of Compounds

General Schemes and Procedures

General Scheme 1.

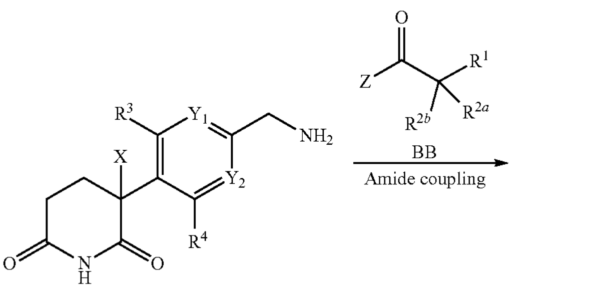

AA

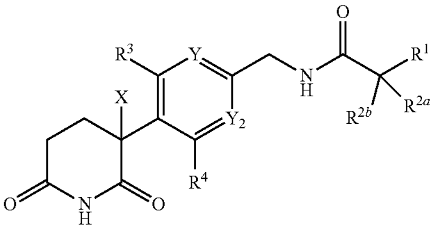

formula (I)

A general synthetic strategy that may be used to prepare compounds of formula (I) is depicted in General Scheme 1. A benzylamine AA, where X is H or halo (for example F) and $Y_1$ and $Y_2$ are C—H or N, wherein at least one of $Y_1$ and $Y_2$ is C—H, may be coupled with compound BB using any suitable amide coupling conditions to afford compounds of formula (I). For example, Mukaiyama's reagent may be used in a polar aprotic solvent such as DMF, in the presence of a base such as DIPEA. $Q^1$ is Cl or OH. The specific groups $R^1$, $R^{2a}$, $R^{2b}$, $R^3$, and $R^4$ are selected on the basis of the desired groups in the compound of formula (I).

General Scheme 2.

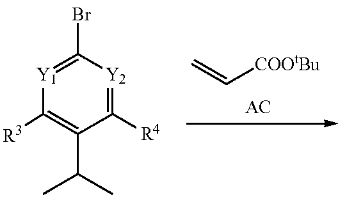

AB

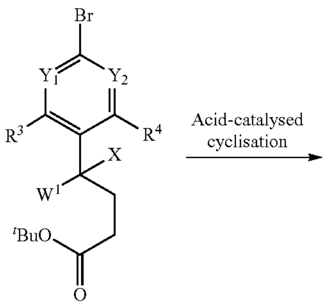

AD

-continued

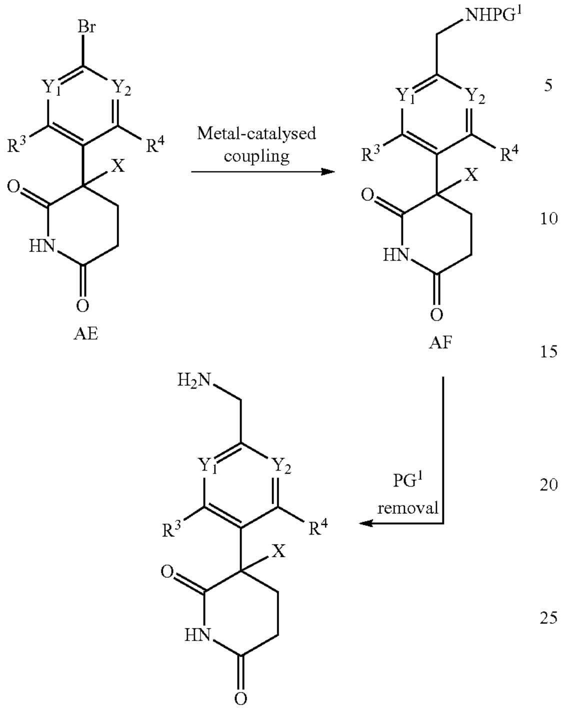

AE AF AA

General Scheme 2 provides an exemplary synthetic procedure for the preparation of starting materials AA used in General Scheme 1. Compound A B, where W1 is an electron-withdrawing group such as a nitrile or an ester, may be converted to a compound of formula AD via a Michael addition reaction with an acrylate of formula AC in the presence of a base (for example, sodium methoxide). Compound AE may be obtained from compound AD via cyclization in acidic medium. A mixture of sulfuric acid in acetic acid may be used at elevated temperature (for example, 90 degrees Celsius). A protected benzylamine of formula AF may be generated from AE via metal-catalysed coupling using a palladium catalyst (for example, Pd(OAc) 2) together with the appropriate potassium trifluoroborate salt. Alternatively, the protected benzylamine may be formed in a two-step process, first by cyanation of AE, then reduction of the cyanide. $PG^1$ is any suitable protecting group that is labile to treatment with acid. Removal of $PG^1$ in the presence of a strong acid such as HCl 2M in EtOAc affords compounds of formula AA. The specific groups $R^3$ and $R^4$ are selected on the basis of the desired groups in the compound of formula (I).

General Scheme 3.

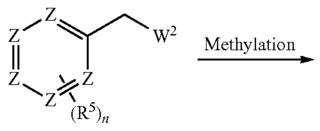

CA

-continued

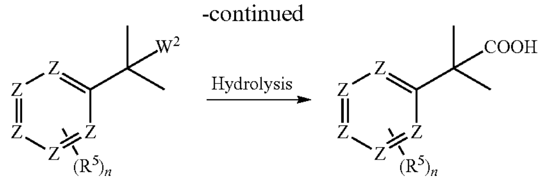

CB CC

General Scheme 3 provides an exemplary synthetic strategy for the preparation of (hetero) cyclic compounds of formula CC, which may be used as starting materials BB in General Scheme 1. Starting from a compound of formula CA, where $W^2$ is a nitrile, ester or carboxylic acid, compounds of formula CB can be obtained via an alkylation reaction with a methylating reagent in the presence of a base. For example, methyl iodide may be used in the presence of sodium hydride, in a solvent such as DMF. Carboxylic acids of formula CC may be obtained via hydrolysis of compound CB in acidic medium. 6 molar HCl may be used as the solvent, and the hydrolysis can be carried out at elevated temperature (for example, 100 degrees Celsius). Z may be N, C—H, or C—$R^5$. $R^5$ is selected on the basis of the desired groups in the compound of formula (I).

General Scheme 4.

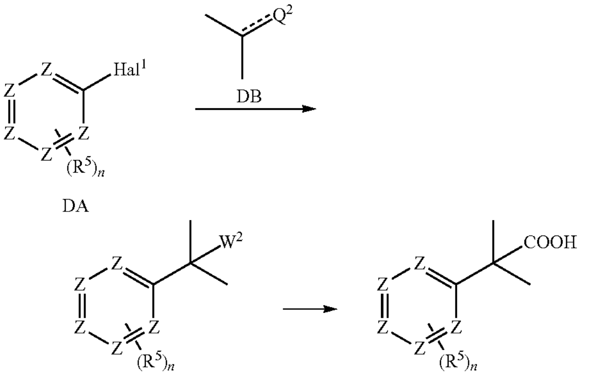

DA DC DD

General Scheme 4 provides an exemplary synthetic strategy for the preparation of (hetero) cyclic compounds of formula DC, which may be used as starting materials BB in General Scheme 1. Starting from a compound of formula DA, where Hall is any suitable halogen (e.g. Cl, Br or I), compounds of formula DC can be obtained via a metal-catalysed coupling reaction with a compound of formula DB, where $Q^2$ is a group such that DB is an α-dimethyl ester, isobutyronitrile, or a silyl ketyl acetal. A palladium catalyst can be used, for example $Pd(P^tBu_3)_2$ in a polar aprotic solvent such as DMF, at elevated temperatures (100 degrees Celsius). Carboxylic acids of formula DD may be obtained via hydrolysis of compound DC in basic medium. A base such as $LiOH*H_2O$ may be used in a solvent mixture such as THF: $H_2O$ 1:1, and the hydrolysis can be carried out at elevated temperature (for example, 100 degrees Celsius). Z may be N, C—H, or C—$R^5$. $R^5$ is selected on the basis of the desired groups in the compound of formula (I).

General Scheme 5.

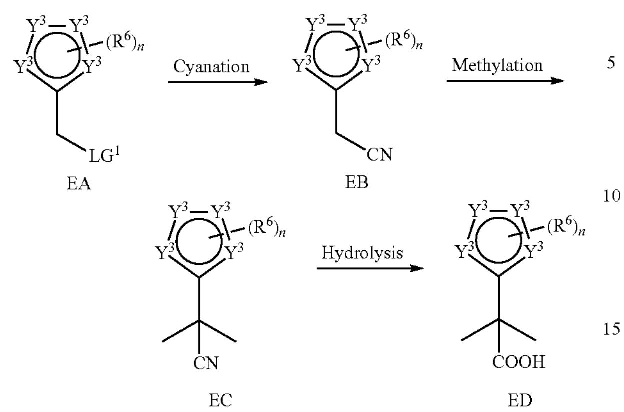

General Scheme 5 provides an exemplary synthetic strategy for the preparation of heterocyclic compounds of formula ED, which may be used as starting materials BB in General Scheme 1. Compounds of formula EB may be obtained from EA via a cyanation reaction. $LG^2$ is any suitable leaving group for nucleophilic substitution reactions (e.g. Cl, Br, I, OMs, OTf) and $Y_3$ may be C—H, C—$R^6$, N, O, or S. Cyanating reagent systems such as TMSCN and TBAF in a polar aprotic solvent (for example, MeCN or THF) may be used. Next, compounds of formula EC may be obtained from EB via an alkylation reaction with a methylating reagent in the presence of a base. For example, methyl iodide may be used in the presence of sodium hydride, in a solvent such as DMF. Carboxylic acids of formula ED may be obtained via hydrolysis of compound EC in acidic medium. 6 molar HCl may be used as the solvent, and the hydrolysis can be carried out at elevated temperature (for example, 60 degrees Celsius). $R^6$ is selected on the basis of the desired groups in the compound of formula (I).

General Scheme 6.

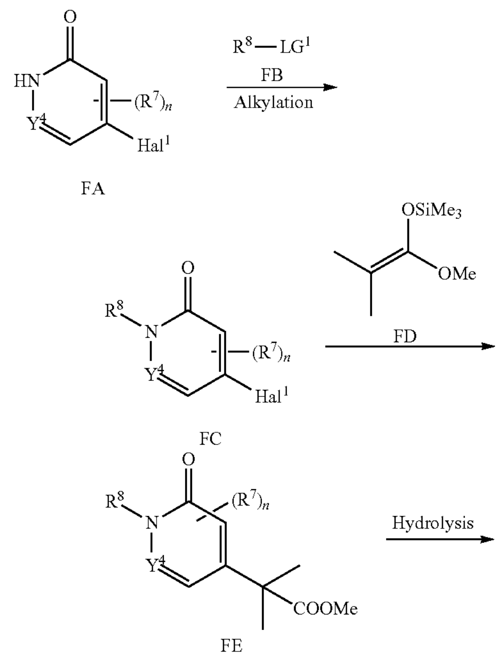

-continued

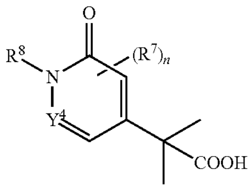

FF

General Scheme 6 provides an exemplary synthetic strategy for the preparation of pyridones or pyridazinones of formula FF, which may be used as starting materials BB in General Scheme 1.

A compound of formula FA may be alkylated with compound FB to afford compounds of formula FC. $LG^1$ is a leaving group suitable for nucleophilic substitution reactions (e.g. Cl, Br, I, OMs, OTf) and $Y_4$ may be C—H, C—$R^7$ or N. The reaction may be carried out in the presence of a base, for example sodium hydride, and in a solvent such as THF. Next, compounds of formula FC may be reacted with intermediate FD under metal-catalysed coupling conditions to afford compounds of formula FE. A palladium catalyst can be used, for example $Pd(P^tBu_3)_2$ in a polar aprotic solvent such as DMF, at elevated temperatures (90 degrees Celsius). Lastly, compounds of formula FE may be hydrolysed in basic medium to afford compounds of formula FF. NaOH may be used as the base in a solvent mixture such as $MeOH{:}H_2O$ 1:1.

General Purification Methods

Purification Method 1:

The residue was purified by Prep-HPLC with a C18 column (type: Phenomenex luna, YMC-Actus Triart, or Welch Xtimate) of the appropriate size. A mobile phase containing a mixture of water (formic acid condition) [Solvent A]and acetonitrile [Solvent B] was used. An appropriate gradient ranging from 0 to 80% of solvent B was applied. The pure compounds were then lyophilized.

Purification Method 2:

The residue was purified by silica gel column chromatography, reversed-phase column chromatography, or prep-TLC (eluting with an appropriate mixture of Petroleum ether and Ethyl acetate for silica gel or acetonitrile and water containing 0.1% formic acid for reversed phase) to afford the desired products.

Exemplary Compound 1

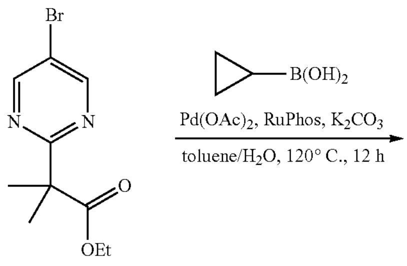

-continued

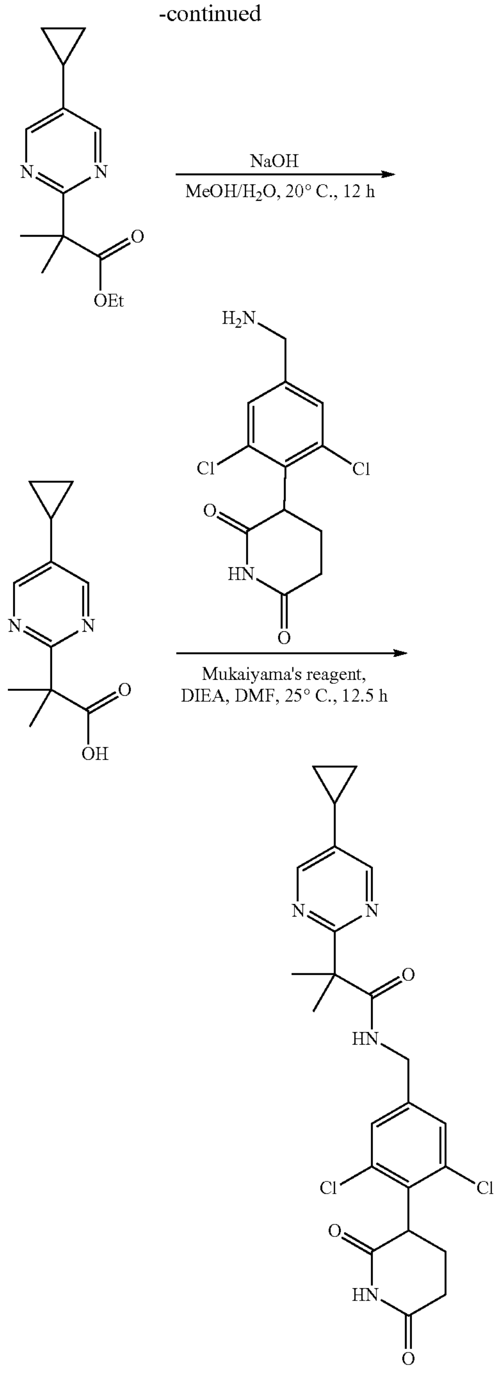

Step 1. To a mixture of ethyl 2-(5-bromopyrimidin-2-yl)-2-methylpropanoate (200 mg, 732 μmol, 1.00 eq.), potassium carbonate (303 mg, 2.20 mmol, 3.00 eq.), palladium (II) acetate (16.4 mg, 73.2 μmol, 0.10 eq.) and 2-dicyclohexylphosphino-2',6'-di-i-propoxy-1,1'-biphenyl (34.1 mg, 73.2 μmol, 0.10 eq.) in toluene (2 mL) and water (0.7 mL) was added cyclopropylboronic acid (125 mg, 1.46 mmol, 2.00 eq.) in portions. The mixture was stirred at 120° C. under nitrogen atmosphere for 12 h. The mixture was cooled to 25° C. then poured into water (20 mL). The mixture was extracted with ethyl acetate (3×20 mL). The combined organic layers were washed with brine (20 mL), dried over anhydrous sodium sulfate, filtered, and the filtrate was concentrated under reduced pressure. The residue was purified via Purification Method 2 to afford ethyl 2-(5-cyclopropylpyrimidin-2-yl)-2-methylpropanoate (150 mg, 512 μmol, 69% yield) as a colourless oil.

Step 2. To a mixture of ethyl 2-(5-cyclopropylpyrimidin-2-yl)-2-methylpropanoate (200 mg, 853 μmol, 1.00 eq.) in methanol (1.5 mL) and water (1.5 mL) was added sodium hydroxide (170 mg, 4.27 mmol, 5.00 eq.) in portions at 20° C. The mixture was stirred at 20° C. for 12 h. The mixture was washed with ethyl acetate (3×10 mL). The aqueous phase was collected, and the pH was adjusted to 2 with 36% aqueous hydrochloric acid, then the mixture was extracted with ethyl acetate (3× 10 mL). The combined organic extracts were washed with brine (10 mL), dried over anhydrous sodium sulfate, filtered, and concentrated under reduced pressure to give 2-(5-cyclopropylpyrimidin-2-yl)-2-methylpropanoic acid (137 mg, 664 μmol, 77% yield) as a white solid.

Step 3. To a mixture of 2-(5-cyclopropylpyrimidin-2-yl)-2-methylpropanoic acid (114 mg, 556 μmol, 1.20 eq.) and 2-chloro-1-methyl-pyridin-1-ium iodide (177 mg, 695 μmol, 1.50 eq.) in dimethylformamide (2 mL) was added diisopropylethylamine (239 mg, 1.85 mmol, 4.00 eq.) dropwise at 25° C. The mixture was stirred at 25° C. for 0.5 h then 3-(4-(aminomethyl)-2,6-dichlorophenyl) piperidine-2,6-dione hydrochloride (150 mg, 463 μmol, 1.00 eq.) was added. The reaction was stirred at 25° C. for 12 h. The mixture was poured into water (50 mL) and extracted with ethyl acetate (3×50 mL). The combined organic layers were washed with brine (50 mL), dried over anhydrous sodium sulfate, filtered, and the filtrate was concentrated under reduced pressure. The residue was purified via Purification Method 1 twice to afford 2-(5-cyclopropylpyrimidin-2-yl)-N-(3,5-dichloro-4-(2,6-dioxopiperidin-3-yl)benzyl)-2-methylpropan-amide (106 mg, 221 μmol, 47% yield) as a white solid.

$^1$H NMR (400 MHZ, DMSO-$d_6$) δ=10.96 (s, 1H), 8.55 (s, 2H), 8.01 (t, J=6.0 Hz, 1H), 7.38 (s, 1H), 7.32 (s, 1H), 4.56 (dd, J=5.6, 12.8 Hz, 1H), 4.24 (d, J=6.0 Hz, 2H), 2.86 (d, J=5.6, 10.0, 16.8 Hz, 1H), 2.56-2.55 (m, 1H), 2.36 (q, J=4.4, 13.2 Hz, 1H), 1.98-1.86-1.84 (m, 2H), 1.52 (s, 6H), 1.06-1.01 (m, 2H), 0.84-0.79 (m, 2H). MS (ESI) m/z 475.2 $[M+H]^+$

Exemplary Compound 2

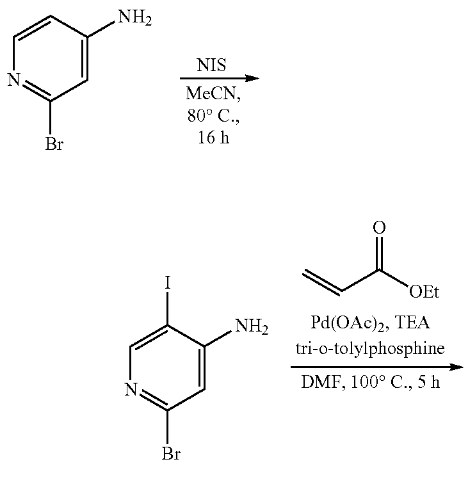

-continued

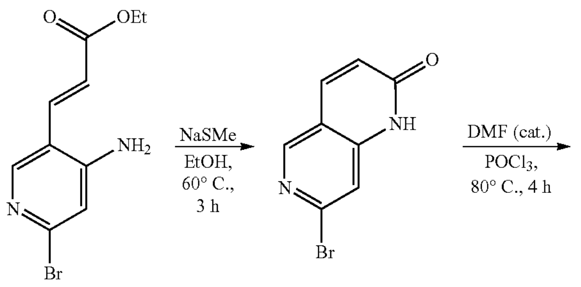

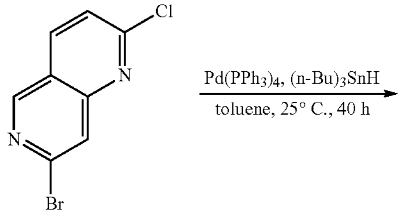

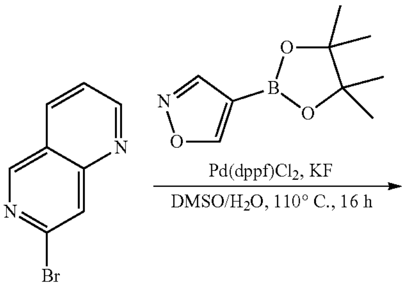

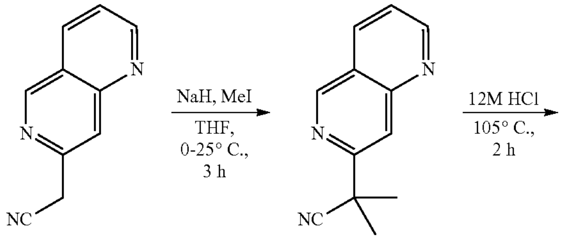

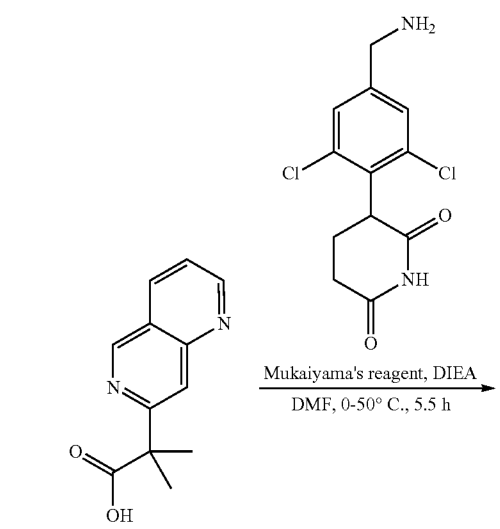

-continued

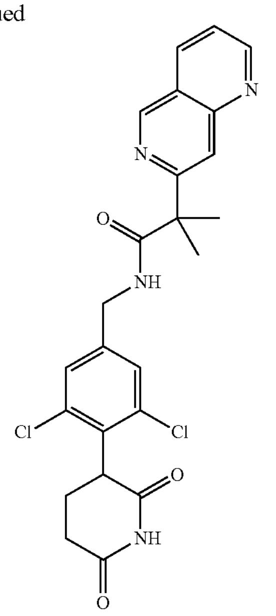

Step 1. To a stirred solution of 2-bromopyridin-4-amine (10.0 g, 57.8 mmol, 1.00 eq.) in acetonitrile (250 mL) was added N-iodosuccinimide (15.6 g, 69.3 mmol, 1.20 eq.). The resulting reaction mixture was stirred at 80° C. for 16 h. The reaction mixture was cooled to 25° C., and concentrated under reduced pressure to give a residue. The residue was diluted with saturated sodium persulfate solution (100 mL), and then extracted with ethyl acetate (5×100 mL). The combined organic layers were dried over anhydrous sodium sulfate, filtered, and concentrated under reduced pressure. The residue was purified via Purification Method 2 to afford 2-bromo-5-iodopyridin-4-amine (7.01 g, 23.2 mmol, 40% yield) as a yellow solid.

Step 2. To a solution of 2-bromo-5-iodopyridin-4-amine (7.00 g, 23.4 mmol, 1.00 eq.) in dimethyl formamide (70 mL) was added ethyl acrylate (5.29 g, 52.8 mmol, 2.26 eq.), palladium acetate (315 mg, 1.41 mmol, 0.06 eq.), triethylamine (4.00 g, 39.5 mmol, 5.5 mL, 1.69 eq.) and tri-o-tolylphosphine (713 mg, 2.34 mmol, 0.10 eq.). The mixture was stirred at 100° C. for 5 h under nitrogen atmosphere. The reaction mixture was cooled to 25° C., diluted with water (100 mL) and extracted with ethyl acetate (8 × 100 mL). The combined organic layers were dried over anhydrous sodium sulfate, filtered, and concentrated under reduced pressure. The residue was purified via Purification Method 2 to afford ethyl(E)-3-(4-amino-6-bromopyridin-3-yl) acrylate (5.70 g, 20.0 mmol, 85% yield) as a yellow solid.

Step 3. To a solution of ethyl(E)-3-(4-amino-6-bromopyridin-3-yl) acrylate (5.70 g, 21.0 mmol, 1.00 eq.) in ethyl alcohol (60 mL) was added sodium methyl mercaptide (3.45 g, 49.2 mmol, 3.1 mL, 2.30 eq.). The mixture was stirred at 60° C. for 3 h. The reaction mixture was cooled to 25° C., diluted with water (30 ml) and then neutralized with 1 N hydrochloric acid to pH 7.0. The solid was filtered, and the filter cake was washed with water (2×50 ml). The filter cake was dried under vacuum to afford 7-bromo-1,6-naphthyridin-2 (1H)-one (3.52 g, 15.5 mmol, 74% yield) as a white solid.

Step 4. To a solution of dimethyl formamide (30.0 mg, 6.22 mmol) in phosphorus oxychloride (90 mL) was added 7-bromo-1,6-naphthyridin-2 (1H)-one (3.52 g, 15.6 mmol, 1.00 eq.). The mixture was stirred at 80° C. for 4 h. The reaction mixture was cooled to 25° C., and concentrated under reduced pressure. The residue was partitioned between ethyl acetate (100 mL) and saturated aqueous sodium bicarbonate solution (100 mL). The aqueous layer was extracted with ethyl acetate (5× 100 mL). The combined organic layers were dried over sodium sulfate, filtered, and concentrated under reduced pressure. The residue was purified via Purification Method 2 to afford 7-bromo-2-chloro-1,6-naphthyridine (3.53 g, 14.3 mmol, 92% yield) as a white solid.

Step 5. To a solution of 7-bromo-2-chloro-1,6-naphthyridine (3.83 g, 15.7 mmol, 1.00 eq.) in toluene (150 mL) was added tetrakis [triphenylphosphine]palladium (0) (2.36 g, 2.05 mmol, 0.13 eq.) and tributylstannane (4.74 g, 16.3 mmol, 4.32 mL, 1.04 eq.). The mixture was stirred at 25° C. for 40 h under nitrogen atmosphere. The reaction mixture was concentrated under reduced pressure. The residue was quenched by addition of saturated aqueous potassium fluoride (100 mL) and diluted with ethyl acetate (100 mL). The mixture was stirred at 25° C. for 0.5 h, then filtered and extracted with ethyl acetate (5× 100 mL). The combined organic layers were dried over anhydrous sodium sulfate, filtered, and concentrated under reduced pressure. The residue was purified via Purification Method 2 to afford 7-bromo-1,6-naphthyridine (2.01 g, 8.65 mmol, 55% yield) as a yellow solid.

Step 6. To a solution of 7-bromo-1,6-naphthyridine (1.00 g, 4.78 mmol, 1.00 eq.) and 4-(4,4,5,5-tetramethyl-1,3,2-dioxaborolan-2-yl) isoxazole (1.40 g, 7.18 mmol, 1.50 eq.) in dimethylsulfoxide (30 mL) and water (15 mL) were added potassium fluoride (833 mg, 14.3 mmol, 3.00 eq.) and [1,1'-bis(diphenylphosphino)ferrocene]dichloropalladium (II) (350 mg, 478 μmol, 0.10 eq.). The reaction was stirred at 110° C. for 16 h under nitrogen atmosphere. The reaction mixture was cooled to 25° C., diluted with water (100 mL), filtered through diatomite, and washed with ethyl acetate (200 mL). The mixture was extracted with ethyl acetate (6×100 mL). The combined organic layers were dried over anhydrous sodium sulfate, filtered, and concentrated in vacuo to give a residue. The residue was purified via Purification Method 2 to afford 2-(1,6-naphthyridin-7-yl) acetonitrile (390 mg, 2.19 mmol, 46% yield) as a yellow solid.

Step 7. To a solution of 2-(1,6-naphthyridin-7-yl) acetonitrile (390 mg, 2.19 mmol, 1.00 eq.) in tetrahydrofuran (20 mL) was added sodium hydride (239 mg, 5.99 mmol, 60% purity, 2.62 eq.) at 0° C. After addition, the mixture was stirred at 0° C. for 0.5 h, and then iodomethane (1.76 g, 12.4 mmol, 0.7 mL, 5.44 eq.) in tetrahydrofuran (2 mL) was added dropwise at 0° C. The reaction was stirred at 25° C. for 2.5 h under nitrogen atmosphere. The reaction mixture was quenched with water (20 mL) and extracted with ethyl acetate (6×20 mL). The combined organic layers were dried over anhydrous sodium sulfate, filtered, and concentrated under reduced pressure. The residue was purified via Purification Method 2 to afford 2-methyl-2-(1,6-naphthyridin-7-yl) propanenitrile (334 mg, 1.68 mmol, 73% yield) as a white solid.

Step 8. A mixture of 2-methyl-2-(1,6-naphthyridin-7-yl) propanenitrile (330 mg, 1.67 mmol, 1.00 eq.) in hydrochloric acid (12 M, 20 mL) was stirred at 105° C. for 2 h. The reaction mixture was concentrated under reduced pressure. The residue was purified via Purification Method 1 to afford 2-methyl-2-(1,6-naphthyridin-7-yl) propanoic acid (310 mg, 1.42 mmol, 42% yield) as a yellow solid.

Step 9. To a solution of 2-methyl-2-(1,6-naphthyridin-7-yl) propanoic acid (133 mg, 618 μmol, 2.50 eq.) in dimethyl formamide (4.0 mL) were added N,N-diisopropylethylamine (95.8 mg, 742 μmol, 3.00 eq.) and 2-chloro-1-methyl-pyridin-1-ium iodide (94.7 mg, 371 μmol, 1.50 eq.) at 0° C.

After addition, the mixture was stirred at 20° C. for 30 min, and then 3-[4-(aminomethyl)-2,6-dichloro-phenyl]piperidine-2,6-dione hydrochloride (80 mg, 247 μmol, 1.00 eq.) was added. The reaction was stirred at 50° C. for 5 h. The mixture was diluted with water (20 mL) and extracted with ethyl acetate (5×20 mL). The organic layers were dried over sodium sulfate, filtered, and concentrated under reduced pressure. The residue was purified via Purification Method I to afford N-(3,5-dichloro-4-(2,6-dioxopiperidin-3-yl)benzyl)-2-methyl-2-(1,6-naphthyridin-7-yl) propanamide (17.3 mg, 35.3 μmol, 14% yield) as a white solid.

$^1$H NMR (400 MHZ, DMSO-$d_6$)>=10.93 (s, 1H), 9.41 (s, 1H), 9.12 (dd, J=1.6, 4.4 Hz, 1H), 8.59 (d, J=8.4 Hz, 1H), 7.93 (t, J=6.4 Hz, 1H), 7.89 (s, 1H), 7.68 (dd, J=4.4, 8.4 Hz, 1H), 7.29 (s, 1H), 7.22 (s, 1H), 4.53 (dd, J=5.6, 12.8 Hz, 1H), 4.23 (d, J=6.0 Hz, 2H), 2.89-2.79 (m, 1H), 2.58-2.53 (m, 1H), 2.36-2.27 (m, 1H), 1.92-1.83 (m, 1H), 1.64 (s, 6H). MS (ESI) m/z 507.2 $[M+Na]^+$

Exemplary Compound 4

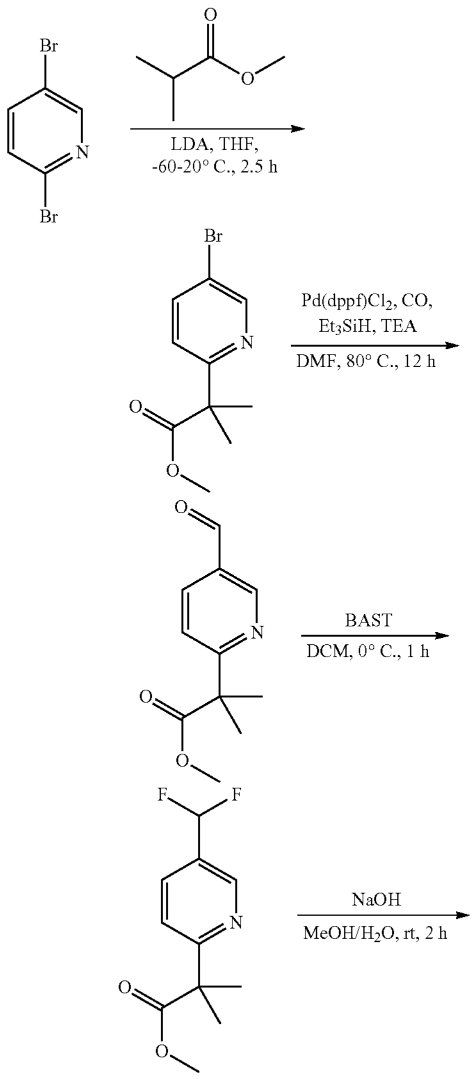

-continued

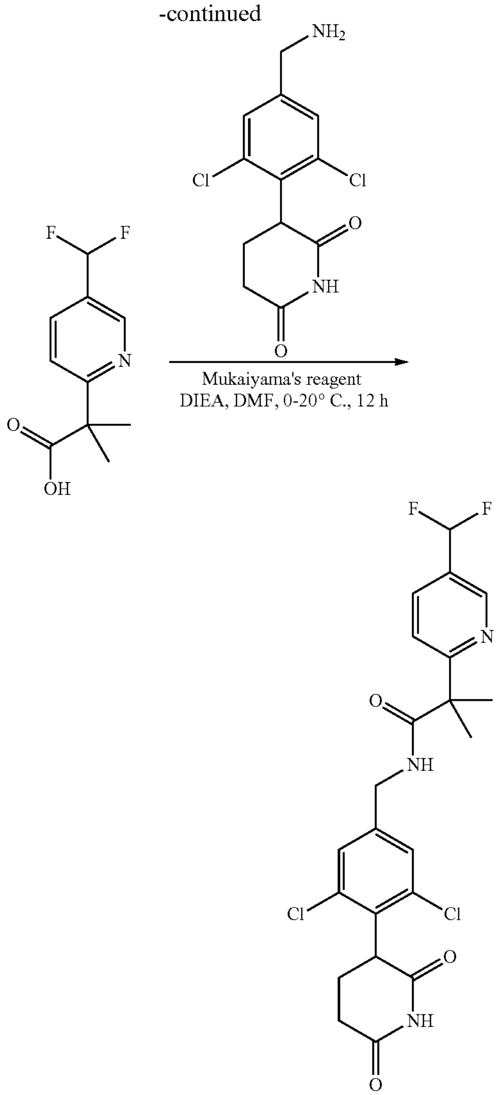

Step 1. To a solution of methyl 2-methylpropanoate (1.30 g, 12.7 mmol, 1.50 eq.) in tetrahydrofuran (5 mL) was added lithium diisopropyl amide (2 M in tetrahydrofuran, 6.33 mL, 1.50 eq.) at −60° C. under nitrogen atmosphere. It was stirred at −60° C. for 30 min. Then a solution of 2,5-dibromopyridine (2.00 g, 8.44 mmol, 1.00 eq.) in tetrahydrofuran (20 mL) was added to the mixture at −60° C. under nitrogen atmosphere. It was stirred at 20° C. for 2 h. The reaction was quenched with saturated ammonium chloride (18 mL) at 0° C. The reaction mixture was diluted with ethyl acetate (30 mL) and water (15 mL). The layers were separated, and the aqueous phase was extracted with ethyl acetate (20 mL). The combined organic layers were washed with brine (30 mL) and dried over anhydrous sodium sulfate, filtered, and concentrated in vacuo. The residue was purified via Purification Method 2 to afford methyl 2-(5-bromopyridin-2-yl)-2-methylpropanoate (1.89 g, 6.59 mmol, 78% yield, 90% purity) as a colourless oil.

Step 2. To a solution of methyl 2-(5-bromopyridin-2-yl)-2-methylpropanoate (1.00 g, 3.87 mmol, 1.00 eq.) in dimethyl formamide (4 mL) were added triethylamine (11.6 mmol, 1.62 mL, 3.00 eq.) and [1,1'-bis(diphenylphosphino)ferrocene]dichloropalladium (II) (142 mg, 194 μmol, 0.05 eq.). The reaction was stirred under carbon monoxide (2.5 bar) at 80° C. for 12 h. The reaction mixture was cool to room temperature, then it was diluted with ethyl acetate (50 mL) and water (40 mL). The layers were separated, and the aqueous phase was extracted with ethyl acetate (2x30 mL). Combined extracts were washed with brine (15 mL), and dried over anhydrous sodium sulfate, filtered, and concentrated in vacuo. The residue was purified via Purification Method 2 to afford methyl 2-(5-formylpyridin-2-yl)-2-methylpropanoate (350 mg, 1.52 mmol, 39% yield, 90% purity) as a colourless oil.

Step 3. To a solution of methyl 2-(5-formylpyridin-2-yl)-2-methylpropanoate (350 mg, 1.69 mmol, 1.00 eq.) in dichloromethane (4 mL) was added (bis-(2-methoxyethyl) amino) sulfur trifluoride (3.38 mmol, 740 μL, 2.00 eq.) at 0° C. under nitrogen. The reaction was stirred at 0° C. for 2 h. The reaction mixture was quenched by addition saturated sodium bicarbonate (15 mL) and extracted with ethyl acetate (3x25 mL). The combined organic layers were dried over anhydrous sodium sulfate, filtered, and concentrated under reduced pressure. The residue was purified via Purification Method 2 to afford methyl 2-(5-(difluoromethyl)pyridin-2-yl)-2-methylpropanoate (250 mg, 981 μmol, 58% yield, 90% purity) as a colourless oil.

Step 4. To a solution of methyl 2-(5-(difluoromethyl) pyridin-2-yl)-2-methylpropanoate (250 mg, 1.09 mmol, 1.00 eq.) in methanol (4 mL) was added a solution of sodium hydroxide (218 mg, 5.45 mmol, 5.00 eq.) in water (4 mL). It was stirred at 20° C. for 2.5 h. The pH of the reaction mixture was adjusted to 6 with 2 M hydrochloric acid at 0° C. Then it was diluted with water and lyophilized to give 2-(5-(difluoromethyl)pyridin-2-yl)-2-methylpropanoic acid (400 mg, crude) as a white solid.

Step 5. To a solution of 2-(5-(difluoromethyl)pyridin-2-yl)-2-methylpropanoic acid (200 mg, crude) in dimethyl formamide (6 mL) was added N,N-diisopropylethylamine (1.86 mmol, 323 μL, 5.00 eq.) and 2-chloro-1-methyl-pyridinium iodide (114 mg, 446 μmol, 1.20 eq.) at 0° C. The reaction was stirred at 20° C. for 5 h. Then 3-(4-(aminomethyl)-2,6-dichlorophenyl) piperidine-2,6-dione hydrochloride (120 mg, 372 μmol, 1.00 eq.) was added to the mixture. It was stirred at 20° C. for 15 h. The mixture was diluted with ethyl acetate (35 mL) and water (40 mL). The layers were separated, and the aqueous phase was extracted with ethyl acetate (2x30 mL). The combined organic layers were washed with brine (30 mL), and dried over anhydrous sodium sulfate, filtered, and concentrated in vacuo. The residue was purified via Purification Method I to afford N-(3,5-dichloro-4-(2,6-dioxopiperidin-3-yl)benzyl)-2-(5-(difluoromethyl)pyridin-2-yl)-2-methylpropanamide (89.17 mg, 184 μmol, 49% yield) as a white solid.

Exemplary Compound 5

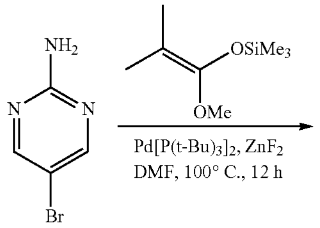

-continued

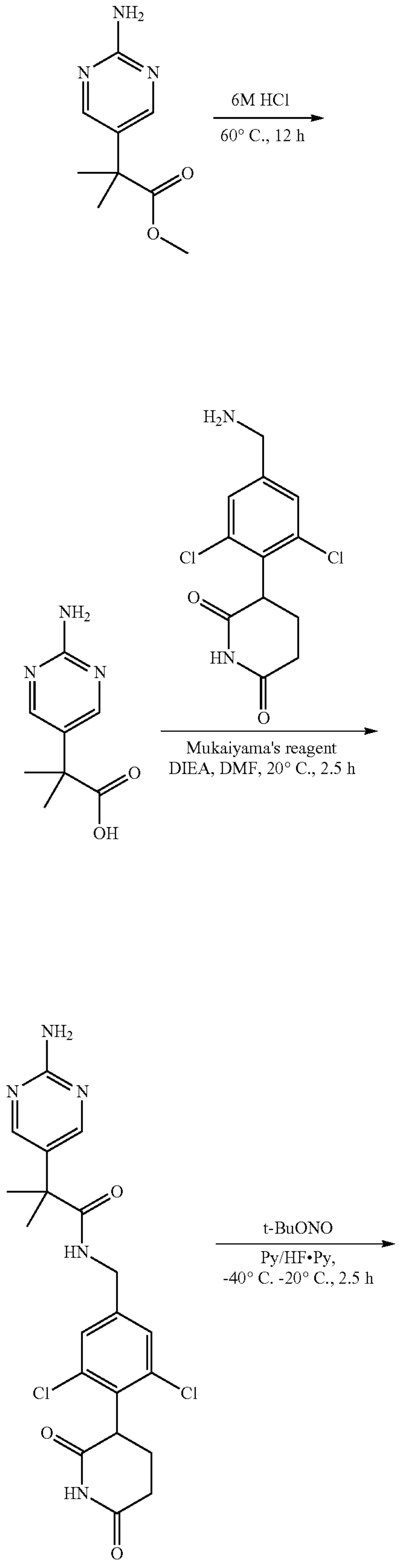

-continued

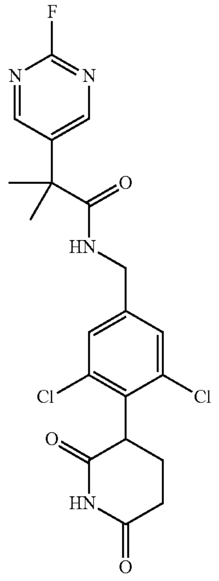 [SMILES: CC(C)(C(=O)NCc1cc(Cl)c(C2CCC(=O)NC2=O)c(Cl)c1)c1cnc(F)nc1]

Step 1. To a solution of 5-bromopyrimidin-2-amine (2.00 g, 11.5 mmol, 1.00 eq.) in N,N-dimethylformamide (20 mL) were added ((1-methoxy-2-methylprop-1-en-1-yl)oxy)trimethylsilane (4.01 g, 23.0 mmol, 2.00 eq.), difluorozine (1.19 g, 11.5 mmol, 1.00 eq.) and bis(tri-tert-butylphosphine) palladium (0) (587 mg, 1.15 mmol, 0.10 eq.). The mixture was stirred at 100° C. under nitrogen atmosphere for 12 h. The mixture was diluted with water (50 mL) and extracted with ethyl acetate (50 mL). The combined organic layers were washed with water (2× 50 mL), dried over sodium sulfate, filtered, and concentrated under reduced pressure. The residue was purified via Purification Method 2 to afford methyl 2-(2-aminopyrimidin-5-yl)-2-methylpropanoate (200 mg, 1.01 mmol, 9% yield) as a white solid.

Step 2. A solution of methyl 2-(2-aminopyrimidin-5-yl)-2-methylpropanoate (100 mg, 512 μmol, 1.00 eq.) in hydrochloric acid (6 M, 5 mL) was stirred at 60° C. for 12 h. The mixture was concentrated to give 2-(2-aminopyrimidin-5-yl)-2-methylpropanoic acid hydrochloride (110 mg, crude) as a white solid, and it was used into next step directly.

Step 3. To a solution of 2-(2-aminopyrimidin-5-yl)-2-methylpropanoic acid hydrochloride (130 mg, crude) in N,N-dimethylformamide (5 mL) were added 2-chloro-1-methyl-pyridin-1-ium iodide (183 mg, 717 μmol, 1.20 eq.) and N,N-diisopropylethylamine (2.99 mmol, 520 μL, 5.00 eq.). The mixture was stirred at 20° C. for 0.5 h. Then 3-(4-(aminomethyl)-2,6-dichlorophenyl) piperidine-2,6-dione hydrochloride (150 mg, 464 μmol, 0.77 eq.) was added to the mixture. The mixture was stirred at 20 for 12 h. The mixture was filtered and concentrated under reduced pressure to give a residue. It was purified via Purification Method 1 to afford 2-(2-aminopyrimidin-5-yl)-N-(3,5-dichloro-4-(2,6-dioxopiperidin-3-yl)benzyl)-2-methylpropanamide (110 mg, 232 μmol, 39% yield) as a white solid.

Step 4. A solution of 2-(2-aminopyrimidin-5-yl)-N-(3,5-dichloro-4-(2,6-dioxopiperidin-3-yl)benzyl)-2-methylpropanamide (140 mg, 311 μmol, 1.00 eq.) in pyridine (5 mL) was cooled to −40° C. Then pyridine hydrofluoride (5 mL, 70% purity) was added to the mixture. The mixture was stirred at −40° C. for 0.5 h. Then tert-butyl nitrite (64.1 mg, 622 μmol, 2.00 eq.) was added to the mixture. The mixture was stirred at 20° C. for 2 h. The mixture was diluted with water (20 mL) and extracted with ethyl acetate (20 mL). The combined organic layers were washed with water (2× 20 L), dried over sodium sulfate, filtered, and concentrated under reduced pressure. The residue was purified via Purification Method 1 to afford N-(3,5-dichloro-4-(2,6-dioxopiperidin-3-yl)benzyl)-2-(2-fluoropyrimidin-5-yl)-2-methylpropanamide (23.67 mg, 51.2 μmol, 16% yield) as a white solid.

$^1$H NMR (400 MHZ, DMSO-$d_6$) δ=10.97 (s, 1H), 8.76 (d, J=1.6 Hz, 2H), 8.22 (t, J=5.6 Hz, 1H), 7.26 (d, J=1.2 Hz, 1H), 7.20 (s, 1H), 4.57 (dd, J=5.6, 12.8 Hz, 1H), 4.23 (d, J=5.6 Hz, 2H), 2.95-2.79 (m, 1H), 2.55 (m, 1H), 2.35 (dq, J=4.4, 13.2 Hz, 1H), 1.97-1.83 (m, 1H), 1.59 (s, 6H). MS (ESI) m/z 453.1 [M+H]$^+$

Exemplary Compound 6

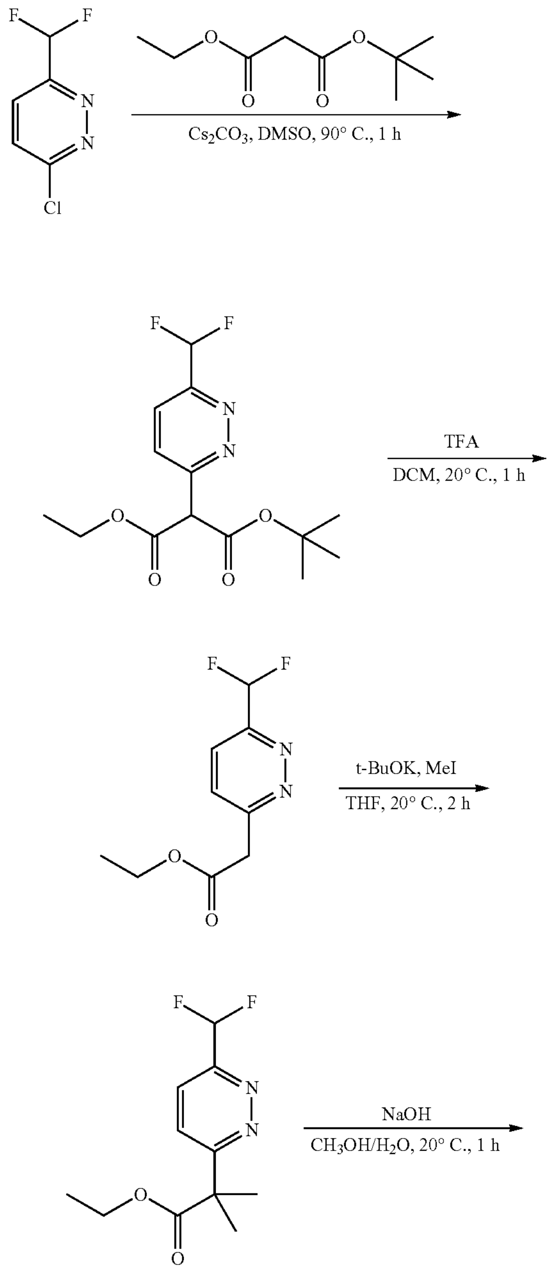

-continued

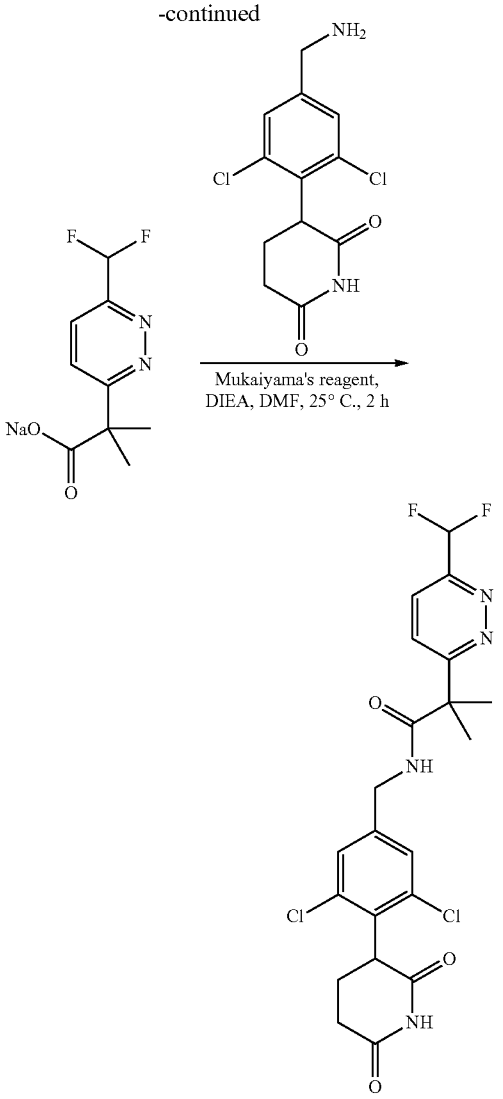

Step 1. To a solution of tert-butyl ethyl malonate (343 mg, 1.82 mmol, 1.50 eq.) in dimethylsulfoxide (8 mL) were added caesium carbonate (792 mg, 2.43 mmol, 2.00 eq.) and 3-chloro-6-(difluoromethyl)pyridazine (200 mg, 1.22 mmol, 1.00 eq.) in portions at 20° C. The mixture was stirred at 90° C. for 1 h. The mixture was cooled to 25° C., and filtered. The filtrate was quenched with water (50 mL) then extracted with ethyl acetate (3×50 mL). The combined organic layers were washed with brine (50 mL), dried over anhydrous sodium sulfate, filtered, and the filtrate was concentrated under reduced pressure. The residue was purified via Purification Method 2 to afford 1-(tert-butyl) 3-ethyl 2-(6-(difluoromethyl)pyridazin-3-yl) malonate (371 mg, 938 μmol, 77% yield) as a yellow oil.

Step 2. To a solution of 1-(tert-butyl) 3-ethyl 2-(6-(difluoromethyl)pyridazin-3-yl) malonate (407 mg, 1.29 mmol, 1.00 eq.) in dichloromethane (5 mL) was added trifluoroacetic acid (5 mL) dropwise at 20° C. The mixture was stirred at 20° C. for 1 h. The reaction was quenched with saturated aqueous sodium bicarbonate (50 mL) and extracted with ethyl acetate (3×50 mL). The combined organic layers were washed with brine (50 mL), dried over anhydrous sodium sulfate, filtered, and the filtrate was concentrated under reduced pressure. The residue was purified via Purification Method 2 to afford ethyl 2-(6-(difluoromethyl)pyridazin-3-yl)acetate (204 mg, 849 μmol, 66% yield) as a yellow solid.

Step 3. To a mixture of ethyl 2-(6-(difluoromethyl) pyridazin-3-yl)acetate (104 mg, 481 μmol, 1.00 eq.) and potassium 2-methylpropan-2-olate (1 M in tetrahydrofuran, 1.44 mL, 3.00 eq.) in tetrahydrofuran (1 mL) was added iodomethane (682 mg, 4.81 mmol, 10.0 eq.) dropwise at 20° C. The mixture was stirred at 20° C. for 2 h. The mixture was poured into water (10 mL) and extracted with ethyl acetate (3×10 mL). The combined organic layers were washed with brine (10 mL), dried over anhydrous sodium sulfate, filtered, and the filtrate was concentrated under reduced pressure. The residue was purified via Purification Method 2 to afford ethyl 2-(6-(difluoromethyl)pyridazin-3-yl)-2-methylpropanoate (105 mg, 429 μmol, 89% yield) as a yellow oil.

Step 4. To a mixture of ethyl 2-(6-(difluoromethyl) pyridazin-3-yl)-2-methylpropanoate (65.0 mg, 266 μmol, 1.00 eq.) in methanol (0.5 mL) and water (0.5 mL) was added sodium hydroxide (53.2 mg, 1.33 mmol, 5.00 eq.) in portions at 20° C. The mixture was stirred at 20° C. for 1 h. The mixture was poured into water (10 mL) and extracted with ethyl acetate (3×10 mL). The aqueous phase was collected and lyophilized to afford sodium 2-(6-(difluoromethyl)pyridazin-3-yl)-2-methylpropanoate (100 mg, crude) as a white solid.

Step 5. To a mixture of sodium 2-(6-(difluoromethyl) pyridazin-3-yl)-2-methylpropanoate (100 mg, 125 μmol, 1.00 eq.) and 2-chloro-1-methyl-pyridin-1-ium; iodide (38.6 mg, 151 μmol, 1.20 eq.) in dimethyl formamide (1 mL) was added diisopropylethylamine (48.8 mg, 377 μmol, 3.00 eq.) dropwise at 25° C. The reaction was stirred at 25° C. for 0.5 h, then 3-(4-(aminomethyl)-2,6-dichlorophenyl) piperidine-2,6-dione (40.7 mg, 125 μmol, 1.00 eq., hydrochloride) was added and the reaction was stirred at 25° C. for 1.5 h. The mixture was poured into water (10 mL) and extracted with ethyl acetate (3× 10 mL). The combined organic layers were washed with brine (10 mL), dried over anhydrous sodium sulfate, filtered, and the filtrate was concentrated under reduced pressure. The residue was purified via Purification Method 1 twice to afford N-(3,5-dichloro-4-(2,6-dioxopiperidin-3-yl)benzyl)-2-(6-(difluoromethyl)pyridazin-3-yl)-2-methylpropanamide (6.32 mg, 12.8 μmol, 10% yield) as a white solid.

$^1$H NMR (400 MHZ, DMSO-$d_6$) δ=10.95 (s, 1H), 8.26 (t, J=6.0 Hz, 1H), 8.03-7.95 (m, 1H), 7.93-7.86 (m, 1H), 7.44-7.09 (m, 3H), 4.55 (dd, J=5.6, 12.8 Hz, 1H), 4.24 (d, J=6.0 Hz, 2H), 2.91-2.79 (m, 1H), 2.59-2.52 (m, 1H), 2.40-2.28 (m, 1H), 1.93-1.83 (m, 1H), 1.64 (s, 6H). MS (ESI) m/z 485.2 $[M+H]^+$

Exemplary Compound 7

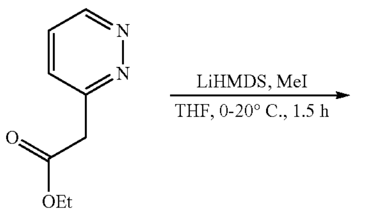

-continued

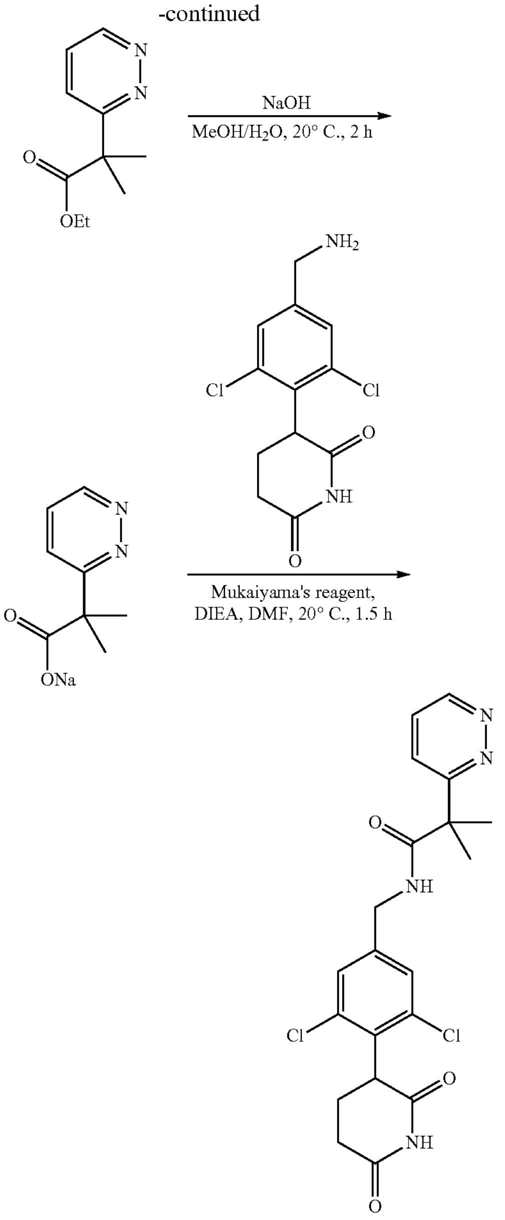

Step 1. To a solution of ethyl 2-(pyridazin-3-yl)acetate (570 mg, 3.43 mmol, 1.00 eq.) in tetrahydrofuran (5 mL) was added lithium bis(trimethylsilyl)amide (1 M in tetrahydrofuran, 10.2 mL, 3.00 eq.) dropwise at 0° C. under nitrogen atmosphere. The mixture was stirred at 0° C. for 0.5 h then iodomethane (2.43 g, 17.1 mmol, 5.00 eq.) was added dropwise at 0° C. The reaction was stirred at 20° C. for 1 h under nitrogen atmosphere, then it was poured into saturated aqueous ammonium chloride (20 mL). The mixture was extracted with ethyl acetate (3× 20 mL). The combined organic layers were washed with brine (10 mL), dried over anhydrous sodium sulfate, filtered, and the filtrate was concentrated under reduced pressure. The residue was purified via Purification Method 2 to afford ethyl 2-methyl-2-(pyridazin-3-yl) propanoate (590 mg, 2.95 mmol, 85% yield) as a brown liquid.

Step 2. To a solution of ethyl 2-methyl-2-(pyridazin-3-yl) propanoate (590 mg, 3.04 mmol, 1.00 eq.) in methanol (3 mL) and water (3 mL) was added sodium hydroxide (607 mg, 15.1 mmol, 5.00 eq.) in one portion at 20° C. The reaction was stirred at 20° C. for 2 h. The mixture was poured into water (10 mL) and adjusted to pH 8-9 with 36% aqueous hydrochloric acid, then lyophilized to give sodium 2-methyl-2-(pyridazin-3-yl) propanoate (1.18 g, 2.63 mmol, 42% purity, 86% yield) as a white solid.

Step 3. To a solution of sodium 2-methyl-2-(pyridazin-3-yl) propanoate (58.1 mg, 309 μmol, 1.00 eq.) and 2-chloro-1-methyl-pyridin-1-1 μm;iodide (94.7 mg, 370 μmol, 1.20 eq.) in dimethyl formamide (1 mL) was added diisopropylethylamine (119 mg, 927 μmol, 3.00 eq.) dropwise at 20° C. The mixture was stirred at 20° C. for 0.5 h, then 3-(4-(aminomethyl)-2,6-dichlorophenyl) piperidine-2,6-dione (100 mg, 309 μmol, 1.00 eq., hydrochloride) was added. The reaction was stirred at 20° C. for 1 h. The mixture was poured into water (20 mL) and extracted with ethyl acetate (3x20 mL). The combined organic layers were washed with brine (10 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-methyl-2-(pyridazin-3-yl) propanamide (58.2 mg, 132 μmol, 42% yield) as a white solid.

$^1H$ NMR (400 MHZ, DMSO-$d_6$) δ=10.96 (s, 1H), 9.15 (t, J=3.2 Hz, 1H), 8.22 (t, J=6.0 Hz, 1H), 7.65 (d, J=3.2 Hz, 2H), 7.27 (d, J=1.2 Hz, 1H), 7.20 (s, 1H), 4.55 (dd, J=5.6, 12.8 Hz, 1H), 4.23 (d, J=6.0 Hz, 2H), 2.93-2.77 (m, 1H), 2.60-2.53 (m, 1H), 2.40-2.30 (m, 1H), 1.94-1.83 (m, 1H), 1.61 (s, 6H). MS (ESI) m/z 435.1 $[M+H]^+$

-continued

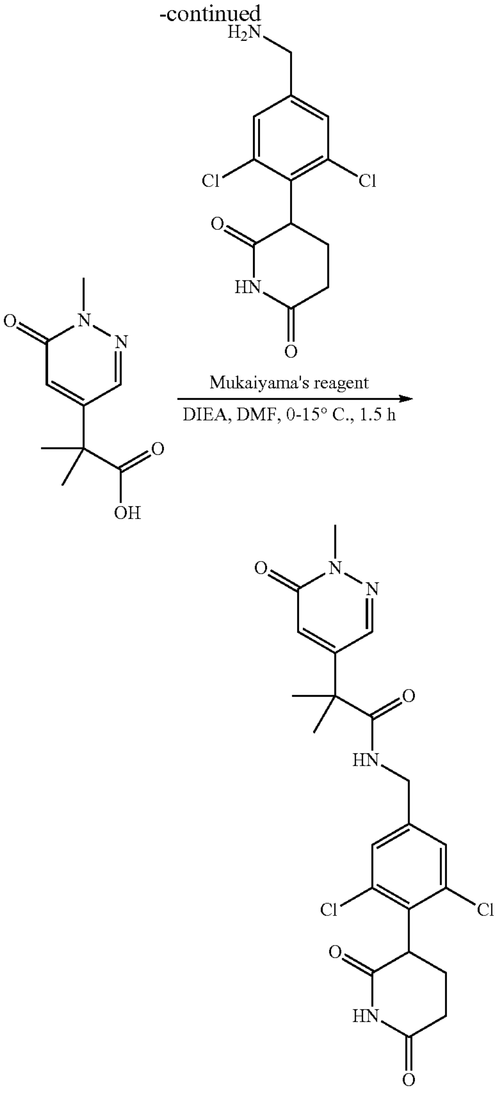

Exemplary Compound 9

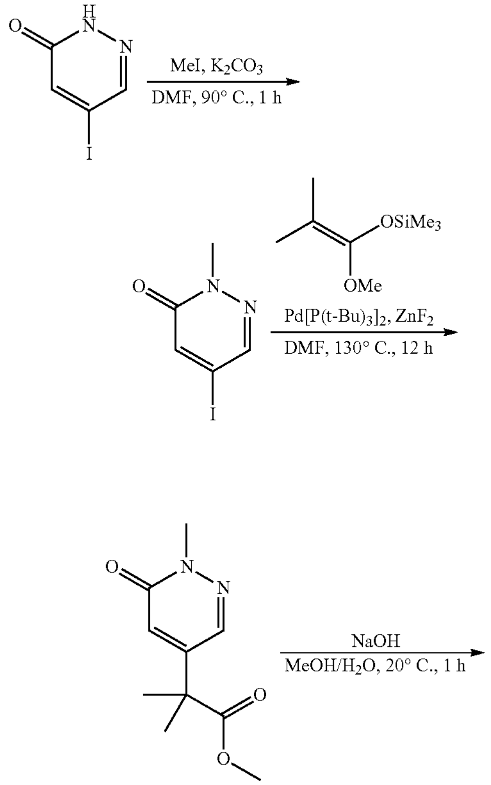

Step 1. To a solution of 5-iodopyridazin-3 (2H)-one (1.55 g, 6.98 mmol, 1.00 eq.) in N,N-dimethylformamide (15 mL) were added potassium carbonate (1.93 g, 14.0 mmol, 2.00 eq.) and iodomethane (7.71 mmol, 480 μL, 1.10 eq.). The mixture was stirred at 90° C. for 1 h. After cooling to 15° C., the mixture was filtered, and the filtrate was concentrated under reduced pressure. The residue was purified via Purification Method 2 to afford 5-iodo-2-methylpyridazin-3 (2H)-one (1.40 g, 5.58 mmol, 80% yield) as off-white solid.

Step 2. To a solution of 5-iodo-2-methylpyridazin-3 (2H)-one (1.40 g, 5.93 mmol, 1.00 eq.) and ((1-methoxy-2-methylprop-1-en-1-yl)oxy)trimethylsilane (1.61 g, 9.24 mmol, 1.56 eq.) in N,N-dimethylformamide (2 mL) were added bis(tri-tert-butylphosphine) palladium (0) (350 mg, 685 μmol, 0.11 eq.) and zinc (II) fluoride (700 mg, 6.77 mmol, 1.14 eq.). The reaction was stirred at 130° C. for 12 h under nitrogen atmosphere. The mixture was filtered through a pad of Celite, and the filter cake was washed with dichloromethane (5 mL) and methanol (5 mL). The filtrate was concentrated under reduced pressure. The crude product was purified via Purification Method 2 then Purification Method 1 to afford methyl 2-methyl-2-(1-methyl-6-oxo-1,6-dihydropyridazin-4-yl) propanoate (130 mg, 606 μmol, 10% yield) as a yellow oil.

Step 3. To a solution of methyl 2-methyl-2-(1-methyl-6-oxo-1,6-dihydropyridazin-4-yl) propanoate (120 mg, 571 μmol, 1.00 eq.) in methanol (2 mL) was added a solution of sodium hydroxide (229 mg, 5.73 mmol, 10.0 eq.) in water (2 mL). The mixture was stirred at 20° C. for 1 h. The mixture was adjusted to pH 2 with 2 M hydrochloric acid. The mixture was extracted with dichloromethane (2×20 mL). The combined organic layers were dried over sodium sulfate, filtered, and concentrated under reduced pressure to give 2-methyl-2-(1-methyl-6-oxo-1,6-dihydropyridazin-4-yl) propanoic acid (90.0 mg, 427 μmol, 75% yield,) as a white solid.

Step 4. To a solution of 2-methyl-2-(1-methyl-6-oxo-1,6-dihydropyridazin-4-yl) propanoic acid (40.0 mg, 204 μmol, 1.00 eq.) in N,N-dimethylformamide (2 mL) were added 2-chloro-1-methylpyridin-1-ium iodide (79.0 mg, 309 μmol, 1.52 eq.) and N-ethyl-N-isopropylpropan-2-amine (861 μmol, 150 μL, 4.22 eq.) at 0° C. The mixture was stirred at 15° C. for 0.5 h. Then 3-(4-(aminomethyl)-2,6-dichlorophenyl) piperidine-2,6-dione hydrochloride (66.0 mg, 204 μmol, 1.00 eq.) was added. The reaction was stirred at 15° C. for 1 h. The mixture was diluted with water (20 mL). The mixture was extracted with dichloromethane (2×20 mL). The combined organic layers were washed with water (2×30 mL) followed by brine (20 mL), dried over sodium sulfate, filtered, and concentrated under reduced pressure. The crude product was purified via Purification Method 2 to afford N-(3,5-dichloro-4-(2,6-dioxopiperidin-3-yl)benzyl)-2-methyl-2-(1-methyl-6-oxo-1,6-dihydropyridazin-4-yl) propanamide (83.4 mg, 179 μmol, 88% yield) as a white solid.

$^1$H NMR (400 MHZ, DMSO-$d_6$) δ=10.96 (s, 1H), 8.24 (t, J=5.6 Hz, 1H), 7.76 (d, J=2.0 Hz, 1H), 7.26 (s, 1H), 7.19 (s, 1H), 6.78 (d, J=2.0 Hz, 1H), 4.56 (dd, J=5.6, 12.8 Hz, 1H), 4.23 (d, J=5.6 Hz, 2H), 3.62 (s, 3H), 2.90-2.80 (m, 1H), 2.58-2.52 (m, 1H), 2.40-2.30 (m, 1H), 1.95-1.82 (m, 1H), 1.45 (s, 6H). MS (ESI) m/z 465.3 $[M+H]^+$

Exemplary Compound 10

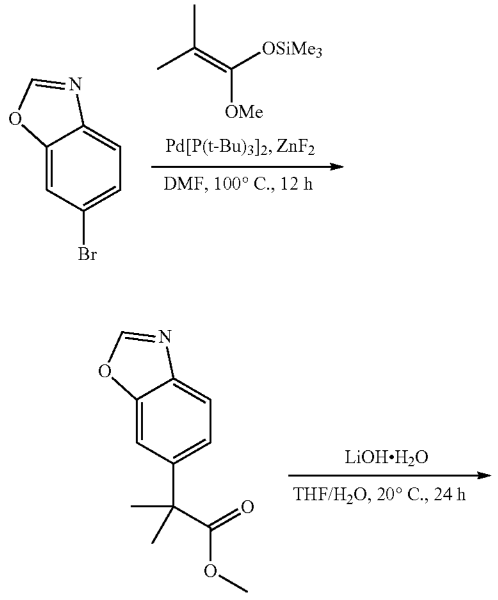

-continued

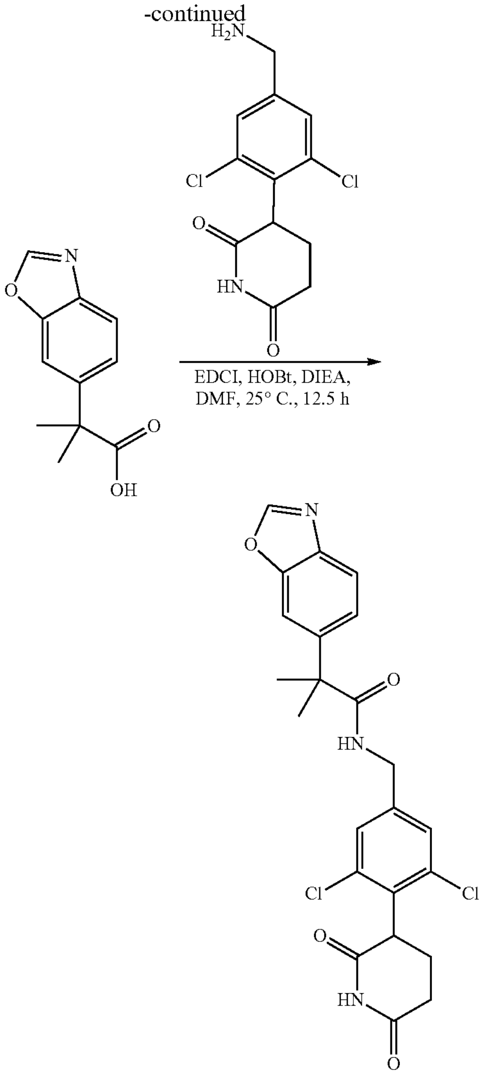

Step 1. To a mixture of 6-bromobenzo[d]oxazole (1.00 g, 5.05 mmol, 1.00 eq.), bis(tri-tert-butylphosphine) palladium (0) (258 mg, 505 μmol, 0.10 eq.) and difluorozinc (1.04 g, 10.1 mmol, 2.00 eq.) in dimethyl formamide (10 mL) was added ((1-methoxy-2-methylprop-1-en-1-yl)oxy)trimethylsilane (1.76 g, 10.1 mmol, 2.00 eq.) dropwise. The mixture was stirred at 100° C. under nitrogen atmosphere for 12 h. The mixture was cooled to 25° C. then filtered. The filtrate was quenched with water (50 mL) and extracted with ethyl acetate (3×50 mL). The combined organic layers were washed with brine (50 mL), dried over anhydrous sodium sulfate, filtered, and the filtrate was concentrated under reduced pressure. The residue was purified via Purification Method 2 to afford methyl 2-(benzo[d]oxazol-6-yl)-2-methylpropanoate (600 mg, 2.74 mmol, 54% yield) as a yellow oil.

Step 2. To a mixture of methyl 2-(benzo[d]oxazol-6-yl)-2-methylpropanoate (200 mg, 912 μmol, 1.00 eq.) in tetrahydrofuran (1.5 mL) and water (1.5 mL) was added lithium hydroxide hydrate (76.5 mg, 1.82 mmol, 2.00 eq.) in one portion 20° C. The reaction was stirred at 20° C. for 24 h. The mixture was poured into water then extracted with ethyl acetate (3× 10 mL). The aqueous phase was collected and adjusted to pH 2 using 36% aqueous hydrochloric acid, and then it was extracted with ethyl acetate (3×10 mL). The combined organic extracts were washed with brine (10 mL), dried over anhydrous sodium sulfate, filtered, and concentrated under reduced pressure to give 2-(benzo[d]oxazol-6-yl)-2-methylpropanoic acid (100 mg, crude) as a yellow solid.

Step 3. To a mixture of 2-(benzo[d]oxazol-6-yl)-2-methylpropanoic acid (56.4 mg, 274 μmol, 1.00 eq.), N1-((ethylimino)methylene)-N3,N3-dimethylpropane-1,3-diamine hydrochloride (63.2 mg, 329 μmol, 1.20 eq.) and 1H-benzo[d][1,2,3]triazol-1-ol (44.5 mg, 329 μmol, 1.20 eq.) in dimethyl formamide (2 mL) was added diisopropylethylamine (142 mg, 1.10 mmol, 4.00 eq.) dropwise at 25° C. The mixture was stirred at 25° C. for 0.5 h, then 3-(4-(aminomethyl)-2,6-dichlorophenyl) piperidine-2,6-dione hydrochloride (80.0 mg, 247 μmol, 0.90 eq.) was added and the mixture was stirred at 25° C. for 12 h. The mixture was poured into water (50 mL) and extracted with ethyl acetate (3×50 mL). The combined organic layers were washed with brine (50 mL), dried over anhydrous sodium sulfate, filtered, and the filtrate was concentrated under reduced pressure. The residue was purified via Purification Method 1 to afford 2-(benzo[d]oxazol-6-yl)-N-(3,5-dichloro-4-(2,6-dioxopiperidin-3-yl)benzyl)-2-methylpropanamide (17.9 mg, 35.1 μmol, 12% yield) as a white solid.

$^1H$ NMR (400 MHZ, DMSO-$d_6$) δ=10.94 (s, 1H), 8.72 (s, 1H), 8.01 (t, J=6.0 Hz, 1H), 7.79-7.70 (m, 2H), 7.33 (dd, J=1.6, 8.4 Hz, 1H), 7.11 (s, 1H), 7.04 (s, 1H), 4.52 (dd, J=5.6, 12.8 Hz, 1H), 4.20 (d, J=6.0 Hz, 2H), 2.94-2.74 (m, 1H), 2.58-2.51 (m, 1H), 2.32 (q, J=4.0, 13.2 Hz, 1H), 1.93-1.80 (m, 1H), 1.57 (s, 6H). MS (ESI) m/z 474.2 $[M+H]^+$

Exemplary Compound 14

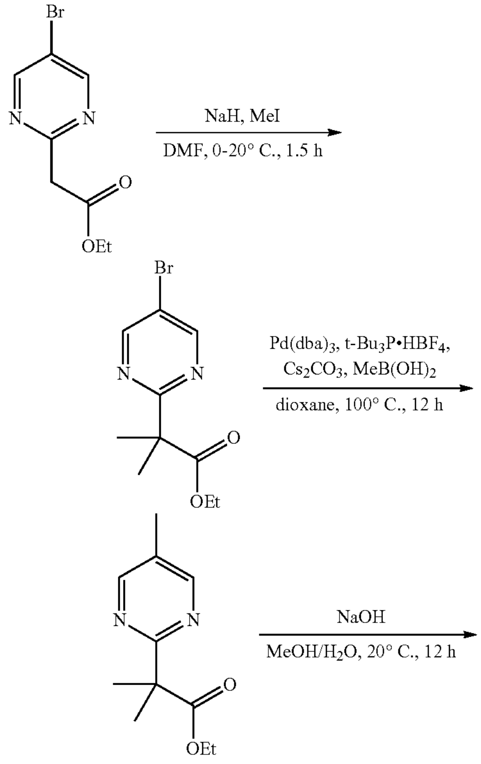

-continued

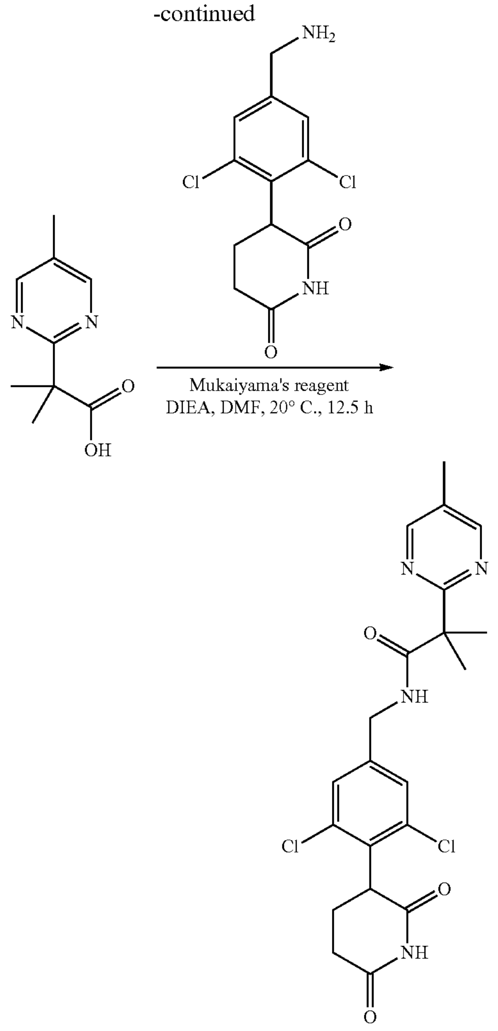

Step 1. To a mixture of ethyl 2-(5-bromopyrimidin-2-yl) acetate (1.00 g, 4.08 mmol, 1.00 eq.) in dimethylformamide (20 mL) was added sodium hydride (489 mg, 12.2 mmol, 60% purity, 3.00 eq.) in portions at 0° C. The mixture was stirred at 0° C. for 0.5 h, then iodomethane (1.74 g, 12.2 mmol, 3.00 eq.) was added. The reaction was stirred at 20° C. for 1 h, then it was quenched with saturated ammonium chloride solution (20 mL) and extracted with ethyl acetate (3× 20 mL). The combined organic layers were washed with brine (20 mL), dried over anhydrous sodium sulfate, filtered, and concentrated under reduced pressure. The residue was purified via Purification Method 2 then Purification Method 1 to afford ethyl 2-(5-bromopyrimidin-2-yl)-2-methylpropanoate (820 mg, 2.94 mmol, 72% yield) as a yellow oil.

Step 2. To a solution of ethyl 2-(5-bromopyrimidin-2-yl)-2-methylpropanoate (620 mg, 2.27 mmol, 1.00 eq.) and methylboronic acid (679 mg, 11.4 mmol, 5.00 eq.) in dioxane (6 mL) were added tris(dibenzylideneacetone)-dipalladium (0) (103 mg, 113 μmol, 0.05 eq.), tri-tert-butylphosphonium tetrafluoroborate (65.8 mg, 227 μmol, 0.10 eq.) and caesium carbonate (2.22 g, 6.81 mmol, 3.00 eq.) in one portion at 20° C. under nitrogen atmosphere. The reaction was stirred at 100° C. for 12 h. The mixture was cooled to 20° C., poured into water (10 mL), and extracted with ethyl acetate (3×10 mL). The combined organic layers were washed with brine (10 mL), dried over anhydrous sodium sulfate, filtered, and the filtrate was concentrated under reduced pressure. The residue was purified via Purification Method 2 to afford ethyl 2-methyl-2-(5-methylpyrimidin-2-yl) propanoate (400 mg, 1.73 mmol, 76% yield) as a yellow oil.

Step 3. To a solution of ethyl 2-methyl-2-(5-methylpyrimidin-2-yl) propanoate (400 mg, 1.92 mmol, 1.00 eq.) in methanol (4 mL) and water (4 mL) was added sodium hydroxide (384 mg, 9.60 mmol, 5.00 eq.) in one portion at 20° C. The reaction was stirred at 20° C. for 12 h. The mixture was poured into water (10 mL) and adjusted to pH 2-3 with 36% aqueous hydrochloric acid. The mixture was extracted with ethyl acetate (3×20 mL). The combined organic layers were washed with brine (10 mL), dried over anhydrous sodium sulfate, filtered, and the filtrate was concentrated under reduced pressure to give 2-methyl-2-(5-methylpyrimidin-2-yl) propanoic acid (300 mg, 1.56 mmol, 81% yield) as a white solid.

Step 4. To a solution of 2-methyl-2-(5-methylpyrimidin-2-yl) propanoic acid (80.0 mg, 443 μmol, 1.00 eq.) and diisopropylethylamine (229 mg, 1.78 mmol, 4.00 eq.) in dimethylformamide (1 mL) was added Mukaiyama's reagent (136 mg, 532 μmol, 1.20 eq.) in one portion at 20° C. The reaction was stirred at 20° C. for 0.5 h, then 3-(4-(aminomethyl)-2,6-dichlorophenyl) piperidine-2,6-dione hydrochloride (143 mg, 443 μmol, 1.00 eq.) was added. The reaction was stirred at 20° C. for 12 h. The mixture was poured into water (10 mL) and extracted with ethyl acetate (3× 20 mL). The combined organic layers were washed with brine (10 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-methyl-2-(5-methylpyrimidin-2-yl)-propanamide (74.8 mg, 166 μmol, 37% yield) as a white solid.

$^1$H NMR (400 MHZ, DMSO-d$_6$) δ=10.96 (s, 1H), 8.64 (s, 2H), 8.03 (t, J=6.0 Hz, 1H), 7.40 (s, 1H), 7.34 (d, J=1.2 Hz, 1H), 4.56 (dd, J=5.6, 12.8 Hz, 1H), 4.25 (d, J=6.0 Hz, 2H), 2.92-2.80 (m, 1H), 2.62-2.52 (m, 1H), 2.36 (dq, J=3.6, 13.2 Hz, 1H), 2.27 (s, 3H), 1.94-1.84 (m, 1H), 1.53 (s, 6H). $^1$H NMR (400 MHZ, DMSO-d$_6$, T=80° C.) ¿=10.95 (s, 1H), 8.62 (s, 2H), 7.84 (s, 1H), 7.44-7.25 (m, 2H), 4.55 (dd, J=5.6, 12.8 Hz, 1H), 4.26 (d, J=6.0 Hz, 2H), 2.84 (ddd, J=6.0, 14.4, 16.8 Hz, 1H), 2.56 (d, J=16.8 Hz, 1H), 2.39 (dq, J=3.6, 13.2 Hz, 1H), 2.27 (s, 3H), 1.99-1.86 (m, 1H), 1.56 (s, 6H). MS (ESI) m/z 449.1 [M+H]$^+$ Exemplary Compound 15

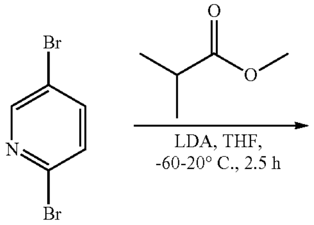

-continued

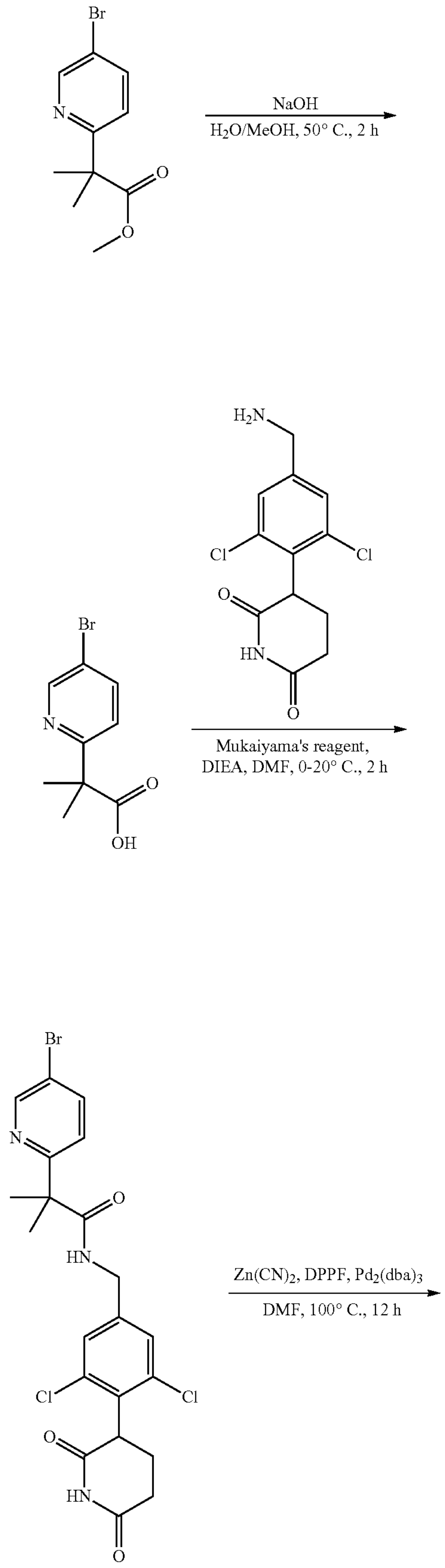

-continued

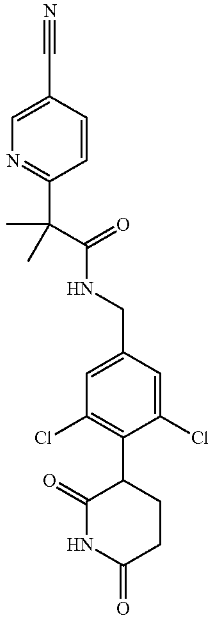

Step 1. To a solution of lithium diisopropylamide (6.20 mL, 2 M, 1.47 eq.) was added methyl isobutyrate (1.29 g, 12.7 mmol, 1.50 eq.) in tetrahydrofuran (5 mL) at −60° C. under nitrogen atmosphere. The reaction was stirred at −60° C. for 30 min, then 2,5-dibromopyridine (2.00 g, 8.44 mmol, 1.00 eq.) in tetrahydrofuran (15 mL) was added to the mixture at −60° C., the reaction was stirred at 20° C. for 2 h. The reaction was quenched with saturated ammonium chloride solution (20 mL) at 0° C. The reaction mixture was diluted with ethyl acetate (30 mL) and water (15 mL). The layers were separated, and the aqueous phase was extracted with ethyl acetate (2×20 mL). The combined organic layers were washed with brine (30 mL) and dried over anhydrous sodium sulfate, filtered, and concentrated in vacuo. The residue was purified via Purification Method 2 to afford methyl 2-(5-bromopyridin-2-yl)-2-methylpropanoate (1.60 g, 6.07 mmol, 72% yield) as a light-yellow oil.

Step 2. To a solution of methyl 2-(5-bromopyridin-2-yl)-2-methylpropanoate (400 mg, 1.55 mmol, 1.00 eq.) in methanol (5 mL) was added sodium hydroxide (186 mg, 4.65 mmol, 3.00 eq.) in water (5 mL) at 0° C. The reaction was stirred at 50° C. for 2 h. After cooling to room temperature, the mixture was concentrated in vacuo. The residue was diluted with ethyl acetate (10 mL) and water (5 mL). The layers were separated, and the aqueous phase was acidified to pH 5 with 1M hydrochloric acid. The aqueous phase was extracted with ethyl acetate (10 mL). The combined organic layers were washed with brine (10 mL) and dried over anhydrous sodium sulfate, filtered, and concentrated in vacuo to afford 2-(5-bromopyridin-2-yl)-2-methylpropanoic acid (300 mg, 1.18 mmol, 76% yield) as a white solid.

Step 3. To a solution of 2-(5-bromopyridin-2-yl)-2-methylpropanoic acid (80.0 mg, 328 μmol, 1.00 eq.) and N,N-diisopropylethylamine (130 mg, 1.00 mmol, 3.07 eq.) in dimethylformamide (2 mL) was added 2-chloro-1-methylpyridin-1-ium iodide (100 mg, 391 μmol, 1.19 eq.) at 0° C. The mixture was stirred at 20° C. for 30 min, then 3-(4-(aminomethyl)-2,6-dichlorophenyl) piperidine-2,6-dione (95.0 mg, 331 μmol, 1.01 eq.) was added to the mixture. The reaction was stirred at 20° C. for 2 h. The mixture was diluted with ethyl acetate (10 mL) and water (10 mL). The layers were separated, and the aqueous phase was extracted with ethyl acetate (2×10 mL). The combined organic layers were washed with brine (15 mL) and dried over anhydrous sodium sulfate, filtered, and concentrated in vacuo. The residue was purified via Purification Method 2 to afford 2-(5-bromopyridin-2-yl)-N-(3,5-dichloro-4-(2,6-dioxopiperidin-3-yl)benzyl)-2-methylpropanamide (160 mg, 302 μmol, 92% yield) as a white solid.

Step 4. To a solution of 2-(5-bromopyridin-2-yl)-N-(3,5-dichloro-4-(2,6-dioxopiperidin-3-yl)benzyl)-2-methylpropanamide (120 mg, 234 μmol, 1.00 eq.) and zinc cyanide (40.0 mg, 341 μmol, 1.46 eq.) in dimethylformamide (2 mL) was added 1,1-bis(diphenylphosphino)ferrocene (12.0 mg, 21.7 μmol, 0.10 eq.) and tris(dibenzylideneacetone) dipalladium (0) (24.0 mg, 26.2 μmol, 0.11 eq.) under nitrogen atmosphere. The reaction was stirred at 100° C. for 12 h. The resulting mixture was filtered, the filtration was diluted with ethyl acetate (5 mL) and water (5 mL). The layers were separated, and the aqueous phase was extracted with ethyl acetate (2×5 mL). The combined organic layers were washed with brine (10 mL) and dried over anhydrous sodium sulfate, filtered, and concentrated in vacuo. The residue was purified via Purification Method 1 to afford 2-(5-cyanopyridin-2-yl)-N-(3,5-dichloro-4-(2,6-dioxopiperidin-3-yl)benzyl)-2-methylpropanamide (24.19 mg, 52.1 μmol, 22% yield) as a white solid.

$^1H$ NMR (400 MHZ, DMSO-$d_6$) δ=10.98 (s, 1H), 9.03-8.95 (m, 1H), 8.32 (dd, J=2.0, 8.4 Hz, 1H), 8.11 (s, 1H), 7.63 (d, J=8.4 Hz, 1H), 7.27 (d, J=1.6 Hz, 1H), 7.20 (d, J=1.6 Hz, 1H), 4.57 (dd, J=5.6, 12.8 Hz, 1H), 4.23 (d, J=6.0 Hz, 2H), 2.90 (s, 1H), 2.59-2.52 (m, 1H), 2.41-2.28 (m, 1H), 1.96-1.83 (m, 1H), 1.55 (s, 6H). MS (ESI) m/z 459.1 $[M+H]^+$.

Exemplry Compound 16

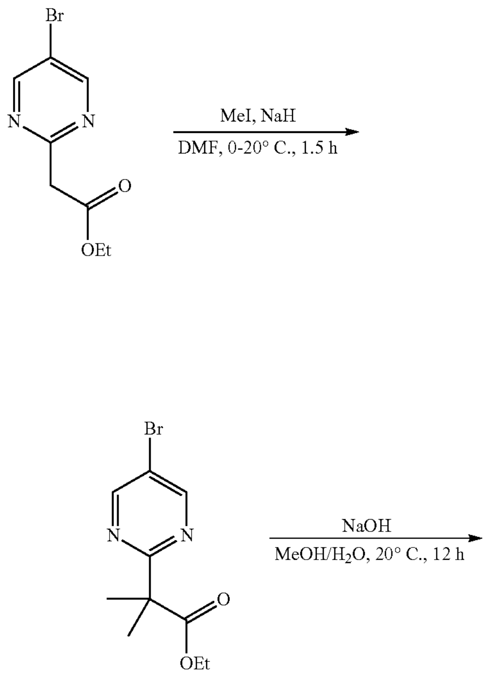

-continued

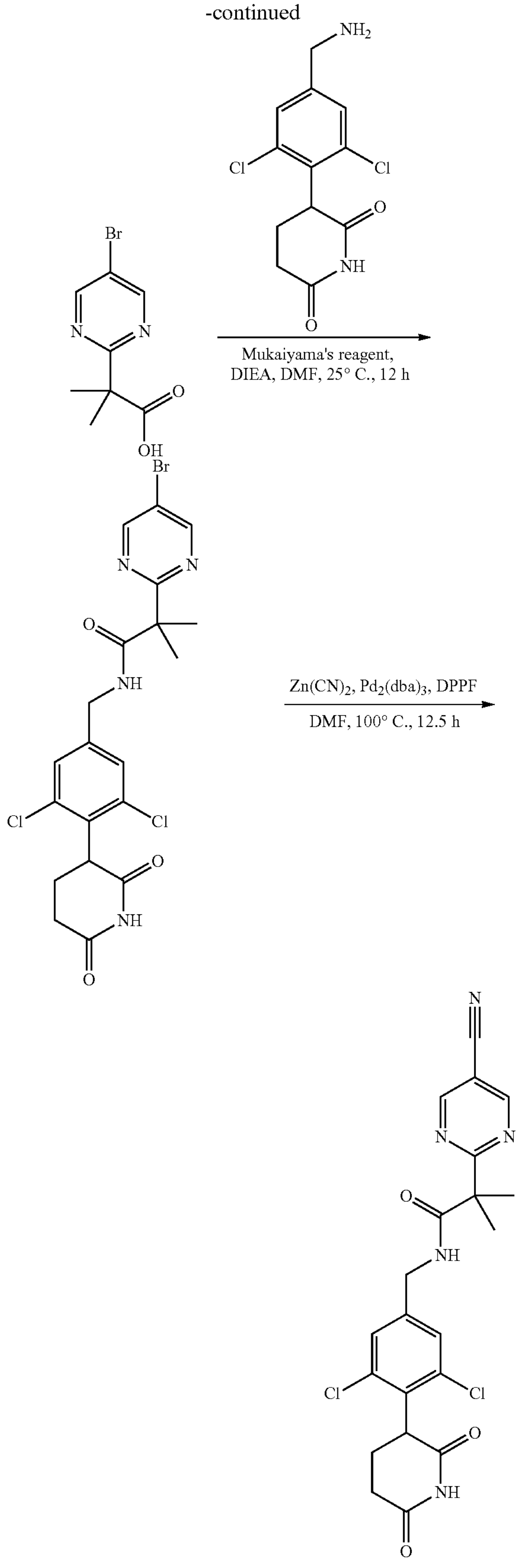

Step 1. To a mixture of ethyl 2-(5-bromopyrimidin-2-yl) acetate (1.00 g, 4.08 mmol, 1.00 eq.) in dimethylformamide (20 mL) was added sodium hydride (489 mg, 12.2 mmol, 60% purity, 3.00 eq.) in portions at 0° C. The mixture was stirred at 0° C. for 0.5 h. Then iodomethane (1.74 g, 12.2 mmol, 3.00 eq.) was added, and the reaction was stirred at 20° C. for 1 h. The reaction was quenched with saturated ammonium chloride solution (20 mL) and extracted with ethyl acetate (3× 20 mL). The combined organic layers were washed with brine (20 mL), dried over anhydrous sodium sulfate, filtered, and the filtrate was concentrated under reduced pressure to give ethyl 2-(5-bromopyrimidin-2-yl)-2-methylpropanoate (1.18 g, 3.93 mmol, 96% yield) as a yellow oil.

Step 2. To a mixture of ethyl 2-(5-bromopyrimidin-2-yl)-2-methylpropanoate (450 mg, 1.65 mmol, 1.00 eq.) in methanol (3 mL) and water (3 mL) was added sodium hydroxide (329 mg, 8.24 mmol, 5.00 eq.) in portions at 20° C. The mixture was stirred at 20° C. for 12 h. The aqueous solution was washed with ethyl acetate (3×10 mL). The aqueous phase was collected and adjusted to pH 2 using 36% aqueous hydrochloric acid, then it was extracted with ethyl acetate (3×10 mL). The combined organic extracts were washed with brine (10 mL), dried over anhydrous sodium sulfate, filtered, and the filtrate was concentrated under reduced pressure to give 2-(5-bromopyrimidin-2-yl)-2-methylpropanoic acid (350 mg, 1.40 mmol, 85% yield) as a white solid.

Step 3. To a mixture of 2-(5-bromopyrimidin-2-yl)-2-methylpropanoic acid (181 mg, 741 μmol, 1.20 eq.) and 2-chloro-1-methyl-pyridin-1-ium iodide (189 mg, 741 μmol, 1.20 eq.) in dimethylformamide (3 mL) was added N,N-diisopropylethylamine (159 mg, 1.24 mmol, 2.00 eq.) drop-wise at 25° C. The reaction was stirred at 25° C. for 0.5 h, then 3-(4-(aminomethyl)-2,6-dichlorophenyl) piperidine-2,6-dione hydrochloride (200 mg, 618 μmol, 1.00 eq.) was added, and the reaction was stirred at 25° C. for 12 h. The mixture was poured into water (10 mL) and extracted with ethyl acetate (3×10 mL). The combined organic layers were washed with brine (10 mL), dried over anhydrous sodium sulfate, filtered, and the filtrate was concentrated under reduced pressure. The residue was purified via Purification Method 2 to afford 2-(5-bromopyrimidin-2-yl)-N-(3,5-dichloro-4-(2,6-dioxopiperidin-3-yl)benzyl)-2-methylpropanamide (210 mg, 367 μmol, 59% yield) as a white solid.

Step 4. To a mixture of 2-(5-bromopyrimidin-2-yl)-N-(3,5-dichloro-4-(2,6-dioxopiperidin-3-yl)benzyl)-2-methylpropanamide (190 mg, 369 μmol, 1.00 eq.), tris(dibenzylideneacetone) dipalladium (0) (33.8 mg, 36.9 μmol, 0.10 eq.) and 1,1'-bis(diphenylphosphino)ferrocene (20.4 mg, 36.9 μmol, 0.10 eq.) in dimethylformamide (3 mL) was added zinc cyanide (70.0 mg, 596 μmol, 1.61 eq.) in portions at 25° C. The mixture was stirred at 100° C. under nitrogen atmosphere for 12 h. The mixture was cooled to 25° C. then filtered. The filtrate was poured into water (50 mL) and extracted with ethyl acetate (3×50 mL). The combined organic layers were washed with brine (30 mL), dried over anhydrous sodium sulfate, filtered, and the filtrate was concentrated under reduced pressure. The residue was purified via Purification Method 1 to afford 2-(5-cyanopyrimidin-2-yl)-N-(3,5-dichloro-4-(2,6-dioxopiperidin-3-yl)benzyl)-2-methyl-propanamide (128 mg, 276 μmol, 74% yield) as a white solid.

$^1$H NMR (400 MHZ, DMSO-$d_6$) δ=10.96 (s, 1H), 9.30 (s, 2H), 8.14 (t, J=6.0 Hz, 1H), 7.35 (s, 1H), 7.29 (d, J=0.8 Hz, 1H), 4.57 (dd, J=5.6, 12.8 Hz, 1H), 4.25 (d, J=6.0 Hz, 2H), 2.93-2.79 (m, 1H), 2.61-2.52 (m, 1H), 2.36 (q, J=4.4, 13.2 Hz, 1H), 1.94-1.83 (m, 1H), 1.57 (s, 6H). MS (ESI) m/z 460.1 $[M+H]^+$

Exemplary Compound 19

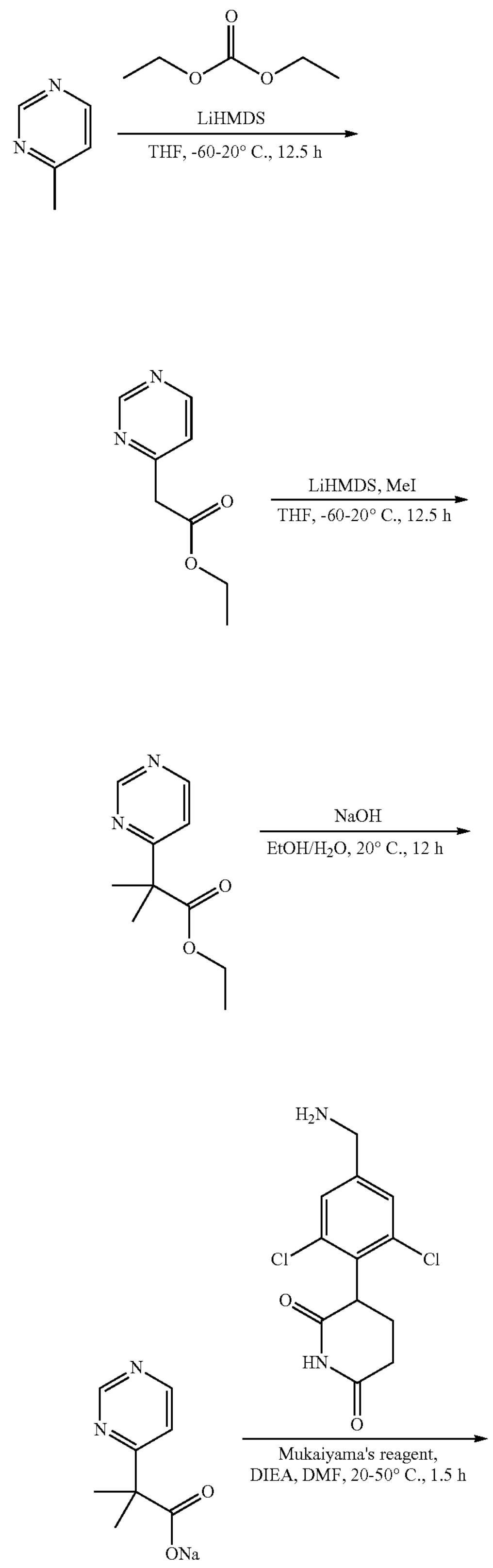

-continued

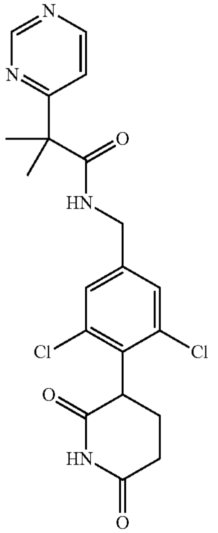

Step 1. To a solution of lithium bis(trimethylsilyl)amide (1 M in tetrahydrofuran, 63.8 mL, 3.00 eq.) was added a solution of 4-methylpyrimidine (2.00 g, 21.3 mmol, 1.00 eq.) in tetrahydrofuran (20 mL) dropwise at −60° C. The solution was stirred at −60° C. for 0.5 h then a solution of diethyl carbonate (3.77 g, 31.9 mmol, 1.50 eq.) in tetrahydrofuran (24 mL) was added. The solution was stirred at 20° C. under nitrogen atmosphere for 12 h. The mixture was poured into 5% citric acid solution (80 mL). The mixture was extracted with ethyl acetate (5× 20 mL). The combined organic layers were washed with brine (20 mL), dried over anhydrous sodium sulfate, filtered, and the filtrate was concentrated under reduced pressure. The residue was purified via Purification Method 2 to afford ethyl 2-(pyrimidin-4-yl)acetate (2.00 g, 12.0 mmol, 56% yield) as a light-yellow oil.

Step 2. To a solution of ethyl 2-(pyrimidin-4-yl)acetate (2.00 g, 12.0 mmol, 1.00 eq.) in tetrahydrofuran (40 mL) was added lithium bis(trimethylsilyl)amide (1 M in tetrahydrofuran, 30.1 mL, 2.50 eq.) dropwise at −60° C. The solution was stirred at −60° C. for 0.5 h then iodomethane (5.12 g, 36.1 mmol, 3.00 eq.) was added. The solution was stirred at 20° C. for 12 h. The mixture was poured into saturated aqueous ammonium chloride solution (50 mL) and extracted with ethyl acetate (5×30 mL). The combined organic layers were washed with brine (30 mL), dried over anhydrous sodium sulfate, filtered, and the filtrate was concentrated under reduced pressure. The residue was purified via Purification Method 2 to afford ethyl 2-methyl-2-(pyrimidin-4-yl) propanoate (560 mg, 2.16 mmol, 17% yield) as a light-yellow oil.

Step 3. To a solution of ethyl 2-methyl-2-(pyrimidin-4-yl) propanoate (560 mg, 2.88 mmol, 1.00 eq.) in ethanol (5 mL) was added a solution of sodium hydroxide (2 M in water, 7.21 mL, 5.00 eq.) dropwise at 20° C. The reaction was stirred at 20° C. for 12 h. Ethanol was removed in vacuo and the remaining solution was diluted with water (20 mL). The pH was adjusted to 7-8 with 36% aqueous hydrochloric acid, then the mixture was lyophilized to give sodium 2-methyl-2-(pyrimidin-4-yl) propanoate (1.26 g, crude) as a white solid.

Step 4. To a mixture of sodium 2-methyl-2-(pyrimidin-4-yl) propanoate (125 mg, 266 μmol, 1.00 eq.) and 2-chloro-1-methyl-pyridin-1-ium iodide (81.5 mg, 319 μmol, 1.20 eq.) in dimethylformamide (1.5 mL) was added diisopropylethylamine (137 mg, 1.06 mmol, 4.00 eq.) dropwise at 20° C. The reaction was stirred at 20° C. for 0.5 h then 3-(4-(aminomethyl)-2,6-dichlorophenyl) piperidine-2,6-dione hydrochloride (77.4 mg, 239 μmol, 0.90 eq.) was added. The reaction was stirred at 50° C. for 1 h. The mixture was cooled to 20° C., and poured into water (10 mL). The mixture was extracted with ethyl acetate (3×10 mL). The combined organic layers were washed with brine (10 mL), dried over anhydrous sodium sulfate, filtered, and the filtrate was concentrated under reduced pressure. The residue was purified via Purification Method I to afford N-(3,5-dichloro-4-(2,6-dioxopiperidin-3-yl)benzyl)-2-methyl-2-(pyrimidin-4-yl) propanamide (43.6 mg, 99.3 μmol, 37% yield) as a white solid.

$^1$H NMR (400 MHZ, DMSO-$d_6$) δ=10.96 (s, 1H), 9.16 (d, J=1.6 Hz, 1H), 8.77 (d, J=5.2 Hz, 1H), 8.16 (t, J=6.0 Hz, 1H), 7.53 (dd, J=1.2, 5.2 Hz, 1H), 7.34 (d, J=1.6 Hz, 1H), 7.28 (d, J=1.2 Hz, 1H), 4.56 (dd, J=5.6, 12.8 Hz, 1H), 4.24 (d, J=6.0 Hz, 2H), 2.93-2.78 (m, 1H), 2.59-2.52 (m, 1H), 2.38-2.30 (m, 1H), 1.95-1.82 (m, 1H), 1.52 (s, 6H). MS (ESI) m/z 435.1 $[M+H]^+$

Exemplary Compound 21

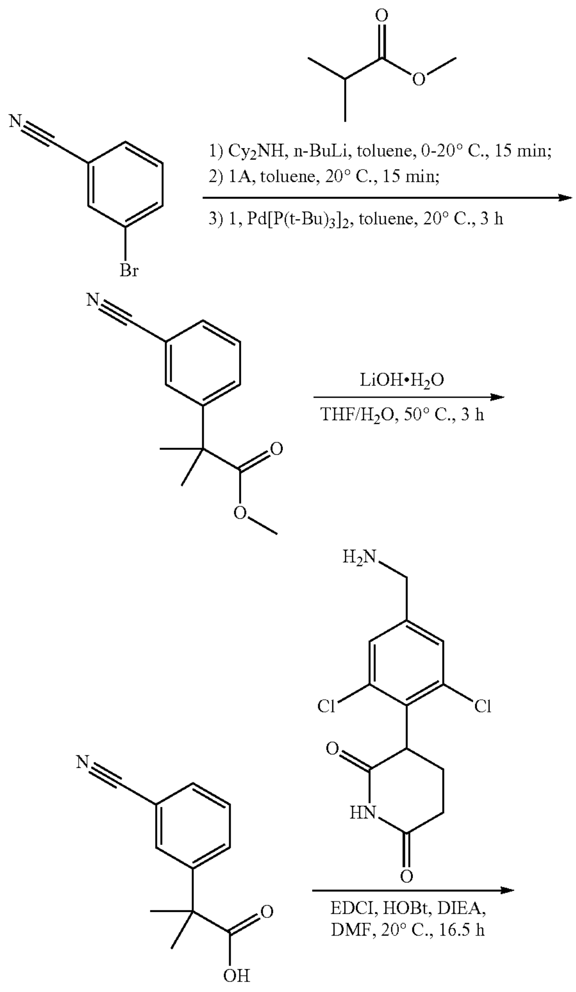

-continued

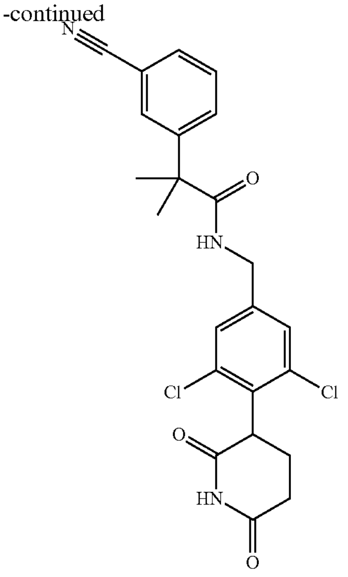

Step 1. To a solution of dicyclohexylamine (2.60 mL, 13.0 mmol, 1.19 eq.) in toluene (30 mL) was added n-butyllithium (2.5 M, 4.80 mL, 1.09 eq.) dropwise at 0° C. under nitrogen atmosphere, and the mixture was stirred at 20° C. for 15 min. Then methyl isobutyrate (1.39 mL, 12.0 mmol, 1.10 eq.) was added dropwise, and the reaction was stirred at 20° C. for 15 min. Palladium tri-tert-butylphosphane (560 mg, 1.10 mmol, 0.01 eq.) and 3-bromobenzonitrile (2.00 g, 11.0 mmol, 1.00 eq.) were added. The reaction was stirred at 20° C. for 3 h under nitrogen atmosphere. The mixture was diluted with water (100 mL) and extracted with ethyl acetate (3×100 mL). The combined organic extracts were washed with brine (100 mL) and dried over sodium sulfate, filtered, and concentrated under reduced pressure. The residue was purified via Purification Method 2 to afford methyl 2-(3-cyanophenyl)-2-methylpropanoate (1.00 g, 4.92 mmol, 44% yield) as a yellow oil.

Step 2. To a solution of methyl 2-(3-cyanophenyl)-2-methylpropanoate (400 mg, 1.97 mmol, 1.00 eq.) in tetrahydrofuran (5 mL) was added lithium hydroxide monohydrate (200 mg, 4.77 mmol, 2.42 eq.) in water (5 mL). The reaction was stirred at 50° C. for 3 h. The mixture was diluted with water (30 mL) and ethyl acetate (30 mL). The layers were separated, and the aqueous phase was washed with ethyl acetate (20 mL). The aqueous phase was adjusted to pH 3~4 with hydrochloric acid (1 M) and extracted with ethyl acetate (3×30 mL). The combined organic extracts were dried over sodium sulfate, filtered, and concentrated under reduced pressure to afford 2-(3-cyanophenyl)-2-methylpropanoic acid (280 mg, 1.18 mmol, 60% yield) as a yellow oil.

Step 3. To a solution of 2-(3-cyanophenyl)-2-methylpropanoic acid (100 mg, 528 μmol, 1.52 eq.) in dimethylformamide (2 mL) was added N,N-diisopropylethylamine (200 uL, 1.09 mmol, 3.14 eq.), 1H-benzo[d][1,2,3]triazol-1-ol (57.1 mg, 422 μmol, 1.21 eq.) and 1-(3-dimethylaminopropyl)-3-ethylcarbodiimide hydrochloride (82.5 mg, 430 μmol, 1.24 eq.). The mixture was stirred at 20° C. for 30 min. Then 3-(4-(aminomethyl)-2,6-dichlorophenyl) piperidine-2,6-dione (100 mg, 348 μmol, 1.00 eq.) was added, and the reaction was stirred at 20° C. for 16 h.

The reaction mixture was diluted with water (20 mL) and extracted with ethyl acetate (2×20 mL). The combined organic extracts were washed with brine (30 mL), dried over sodium sulfate, filtered, and concentrated under reduced pressure. The residue was purified via Purification Method 1 to afford 2-(3-cyanophenyl)-N-(3,5-dichloro-4-(2,6-dioxopiperidin-3-yl)benzyl)-2-methylpropanamide (41.61 mg, 86.2 μmol, 24% yield) as a white solid.

$^1H$ NMR (400 MHZ, DMSO-$d_6$) δ=10.95 (s, 1H), 8.12 (t, J=5.6 Hz, 1H), 7.78-7.69 (m, 2H), 7.68-7.60 (m, 1H), 7.59-7.51 (m, 1H), 7.17 (s, 1H), 7.10 (s, 1H), 4.60-4.49 (m, 1H), 4.22 (d, J=6.0 Hz, 2H), 2.92-2.78 (m, 1H), 2.60-2.53 (m, 1H), 2.43-2.28 (m, 1H), 1.98-1.82 (m, 1H), 1.53 (s, 6H). MS (ESI) m/z 458.2 $[M+H]^+$

Exemplary Compound 25

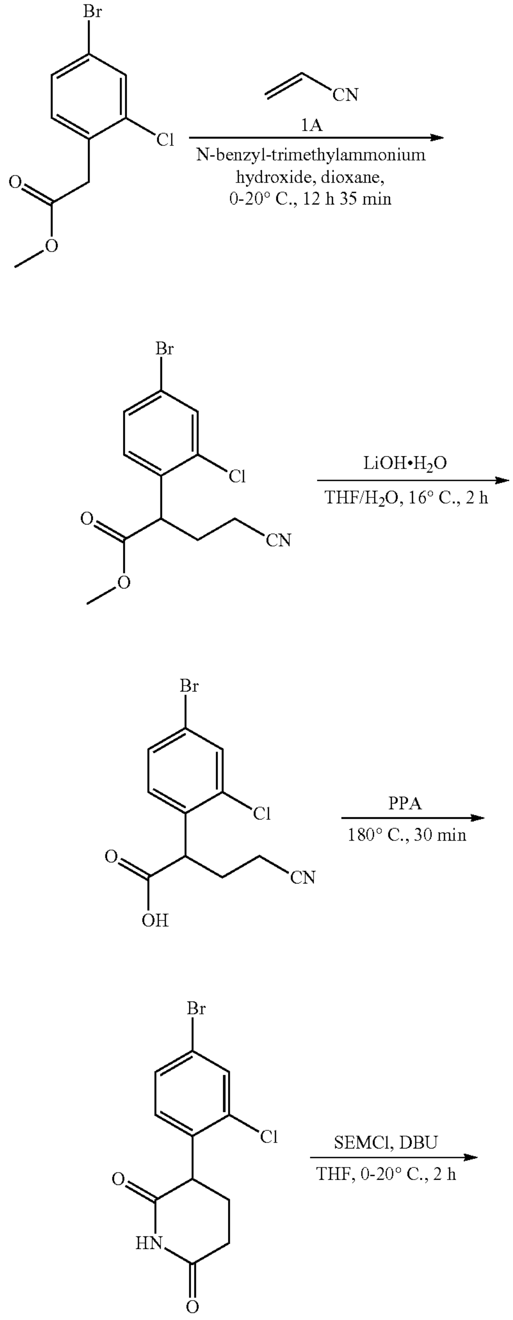

-continued

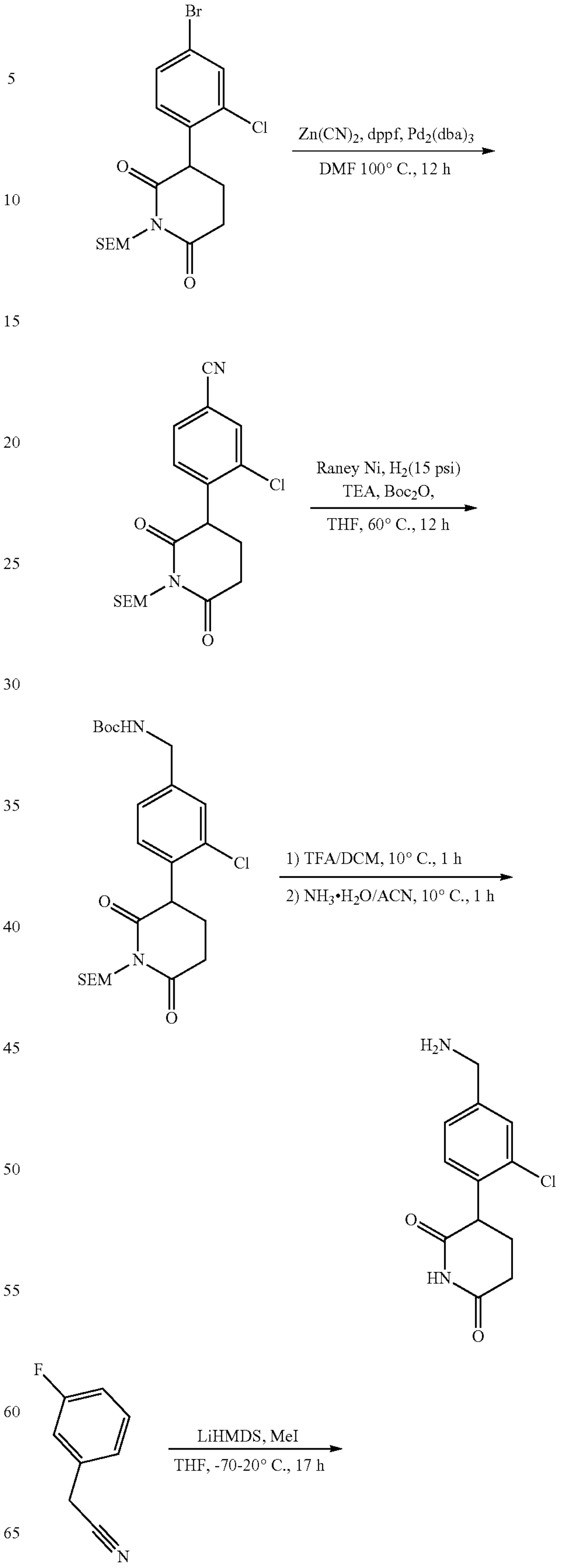

-continued

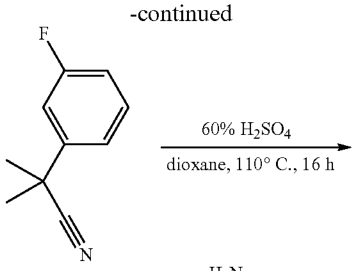

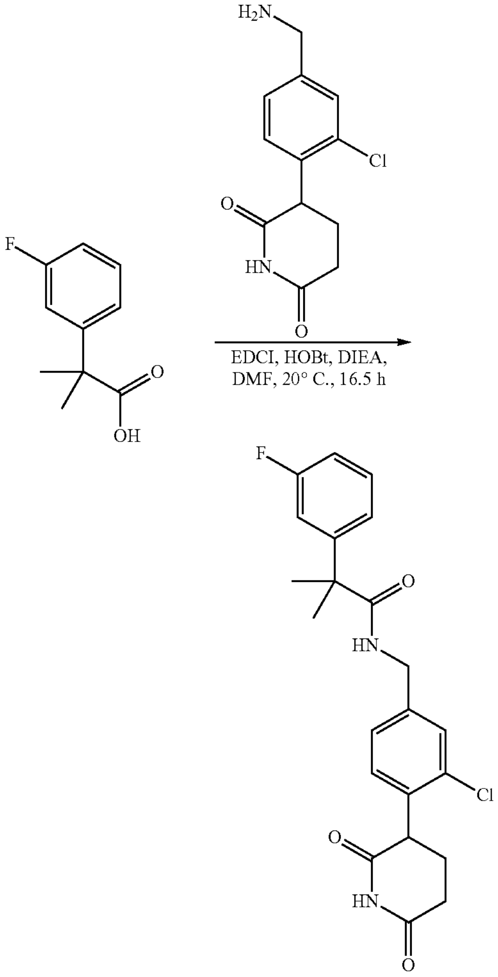

Step 1: A solution of methyl 2-(4-bromo-2-chlorophenyl) acetate (15.0 g, 56.9 mmol, 1.00 eq.) and acrylonitrile (6.04 g, 113 mmol, 2.00 eq.) in dioxane (80 mL) was stirred at 0° C. for 5 min. Then N-benzyl-trimethylammonium hydroxide (4.76 g, 28.4 mmol, 0.50 eq.) was added, and the reaction was stirred at 0° C. for 30 min, then at 20° C. for 12 h. The mixture was diluted with water (100 mL) and ethyl acetate (200 mL). The layers were separated, and the combined organic layers were washed with brine (50 mL), dried over sodium sulfate, filtered, and concentrated under reduced pressure to give a residue. The residue was purified via Purification Method 2 to afford methyl 2-(4-bromo-2-chlorophenyl)-4-cyanobutanoate (10.9 g, 30.9 mmol, 54% yield, 90% purity) as red oil.

Step 2: To a solution of methyl 2-(4-bromo-2-chlorophenyl)-4-cyanobutanoate (4.80 g, 15.2 mmol, 1.00 eq.) in THF (10 mL) and water (10 mL) was added lithium hydroxide monohydrate (3.18 g, 75.8 mmol, 5.00 eq.). The reaction was stirred at 16° C. for 2 h, then THE was removed in vacuo and the remaining aqueous solution was adjusted to pH 6 with hydrochloric acid (2 M). The mixture was concentrated under reduced pressure to give a residue. The residue was concentrated under vacuum. The residue was purified via Purification Method 2 to afford 2-(4-bromo-2-chlorophenyl)-4-cyanobutanoic acid (4.20 g, 13.7 mmol, 90% yield) as a white solid.

Step 3: A solution of 2-(4-bromo-2-chlorophenyl)-4-cyanobutanoic acid (2.00 g, 6.61 mmol, 1.00 eq.) in polyphosphoric acid (20 mL) was stirred at 180° C. for 30 min. Then the mixture was diluted with ice water (50 mL) and extracted with dichloromethane (50 mL). The combined organic layers were washed with brine (20 mL), dried over sodium sulfate, filtered, and concentrated under reduced pressure to give a residue. The residue was purified via Purification Method 2 to afford 3-(4-bromo-2-chlorophenyl) piperidine-2,6-dione (1.50 g, 4.71 mmol, 71% yield) as a white solid.

Step 4: To a solution of 3-(4-bromo-2-chlorophenyl) piperidine-2,6-dione (1.80 g, 5.95 mmol, 1.00 eq.) in THF (20 mL) were added DBU (1.81 g, 11.9 mmol, 2.00 eq.) and 2-(trimethylsilyl) ethoxymethyl chloride (1.79 g, 10.7 mmol, 1.80 eq.) at 0° C. The reaction was stirred at 20° C. for 2 h, then it was diluted with water (50 mL) and extracted with ethyl acetate (100 mL). The combined organic layers were washed with brine (50 mL), dried over sodium sulfate, filtered, and concentrated under reduced pressure to give a residue. The residue was purified via Purification Method 2 to afford 3-(4-bromo-2-chlorophenyl)-1-((2-(trimethylsilyl) ethoxy)methyl) piperidine-2,6-dione (2.20 g, 4.78 mmol, 80% yield) as a yellow oil.

Step 5: To a solution of 3-(4-bromo-2-chloro-phenyl)-1-(2-trimethylsilylethoxymethyl) piperidine-2,6-dione (1.00 g, 2.31 mmol, 1.00 eq.) in DMF (20 mL) were added zinc cyanide (353 mg, 3.00 mmol, 1.30 eq.), $Pd_2(dba)_3$ (212 mg, 0.23 mmol, 0.10 eq.) and 1,1-bis(diphenylphosphino)-ferrocene (128 mg, 0.23 mmol, 0.10 eq.). The reaction was stirred at 100° C. under nitrogen for 12 h. The mixture was cooled to 20° C., and poured into water (50 mL). The aqueous layer was extracted with ethyl acetate (3× 50 mL). The combined organic layers were washed with brine (80 mL), dried over anhydrous sodium sulfate, filtered, and concentrated under reduced pressure to give a residue. The residue was purified via Purification Method 2 to afford 3-chloro-4-(2,6-dioxo-1-((2-(trimethylsilyl) ethoxy)methyl) piperidin-3-yl)benzonitrile (2.20 g, 5.69 mmol, 82% yield) as a light-yellow oil.

Step 6: To a suspension of Raney-nickel (1.24 g, 14.5 mmol, 2.50 eq.) in THF (20 mL) was added a solution of 3-chloro-4-(2,6-dioxo-1-((2-(trimethylsilyl) ethoxy)methyl) piperidin-3-yl)benzonitrile (2.20 g, 5.81 mmol, 1.00 eq.), $Boc_2O$(2.53 g, 11.6 mmol, 2.00 eq.) and TEA (881 mg, 8.71 mmol, 1.50 eq.) in THF (50 mL). The reaction was stirred at 60° C. under hydrogen atmosphere (15 psi) for 12 h. The mixture was cooled to 20° C., filtered, and concentrated under reduced pressure to give a residue. The residue was purified via Purification Method 2 to afford tert-butyl 3-chloro-4-(2,6-dioxo-1-((2-(trimethylsilyl) ethoxy)methyl) piperidin-3-yl)benzylcarbamate (2.30 g, 4.76 mmol, 82% yield) as a colourless oil.

Step 7: To a solution of tert-butyl 3-chloro-4-(2,6-dioxo-1-((2-(trimethylsilyl) ethoxy)methyl) piperidin-3-yl)benzylcarbamate (2.30 g, 4.76 mmol, 1.00 eq.) in DCM (80 mL) was added TFA (24.6 g, 216 mmol, 45.4 eq.) dropwise at 10° C. The reaction was stirred at 10° C. for 1 h, then it was concentrated under reduced pressure to give a residue. The residue was dissolved in MeCN(40 mL) and cooled to 0° C. An ammonia solution (2 mL, 28% purity) was added to reach pH >8. The reaction was stirred at 10° C. for 1 h, then the mixture was adjusted to pH<6 with formic acid. The mixture was concentrated under reduced pressure to give a residue. The residue was purified via Purification Method 2 to afford 3-(4-(aminomethyl)-2-chlorophenyl) piperidine-2, 6-dione (700 mg, 2.77 mmol, 58% yield) as a light-yellow solid.

$^1$H NMR (400 MHZ, DMSO-$d_6$) δ=10.94 (s, 1H), 8.54-8.05 (m, 2H), 7.60 (s, 1H), 7.41 (s, 2H), 4.23 (dd, J=5.2, 12.8 Hz, 1H), 4.05 (s, 2H), 2.85-2.71 (m, 1H), 2.55 (d, J=3.2 Hz, 1H), 2.31 (dq, J=4.4, 13.2 Hz, 1H), 2.02-1.90 (m, 1H).

Step 8. To a solution of 2-(3-fluorophenyl) acetonitrile (2.00 g, 14.8 mmol, 1.00 eq.) in tetrahydrofuran (30 mL) was added lithium bis(trimethylsilyl)amide (1 M in tetrahydrofuran, 30.0 mL, 2.03 eq.) at −60° C. under nitrogen, and the reaction was stirred at −60° C. for 1 h. Then iodomethane (3.70 mL, 59.4 mmol, 4.02 eq.) was added at −60° C. under nitrogen. The reaction was stirred at 20° C. for 16 h. The reaction was quenched with saturated aqueous ammonium chloride solution (10 mL) at 0° C., then diluted with water (50 mL) and extracted with ethyl acetate (2×50 mL). The combined organic layers were washed with brine (60 mL), dried over sodium sulfate, filtered, and concentrated under reduced pressure to afford 2-(3-fluorophenyl)-2-methylpropanenitrile (2.40 g, 14.7 mmol, 99% yield) as a brown oil.

Step 2. To a solution of 2-(3-fluorophenyl)-2-methylpropanenitrile (1.00 g, 6.13 mmol, 1.00 eq.) in dioxane (10 mL) was added sulfuric acid (6 mL) and water (4 mL). The mixture was stirred at 110° C. for 16 h. The reaction mixture was diluted with water (30 mL) and extracted with dichloromethane (2×30 mL). The combined organic extracts were washed with brine (40 mL) and dried over sodium sulfate, filtered, and concentrated under reduced pressure to afford 2-(3-fluorophenyl)-2-methylpropanoic acid (1.00 g, 5.49 mmol, 89% yield) as a brown oil.

Step 3. To a solution of 2-(3-fluorophenyl)-2-methylpropanoic acid (70.0 mg, 384 μmol, 1.00 eq.) in dimethylformamide (2 mL) was added N,N-diisopropylethylamine (210 μL, 1.21 mmol, 3.14 eq.), 1H-benzo[d][1,2,3]triazol-1-ol (63.0 mg, 466 μmol, 1.21 eq.) and 1-(3-dimethylaminopropyl)-3-ethylcarbodiimide hydrochloride (91.0 mg, 475 μmol, 1.24 eq.). The mixture was stirred for 30 min at 20° C., then 3-(4-(aminomethyl)-2-chlorophenyl) piperidine-2, 6-dione (80.0 mg, 316 μmol, 0.82 eq.) was added to the mixture. The mixture was stirred at 20° C. for 16 h. The reaction mixture was diluted with water (20 mL) and extracted with ethyl acetate (2× 20 mL). The combined organic extracts were washed with brine (40 mL), dried over sodium sulfate, filtered, and concentrated under reduced pressure. The residue was purified via Purification Method 1 afford N-(3-chloro-4-(2,6-dioxopiperidin-3-yl)benzyl)-2-(3-fluorophenyl)-2-methylpropanamide (74.54 mg, 177 μmol, 46% yield) as a white solid.

$^1$H NMR (400 MHZ, DMSO-$d_6$) δ=10.89 (s, 1H), 8.05 (t, J=6.0 Hz, 1H), 7.44-7.32 (m, 1H), 7.23 (d, J=8.0 Hz, 1H), 7.17-7.02 (m, 5H), 4.21 (d, J=6.0 Hz, 2H), 4.18-4.10 (m, 1H), 2.83-2.69 (m, 1H), 2.53 (d, J=3.6 Hz, 1H), 2.35-2.18 (m, 1H), 2.00-1.89 (m, 1H), 1.49 (s, 6H). MS (ESI) m/z 416.9 $[M+H]^+$.

Exemplary Compound 32

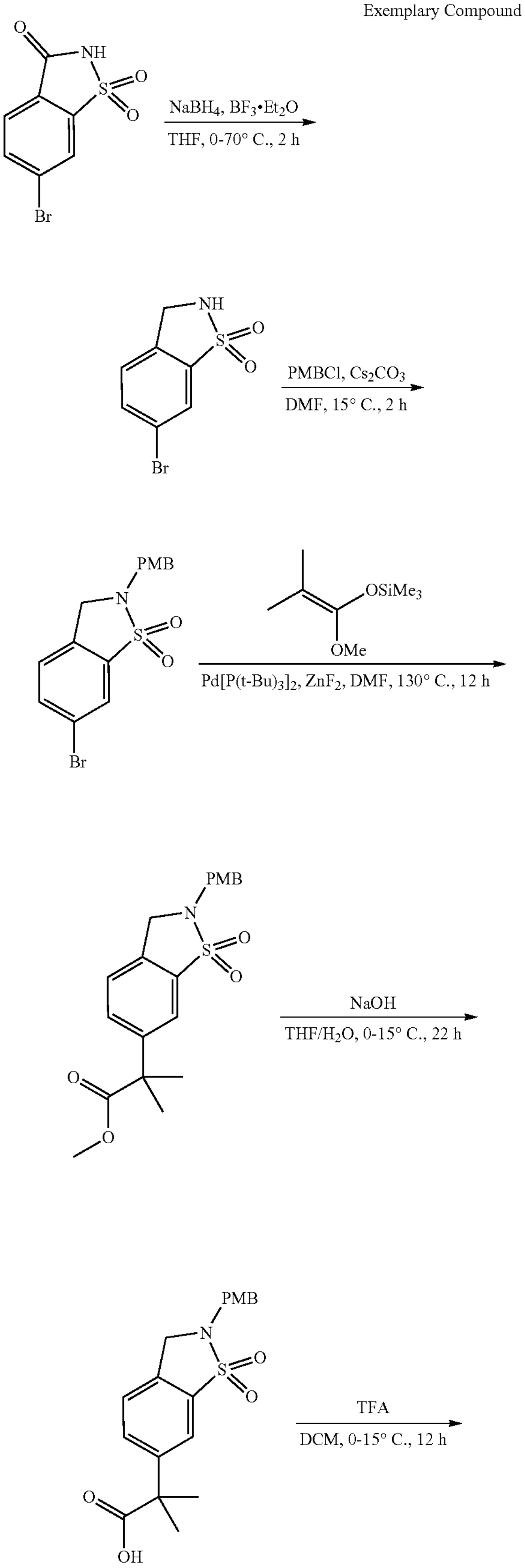

-continued

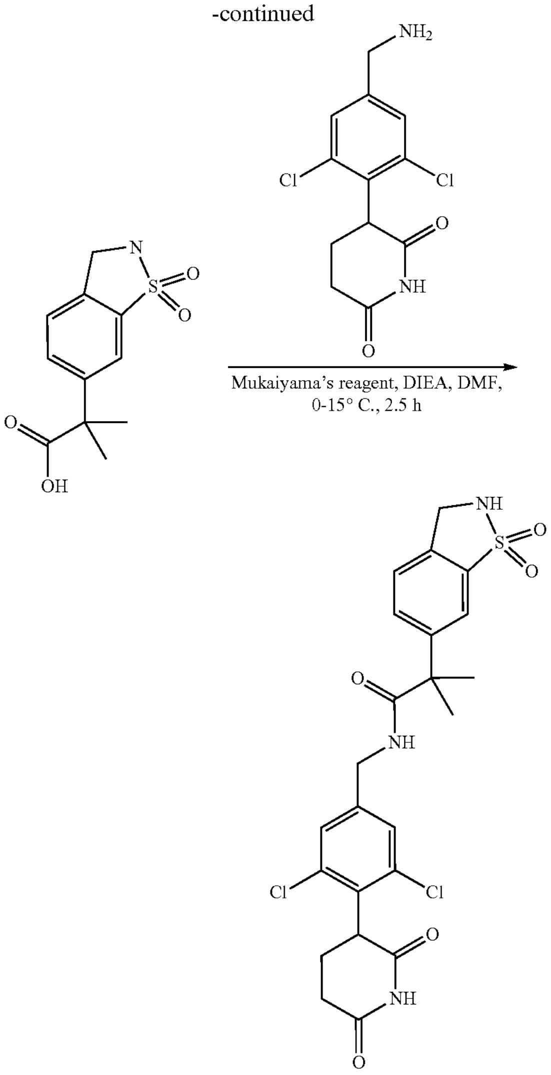

Step 1. To a solution of 6-bromobenzo[d]isothiazol-3 (2H)-one 1,1-dioxide (1.00 g, 3.82 mmol, 1.00 eq.) in tetrahydrofuran (20 mL) was added sodium borohydride (1.36 g, 36.0 mmol, 9.42 eq.) at 0° C. The reaction was stirred at 0° C. for 15 min, then boron trifluoride diethyl ether (5.00 mL, 40.7 mmol, 10.7 eq.) was added to the mixture at 0° C., and the reaction was stirred at 70° C. for 2 h. The reaction was quenched with saturated ammonium chloride solution (30 mL) at 0° C. The mixture was diluted with ethyl acetate (25 mL) and water (10 mL). The layers were separated, and the aqueous phase was extracted with ethyl acetate (2×15 mL). The combined organic layers were washed with brine (30 mL) and dried over anhydrous sodium sulfate, filtered, and concentrated in vacuo. The residue was purified via Purification Method 2 to afford 6-bromo-2,3-dihydrobenzo[d]isothiazole 1,1-dioxide (830 mg, 3.31 mmol, 87% yield) as a white solid.

Step 2. To a solution of 6-bromo-2,3-dihydro-1,2-benzothiazole 1,1-dioxide (830 mg, 3.35 mmol, 1.00 eq.) in dimethylformamide (5 mL) were added 1-(chloromethyl)-4-methoxybenzene (680 μL, 5.01 mmol, 1.50 eq.) and caesium carbonate (3.28 g, 10.1 mmol, 3.01 eq.). The reaction was stirred at 15° C. for 2 h. The mixture was diluted with ethyl acetate (10 mL) and water (10 mL). The layers were separated, and the aqueous phase was extracted with ethyl acetate (2×10 mL). The combined organic layers were washed with brine (20 mL) and dried over anhydrous sodium sulfate, filtered, and concentrated in vacuo. The residue was purified via Purification Method 2 to afford 6-bromo-2-(4-methoxybenzyl)-2,3-dihydrobenzo[d]isothiazole 1,1-dioxide (540 mg, 1.41 mmol, 42% yield) as a white solid.

Step 3. To a solution of 6-bromo-2-(4-methoxybenzyl)-2,3-dihydrobenzo[d]isothiazole 1,1-dioxide (450 mg, 1.22 mmol, 1.00 eq.) and ((1-methoxy-2-methylprop-1-en-1-yl) oxy)trimethylsilane (450 mg, 2.58 mmol, 2.11 eq.) in dimethylformamide (10 mL) were added difluorozinc (270 mg, 2.61 mmol, 2.14 eq.) and palladium;tri-tert-butylphosphane (90.0 mg, 176 μmol, 0.14 eq.) . . . . The reaction was stirred at 130° C. for 12 h under nitrogen atmosphere. The reaction mixture was cooled to room temperature and diluted with ethyl acetate (10 mL) and water (10 mL). The layers were separated, and the aqueous phase was extracted with ethyl acetate (2×10 mL). The combined organic layers were washed with brine (25 mL) and dried over anhydrous sodium sulfate, filtered, and concentrated in vacuo. The residue was purified via Purification Method 2 to afford methyl 2-(2-(4-methoxybenzyl)-1,1-dioxido-2,3-dihydrobenzo[d]isothiazol-6-yl)-2-methylpropanoate (330 mg, 796 μmol, 65% yield) as a white solid.

Step 4. To a solution of methyl 2-(2-(4-methoxybenzyl)-1,1-dioxido-2,3-dihydrobenzo[d]isothiazol-6-yl)-2-methylpropanoate (330 mg, 847 μmol, 1.00 eq.) in tetrahydrofuran (3 mL) was added sodium hydroxide (170 mg, 4.25 mmol, 5.02 eq.) in water (3 mL) at 0° C. The reaction was stirred at 15° C. for 22 h, then it was concentrated in vacuo. The residue was diluted with ethyl acetate (15 mL) and water (10 mL). The layers were separated, and the aqueous phase was acidified to pH 5 with 1M hydrochloric acid. The aqueous phase was extracted with ethyl acetate (15 mL).

The combined organic layers were washed with brine (20 mL) and dried over anhydrous sodium sulfate, filtered, and concentrated in vacuo to afford 2-(2-(4-methoxybenzyl)-1,1-dioxido-2,3-dihydrobenzo[d]isothiazol-6-yl)-2-methylpropanoic acid (280 mg, crude) as a white solid.

Step 5. To a solution of 2-(2-(4-methoxybenzyl)-1,1-dioxido-2,3-dihydrobenzo[d]isothiazol-6-yl)-2-methylpropanoic acid (280 mg, 746 μmol, 1.00 eq.) in dichloromethane (5 mL) was added trifluoroacetic acid (5 mL) at 0° C. The reaction was stirred at 15° C. for 12 h, then it was concentrated in vacuo. The residue was diluted with ethyl acetate (10 mL) and water (10 mL). The layers were separated, and the aqueous phase was acidified to pH 5 with 1M hydrochloric acid. The aqueous phase was extracted with ethyl acetate (3× 10 mL). The combined organic layers were washed with brine (20 mL) and dried over anhydrous sodium sulfate, filtered, and concentrated in vacuo. The residue was purified via Purification Method 1 to afford 2-(1,1-dioxido-2,3-dihydrobenzo[d]isothiazol-6-yl)-2-methylpropanoic acid (80.0 mg, 310 μmol, 42% yield) as a white solid.

Step 6. To a solution of 2-(1,1-dioxo-2,3-dihydro-1,2-benzothiazol-6-yl)-2-methyl-propanoic acid (65.0 mg, 255 μmol, 1.00 eq.) and N,N-diisopropylethylamine (98.7 mg, 764 μmol, 3.00 eq.) in dimethylformamide (1 mL) was added 2-chloro-1-methyl-pyridin-1-ium iodide (78.1 mg, 306 μmol, 1.20 eq.) at 0° C. The reaction was stirred at 15° C. for 0.5 h, then 3-(4-(aminomethyl)-2,6-dichlorophenyl) piperidine-2,6-dione (75.0 mg, 261 μmol, 1.03 eq.) was added, and the reaction was stirred at 15° C. for 2 h. The mixture was diluted with ethyl acetate (10 mL) and water (5 mL).

The layers were separated, and the aqueous phase was extracted with ethyl acetate (2× 8 mL). The combined organic layers were washed with brine (15 mL) and dried over anhydrous sodium sulfate, filtered, and concentrated in vacuo. The residue was purified via Purification Method I to afford N-(3,5-dichloro-4-(2,6-dioxopiperidin-3-yl)benzyl)-2-(1,1-dioxido-2,3-dihydrobenzo[d]isothiazol-6-yl)-2-methylpropanamide (15.87 mg, 30.0 μmol, 12% yield) as a white solid.

$^{1}H$ NMR (400 MHZ, DMSO-$d_6$) δ=10.96 (s, 1H), 8.19 (s, 1H), 7.80 (br s, 1H), 7.69 (s, 1H), 7.60-7.44 (m, 2H), 7.20 (s, 1H), 7.11 (s, 1H), 4.55 (dd, J=5.6, 12.8 Hz, 1H), 4.37 (br s, 2H), 4.21 (br d, J=5.6 Hz, 2H), 2.94-2.74 (m, 1H), 2.60-2.52 (m, 1H), 2.37-2.25 (m, 1H), 1.96-1.81 (m, 1H), 1.54 (s, 6H). MS (ESI) m/z 524.1 $[M+H]^+$

Exemplary Compound 35

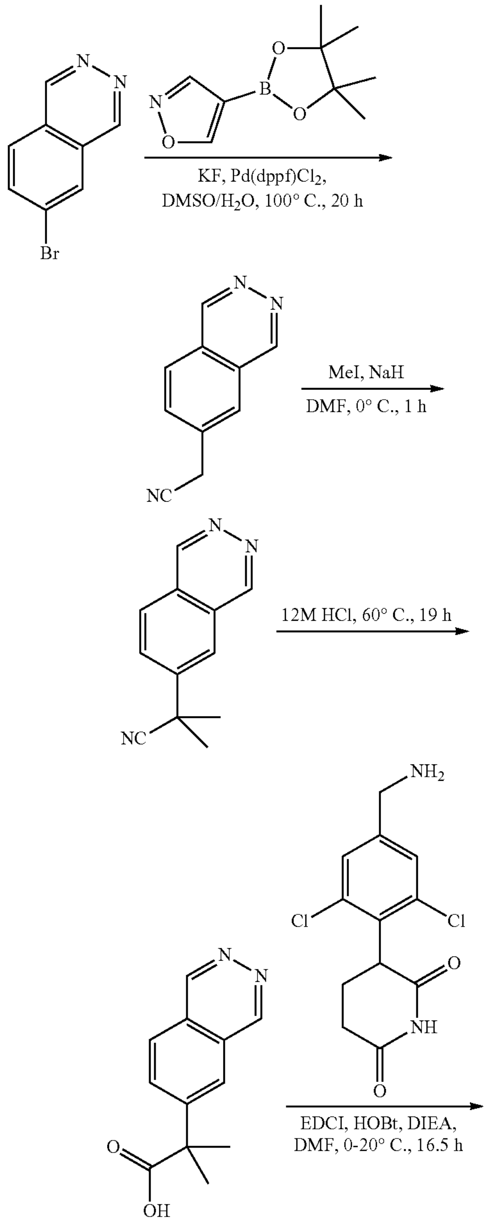

-continued

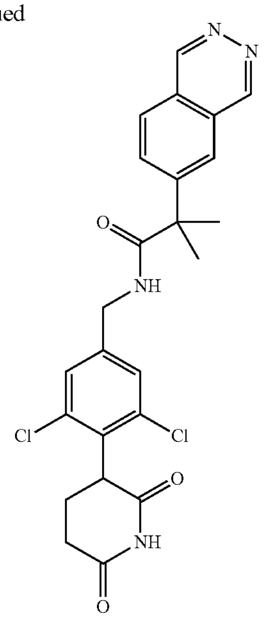

Step 1. To a solution of 6-bromophthalazine (1.00 g, 4.78 mmol, 1.00 eq.) and 4-(4,4,5,5-tetramethyl-1,3,2-dioxaborolan-2-yl) isoxazole (1.43 g, 7.33 mmol, 1.53 eq.) in dimethylsulfoxide (10 mL) and water (2 mL) was added potassium fluoride (840 mg, 14.4 mmol, 3.02 eq.) and [1,1-bis(diphenylphosphino)ferrocene]dichloropalladium (II) (360 mg, 492 μmol, 0.10 eq.) under nitrogen atmosphere. The mixture was stirred at 100° C. for 20 h. Then the mixture was filtered, and the filtrate was purified via Purification Method 2 to afford 2-(phthalazin-6-yl) acetonitrile (120 mg, 709 μmol, 15% yield) as a brown solid.

Step 2. To a solution of 2-(phthalazin-6-yl) acetonitrile (120 mg, 709 μmol, 1.00 eq.) in dimethylformamide (10 mL) was added sodium hydride (120 mg, 3.00 mmol, 60% purity, 4.23 eq.) in portions at 0° C. under nitrogen atmosphere. The mixture was stirred at 0° C. for 15 min, then iodomethane (180 μL, 2.89 mmol, 4.08 eq.) was added to the mixture. The mixture was stirred at 0° C. for 45 min. The reaction mixture was quenched with ice water (20 mL) at 0° C., and diluted with ethyl acetate (20 mL). The layers were separated, and the aqueous phase was extracted with ethyl acetate (2×20 mL). The combined organic layers were washed with brine (30 mL), dried over sodium sulfate, filtered, and concentrated under reduced pressure. The residue was purified via Purification Method 2 to afford 2-methyl-2-(phthalazin-6-yl) propanenitrile (100 mg, 486 μmol, 69% yield) as a brown solid.

Step 3. A solution of 2-methyl-2-phthalazin-6-yl-propanenitrile (100 mg, 507 μmol, 1.00 eq.) in concentrated hydrochloric acid (12 M, 10 mL) was stirred at 60° C. for 19 h. The reaction mixture was concentrated in vacuo. The residue was purified via Purification Method 1 to afford 2-methyl-2-phthalazin-6-yl-propanoic acid (55.0 mg, 249 μmol, 49% yield) as a yellow solid.

Step 4. To a solution of 2-methyl-2-(phthalazin-6-yl) propanoic acid (55.0 mg, 254 μmol, 1.00 eq.) in dimethylformamide (2 mL) was added N,N-diisopropylethylamine (130 μL, 773 μmol,, 3.04 eq.), 1H-benzo[d][1,2,3]triazol-1-ol (45.0 mg, 333 μmol, 1.31 eq.) and 1-(3-dimethylaminopropyl)-3-ethylcarbodiimide hydrochloride (60.0 mg, 313 μmol, 1.23 eq.) at 0° C. The reaction was stirred for 30 min at 20° C., then 3-(4-(aminomethyl)-2,6-dichlorophenyl) piperidine-2,6-dione (80.0 mg, 278. umol, 1.10 eq.) added. The reaction was stirred at 20° C. for 16 h. The mixture was diluted with water (10 mL) and extracted with ethyl acetate (2×10 mL). The combined organic layers were washed with brine (20 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-methyl-2-(phthalazin-6-yl) propanamide (47.6 mg, 95.2 μmol, 37% yield) as a white solid.

$^{1}$H NMR (400 MHZ, DMSO-$d_6$) δ=10.96 (s, 1H), 9.69 (s, 1H), 9.66 (d, J=1.2 Hz, 1H), 8.18-8.06 (m, 3H), 7.98-7.91 (m, 1H), 7.11 (d, J=1.6 Hz, 1H), 7.04 (d, J=1.2 Hz, 1H), 4.57-4.47 (m, 1H), 4.21 (d, J=6.0 Hz, 2H), 2.91-2.75 (m, 1H), 2.59-2.52 (m, 1H), 2.38-2.24 (m, 1H), 1.92-1.79 (m, 1H), 1.63 (s, 6H). MS (ESI) m/z 485.2 [M+H]$^+$

Exemplary Compound 36

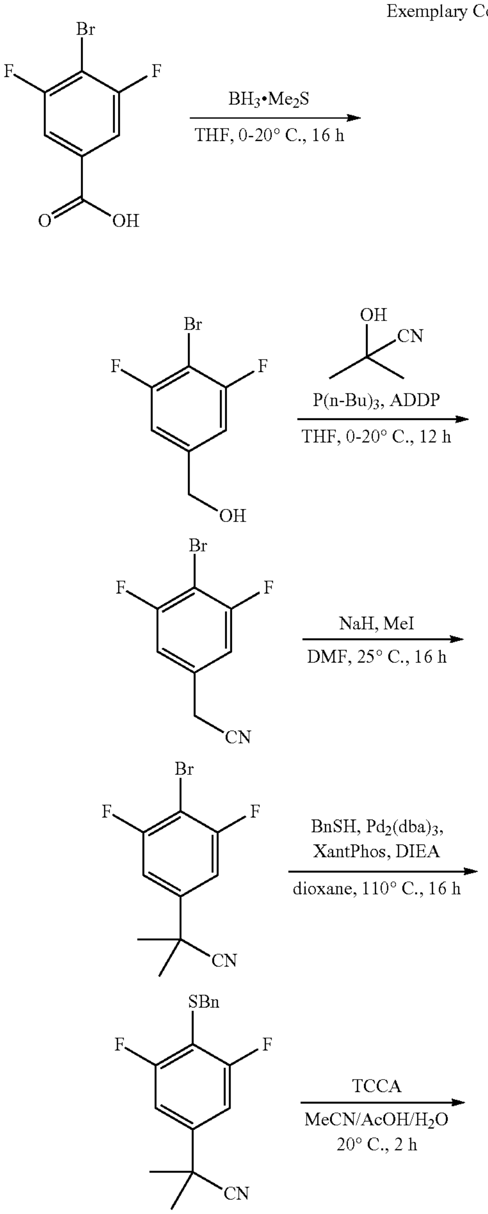

-continued

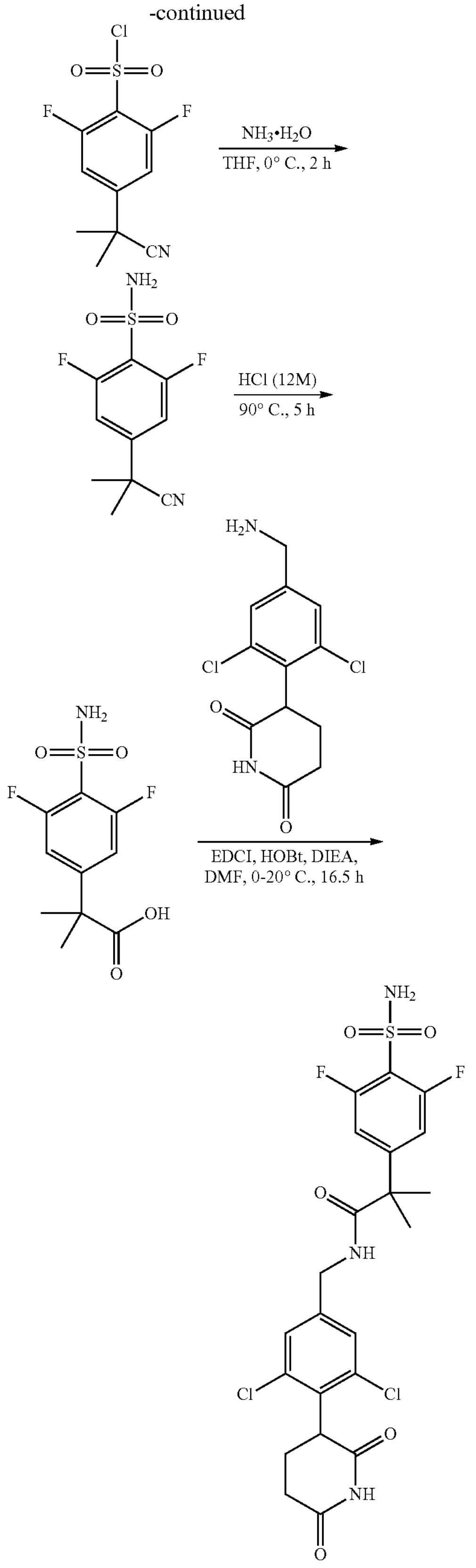

Step 1. To a solution of 4-bromo-3,5-difluoro-benzoic acid (2.00 g, 8.44 mmol, 1.00 eq.) in tetrahydrofuran (15 mL) was added dropwise borane dimethyl sulfide complex (10 M, 2.53 mL, 3.00 eq.) at 0° C. The reaction was stirred at 20° C. for 16 h. The reaction was quenched with ethyl alcohol at 0° C. under nitrogen atmosphere. The pH was adjusted to 2 with 2M hydrochloric acid (2 mL). The mixture was concentrated in vacuo. The residue was purified via Purification Method 2 to afford (4-bromo-3,5-difluorophenyl) methanol (1.41 g, 5.70 mmol, 68% yield, 90% purity) as a white solid.

Step 2. To a solution of (4-bromo-3,5-difluoro-phenyl) methanol (1.31 g, 5.87 mmol, 1.00 eq.) in tetrahydrofuran (15 mL) were added 2-hydroxy-2-methyl-propanenitrile (2.54 g, 29.9 mmol, 2.73 mL, 5.08 eq.) and tributylphosphane (2.38 g, 11.8 mmol, 2.90 mL, 2.00 eq.). The mixture was cooled to 0° C. Then azodicarboxylic acid dipiperidide (2.96 g, 11.8 mmol, 2.00 eq.) was added dropwise at 0° C. The reaction was stirred at 20° C. under nitrogen atmosphere for 12 h. The mixture was quenched with water (30 mL) and extracted with ethyl acetate (30 mL). The combined organic layers were washed with brine (30 mL), dried over sodium sulfate, filtered, and concentrated in vacuo. The residue was purified via Purification Method 2 to afford 2-(4-bromo-3,5-difluorophenyl) acetonitrile (1.75 g, crude) as a white solid.

Step 3. To a solution of 2-(4-bromo-3,5-difluoro-phenyl) acetonitrile (1.75 g, 7.54 mmol, 1.00 eq.) in dimethyl formamide (15 mL) was added sodium hydride (905 mg, 22.6 mmol, 60% purity, 3.00 eq.) at 0° C. under nitrogen atmosphere. After the mixture was stirred at 25° C. for 12 min, methyl iodide (5.35 g, 37.7 mmol, 2.35 mL, 5.00 eq.) was added to the mixture. The reaction was stirred at 25° C. under nitrogen atmosphere for 16 h. The reaction was quenched with saturated ammonium chloride, and the pH was adjusted to 5 with glacial acetic acid at 0° C. The mixture was diluted with water (30 mL) and extracted with ethyl acetate (30 mL). The combined organic layers were washed with brine (3×30 mL), dried over sodium sulfate, filtered, and concentrated in vacuo. The residue was purified via Purification Method 2 to afford 2-(4-bromo-3,5-difluorophenyl)-2-methylpropanenitrile (925 mg, 3.20 mmol, 42% yield) as a white solid.

Step 4. To a mixture of 2-(4-bromo-3,5-difluoro-phenyl)-2-methyl-propanenitrile (750 mg, 2.88 mmol, 1.00 eq.), tris(dibenzylideneacetone) dipalladium (0) (264 mg, 288 μmol, 0.10 eq.) and 4,5-bis(diphenylphosphino)-9,9-dimethylxanthene (334 mg, 577 μmol, 0.20 eq.) in dioxane (6 mL) were added N,N-diisopropylethylamine (1.12 g, 8.65 mmol, 1.51 mL, 3.00 eq.) and benzyl mercaptane (1.08 g, 8.70 mmol, 1.02 mL, 3.02 eq.) in one portion. The reaction was stirred at 110° C. under nitrogen atmosphere for 16 h. The mixture was concentrated under reduced pressure. The residue was purified via Purification Method 2 then Purification Method 1 to afford 2-(4-(benzylthio)-3,5-difluorophenyl)-2-methylpropanenitrile (640 mg, 1.90 mmol, 66% yield) as a colourless oil.

Step 5. To a solution of 2-(4-benzylsulfanyl-3,5-difluoro-phenyl)-2-methyl-propanenitrile (490 mg, 1.62 mmol, 1.00 eq.) in acetonitrile (5 mL), acetic acid (0.25 mL) and water (0.15 mL) was added 1,3,5-trichloro-1,3,5-triazinane-2,4,6-trione (808 mg, 3.48 mmol, 2.15 eq.). The mixture was stirred at 20° C. for 2 h. The mixture was diluted with water (20 mL) and extracted with ethyl acetate (20 mL). The combined organic layers were washed with water (20 mL) and brine (20 mL), dried over sodium sulfate, filtered, and concentrated under reduced pressure. The residue was purified via Purification Method 2 to afford 4-(2-cyanopropan-2-yl)-2,6-difluorobenzenesulfonyl chloride (410 mg, 1.32 mmol, 82% yield) as a white solid.

Step 6. To a solution of 4-(1-cyano-1-methyl-ethyl)-2,6-difluoro-benzenesulfonyl chloride (410 mg, 1.47 mmol, 1.00 eq.) in tetrahydrofuran (5 mL) was added ammonium hydroxide (14.7 mmol, 2.26 mL, 25% purity, 10.0 eq.) at 0° C. The mixture was stirred at 0° C. for 2 h. The mixture was diluted with water (20 mL) and extracted with ethyl acetate (20 mL). The combined organic layers were washed with water (20 mL) and brine (20 mL), dried over sodium sulfate, filtered, and concentrated under reduced pressure. The residue was purified by Prep-TLC (petroleum ether/ethyl acetate=1/1) to give 4-(2-cyanopropan-2-yl)-2,6-difluorobenzenesulfonamide (306 mg, 1.06 mmol, 72% yield) as a white solid.

Step 7. A solution of 4-(1-cyano-1-methyl-ethyl)-2,6-difluoro-benzenesulfonamide (220 mg, 845 μmol, 1.00 eq.) in hydrochloric acid (12 M, 5 mL) was stirred at 90° C. for 5 h. The reaction mixture was concentrated in vacuo. The residue was purified via Purification Method 1 to afford 2-(3,5-difluoro-4-sulfamoylphenyl)-2-methylpropanoic acid (141 mg, 454 μmol, 54% yield) as a yellow oil.

Step 8. To a solution of 2-(3,5-difluoro-4-sulfamoylphenyl)-2-methyl-propanoic acid (104 mg, 371 μmol, 1.20 eq.) in dimethyl formamide (3 mL) were added N,N-diisopropylethylamine (927 μmol, 161 μL, 3.00 eq.), N-[3-(dimethylamino) propyl]-N-ethylcarbodiimide hydrochloride (71.1 mg, 371 μmol, 1.20 eq.) and 1-Hydroxybenzotriazole (50.1 mg, 371 μmol, 1.20 eq.) at 0° C. After 30 min, 3-(4-(aminomethyl)-2,6-dichlorophenyl) piperidine-2,6-dione hydrochloride (100 mg, 309 μmol, 1.00 eq.) was added. The reaction was stirred at 20° C. for 16 h. The mixture was diluted with water (10 mL) and extracted with ethyl acetate (10 mL). The combined organic layers were washed with water (2×10 mL) and brine (10 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-(3,5-difluoro-4-sulfamoylphenyl)-2-methylpropanamide (84.9 mg, 150 μmol, 49% yield) as a white solid.

$^1H$ NMR (400 MHZ, DMSO-$d_6$) δ=10.97 (s, 1H), 8.20 (t, J=6.0 Hz, 1H), 7.98 (s, 2H), 7.21 (d, J=1.6 Hz, 1H), 7.18-7.13 (m, 3H), 4.56 (dd, J=5.6, 12.8 Hz, 1H), 4.23 (d, J=6.0 Hz, 2H), 2.86 (ddd, J=6.0, 14.0, 16.8 Hz, 1H), 2.58-2.53 (m, 1H), 2.35 (dq, J=4.4, 13.2 Hz, 1H), 1.93-1.84 (m, 1H), 1.55-1.46 (m, 6H). MS (ESI) m/z 548.1 $[M+H]^+$ Exemplary Compound 37

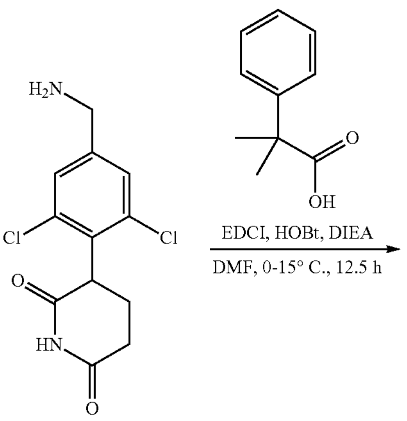

-continued

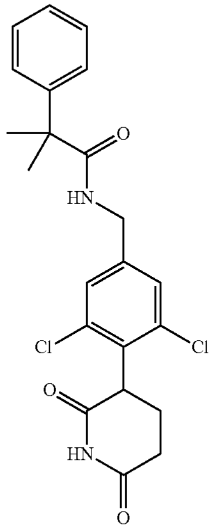

Step 1. To a solution of 2-methyl-2-phenylpropanoic acid (80.0 mg, 487 µmol, 1.00 eq.) and N,N-diisopropylethylamine (193 mg, 1.49 mmol, 3.06 eq.) in dimethylformamide (1 mL) were added 1-(3-dimethylaminopropyl)-3-ethylcarbodiimide hydrochloride (140 mg, 730 µmol, 1.50 eq.) and 1-Hydroxybenzotriazole hydrate (100 mg, 740 µmol, 1.52 eq.) at 0° C. The mixture was stirred at 15° C. for 30 min, then 3-(4-(aminomethyl)-2,6-dichlorophenyl) piperidine-2,6-dione (100 mg, 348 µmol, 0.72 eq.) was added, and the reaction was stirred at 15° C. for 12 h. The mixture was diluted with ethyl acetate (8 mL) and water (5 mL). The layers were separated, and the aqueous phase was extracted with ethyl acetate (2×5 mL). The combined organic layers were washed with brine (15 mL) and dried over anhydrous sodium sulfate, filtered, and concentrated in vacuo. The residue was purified via Purification Method 1 to afford N-(3,5-dichloro-4-(2,6-dioxopiperidin-3-yl)benzyl)-2-methyl-2-phenylpropanamide (71.65 mg, 164 µmol, 34% yield) as a white solid.

$^1$H NMR (400 MHZ, DMSO-$d_6$) δ=10.96 (s, 1H), 8.02 (t, J=6.0 Hz, 1H), 7.38-7.28 (m, 4H), 7.28-7.22 (m, 1H), 7.21 (s, 1H), 7.14 (s, 1H), 4.56 (dd, J=5.6, 12.8 Hz, 1H), 4.21 (d, J=6.0 Hz, 2H), 2.93-2.79 (m, 1H), 2.59-2.52 (m, 1H), 2.42-2.27 (m, 1H), 1.95-1.83 (m, 1H), 1.49 (s, 6H). MS (ESI) m/z 433.1 [M+H]$^+$

Exemplary Compound 38

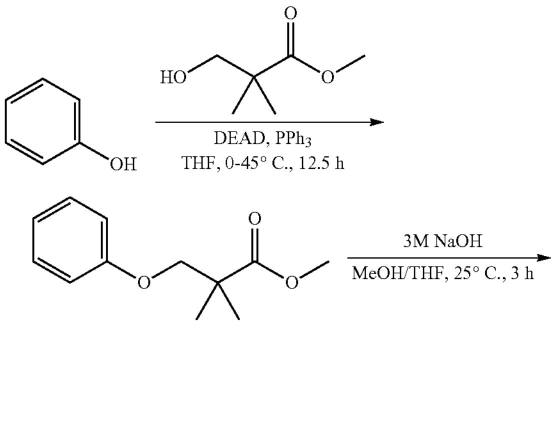

-continued

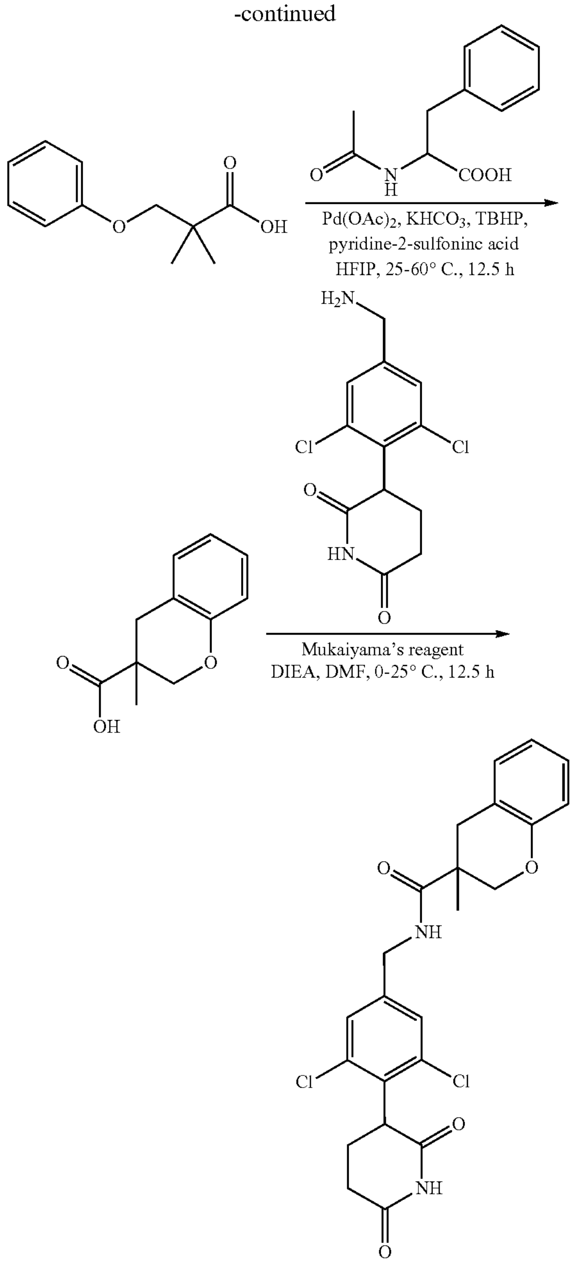

Step 1. To a solution of phenol (5.00 g, 53.1 mmol, 4.67 mL, 1.00 eq.) in tetrahydrofuran (50.0 mL) was added methyl 3-hydroxy-2,2-dimethyl-propanoate (8.43 g, 63.7 mmol, 8.13 mL, 1.20 eq.) and triphenylphosphine (20.9 g, 79.6 mmol, 1.50 eq.). After 0.5 h, diethyl azodiformate (13.8 g, 79.6 mmol, 14.4 mL, 1.50 eq.) was added. Then the mixture was stirred at 45° C. for 12 h under nitrogen atmosphere. The mixture was concentrated under reduced pressure. The residue was purified via Purification Method 2 to afford methyl 2,2-dimethyl-3-phenoxypropanoate (4.99 g, 21.5 mmol, 40% yield, 90% purity) as a white oil.

Step 2. To a solution of methyl 2,2-dimethyl-3-phenoxypropanoate (4.99 g, 23.9 mmol, 1.00 eq.) in methanol (1.5 mL) and tetrahydrofuran (1.5 mL) was added sodium hydroxide (3 M, 44.3 mL, 5.55 eq.). The mixture was stirred at 25° C. for 3 h. Dichloromethane (50.0 mL) was added, and the reaction was stirred at room temperature for 5 min.

The pH was adjusted to 2 by adding 1M hydrochloric acid. The mixture was diluted with water (20.0 mL) and extracted with ethyl acetate (3×50.0 mL). The combined organic layers were washed with brine (3×50.0 mL), dried over anhydrous sodium sulfate, filtered, and concentrated under reduced pressure to afford 2,2-dimethyl-3-phenoxypropanoic acid (3.93 g, 20.2 mmol, 84% yield) as a white solid.

Step 3. A solution of palladium (II) acetate (14.4 mg, 64.3 μmol, 0.05 eq.) and (2R)-2-acetamido-3-phenyl-propanoic acid (26.6 mg, 128 μmol, 0.100 eq.) in anhydrous hexafluoroisopropanol (5.00 mL) was stirred at 25° C. for 0.5 h. 2,2-dimethyl-3-phenoxy-propanoic acid (250 mg, 1.29 mmol, 1.00 eq.), potassium bicarbonate (193 mg, 1.93 mmol, 1.50 eq.), tert-butyl hydroperoxide (174 mg, 1.93 mmol, 185 μL, 1.50 eq.) and pyridine-2-sulfonic acid (20.4 mg, 128 μmol, 0.100 eq.) were added, and the reaction was stirred at 60° C. for 12 h. The pH of the mixture was adjusted to 2 by adding 1M hydrochloric acid. The mixture was quenched with water (20.0 mL) and extracted with dichloromethane (3×50.0 mL). The combined organic layers were washed with brine (3×50.0 mL), dried over anhydrous sodium sulfate, filtered, and concentrated under reduced pressure. The residue was purified via Purification Method 2 to afford 3-methylchromane-3-carboxylic acid (228 mg, 1.19 mmol, 46% yield) as a yellow solid.

Step 4. To a solution of 3-methylchromane-3-carboxylic acid (67.0 mg, 348 μmol, 1.00 eq.) in N,N-dimethylformamide (2.0 mL) was added 2-chloro-1-methyl-pyridin-1-ium iodide (133 mg, 522 μmol, 1.50 eq.) and N,N-diisopropylethylamine (180 mg, 1.39 mmol, 4.00 eq . . . ). The reaction was stirred at 0° C. for 0.5 h, then 3-(4-(aminomethyl)-2,6-dichlorophenyl) piperidine-2,6-dione (110 mg, 383 μmol, 1.10 eq.) was added. The reaction was stirred at 25° C. for 12 h. The mixture was concentrated under reduced pressure to give a residue. The residue was purified via Purification Method 1 to afford N-(3,5-dichloro-4-(2,6-dioxopiperidin-3-yl)benzyl)-3-methylchromane-3-carboxamide (44.93 mg, 94.5 μmol, 27% yield) as a yellow solid.

$^1$H NMR (400 MHZ, DMSO-$d_6$) δ=10.96 (s, 1H), 8.46 (t, J=5.6 Hz, 1H), 7.27-7.23 (m, 1H), 7.17 (s, 1H), 7.09-7.02 (m, 2H), 6.86-6.80 (m, 1H), 6.76 (d, J=7.6 Hz, 1H), 4.60-4.49 (m, 1H), 4.35 (d, J=10.8 Hz, 1H), 4.29-4.19 (m, 2H), 3.94 (d, J=10.8 Hz, 1H), 3.21 (d, J=16.4 Hz, 1H), 2.90-2.79 (m, 1H), 2.68 (d, J=16.0 Hz, 1H), 2.54 (d, J=2.0 Hz, 1H), 2.38-2.27 (m, 1H), 1.93-1.80 (m, 1H), 1.20 (s, 3H). MS (ESI) m/z 461.1 [M+H]$^+$

Exemplary Compound 39

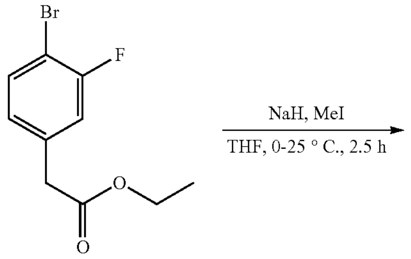

-continued

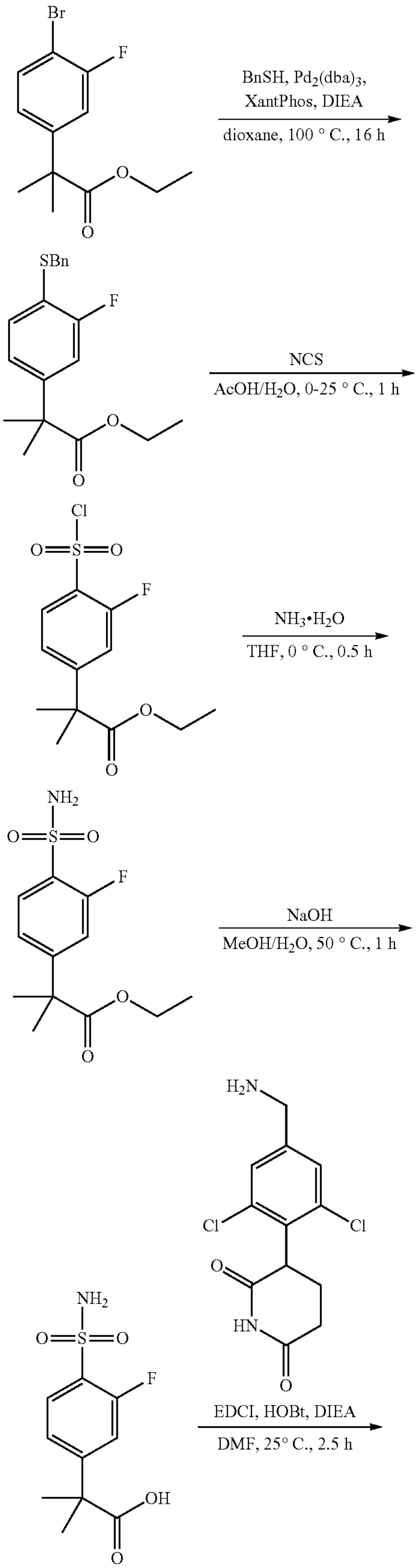

-continued

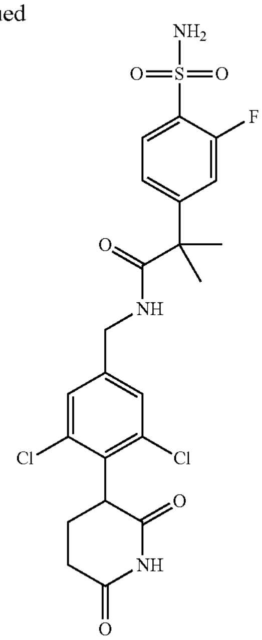

Step 1. To a mixture of ethyl 2-(4-bromo-3-fluorophenyl) acetate (5.00 g, 19.1 mmol, 1.00 eq.) in tetrahydrofuran (50 mL) was added sodium hydride (3.06 g, 76.6 mmol, 60% purity, 4.00 eq.) in portions at 0° C. The reaction was stirred at 0° C. for 0.5 h, then iodomethane (8.15 g, 57.4 mmol, 3.00 eq.) was added, and the mixture was stirred at 0° C. under nitrogen atmosphere for 2 h. The reaction was quenched with saturated aqueous ammonium chloride (50 mL) and extracted with ethyl acetate (3×50 mL). The combined organic layers were washed with brine (50 mL), dried over anhydrous sodium sulfate, filtered, and the filtrate was concentrated under reduced pressure. The residue was purified via Purification Method 2 to afford ethyl 2-(4-bromo-3-fluorophenyl)-2-methylpropanoate (5.00 g, 17.2 mmol, 90% yield) as a colourless oil.

Step 2. To a mixture of ethyl 2-(4-bromo-3-fluorophenyl)-2-methylpropanoate (200 mg, 691 μmol, 1.00 eq.), tris (dibenzylideneacetone) dipalladium (0) (63.3 mg, 69.2 μmol, 0.10 eq.) and 4,5-bis(diphenylphosphino)-9,9-dimethylxanthene (80.1 mg, 138 μmol, 0.20 eq.) in dioxane (2 mL) were added diisopropylethylamine (268 mg, 2.08 mmol, 3.00 eq.) and phenylmethanethiol (510 mg, 4.11 mmol, 5.94 eq.) in one portion at 25° C. The mixture was stirred at 100° C. under nitrogen atmosphere for 16 h. The mixture was cooled to 25° C. then poured into water (10 mL). The mixture was extracted with ethyl acetate (3×20 mL). The combined organic layers were washed with brine (20 mL), dried over anhydrous sodium sulfate, filtered, and the filtrate was concentrated under reduced pressure. The residue was purified by Prep-TLC (petroleum ether:ethyl acetate=10:1) to give ethyl 2-(4-(benzylthio)-3-fluorophenyl)-2-methylpropanoate (80.0 mg, 240 μmol, 34% yield) as a colourless oil.

Step 3. To a solution of ethyl 2-(4-(benzylthio)-3-fluorophenyl)-2-methylpropanoate (400 mg, 1.20 mmol, 1.00 eq.) in water (0.4 mL) and acetic acid (2 mL) was added 1-chloropyrrolidine-2,5-dione (750 mg, 5.62 mmol, 4.67 eq.) at 0° C. The reaction was stirred at 25° C. for 1 h. The mixture was poured into water (10 mL) and extracted with ethyl acetate (3× 20 mL). The combined organic layers were washed with brine (20 mL), dried over anhydrous sodium sulfate, filtered, and the filtrate was concentrated under reduced pressure. The residue was purified via Purification Method 2 to afford ethyl 2-(4-(chlorosulfonyl)-3-fluorophenyl)-2-methylpropanoate (300 mg, 971 μmol, 80% yield) as a colourless oil.

Step 4. To a solution of ethyl 2-(4-(chlorosulfonyl)-3-fluorophenyl)-2-methylpropanoate (300 mg, 971 μmol, 1.00 eq.) in tetrahydrofuran (1 mL) was added ammonium hydroxide (1.36 g, 9.72 mmol, 10.0 eq.) in one portion at 0° C. The reaction was stirred at 0° C. for 0.5 h. The mixture was poured into water (10 mL) and extracted with ethyl acetate (3× 20 mL). The combined organic layers were washed with brine (20 mL), dried over anhydrous sodium sulfate, filtered, and the filtrate was concentrated under reduced pressure. The residue was purified via Purification Method 2 to afford ethyl 2-(3-fluoro-4-sulfamoylphenyl)-2-methylpropanoate (160 mg, 536 μmol, 55% yield) as a white solid.

Step 5. To a mixture of ethyl 2-(3-fluoro-4-sulfamoylphenyl)-2-methylpropanoate (150 mg, 518 μmol, 1.00 eq.) in methanol (0.5 mL) and water (0.5 mL) was added sodium hydroxide (165 mg, 4.15 mmol, 8.00 eq.) in one portion at 20° C. The reaction was stirred at 50° C. for 1 h. The mixture was cooled to 20° C., and washed with ethyl acetate (3×30 mL). The aqueous phase was collected and adjusted pH to 2 using 36% aqueous hydrochloric acid, and then extracted with ethyl acetate (3× 20 mL). The combined organic extracts were washed with brine (30 mL), dried over anhydrous sodium sulfate, filtered, and concentrated under reduced pressure to give 2-(3-fluoro-4-sulfamoylphenyl)-2-methylpropanoic acid (80.0 mg, 275 μmol, 53% yield) as a white solid.

Step 6. To a mixture of 2-(3-fluoro-4-sulfamoylphenyl)-2-methylpropanoic acid (60.0 mg, 229 μmol, 1.00 eq.), N1-((ethylimino)methylene)-N3,N3-dimethylpropane-1,3-diamine hydrochloride (52.8 mg, 275 μmol, 1.20 eq.) and 1H-benzo[d][1,2,3]triazol-1-ol (37.2 mg, 275 μmol, 1.20 eq.) in dimethyl formamide (2 mL) was added diisopropylethylamine (89.0 mg, 688 μmol, 3.00 eq.) dropwise at 25° C. The mixture was stirred at 25° C. for 0.5 h, and then 3-(4-(aminomethyl)-2,6-dichlorophenyl) piperidine-2,6-dione (89.2 mg, 275 μmol, 1.20 eq., hydrochloride) was added. The reaction was stirred at 25° C. for 2 h. The mixture was poured into water (10 mL) and extracted with ethyl acetate (3×20 mL). The combined organic layers were washed with brine (20 mL), dried over anhydrous sodium sulfate, filtered, and concentrated under reduced pressure. The residue was purified via Purification Method 1 to afford N-(3,5-dichloro-4-(2,6-dioxopiperidin-3-yl)benzyl)-2-(3-fluoro-4-sulfamoylphenyl)-2-methylpropanamide (61.8 mg, 117 μmol, 61% yield) as an off-white solid.

$^1$H NMR (400 MHZ, DMSO-$d_6$) δ=10.95 (s, 1H), 8.16 (t, J=6.0 Hz, 1H), 7.74 (t, J=8.0 Hz, 1H), 7.63 (s, 2H), 7.31 (dd, J=1.6, 12.0 Hz, 1H), 7.26 (dd, J=1.6, 8.0 Hz, 1H), 7.20 (d, J=1.2 Hz, 1H), 7.14 (d, J=1.6 Hz, 1H), 4.55 (dd, J=6.0, 12.8 Hz, 1H), 4.22 (d, J=5.6 Hz, 2H), 2.91-2.78 (m, 1H), 2.59-2.51 (m, 1H), 2.39-2.29 (m, 1H), 1.93-1.82 (m, 1H), 1.51 (s, 6H). MS (ESI) m/z 530.3, 532.3 $[M+H]^+$

Exemplary Compound 42

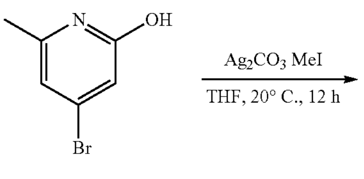

-continued

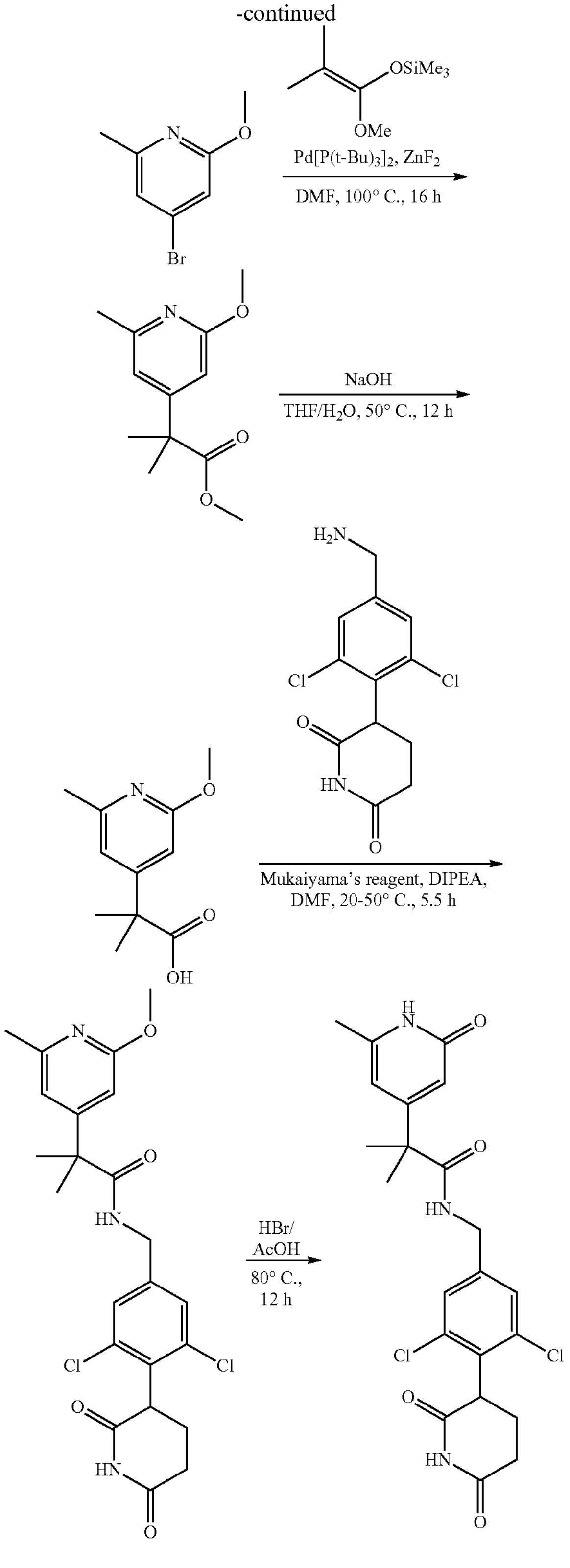

Step 1. To a solution of 4-bromo-6-methylpyridin-2-ol (2.00 g, 10.6 mmol, 1.00 eq.) in tetrahydrofuran (10 mL) was added iodomethane (3.02 g, 21.2 mmol, 2.00 eq.) and silver (I) carbonate (3.81 g, 13.8 mmol, 1.30 eq.) in one portion at 20° C. The mixture was stirred for 12 h at 20° C. in the dark. The mixture was filtered directly, and the filtrate was concentrated under reduced pressure. The residue was purified via Purification Method 2 to afford 4-bromo-2-methoxy-6-methylpyridine (1.40 g, 6.65 mmol, 62% yield) as a light-yellow liquid.

Step 2. A mixture of 4-bromo-2-methoxy-6-methylpyridine (500 mg, 2.47 mmol, 1.00 eq.), difluorozinc (255 mg, 2.47 mmol, 1.00 eq.), palladium tri-tert-butylphosphane (126 mg, 247 μmol, 0.10 eq.) and ((1-methoxy-2-methylprop-1-en-1-yl)oxy)trimethylsilane (862 mg, 4.95 mmol, 2.00 eq.) in dimethyl formamide (5 mL) was stirred at 100° C. for 16 h under nitrogen atmosphere. The mixture was cooled to 20° C., and poured into water (10 mL). The mixture was extracted with ethyl acetate (3×10 mL). The combined organic layers were washed with brine (20 mL), dried over anhydrous sodium sulfate, filtered, and concentrated under reduced pressure. The residue was purified via Purification Method 2 to afford methyl 2-(2-methoxy-6-methylpyridin-4-yl)-2-methylpropanoate (450 mg, 1.77 mmol, 71% yield) as a light-yellow liquid.

Step 3. To a solution of methyl 2-(2-methoxy-6-methylpyridin-4-yl)-2-methylpropanoate (450 mg, 2.02 mmol, 1.00 eq.) in tetrahydrofuran (5 mL) and water (5 mL) was added sodium hydroxide (403 mg, 10.0 mmol, 5.00 eq.) at 20° C. The reaction was stirred at 50° C. for 12 h. The mixture was poured into water (10 mL) and adjusted pH=2-3 with 36% aqueous hydrochloric acid. The mixture was extracted with ethyl acetate (3× 10 mL). The combined organic layers were washed with brine (10 mL), dried over anhydrous sodium sulfate, filtered, and the filtrate was concentrated under reduced pressure to give 2-(2-methoxy-6-methylpyridin-4-yl)-2-methylpropanoic acid (200 mg, 850 μmol, 42% yield) as a white solid.

Step 4. To a solution of 2-(2-methoxy-6-methylpyridin-4-yl)-2-methylpropanoic acid (64.6 mg, 309 μmol, 1.00 eq.) and diisopropylethylamine (119 mg, 927 μmol, 3.00 eq.) in dimethyl formamide (0.5 mL) was added 2-chloro-1-methyl-pyridin-1-ium iodide (94.7 mg, 370 μmol, 1.20 eq.) in one portion at 20° C. The mixture was stirred at 20° C. for 0.5 h, then 3-(4-(aminomethyl)-2,6-dichlorophenyl) piperidine-2,6-dione hydrochloride (100 mg, 309 μmol, 1.00 eq.) was added. The mixture was stirred at 50° C. for 5 h. The reaction mixture was poured into water (10 mL) and extracted with ethyl acetate (3×10 mL). The combined organic layers were washed with brine (20 mL), dried over anhydrous sodium sulfate, filtered, and concentrated under reduced pressure. The residue was purified via Purification Method 2 to afford N-(3,5-dichloro-4-(2,6-dioxopiperidin-3-yl)benzyl)-2-(2-methoxy-6-methylpyridin-4-yl)-2-methylpropanamide (70.0 mg, 146 μmol, 47% yield) as a white solid.

Step 5. A solution of N-(3,5-dichloro-4-(2,6-dioxopiperidin-3-yl)benzyl)-2-(2-methoxy-6-methylpyridin-4-yl)-2-methylpropanamide (50.0 mg, 104 μmol, 1.00 eq.) in hydrogen bromide (2 mL, 35% in acetic acid) was stirred at 80° C. for 12 h. The solution was cooled to 20° C., and concentrated under reduced pressure. The residue was purified via Purification Method 1 to afford N-(3,5-dichloro-4-(2,6-dioxopiperidin-3-yl)benzyl)-2-methyl-2-(6-methyl-2-oxo-1,2-dihydropyridin-4-yl) propanamide (30.4 mg, 64.9 μmol, 62% yield) as a white solid.

$^1$H NMR (400 MHZ, DMSO-$d_6$) 0=11.43 (s, 1H), 10.95 (s, 1H), 8.08 (t, J=6.0 Hz, 1H), 7.22 (s, 1H), 7.15 (s, 1H), 6.09 (s, 1H), 5.78 (s, 1H), 4.55 (dd, J=5.4, 12.8 Hz, 1H), 4.21 (d, J=6.0 Hz, 2H), 2.85 (ddd, J=5.6, 14.4, 16.4 Hz, 1H), 2.55 (s, 1H), 2.39-2.29 (m, 1H), 2.11 (s, 3H), 1.88 (td, J=5.6, 11.2 Hz, 1H), 1.37 (s, 6H). MS (ESI) m/z 464.1 $[M+H]^+$ Exemplary Compound 43

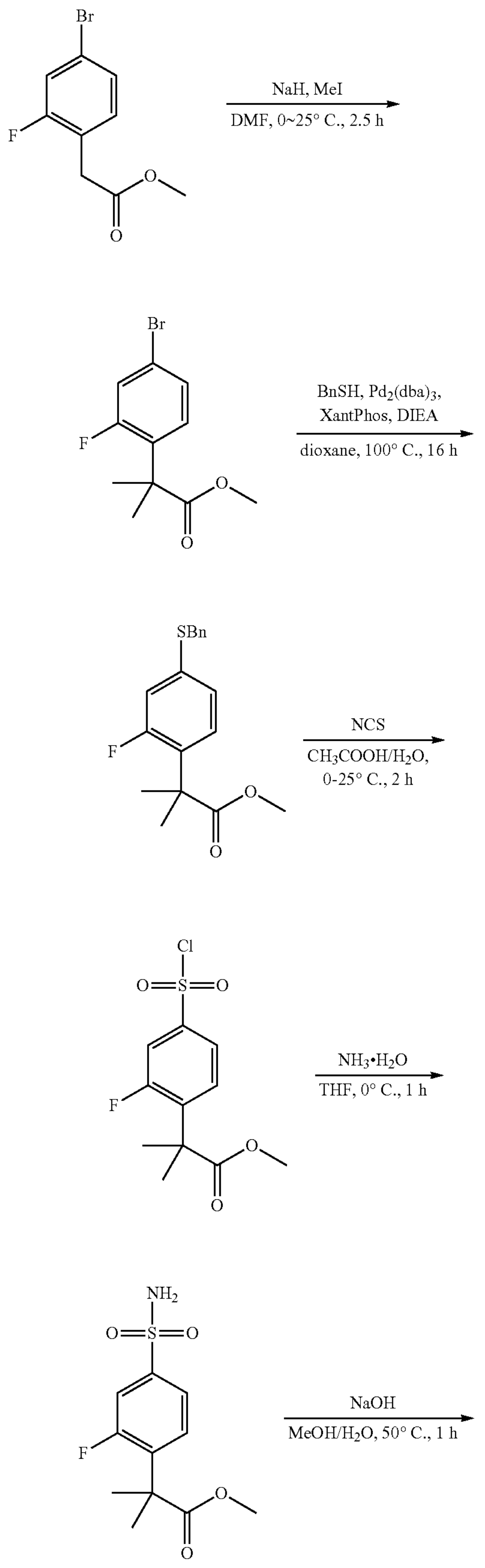

-continued

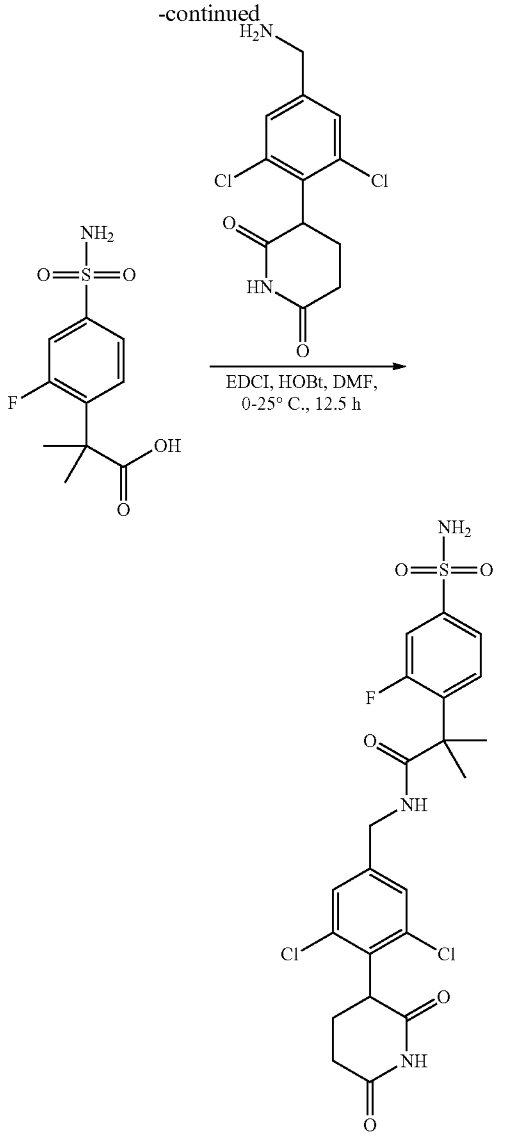

Step 1. To a solution of methyl 2-(4-bromo-2-fluorophenyl)acetate (1.73 g, 6.99 mmol, 1.00 eq.) in N,N-dimethylformamide (20.0 mL) was added sodium hydride (838 mg, 20.9 mmol, 60% purity, 3.00 eq.) at 0° C. After stirring at 0° C. for 0.5 h, iodomethane (4.96 g, 34.9 mmol, 2.17 mL, 5.00 eq.) was added, and the reaction was stirred at 25° C. for 2 h. The mixture was quenched with water (20.0 mL) and extracted with ethyl acetate (3× 20.0 mL). The combined organic layers were washed with brine (3×20.0 mL), dried over anhydrous sodium sulfate, filtered, and concentrated under reduced pressure. The residue was purified via Purification Method 2 to afford methyl 2-(4-bromo-2-fluorophenyl)-2-methylpropanoate (1.60 g, 5.82 mmol, 83% yield) as a transparent oil.

Step 2. To a solution of methyl 2-(4-bromo-2-fluorophenyl)-2-methylpropanoate (1.84 g, 6.69 mmol, 1.00 eq.) in dioxane (18.0 mL) was added phenylmethanethiol (1.16 g, 9.36 mmol, 1.10 mL, 1.40 eq.), tris(dibenzylideneacetone) dipalladium (0) (612 mg, 668 μmol, 0.100 eq.), 4,5-bis (diphenylphosphino)-9,9-dimethylxanthene (773 mg, 1.34 mmol, 0.200 eq.) and N,N-diisopropylethylamine (2.59 g, 20.0 mmol, 3.49 mL, 3.00 eq.). The mixture was stirred at 100° C. for 12 h under nitrogen atmosphere. After cooling to room temperature, the mixture was filtered.

The filtrate was poured into water (20.0 ml) and extracted with ethyl acetate (3×10.0 ml). The combined organic layers were washed with brine (20.0 mL), dried over anhydrous sodium sulfate, filtered, and concentrated under reduced pressure. The residue was purified via Purification Method 2 to afford methyl 2-(4-(benzylthio)-2-fluorophenyl)-2-methylpropanoate (757 mg, 2.31 mmol, 34% yield) as a yellow oil.

Step 3. To a solution of methyl 2-(4-(benzylthio)-2-fluorophenyl)-2-methylpropanoate (757 mg, 2.38 mmol, 1.00 eq.) in acetic acid (1.00 mL) and water (0.350 mL) was added 1-chloropyrrolidine-2,5-dione (1.48 g, 11.1 mmol, 4.67 eq.) at 0° C. The mixture was stirred at 25° C. for 2 h. The mixture was quenched with water (20.0 mL) and extracted with ethyl acetate (3×20.0 mL). The combined organic layers were washed with brine (3× 20.0 mL), dried over anhydrous sodium sulfate, filtered, and concentrated under reduced pressure. The residue was purified via Purification Method 2 to afford methyl 2-(4-(chlorosulfonyl)-2-fluorophenyl)-2-methylpropanoate (427 mg, 1.30 mmol, 54% yield, 90% purity) as a white solid.

Step 4. To a solution of methyl 2-(4-(chlorosulfonyl)-2-fluorophenyl)-2-methylpropanoate (300 mg, 1.02 mmol, 1.00 eq.) in tetrahydrofuran (3.00 mL) was added ammonium hydroxide (1.43 g, 10.1 mmol, 1.57 mL, 25% purity, 10.0 eq.). The reaction was stirred at 0° C. for 1 h. The mixture was diluted with water (20 mL) and extracted with ethyl acetate (3×20.0 mL). The combined organic layers were washed with brine (3×20.0 mL), dried over anhydrous sodium sulfate, filtered, and concentrated under reduced pressure. The residue was purified via Purification Method 2 to afford methyl 2-(2-fluoro-4-sulfamoylphenyl)-2-methylpropanoate (280 mg, 915 μmol, 89% yield, 90% purity) as a white solid.

Step 5. To a solution of methyl 2-(2-fluoro-4-sulfamoylphenyl)-2-methylpropanoate (175 mg, 572 μmol, 1.00 eq.) in methanol (0.500 mL) and water (0.500 mL) was added sodium hydroxide (183 mg, 4.58 mmol, 8.00 eq.). The mixture was stirred at 50° C. for 1 h. The pH of the mixture was adjusted to 7 with 1 M hydrochloric acid. The mixture was purified via Purification Method 1 to afford 2-(2-fluoro-4-sulfamoylphenyl)-2-methylpropanoic acid (50.0 mg, 191.3 μmol, 33% yield) as a white solid.

Step 6. To a solution of 2-(2-fluoro-4-sulfamoylphenyl)-2-methylpropanoic acid (21.0 mg, 80.3 μmol, 1.00 eq.) in N,N-dimethylformamide (1.00 mL) was added benzotriazol-1-ol (13.0 mg, 96.4 μmol, 1.20 eq.) and 1-(3-dimethylaminopropyl)-3-ethylcarbodiimide hydrochloride (18.4 mg, 96.4 μmol, 1.20 eq.). The mixture was stirred at 0° C. for 0.5 h, then 3-[4-(aminomethyl)-2,6-dichloro-phenyl]piperidine-2,6-dione (25.3 mg, 88.4 μmol, 1.10 eq.) was added. The reaction was stirred at 25° C. for 12 h. The mixture was concentrated under reduced pressure. The residue was purified via Purification Method 1 to afford N-(3,5-dichloro-4-(2,6-dioxopiperidin-3-yl)benzyl)-2-(2-fluoro-4-sulfamoylphenyl)-2-methylpropanamide (26.19 mg, 48.88 μmol, 60% yield) as a white solid.

$^1$H NMR (400 MHZ, DMSO-$d_6$) δ=10.97 (s, 1H), 8.44 (s, 1H), 8.06 (t, J=5.6 Hz, 1H), 7.68-7.62 (m, 2H), 7.58-7.35 (m, 3H), 7.31 (s, 1H), 7.24 (s, 1H), 4.62-4.52 (m, 1H), 4.22 (d, J=5.6 Hz, 2H), 2.91-2.80 (m, 1H), 2.55 (d, J=2.0 Hz, 1H), 2.39-2.32 (m, 1H), 1.95-1.86 (m, 1H), 1.50 (s, 6H). MS (ESI) m/z 529.9 [M+H]$^+$

Exemplary Compound 44

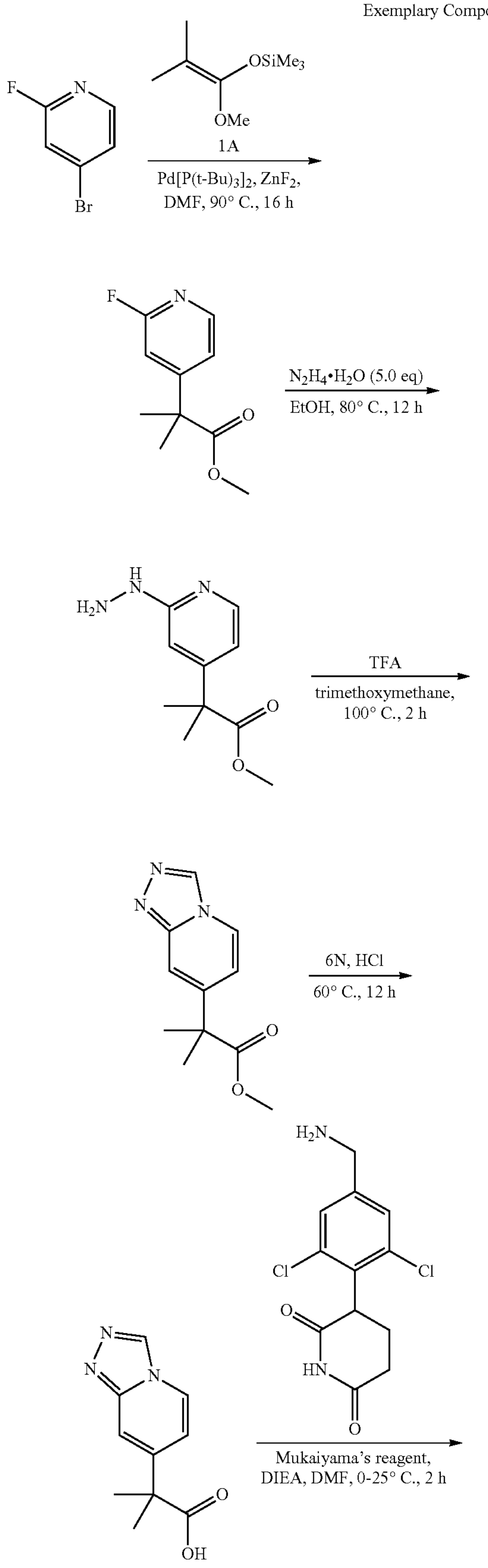

-continued

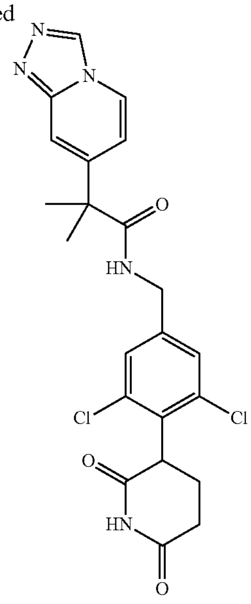

Step 1. To a solution of 4-bromo-2-fluoropyridine (5.00 g, 28.4 mmol, 1.00 eq.) and ((1-methoxy-2-methylprop-1-en-1-yl)oxy)trimethylsilane (7.43 g, 42.6 mmol, 1.50 eq.) in N,N-dimethylformamide (30 mL) were added bis(tri-tert-butylphosphine) palladium (0) (800 mg, 1.57 mmol, 0.55 eq.) and zinc (II) fluoride (2.94 g, 28.4 mmol, 1.00 eq.). The reaction was stirred at 90° C. for 16 h under nitrogen. The mixture was filtered, and the filtrate was diluted with water (100 mL) and extracted with ethyl acetate (3×50 mL). The combined organic layers were washed with water (3×50 mL), dried over sodium sulfate, filtered, and concentrated under reduced pressure. The crude product was purified via Purification Method 2 to afford methyl 2-(2-fluoropyridin-4-yl)-2-methylpropanoate (3.56 g, 17.9 mmol, 63% yield) as a light-yellow liquid.

Step 2. To a solution of methyl 2-(2-fluoropyridin-4-yl)-2-methylpropanoate (500 mg, 2.54 mmol, 1.00 eq.) in ethanol (5 mL) was added hydrazine hydrate (14.7 mmol, 720 μL, 98% purity, 5.79 eq.). The mixture was stirred at 80° C. for 12 h. After cooling to 20° C., the mixture was concentrated under reduced pressure. The crude product was purified via Purification Method 2 to afford methyl 2-(2-hydrazineylpyridin-4-yl)-2-methylpropanoate formate (210 mg, 773 μmol, 31% yield) as an off-white solid.

Step 3. To a solution of methyl 2-(2-hydrazineylpyridin-4-yl)-2-methylpropanoate formate (170 mg, 666 μmol, 1.00 eq.) in trimethoxymethane (5 mL) was added trifluoroacetic acid (8.00 mg, 70.2 μmol, 0.11 eq.). The mixture was stirred at 100° C. for 2 h. The mixture was concentrated under reduced pressure. The crude product was purified via Purification Method 2 to afford methyl 2-([1,2,4]triazolo[4,3-a]pyridin-7-yl)-2-methylpropanoate (70.0 mg, 303 μmol, 46% yield) as a yellow oil.

Step 4. A mixture of methyl 2-([1,2,4]triazolo[4,3-a]pyridin-7-yl)-2-methylpropanoate (80.0 mg, 365 μmol, 1.00 eq.) in hydrochloric acid (4 mL) (6 N in water) was stirred at 60° C. for 12 h. The mixture was concentrated under reduced pressure to give 2-([1,2,4]triazolo[4,3-a]pyridin-7-yl)-2-methylpropanoic acid (80.0 mg, 363 μmol, 99% yield) as a light-yellow solid.

Step 5. To a solution of 2-([1,2,4]triazolo[4,3-a]pyridin-7-yl)-2-methylpropanoic acid (70.0 mg, 341 μmol, 1.00 eq.) in N,N-dimethylformamide (2 mL) were added N,N-diisopropylethylamine (1.61 mmol, 280 μL, 4.71 eq.) and 2-chloro-1-methylpyridin-1-ium iodide (126 mg, 493 μmol, 1.45 eq.) at 0° C. The mixture was stirred at 15° C. for 0.5 h. Then 3-(4-(aminomethyl)-2,6-dichlorophenyl) piperidine-2,6-dione hydrochloride (100 mg, 309 μmol, 0.90 eq.) was added. The reaction was stirred at 25° C. for 1.5 h. The mixture was diluted with water (20 mL) and extracted with dichloromethane (2×20 mL). The combined organic layers were dried over sodium sulfate, filtered, and concentrated under reduced pressure. The crude product was purified via Purification Method 1 to afford 2-([1,2,4]triazolo[4,3-a]pyridin-7-yl)-N-(3,5-dichloro-4-(2,6-dioxopiperidin-3-yl) benzyl)-2-methylpropanami-de (75.8 mg, 158 μmol, 46% yield) as a pink solid.

$^{1}$H NMR (400 MHZ, DMSO-$d_6$)>=10.95 (s, 1H), 9.22 (s, 1H), 8.49 (dd, J=0.8, 7.2 Hz, 1H), 8.11 (t, J=6.0 Hz, 1H), 7.67 (s, 1H), 7.16 (d, J=1.2 Hz, 1H), 7.08 (d, J=1.2 Hz, 1H), 6.80 (dd, J=1.6, 7.2 Hz, 1H), 4.53 (dd, J=5.6, 12.8 Hz, 1H), 4.20 (d, J=6.0 Hz, 2H), 2.90-2.78 (m, 1H), 2.57-2.52 (m, 1H), 2.32 (dq, J=4.4, 13.2 Hz, 1H), 1.91-1.82 (m, 1H), 1.54 (s, 6H). MS (ESI) m/z 474.1 $[M+H]^+$

Exemplary Compound 47

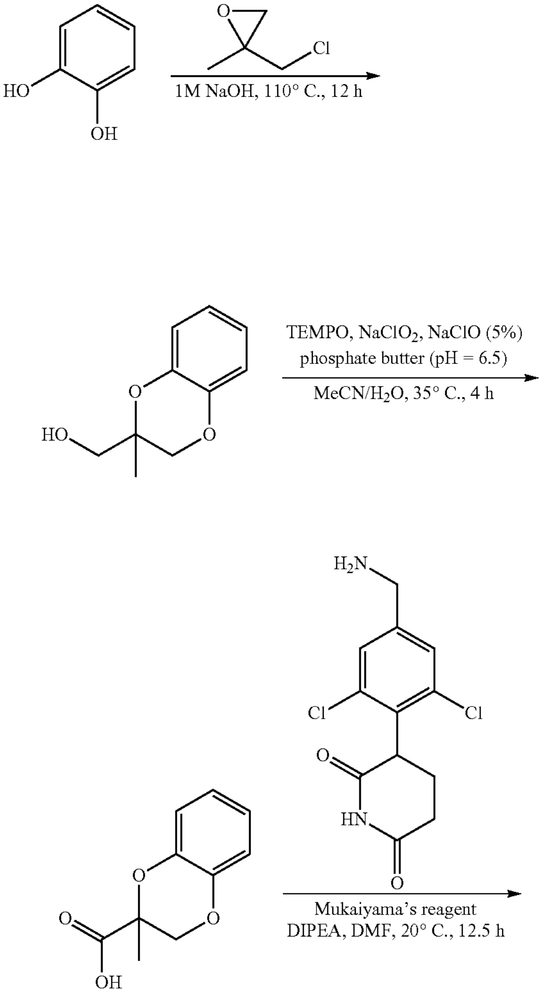

-continued

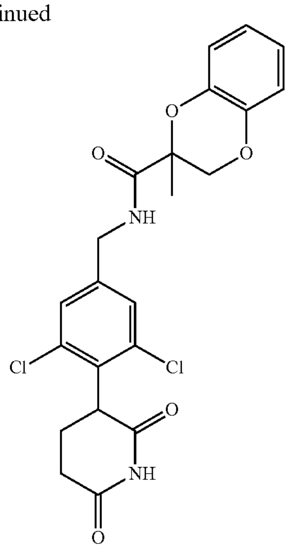

Step 1. To a solution of 2-(chloromethyl)-2-methyloxirane (5.08 g, 47.7 mmol, 1.05 eq.) in sodium hydroxide (1 M, 50 mL) was added pyrocatechol (5.00 g, 45.4 mmol, 1.00 eq.) and the reaction was stirred at 110° C. for 12 h. The mixture was diluted with water (50 mL) and extracted with ethyl acetate (3'25 mL). The combined organic layers were washed with brine (50 mL), dried over sodium sulfate, filtered, and concentrated under reduced pressure to give a residue. The residue was purified via Purification Method 2 to afford (2-methyl-2,3-dihydrobenzo[b][1,4]dioxin-2-yl) methanol (7.30 g, crude) as a colourless oil.

Step 2. To a solution of (2-methyl-2,3-dihydrobenzo[b][1,4]dioxin-2-yl) methanol (1.00 g, 5.55 mmol, 1.00 eq.) in acetonitrile (10 mL) and phosphate buffer (10 mL, disodium hydrogenphosphate in water, pH=6.5) was added 1-oxidanyl-2,2,6,6-tetramethyl-piperidine (87.3 mg, 555 μmol, 0.10 eq.) followed by a solution of sodium chlorite (1.00 g, 11.1 mmol, 2.00 eq.) in water (1.25 mL) and sodium hypochlorite (8.26 g, 5.55 mmol, 6.85 mL, 5% purity, 1.00 eq.) in portions. The mixture was stirred at 35° C. for 4 h. After cooling to room temperature, the mixture was diluted with water (15 mL) and adjusted to pH 9-10 with 1 M sodium hydroxide. The mixture was washed with ethyl acetate (20 mL). The aqueous phase was adjusted to pH 2-3 with 1 M hydrochloric acid and extracted with ethyl acetate (2' 20 mL). The combined organic layers were washed with brine (20 mL), dried over sodium sulfate, filtered, and concentrated under reduced pressure to give a residue. The residue was purified via Purification Method 2 to afford 2-methyl-2,3-dihydrobenzo[b][1,4]dioxine-2-carboxylic acid (432 mg, 2.00 mmol, 36% yield, 90% purity) as a yellow solid.

Step 3. To a solution of 2-methyl-2,3-dihydrobenzo[b][1,4]dioxine-2-carboxylic acid (50.0 mg, 257 μmol, 1.20 eq.) in N,N-dimethylformamide (2 mL) were added 2-chloro-1-methyl-pyridin-1-ium iodide (82.2 mg, 322 μmol, 1.50 eq.) and N,N-diisopropylethylamine (83.2 mg, 644 μmol, 3.00 eq.), the mixture was stirred at 20° C. for 30 min. Then 3-(4-(aminomethyl)-2,6-dichlorophenyl) piperidine-2,6-dione hydrochloride (61.6 mg, 215 μmol, 1.00 eq.) was added, and the reaction was stirred at 20° C. for 12 h. The mixture diluted with water (15 mL) and extracted with ethyl acetate (3'10 mL). The combined organic layers were washed with water (10 mL) and brine (10 mL), dried over sodium sulfate, filtered, and concentrated under reduced pressure to give a residue. The residue was purified via Purification Method 1 to afford N-(3,5-dichloro-4-(2,6-dioxopiperidin-3-yl)benzyl)-2-methyl-2,3-dihydrobenzo[b][1,4]dioxine-2-carboxamide (41.1 mg, 86.9 μmol, 40% yield, 97.9% purity) as a white solid.

$^1$H NMR (400 MHZ, DMSO-$d_6$) δ=10.94 (s, 1H), 8.62 (t, J=6.0 Hz, 1H), 7.12-7.08 (m, 1H), 7.03-6.99 (m, 2H), 6.92-6.86 (m, 3H), 4.55-4.50 (m, 2H), 4.38-4.32 (m, 1H), 4.17-4.11 (m, 1H), 3.87 (d, J=11.2 Hz, 1H), 2.88-2.78 (m, 1H), 2.54-2.53 (m, 1H), 2.37-2.27 (m, 1H), 1.88-1.83 (m, 1H), 1.47 (s, 3H). MS (ESI) m/z 463.1 [M+H]$^+$

Exemplary Compound 48

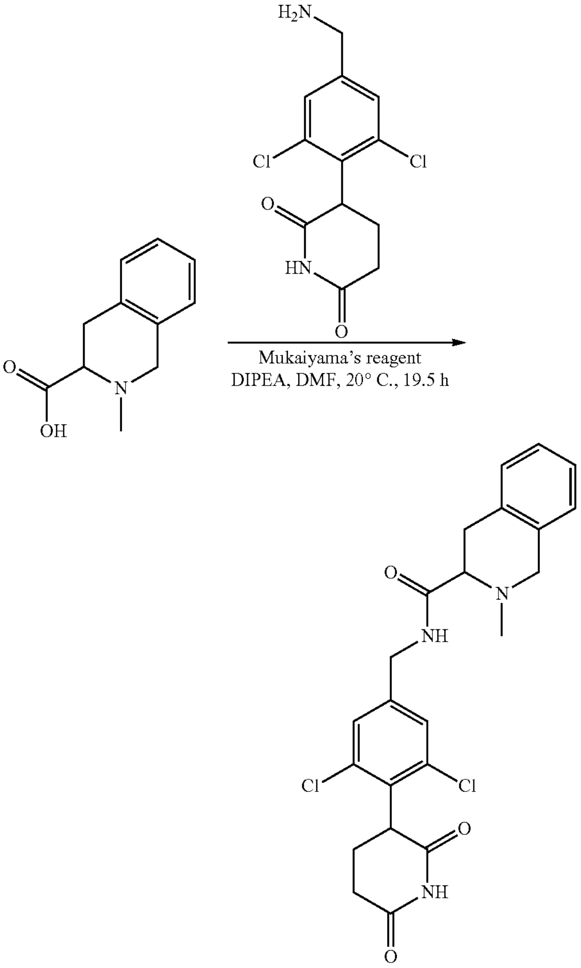

To a solution of 2-methyl-1,2,3,4-tetrahydroisoquinoline-3-carboxylic acid (100 mg, 518 μmol, 1.67 eq.) in dimethyl formamide (3 mL) were added N,N-diisopropylethylamine (120 mg, 927 μmol, 3.00 eq.) and 2-chloro-1-methyl-pyridin-1-ium iodide (150 mg, 587 μmol, 1.90 eq.). After addition, the mixture was stirred at 20° C. for 30 min, then 3-(4-(aminomethyl)-2,6-dichlorophenyl) piperidine-2,6-dione hydrochloride (100 mg, 309 μmol, 1.00 eq.) was added. The reaction was stirred at 20° C. for 19 h. The mixture was diluted with water (20 mL) and extracted with ethyl acetate (20 mL). The combined organic layers were washed with water (2×20 mL) and brine (20 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-methyl-1,2,3,4-tetrahydroisoquinoline-3-carboxamide formate (52.92 mg, 103 μmol, 33.5% yield) as a purple solid.

$^1$H NMR (400 MHZ, DMSO-$d_6$) δ=10.97 (s, 1H), 8.63 (t, J=6.0 Hz, 1H), 7.35 (s, 1H), 7.27 (s, 1H), 7.16-7.09 (m, 3H), 7.07 (d, J=3.2 Hz, 1H), 4.57 (dd, J=5.6, 12.8 Hz, 1H), 4.35-4.20 (m, 2H), 3.89 (d, J=15.2 Hz, 1H), 3.56 (d, J=15.2 Hz, 1H), 3.24 (t, J=6.8 Hz, 1H), 3.01-2.80 (m, 3H), 2.55 (m, 1H), 2.43-2.28 (m, 4H), 1.95-1.85 (m, 1H). MS (ESI) m/z 460.2 [M+H]$^+$

Exemplary Compound 50

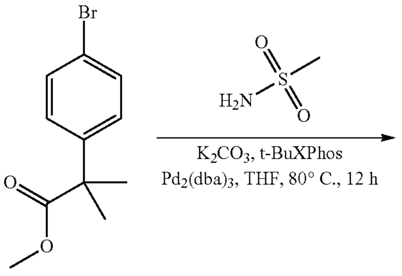

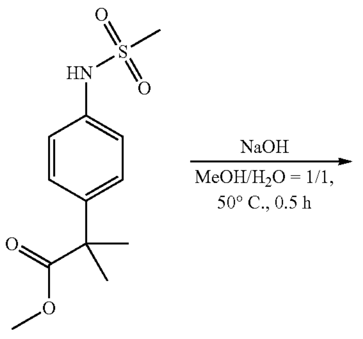

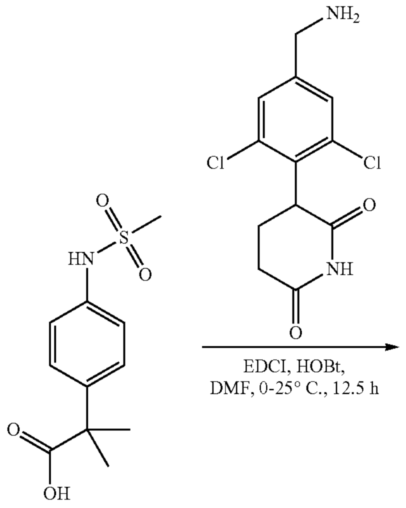

-continued

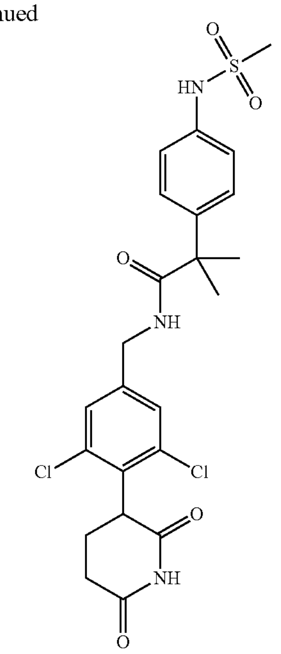

Step 1. To a solution of methyl 2-(4-bromophenyl)-2-methyl-propanoate (1.00 g, 3.89 mmol, 1.00 eq.) in tetrahydrofuran (10 mL) was added potassium carbonate (1.08 g, 7.78 mmol, 2.00 eq.), methanesulfonamide (443 mg, 4.67 mmol, 1.20 eq.), tris(dibenzylideneacetone) dipalladium (0) (178 mg, 194 μmol, 0.050 eq.) and di-tert-butyl-[2-(2,4,6-triisopropylphenyl)phenyl]phosphane (330 mg, 777 μmol, 0.200 eq.). The reaction was stirred at 80° C. for 12 h under nitrogen atmosphere. The mixture was filtered, and the filtrate was concentrated under reduced pressure to give a crude product. The crude product was purified via Purification Method 2 to afford methyl 2-methyl-2-(4-(methylsulfonamido)phenyl) propanoate (333 mg, 1.20 mmol, 30% yield) as a yellow solid.

Step 2. To a solution of methyl 2-methyl-2-(4-(methylsulfonamido)phenyl) propanoate (100 mg, 368 μmol, 1.00 eq.) in methanol (1 mL) and water (1 mL) was added sodium hydroxide (117 mg, 2.95 mmol, 8.00 eq.). The mixture was stirred at 50° C. for 0.5 h. The pH of the mixture was adjusted to 7 with 1M hydrochloric acid. The mixture was purified via Purification Method 1 to afford 2-methyl-2-(4-(methylsulfonamido)phenyl) propanoic acid (71.0 mg, 273 μmol, 74% yield) as a white solid.

Step 3. To a solution of 2-methyl-2-(4-(methylsulfonamido)phenyl) propanoic acid (41.0 mg, 159 μmol, 1.00 eq.) in dimethylformamide (1 mL) were added 1-hydroxybenzotriazole (25.8 mg, 191 μmol, 1.20 eq.) and 1-(3-dimethylaminopropyl)-3-ethylcarbodiimide hydrochloride (36.6 mg, 191 μmol, 1.20 eq.). The reaction was stirred at 0° C. for 0.5 h, then 3-(4-(aminomethyl)-2,6-dichlorophenyl) piperidine-2,6-dione (50.3 mg, 175 μmol, 1.10 eq.) was added. The reaction was stirred at 25° C. for 12 h. The mixture was concentrated under reduced pressure. The residue was purified via Purification Method 1 to afford N-(3,5-dichloro-4-(2,6-dioxopiperidin-3-yl)benzyl)-2-methyl-2-(4-(methylsulfonamido)phenyl) propanamide (23.97 mg, 45.1 μmol, 28% yield) as a white solid.

$^1$H NMR (400 MHZ, DMSO-$d_6$) δ=10.95 (s, 1H), 9.68 (s, 1H), 7.98 (t, J=6.0 Hz, 1H), 7.31-7.25 (m, 2H), 7.20-7.15 (m, 3H), 7.11 (d, J=1.6 Hz, 1H), 4.59-4.50 (m, 1H), 4.20 (d,

J=5.6 Hz, 2H), 2.95 (s, 3H), 2.90-2.80 (m, 1H), 2.58-2.52 (m, 1H), 2.40-2.29 (m, 1H), 1.92-1.83 (m, 1H), 1.46 (s, 6H). MS (ESI) m/z 527.8 $[M+H]^+$

Exemplary Compound 51

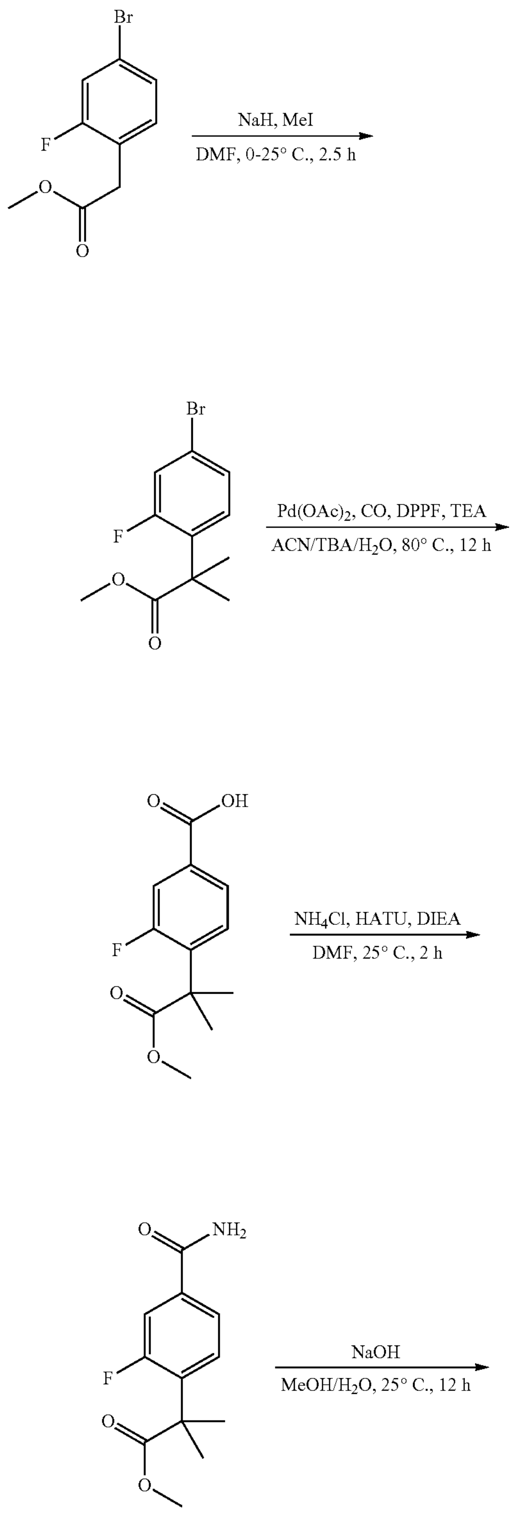

-continued

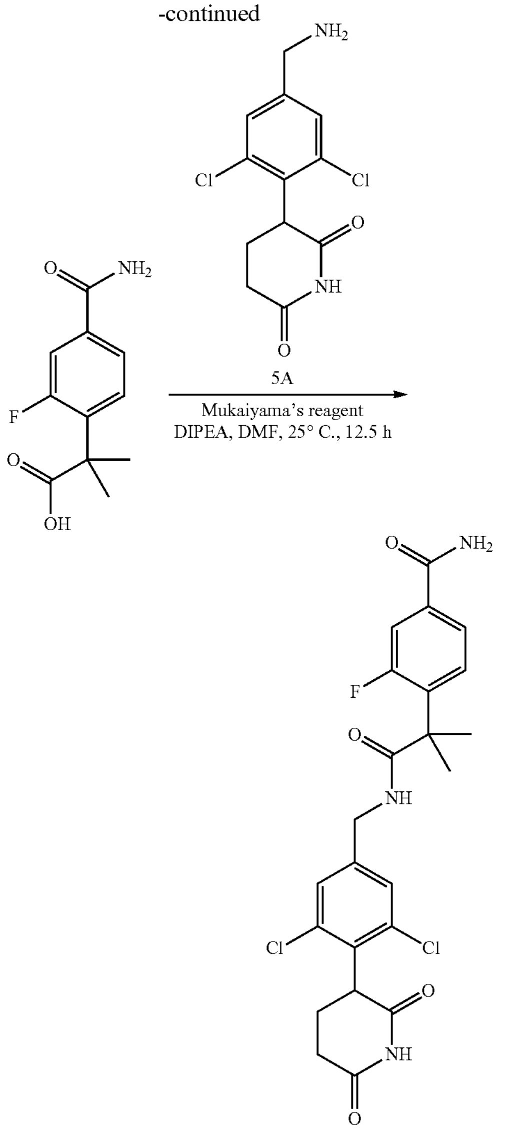

Step 1. To a mixture of methyl 2-(4-bromo-2-fluorophenyl)acetate (2.00 g, 8.10 mmol, 1.00 eq.) in dimethyl formamide (10 mL) was added sodium hydride (1.30 g, 32.4 mmol, 60% purity, 4.00 eq.) in portions at 0° C. The mixture was stirred at 0° C. for 0.5 h, then iodomethane (5.75 g, 40.4 mmol, 5.00 eq.) was added and the mixture was stirred at 25° C. for 2 h. The reaction was quenched with saturated aqueous ammonium chloride (20 mL) and extracted with ethyl acetate (3× 20 mL). The combined organic layers were washed with brine (20 mL), dried over anhydrous sodium sulfate, filtered, and concentrated under reduced pressure. The residue was purified via Purification Method 2 to afford methyl 2-(4-bromo-2-fluorophenyl)-2-methylpropanoate (900 mg, 3.27 mmol, 40% yield) as a colourless oil.

Step 2. To a solution of methyl 2-(4-bromo-2-fluorophenyl)-2-methylpropanoate (1.00 g, 3.63 mmol, 1.00 eq.) in water (1.20 mL), 2-methylpropan-2-ol (12 mL) and acetonitrile (18 mL) were added 1,1'-bis(diphenylphosphino)ferrocene (403 mg, 726 μmol, 0.20 eq.), diacetoxypalladium (81.6 mg, 363 μmol, 0.10 eq.) and triethylamine (1.10 g, 10.9 mmol, 3.00 eq.). The mixture was stirred under carbon monoxide (50 Psi) at 80° C. for 12 h. The mixture was cooled to 20° C., and poured into water (10 mL). The mixture was adjusted to pH 10 using 10% aqueous sodium carbonate. The mixture was washed with ethyl acetate (3×30 mL). The aqueous phase was collected and adjusted to pH 2 using 36% aqueous hydrochloric acid. The mixture was extracted with ethyl acetate (3×30 mL). The combined organic layers were washed with brine (50 mL), dried over anhydrous sodium sulfate, filtered, and the filtrate was concentrated in vacuo to give 3-fluoro-4-(1-methoxy-2-methyl-1-oxopropan-2-yl)benzoic acid (900 mg, 3.00 mmol, 82% yield) as a yellow solid.

Step 3. A solution of 3-fluoro-4-(1-methoxy-2-methyl-1-oxopropan-2-yl)benzoic acid (900 mg, 3.75 mmol, 1.00 eq.), ammonium chloride (601 mg, 11.2 mmol, 3.00 eq.), 2-(3H-[1,2,3]triazolo[4,5-b]pyridin-3-yl)-1,1,3,3-tetramethylisouronium hexafluorophosphate (V) (2.14 g, 5.62 mmol, 1.50 eq.) and diisopropylethylamine (1.45 g, 11.2 mmol, 3.00 eq.) in dimethyl formamide (10 mL) was stirred at 25° C. for 2 h. The mixture was poured into water (20 mL) and extracted with ethyl acetate (3×20 mL). The combined organic layers were washed with brine (20 mL), dried over anhydrous sodium sulfate, filtered, and the filtrate was concentrated under reduced pressure to give methyl 2-(4-carbamoyl-2-fluorophenyl)-2-methylpropanoate (700 mg, 2.25 mmol, 60% yield) as a yellow solid.

Step 4. To a mixture of methyl 2-(4-carbamoyl-2-fluorophenyl)-2-methylpropanoate (120 mg, 501 μmol, 1.00 eq.) in water (1 mL) and methanol (1 mL) was added sodium hydroxide (100 mg, 2.51 mmol, 5.00 eq.) in one portion at 25° C. The reaction was stirred at 25° C. for 12 h. The mixture was poured into water (10 mL) and washed with ethyl acetate (3×30 mL). The aqueous phase was collected and adjusted to pH 2 using 36% aqueous hydrochloric acid. The mixture was extracted with ethyl acetate (3×30 mL). The combined organic layers were washed with brine (20 mL), dried over anhydrous sodium sulfate, filtered, and the filtrate was concentrated in vacuo. The residue was purified via Purification Method I to afford 2-(4-carbamoyl-2-fluorophenyl)-2-methylpropanoic acid (40.0 mg, 174. μmol, 34% yield) as a white solid.

Step 5. To a solution of 2-(4-carbamoyl-2-fluorophenyl)-2-methylpropanoic acid (40.0 mg, 177 μmol, 1.00 eq.) and 2-chloro-1-methyl-pyridin-1-ium iodide (54.4 mg, 213 μmol, 1.20 eq.) in dimethyl formamide (1 mL) was added diisopropylethylamine (68.8 mg, 532 μmol, 3.00 eq.) dropwise at 25° C. The reaction was stirred at 25° C. for 0.5 h, then 3-(4-(aminomethyl)-2,6-dichlorophenyl) piperidine-2,6-dione hydrochloride (57.4 mg, 177 μmol, 1.00 eq.) was added. The reaction was stirred at 25° C. for 12 h. The mixture was poured into water (10 mL) and extracted with ethyl acetate (3×20 mL). The combined organic layers were washed with brine (20 mL), dried over anhydrous sodium sulfate, filtered, and the filtrate was concentrated under reduced pressure. The residue was purified via Purification Method I to afford 4-(1-((3,5-dichloro-4-(2,6-dioxopiperidin-3-yl)benzyl)amino)-2-methyl-1-oxopropan-2-yl)-3-fluorobenzamide (37.7 mg, 75.5 μmol, 42% yield) as a white solid.

$^1$H NMR (400 MHZ, DMSO-$d_6$) δ=10.97 (s, 1H), 8.04 (s, 1H), 7.96 (s, 1H), 7.74 (dd, J=1.6, 8.0 Hz, 1H), 7.62 (dd, J=1.6, 12.4 Hz, 1H), 7.53 (t, J=8.0 Hz, 1H), 7.48 (s, 1H), 7.30 (s, 1H), 7.23 (d, J=0.8 Hz, 1H), 4.57 (dd, J=5.6, 12.4 Hz, 1H), 4.21 (d, J=6.0 Hz, 2H), 2.85 (dd, J=5.6, 14.0, 16.8 Hz, 1H), 2.55 (d, J=2.0 Hz, 1H), 2.35 (dq, J=4.0, 13.2 Hz, 1H), 1.94-1.85 (m, 1H), 1.49 (s, 6H). MS (ESI) m/z 494.1 $[M+H]^+$

Exemplary Compound 52

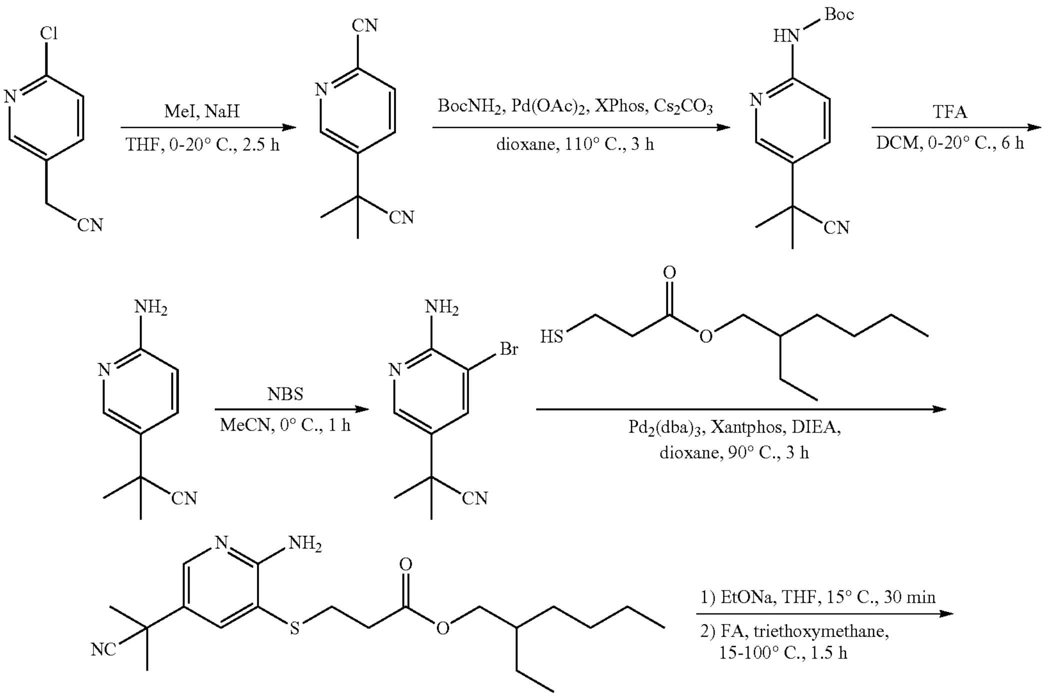

-continued

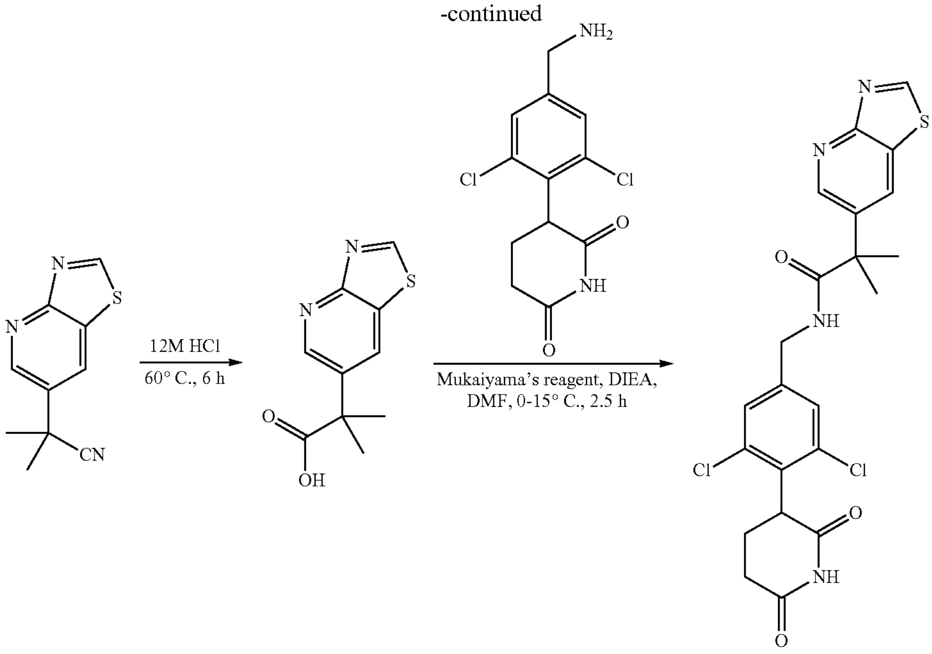

Step 1. To a solution of 2-(6-chloropyridin-3-yl) acetonitrile (2.00 g, 13.1 mmol, 1.00 eq.) in tetrahydrofuran (20 mL) was added sodium hydride (1.30 g, 32.5 mmol, 60% purity, 2.48 eq.) at 0° C. under nitrogen atmosphere. The reaction was stirred at 0° C. for 30 min, then iodomethane (2.10 mL, 33.7 mmol, 2.57 eq.) was added dropwise at 0° C. The reaction was stirred at 20° C. for 2 h. The reaction was quenched with saturated ammonium chloride solution (25 mL). The mixture was diluted with ethyl acetate (30 mL) and water (15 mL). The layers were separated, and the combined organic layers were washed with brine (30 mL), dried over anhydrous sodium sulfate, filtered, and concentrated in vacuo. The residue was purified via Purification Method 2 to afford 2-(6-chloropyridin-3-yl)-2-methylpropanenitrile (1.80 g, 9.67 mmol, 74% yield) as a white solid.

Step 2. To a solution of 2-(6-chloropyridin-3-yl)-2-methylpropanenitrile (1.80 g, 9.96 mmol, 1.00 eq.) and tert-butyl carbamate (1.76 g, 15.0 mmol, 1.51 eq.) in dioxane (30 mL) were added di-tert-butyl (2',4',6'-triisopropyl-[1,1'-biphenyl]-2-yl)phosphane (1.43 g, 2.99 mmol, 0.30 eq.), caesium carbonate (4.87 g, 15.0 mmol, 1.50 eq.) and palladium (II) acetate (340 mg, 1.51 mmol, 0.15 eq.) under nitrogen atmosphere. The reaction was stirred at 110° C. for 3 h. The mixture was diluted with ethyl acetate (30 mL) and water (30 mL). The layers were separated, and the aqueous phase was extracted with ethyl acetate (2×30 mL). The combined organic layers were washed with brine (30 mL), dried over anhydrous sodium sulfate, filtered, and concentrated in vacuo. The residue was purified via Purification Method 2 to afford tert-butyl (5-(2-cyanopropan-2-yl)pyridin-2-yl) carbamate (900 mg, 3.17 mmol, 32% yield) as a yellow solid.

Step 3. To a solution of tert-butyl (5-(2-cyanopropan-2-yl)pyridin-2-yl) carbamate (900 mg, 3.44 mmol, 1.00 eq.) in dichloromethane (10 mL) was added dropwise trifluoroacetic acid (5.20 mL, 70.0 mmol, 20.3 eq.) at 0° C. The reaction was stirred at 20° C. for 6 h. The mixture was diluted with dichloromethane (15 mL) and water (15 mL). The layers were separated, and the aqueous phase was extracted with dichloromethane (2×15 mL). The combined organic layers were washed with sodium bicarbonate (2×20 mL), brine (20 mL), and dried over anhydrous sodium sulfate. The aqueous phase was basified to pH 7 with saturated sodium bicarbonate solution and extracted with ethyl acetate (2× 20 mL). The layers were separated, and the combined organic layers were washed with brine (20 mL), dried over anhydrous sodium sulfate, and concentrated in vacuo to afford 2-(6-aminopyridin-3-yl)-2-methylpropanenitrile (350 mg, 1.95 mmol, 57% yield) as a yellow solid.

Step 4. To a solution of 2-(6-aminopyridin-3-yl)-2-methylpropanenitrile (250 mg, 1.55 mmol, 1.00 eq.) in acetonitrile (6 mL) was added N-bromosuccinimide (340 mg, 1.91 mmol, 1.23 eq.) at 0° C. The reaction was stirred at 0° C. for 1 h. The resulting mixture was concentrated in vacuo. The residue was purified via Purification Method 2 to afford 2-(6-amino-5-bromopyridin-3-yl)-2-methylpropanenitrile (180 mg, 720 μmol, 46% yield) as a brown solid.

Step 5. To a solution of 2-(6-amino-5-bromopyridin-3-yl)-2-methylpropanenitrile (280 mg, 1.17 mmol, 1.00 eq.) and 2-ethylhexyl 3-mercaptopropanoate (280 mg, 1.28 mmol, 1.10 eq.) in dioxane (6 mL) were added 4,5-bis (diphenylphosphino)-9,9-dimethylxanthene (70.0 mg, 121 μmol, 0.10 eq.), tris(dibenzylideneacetone)-dipalladium (0) (112 mg, 122 μmol, 0.10 eq.) and N,N-diisopropylethylamine (238 mg, 1.84 mmol, 1.58 eq.). The reaction was stirred at 90° C. for 3 h under nitrogen atmosphere. The resulting mixture was filtered over a pad of celite and diluted with ethyl acetate (15 mL) and water (15 mL). The layers were separated, and the aqueous phase was extracted with ethyl acetate (2×10 mL). The combined organic layers were washed with brine (30 mL) and dried over anhydrous sodium sulfate, filtered, and concentrated in vacuo. The residue was purified via Purification Method 2 to afford 2-ethylhexyl 3-((2-amino-5-(2-cyanopropan-2-yl)pyridin-3-yl)thio) propanoate (380 mg, 906 μmol, 78% yield) as a brown oil.

Step 6. To a solution of 2-ethylhexyl 3-((2-amino-5-(2-cyanopropan-2-yl)pyridin-3-yl)thio) propanoate (300 mg, 795 μmol, 1.00 eq.) in tetrahydrofuran (5 mL) was added sodium ethanolate (1.50 mL, 795 μmol, 20% purity in ethyl alcohol, 1.00 eq.). The reaction was stirred at 15° C. for 30 min, then formic acid (2.50 mL, 66.3 mmol, 83.4 eq.) and triethoxymethane (4.00 mL, 24.1 mmol, 30.3 eq.) was added. The reaction was stirred at 15° C. for 30 min, then warmed and stirred at 100° C. for 1 h. The mixture was basified to pH 7 with saturated sodium bicarbonate solution, then it was diluted with ethyl acetate (10 mL) and water (10 mL). The layers were separated, and the aqueous phase was extracted with ethyl acetate (2× 10 mL). The combined organic layers were washed with brine (20 mL), dried over anhydrous sodium sulfate, filtered, and concentrated in vacuo. The residue was purified via Purification Method 2 to afford 2-methyl-2-(thiazolo[4,5-b]pyridin-6-yl) propanenitrile (90.0 mg, 438 μmol, 55% yield) as a yellow solid.

Step 7. A solution of 2-methyl-2-(thiazolo[4,5-b]pyridin-6-yl) propanenitrile (90.0 mg, 443 μmol, 1.00 eq.) in concentrated hydrochloric acid (12 M, 4 mL) was stirred at 60° C. for 6 h. The reaction mixture was concentrated in vacuo. The residue was purified via Purification Method 1 to afford 2-methyl-2-(thiazolo[4,5-b]pyridin-6-yl) propanoic acid (60.0 mg, 262 μmol, 59% yield) as a white solid.

Step 8. To a solution of 2-methyl-2-(thiazolo[4,5-b]pyridin-6-yl) propanoic acid (50.0 mg, 225 μmol, 1.00 eq.) in dimethylformamide (1.5 mL) were added 2-chloro-1-methyl-pyridin-1-ium iodide (70.0 mg, 274 μmol, 1.22 eq.) and N,N-diisopropylethylamine (90.0 mg, 696 μmol, 3.10 eq.) at 0° C. The reaction was stirred at 15° C. for 30 min, then 3-(4-(aminomethyl)-2,6-dichlorophenyl) piperidine-2,6-dione (65.0 mg, 226 μmol, 1.01 eq.) was added, and the reaction was stirred at 15° C. for 2 h. The mixture was diluted with ethyl acetate (8 mL) and water (8 mL). The layers were separated, and the aqueous phase was extracted with ethyl acetate (2×5 mL). The combined organic layers were washed with brine (15 mL), dried over anhydrous sodium sulfate, filtered, and concentrated in vacuo. The residue was purified via Purification Method 1 to afford N-(3,5-dichloro-4-(2,6-dioxopiperidin-3-yl)benzyl)-2-methyl-2-(thiazolo[4,5-b]pyridin-6-yl) propanamide (32.65 mg, 65.1 μmol, 29% yield) as a white solid.

$^1$H NMR (400 MHZ, DMSO-$d_6$) δ=10.96 (s, 1H), 9.67 (s, 1H), 8.70 (d, J=2.4 Hz, 1H), 8.65 (d, J=2.4 Hz, 1H), 8.16 (s, 1H), 7.17 (d, J=1.6 Hz, 1H), 7.10 (d, J=1.2 Hz, 1H), 4.54 (dd, J=5.6, 12.8 Hz, 1H), 4.23 (d, J=6.0 Hz, 2H), 2.94-2.78 (m, 1H), 2.59-2.52 (m, 1H), 2.39-2.25 (m, 1H), 1.95-1.81 (m, 1H), 1.73-1.56 (m, 6H). MS (ESI) m/z 491.2 $[M+H]^+$

Exemplary Compound 56

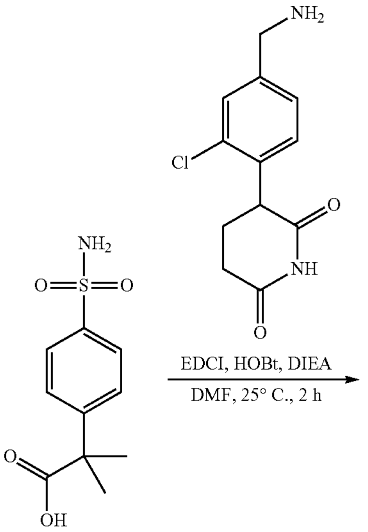

-continued

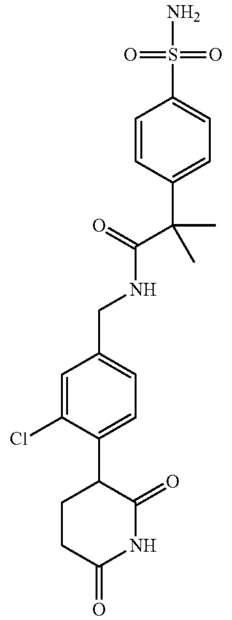

To a solution of 2-methyl-2-(4-sulfamoylphenyl) propanoic acid (100 mg, 411 μmol, 1.00 eq.), N1-((ethylimino) methylene)-N3,N3-dimethylpropane-1,3-diamine hydrochloride (94.6 mg, 493 μmol, 1.20 eq.) and 1H-benzo[d][1,2,3]triazol-1-ol (66.7 mg, 493 μmol, 1.20 eq.) in dimethyl formamide (2 mL) were added 3-(4-(aminomethyl)-2-chlorophenyl) piperidine-2,6-dione (104 mg, 411 μmol, 1.00 eq.) and diisopropylethylamine (159 mg, 1.23 mmol, 3.00 eq.) in one portion. The reaction was stirred at 25° C. for 2 h. The mixture was poured into water (10 mL) and extracted with ethyl acetate (3×10 mL). The combined organic layers were washed with brine (10 mL), dried over anhydrous sodium sulfate, filtered, and the filtrate was concentrated under reduced pressure. The residue was purified via Purification Method 1 to afford N-(3-chloro-4-(2,6-dioxopiperidin-3-yl) benzyl)-2-methyl-2-(4-sulfamoylphenyl) propanamide (102 mg, 211 μmol, 51% yield) as a white solid.

$^1$H NMR (400 MHZ, DMSO-$d_6$) δ=10.89 (s, 1H), 8.08 (t, J=6.0 Hz, 1H), 7.77 (d, J=8.4 Hz, 2H), 7.49 (d, J=8.4 Hz, 2H), 7.31 (s, 2H), 7.24 (d, J=8.0 Hz, 1H), 7.17 (s, 1H), 7.09 (dd, J=1.2, 8.0 Hz, 1H), 4.22 (d, J=6.0 Hz, 2H), 4.15 (dd, J=4.8, 12.3 Hz, 1H), 2.81-2.71 (m, 1H), 2.53 (d, J=3.6 Hz, 1H), 2.26 (dq, J=4.4, 12.8 Hz, 1H), 1.99-1.91 (m, 1H), 1.51 (s, 6H). MS (ESI) m/z 461.1 $[M-NH_2]^+$

Exemplary Compound 59

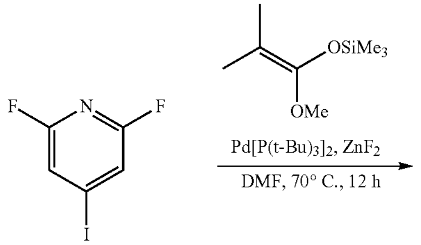

-continued

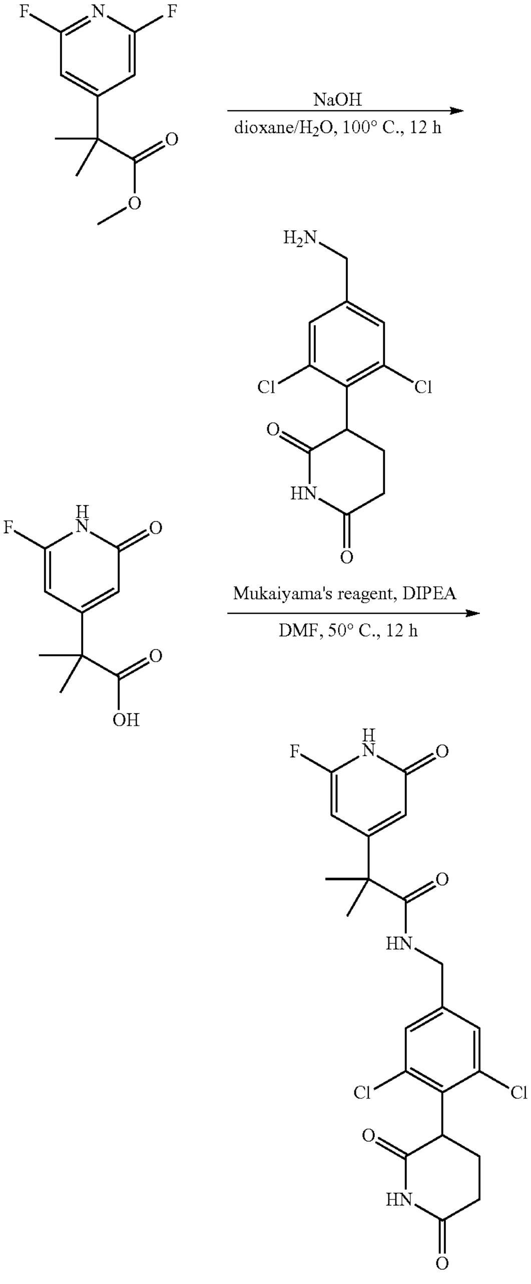

Step 1. To a mixture of 2,6-difluoro-4-iodo-pyridine (1.00 g, 4.15 mmol, 1.00 eq.) in dimethyl formamide (10 mL) were added difluorozinc (429 mg, 4.15 mmol, 1.00 eq.), tri-tert-butylphosphane palladium (212 mg, 415 μmol, 0.10 eq.) and (1-methoxy-2-methyl-prop-1-enoxy)-trimethyl-silane (1.45 g, 8.30 mmol, 2.00 eq.) in one portion under nitrogen. The reaction was stirred at 70° C. for 12 h under nitrogen atmosphere, then it was cooled to 20° C., and poured into water (10 mL). The mixture was extracted with ethyl acetate (3x10 mL). The combined organic layers were washed with brine (20 mL), dried over anhydrous sodium sulfate, filtered, and the filtrate was concentrated under reduced pressure. The residue was purified via Purification Method 2 then Purification Method 1 to afford methyl 2-(2,6-difluoropyridin-4-yl)-2-methylpropanoate (66.0 mg, 294 μmol, 7% yield) as a light-yellow oil.

Step 2. To a mixture of methyl 2-(2,6-difluoropyridin-4-yl)-2-methylpropanoate (60.0 mg, 279 μmol, 1.00 eq.) in dioxane (0.5 mL) and water (0.5 mL) was added sodium hydroxide (111 mg, 2.79 mmol, 10.0 eq.) in one portion. The reaction was stirred at 100° C. for 12 h. The mixture was cooled to 20° C., and poured into water (10 mL), then the pH was adjusted to 3-4 with 36% aqueous hydrochloric acid. The mixture was extracted with ethyl acetate (3x10 mL). The combined organic layers were washed with brine (10 mL), dried over anhydrous sodium sulfate, filtered, and the filtrate was concentrated under reduced pressure. The residue was purified via Purification Method 2 to afford 2-(6-fluoro-2-oxo-1,2-dihydropyridin-4-yl)-2-methylpropanoic acid (30.0 mg, 119 μmol, 42% yield) as a white solid.

Step 3. To a solution of 2-(6-fluoro-2-oxo-1,2-dihydropyridin-4-yl)-2-methylpropanoic acid (30.0 mg, 151 μmol, 1.00 eq.) and diisopropylethylamine (77.9 mg, 602 μmol, 4.00 eq.) in dimethyl formamide (1 mL) was added 2-chloro-1-methyl-pyridin-1-ium iodide (46.2 mg, 181 μmol, 1.20 eq.) in one portion at 20° C. The mixture was stirred at 20° C. for 0.5 h, and then 3-(4-(aminomethyl)-2,6-dichlorophenyl) piperidine-2,6-dione hydrochloride (58.5 mg, 181 μmol, 1.20 eq.) was added. The reaction was stirred at 20° C. for 1.5 h. The mixture was poured into water (20 mL) and extracted with ethyl acetate (3x20 mL). The combined organic layers were washed with brine (10 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-(6-fluoro-2-oxo-1,2-dihydropyridin-4-yl)-2-methylpropanamide (62.0 mg, 132 μmol, 87% yield) as a white solid.

$^1$H NMR (400 MHZ, DMSO-$d_6$) δ=11.29 (s, 1H), 10.96 (s, 1H), 8.14 (t, J=6.0 Hz, 1H), 7.21 (d, J=1.6 Hz, 1H), 7.15 (d, J=1.2 Hz, 1H), 6.45 (d, J=13.6 Hz, 2H), 4.55 (dd, J=5.6, 12.4 Hz, 1H), 4.22 (d, J=6.0 Hz, 2H), 2.85 (ddd, J=6.0, 14.0, 17.2 Hz, 1H), 2.54 (d, J=2.0 Hz, 1H), 2.37-2.27 (m, 1H), 1.95-1.81 (m, 1H), 1.46 (s, 6H). MS (ESI) m/z 468.2 $[M+H]^+$ Exemplary Compound 64

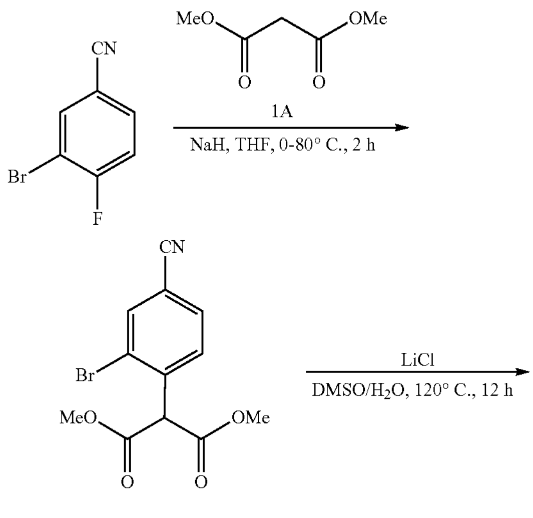

-continued

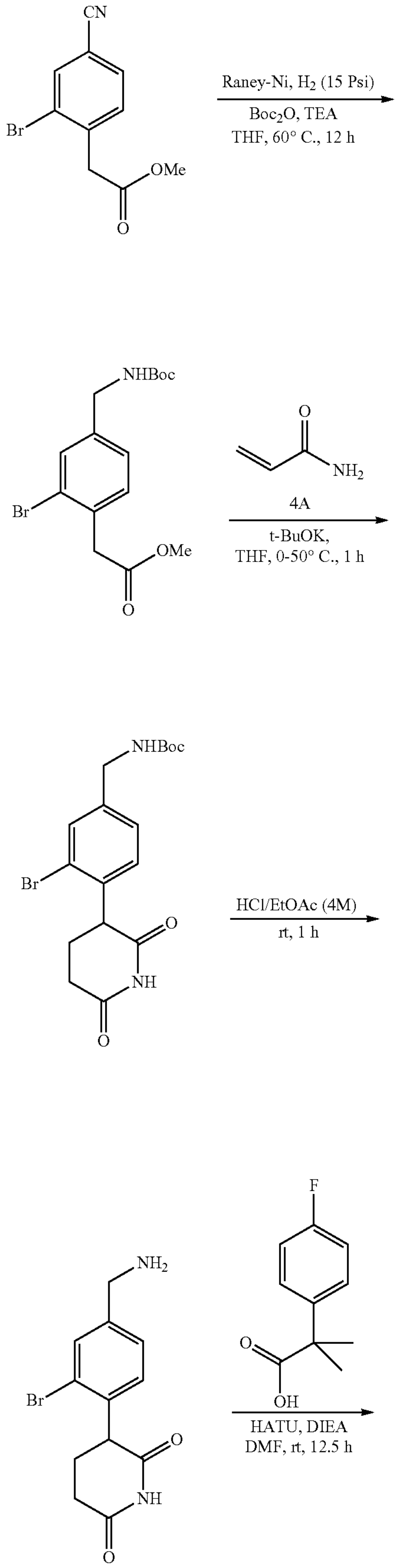

-continued

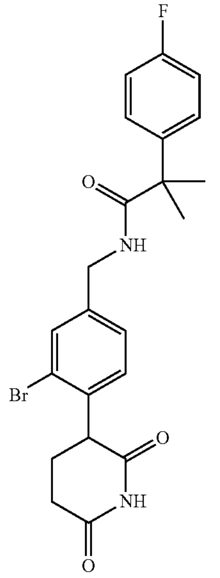

Step 1: To a solution of dimethyl malonate (3.96 g, 30.0 mmol, 1.20 eq.) in THF (50 mL) was added sodium hydride (1.50 g, 37.5 mmol, 60% purity, 1.50 eq.) at 0° C. under nitrogen. The reaction was stirred at 0° C. for 30 min, then 3-bromo-4-fluorobenzonitrile (5.00 g, 25.0 mmol, 1.00 eq.) was added. The reaction was stirred at 80° C. for 1.5 h, then it was quenched with water (200 mL) at 0° C. The aqueous layer was extracted with ethyl acetate (200 mL). The combined organic layers were washed with brine (3×200 mL), dried over sodium sulfate, filtered, and concentrated under reduced pressure to give a residue. The residue was purified via Purification Method 2 to afford dimethyl 2-(2-bromo-4-cyanophenyl) malonate (4.00 g, 12.2 mmol, 49% yield) as a white solid.

Step 2: To a solution of dimethyl 2-(2-bromo-4-cyanophenyl) malonate (2.00 g, 6.41 mmol, 1.00 eq.) in DMSO(10 mL) and water (1 mL) was added lithium chloride (407 mg, 9.61 mmol, 1.50 eq.). The reaction was stirred at 120° C. for 12 h, then it was diluted with water (50 mL), and the aqueous layer was extracted with ethyl acetate (50 mL). The combined organic layers were washed with brine (3×50 mL), dried over sodium sulfate, filtered, and concentrated under reduced pressure to give a residue. The residue was purified via Purification Method 2 to afford methyl 2-(2-bromo-4-cyanophenyl)acetate (1.00 g, 3.74 mmol, 58% yield) as a yellow oil.

Step 3: To a solution of methyl 2-(2-bromo-4-cyanophenyl)acetate (500 mg, 1.97 mmol, 1.00 eq.) in THF (10 mL) were added $Boc_2O$(859 mg, 3.94 mmol, 2.00 eq.), TEA (2.95 mmol, 410 μL, 1.50 eq.) and Raney-Ni (200 mg, 2.33 mmol, 1.19 eq.). The reaction was stirred at 60° C. under hydrogen (15 Psi) for 12 h. The mixture was filtered, and the filtrate was concentrated under reduced pressure to give a residue. The residue was purified via Purification Method 2 to afford methyl 2-(2-bromo-4-(((tert-butoxycarbonyl) amino) methyl)phenyl)acetate (700 mg, 1.17 mmol, 60% yield) as a colourless oil.

Step 4: To a solution of methyl 2-(2-bromo-4-(((tert-butoxycarbonyl)amino) methyl)phenyl)acetate (650 mg, 1.81 mmol, 1.00 eq.) and acrylamide (130 mg, 1.81 mmol, 1.00 eq.) in THF (10 mL) was added KO'Bu (1 M in THF, 1.81 mL, 1.00 eq.) at 0° C. The reaction was stirred at 50° C. for 1 h, then it was acidified with aqueous hydrochloric acid (1 M) to reach pH 6.

The mixture was diluted with water (20 mL), and the aqueous layer was extracted with ethyl acetate (20 mL). The combined organic layers were washed with brine (3× 20 mL), dried over sodium sulfate, filtered, and concentrated under reduced pressure to give a residue. The residue was purified via Purification Method 2 to afford tert-butyl (3-bromo-4-(2,6-dioxopiperidin-3-yl)benzyl) carbamate (110 mg, 249 μmol, 14% yield) as a white solid.

Step 5: A solution of tert-butyl (3-bromo-4-(2,6-dioxopiperidin-3-yl)benzyl) carbamate (110 mg, 277 μmol, 1.00 eq.) in HCl/ethyl acetate (4 M, 5 mL) was stirred at 20° C. for 1 h. The mixture was concentrated under reduced pressure to afford 3-(4-(aminomethyl)-2-bromophenyl) piperidine-2,6-dione hydrochloride (100 mg, crude) as a white solid. MS (ESI) m/z 595.2 $[2M+H]^+$ Step 6. To a solution of 2-(4-fluorophenyl)-2-methylpropanoic acid (54.6 mg, 300 μmol, 1.00 eq.) in N,N-dimethylformamide (3 mL) were added O-(7-Azabenzotriazol-1-yl)-N,N,N',N'-tetramethyluronium hexafluorophosphate (137 mg, 360 μmol, 1.20 eq.) and N,N-diisopropylethylamine (900 μmol, 157 μL, 3.00 eq.). The mixture was stirred at 20° C. for 30 min. Then 3-(4-(aminomethyl)-2-bromophenyl) piperidine-2,6-dione hydrochloride (100 mg, crude) was added, and the reaction was stirred at 20° C. for 12 h. The mixture was diluted with water (20 mL) and extracted with ethyl acetate (20 mL). The combined organic layers were washed with water (2×20 mL), dried over sodium sulfate, filtered, and concentrated under reduced pressure. The residue was purified via Purification Method 1 to afford N-(3-bromo-4-(2,6-dioxopiperidin-3-yl)benzyl)-2-(4-fluorophenyl)-2-methylpropanamide (38.86 mg, 82.6 μmol, 28% yield) as a white solid.

$^1$H NMR (400 MHZ, DMSO-$d_6$)>=10.90 (s, 1H), 8.00 (t, J=6.0 Hz, 1H), 7.39-7.31 (m, 2H), 7.28 (d, J=1.2 Hz, 1H), 7.22 (d, J=8.0 Hz, 1H), 7.19-7.09 (m, 3H), 4.21 (d, J=6.0 Hz, 2H), 4.15 (dd, J=5.2, 12.0 Hz, 1H), 2.77 (m, 1H), 2.56-2.53 (m, 1H), 2.26 (dq, J=4.4, 12.8 Hz, 1H), 2.02-1.91 (m, 1H), 1.49 (s, 6H). MS (ESI) m/z 461.2 $[M+H]^+$

Exemplary Compound 65

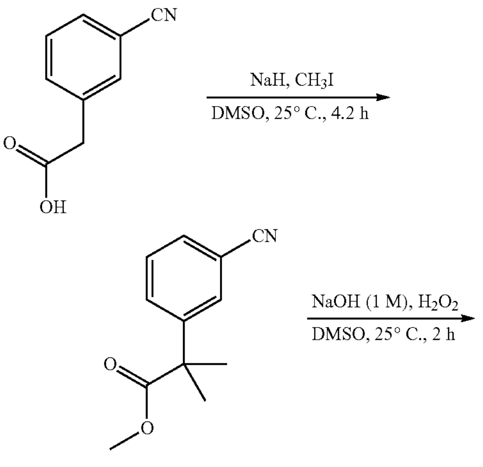

-continued

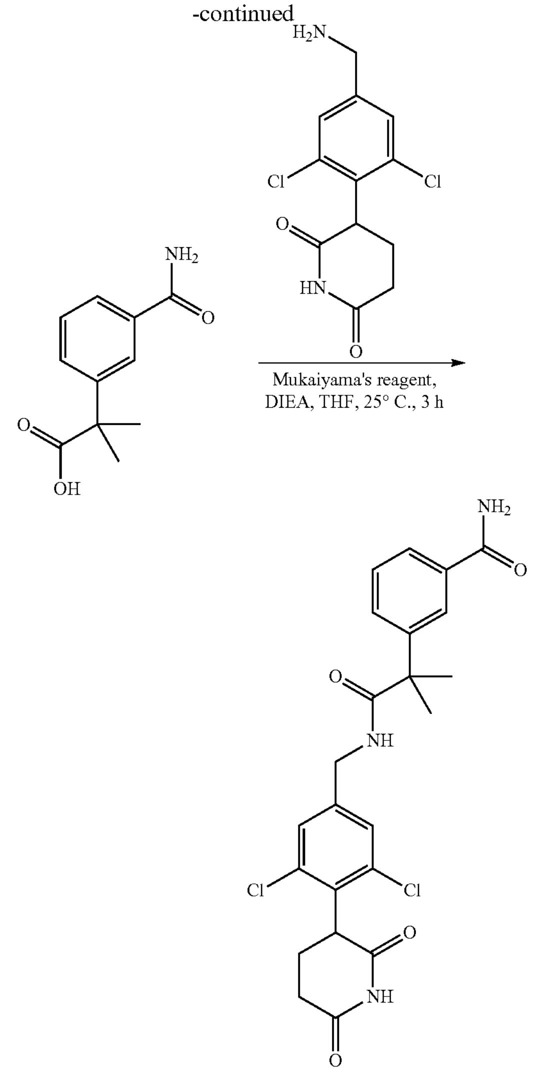

Step 1. To a solution of 2-(3-cyanophenyl) acetic acid (800 mg, 4.96 mmol, 1.00 eq.) in dimethylsulfoxide (10 mL) was added sodium hydride (993 mg, 24.8 mmol, 60% purity, 5.00 eq.). After 12 minutes, methyl iodide (4.93 g, 34.7 mmol, 7.00 eq.) was added. The reaction was stirred at 25° C. under nitrogen atmosphere for 4 h. The mixture was diluted with water (50 mL), and adjusted to pH 5 with glacial acetic acid at 0° C. The mixture was extracted with ethyl acetate (50 mL). The combined organic layers were washed with brine (30 mL) and dried over anhydrous sodium sulfate, filtered, and concentrated in vacuo. The residue was purified via Purification Method 2 to afford methyl 2-(3-cyanophenyl)-2-methylpropanoate (536 mg, 2.03 mmol, 41% yield, 77% purity) as a colourless oil.

Step 2. To a solution of methyl 2-(3-cyanophenyl)-2-methylpropanoate (450 mg, 2.21 mmol, 1.00 eq.) in dimethylsulfoxide (5 mL) were added hydrogen peroxide (2.5 mL, 30% purity) and sodium hydroxide (1 M, 2.5 mL). The mixture was stirred at 25° C. for 2 h. The mixture was diluted with water (20 mL), extracted with ethyl acetate (20 mL), and washed with saturated sodium thiosulfate (20 mL). The combined organic layers were dried over anhydrous sodium sulfate, filtered, and concentrated under reduced pressure to give 2-(3-carbamoylphenyl)-2-methylpropanoic acid (243 mg, crude) as a white solid.

Step 3. To a solution of 2-(3-carbamoylphenyl)-2-methylpropanoic acid (96.0 mg, 463 μmol, 1.50 eq.) in tetrahydrofuran (5 mL) were added N,N-diisopropylethylamine (120 mg, 927 μmol, 3.00 eq.), 2-chloro-1-methyl-pyridin-1-ium iodide (118 mg, 463 μmol, 1.50 eq.) and 3-[4-(aminomethyl)-2,6-dichloro-phenyl]piperidine-2,6-dione hydrochloride (100 mg, 309 μmol, 1.00 eq.). The reaction was stirred at 25° C. for 3 h. The mixture was diluted with ethyl acetate (30 mL) and water (10 mL). The layers were separated, and the combined organic layers were washed with brine (30 mL), dried over anhydrous sodium sulfate, filtered, and concentrated in vacuo. The residue was purified via Purification Method 1 to afford 3-(1-((3,5-dichloro-4-(2,6-dioxopiperidin-3-yl)benzyl)amino)-2-methyl-1-oxopropan-2-yl)benzamide (35.27 mg, 71 μmol, 23% yield) as a white solid.

$^1H$ NMR (400 MHZ, DMSO-$d_6$)>=10.94 (s, 1H), 8.06-7.96 (m, 2H), 7.90 (s, 1H), 7.81-7.73 (m, 1H), 7.45-7.37 (m, 2H), 7.34 (s, 1H), 7.17 (s, 1H), 7.09 (d, J=1.2 Hz, 1H), 4.54 (dd, J=5.6, 12.8 Hz, 1H), 4.20 (d, J=6.0 Hz, 2H), 2.84 (m, 1H), 2.58-2.52 (m, 1H), 2.33 (dq, J=4.4, 13.2 Hz, 1H), 1.93-1.80 (m, 1H), 1.52 (s, 6H). MS (ESI) m/z 476.1 $[M+H]^+$

Exemplary Compound 67

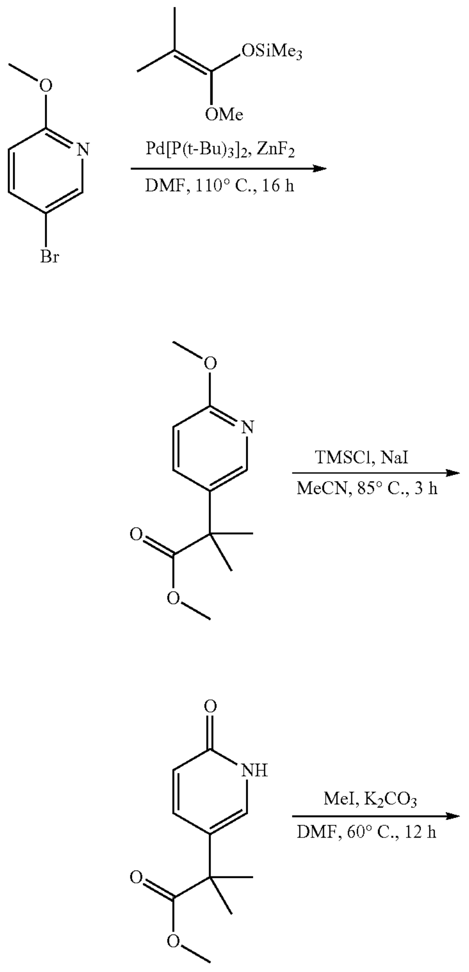

-continued

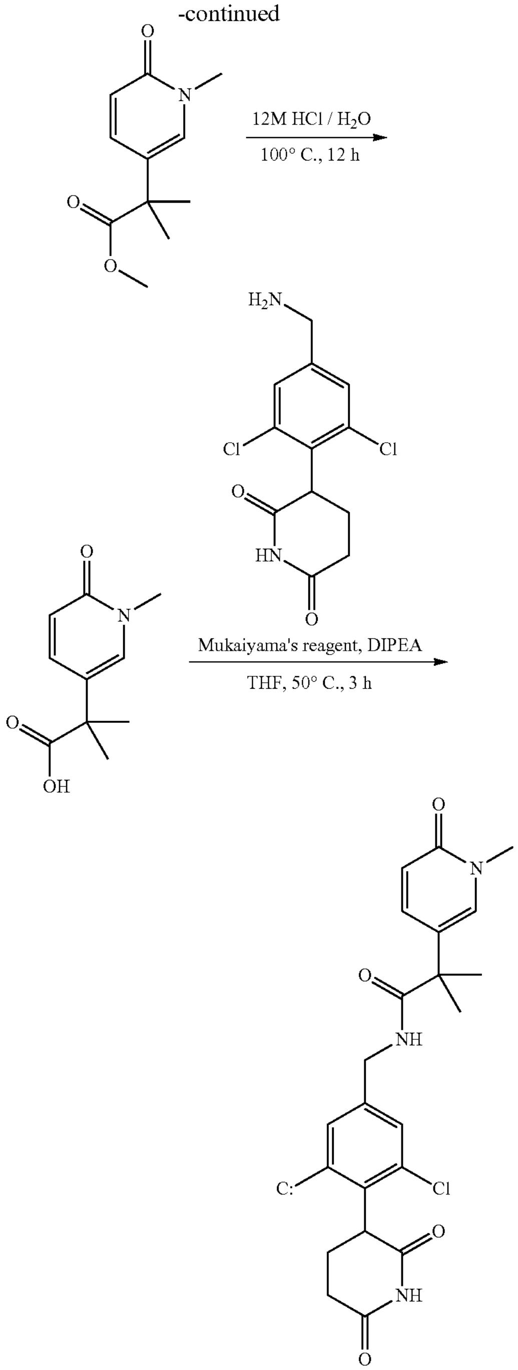

Step 1. To a solution of 5-bromo-2-methoxy-pyridine (2.00 g, 10.6 mmol, 1.00 eq.) and (1-methoxy-2-methyl-prop-1-enoxy)-trimethyl-silane (3.00 g, 17.2 mmol, 1.62 eq.) in N,N-dimethylformamide (30 mL) was added difluorozinc (1.10 g, 10.6 mmol, 1.00 eq.) and tri-tert-butylphosphane palladium (600 mg, 1.17 mmol, 0.11 eq.). The mixture was stirred at 110° C. for 16 h under nitrogen atmosphere. The mixture was cooled to 25° C., and poured into water (300 mL). The aqueous phase was extracted with ethyl acetate (3 '150 mL). The combined organic layers were washed with brine (300 mL), dried over anhydrous sodium sulfate, filtered, and concentrated under reduced pressure. The residue was purified via Purification Method 2 to afford methyl 2-(6-methoxypyridin-3-yl)-2-methylpropanoate (1.60 g, 7.07 mmol, 66% yield) as a yellow oil.

Step 2. To a solution of methyl 2-(6-methoxypyridin-3-yl)-2-methylpropanoate (800 mg, 3.82 mmol, 1.00 eq.) in acetonitrile (20 mL) was added sodium iodide (1.75 g, 11.7 mmol, 3.05 eq.) and chlorotrimethylsilane (1.28 g, 11.8 mmol, 3.09 eq.). The mixture was stirred at 85° C. for 3 h, then it was poured into water (100 mL). The aqueous phase was extracted with ethyl acetate (3' 50 mL). The combined organic layers were washed with brine (100 mL), dried over anhydrous sodium sulfate, filtered, and concentrated under vacuum to afford methyl 2-methyl-2-(6-oxo-1,6-dihydropyridin-3-yl) propanoate (800 mg, crude) as a brown oil.

Step 3. To a solution of methyl 2-methyl-2-(6-oxo-1,6-dihydropyridin-3-yl) propanoate (800 mg, 4.10 mmol, 1.00 eq.) in N, N-dimethylformamide (10 mL) was added potassium carbonate (1.70 g, 12.3 mmol, 3.00 eq.) and iodomethane (912 mg, 6.43 mmol, 1.57 eq.). The mixture was stirred at 60° C. for 12 h under nitrogen atmosphere. The mixture was poured into water (50 mL). The aqueous phase was extracted with ethyl acetate (3'30 mL). The combined organic layers were washed with brine (50 mL), dried over anhydrous sodium sulfate, filtered, and concentrated under reduced pressure. The residue was purified via Purification Method 2 to afford methyl 2-methyl-2-(1-methyl-6-oxo-1,6-dihydropyridin-3-yl) propanoate (400 mg, 1.87 mmol, 45.7% yield) as a yellow oil.

Step 4. To a solution of methyl 2-methyl-2-(1-methyl-6-oxo-1,6-dihydropyridin-3-yl) propanoate (400 mg, 1.91 mmol, 1.00 eq.) was added hydrochloric acid (12M, 15 mL). The mixture was stirred at 100° C. for 12 h under nitrogen atmosphere. The reaction mixture was concentrated under reduced pressure to afford 2-methyl-2-(1-methyl-6-oxo-1,6-dihydropyridin-3-yl) propanoic acid (290 mg, crude) as a yellow solid.

Step 5. To a solution of 3-(4-(aminomethyl)-2,6-dichlorophenyl) piperidine-2,6-dione (200 mg, 0.695 mmol, 1.00 eq.), 2-methyl-2-(1-methyl-6-oxo-1,6-dihydropyridin-3-yl) propanoic acid (160 mg, 0.819 mmol, 1.18 eq.), and N-ethyl-N-propan-2-ylpropan-2-amine (445 mg, 3.44 mmol, 0.600 mL, 4.95 eq.) in tetrahydrofuran (10 mL) was added 2-chloro-1-methyl-pyridin-1-ium iodide (240 mg, 0.939 mmol, 1.35 eq.) and the mixture was stirred at 50° C. for 3 h under nitrogen atmosphere.

The mixture was poured into water (30 mL). The aqueous phase was extracted with ethyl acetate (3'10 mL). The combined organic layers were washed with brine (30 mL), dried over anhydrous sodium sulfate, filtered, and concentrated under reduced pressure. The residue was purified via Purification Method 1 to afford N-(3,5-dichloro-4-(2,6-dioxopiperidin-3-yl)benzyl)-2-methyl-2-(1-methyl-6-oxo-1,6-dihydropyridin-3-yl) propanamide (53.8 mg, 116 μmol, 16% yield) as a white solid.

$^1$H NMR (400 MHZ, DMSO-$d_6$) δ=10.97 (s, 1H), 8.04 (t, J=6.0 Hz, 1H), 7.57 (d, J=2.8 Hz, 1H), 7.31 (dd, J=2.8, 9.6 Hz, 1H), 7.23 (s, 1H), 7.17 (s, 1H), 6.36 (d, J=9.2 Hz, 1H), 4.56 (dd, J=5.6, 12.4 Hz, 1H), 4.20 (d, J=6.0 Hz, 2H), 3.43 (s, 3H), 2.85 (ddd, J=6.0, 14.0, 16.8 Hz, 1H), 2.55 (br d, J=2.0 Hz, 1H), 2.34 (dq, J=4.4, 13.2 Hz, 1H), 1.95-1.81 (m, 1H), 1.40 (s, 6H). MS (ESI) m/z 464.0 [M+H]$^+$ Exemplary Compound 68

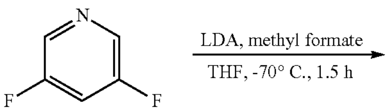

-continued

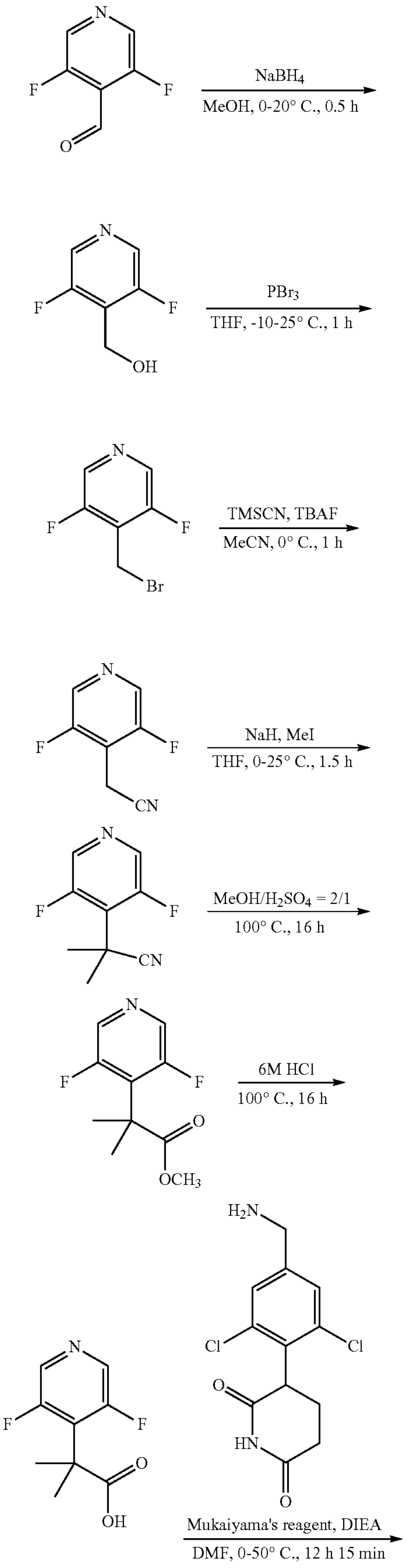

-continued

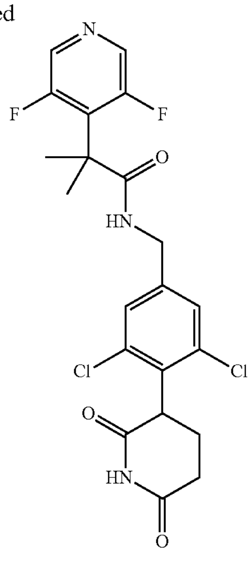

Step 1. To a solution of lithium diisopropylamide (2 M, 26.0 mL, 1.20 eq.) in tetrahydrofuran (40 mL) was added a solution of 3,5-difluoropyridine (5.00 g, 43.5 mmol, 1.00 eq.) in tetrahydrofuran (15 mL) dropwise at −70° C. under nitrogen atmosphere. After stirring at −70° C. for 30 min, a solution of methyl formate (5.22 g, 86.9 mmol, 2.00 eq.) in tetrahydrofuran (15 mL) was added dropwise. The reaction was stirred at −70° C. for 1 h. The mixture was poured into saturated sodium bicarbonate solution (50 mL) and ethyl acetate (50 mL). The layers were separated, and the aqueous phase was extracted with ethyl acetate (2×30 mL). The combined organic layers were washed with brine (80 mL) and dried over anhydrous sodium sulfate, filtered, and concentrated in vacuo. The residue was purified via Purification Method 2 to afford 3,5-difluoroisonicotinaldehyde (3.00 g, 18.9 mmol, 43% yield) as a yellow solid.

Step 2. To a solution of 3,5-difluoroisonicotinaldehyde (3.00 g, 21.0 mmol, 1.00 eq.) in methanol (30 mL) was added sodium borohydride (960 mg, 25.4 mmol, 1.21 eq.) at 0° C. The reaction was stirred at 25° C. for 0.5 h. The reaction was quenched with saturated ammonium chloride solution (25 mL) at 0° C., and diluted with ethyl acetate (30 mL) and water (15 mL). The layers were separated, and the aqueous phase was extracted with ethyl acetate (2×25 mL). The combined organic layers were washed with brine (30 mL) and dried over anhydrous sodium sulfate, filtered, and concentrated in vacuo. The residue was purified via Purification Method 2 to afford (3,5-difluoropyridin-4-yl) methanol (2.30 g, 15.1 mmol, 72% yield) as a white solid.

Step 3. To a solution of (3,5-difluoropyridin-4-yl) methanol (3.90 g, 26.9 mmol, 1.00 eq.) in tetrahydrofuran (40 mL) was added phosphorus tribromide (18.2 g, 67.4 mmol, 2.51 eq.) at −10° C. The reaction was stirred at 25° C. for 1 h. The reaction was quenched by pouring into ice water (30 mL). The mixture was diluted with dichloromethane (35 mL) and water (10 mL). The combined organic layers were washed with brine (35 mL) and dried over anhydrous sodium sulfate, filtered, and concentrated in vacuo to afford 4-(bromomethyl)-3,5-difluoropyridine (4.5 g, crude) as a yellow oil.

Step 4. To a solution of 4-(bromomethyl)-3,5-difluoropyridine (4.30 g, 20.7 mmol, 1.00 eq.) in acetonitrile (40 mL) were added trimethylsilyl cyanide (3.20 mL, 25.6 mmol, 1.24 eq.) and tetrabutylammonium fluoride (1 M, 27.0 mL, 1.31 eq.) at 0° C. The reaction was stirred at 0° C. for 1 h. The mixture was diluted with ethyl acetate (40 mL) and water (30 mL). The layers were separated, and the aqueous phase was extracted with ethyl acetate (2×25 mL). The combined organic layers were washed with brine (30 mL), dried over anhydrous sodium sulfate, filtered, and concentrated in vacuo. The residue was purified via Purification Method 2 to afford 2-(3,5-difluoropyridin-4-yl) acetonitrile (1.40 g, 6.00 mmol, 29% yield) as a white solid.

Step 5. To a solution of 2-(3,5-difluoropyridin-4-yl) acetonitrile (1.40 g, 9.08 mmol, 1.00 eq.) in tetrahydrofuran (20 mL) was added sodium hydride (1.10 g, 27.5 mmol, 60% purity, 3.03 eq.) at 0° C. under nitrogen atmosphere. The reaction was stirred at 0° C. for 30 min, then methyl iodide (6.84 g, 48.2 mmol, 5.30 eq.) was added and the reaction was stirred at 25° C. for 1 h. The reaction was quenched with water (25 mL), then diluted with ethyl acetate (30 mL) and water (15 mL). The layers were separated, and the combined organic layers were washed with brine (30 mL), dried over anhydrous sodium sulfate, filtered, and concentrated in vacuo. The residue was purified via Purification Method 2 to afford 2-(3,5-difluoropyridin-4-yl)-2-methylpropanenitrile (1.17 g, 5.91 mmol, 65% yield) as a white solid.

Step 6. To a solution of 2-(3,5-difluoropyridin-4-yl)-2-methylpropanenitrile (500 mg, 2.74 mmol, 1.00 eq.) in methanol (6 mL) was added sulfuric acid (3 mL). The reaction was stirred at 100° C. for 16 h. After cooling to room temperature, the mixture was diluted with ethyl acetate (20 mL) and water (20 mL). The layers were separated, and the aqueous phase was extracted with ethyl acetate (2× 15 mL). The combined organic layers were washed with brine (25 mL), dried over anhydrous sodium sulfate, filtered, and concentrated in vacuo. The residue was purified via Purification Method 2 to afford methyl 2-(3,5-difluoropyridin-4-yl)-2-methylpropanoate (200 mg, 836 μmol, 30% yield) as a white solid.

Step 7. A mixture of methyl 2-(3,5-difluoropyridin-4-yl)-2-methylpropanoate (130 mg, 604 μmol, 1.00 eq.) and hydrochloric acid (12 M, 3 mL) in water (3 mL) was stirred at 100° C. for 16 h. The reaction mixture was concentrated in vacuo. The residue was purified via Purification Method 2 to afford 2-(3,5-difluoropyridin-4-yl)-2-methylpropanoic acid (30.0 mg, 134 μmol, 22% yield) as a white solid.

Step 8. To a solution of 2-(3,5-difluoro-4-pyridyl)-2-methyl-propanoic acid (60.0 mg, 298 μmol, 1.00 eq.) in dimethylformamide (2 mL) were added 2-chloro-1-methyl-pyridin-1-ium iodide (115 mg, 450 μmol, 1.51 eq.) and N,N-diisopropylethylamine (115 mg, 890 μmol, 2.98 eq.) at 0° C.

The reaction was stirred at 25° C. for 15 min, then 3-(4-(aminomethyl)-2,6-dichlorophenyl) piperidine-2,6-dione (90.0 mg, 313 μmol, 1.05 eq.) was added, and the reaction was stirred at 50° C. for 12 h. The mixture was diluted with ethyl acetate (30 mL) and water (30 mL). The layers were separated, and the aqueous phase was extracted with ethyl acetate (2× 30 mL). The combined organic layers were washed with brine (30 mL), dried over anhydrous sodium sulfate, filtered, and concentrated in vacuo. The residue was purified via Purification Method I to afford N-(3,5-dichloro-4-(2,6-dioxopiperidin-3-yl)benzyl)-2-(3,5-difluoropyridin-4-yl)-2-methylpropanamide (31.99 mg, 66.0 μmol, 22% yield) as a white solid.

$^1$H NMR (400 MHZ, DMSO-$d_6$) δ=10.96 (s, 1H), 8.44 (d, J=1.6 Hz, 2H), 8.30 (t, J=5.6 Hz, 1H), 7.32 (d, J=1.6 Hz, 1H), 7.25 (d, J=1.6 Hz, 1H), 4.57 (dd, J=5.6, 12.8 Hz, 1H), 4.24 (d, J=6.0 Hz, 2H), 2.93-2.77 (m, 1H), 2.58-2.52 (m, 1H), 2.39-2.29 (m, 1H), 1.95-1.82 (m, 1H), 1.58 (s, 6H). MS (ESI) m/z 470.0 [M+H]$^+$

Exemplary Compound 69
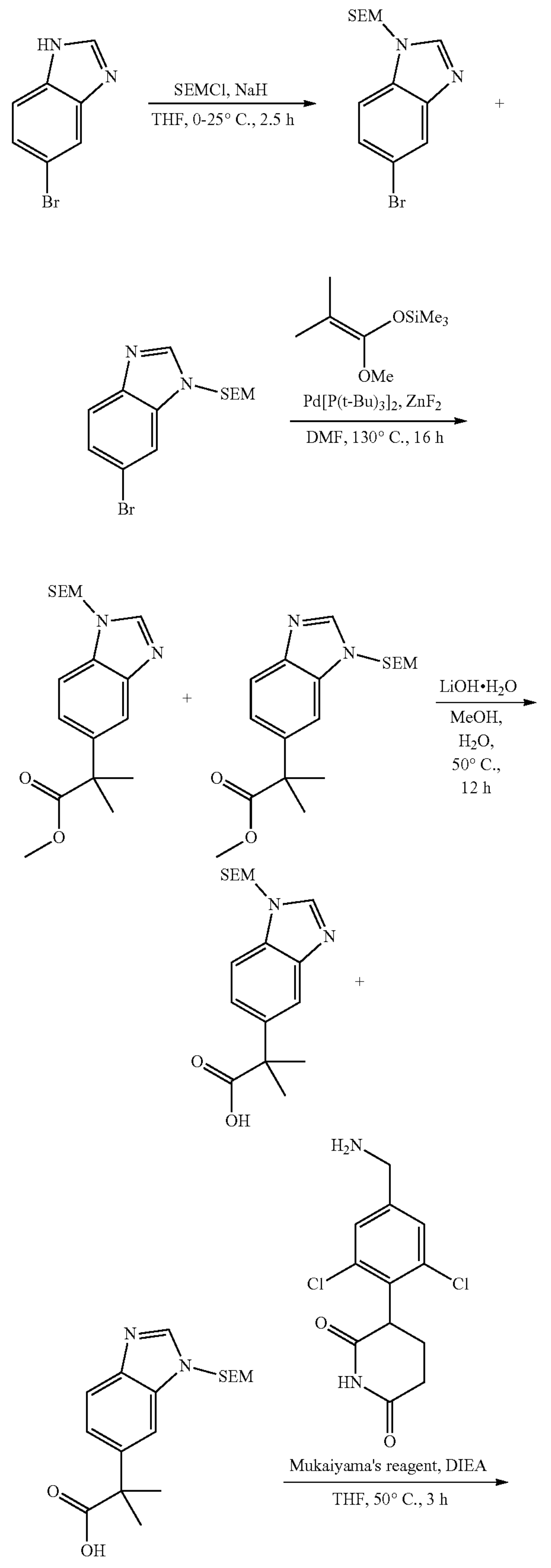
-continued
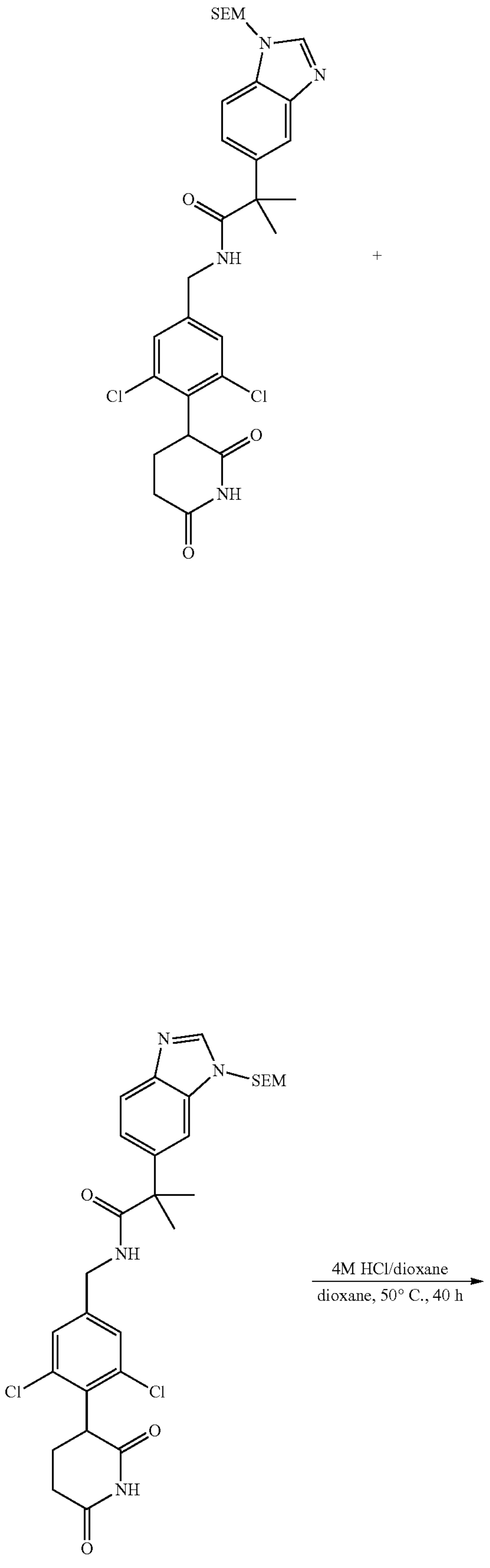

-continued

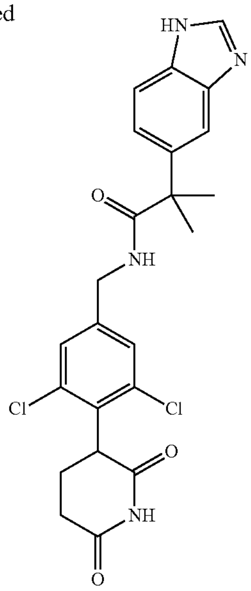

Step 1. To a solution of 5-bromo-1H-benzimidazole (1.00 g, 5.08 mmol, 1.00 eq.) in tetrahydrofuran (15 mL) was added sodium hydride (267 mg, 6.68 mmol, 60.0% purity, 1.31 eq.) at 0° C. The mixture was stirred at 0° C. for 30 min, then 2-(trimethylsilyl) ethoxymethyl chloride (1.13 g, 6.78 mmol, 1.33 eq.) was added. The reaction was stirred at 25° C. for 2 h under nitrogen atmosphere. The reaction was quenched by addition of saturated ammonium chloride solution (20 mL) under nitrogen and extracted with ethyl acetate (3×20 mL). The combined organic layers were washed with brine (2×50 mL), dried over anhydrous sodium sulfate, filtered, and concentrated under reduced pressure. The residue was purified via Purification Method 2 to afford a mixture of 5-bromo-1-((2-(trimethylsilyl) ethoxy)methyl)-1H-benzo[d]imidazole and 6-bromo-1-((2-(trimethylsilyl) ethoxy)methyl)-1H-benzo[d]imidazole (1.42 g, 2.17 mmol, 43% yield) as a colourless oil.

Step 2. To a solution of (1-methoxy-2-methyl-prop-1-enoxy)-trimethyl-silane (2.90 g, 16.6 mmol, 6.40 eq.), 5-bromo-1-((2-(trimethylsilyl) ethoxy)methyl)-1H-benzo[d] imidazole and 6-bromo-1-((2-(trimethylsilyl) ethoxy) methyl)-1H-benzo[d]imidazole (1.70 g, 2.60 mmol, 1.00 eq.), and difluorozinc (1.07 g, 10.4 mmol, 4.00 eq.) in N, N-dimethylformamide (15 mL) was added bis(tri-tert-butylphosphine) palladium (0) (531 mg, 1.04 mmol, 0.400 eq.) under nitrogen atmosphere. The mixture was stirred at 130° C. for 16 h. The reaction was quenched with water (100 mL) and extracted with ethyl acetate (3×100 mL). The combined organic layers were washed with brine (3× 100 mL), dried over anhydrous sodium sulfate, filtered, and concentrated under reduced pressure. The residue was purified via Purification Method 2 to afford a mixture of methyl 2-methyl-2-(1-((2-(trimethylsilyl) ethoxy)methyl)-1H-benzo[d]imidazol-5-yl) propanoate and methyl 2-methyl-2-(1-((2-(trimethylsilyl) ethoxy)methyl)-1H-benzo[d]imidazol-6-yl) propanoate (1.06 g, crude) as a colourless oil.

Step 3. To a solution of methyl 2-methyl-2-(1-((2-(trimethylsilyl) ethoxy)methyl)-1H-benzo[d]imidazol-5-yl) propanoate and methyl 2-methyl-2-(1-((2-(trimethylsilyl) ethoxy)methyl)-1H-benzo[d]imidazol-6-yl) propanoate (370 mg, 531 µmol, 1.00 eq.) in methanol (30 mL) and water (15 mL) was added lithium hydroxide monohydrate (446 mg, 10.6 mmol, 20.0 eq.) at 25° C. The reaction was stirred at 50° C. for 12 h. The mixture was concentrated under reduced pressure. The residue was acidified to pH ~ 5 with 2N hydrochloric acid. The resulting mixture was extracted with ethyl acetate (3×30 mL). The combined organic layers were washed with brine (3×30 mL), dried over anhydrous sodium sulfate, filtered, and concentrated under reduced pressure to afford a colourless oil. The crude product was purified via Purification Method 2 to afford a mixture of 2-methyl-2-(1-((2-(trimethylsilyl) ethoxy)methyl)-1H-benzo[d]imidazol-5-yl) propanoic acid and 2-methyl-2-(1-((2-(trimethylsilyl) ethoxy)methyl)-1H-benzo[d]imidazol-6-yl) propanoic acid (130 mg, 194 µmol, 37% yield) as a colourless oil.

Step 4. To a solution of 3-[4-(aminomethyl)-2,6-dichloro-phenyl]piperidine-2,6-dione hydrochloride (130 mg, 402 µmol, 1.00 eq.) and 2-methyl-2-(1-((2-(trimethylsilyl) ethoxy)methyl)-1H-benzo[d]imidazol-5-yl) propanoic acid and 2-methyl-2-(1-((2-(trimethylsilyl) ethoxy)methyl)-1H-benzo[d]imidazol-6-yl) propanoic acid (130 mg, 194 µmol, 0.97 eq.) in tetrahydrofuran (5 mL) were added 2-chloro-1-methyl-pyridin-1-ium iodide (165 mg, 646 µmol, 1.61 eq.) and N-ethyl-N-propan-2-ylpropan-2-amine (165 mg, 1.28 mmol, 0.222 mL, 3.18 eq.). The mixture was stirred at 50° C. for 3 h under nitrogen atmosphere. The reaction was quenched with water (60 mL) and extracted with ethyl acetate (3×20 mL). The combined organic layers were washed with brine (3× 30 mL), dried over anhydrous sodium sulfate, filtered, and concentrated under reduced pressure. The residue was purified via Purification Method 2 to afford a mixture of N-(3,5-dichloro-4-(2,6-dioxopiperidin-3-yl) benzyl)-2-methyl-2-(1-((2-(trimethylsilyl) ethoxy)methyl)-1H-benzo[d]imidazol-5-yl) propanamide and N-(3,5-dichloro-4-(2,6-dioxopiperidin-3-yl)benzyl)-2-methyl-2-(1-((2-(trimethylsilyl) ethoxy)methyl)-1H-benzo[d]imidazol-6-yl) propanamide (54.0 mg, 44.7 µmol, 11% yield) as a yellow oil.

Step 5. To a solution of the mixture of N-(3,5-dichloro-4-(2,6-dioxopiperidin-3-yl)benzyl)-2-methyl-2-(1-((2-(trimethylsilyl) ethoxy)methyl)-1H-benzo[d]imidazol-5-yl) propanamide and N-(3,5-dichloro-4-(2,6-dioxopiperidin-3-yl)benzyl)-2-methyl-2-(1-((2-(trimethylsilyl) ethoxy) methyl)-1H-benzo[d]imidazol-6-yl) propanamide (37.0 mg, 61.3 µmol, 1.00 eq.) in dioxane (18.5 mL) was added 4 M hydrogen chloride in dioxane (37.0 mL). The mixture was stirred at 50° C. for 40 h. The mixture was concentrated under reduced pressure. The residue was purified via Purification Method 1 to afford 2-(1H-benzo[d]imidazol-5-yl)-N-(3,5-dichloro-4-(2,6-dioxopiperidin-3-yl)benzyl)-2-methylpropanamide formate (25.1 mg, 51.9 µmol, 85% yield) as a white solid.

$^1$H NMR (400 MHZ, DMSO-$d_6$) δ=12.36 (s, 1H), 10.95 (s, 1H), 8.18 (s, 1H), 7.90 (t, J=5.6 Hz, 1H), 7.74-7.38 (m, 2H), 7.18-7.08 (m, 2H), 7.04 (s, 1H), 4.52 (dd, J=5.6, 12.8 Hz, 1H), 4.18 (d, J=6.0 Hz, 2H), 2.83 (ddd, J=5.6, 14.0, 17.2 Hz, 1H), 2.54 (d, J=2.0 Hz, 1H), 2.39-2.24 (m, 1H), 1.93-1.80 (m, 1H), 1.55 (s, 6H). MS (ESI) m/z 473.2 $[M+H]^+$ Exemplary Compound 70

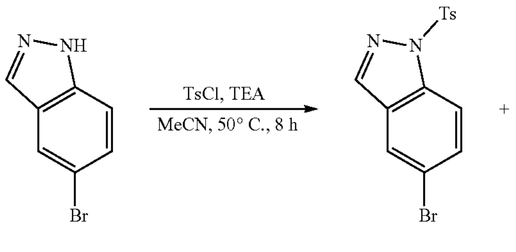

-continued

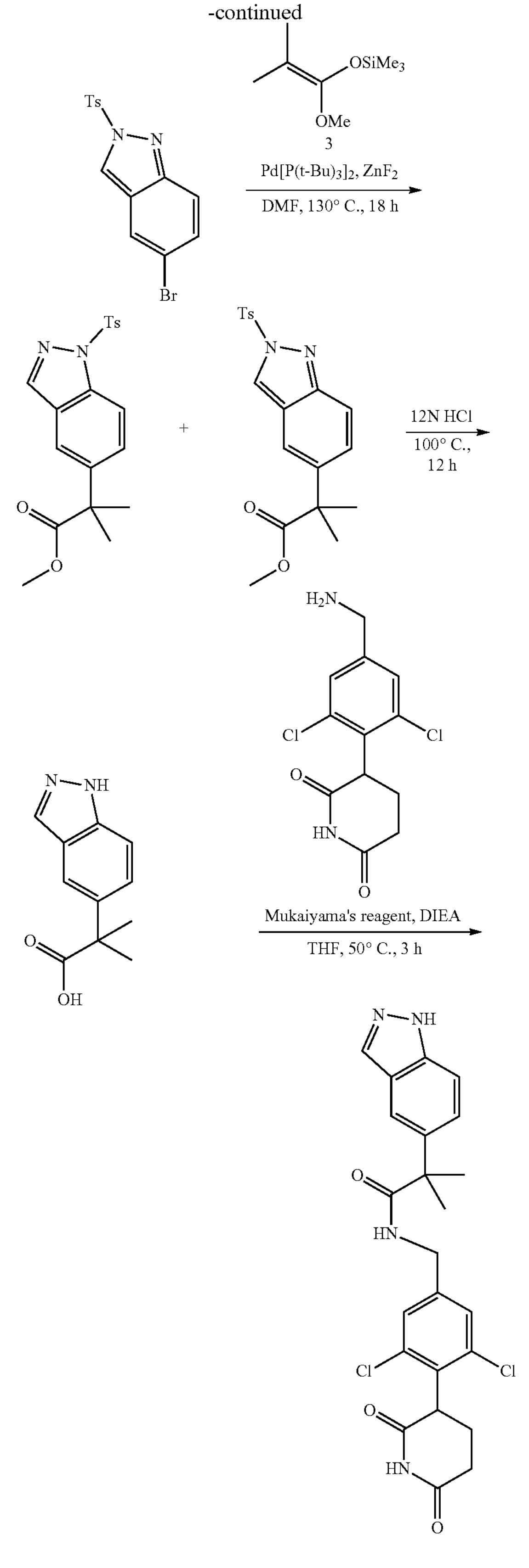

Step 1. To a solution of 5-bromo-1H-indazole (200 mg, 1.02 mmol, 1.00 eq.) in acetonitrile (5 mL) was added triethylamine (436 mg, 4.31 mmol, 4.25 eq.) and 4-methylbenzenesulfonyl chloride (220 mg, 1.15 mmol, 1.14 eq.). The reaction was stirred at 50° C. for 8 h under nitrogen atmosphere. The mixture was quenched with water (20 mL) and then extracted with ethyl acetate (3× 20 mL). The combined organic layers were washed with brine (50 mL), dried over anhydrous sodium sulfate, filtered, and concentrated under reduced pressure. The residue was purified via Purification Method 2 to afford a mixture of 5-bromo-1-tosyl-1H-indazole and 5-bromo-2-tosyl-2H-indazole (570 mg, crude) as a white solid.

Step 2. To a solution of (1-methoxy-2-methyl-prop-1-enoxy)-trimethyl-silane (300 mg, 1.72 mmol, 1.63 eq.) and a mixture of 5-bromo-1-tosyl-1H-indazole and 5-bromo-2-tosyl-2H-indazole (370 mg, 1.05 mmol, 1.00 eq.) in N, N-dimethylformamide (10 mL) was added difluorozinc (110 mg, 1.06 mmol, 1.01 eq.) and bis(tri-tert-butylphosphine) palladium (0) (55.0 mg, 0.108 mmol, 0.102 eq.). The mixture was stirred at 130° C. for 18 h under nitrogen atmosphere. The mixture was poured into water (70 mL) and extracted with ethyl acetate (3× 30 mL). The combined organic layers were washed with brine (50 mL), dried over anhydrous sodium sulfate, filtered, and concentrated under reduced pressure. The residue was purified via Purification Method 2 to afford a mixture of methyl 2-methyl-2-(1-tosyl-1H-indazol-5-yl) propanoate and methyl 2-methyl-2-(2-tosyl-2H-indazol-5-yl) propanoate (200 mg, 0.534 mmol, 51% yield) as a white solid.

Step 3. A mixture of methyl 2-methyl-2-(1-tosyl-1H-indazol-5-yl) propanoate and methyl 2-methyl-2-(2-tosyl-2H-indazol-5-yl) propanoate (180 mg, 0.483 mmol, 1.00 eq.) in hydrochloric acid (12N, 10 mL) was stirred at 100° C. for 12 h under nitrogen atmosphere. The mixture was poured into water (50 mL) and extracted with ethyl acetate (3 '20 mL). The combined organic layers were washed with brine (50 mL), dried over anhydrous sodium sulfate, filtered, and concentrated under reduced pressure to afford 2-(1H-indazol-5-yl)-2-methyl-propanoic acid (100 mg, crude) as a yellow solid.

Step 4. To a solution of 3-(4-(aminomethyl)-2,6-dichlorophenyl) piperidine-2,6-dione (140 mg, 0.488 mmol, 1.00 eq.) and 2-(1H-indazol-5-yl)-2-methyl-propanoic acid (100 mg, 0.489 mmol, 1.00 eq.) in tetrahydrofuran (5 mL) was added 2-chloro-1-methyl-pyridin-1-ium iodide (200 mg, 0.783 mmol, 1.61 eq.) and N-ethyl-N-propan-2-ylpropan-2-amine (350 mg, 2.71 mmol, 5.55 eq.). The reaction was stirred at 50° C. for 3 h under nitrogen atmosphere. The mixture was poured into water (20 mL) and extracted with ethyl acetate (3' 15 mL). The combined organic layers were washed with brine (30 mL), dried over anhydrous sodium sulfate, filtered, and concentrated under reduced pressure. The residue was purified via Purification Method I to afford N-[[3,5-dichloro-4-(2,6-dioxo-3-piperidyl)phenyl]methyl]-2-(1H-indazol-5-yl)-2-methyl-propanamide (34.2 mg, 72.3 μmol, 15% yield) as a white solid.

$^1$H NMR (400 MHZ, DMSO-$d_6$) 0=12.99 (s, 1H), 10.95 (s, 1H), 8.04 (s, 1H), 7.92 (t, J=6.0 Hz, 1H), 7.70 (s, 1H), 7.48 (d, J=8.4 Hz, 1H), 7.26 (dd, J=2.0, 8.8 Hz, 1H), 7.14 (s, 1H), 7.05 (s, 1H), 4.53 (dd, J=5.6, 12.4 Hz, 1H), 4.18 (d, J=6.0 Hz, 2H), 2.92-2.75 (m, 1H), 2.54 (s, 1H), 2.41-2.25 (m, 1H), 1.92-1.79 (m, 1H), 1.54 (s, 6H). MS (ESI) m/z 473.0 $[M+H]^+$

Exemplary Compound 71

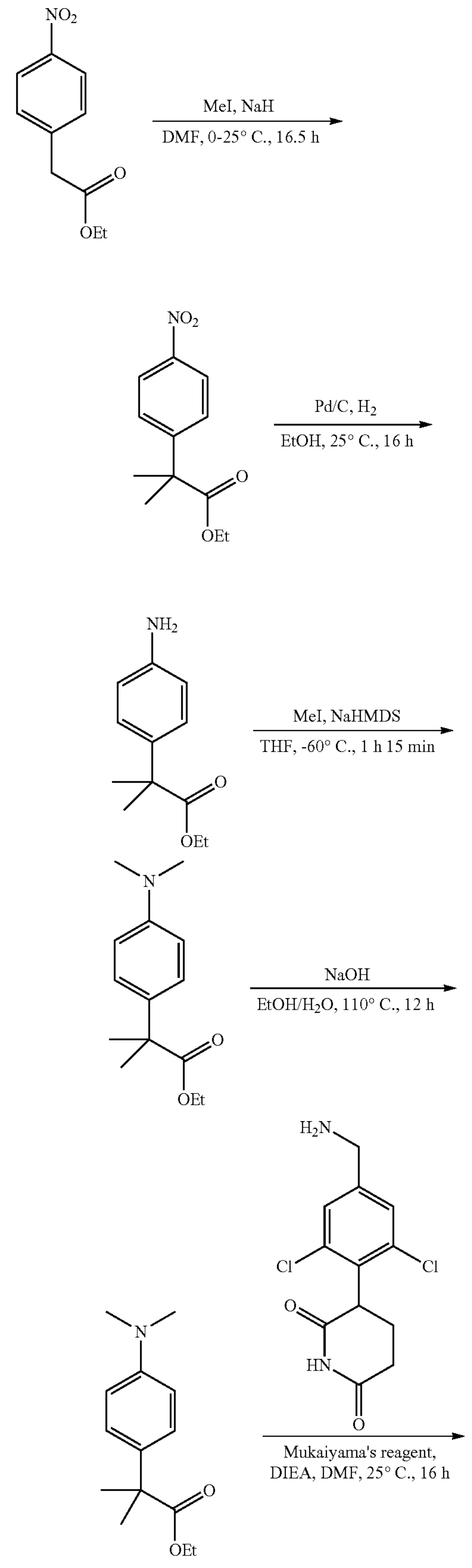

-continued

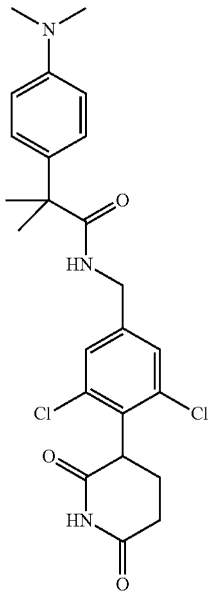

Step 1. To a suspension of sodium hydride (1.15 g, 28.7 mmol, 60% purity, 3.00 eq.) in N,N-dimethylformamide (10 mL) was added ethyl 2-(4-nitrophenyl)acetate (2.00 g, 9.56 mmol, 1.00 eq.) in portions at 0° C. under nitrogen atmosphere. The mixture was stirred at 25° C. for 0.5 h under nitrogen, then the mixture was cooled to 0° C., and a solution of iodomethane (48.2 mmol, 3 mL, 5.04 eq.) in N,N-dimethylformamide (10 mL) was added dropwise. The reaction was stirred at 25° C. for 16 h under nitrogen. The reaction was quenched with saturated ammonium chloride (80 mL) at 0° C. The mixture was extracted with ethyl acetate (2×50 mL). The combined organic layers were washed with brine (2×50 mL), dried over sodium sulfate, filtered, and concentrated under reduced pressure. The crude product was purified via Purification Method 2 to afford ethyl 2-methyl-2-(4-nitrophenyl) propanoate (1.69 g, 7.12 mmol, 74% yield) as a yellow liquid.

Step 2. To a suspension of palladium on carbon (500 mg, 10% purity) in ethanol (10 mL) was added ethyl 2-methyl-2-(4-nitrophenyl) propanoate (1.00 g, 4.21 mmol, 1.00 eq.). The reaction was stirred at 25° C. for 16 h under hydrogen (15 psi). The mixture was filtered through a pad of Celite, and the filtrate was concentrated under reduced pressure to give ethyl 2-(4-aminophenyl)-2-methylpropanoate (830 mg, 3.72 mmol, 88% yield) as a light-yellow oil.

Step 3. To a solution of ethyl 2-(4-aminophenyl)-2-methylpropanoate (780 mg, 3.76 mmol, 1.00 eq.) in tetrahydrofuran (15 mL) was added dropwise sodium bis(trimethylsilyl)amide (1 M, 11.6 mL, 3.07 eq.) at −60° C. under nitrogen atmosphere. The mixture was stirred at −60° C. for 15 min under nitrogen. Then a solution of iodomethane (9.96 mmol, 620 μL, 2.65 eq.) in tetrahydrofuran (2 mL) was added at −60° C. The mixture was stirred at −60° C. for 1 h under nitrogen. The reaction was warmed to 0° C., then it was quenched with saturated ammonium chloride (50 mL) at 0° C. The mixture was extracted with ethyl acetate (2×50 mL). The combined organic layers were washed with brine (2×50 mL), dried over sodium sulfate, filtered, and concentrated under reduced pressure. The crude product was purified via Purification Method 2 to afford ethyl 2-(4-(dimethylamino) phenyl)-2-methylpropanoate (680 mg, 2.77 mmol, 74% yield) as a yellow oil.

Step 4. A mixture of ethyl 2-(4-(dimethylamino)phenyl)-2-methylpropanoate (680 mg, 2.89 mmol, 1.00 eq.) and sodium hydroxide (1.16 g, 28.9 mmol, 10.0 eq.) in ethanol (10 mL) and water (5 mL) was stirred at 110° C. for 12 h. After cooling to 25° C., the mixture was diluted with water (30 mL) and washed with ethyl acetate (30 mL). The organic layers were discarded. The aqueous layer was adjusted to pH 5 with hydrochloric acid (12 M). The mixture was extracted with ethyl acetate (2×20 mL). The combined organic layers were dried over sodium sulfate, filtered, and concentrated under reduced pressure to give 2-(4-(dimethylamino)phenyl)-2-methylpropanoic acid (630 mg, 2.86 mmol, 99% yield) as off-white solid.

Step 5. To a solution of 2-(4-(dimethylamino)phenyl)-2-methylpropanoic acid (100 mg, 482 μmol, 1.00 eq.) and 3-(4-(aminomethyl)-2,6-dichlorophenyl) piperidine-2,6-dione hydrochloride (160 mg, 494 μmol, 1.02 eq.) in N,N-dimethylformamide (2 mL) were added N,N-diisopropylethylamine (1.72 mmol, 300 μL, 3.57 eq.) and 2-chloro-1-methylpyridin-1-ium iodide (250 mg, 979 μmol, 2.03 eq.). The reaction was stirred at 25° C. for 16 h. The mixture was diluted with ethyl acetate (20 mL) and washed with water (2×20 mL). The combined organic layers were dried over sodium sulfate, filtered, and concentrated under reduced pressure. The crude product was purified via Purification Method 1 to afford N-(3,5-dichloro-4-(2,6-dioxopiperidin-3-yl)benzyl)-2-(4-(dimethylamino)phenyl)-2-methylpropanamide (115 mg, 232 μmol, 48% yield) as a white solid.

$^1$H NMR (400 MHZ, DMSO-$d_6$) δ=10.94 (s, 1H), 7.84 (t, J=6.0 Hz, 1H), 7.16 (d, J=1.2 Hz, 1H), 7.15-7.11 (m, 2H), 7.09 (s, 1H), 6.70 (d, J=8.8 Hz, 2H), 4.54 (dd, J=5.2, 12.4 Hz, 1H), 4.18 (d, J=6.0 Hz, 2H), 2.89-2.79 (m, 7H), 2.57-2.52 (m, 1H), 2.39-2.28 (m, 1H), 1.92-1.82 (m, 1H), 1.44 (s, 6H). MS (ESI) m/z 476.3 $[M+H]^+$

Exemplary Compound 79

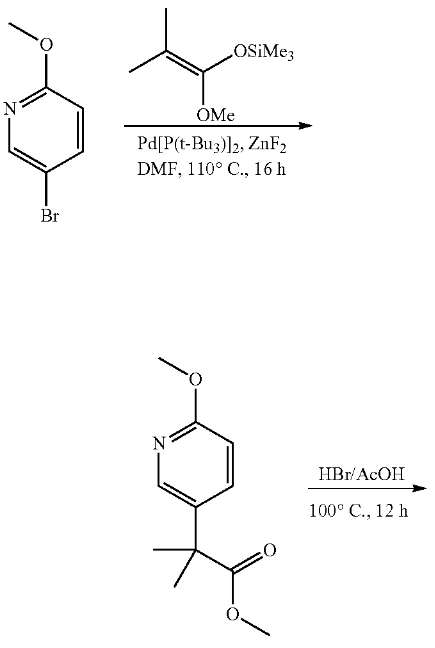

-continued

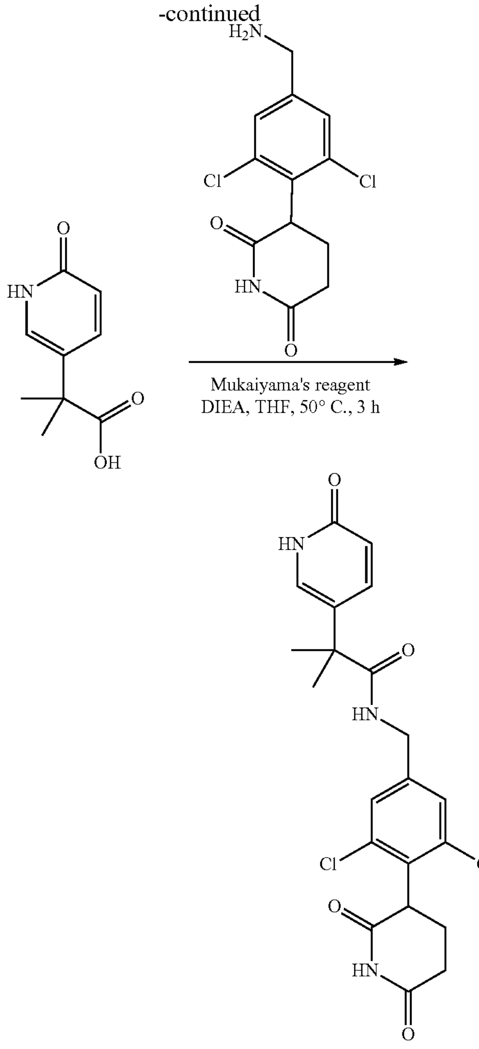

Step 1. To an oven-dried three neck round bottom flask were added difluorozinc (550 mg, 5.32 mmol, 1.00 eq.) and palladium tri-tert-butylphosphane (272 mg, 0.532 mol, 0.10 eq.). N, N-dimethylformamide (40 mL), (1-methoxy-2-methyl-prop-1-enoxy)-trimethyl-silane (1.48 g, 8.51 mmol, 1.60 eq.) and 5-bromo-2-methoxy-pyridine (1.00 g, 5.32 mmol, 1.00 eq.) were added, and the mixture was degassed by purging with nitrogen. The reaction was stirred at 110° C. for 16 h under nitrogen, then it was cooled to 25° C., and poured into water (300 mL) and extracted with ethyl acetate (3×100 mL). The combined organic layers were washed with brine (2×100 mL), dried over anhydrous sodium sulfate, filtered, and concentrated under reduced pressure. The residue was purified via Purification Method 2 to afford methyl 2-(6-methoxypyridin-3-yl)-2-methylpropanoate (980 mg, 3.80 mmol, 71% yield) as a yellow oil.

Step 2. A solution of methyl 2-(6-methoxy-3-pyridyl)-2-methyl-propanoate (300 mg, 1.43 mmol, 1.00 eq.) and hydrobromic acid in acetic acid (7.5 mL) was stirred at 100° C. for 12 h. The reaction mixture was concentrated under reduced pressure to afford 2-methyl-2-(6-oxo-1,6-dihydropyridin-3-yl) propanoic acid (645 mg, crude) as a white solid.

Step 3. To a solution of 3-[4-(aminomethyl)-2,6-dichlorophenyl]piperidine-2,6-dione (100 mg, 0.348 mol, 1.00 eq.) and 2-methyl-2-(6-oxo-1H-pyridin-3-yl) propanoic acid (200 mg, 0.828 mol, 2.38 eq.) in tetrahydrofuran (5 mL) were added 2-chloro-1-methylpyridinium iodide (140 mg, 0.548 mol, 1.57 eq.) and N-ethyl-N-propan-2-ylpropan-2-amine (140 mg, 1.08 mmol, 3.11 eq.). The reaction was stirred at 50° C. for 3 h under nitrogen atmosphere. The mixture was concentrated under reduced pressure. The residue was purified via Purification Method 2 then Purification method 1 to afford N-(3,5-dichloro-4-(2,6-dioxopiperidin-3-yl)benzyl)-2-methyl-2-(6-oxo-1,6-dihydropyridin-3-yl) propanamide (20.1 mg, 445 mmol, 13% yield) as a white solid.

$^1$H NMR (400 MHZ, DMSO-$d_6$) δ=11.49 (s, 1H), 10.95 (s, 1H), 8.05 (t, J=6.0 Hz, 1H), 7.31 (dd, J=2.8, 9.6 Hz, 1H), 7.22-7.16 (m, 3H), 6.30 (d, J=9.6 Hz, 1H), 4.56 (dd, J=5.2, 12.4 Hz, 1H), 4.20 (d, J=5.2 Hz, 2H), 2.92-2.78 (m, 1H), 2.53 (s, 1H), 2.38-2.33 (m, 1H), 1.94-1.84 (m, 1H), 1.39 (s, 6H). MS (ESI) m/z 450.0 $[M+H]^+$

Exemplary Compound 80

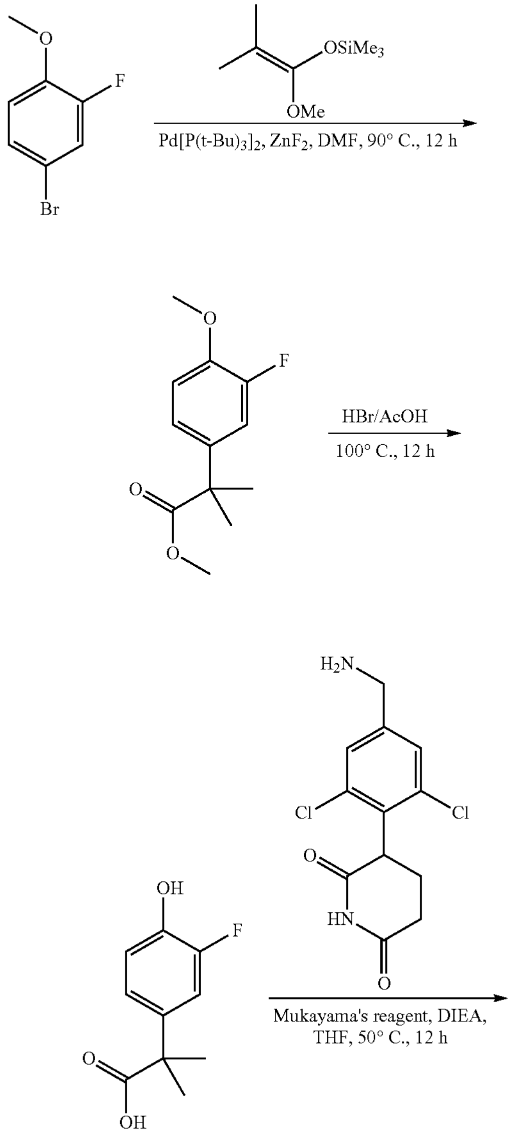

-continued

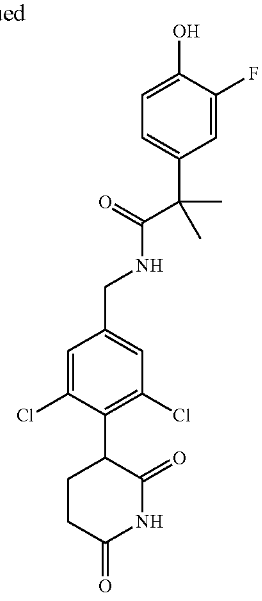

Step 1. A mixture of 4-bromo-2-fluoro-1-methoxybenzene (2.00 g, 9.75 mmol, 1.00 eq.), ((1-methoxy-2-methyl-prop-1-en-1-yl)oxy)trimethylsilane (2.55 g, 14.6 mmol, 1.50 eq.), palladium tri-tert-butylphosphane (500 mg, 978 μmol, 0.10 eq.) and difluorozinc (1.01 g, 9.75 mmol, 1.00 eq.) in dimethyl formamide (10 mL) was stirred at 90° C. for 12 h under nitrogen atmosphere. The reaction was quenched with water (45 mL) and extracted with ethyl acetate (2×35 mL). The combined organic layers were washed with brine (4×30 mL), dried over anhydrous sodium sulfate, filtered, and concentrated under reduced pressure. The residue was purified via Purification Method 2 to afford methyl 2-(3-fluoro-4-methoxyphenyl)-2-methylpropanoate (1.13 g, 3.98 mmol, 41% yield) as a yellow oil.

Step 2. A mixture of methyl 2-(3-fluoro-4-methoxyphenyl)-2-methylpropanoate (1.13 g, 4.99 mmol, 1.00 eq.) in 33 wt % hydrobromic acid in acetic acid (10 mL) was degassed by purging with nitrogen, then the reaction was stirred at 100° C. for 12 h under nitrogen atmosphere. The mixture was concentrated under reduced pressure to afford 2-(3-fluoro-4-hydroxyphenyl)-2-methylpropanoic acid (1.02 g, crude) as a yellow oil.

Step 3. To a solution of 2-(3-fluoro-4-hydroxyphenyl)-2-methylpropanoic acid (70.0 mg, 353 μmol, 1.00 eq.) in tetrahydrofuran (5 mL) was added 3-(4-(aminomethyl)-2,6-dichlorophenyl) piperidine-2,6-dione (101 mg, 351 μmol, 1.00 eq.), 2-chloro-1-methylpyridinium iodide (108 mg, 423 μmol, 1.20 eq.) and N,N-diisopropyl ethylamine (137 mg, 1.06 mmol, 3.00 eq.). The mixture was stirred at 50° C. for 12 h. The reaction mixture was quenched with water (20 mL) and extracted with ethyl acetate (2×20 mL). The combined organic layers were washed with brine (2×20 mL), dried over anhydrous sodium sulfate, filtered, and concentrated under reduced pressure. The residue was purified via Purification Method 1 to afford N-(3,5-dichloro-4-(2,6-dioxopiperidin-3-yl)benzyl)-2-(3-fluoro-4-hydroxyphenyl)-2-methylpropanamide (27.3 mg, 58.4 μmol, 16% yield) as a white solid.

$^1$H NMR (400 MHZ, DMSO-$d_6$) δ=10.94 (s, 1H), 9.74 (s, 1H), 7.95 (t, J=6.0 Hz, 1H), 7.15 (s, 1H), 7.09-7.01 (m, 2H), 6.95-6.85 (m, 2H), 4.54 (dd, J=5.6, 12.8 Hz, 1H), 4.19 (d, J=6.0 Hz, 2H), 2.84 (ddd, J=5.6, 14.0, 16.8 Hz, 1H), 2.33

(qd, J=4.0, 13.2 Hz, 1H), 1.92-1.82 (m, 1H), 2.56-2.51 (m, 1H), 1.44 (s, 6H). MS (ESI) m/z 489.0 [M+Na]+

Exemplary Compound 87

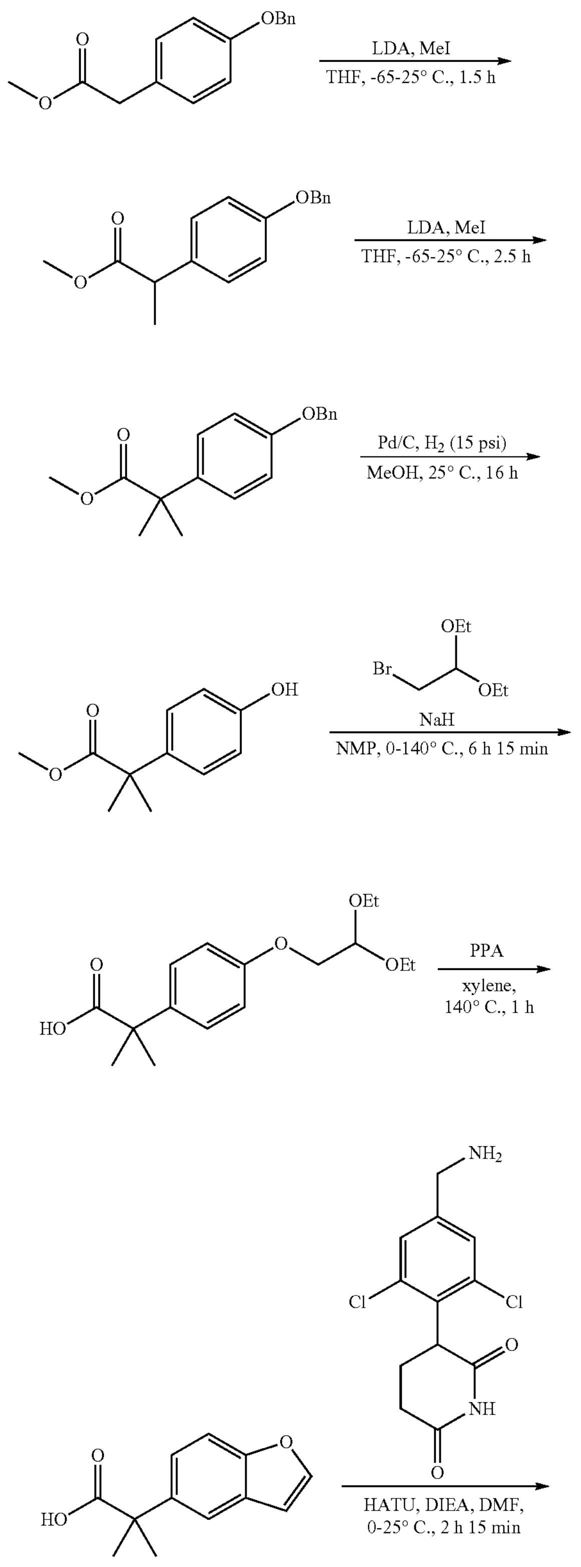

-continued

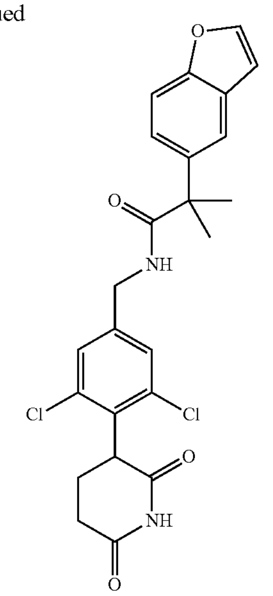

Step 1. To a solution of methyl 2-(4-(benzyloxy)phenyl) acetate (5.00 g, 19.5 mmol, 1.00 eq.) in tetrahydrofuran (50 mL) was added lithium diisopropylamide (2 M in tetrahydrofuran, 19.5 mL, 2.00 eq.) at −65° C. under nitrogen atmosphere. The reaction was stirred at −65° C. for 30 min, then iodomethane (3.70 mL, 59.4 mmol, 3.05 eq.) was added dropwise. The reaction was stirred at 25° C. for 1 h. The reaction was quenched with saturated ammonium chloride solution (40 mL) at 0° C. The mixture was extracted with ethyl acetate (2×40 mL). The combined organic layers were washed with brine (50 mL), dried over anhydrous sodium sulfate, and concentrated in vacuo. The residue was purified via Purification Method 2 to afford methyl 2-(4-(benzyloxy) phenyl) propanoate (4.54 g, 16.8 mmol, 86% yield) as a colourless oil.

Step 2. To a solution of methyl 2-(4-(benzyloxy)phenyl) propanoate (4.54 g, 16.8 mmol, 1.00 eq.) in tetrahydrofuran (50 mL) was added lithium diisopropylamide (2 M, 16.8 mL, 2.00 eq.) at −65° C. under nitrogen atmosphere. The reaction was stirred at −65° C. for 30 min, then iodomethane (3.20 mL, 51.4 mmol, 3.06 eq.) was added dropwise. The reaction was stirred at 25° C. for 2 h. The reaction was quenched with saturated ammonium chloride solution (45 mL) at 0° C. The mixture was extracted with ethyl acetate (2×40 mL). The combined organic layers were washed with brine (50 mL), dried over anhydrous sodium sulfate, and concentrated in vacuo. The residue was purified via Purification Method 2 to afford methyl 2-(4-(benzyloxy)phenyl)-2-methylpropanoate (4.70 g, 14.9 mmol, 89% yield) as a yellow solid.

Step 3. To a solution of palladium on carbon (940 mg, 10% purity) in methanol (50 mL) was added a solution of methyl 2-(4-(benzyloxy)phenyl)-2-methylpropanoate (4.70 g, 16.5 mmol, 1.00 eq.) in methanol (20 mL). The reaction was stirred at 25° C. for 16 h under hydrogen atmosphere (15 psi). The mixture was filtered over a pad of celite, and the filtrate was concentrated under reduced pressure. The residue was purified via Purification Method 2 to afford methyl 2-(4-hydroxyphenyl)-2-methylpropanoate (2.70 g, 13.9 mmol, 84% yield) as a white solid.

Step 4. To a solution of methyl 2-(4-hydroxyphenyl)-2-methyl-propanoate (2.70 g, 13.9 mmol, 1.00 eq.) in N-methyl pyrrolidone (40 mL) was added sodium hydride (1.13 g, 28.2 mmol, 60% purity, 2.03 eq.) at 0° C. The reaction was stirred at 0° C. for 15 min. Then 2-bromo-1,1-diethoxy-ethane (2.10 mL, 14.0 mmol, 1.00 eq.) was added dropwise to the mixture. The reaction was stirred at 140° C. for 6 h under nitrogen atmosphere. The reaction was quenched with water (50 mL) at 0° C. The mixture was washed with ethyl acetate (50 mL). The layers were separated, and the aqueous phase was acidified to PH ~5 with 1 M hydrochloric acid. The aqueous phase was extracted with ethyl acetate (2×50 mL). The combined organic layers were washed with brine (50 mL) and dried over anhydrous sodium sulfate, filtered, and concentrated in vacuo. The residue was purified via Purification Method 2 to afford 2-(4-(2,2-diethoxyethoxy)phenyl)-2-methylpropanoic acid (2.50 g, 7.17 mmol, 52% yield) as a colourless oil.

Step 5. To a solution of 2-(4-(2,2-diethoxyethoxy)phenyl)-2-methylpropanoic acid (1.00 g, 3.37 mmol, 1.00 eq.) in xylene (10 mL) was added polyphosphoric acid (1.14 g, 3.37 mmol, 1.00 eq.) at 25° C. The reaction was stirred at 140° C. for 1 h. The reaction was quenched with water (50 mL) at 0° C. The mixture was extracted with ethyl acetate (3× 40 mL). The combined organic layers were washed with brine (50 mL) and dried over anhydrous sodium sulfate, filtered, and concentrated in vacuo. The residue was purified via Purification Method 2 to afford 2-(benzofuran-5-yl)-2-methylpropanoic acid (350 mg, 1.65 mmol, 49% yield) as a white solid.

Step 6. To a solution of 2-(benzofuran-5-yl)-2-methylpropanoic acid (80 mg, 391.73 μmol, 1.00 eq.) and N,N-diisopropylethylamine (154 mg, 1.19 mmol, 3.03 eq.) in dimethylformamide (6 mL) was added O-(7-azabenzotriazol-1-yl)-N,N,N,N-tetramethyluroniumhexafluorophosphate (224 mg, 589 μmol, 1.50 eq.) at 0° C. The reaction was stirred at 25° C. for 15 min. Then 3-(4-(aminomethyl)-2,6-dichlorophenyl) piperidine-2,6-dione (100 mg, 348 μmol, 0.89 eq.) was added to the mixture, and the reaction was stirred at 25° C. for 2 h. The mixture was diluted with ethyl acetate (30 mL) and water (30 mL). The layers were separated, and the aqueous phase was extracted with ethyl acetate (2× 30 mL). The combined organic layers were washed with saturated sodium bicarbonate (3×20 mL) and brine (30 mL), dried over anhydrous sodium sulfate, filtered, and concentrated in vacuo. The residue was purified via Purification Method I to afford 2-(benzofuran-5-yl)-N-(3,5-dichloro-4-(2,6-dioxopiperidin-3-yl)benzyl)-2-methylpropanamide (51.34 mg, 105 μmol, 27% yield) as an off-white solid.

$^1$H NMR (400 MHZ, DMSO-$d_6$) δ=10.95 (s, 1H), 8.02-7.91 (m, 2H), 7.62 (d, J=1.6 Hz, 1H), 7.54 (d, J=8.8 Hz, 1H), 7.25 (dd, J=2.0, 8.8 Hz, 1H), 7.15 (s, 1H), 7.07 (d, J=1.2 Hz, 1H), 6.94 (dd, J=0.8, 2.0 Hz, 1H), 4.54 (dd, J=5.6, 12.8 Hz, 1H), 4.20 (d, J=6.0 Hz, 2H), 2.92-2.77 (m, 1H), 2.59-2.52 (m, 1H), 2.40-2.25 (m, 1H), 1.93-1.80 (m, 1H), 1.55 (s, 6H). MS (ESI) m/z 473.1 [M+H]$^+$

Exemplary Compound 89

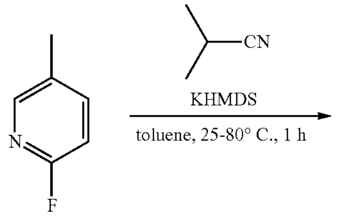

-continued

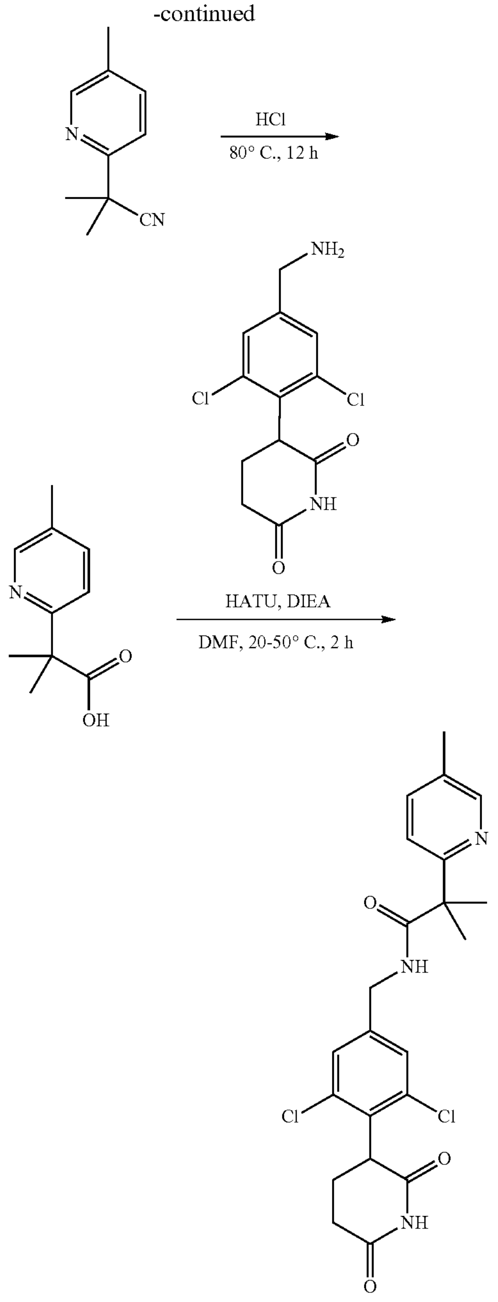

Step 1. To a solution of 2-fluoro-5-methylpyridine (2.00 g, 18.0 mmol, 1.00 eq.) and isobutyronitrile (2.80 g, 40.5 mmol, 2.25 eq.) in toluene (60 mL) was added potassium bis(trimethylsilyl)amide (1 M, 27.0 mL, 1.50 eq.) dropwise at 25° C. under nitrogen. The mixture was stirred at 80° C. for 1 h under nitrogen. After reaction completion, the mixture was cooled to 25° C., quenched with saturated aqueous ammonium chloride solution (80 mL) and extracted with ethyl acetate (5× 100 mL). The combined organic layers were dried over sodium sulfate, filtered, and concentrated under reduced pressure to give a residue, which was purified via Purification Method 2 to afford 2-methyl-2-(5-methylpyridin-2-yl) propanenitrile (2.30 g, 12.4 mmol, 69% yield) as a colourless liquid.

Step 2. A mixture of 2-methyl-2-(5-methylpyridin-2-yl) propanenitrile (2.30 g, 12.4 mmol, 1.00 eq.) in concentrated hydrochloric acid (12 M, 20 mL) was stirred at 80° C. for 12 h. The reaction mixture was concentrated under reduced pressure, then diluted with water (15 mL) and lyophilized to give a brown oil. The brown oil was triturated with dichloromethane (10 mL) and methanol (10 mL) at 25° C. for 5 min. The suspension was filtered, and the filtrate was concentrated under reduced pressure to give 2-methyl-2-(5-methylpyridin-2-yl) propanoic acid (818 mg, 3.42 mmol, 28% yield, 75% purity) as a brown oil.

Step 3. To a solution of 2-methyl-2-(5-methylpyridin-2-yl) propanoic acid (100 mg, 418 μmol, 1.50 eq.) in dimethylformamide (2 mL) were added O-(7-azabenzotriazol-1-yl)-N,N,N,N-tetramethyluronium hexafluorophosphate (159 mg, 418 μmol, 1.50 eq.) and diisopropylethylamine (72.0 mg, 558 μmol, 97.2 μL, 2.00 eq.). The reaction was stirred at 20° C. for 0.5 h, then 3-(4-(aminomethyl)-2,6-dichlorophenyl) piperidine-2,6-dione hydrochloride (90.3 mg, 279 μmol, 1.00 eq.) in dimethylformamide (1 mL) was added. The reaction was stirred at 50° C. for 1.5 h. After reaction completion, the mixture was cooled to 25° C., then it was diluted with water (10 mL) and extracted with ethyl acetate (3× 20 mL). The combined organic layers were washed with saturated aqueous sodium bicarbonate solution (2× 20 mL), dried over sodium sulfate, filtered, and concentrated under reduced pressure to give a residue, which was purified via Purification Method 1 to afford N-(3,5-dichloro-4-(2,6-dioxopiperidin-3-yl)benzyl)-2-methyl-2-(5-methylpyridin-2-yl) propanamide (31.9 mg, 70.3 μmol, 19% yield) as an off-white solid.

$^1$H NMR (400 MHZ, DMSO-$d_6$) δ=10.95 (s, 1H), 8.46 (s, 1H), 8.17-8.00 (m, 1H), 7.82-7.66 (m, 1H), 7.47-7.35 (m, 1H), 7.32-7.27 (m, 1H), 7.25-7.21 (s, 1H), 4.55 (dd, J=5.6, 12.8 Hz, 1H), 4.23 (d, J=6.0 Hz, 2H), 2.90-2.81 (m, 1H), 2.58-2.53 (m, 1H), 2.41-2.33 (m, 1H), 2.32 (s, 3H), 1.93-1.83 (m, 1H), 1.54 (s, 6H). MS (ESI) m/z 448.2 [M+1]$^+$

Exemplary Compound 90

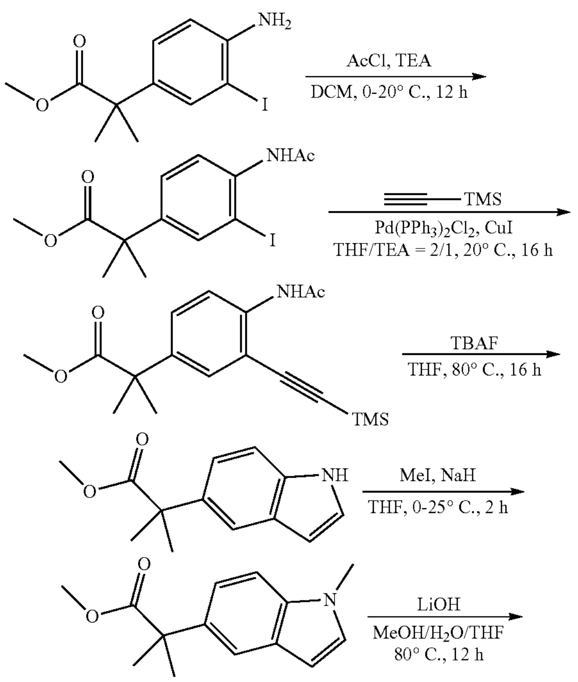

-continued

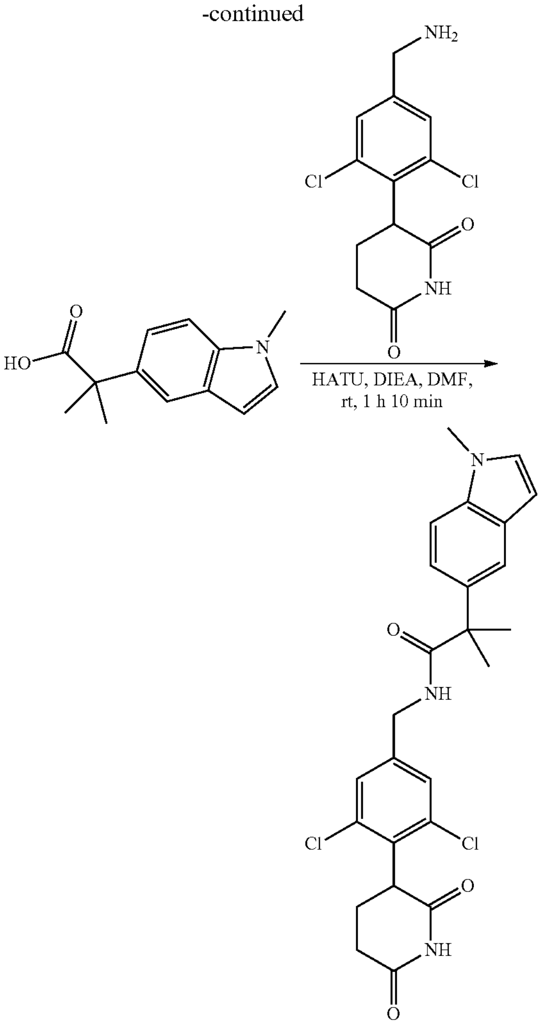

Step 1. A solution of methyl 2-(4-amino-3-iodophenyl)-2-methylpropanoate (3.30 g, 10.3 mmol, 1.00 eq.) and triethylamine (2.09 g, 20.7 mmol, 2.00 eq.) in dichloromethane (50 mL) was cooled to 0° C. Then acetyl chloride (12.4 mmol, 885 μL, 1.20 eq.) was added. The reaction was stirred at 20° C. for 12 h. The mixture was concentrated under reduced pressure. The residue was purified via Purification Method 2 to afford methyl 2-(4-acetamido-3-iodophenyl)-2-methylpropanoate (2.88 g, 7.58 mmol, 73% yield) as a colourless oil.

Step 2. To a solution of methyl 2-(4-acetamido-3-iodophenyl)-2-methylpropanoate (1.00 g, 2.77 mmol, 1.00 eq.) in triethylamine (5 mL) and tetrahydrofuran (10 mL) were added ethynyl(trimethyl) silane (1.36 g, 13.8 mmol, 1.92 mL, 5.00 eq.), bis(triphenylphosphine) palladium (II) dichloride (194 mg, 277 μmol, 0.10 eq.) and cuprous iodide (52.7 mg, 277 μmol, 0.10 eq.). The mixture was stirred at 20° C. under nitrogen atmosphere for 16 h. The mixture was diluted with water (50 mL) and extracted with ethyl acetate (50 mL). The combined organic layers were washed with brine (3×50 mL), dried over sodium sulfate, filtered, and concentrated in vacuo. The residue was purified via Purification Method 2 to afford methyl 2-(4-acetamido-3-((trimethylsilyl) ethynyl)phenyl)-2-methylpropanoate (900 mg, 2.44 mmol, 88% yield) as a yellow oil.

Step 3. To a solution of methyl 2-(4-acetamido-3-((trimethylsilyl) ethynyl)phenyl)-2-methylpropanoate (900 mg, 2.72 mmol, 1.00 eq.) in tetrahydrofuran (20 mL) was added tetrabutylammonium fluoride (1M in tetrahydrofuran, 5.43 mL, 2.00 eq.). The mixture was stirred at 80° C. under nitrogen atmosphere for 16 h. The mixture was concentrated under reduced pressure. The residue was purified via Purification Method 2 to afford methyl 2-(1H-indol-5-yl)-2-methylpropanoate (400 mg, 1.75 mmol, 64% yield) as a yellow solid.

Step 4. To a solution of methyl 2-(1H-indol-5-yl)-2-methylpropanoate (400 mg, 1.84 mmol, 1.00 eq.) in tetrahydrofuran (10 mL) was added sodium hydride (110 mg, 2.76 mmol, 60% purity, 1.50 eq.) at 0° C. The mixture was stirred at 0° C. for 0.5 h. Then methyl iodide (287 mg, 2.03 mmol, 1.10 eq.) was added at 0° C. The mixture was stirred 25° C. for 1.5 h. The reaction was quenched with saturated ammonium chloride solution (50 mL) and extracted with ethyl acetate (3×50 mL). The combined organic extracts were washed with saturated ammonium chloride (50 mL) and brine (50 mL), dried over sodium sulfate, filtered, and concentrated. The residue was purified via Purification Method 2 to afford methyl 2-methyl-2-(1-methyl-1H-indol-5-yl) propanoate (270 mg, 1.05 mmol, 57% yield) as a colourless oil.

Step 5. To a solution of methyl 2-methyl-2-(1-methyl-1H-indol-5-yl) propanoate (270 mg, 1.17 mmol, 1.00 eq.) in methanol (2 mL), tetrahydrofuran (2 mL) and water (2 mL) was added lithium hydroxide monohydrate (245 mg, 5.84 mmol, 5.00 eq.). The mixture was stirred at 80° C. for 12 h. The reaction was acidified with formic acid until pH 5. The mixture was filtered, and the filtrate was purified via Purification Method 2 to afford 2-methyl-2-(1-methyl-1H-indol-5-yl) propanoic acid (150 mg, 684 μmol, 59% yield) as a white solid.

Step 6. To a solution of 2-methyl-2-(1-methyl-1H-indol-5-yl) propanoic acid (100 mg, 460 μmol, 1.00 eq.) in N,N-dimethylformamide (3 mL) were added O-(7-azabenzotriazol-1-yl)-N,N,N',N'-tetramethyluronium hexafluorophosphate (210 mg, 552 μmol, 1.20 eq.) and N,N-diisopropylethylamine (1.38 mmol, 240 μL, 3.00 eq.). The mixture was stirred at 25° C. for 10 min, then 3-(4-(aminomethyl)-2,6-dichlorophenyl) piperidine-2,6-dione hydrochloride (149 mg, 460 μmol, 1.00 eq.) was added. The reaction was stirred at 25° C. for 1 h. The mixture was diluted with water (20 mL) and extracted with ethyl acetate (20 mL). The combined organic layers were washed with brine (3× 20 mL), dried over sodium sulfate, filtered, and concentrated in vacuo. The residue was purified via Purification Method 1 to afford N-(3,5-dichloro-4-(2,6-dioxopiperidin-3-yl)benzyl)-2-methyl-2-(1-methyl-1H-indol-5-yl) propanamide (113.62 mg, 231 μmol, 50% yield) as a white solid.

$^1$H NMR (400 MHZ, DMSO-$d_6$) δ=10.94 (s, 1H), 7.82 (t, J=6.0 Hz, 1H), 7.51 (s, 1H), 7.37 (d, J=8.4 Hz, 1H), 7.29 (d, J=2.8 Hz, 1H), 7.15 (s, 1H), 7.11-7.02 (m, 2H), 6.39 (d, J=2.8 Hz, 1H), 4.53 (dd, J=5.2, 12.8 Hz, 1H), 4.18 (d, J=6.0 Hz, 2H), 3.76 (s, 3H), 2.89-2.76 (m, 1H), 2.54 (m, 1H), 2.33 (dq, J=4.0, 13.2 Hz, 1H), 1.94-1.79 (m, 1H), 1.53 (s, 6H). MS (ESI) m/z 486.2 $[M+H]^+$

Exemplary Compound 91

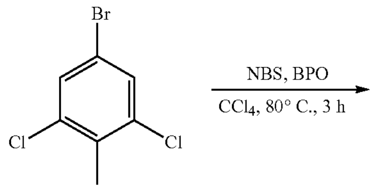

-continued

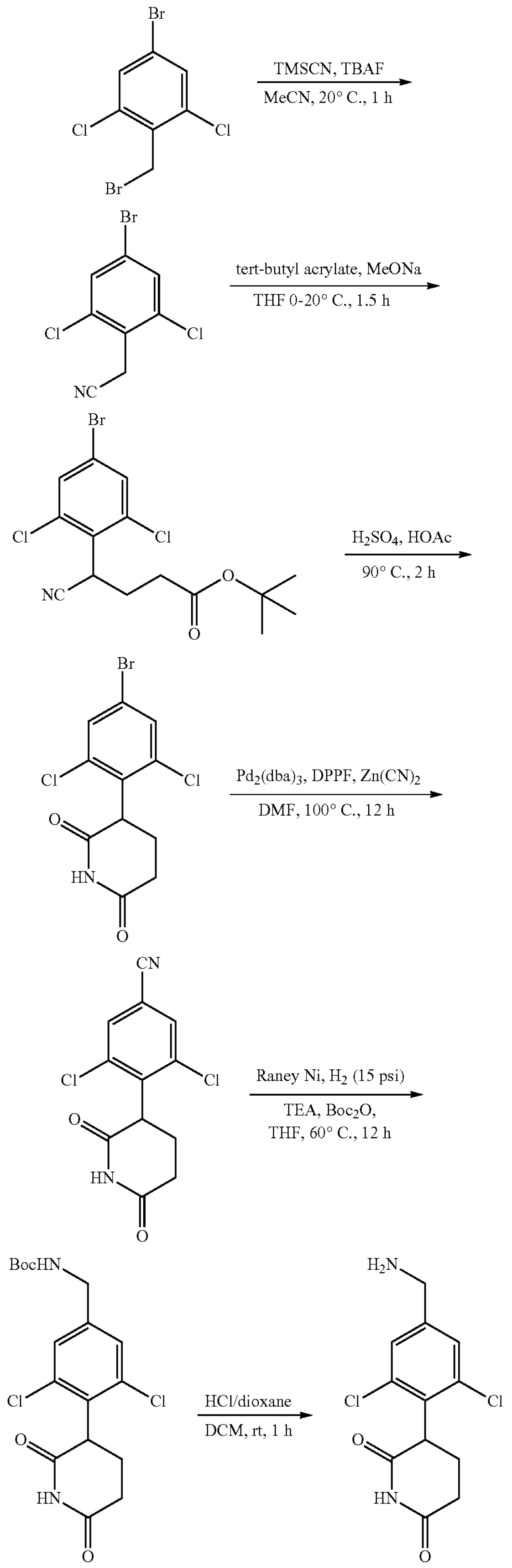

-continued

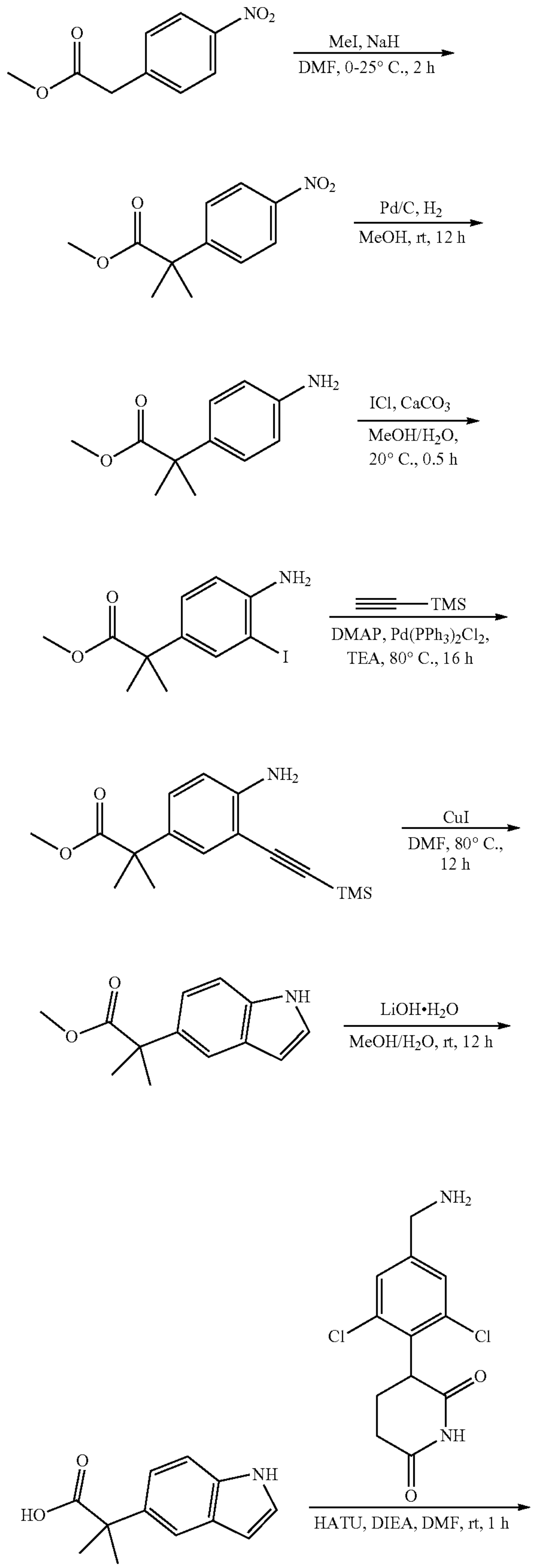

-continued

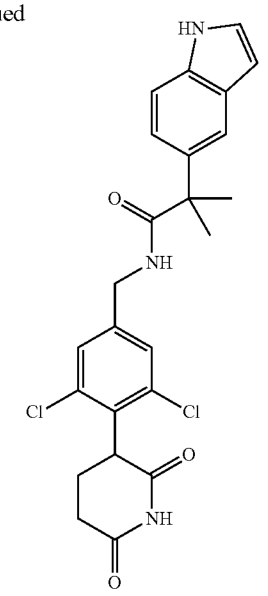

Step 1. To a solution of 5-bromo-1,3-dichloro-2-methylbenzene (30.0 g, 125 mmol, 1.00 eq.) in carbon tetrachloride (200 mL) was added N-bromosuccinimide (23.4 g, 131 mmol, 1.05 eq.) followed by benzoic peroxyanhydride (1.51 g, 6.25 mmol, 0.05 eq.) in portions. The reaction was stirred at 80° C. for 3 h under nitrogen atmosphere. The mixture was cooled to room temperature. It was filtered, and the filtrate was concentrated under reduced pressure to give a residue. The residue was purified via Purification Method 2 to afford 5-bromo-2-(bromomethyl)-1,3-dichlorobenzene (86.7 g, 245 mmol, 98% yield) as a white solid.

Step 2. To a solution of 5-bromo-2-(bromomethyl)-1,3-dichlorobenzene (43.3 g, 136 mmol, 1.00 eq.) and TMSCN (20.2 g, 204 mmol, 1.50 eq.) in MeCN(100 mL) was added a solution of TBAF (1 M in THF, 204 mL, 1.50 eq.) dropwise at 0° cover 30 min. After 30 min at room temperature, the reaction was concentrated under reduced pressure to give a residue. The residue was purified via Purification Method 2 to afford 2-(4-bromo-2,6-dichlorophenyl) acetonitrile (63.7 g, 216 mmol, 80% yield) as a white solid.

Step 3. To a solution of 2-(4-bromo-2,6-dichlorophenyl) acetonitrile (78.8 g, 297 mmol, 1.00 eq.) in THF (400 mL) were added tert-butyl acrylate (38.1 g, 297 mmol, 1.00 eq.) and sodium methoxide (1.61 g, 29.7 mmol, 0.10 eq.) at 0° C. Then the reaction was stirred at 20° C. for 1.5 h. The mixture was diluted with water (500 mL) and extracted with ethyl acetate (3'200 mL). The combined organic layers were washed with brine (150 mL), dried over sodium sulfate, filtered, and concentrated under reduced pressure to afford tert-butyl 4-(4-bromo-2,6-dichlorophenyl)-4-cyanobutanoate (115.3 g, crude) as a yellow oil.

Step 4. To a solution of tert-butyl 4-(4-bromo-2,6-dichlorophenyl)-4-cyanobutanoate (115 g, 293 mmol, 1.00 eq.) in acetic acid (500 mL) was added sulfuric acid (109 mL). The reaction was stirred at 90° C. for 2 h. The mixture was cooled to room temperature and poured into ice water (500 mL). The resulting precipitate was filtered, washed with ethyl acetate (200 mL), and dried under vacuum to afford 3-(4-bromo-2,6-dichlorophenyl) piperidine-2,6-dione (88.0 g, 248 mmol, 85% yield) as a white solid.

Step 5. To a solution of 3-(4-bromo-2,6-dichlorophenyl) piperidine-2,6-dione (10.0 g, 29.7 mmol, 1.00 eq.) in DMF (150 mL) were added zinc cyanide (5.23 g, 44.5 mmol, 1.50 eq.), 1,1'-bis (diphenylphosphino)ferrocene (823 mg, 1.48 mmol, 0.05 eq.) and $Pd_2$ (dba) 3 (1.36 g, 1.48 mmol, 0.05 eq.). The reaction was stirred at 100° C. under nitrogen for 12 h. The mixture was cooled to 20° C., and poured into water (500 mL), and the aqueous layer was extracted with ethyl acetate (500 mL). The combined organic layers were washed with brine (500 mL), dried over anhydrous sodium sulfate, filtered, and concentrated under reduced pressure to give a residue. The residue was triturated with ethyl acetate (100 mL) at 100° C. for 30 min, then the resulting solid was filtered to afford 3,5-dichloro-4-(2,6-dioxopiperidin-3-yl) benzonitrile (8.50 g, 27.0 mmol, 91% yield) as a yellow solid.

Step 6. To a solution of 3,5-dichloro-4-(2,6-dioxopiperidin-3-yl)benzonitrile (4.00 g, 14.1 mmol, 1.00 eq.) in THF (50 mL) were added TEA (21.2 mmol, 2.95 mL, 1.50 eq.), $Boc_2O$(6.17 g, 28.3 mmol, 2.00 eq.) and Raney-Ni (1.00 g). The reaction was stirred at 60° C. under hydrogen atmosphere (15 psi) for 12 h. The mixture was filtered, and the filtrate was concentrated under reduced pressure to give a residue. The residue was purified via Purification Method 2 to afford tert-butyl (3,5-dichloro-4-(2,6-dioxopiperidin-3-yl) benzyl) carbamate (9.00 g, 22.1 mmol, 78% yield) as a white solid.

Step 7. To a solution of tert-butyl (3,5-dichloro-4-(2,6-dioxopiperidin-3-yl)benzyl) carbamate (10.1 g, 26.1 mmol, 1.00 eq.) in DCM (50 mL) was added hydrogen chloride/dioxane (4 M, 50 mL). The mixture was stirred at 20° C. for 1 h, then concentrated under reduced pressure to afford 3-(4-(aminomethyl)-2,6-dichlorophenyl) piperidine-2,6-dione hydrochloride (8.00 g, 23.5 mmol, 90% yield) as a white solid.

$^1$H NMR (400 MHZ, DMSO-$d_6$) δ=11.01 (s, 1H), 8.64 (s, 3H), 7.75 (d, J=1.2 Hz, 1H), 7.68 (d, J=1.2 Hz, 1H), 4.63 (dd, J=5.2, 12.8 Hz, 1H), 4.04 (d, J=5.6 Hz, 2H), 2.88 (ddd, J=5.6, 14.0, 16.8 Hz, 1H), 2.57 (d, J=2.0 Hz, 1H), 2.38 (dq, J=4.4, 13.2 Hz, 1H), 1.97-1.87 (m, 1H). MS (ESI) m/z 287.1 $[M+H]^+$ Step 8. To a solution of methyl 2-(4-nitrophenyl)acetate (4.00 g, 20.5 mmol, 1.00 eq.) in N,N-dimethylformamide (20 mL) was added sodium hydride (2.05 g, 51.2 mmol, 60% purity, 2.50 eq.) at 0° C. under nitrogen atmosphere. The mixture was stirred at 0° C. for 0.5 h. Then methyl iodide (82.0 mmol, 5.10 mL, 4.00 eq.) was added. The mixture was stirred at 25° C. under nitrogen for 1.5 h. The reaction was quenched with saturated ammonium chloride solution (200 mL). The mixture was extracted with ethyl acetate (3×200 mL). The combined organic extracts were washed with saturated ammonium chloride (200 mL) and brine (500 mL), dried over sodium sulfate, filtered, and concentrated under reduce pressure. The residue was purified via Purification Method 2 to afford methyl 2-methyl-2-(4-nitrophenyl) propanoate (4.60 g, 19.6 mmol, 96% yield) as a yellow oil.

Step 9. To a solution of methyl 2-methyl-2-(4-nitrophenyl) propanoate (4.60 g, 20.6 mmol, 1.00 eq.) in methanol (30 mL) was added palladium on carbon (500 mg, 10% purity). The mixture was stirred at 20° C. under hydrogen atmosphere (15 psi) for 12 h. The mixture was filtered through a pad of celite. The filtrate was concentrated to give methyl 2-(4-aminophenyl)-2-methylpropanoate (4.00 g, 19.7 mmol, 95% yield) as a yellow oil.

Step 10. To a solution of methyl 2-(4-aminophenyl)-2-methylpropanoate (4.00 g, 20.7 mmol, 1.00 eq.) in methanol (40 mL) and water (20 mL) was added calcium carbonate (3.11 g, 31.1 mmol, 1.50 eq.). Then a solution of iodine chloride (3.36 g, 20.7 mmol, 1.00 eq.) in methanol (5 mL) was added. The mixture was stirred at 20° C. for 0.5 h. The mixture was diluted with water (200 mL) and extracted with ethyl acetate (200 mL). The combined organic layers were washed with brine (3× 200 mL), dried over sodium sulfate, filtered, and concentrated in vacuo. The residue was purified via Purification Method 2 to afford methyl 2-(4-amino-3-iodophenyl)-2-methylpropanoate (5.70 g, 17.0 mmol, 82% yield) as a yellow oil.

Step 11. To a solution of methyl 2-(4-amino-3-iodophenyl)-2-methylpropanoate (2.00 g, 6.27 mmol, 1.00 eq.) in triethylamine (10 mL) were added ethynyl(trimethyl) silane (6.16 g, 62.7 mmol, 10.0 eq.), bis(triphenylphosphine) palladium (II) dichloride (220 mg, 313 μmol, 0.05 eq.) and 4-dimethylaminopyridin (38.3 mg, 313 μmol, 0.05 eq.). The reaction was stirred at 80° C. under nitrogen atmosphere for 16 h. The mixture was diluted with water (50 mL) and extracted with ethyl acetate (50 mL). The combined organic layers were washed with brine (3×50 mL), dried over sodium sulfate, filtered, and concentrated in vacuo. The residue was purified via Purification Method 2 to afford methyl 2-(4-amino-3-((trimethylsilyl) ethynyl)phenyl)-2-methylpropanoate (900 mg, 2.80 mmol, 45% yield, 90% purity) as a yellow oil.

Step 12. To a solution of methyl 2-(4-amino-3-((trimethylsilyl) ethynyl)phenyl)-2-methylpropanoate (800 mg, 2.76 mmol, 1.00 eq.) in N,N-dimethylformamide (20 mL) was added cuprous iodide (263 mg, 1.38 mmol, 0.50 eq.). The mixture was stirred at 80° C. under nitrogen atmosphere for 12 h. The mixture was diluted with water (20 mL) and extracted with ethyl acetate (20 mL). The combined organic layers were washed with brine (3× 20 mL), dried over sodium sulfate, filtered, and concentrated in vacuo. The residue was purified via Purification Method 2 to afford methyl 2-(1H-indol-5-yl)-2-methylpropanoate (120 mg, 331 μmol, 12% yield, 60% purity) as a yellow oil.

Step 13. To a solution of methyl 2-(1H-indol-5-yl)-2-methylpropanoate (120 mg, 331 μmol, 60% purity, 1.00 eq.) in methanol (5 mL) and water (2 mL) was added lithium hydroxide monohydrate (55.6 mg, 1.33 mmol, 4.00 eq.). The mixture was stirred at 20° C. for 12 h. The reaction was acidified with formic acid to pH 6 and filtered. The filtrate was purified via Purification Method 2 to afford 2-(1H-indol-5-yl)-2-methylpropanoic acid (50.0 mg, 234 μmol, 71% yield) as a yellow solid.

Step 14. To a solution of 2-(1H-indol-5-yl)-2-methylpropanoic acid (30.0 mg, 148 μmol, 1.00 eq.) in N,N-dimethylformamide (3 mL) were added 2-(3H-[1,2,3]triazolo[4,5-b]pyridin-3-yl)-1,1,3,3-tetramethyluronium hexafluorophosphate (V) (67.4 mg, 177 μmol, 1.20 eq.), N,N-diisopropylethylamine (443 μmol, 77.1 μL, 3.00 eq.) and 3-(4-(aminomethyl)-2,6-dichlorophenyl) piperidine-2,6-dione hydrochloride (47.8 mg, 148 μmol, 1.00 eq.). The reaction was stirred at 20° C. for 1 h. The mixture was diluted with water (20 mL) and extracted with ethyl acetate (20 mL). The combined organic layers were washed with brine (3× 20 mL), dried over sodium sulfate, filtered, and concentrated in vacuo. The residue was purified via Purification Method 1 to afford N-(3,5-dichloro-4-(2,6-dioxopiperidin-3-yl)benzyl)-2-(1H-indol-5-yl)-2-methylpropanamide (47.32 mg, 99.1 μmol, 67% yield) as a white solid.

$^1$H NMR (400 MHZ, DMSO-$d_6$)>=11.01 (s, 1H), 10.95 (s, 1H), 7.83 (t, J=6.0 Hz, 1H), 7.51 (d, J=1.2 Hz, 1H), 7.37-7.28 (m, 2H), 7.18 (d, J=1.6 Hz, 1H), 7.09 (d, J=1.2 Hz, 1H), 7.02 (dd, J=1.6, 8.4 Hz, 1H), 6.39 (d, J=2.0 Hz, 1H), 4.53 (dd, J=5.6, 12.8 Hz, 1H), 4.18 (d, J=6.0 Hz, 2H), 2.84 (ddd, J=5.6, 14.0, 16.8 Hz, 1H), 2.56-2.53 (m, 1H), 2.39-2.24 (m, 1H), 1.91-1.79 (m, 1H), 1.52 (s, 6H). MS (ESI) m/z 472.2 $[M+H]^+$ Exemplary Compound 94

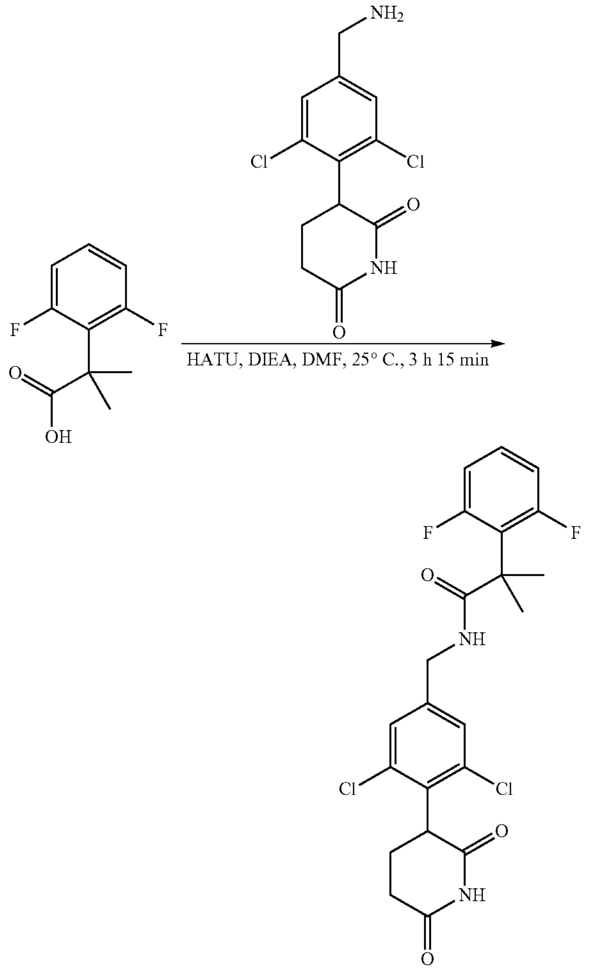

Step 1. To a solution of 2-(2,6-difluorophenyl)-2-methylpropanoic acid (50.0 mg, 250 μmol, 1.00 eq.) and N,N-diisopropylethylamine (100 mg, 774 μmol, 3.10 eq.) in dimethylformamide (4 mL) was added O-(7-Azabenzotriazol-1-yl)-N,N,N',N'-tetramethyluronium hexafluorophosphate (120 mg, 316 μmol, 1.26 eq.) at 0° C. The reaction was stirred at 25° C. for 15 min. Then 3-(4-(aminomethyl)-2,6-dichlorophenyl) piperidine-2,6-dione (75.0 mg, 261 μmol, 1.05 eq.) was added, and the reaction was stirred at 25° C. for 3 h. The reaction mixture was diluted with ethyl acetate (15 mL) and water (15 mL). The layers were separated, and the aqueous phase was extracted with ethyl acetate (15 mL). The combined organic layers were washed with saturated sodium bicarbonate solution (2×15 mL) and brine (20 mL), dried over anhydrous sodium sulfate, filtered, and concentrated in vacuo. The residue was purified via Purification Method 1 to afford N-(3,5-dichloro-4-(2,6-dioxopiperidin-3-yl)benzyl)-2-(2,6-difluorophenyl)-2-methylpropanamide (36.48 mg, 77.0 μmol, 31% yield) as a white solid.

$^1$H NMR (400 MHZ, DMSO-$d_6$) δ=10.96 (s, 1H), 8.14 (t, J=5.8 Hz, 1H), 7.40-7.33 (m, 1H), 7.32 (s, 1H), 7.25 (d, J=1.2 Hz, 1H), 7.09-6.97 (m, 2H), 4.57 (dd, J=5.6, 12.8 Hz, 1H), 4.27-4.17 (m, 2H), 2.94-2.78 (m, 1H), 2.59-2.52 (m, 1H), 2.39-2.28 (m, 1H), 1.96-1.83 (m, 1H), 1.55 (s, 6H). MS (ESI) m/z 469.1 $[M+H]^+$

Exemplary Compound 99

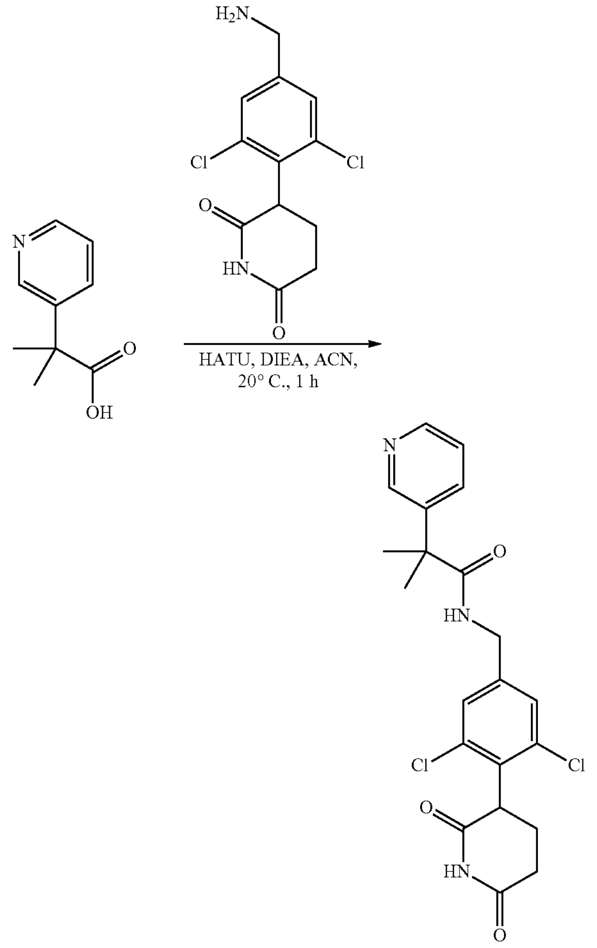

To a mixture of 2-methyl-2-(3-pyridyl) propanoic acid (50.0 mg, 0.30 mmol, 1.00 eq.), diisopropylethylamine (156 mg, 1.21 mmol, 4.00 eq.) and 2-(3H-[1,2,3]triazolo[4,5-b]pyridin-3-yl)-1,1,3,3-tetramethylisouronium hexafluorophosphate (V) (138 mg, 0.36 mmol, 1.20 eq.) in acetonitrile (4 mL) was added 3-(4-(aminomethyl)-2,6-dichlorophenyl) piperidine-2,6-dione hydrochloride (49.0 mg, 0.15 mmol, 0.50 eq.) in one portion at 20° C. The mixture was stirred at 20° C. for 1 h. The mixture was poured into saturated aqueous sodium bicarbonate (10 mL) and extracted with ethyl acetate (3×20 mL). The combined organic layers were washed with brine (50 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-methyl-2-(pyridin-3-yl) propanamide (45.8 mg, 0.10 mmol, 34% yield) as a white solid.

$^1$H NMR (400 MHZ, DMSO-$d_6$)>=10.95 (s, 1H), 8.57 (d, J=2.4 Hz, 1H), 8.46 (dd, J=1.6, 4.8 Hz, 1H), 8.15 (t, J=6.0 Hz, 1H), 7.68 (td, J=2.0, 8.0 Hz, 1H), 7.35 (dd, J=4.4, 8.0 Hz, 1H), 7.20 (s, 1H), 7.14 (s, 1H), 4.55 (dd, J=5.6, 12.8 Hz, 1H), 4.21 (d, J=6.0 Hz, 2H), 2.91-2.76 (m, 1H), 2.57-2.52 (m, 1H), 2.34-2.27 (m, 1H), 1.94-1.81 (m, 1H), 1.53 (s, 6H). MS (ESI) m/z 434.1/436.1 $[M+H]^+$

Exemplary Compound 106

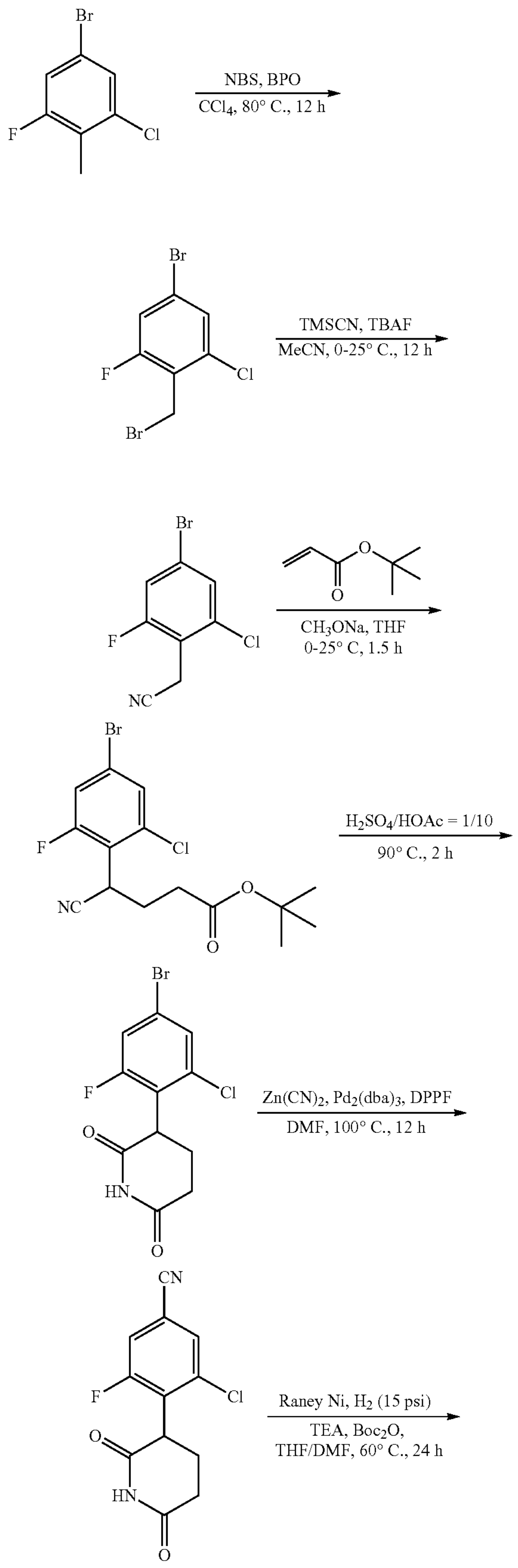

-continued

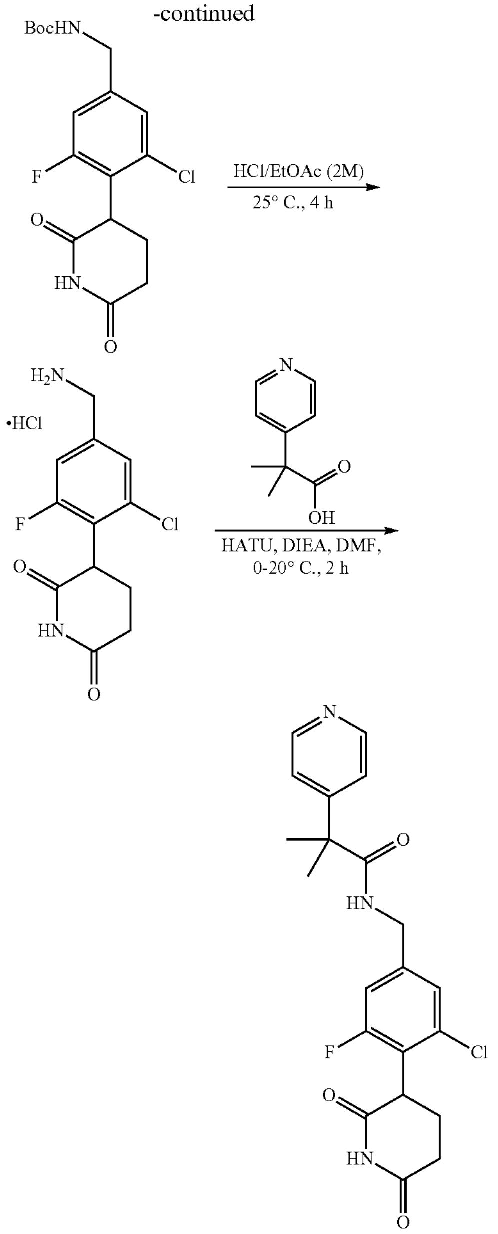

Step 1: To a solution of 5-bromo-1-chloro-3-fluoro-2-methylbenzene (8.00 g, 35.8 mmol, 1.00 eq.) in carbon tetrachloride (80 mL) were added N-bromosuccinimide (6.69 g, 37.6 mmol, 1.05 eq.) and benzoic peroxyanhydride (434 mg, 1.79 mmol, 0.05 eq.). The reaction was stirred at 80° C. under nitrogen atmosphere for 12 h. After cooling to room temperature, the mixture was concentrated under reduced pressure to give a residue. The residue was purified via Purification Method 2 to afford 5-bromo-2-(bromomethyl)-1-chloro-3-fluorobenzene (10.8 g, 33.9 mmol, 95% yield) as a yellow oil.

Step 2: To a solution of 5-bromo-2-(bromomethyl)-1-chloro-3-fluorobenzene (10.8 g, 35.7 mmol, 1.00 eq.) and TMSCN(5.37 g, 54.1 mmol, 1.52 eq.) in MeCN(100 mL) was added TBAF (1 M in THF, 53.6 mL, 1.50 eq.) at 0° C. The reaction was stirred at 25° C. for 12 h, then it was concentrated under reduced pressure to give a residue. The residue was purified via Purification Method 2 to afford the 2-(4-bromo-2-chloro-6-fluorophenyl) acetonitrile (8.20 g, 31.4 mmol, 88% yield) as a white solid.

Step 3: To a solution of 2-(4-bromo-2-chloro-6-fluorophenyl) acetonitrile (8.20 g, 33.0 mmol, 1.00 eq.) in THF (80 mL) were added tert-butyl acrylate (4.23 g, 33.0 mmol, 1.00 eq.) and sodium methoxide (178 mg, 3.30 mmol, 0.10 eq.) at 0° C. The reaction was stirred at 25° C. for 1.5 h. The mixture was diluted with water (150 mL) and extracted with ethyl acetate (3×50 mL). The combined organic layers were washed with brine (50 mL), dried over sodium sulfate, filtered, and concentrated under reduced pressure to afford tert-butyl 4-(4-bromo-2-chloro-6-fluorophenyl)-4-cyanobutanoate (11.4 g, 27.2 mmol, 82% yield) as a yellow oil.

Step 4: To a solution of tert-butyl 4-(4-bromo-2-chloro-6-fluorophenyl)-4-cyanobutanoate (14.2 g, 37.6 mmol, 1.00 eq.) in acetic acid (150 mL) was added sulfuric acid (15 mL). The reaction mixture stirred at 90° C. for 2 h. The mixture was cooled to room temperature and poured into ice water (300 mL). The resulting precipitate was filtered and washed with water (100 mL), then dried under vacuum to afford 3-(4-bromo-2-chloro-6-fluorophenyl) piperidine-2,6-dione (10.9 g, 32.3 mmol, 86% yield) as a white solid.

Step 5: To a solution of 3-(4-bromo-2-chloro-6-fluorophenyl) piperidine-2,6-dione (10.9 g, 34.0 mmol, 1.00 eq.) in DMF (100 mL) were added $Pd_2$ (dba) 3 (1.56 g, 1.70 mmol, 0.05 eq.), 1,1'-Bis(diphenylphosphino)ferrocene (943 mg, 1.70 mmol, 0.05 eq.) and zinc cyanide (6.08 g, 51.8 mmol, 1.52 eq.). The reaction was stirred at 100° C. for 12 h under nitrogen. The mixture was filtered, and the filtrate was poured into water (150 mL). The aqueous layer was extracted with ethyl acetate (3×50 mL). The combined organic layers were washed with water (100 mL) and brine (100 mL), dried over anhydrous sodium sulfate, filtered, and concentrated under reduced pressure to give a residue. The residue was triturated with ethyl acetate (15 mL) at 25° C. for 1 h to afford 3-chloro-4-(2,6-dioxopiperidin-3-yl)-5-fluorobenzonitrile (7.60 g, 25.7 mmol, 75% yield) as a brown solid.

Step 6: To a solution of 3-chloro-4-(2,6-dioxopiperidin-3-yl)-5-fluorobenzonitrile (3.80 g, 14.3 mmol, 1.00 eq.) in DMF (15 mL) and THF (15 mL) were added $Boc_2O$(6.22 g, 28.5 mmol, 2.00 eq.), TEA (2.16 g, 21.4 mmol, 1.50 eq.), and Raney-Ni (1 g). The reaction was stirred at 60° C. under hydrogen (15 psi) for 24 h. The mixture was filtered and diluted with water (100 mL) then extracted with ethyl acetate (3×50 mL). The combined organic layers were washed with water (50 mL) and brine (50 mL), dried over sodium sulfate, filtered, and concentrated under reduced pressure to give a residue. The residue was purified via Purification Method 2 to afford tert-butyl (3-chloro-4-(2,6-dioxopiperidin-3-yl)-5-fluorobenzyl) carbamate (7.40 g, 19.0 mmol, 66.5% yield) as a yellow oil.

Step 7: A solution of tert-butyl (3-chloro-4-(2,6-dioxopiperidin-3-yl)-5-fluorobenzyl) carbamate (7.40 g, 20.0 mmol, 1.00 eq.) in hydrogen chloride (2 M in ethyl acetate, 50 mL) was stirred at 25° C. for 4 h. The resulting precipitate was filtered to afford 3-(4- (aminomethyl)-2-chloro-6-fluorophenyl) piperidine-2,6-dione (5.03 g, 16.1 mmol, 80% yield) as a white solid.

$^1$H NMR (400 MHz, DMSO-$d_6$) δ=10.99 (s, 1H), 8.63 (s, 3H), 7.57 (s, 1H), 7.46 (d, J=10.8 Hz, 1H), 4.37-4.43 (m, 1H), 4.13-3.96 (m, 2H), 2.89-2.79 (m, 1H), 2.56-2.51 (m, 1H), 2.35-2.03 (m, 1H), 1.99-1.92 (m, 1H). MS (ESI) m/z 271.0 [M+H]$^+$

Step 8. To a solution of 2-methyl-2-(pyridin-4-yl) propanoic acid (80.0 mg, 485 μmol, 1.40 eq.) in dimethylformamide (3 mL) was added N,N-diisopropylethylamine (180 μL, 1.00 mmol, 3.00 eq.). O-(7-azabenzotriazol-1-yl)-N,N,N,N-tetramethyluroniumhexafluorophosphate (160 mg, 422 μmol, 1.20 eq.) was added to the reaction mixture at 0° C. 3-(4-(aminomethyl)-2-chloro-6-fluorophenyl) piperidine-2,6-dione (110 mg, 347 μmol, 1 eq.) was added, and the reaction was stirred at 20° C. for 2 h. The mixture was diluted with water (15 mL) and extracted with ethyl acetate (4×20 mL). The combined organic extracts were washed with saturated sodium bicarbonate solution (2× 20 mL), dried over sodium sulfate, filtered, and concentrated under reduced pressure. The residue was purified via Purification Method I to afford N-(3-chloro-4-(2,6-dioxopiperidin-3-yl)-5-fluorobenzyl)-2-methyl-2-(pyridin-4-yl)-propanamide (38.9 mg, 92.2 μmol, 27% yield) as a white solid.

$^1$H NMR (400 MHZ, DMSO-$d_6$) δ=10.96 (s, 1H), 8.58-8.44 (m, 2H), 8.15 (t, J=6.0 Hz, 1H), 7.34-7.24 (m, 2H), 7.05 (s, 1H), 6.94 (d, J=11.2 Hz, 1H), 4.33 (dd, J=4.8, 12.4 Hz, 1H), 4.22 (d, J=6.0 Hz, 2H), 2.82 (s, 1H), 2.54 (d, J=2.4 Hz, 1H), 2.20-2.05 (m, 1H), 2.00-1.86 (m, 1H), 1.49 (s, 6H). $^1$H NMR (400 MHZ, MeOH-$d_6$) δ=8.50 (d, J=6.0 Hz, 2H), 7.44-7.37 (m, 2H), 7.08 (s, 1H), 6.92 (d, J=10.8 Hz, 1H), 4.39 (dd, J=5.2, 12.4 Hz, 1H), 4.33-4.29 (m, 2H), 2.88-2.76 (m, 1H), 2.70 (br d, J=2.8 Hz, 1H), 2.42-2.22 (m, 1H), 2.13-2.01 (m, 1H), 1.59 (s, 6H). MS (ESI) m/z 418.1 [M+H]$^+$

Exemplary Compound 107

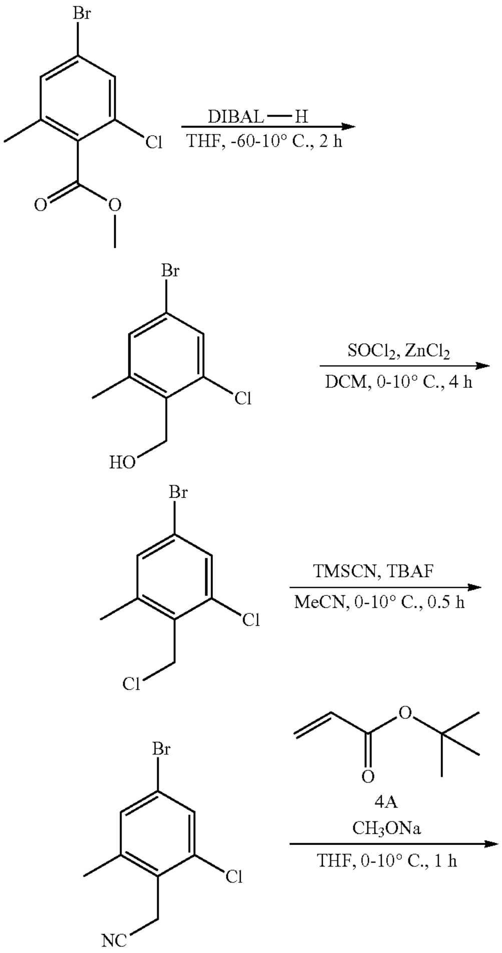

-continued

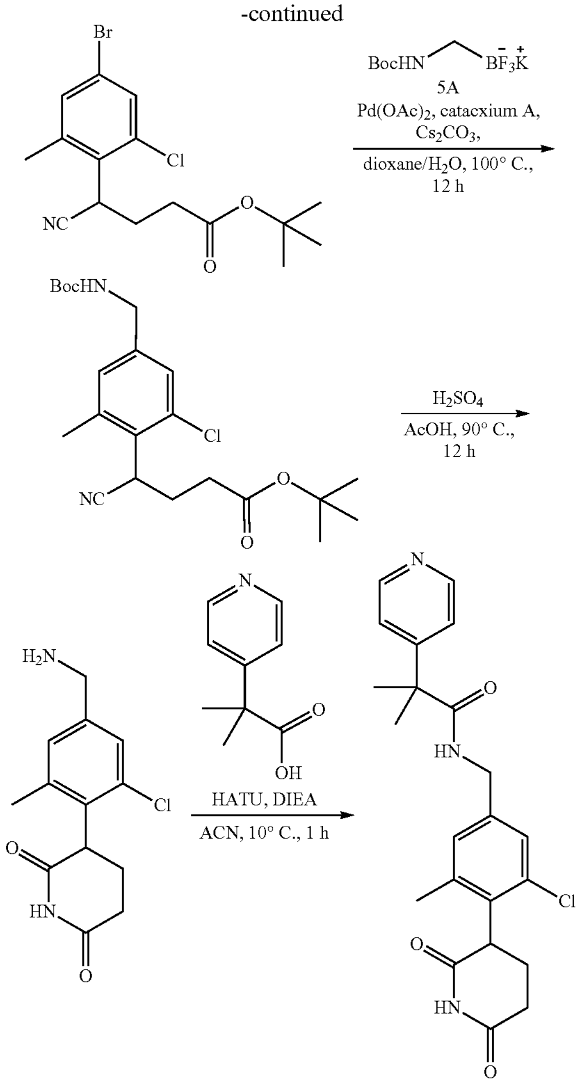

Step 1: To a solution of methyl 4-bromo-2-chloro-6-methylbenzoate (2.00 g, 7.59 mmol, 1.00 eq.) in THF (40 mL) was added a solution of DIBAL-H (1 M in toluene, 22.8 mL, 3.00 eq.) dropwise at −60° C. The reaction was stirred at −60° C. for 30 min, then warmed to 10° C., and stirred for 1.5 h. The reaction was cooled to 0° C., and quenched with water (1 mL) followed by 5 N aqueous sodium hydroxide (2 mL). The mixture was filtered, and the filtrate was concentrated under reduced pressure to afford (4-bromo-2-chloro-6-methylphenyl)-methanol (1.75 g, 7.43 mmol, 97% yield) as a light-yellow solid.

Step 2: To a solution of (4-bromo-2-chloro-6-methylphenyl) methanol (1.75 g, 7.43 mmol, 1.00 eq.) $ZnCl_2$ (50.6 mg, 0.372 mmol, 0.05 eq.) in DCM (20 mL) was added $SOCl_2$ (1.77 g, 14.9 mmol, 2.00 eq.) dropwise at 0° C. The reaction was stirred at 10° C. for 4 h, then it was poured into water (20 mL). The aqueous layer was extracted with ethyl acetate (3× 20 mL). The combined organic layers were washed with brine (30 mL), dried over anhydrous sodium sulfate, filtered, and concentrated under reduced pressure to afford 5-bromo-1-chloro-2-(chloromethyl)-3-methylbenzene (1.80 g, 7.09 mmol, 95% yield) as a brown oil.

Step 3: To a solution of 5-bromo-1-chloro-2-(chloromethyl)-3-methylbenzene (1.80 g, 7.09 mmol, 1.00 eq.) and TMSCN(1.05 g, 10.6 mmol, 1.50 eq.) in MeCN(20 mL) was added TBAF (1 M in tetrahydrofuran, 10.6 mL, 1.50 eq.) dropwise at 0° C. The reaction was stirred at 10° C. for 30 min, then it was concentrated under reduced pressure to give a residue. The residue was purified via Purification Method 2 to afford 2-(4-bromo-2-chloro-6-methylphenyl)-acetonitrile (1.65 g, 6.75 mmol, 95% yield) as a white solid.

Step 4: To a solution of 2-(4-bromo-2-chloro-6-methylphenyl) acetonitrile (500 mg, 2.04 mmol, 1.00 eq.) and tert-butyl prop-2-enoate (262.09 mg, 2.04 mmol, 1.00 eq.) in THF (10 mL) was added sodium methoxide (11.1 mg, 0.204 mmol, 0.10 eq.) in one portion at 0° C. The reaction was stirred at 10° C. for 1 h, then it was poured into water (10 mL). The aqueous layer was extracted with ethyl acetate (3×10 mL). The combined organic layers were washed with brine (10 mL), dried over anhydrous sodium sulfate, filtered, and concentrated under reduced pressure to give a residue. The residue was purified via Purification Method 2 then Purification Method I to afford tert-butyl 4-(4-bromo-2-chloro-6-methylphenyl)-4-cyanobutanoate (330 mg, 0.885 mmol, 43% yield) as a light-yellow oil.

Step 5: To a mixture of tert-butyl 4-(4-bromo-2-chloro-6-methylphenyl)-4-cyanobutanoate (500 mg, 1.34 mmol, 1.00 eq.) and potassium (((tert-butoxycarbonyl)amino) methyl)trifluoroborate (477 mg, 2.01 mmol, 1.50 eq.) in dioxane (15 mL) and water (1.5 mL) were added caesium carbonate (1.31 g, 4.02 mmol, 3.00 eq.), Pd(OAc) 2 (60.2 mg, 0.268 mmol, 0.20 eq.) and di (1-adamantyl)-n-butylphosphine hydriodide (96.2 mg, 0.268 mmol, 0.20 eq.) in one portion. The reaction was stirred at 100° C. under nitrogen. After 12 h, it was cooled to 20° C., and poured into water (20 mL). The aqueous layer was extracted with ethyl acetate (3×20 mL). The combined organic layers were washed with brine (50 mL), dried over anhydrous sodium sulfate, filtered, and concentrated under reduced pressure to give a residue. The residue was purified via Purification Method 1 to afford tert-butyl 4-(4-(((tert-butoxycarbonyl) amino)methyl)-2-chloro-6-methyl-phenyl)-4-cyanobutanoate (245 mg, 0.579 mmol, 43% yield) as a colourless oil.

Step 6: To a solution of tert-butyl 4-(4-(((tert-butoxycarbonyl)amino)methyl)-2-chloro-6-methylphenyl)-4-cyanobutanoate (240 mg, 0.567 mmol, 1.00 eq.) in acetic acid (40 mL) was added sulfuric acid (557 mg, 5.67 mmol, 10.0 eq.) dropwise. The reaction was stirred at 90° C. for 12 h. The mixture was cooled to 20° C., and concentrated under reduced pressure to give a residue. The residue was purified via Purification Method 1 to afford 3-(4-(aminomethyl)-2-chloro-6-methylphenyl) piperidine-2,6-dione (115 mg, 0.302 mmol, 53% yield) as a white solid.

$^1$H NMR (400 MHZ, DMSO-$d_6$)>=10.89 (s, 1H), 8.31-8.06 (m, 2H), 7.40 (s, 1H), 7.29 (s, 1H), 4.28 (dd, J=5.6, 12.8 Hz, 1H), 3.99 (s, 2H), 2.88-2.78 (m, 1H), 2.45-2.35 (m, 3H), 2.33 (d, J=1.6 Hz, 1H), 2.22-2.15 (m, 1H), 1.96-1.86 (m, 1H).

Step 7. To a solution of 2-methyl-2-(4-pyridyl) propanoic acid (47.7 mg, 0.289 mmol, 1.10 eq.), diisopropylethylamine (136 mg, 1.05 mmol, 4.00 eq.) and 2-(3H-[1,2,3]triazolo [4,5-b]pyridin-3-yl)-1,1,3,3-tetramethylisouronium hexafluorophosphate (V) (120 mg, 0.315 mmol, 1.20 eq.) in acetonitrile (5 mL) was added 3-(4-(aminomethyl)-2-chloro-6-methylphenyl) piperidine-2,6-dione (100 mg, 0.263 mmol, 1.00 eq.) in one portion at 10° C. The mixture was stirred at 10° C. for 1 h. The mixture was poured into saturated aqueous sodium bicarbonate (20 mL) and extracted with ethyl acetate (5× 20 mL). The combined organic layers were washed with brine (50 mL), dried over anhydrous sodium sulfate, filtered, and the filtrate was concentrated under reduced pressure. The residue was purified via Purification Method 1 to afford N-(3-chloro-4-(2,6-dioxopiperidin-3-yl)-5-methylbenzyl)-2-methyl-2-(pyridin-4-yl) propanamide (27.9 mg, 0.0667 mmol, 27% yield) as a white solid.

$^1$H NMR (400 MHZ, DMSO-$d_6$) δ=10.97-10.80 (m, 1H), 8.85 (d, J=6.8 Hz, 2H), 8.34 (t, J=6.0 Hz, 1H), 7.93 (d, J=6.4 Hz, 2H), 7.05-6.88 (m, 2H), 4.51 (dd, J=5.5, 13.0 Hz, 1H), 4.19 (d, J=5.6 Hz, 3H), 2.86-2.77 (m, 1H), 2.56-2.53 (m, 1H), 2.32 (s, 3H), 2.10 (s, 1H), 1.94-1.81 (m, 1H), 1.60 (s, 6H). $^1$H NMR (400 MHZ, DMSO-$d_6$, T=80° C.) δ=10.55 (s, 1H), 8.74 (d, J=6.8 Hz, 2H), 8.12-8.03 (m, 1H), 7.79 (d, J=6.4 Hz, 2H), 7.03 (s, 1H), 6.96 (s, 1H), 4.22 (d, J=6.0 Hz, 3H), 2.81 (ddd, J=6.0, 13.6, 16.8 Hz, 1H), 2.57 (s, 1H), 2.42-2.14 (m, 4H), 1.97-1.86 (m, 1H), 1.60 (s, 6H). MS (ESI) m/z 414.2, 416.2 $[M+H]^+$ Exemplary Compound 120

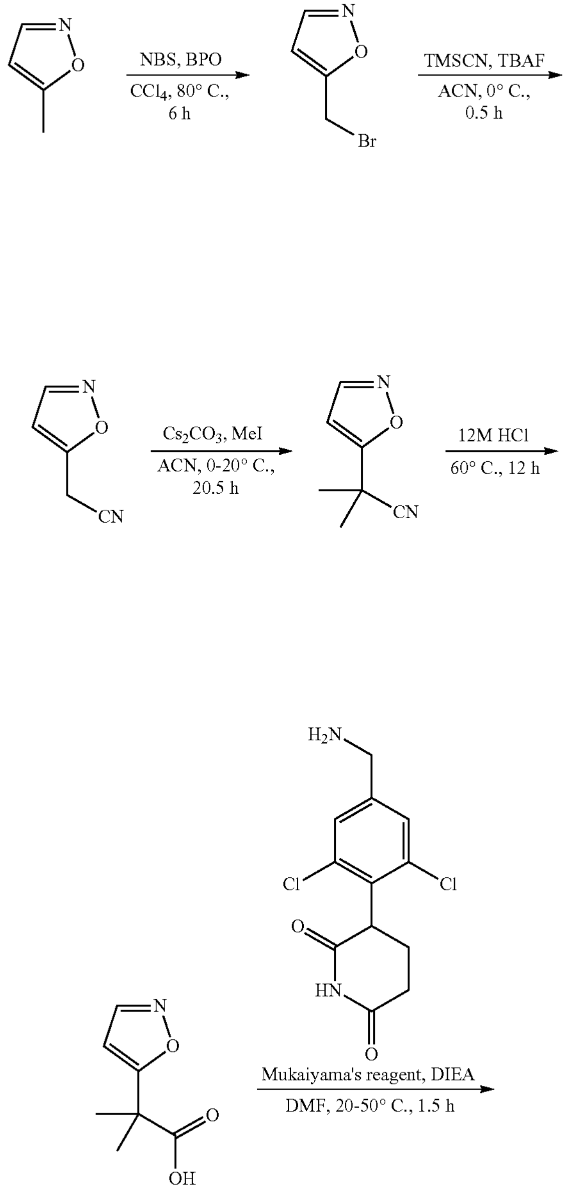

-continued

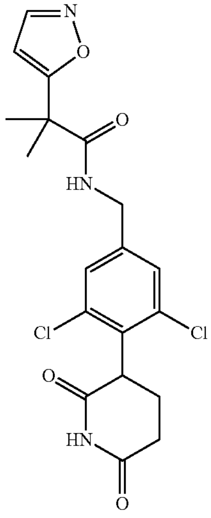

Step 1. To a solution of 5-methylisoxazole (5.00 g, 60.2 mmol, 1.00 eq.) in perchloromethane (125 mL) were added benzoyl benzenecarboperoxoate (1.46 g, 6.02 mmol, 0.10 eq.) and 1-bromopyrrolidine-2,5-dione (10.7 g, 60.2 mmol, 1.00 eq.) in portions at 20° C. The mixture was stirred at 80° C. for 6 h. The mixture was cooled to 20° C., and filtered, the filtrate was concentrated under reduced pressure. The residue was purified via Purification Method 2 to afford 5-(bromomethyl) isoxazole (5.20 g, 32.1 mmol, 53% yield) as a light-yellow oil.

Step 2. To a solution of 5-(bromomethyl) isoxazole (5.00 g, 30.9 mmol, 1.00 eq.) and trimethylsilyl cyanide (4.59 g, 46.3 mmol, 1.50 eq.) in acetonitrile (50 mL) was added tetrabutylammonium fluoride (1 M in tetrahydrofuran, 46.3 mL, 1.50 eq.) dropwise at 0° C. The solution was stirred at 0° C. under nitrogen atmosphere for 0.5 h. The mixture was poured into water (100 mL) and extracted with ethyl acetate (3×50 mL). The combined organic layers were washed with brine (30 mL), dried over anhydrous sodium sulfate, filtered, and the filtrate was concentrated under reduced pressure. The residue was purified via Purification Method 2 to afford 2-isoxazol-5-ylacetonitrile (1.50 g, 13.9 mmol, 44% yield) as a light-yellow oil.

Step 3. To a solution of 2-isoxazol-5-ylacetonitrile (500 mg, 4.63 mmol, 1.00 eq.) in acetonitrile (20 mL) was added caesium carbonate (4.52 g, 13.9 mmol, 3.00 eq.) in portions at 20° C. The mixture was stirred at 20° C. for 0.5 h, then it was cooled to 0° C., and iodomethane (6.57 g, 46.3 mmol, 10.0 eq.) was added dropwise. The mixture was stirred at 20° C. for 20 h. The mixture was filtered, and the filtrate was concentrated under reduced pressure. The residue was purified via Purification Method 2 to afford 2-isoxazol-5-yl-2-methyl-propanenitrile (560 mg, 4.11 mmol, 88% yield) as a colourless oil.

Step 4. A mixture of 2-isoxazol-5-yl-2-methyl-propanenitrile (300 mg, 2.20 mmol, 1.00 eq.) in concentrated hydrochloric acid (5 mL, 36% purity) was stirred at 60° C. for 12 h. The mixture was poured into water (30 mL) and extracted with dichloromethane (3×30 mL). The combined organic layers were washed with brine (10 mL), dried over anhydrous sodium sulfate, filtered, and the filtrate was concentrated under reduced pressure to give 2-isoxazol-5-yl-2-methyl-propanoic acid (200 mg, 1.28 mmol, 57% yield) as a white solid.

Step 5. To a mixture of 2-isoxazol-5-yl-2-methyl-propanoic acid (40.0 mg, 258 µmol, 1.00 eq.) and 2-chloro-1-methyl-pyridin-1-ium iodide (79.0 mg, 309 µmol, 1.20 eq.) in dimethylformamide (1.5 mL) was added diisopropylethylamine (133 mg, 1.03 mmol, 4.00 eq.) dropwise at 20° C. The mixture was stirred at 20° C. for 0.5 h, then 3-(4-(aminomethyl)-2,6-dichlorophenyl) piperidine-2,6-dione hydrochloride (83.4 mg, 258 µmol, 1.00 eq.) was added. The mixture was stirred at 50° C. for 1 h, then it was cooled to 20° C., and poured into water (10 mL). The mixture was extracted with ethyl acetate (3× 10 mL). The combined organic layers were washed with brine (10 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-(isoxazol-5-yl)-2-methylpropanamide (78.5 mg, 185 µmol, 71% yield) as a white solid.

$^1$H NMR (400 MHZ, DMSO-d$_6$) δ=10.96 (s, 1H), 8.51 (d, J=2.0 Hz, 1H), 8.26 (t, J=5.6 Hz, 1H), 7.26 (s, 1H), 7.20 (d, J=1.2 Hz, 1H), 6.40 (d, J=1.6 Hz, 1H), 4.56 (dd, J=5.6, 12.8 Hz, 1H), 4.23 (d, J=6.0 Hz, 2H), 2.91-2.78 (m, 1H), 2.58-2.51 (m, 1H), 2.39-2.29 (m, 1H), 1.95-1.83 (m, 1H), 1.54 (s, 6H). MS (ESI) m/z 424.2 [M+H]$^+$

Exemplary Compound 126

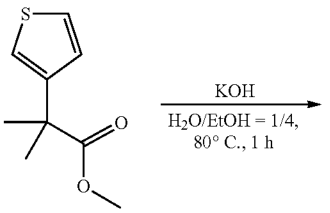

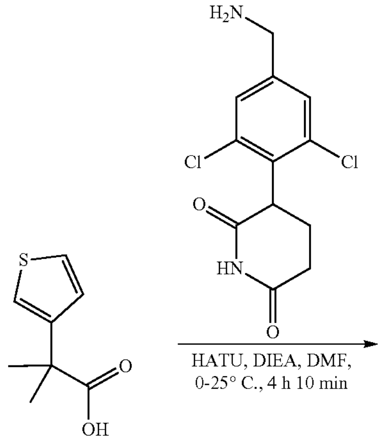

-continued

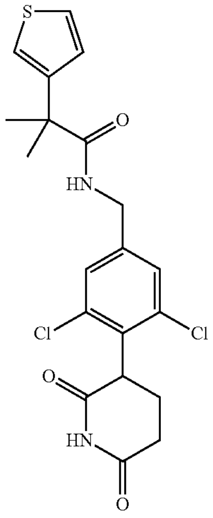

Step 1. To a solution of methyl 2-methyl-2-(thiophen-3-yl) propanoate (90.0 mg, 488 µmol, 1.00 eq.) in ethanol (4 mL) was added a solution of potassium hydroxide (36.0 mg, 642 µmol, 1.31 eq.) in water (1 mL). The reaction was stirred at 80° C. for 1 h. After cooling to room temperature, the mixture was concentrated in vacuo. The residue was diluted with ethyl acetate (10 mL) and water (10 mL). The layers were separated, and the pH of aqueous phase was acidified to 5 with 1M hydrochloric acid. The aqueous phase was extracted with ethyl acetate (3×10 mL). The combined organic layers were washed with brine (30 mL) and dried over anhydrous sodium sulfate, filtered, and concentrated in vacuo to afford 2-methyl-2-(thiophen-3-yl) propanoic acid (30.0 mg, 176 µmol, 36% yield) as a colourless solid.

Step 2. To a solution of 2-methyl-2-(thiophen-3-yl) propanoic acid (25.0 mg, 147 µmol, 1.00 eq.) and N,N-diisopropylethylamine (57.0 mg, 441 µmol, 3.00 eq.) in dimethylformamide (2.5 mL) was added O-(7-Azabenzotriazol-1-yl)-N,N,N',N'-tetramethyluronium Hexafluorophosphate (60.0 mg, 158 µmol, 1.07 eq.) at 0° C. The reaction was stirred at 0° C. for 10 min, then 3-(4-(aminomethyl)-2,6-dichlorophenyl) piperidine-2,6-dione (40.0 mg, 139 µmol, 0.95 eq.) was added to the mixture. The reaction was stirred at 20° C. for 4 h. The reaction mixture was diluted with ethyl acetate (10 mL) and water (10 mL). The layers were separated, and the aqueous phase was extracted with ethyl acetate (2×10 mL). The combined organic layers were washed with saturated sodium bicarbonate solution (2×20 mL) and brine (20 mL), dried over anhydrous sodium sulfate, filtered, and concentrated in vacuo. The residue was purified via Purification Method I to afford N-(3,5-dichloro-4-(2,6-dioxopiperidin-3-yl)benzyl)-2-methyl-2-(thiophen-3-yl) propanamide (24.72 mg, 55.7 µmol, 38% yield) as a white solid.

Exemplary Compound 127

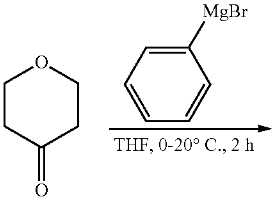

-continued

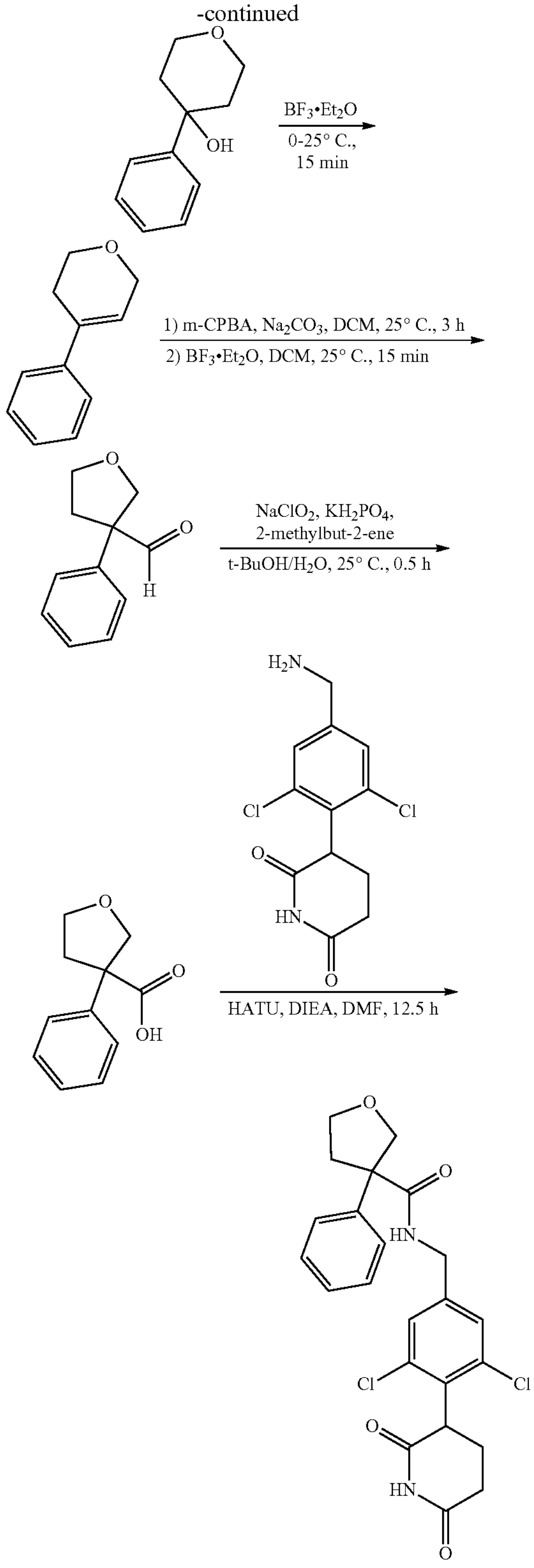

Step 1. To a solution of tetrahydro-4H-pyran-4-one (3.00 g, 30.0 mmol, 1.00 eq.) in tetrahydrofuran (30 mL) was added phenylmagnesium bromide (3 M in tetrahydrofuran, 18 mL, 1.80 eq.) at 0° C. under nitrogen. The mixture was stirred at 0° C. under nitrogen for 1 h, then at 20° C. for 1 h. The reaction was quenched with saturated ammonium chloride (75 mL), and the mixture was extracted with ethyl acetate (3x30 mL). The combined organic extracts were washed with brine (25 mL), dried over sodium sulfate, filtered, and concentrated under reduced pressure to give a residue. The residue was purified via Purification Method 2 to afford 4-phenyltetrahydro-2H-pyran-4-ol (2.45 g, 13.0 mmol, 44% yield) as a white solid.

Step 2. A mixture of 4-phenyltetrahydro-2H-pyran-4-ol (2.20 g, 12.3 mmol, 1.00 eq.) in boron trifluoride diethyl etherate (5 mL) was stirred at 25° C. for 15 min. The reaction mixture was quenched with saturated sodium bicarbonate solution (50 mL) and extracted with ethyl acetate (3x 35 mL). The combined organic layers were dried over sodium sulfate, filtered, and concentrated under reduced pressure. The residue was purified via Purification Method 2 to afford 4-phenyl-3,6-dihydro-2H-pyran (1.70 g, 10.1 mmol, 82% yield) as a white solid.

Step 3. To a solution of 4-phenyl-3,6-dihydro-2H-pyran (1.00 g, 6.24 mmol, 1.00 eq.) and sodium carbonate (1.65 g, 15.6 mmol, 2.50 eq.) in dichloromethane (15 mL) was added 3-chlorobenzoperoxoic acid (2.53 g, 12.5 mmol, 85% purity, 2.00 eq.). The mixture was stirred at 25° C. for 3 h. The reaction was quenched with sodium carbonate aqueous solution (40 mL) at 25° C., and then extracted with methylene chloride (25 mL). The combined organic layers were washed with water (15 mL), dried over sodium sulfate, filtered, and concentrated under reduced pressure to give a residue. Boron trifluoride diethyl etherate (1.15 g, 8.13 mmol, 1.30 eq.) was added dropwise to the solution of the residue in dichloromethane (15 mL) at 20° C., the mixture was stirred at 25° C. for 15 min. The reaction mixture was quenched with saturated sodium bicarbonate aqueous solution (40 mL) at 25° C., and then extracted with methylene chloride (30 mL). The combined organic layers were washed with water (15 mL), dried over sodium sulfate, filtered, and concentrated under reduced pressure. The residue was purified via Purification Method 2 to afford 3-phenyltetrahydrofuran-3-carbaldehyde (471 mg, 2.54 mmol, 41% yield) as a colourless oil.

Step 4. To a solution of 3-phenyltetrahydrofuran-3-carbaldehyde (471 mg, 2.67 mmol, 1.00 eq.) and 2-methyl-2-butene (265 mg, 3.78 mmol, 1.41 eq.) in 2-methylpropan-2-ol (5 mL) was added a solution of potassium dihydrogen phosphate (909 mg, 6.68 mmol, 2.50 eq.) and sodium chlorite (725 mg, 8.02 mmol, 3.00 eq.) in water (3 mL). The mixture was stirred at 25° C. for 30 min, then it was diluted with water (50 mL) and extracted with ethyl acetate (3'30 mL). The combined organic layers were washed with brine (20 mL), dried over sodium sulfate, filtered, and concentrated under reduced pressure to give 3-phenyltetrahydrofuran-3-carboxylic acid (531 mg, crude) as a white solid.

Step 5. To a solution of 3-phenyltetrahydrofuran-3-carboxylic acid (71.3 mg, 371 μmol, 1.50 eq.) in N,N-dimethylformamide (3 mL) were added O-(7-azabenzotriazol-1-yl)-N,N,N',N'-tetramethyluronium hexafluorophosphate (113 mg, 297 μmol, 1.20 eq.) and N,N-diisopropylethylamine (63.9 mg, 494 μmol, 2.00 eq.). The mixture was stirred at 20° C. for 30 min, then 3-(4-(aminomethyl)-2,6-dichlorophenyl) piperidine-2,6-dione hydrochloride (80.0 mg, 247 μmol, 1.00 eq.) was added. The reaction was stirred at 20° C. for 12 h. The mixture was diluted with water (15 mL) and extracted with ethyl acetate (3'10 mL). The combined organic layers were washed with water (10 mL) and brine (10 mL), dried over sodium sulfate, filtered, and concentrated under reduced pressure. The residue was purified via Purification Method I to afford N-(3,5-dichloro-4-(2,6-dioxopiperidin-3-yl)benzyl)-3-phenyltetrahydrofuran-3-carboxamide (66.7 mg, 143.11 μmol, 58% yield) as a white solid.

$^1$H NMR (400 MHZ, DMSO-$d_6$) δ=10.95 (s, 1H), 8.42 (t, J=6.0 Hz, 1H), 7.38-7.27 (m, 5H), 7.10 (s, 1H), 7.02 (s, 1H), 4.58-4.50 (m, 2H), 4.22 (d, J=6.0 Hz, 2H), 3.88-3.82 (m, 1H), 3.81-3.74 (m, 2H), 2.93-2.79 (m, 2H), 2.53 (s, 1H), 2.37-2.26 (m, 1H), 2.24-2.17 (m, 1H), 1.89-1.83 (m, 1H). MS (ESI) m/z 461.0 $[M+H]^+$

Exemplary Compound 128

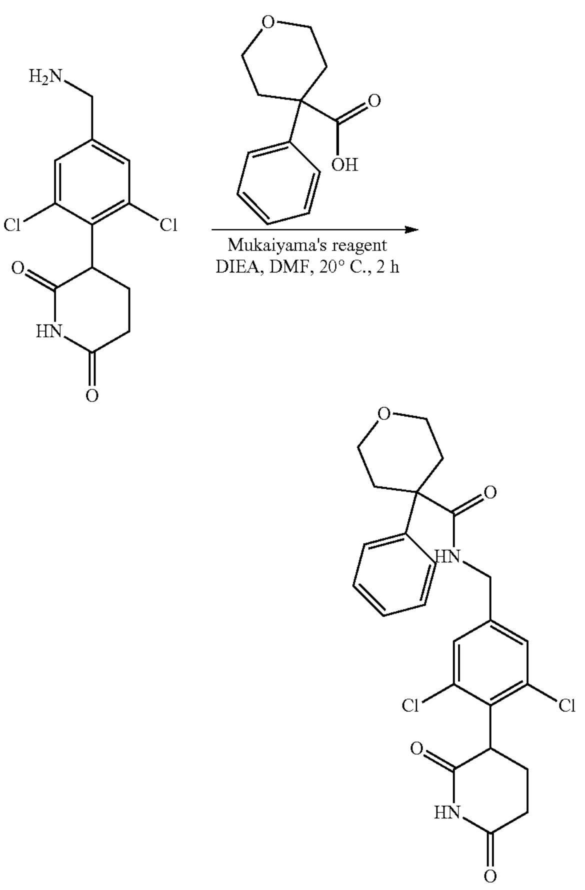

Step 1. To a solution of 4-phenyltetrahydropyran-4-carboxylic acid (76.5 mg, 371 μmol, 1.20 eq.) in dimethyl formamide (3.00 mL) were added N,N-diisopropylethylamine (200 mg, 1.55 mmol, 269 μL, 5.00 eq.) and 2-chloro-1-methyl-pyridin-1-ium iodide (94.7 mg, 371 μmol, 1.20 eq.). The reaction was stirred at 20° C. for 30 min, then 3-[4-(aminomethyl)-2,6-dichloro-phenyl]piperidine-2,6-dione hydrochloride (100 mg, 309 μmol, 1.00 eq.) was added. The reaction was stirred at 20° C. for 1.5 h. The mixture was diluted with water (10 mL) and extracted with ethyl acetate (10 mL). The combined organic layers were washed with water (2×10 mL) and brine (10 mL), dried over sodium sulfate, filtered, and concentrated under reduced pressure. The residue was purified via Purification Method 1 to afford N-(3,5-dichloro-4-(2,6-dioxopiperidin-3-yl)benzyl)-4-phenyltetrahydro-2H-pyran-4-carboxamide (65.63 mg, 137 μmol, 44% yield) as a white solid.

$^1$H NMR (400 MHZ, DMSO-$d_6$, T=80° C.) δ=10.67 (br s, 1H), 8.05 (t, J=5.6 Hz, 1H), 7.40-7.34 (m, 4H), 7.30-7.25 (m, 1H), 7.10-7.04 (m, 2H), 4.54-4.50 (dd, J=5.6, 12.8 Hz, 1H), 4.26-4.25 (d, J=6.0 Hz, 2H), 3.79-3.74 (td, J=4.0, 11.6 Hz, 2H), 3.56-3.51 (t, J=10.8 Hz, 2H), 2.88-2.79 (ddd, J=5.6, 14.0, 16.8 Hz, 1H), 2.59-2.54 (m, 1H), 2.46 (m, 2H), 2.42-2.31 (dq, J=4.4, 13.2 Hz, 1H), 1.99-1.89 (m, 3H). MS (ESI) m/z 475.2 $[M+H]^+$ Exemplary Compound 130

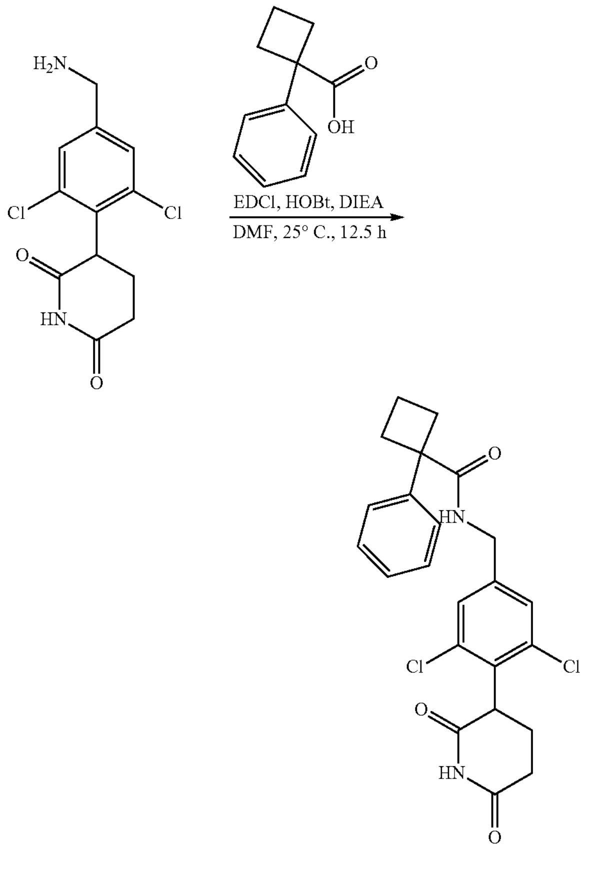

Step 1. To a mixture of 1-phenylcyclobutane-1-carboxylic acid (52.2 mg, 296 μmol, 1.20 eq.), $N^1$-((ethylimino)-methylene)-$N^3$,$N^3$-dimethylpropane-1,3-diamine hydrochloride (56.8 mg, 296 μmol, 1.20 eq.) and 1H-benzo[d][1,2,3]triazol-1-ol (40.1 mg, 296 μmol, 1.20 eq.) in dimethyl formamide (2 mL) was added diisopropylethylamine (159 mg, 1.24 mmol, 5.00 eq.) dropwise at 25° C. The reaction was stirred at 25° C. for 0.5 h, then 3-(4-(aminomethyl)-2,6-dichlorophenyl) piperidine-2,6-dione (80.0 mg, 247 μmol, 1.00 eq., hydrochloride) was added. The reaction was stirred at 25° C. for 12 h. The mixture was poured into water (10 mL) and extracted with ethyl acetate (3×10 mL). The combined organic layers were washed with brine (10 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-1-phenylcyclobutane-1-carboxamide (55.5 mg, 124 μmol, 50% yield) as a white solid.

$^1$H NMR (400 MHZ, DMSO-$d_6$) δ=10.95 (s, 1H), 8.26 (t, J=6.0 Hz, 1H), 7.35 (d, J=4.4 Hz, 4H), 7.28-7.22 (m, 1H), 7.07 (s, 1H), 6.99 (d, J=0.8 Hz, 1H), 4.52 (dd, J=5.6, 12.8 Hz, 1H), 4.20 (d, J=6.0 Hz, 2H), 2.97-2.71 (m, 3H), 2.59-2.52 (m, 1H), 2.43-2.23 (m, 3H), 1.88-1.72 (m, 3H). MS (ESI) m/z 445.1 $[M+1]^+$

Exemplary Compound 131

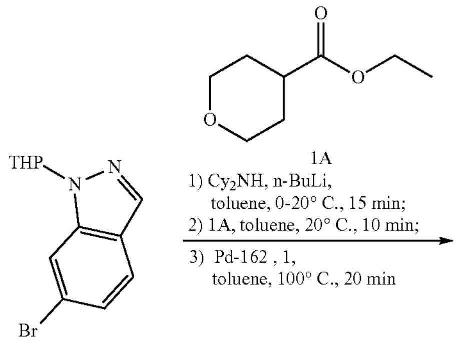

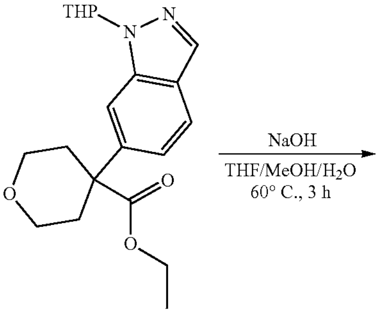

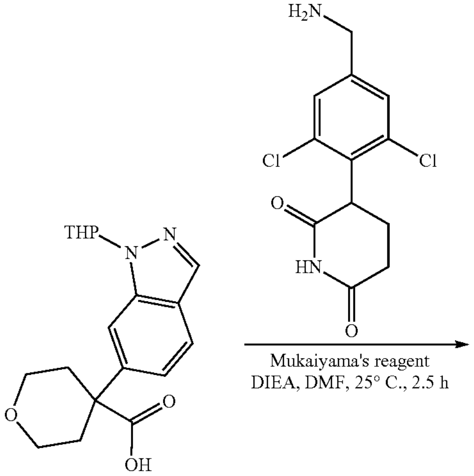

-continued

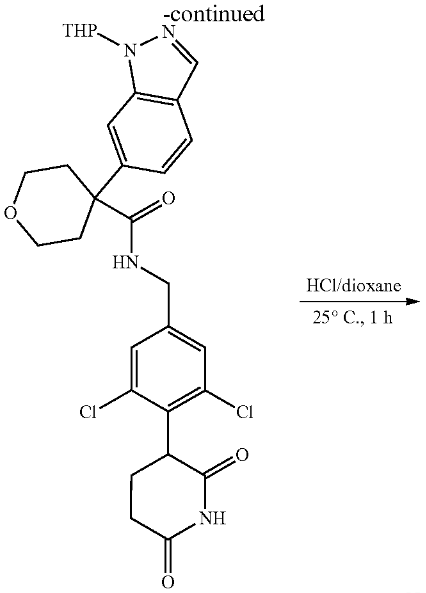

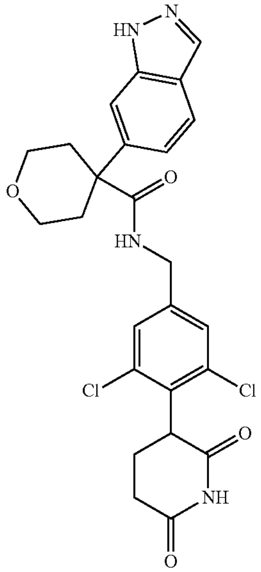

Step 1. To a solution of N-cyclohexylcyclohexanamine (1.10 g, 6.05 mmol, 1.20 mL, 1.70 eq.) in toluene (10.0 mL) was added n-butyllithium (2.50 M, 2.42 mL, 1.70 eq.) at 0° C. under nitrogen atmosphere. The mixture was stirred at 20° C. for 15 min, then ethyl tetrahydro-2H-pyran-4-carboxylate (900 mg, 5.69 mmol, 1.60 eq.) was added. The reaction was stirred at 20° C. for 10 min. Then chloro (crotyl) (tri-tert-butylphosphine) palladium (II) (129 mg, 355 μmol, 0.100 eq.) and 6-bromo-1-(tetrahydro-2H-pyran-2-yl)-1H-indazole (1.00 g, 3.56 mmol, 1.00 eq.) were added, and the reaction was stirred at 100° C. under nitrogen atmosphere for 20 min. The mixture was quenched with water (20.0 mL), extracted with ethyl acetate (3× 20.0 mL), washed with brine (3× 20.0 mL), and dried over anhydrous sodium sulfate, filtered, and concentrated under reduced pressure to give a residue. The residue was purified via Purification Method 2 to afford ethyl 4-(1-(tetrahydro-2H-pyran-2-yl)-1H-indazol-6-yl)tetrahydro-2H-pyran-4-carboxylate (863 mg, 2.41 mmol, 67.6% yield) as a yellow oil.

Step 2. To a solution of ethyl 4-(1-(tetrahydro-2H-pyran-2-yl)-1H-indazol-6-yl)tetrahydro-2H-pyran-4-carboxylate (763 mg, 2.13 mmol, 1.00 eq.) in methanol (3.00 mL), water (3.00 mL) and tetrahydrofuran (3.00 mL) was added sodium hydroxide (425 mg, 10.6 mmol, 232 μL, 5.00 eq.). The mixture was stirred at 60° C. for 3 h. The pH was adjusted to 2 with 1M hydrochloric acid.

The resulting precipitate was filtered and dried under vacuum to afford 4-(1-(tetrahydro-2H-pyran-2-yl)-1H-indazol-6-yl)tetrahydro-2H-pyran-4-carboxylic acid (703 mg, 2.13 mmol, 99.9% yield) as a brown solid.

Step 3. To a solution of 4-(1-(tetrahydro-2H-pyran-2-yl)-1H-indazol-6-yl)tetrahydro-2HI-pyran-4-carboxylic acid (207 mg, 626 μmol, 1.00 eq.) in N,N-dimethylformamide (3.00 mL) was added 2-chloro-1-methylpyridinium; iodide (192 mg, 752 μmol, 1.20 eq.) and N,N-diisopropylethylamine (243 mg, 1.88 mmol, 327 μL, 3.00 eq.). The reaction was stirred at 0° C. for 0.5 h. 3-(4-(aminomethyl)-2,6-dichlorophenyl) piperidine-2,6-dione (180 mg, 626 μmol, 1.00 eq.) was added, and the reaction was stirred at 25° C. for 2 h. The mixture was concentrated under reduced pressure to give a residue. The residue was purified via Purification Method 1 to afford N-(3,5-dichloro-4-(2,6-dioxopiperidin-3-yl)benzyl)-4-(1-(tetrahydro-2H-pyran-2-yl)-1H-indazol-6-yl)tetrahydro-2H-pyran-4-carboxamide (128 mg, 192 μmol, 30.6% yield) as a white solid.

Step 4. A solution of N-(3,5-dichloro-4-(2,6-dioxopiperidin-3-yl)benzyl)-4-(1-(tetrahydro-2H-pyran-2-yl)-1H-indazol-6-yl)tetrahydro-2H-pyran-4-carboxamide (128 mg, 213 μmol, 1.00 eq.) in hydrochloric acid/dioxane (4M, 2.00 mL) was stirred at 25° C. for 1 h. The mixture was concentrated under reduced pressure to give a residue. The residue was purified via Purification Method 1 to afford N-(3,5-dichloro-4-(2,6-dioxopiperidin-3-yl)benzyl)-4-(1H-indazol-6-yl)tetrahydro-2H-pyran-4-carboxamide (77.1 mg, 148.10 μmol, 69% yield) as a white solid.

$^1H$ NMR (400 MHZ, DMSO-$d_6$) δ=13.04 (s, 1H), 10.94 (s, 1H), 8.29 (t, J=5.6 Hz, 1H), 8.03 (s, 1H), 7.73 (d, J=8.4 Hz, 1H), 7.51 (s, 1H), 7.14 (d, J=8.8 Hz, 1H), 6.92 (s, 1H), 6.84 (s, 1H), 4.51-4.43 (m, 1H), 4.22 (br d, J=5.6 Hz, 2H), 3.82 (br d, J=11.6 Hz, 2H), 3.52 (br t, J=10.8 Hz, 2H), 2.90-2.76 (m, 1H), 2.57 (br d, J=13.2 Hz, 2H), 2.53 (br s, 1H), 2.32-2.20 (m, 1H), 2.01-1.91 (m, 2H), 1.85-1.76 (m, 1H). MS (ESI) m/z 515.2 $[M+H]^+$

Exemplary Compound 132

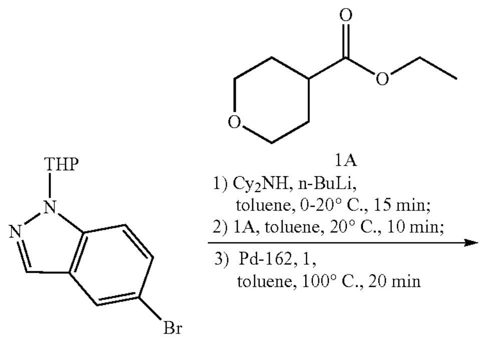

-continued

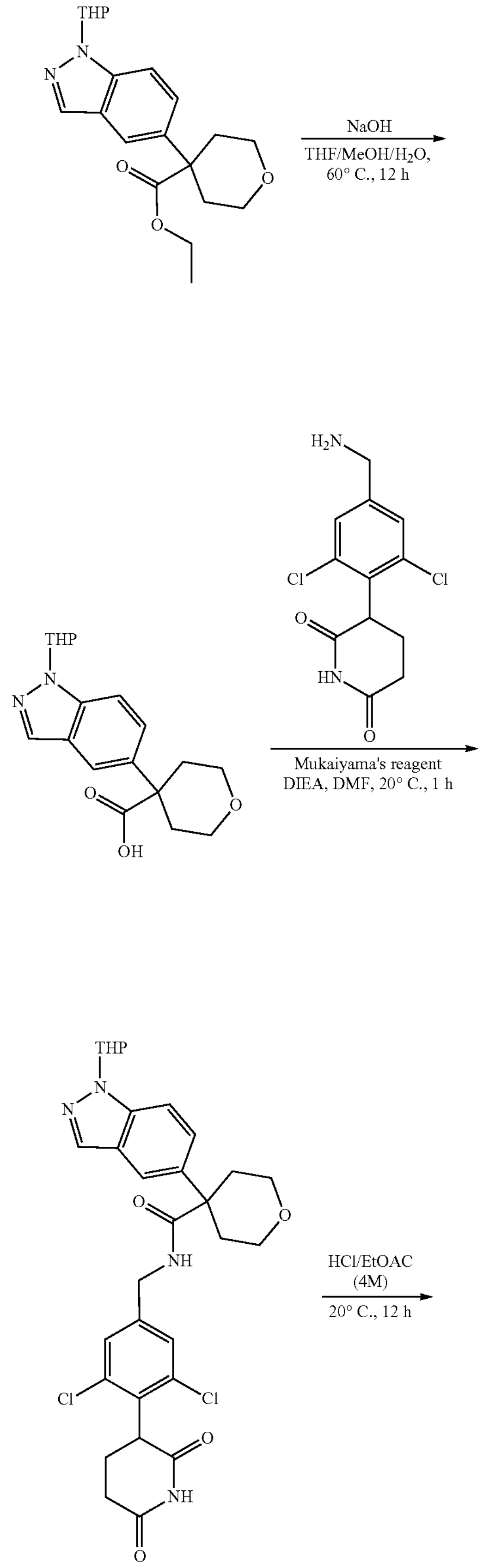

-continued

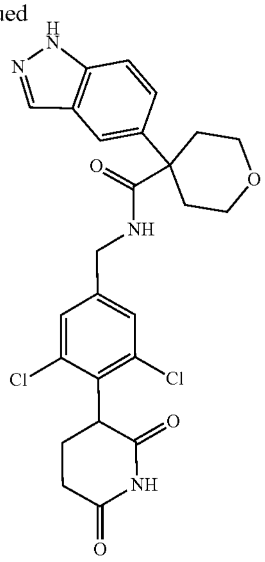

To a solution of dicyclohexylamine (219 mg, 1.21 mmol, 1.70 eq.) in toluene (5 mL) was added n-butyllithium (2.5 M in n-hexane, 484 μL, 1.70 eq.) at 0° C. under nitrogen atmosphere. The mixture was stirred at 20° C. for 15 min. Then ethyl tetrahydro-2H-pyran-4-carboxylate (180 mg, 1.14 mmol, 1.60 eq.) was added to the mixture, and stirred at 20° C. for 10 min. Then chloro (crotyl) (tri-tert-butylphosphine) palladium (II) (26.0 mg, 71.1 μmol, 0.10 eq.) and 5-bromo-1-(tetrahydro-2H-pyran-2-yl)-1H-indazole (200 mg, 711 μmol, 1.00 eq.) were added to the mixture and stirred at 100° C. under nitrogen atmosphere for 20 min. The mixture was cooled to 0° C. Then it was quenched with water (20 mL) and extracted with ethyl acetate (20 mL). The organic layer was washed with water (2×20 mL), dried over sodium sulfate, filtered, and concentrated under reduced pressure. The residue was purified via Purification Method 2 to afford ethyl 4-(1-(tetrahydro-2H-pyran-2-yl)-1H-indazol-5-yl)tetrahydro-2H-pyran-4-carboxylate (110 mg, 276 μmol, 39% yield) as a yellow oil.

To a solution of ethyl 4-(1-(tetrahydro-2H-pyran-2-yl)-1H-indazol-5-yl)tetrahydro-2H-pyran-4-carboxylate (110 mg, 307 μmol, 1.00 eq.) in methanol (2 mL), tetrahydrofuran (2 mL) and water (2 mL) was added sodium hydroxide (49.1 mg, 1.23 mmol, 4.00 eq.). The mixture was stirred at 60° C. for 12 h. The mixture was acidified with aqueous hydrochloric acid (6 M) until pH 5. Then it was concentrated to give a residue. The residue was purified via Purification Method I to afford 4-(1-(tetrahydro-2H-pyran-2-yl)-1H-indazol-5-yl)tetrahydro-2H-pyran-4-carboxylic acid (60.0 mg, 173 μmol, 56% yield) as a white solid.

To a solution of 4-(1-(tetrahydro-2H-pyran-2-yl)-1H-indazol-5-yl)tetrahydro-2H-pyran-4-carboxylic acid (60.0 mg, 182 μmol, 1.00 eq.) in N,N-dimethylformamide (3 mL) were added 2-chloro-1-methyl-pyridin-1-ium iodide (55.7 mg, 218 μmol, 1.20 eq.) and N,N-diisopropylethylamine (70.4 mg, 545 μmol, 3.00 eq.). The mixture was stirred at 20° C. for 0.5 h. Then 3-(4-(aminomethyl)-2,6-dichlorophenyl) piperidine-2,6-dione hydrochloride (58.8 mg, 182 μmol, 1.00 eq.) was added. The mixture was stirred at 20° C. for 1 h. The mixture was diluted with water (20 mL) and extracted with ethyl acetate (20 mL). The organic layer was washed with water (2× 20 mL), dried over sodium sulfate, filtered, and concentrated under reduced pressure. The residue was purified by Prep-TLC (petroleum ether/ethyl acetate=0/1) to give N-(3,5-dichloro-4-(2,6-dioxopiperidin-3-yl)benzyl)-4-(1-(tetrahydro-2H-pyran-2-yl)-1H-indazol-5-yl)tetrahydro-2H-pyran-4-carboxamide (30.0 mg, 47.5 μmol, 26% yield) as a white solid.

A solution of N-(3,5-dichloro-4-(2,6-dioxopiperidin-3-yl) benzyl)-4-(1-(tetrahydro-2H-pyran-2-yl)-1H-indazol-5-yl) tetrahydro-2H-pyran-4-carboxamide (30.0 mg, 50.0 μmol, 1.00 eq.) in hydrogen chloride/ethyl acetate (4 M, 5 mL) was stirred at 20° C. for 12 h. The mixture was concentrated under reduced pressure to give a residue. The residue was purified via Purification Method 1 to afford N-(3,5-dichloro-4-(2,6-dioxopiperidin-3-yl)benzyl)-4-(1H-indazol-5-yl)tetrahydro-2H-pyran-4-carboxamide (12.26 mg, 23.6 μmol, 47% yield) as a white solid.

$^1$H NMR (400 MHZ, DMSO-$d_6$) δ=13.00 (s, 1H), 10.91 (s, 1H), 8.22 (t, J=6.0 Hz, 1H), 8.06 (s, 1H), 7.76 (s, 1H), 7.51 (d, J=8.8 Hz, 1H), 7.37 (dd, J=1.2, 8.8 Hz, 1H), 6.92 (s, 1H), 6.80 (s, 1H), 4.47 (dd, J=5.6, 12.8 Hz, 1H), 4.22 (d, J=5.6 Hz, 2H), 3.80 (d, J=11.2 Hz, 2H), 3.53 (t, J=10.8 Hz, 2H), 2.92-2.73 (m, 1H), 2.62-2.53 (m, 3H), 2.26 (dq, J=4.4, 13.2 Hz, 1H), 2.05-1.90 (m, 2H), 1.87-1.76 (m, 1H). MS (ESI) m/z 515.2 [M+H]$^+$

Exemplary Compound 134

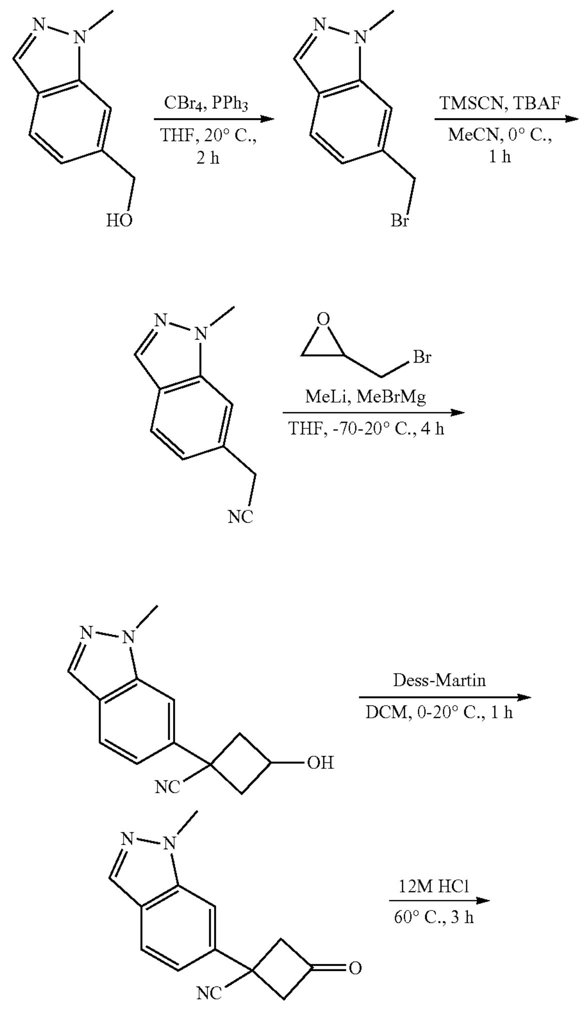

-continued

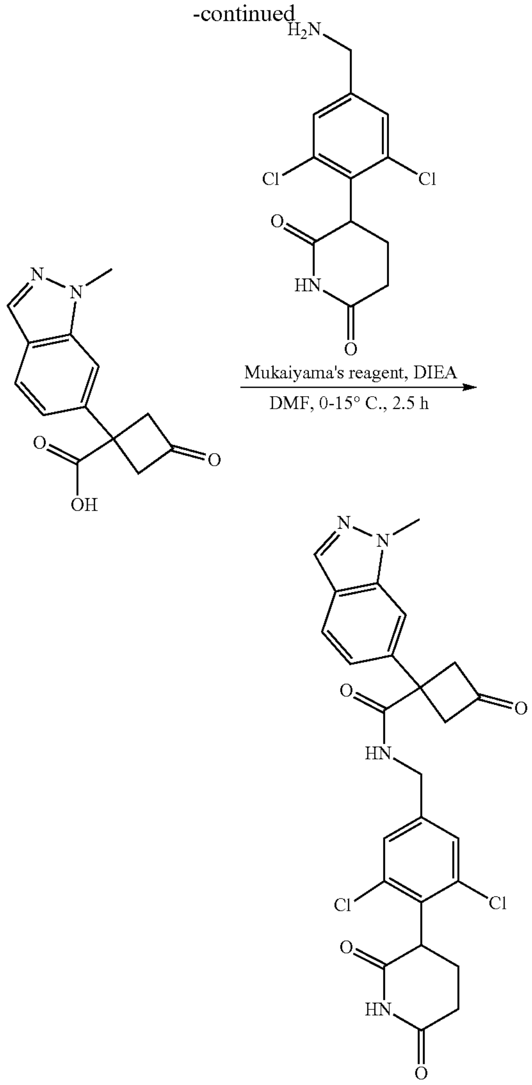

Step 1. To a solution of (1-methyl-1H-indazol-6-yl) methanol (1.00 g, 6.17 mmol, 1.00 eq.) in tetrahydrofuran (15 mL) were added triphenylphosphine (2.43 g, 9.25 mmol, 1.50 eq.) and carbon tetrabromide (3.07 g, 9.25 mmol, 1.50 eq.). The reaction was stirred at 20° C. for 2 h. The resulting mixture was filtered, and the filtrate was diluted with ethyl acetate (20 mL) and water (20 mL). The layers were separated, and the combined organic layers were washed with brine (20 mL) and dried over anhydrous sodium sulfate, filtered, and concentrated in vacuo. The residue was purified via Purification Method 2 to afford 6-(bromomethyl)-1-methyl-1H-indazole (1.10 g, 4.06 mmol, 66% yield) as a yellow solid.

Step 2. To a solution of 6-(bromomethyl)-1-methyl-1H-indazole (1.00 g, 4.44 mmol, 1.00 eq.) in acetonitrile (10 mL) were added trimethylsilyl cyanide (700 μL, 5.60 mmol, 1.26 eq.) and tetrabutylammonium fluoride (1.0 M in tetrahydrofuran, 5.50 mL, 1.24 eq.) at 0° C. The reaction was stirred at 0° C. for 1 h. The reaction mixture was diluted with ethyl acetate (15 mL) and water (15 mL). The layers were separated, and the combined organic layers were washed with brine (15 mL), dried over anhydrous sodium sulfate, filtered, and concentrated in vacuo. The residue was purified via Purification Method 2 to afford 2-(1-methyl-1H-indazol-6-yl) acetonitrile (700 mg, 3.97 mmol, 89% yield) as a light-yellow solid.

Step 3. To a solution of 2-(1-methyl-1H-indazol-6-yl) acetonitrile (350 mg, 2.04 mmol, 1.00 eq.) in tetrahydrofuran (5 mL) was added dropwise methyllithium (1.0 M, 2.30 mL, 1.13 eq.) at −70° C. under nitrogen atmosphere. The reaction was stirred at −70° C. for 1 h. Then 2-(bromomethyl) oxirane (310 mg, 2.26 mmol, 1.11 eq.) in tetrahydrofuran (1 mL) was added dropwise to the mixture slowly at −70° C. The reaction was stirred at −70° C. for 1 h. Then methylmagnesium bromide (3.0 M, 750 μL, 1.10 eq.) was added dropwise to the mixture at −70° C. and the reaction mixture was warmed to 20° C., and stirred for 2 h. The reaction was quenched with water (10 mL) and 3M hydrochloric acid solution (2 mL) at 0° C. The reaction mixture was diluted with ethyl acetate (10 mL) and water (10 mL). The layers were separated, and the aqueous phase was extracted with ethyl acetate (2×10 mL). The combined organic layers were washed with brine (20 mL) and dried over anhydrous sodium sulfate, filtered, and concentrated in vacuo. The residue was purified via Purification Method 2 to afford 3-hydroxy-1-(1-methyl-1H-indazol-6-yl)cyclobutane-1-carbonitrile (210 mg, 822 μmol, 40% yield) as a white solid.

Step 4. To a solution of 3-hydroxy-1-(1-methyl-1H-indazol-6-yl)cyclobutane-1-carbonitrile (200 mg, 880 μmol, 1.00 eq.) in dichloromethane (5 mL) was added (1,1-diacetoxy-3-oxo-1,2-benziodoxol-1-yl)acetate (560 mg, 1.32 mmol, 1.50 eq.) at 0° C. The reaction was stirred at 20° C. for 1 h. The reaction mixture was diluted with dichloromethane (10 mL) and water (10 mL). The layers were separated, and the aqueous phase was extracted with dichloromethane (2×10 mL). The combined organic layers were washed with brine (20 mL) and dried over anhydrous sodium sulfate, filtered, and concentrated in vacuo. The residue was purified via Purification Method 2 then Purification Method 1 to afford 1-(1-methyl-1H-indazol-6-yl)-3-oxocyclobutane-1-carbonitrile (60.0 mg, 240 μmol, 27% yield) as a white solid.

Step 5. A solution of 1-(1-methyl-1H-indazol-6-yl)-3-oxocyclobutane-1-carbonitrile (50.0 mg, 222 μmol, 1.00 eq.) in concentrated hydrochloric acid (12 M, 5 mL) was stirred at 60° C. for 3 h. The reaction mixture was concentrated in vacuo. The residue was purified via Purification Method 1 to afford 1-(1-methyl-1H-indazol-6-yl)-3-oxocyclobutane-1-carboxylic acid (50.0 mg, 186 μmol, 84% yield) as a yellow solid.

Step 6. To a solution of 1-(1-methyl-1H-indazol-6-yl)-3-oxocyclobutane-1-carboxylic acid (40.0 mg, 164 μmol, 1.00 eq.) in dimethylformamide (1.5 mL) were added N,N-diisopropylethylamine (63.5 mg, 491 μmol, 3.00 eq.) and 2-chloro-1-methyl-pyridin-1-ium iodide (52.0 mg, 204 μmol, 1.24 eq.) at 0° C. The reaction was stirred at 15° C. for 30 min, then 3-(4-(aminomethyl)-2,6-dichlorophenyl) piperidine-2,6-dione (50.0 mg, 174 μmol, 1.06 eq.) was added. The reaction was stirred at 15° C. for 2 h. The mixture was diluted with ethyl acetate (8 mL) and water (8 mL). The layers were separated, and the aqueous phase was extracted with ethyl acetate (2×5 mL). The combined organic layers were washed with brine (15 mL) and dried over anhydrous sodium sulfate, filtered, and concentrated in vacuo. The residue was purified via Purification Method 1 to afford N-(3,5-dichloro-4-(2,6-dioxopiperidin-3-yl)benzyl)-1-(1-methyl-1H-indazol-6-yl)-3-oxocyclobutane-1-carboxamide (37.46 mg, 70.8 μmol, 43% yield) as a white solid.

$^1$H NMR (400 MHZ, DMSO-$d_6$) δ=10.94 (s, 1H), 8.22 (s, 1H), 8.05 (s, 1H), 7.82-7.75 (m, 2H), 7.16 (d, J=8.4 Hz, 1H), 7.08 (s, 1H), 6.99 (s, 1H), 4.50 (dd, J=5.6, 12.8 Hz, 1H), 4.22 (d, J=5.6 Hz, 2H), 4.07 (s, 3H), 3.91-3.78 (m, 2H), 3.73-3.60 (m, 2H), 2.90-2.76 (m, 1H), 2.59-2.52 (m, 1H), 2.37-2.21 (m, 1H), 1.92-1.76 (m, 1H). MS (ESI) m/z 513.1 $[M+H]^+$

Exemplary Compound 135

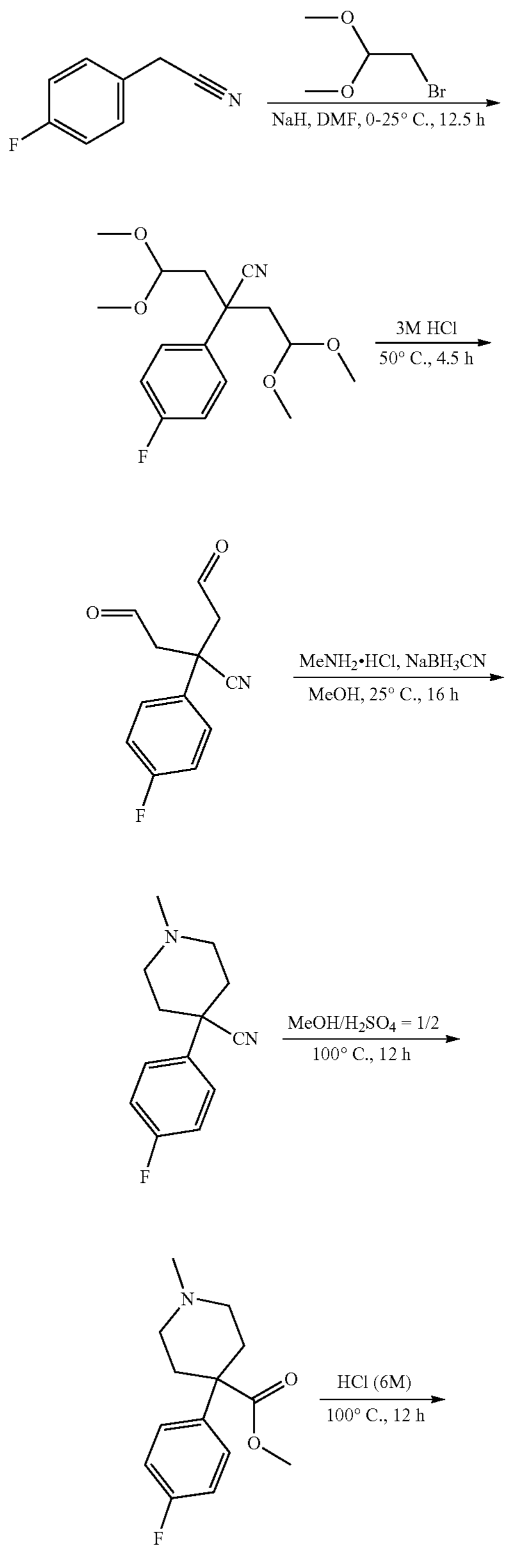

-continued

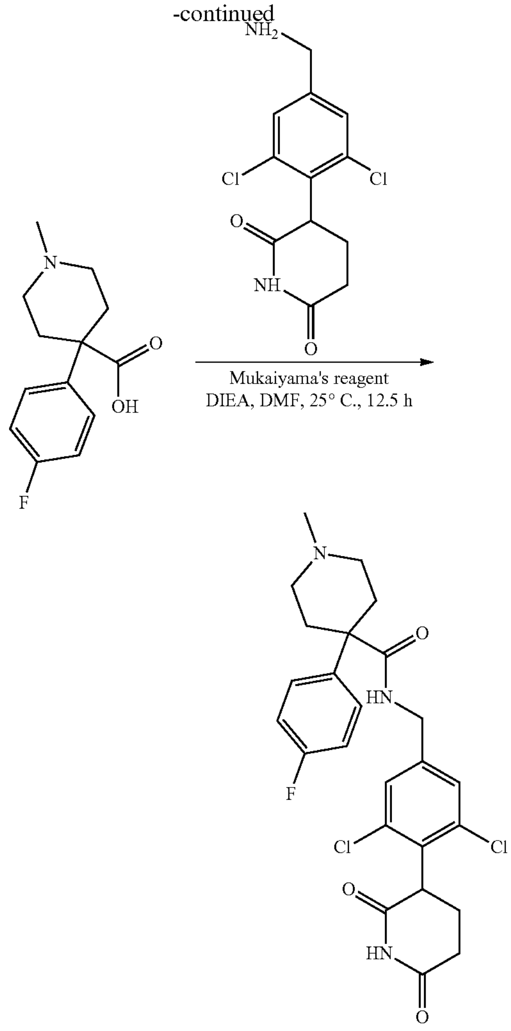

Step 1. To a solution of 2-(4-fluorophenyl) acetonitrile (5.00 g, 37.00 mmol, 1.00 eq.) in N,N-dimethylformamide (100 mL) was added sodium hydride (5.92 g, 148 mmol, 60% purity, 4.00 eq.) under nitrogen atmosphere at 0° C. The mixture was stirred at 25° C. for 0.5 h. Then 2-bromo-1,1-dimethoxy-ethane (25.0 g, 148 mmol, 4.00 eq.) was added, and the reaction was stirred at 25° C. for 12 h. The reaction was quenched with saturated ammonium chloride (100 mL) at 0° C., and extracted with ethyl acetate (2' 100 mL). The combined organic layers were washed with water (2× 70 mL), dried over sodium sulfate, filtered, and concentrated under reduced pressure. The residue was purified via Purification Method 2 to afford 2-(2,2-dimethoxyethyl)-2-(4-fluorophenyl)-4,4-dimethoxybutanenitrile (8.30 g, 20.8 mmol, 56% yield) as a yellow oil.

Step 2. A solution of 2-(2,2-dimethoxyethyl)-2-(4-fluorophenyl)-4,4-dimethoxybutanenitrile (8.30 g, 26.7 mmol, 1.00 eq.) in hydrochloric acid (3 M, 100 mL) was stirred at 50° C. for 4.5 h. The reaction mixture was extracted with ethyl acetate (150 mL). The organic phase was washed with saturated sodium bicarbonate (100 mL), dried over sodium sulfate, filtered, and concentrated under reduced pressure to give 2-(4-fluorophenyl)-4-oxo-2-(2-oxoethyl) butanenitrile (7.00 g, 16.0 mmol, 60% yield) as a yellow oil.

Step 3. To a solution of 2-(4-fluorophenyl)-4-oxo-2-(2-oxoethyl) butanenitrile (3.50 g, 16.0 mmol, 1.00 eq.) in methanol (50 mL) were added sodium cyanoborohydride (2.01 g, 31.9 mmol, 2.00 eq.) and methanamine hydrochloride (3.23 g, 47.9 mmol, 3.00 eq.). The reaction was stirred at 25° C. for 16 h. The mixture was concentrated under reduced pressure to give a residue. The residue was treated with saturated sodium bicarbonate (100 mL) and extracted with ethyl acetate (2 ‘100 mL). The combined organic layers were dried over sodium sulfate, filtered, and the solvent was removed under reduced pressure. The residue was purified via Purification Method 2 to afford 4-(4-fluorophenyl)-1-methyl-piperidine-4-carbonitrile (1.30 g, 5.36 mmol, 33.6% yield) as a yellow oil.

Step 4. To a solution of 4-(4-fluorophenyl)-1-methyl-piperidine-4-carbonitrile (1.10 g, 5.04 mmol, 1.00 eq.) in methanol (3 mL) was added sulfuric acid (6 mL) dropwise. The mixture was stirred at 100° C. for 12 h. The pH of the reaction mixture was adjusted to 7-8 with sodium bicarbonate, and the mixture was diluted with water (30 mL) and extracted with ethyl acetate (2’ 20 mL). The combined organic layers were washed with brine (15 mL), dried over sodium sulfate, filtered, and concentrated under reduced pressure. The residue was purified via Purification Method 2 to afford methyl 4-(4-fluorophenyl)-1-methylpiperidine-4-carboxylate (342 mg, 1.36 mmol, 27% yield) as a white solid.

Step 5. A solution of methyl 4-(4-fluorophenyl)-1-methyl-piperidine-4-carboxylate (170 mg, 676 μmol, 1.00 eq.) in hydrochloric acid (6 M, 20 mL) was stirred at 100° C. for 12 h. The mixture was concentrated to give 4-(4-fluorophenyl)-1-methyl-piperidine-4-carboxylic acid (162 mg, 614 μmol, 90% yield) as a white solid.

Step 5. To a solution of 4-(4-fluorophenyl)-1-methyl-piperidine-4-carboxylic acid (99.2 mg, 418 μmol, 1.20 eq.) in dimethylformamide (3 mL) were added N,N-diisopropylethylamine (135 mg, 1.04 mmol, 3.00 eq.) and 2-chloro-1-methyl-pyridin-1-ium iodide (107 mg, 418 μmol, 1.20 eq.). The mixture was stirred at 25° C. for 30 min, then 3-(4-(aminomethyl)-2,6-dichlorophenyl) piperidine-2,6-dione hydrochloride (100 mg, 348 μmol, 1.00 eq.) was added. The reaction was stirred at 25° C. for 12 h. The mixture was diluted with water (20 mL) and extracted with ethyl acetate (20 mL). The combined organic layers were washed with brine (10 mL), dried over sodium sulfate, filtered, and concentrated under reduced pressure. The residue was purified via Purification Method 1 to afford N-(3,5-dichloro-4-(2,6-dioxopiperidin-3-yl)benzyl)-4-(4-fluorophenyl)-1-methylpiperidine-4-carboxamide formate (22.0 mg, 39.0 μmol, 11% yield) as a white solid.

$^1$H NMR (400 MHZ, DMSO-$d_6$) δ=10.94 (s, 1H), 8.28 (t, J=5.6 Hz, 1H), 7.43-7.36 (m, 2H), 7.16 (t, J=8.8 Hz, 2H), 7.00 (s, 1H), 6.94 (s, 1H), 4.56-4.48 (m, 1H), 4.21 (d, J=5.6 Hz, 2H), 2.88-2.79 (m, 1H), 2.70-2.61 (m, 2H), 2.59-2.52 (m, 3H), 2.34-2.28 (m, 1H), 2.16 (m, 5H), 1.94-1.76 (m, 3H). MS (ESI) m/z 506.0 [M+H]$^+$

Exemplary Compound 136

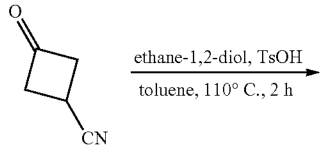

-continued

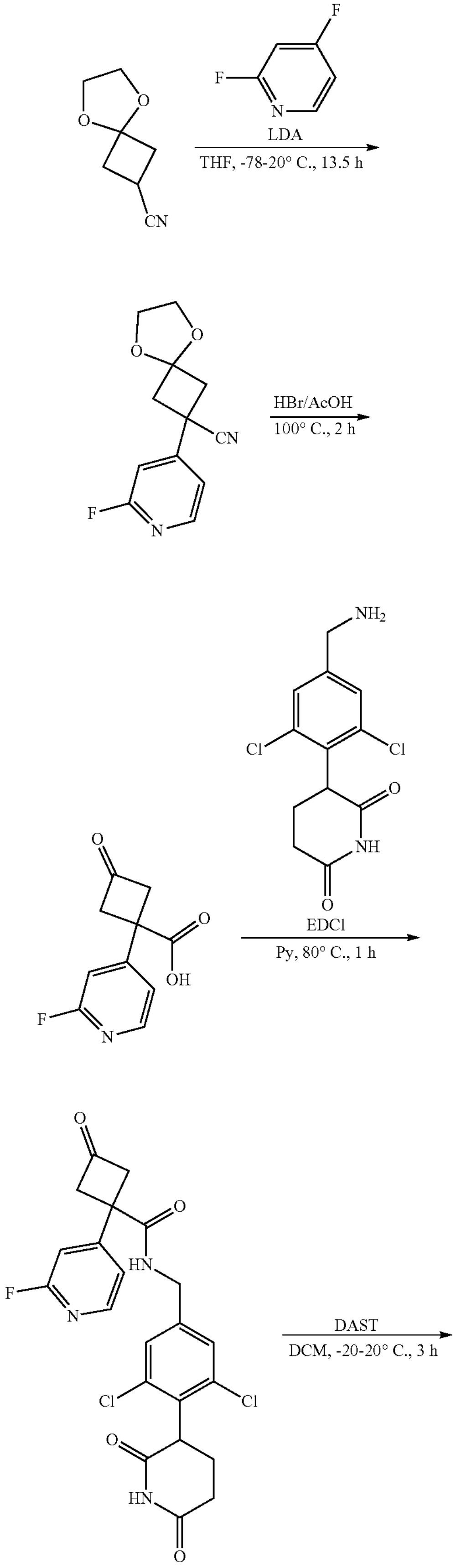

-continued

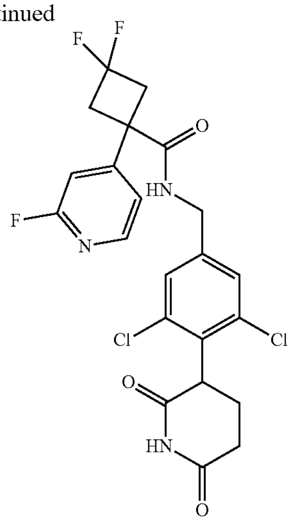

Step 1. A mixture of 3-oxocyclobutane-1-carbonitrile (3.80 g, 39.9 mmol, 1.00 eq.), ethane-1,2-diol (2.48 g, 39.9 mmol, 1.00 eq.) and 4-methylbenzenesulfonic acid (688 mg, 4.00 mmol, 0.10 eq.) in toluene (20 mL) was stirred at 110° C. for 2 h under nitrogen. The mixture was concentrated under reduced pressure to afford 5,8-dioxaspiro[3.4]octane-2-carbonitrile (4.46 g, crude) as a yellow oil.

Step 2. To a mixture of 5,8-dioxaspiro[3.4]octane-2-carbonitrile (4.20 g, 30.2 mmol, 1.00 eq.) in tetrahydrofuran (30 mL) was added lithium diisopropylamide (2 M, 18.0 mL, 1.20 eq.) at −78° C. under nitrogen. The mixture was stirred at −78° C. for 1.5 h, then 2,4-difluoropyridine (3.49 g, 30.3 mmol, 1.00 eq.) was added. The reaction was stirred at 20° C. for 12 h under nitrogen atmosphere. The reaction was quenched with water (100 mL) and extracted with dichloromethane (3×100 mL). The combined organic layers were washed with saturated ammonium chloride aqueous solution (2×100 mL), brine (2× 100 mL), dried over anhydrous sodium sulfate, filtered, and concentrated under reduced pressure. The residue was purified via Purification Method 2 to afford 2-(2-fluoropyridin-4-yl)-5,8-dioxaspiro[3.4]octane-2-carbonitrile (1.46 g, 6.23 mmol, 21% yield) as a yellow oil.

Step 3. A solution of 2-(2-fluoropyridin-4-yl)-5,8-dioxaspiro[3.4]octane-2-carbonitrile (200 mg, 854 μmol, 1.00 eq.) in hydrobromic acid (33 wt. % solution in acetic acid, 3.0 mL) was stirred at 100° C. for 2 h under nitrogen atmosphere. The reaction mixture was concentrated under reduced pressure to give 1-(2-fluoropyridin-4-yl)-3-oxocyclobutane-1-carboxylic acid (160 mg, crude) as a yellow oil.

Step 5. A solution of 3-(4-(aminomethyl)-2,6-dichlorophenyl) piperidine-2,6-dione (200 mg, 697 μmol, 1.00 eq.), 1-(2-fluoropyridin-4-yl)-3-oxocyclobutane-1-carboxylic acid (160 mg, 765 μmol, 1.10 eq.) and 3-(ethyliminomethyleneamino)-N,N-dimethyl-propan-1-amine hydrochloride (160 mg, 835 μmol, 1.20 eq.) in pyridine (5.0 mL) was stirred at 80° C. for 1 h under nitrogen atmosphere. The reaction mixture was concentrated under reduced pressure. The residue was purified via Purification Method 2 to afford N-(3,5-dichloro-4-(2,6-dioxopiperidin-3-yl)benzyl)-1-(2-fluoropyridin-4-yl)-3-oxocyclobutane-1-carboxamide (250 mg, 310 μmol, 45% yield, 59% purity) as a yellow solid.

Step 6. To a solution of N-[3,5-dichloro-4-(2,6-dioxo-3-piperidyl)phenyl]methyl]-1-(2-fluoro-4-pyridyl)-3-oxo-cyclobutanecarboxamide (200 mg, 418 μmol, 1.00 eq.) in dichloromethane (5 mL) was added N,N-diethyl-1,1,1-trifluoro-24-sulfanamine (134 mg, 833 μmol, 1.99 eq.) dropwise at −20° C. over 1 min. The reaction was stirred at 20° C. for 3 h. The mixture was concentrated under reduced pressure. The residue was diluted with water (20 mL) and extracted with ethyl acetate (3× 25 mL). The combined organic layers were washed with water (3×60 mL) and brine (2× 60 mL), dried over anhydrous sodium sulfate, filtered, and concentrated under reduced pressure. The residue was purified via Purification Method 1 to afford N-(3,5-dichloro-4-(2,6-dioxopiperidin-3-yl)benzyl)-3,3-difluoro-1-(2-fluoropyridin-4-yl)cyclobutane-1-carboxamide (12.0 mg, 24.0 μmol, 6% yield) as a white solid.

$^1$H NMR (400 MHZ, DMSO-$d_6$) δ=10.96 (s, 1H), 8.73 (t, J=6.0 Hz, 1H), 8.27 (d, J=5.2 Hz, 1H), 7.36 (d, J=5.2 Hz, 1H), 7.26 (s, 1H), 7.13-7.01 (m, 2H), 4.54 (dd, J=6.0, 13.2 Hz, 1H), 4.25 (d, J=5.6 Hz, 2H), 3.46-3.39 (m, 2H), 3.24-3.16 (m, 2H), 2.90-2.79 (m, 1H), 2.57-2.53 (m, 1H), 2.35-2.30 (m, 1H), 1.93-1.81 (m, 1H). MS (ESI) m/z 500.0 $[M+H]^+$

Exemplary Compound 137

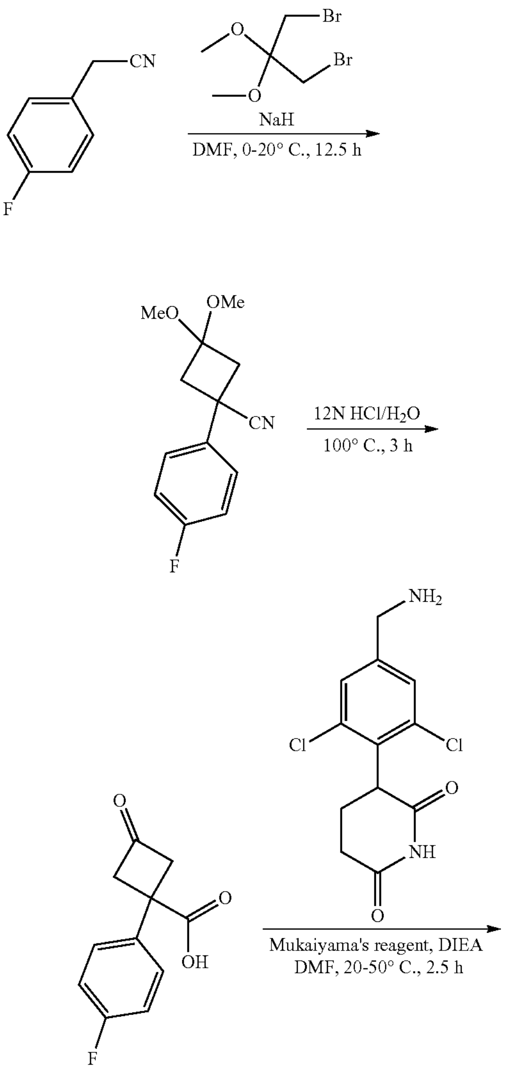

-continued

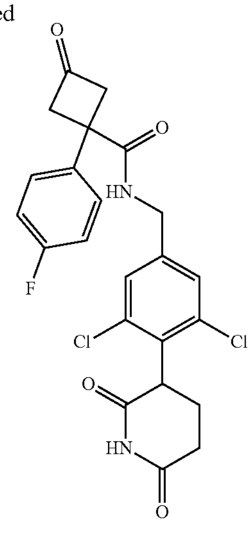

Step 1. To a solution of sodium hydride (1.48 g, 37.0 mmol, 60% purity in mineral oil, 2.50 eq.) in N,N-dimethylformamide (10 mL) was added 2-(4-fluorophenyl) acetonitrile (2.00 g, 14.8 mmol, 1.00 eq.) in N,N-dimethylformamide (5 mL) dropwise at 0° C. over 1 min. After addition, the mixture was stirred at this temperature for 30 minutes under nitrogen atmosphere, and then 1,3-dibromo-2,2-dimethoxypropane (3.88 g, 14.8 mmol, 1.00 eq.) in N,N-dimethylformamide (5.0 mL) was added dropwise at 0° C. The reaction was stirred at 20° C. for 12 h, then it was quenched with saturated ammonium chloride aqueous solution (50 mL) and extracted with ethyl acetate (3× 60 mL). The combined organic layers were washed with brine (3×100 mL), dried over anhydrous sodium sulfate, filtered, and concentrated under reduced pressure. The residue was purified via Purification Method 2 to afford 1-(4-fluorophenyl)-3,3-dimethoxycyclobutane-1-carbonitrile (1.72 g, 5.86 mmol, 40% yield, 80% purity) as a yellow oil.

Step 2. A mixture of 1-(4-fluorophenyl)-3,3-dimethoxycyclobutane-1-carbonitrile (500 mg, 2.13 mmol, 1.00 eq.) in hydrochloric acid (12 M, 2 mL) was stirred at 100° C. for 3 h. The reaction mixture was diluted with water (10 mL) and extracted with ethyl acetate (3× 10 mL). The combined organic layers were washed with water (3×20 mL) and brine (2×20 mL), dried over anhydrous sodium sulfate, filtered, and concentrated under reduced pressure to afford 1-(4-fluorophenyl)-3-oxocyclobutane-1-carboxylic acid (320 mg, crude) as a yellow oil.

Step 3. To a solution of 1-(4-fluorophenyl)-3-oxocyclobutane-1-carboxylic acid (72.5 mg, 348 μmol, 1.00 eq.) in N,N-dimethylformamide (5 mL) was added N,N-diisopropylethylamine (178 mg, 1.38 mmol, 3.96 eq.) and 2-chloro-1-methyl-pyridin-1-ium iodide (98.0 mg, 384 μmol, 1.10 eq.) at 20° C. over 1 min. After addition, the mixture was stirred for 30 min, then 3-(4-(aminomethyl)-2,6-dichlorophenyl) piperidine-2,6-dione (100 mg, 348 μmol, 1.00 eq.) was added at 20° C. The reaction was stirred at 50° C. for 2 h. The reaction mixture was diluted with water (10 mL) and extracted with ethyl acetate (3× 10 mL). The combined organic layers were washed with water (3×20 mL) and brine (2× 20 mL), dried over anhydrous sodium sulfate, filtered, and concentrated under reduced pressure. The residue was purified via Purification Method I to afford N-(3,5-dichloro-4-(2,6-dioxopiperidin-3-yl)benzyl)-1-(4-fluorophenyl)-3-oxocyclobutane-1-carboxamide (21.4 mg, 43.1 μmol, 12% yield) as a yellow solid.

$^1$H NMR (400 MHZ, DMSO-$d_6$) δ=10.95 (s, 1H), 8.36 (t, J=6.0 Hz, 1H), 7.50 (dd, J=8.8, 5.2 Hz, 2H), 7.24 (t, J=8.8 Hz, 2H), 7.06 (s, 1H), 6.99 (s, 1H), 4.53 (dd, J=5.6, 12.8 Hz, 1H), 4.22 (d, J=6.0 Hz, 2H), 3.84-3.73 (m, 2H), 3.57-3.49 (m, 2H), 2.88-2.79 (m, 1H), 2.53 (s, 1H), 2.40-2.32 (m, 1H), 1.90-1.81 (m, 1H). MS (ESI) m/z 499.0 [M+Na]$^+$

Exemplary Compound 139

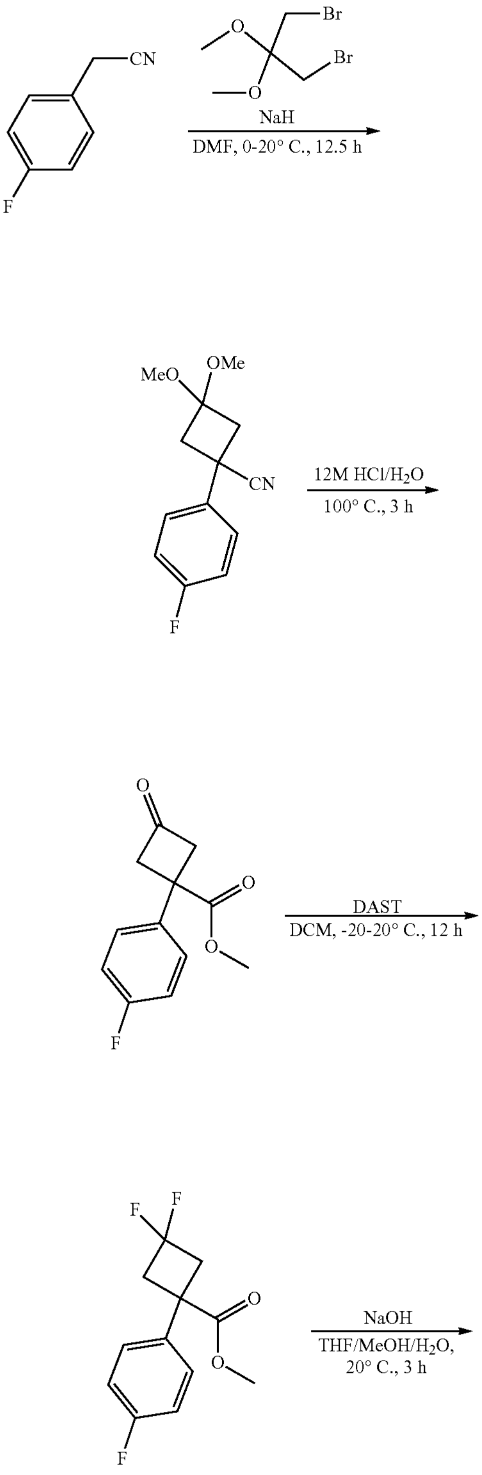

-continued

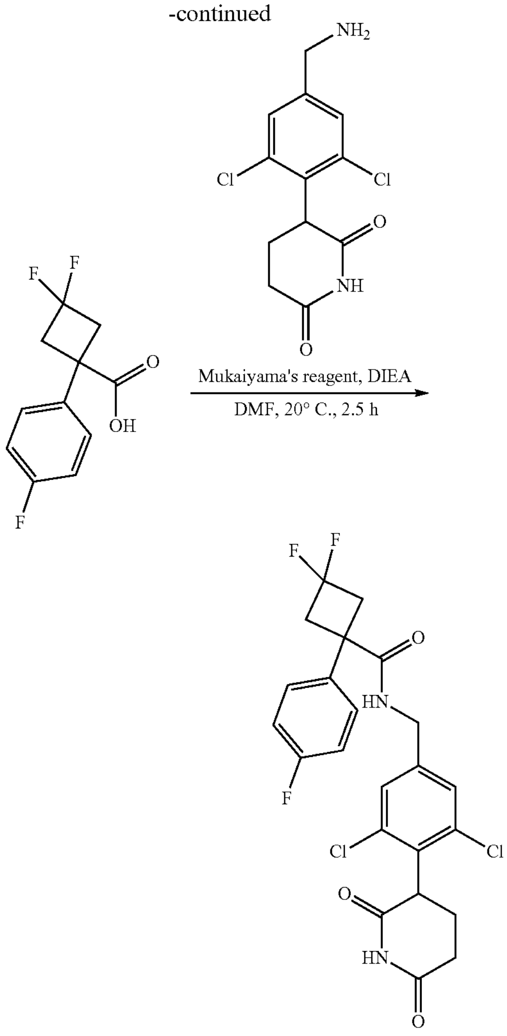

Step 1. To a solution of sodium hydride (1.48 g, 37.0 mmol, 60.0% purity, 2.50 eq.) in N,N-dimethylformamide (10 mL) was added a solution of 2-(4-fluorophenyl) acetonitrile (2.00 g, 14.8 mmol, 1.00 eq.) in N,N-dimethylformamide (5 mL) dropwise at 0° C. over 1 min. After the addition, the mixture was stirred at this temperature for 30 minutes under nitrogen atmosphere, and then a solution of 1,3-dibromo-2,2-dimethoxypropane (3.88 g, 14.8 mmol, 1.00 eq.) in N,N-dimethylformamide (5 mL) was added dropwise at 0° C. The reaction was stirred at 20° C. for 12 h under nitrogen atmosphere. The reaction was quenched with saturated ammonium chloride aqueous solution (50 mL) and extracted with ethyl acetate (3× 60 mL). The combined organic layers were washed with brine (3×100 mL), dried over anhydrous sodium sulfate, filtered, and concentrated under reduced pressure. The residue was purified via Purification Method 2 to afford 1-(4-fluorophenyl)-3,3-dimethoxy-cyclobutanecarbonitrile (1.95 g, 6.15 mmol, 42% yield, 74% purity) as a yellow oil.

Step 2. A mixture of 1-(4-fluorophenyl)-3,3-dimethoxy-cyclobutanecarbonitrile (1.00 g, 4.25 mmol, 1.00 eq.) in hydrochloric acid (12 M, 5 mL) was stirred at 100° C. for 3 h under nitrogen atmosphere. Methanol (10 mL) was added, and the reaction mixture was concentrated under reduced pressure. The residue was purified via Purification Method 2 to afford methyl 1-(4-fluorophenyl)-3-oxocyclobutanecarboxylate (460 mg, 1.85 mmol, 44% yield, 90% purity) as a yellow oil.

Step 3. To a solution of methyl 1-(4-fluorophenyl)-3-oxocyclobutanecarboxylate (460 mg, 2.07 mmol, 1.00 eq.) in dichloromethane (5 mL) was added diethylaminosulfur trifluoride (512 mg, 3.18 mmol, 1.54 eq.) dropwise at −20° C. over 5 min. The reaction was stirred at 20° C. for 12 h. The reaction mixture was diluted with water (10 mL) and extracted with ethyl acetate (3× 15 mL). The combined organic layers were washed with water (3×25 mL) and brine (2×25 mL), dried over anhydrous sodium sulfate, filtered, and concentrated under reduced pressure to afford methyl 3,3-difluoro-1-(4-fluorophenyl)cyclobutanecarboxylate (379 mg, crude) as a yellow oil.

Step 4. To a solution of methyl 3,3-difluoro-1-(4-fluorophenyl)cyclobutanecarboxylate (150 mg, 614 μmol, 1.00 eq.) in tetrahydrofuran (1.2 mL), methanol (3.0 mL) and water (1.2 mL) was added sodium hydroxide (74 mg, 1.85 mmol, 3.01 eq.). The mixture was stirred at 20° C. for 3 h under nitrogen atmosphere. The reaction mixture was concentrated under reduced pressure. The residue was diluted with hydrochloric acid (1M, 10 mL) and extracted with ethyl acetate (3×15 mL). The combined organic layers were washed with brine (2×30 mL), dried over anhydrous sodium sulfate, filtered, and concentrated under reduced pressure to give 3,3-difluoro-1-(4-fluorophenyl)cyclobutanecarboxylic acid (140 mg, crude) as a yellow oil.

Step 5. To a solution of 3,3-difluoro-1-(4-fluorophenyl) cyclobutanecarboxylic acid (70.0 mg, 304 μmol, 1.00 eq.) in N,N-dimethylformamide (1 mL) was added N,N-diisopropylethylamine (163 mg, 1.26 mmol, 4.15 eq.) and 2-chloro-1-methylpyridin-1-ium iodide (94.0 mg, 368 μmol, 1.21 eq.) at 20° C. over 1 min. After the addition, the mixture was stirred at this temperature for 30 min, and then 3-(4-(aminomethyl)-2,6-dichlorophenyl) piperidine-2,6-dione (100 mg, 348 μmol, 1.15 eq.) was added at 20° C. The reaction was stirred at 20° C. for 2 h. The reaction mixture was diluted with water (10 mL) and extracted with ethyl acetate (3×10 mL). The combined organic layers were washed with water (3×20 mL) and brine (2×20 mL), dried over anhydrous sodium sulfate, filtered, and concentrated under reduced pressure. The residue was purified via Purification Method 1 to afford N-(3,5-dichloro-4-(2,6-dioxopiperidin-3-yl)benzyl)-3,3-difluoro-1-(4-fluorophenyl)cyclobutane-carboxamide (43.8 mg, 83.5 μmol, 28% yield) as a white solid.

$^1H$ NMR (400 MHZ, DMSO-$d_6$) δ=10.93 (s, 1H), 8.58 (t, J=6.0 Hz, 1H), 7.38-7.50 (m, 2H), 7.22 (t, J=8.8 Hz, 2H), 6.99 (s, 1H), 6.93 (s, 1H), 6.96-6.86 (m, 1H), 4.52 (dd, J=5.6, 12.4 Hz, 1H), 4.22 (d, J=6.0 Hz, 2H), 3.46-3.36 (m, 2H), 3.07 (q, J=13.6 Hz, 2H), 2.90-2.76 (m, 1H), 2.55-2.52 (m, 1H), 2.29-2.34 (m, 1H), 1.78-1.92 (m, 1H). MS (ESI) m/z 499.0 $[M+H]^+$

Exemplary Compound 143

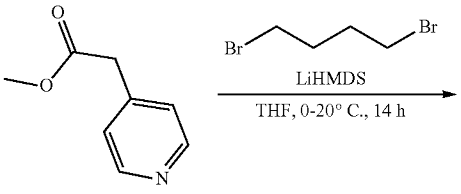

-continued

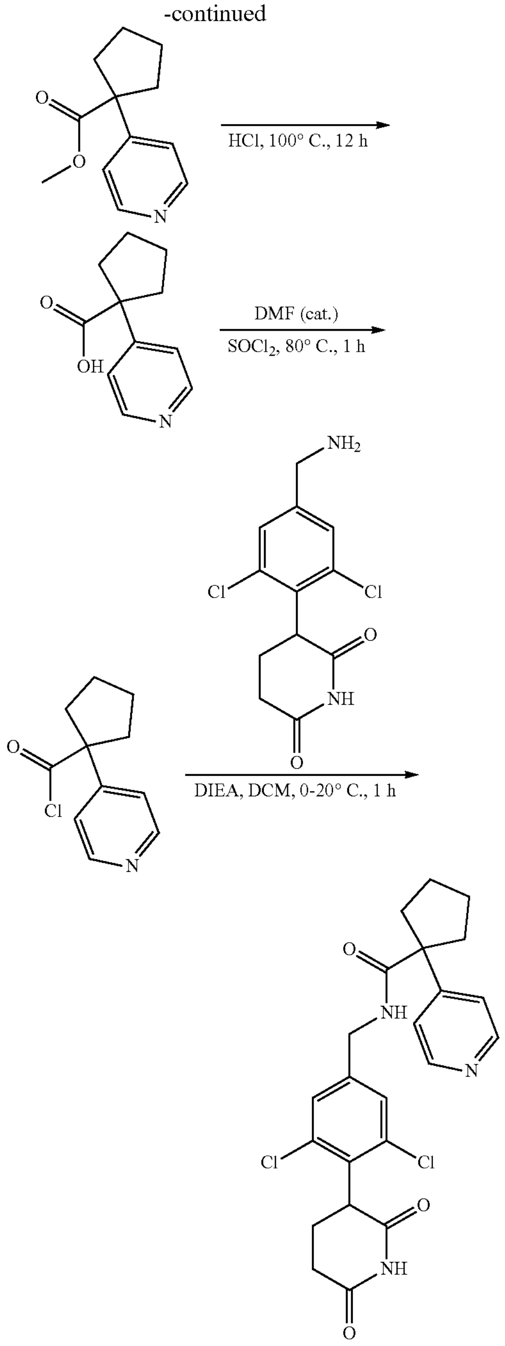

Step 1. To a solution of methyl 2-(pyridin-4-yl)acetate (4.00 g, 26.4 mmol, 1.00 eq.) and 1,4-dibromobutane (8.57 g, 39.6 mmol, 1.50 eq.) in tetrahydrofuran (200 mL) was added lithium bis(trimethylsilyl)amide (1.00 M in tetrahydrofuran, 33 mL, 1.25 eq.) dropwise at 0° C. The reaction was stirred at 20° C. for 2 h, then lithium bis(trimethylsilyl) amide (1.00 M in tetrahydrofuran, 33 mL, 1.25 eq.) was added. The reaction was stirred at 20° C. under nitrogen atmosphere for 12 h. The reaction mixture was quenched with saturated aqueous ammonium chloride (30 mL) then extracted with ethyl acetate (3×10 mL). The combined organic layers were washed with brine (10 mL), dried over anhydrous sodium sulfate, filtered, and concentrated under reduced pressure. The crude product was purified via Purification Method 2 to afford methyl 1-(pyridin-4-yl)cyclopentane-1-carboxylate (4.20 g, 20.0 mmol, 75% yield) as a white solid.

Step 2. A solution of methyl 1-(pyridin-4-yl)cyclopentane-1-carboxylate (200 mg, 974 μmol, 1.00 eq.) in hydrochloric acid (4 mL, 12 M) was stirred at 100° C. for 12 h. The mixture was cooled to 20° C., and concentrated under reduced pressure to give 1-(pyridin-4-yl)cyclopentane-1-carboxylic acid (150 mg, 721 μmol, 74% yield) as a yellow solid.

Step 3. 1-(pyridin-4-yl)cyclopentane-1-carboxylic acid (50.0 mg, 261 μmol, 1.00 eq.) was added portion-wise to sulfurous dichloride (1 mL) containing dimethyl formamide (19.1 mg, 261 μmol, 1.00 eq.), and the mixture was heated at 80° C. for 1 h. The mixture was cooled to 20° C., and concentrated under reduced pressure to give 1-(pyridin-4-yl)cyclopentane-1-carbonyl chloride (54.0 mg, 247 μmol, 94% yield) as a yellow solid.

Step 4. To a solution of 3-(4-(aminomethyl)-2,6-dichlorophenyl) piperidine-2,6-dione (83.3 mg, 257 μmol, 1.00 eq., hydrochloride) in dichloromethane (2 mL) was added diisopropylethylamine (133 mg, 1.03 mmol, 4.00 eq.). The mixture was cooled to 0° C., then 1-(pyridin-4-yl)cyclopentane-1-carbonyl chloride (54.0 mg, 257 μmol, 1.00 eq.) was added. The mixture was stirred at 20° C. for 1 h. The mixture was concentrated under reduced pressure. The crude product was purified via Purification Method 1 to afford N-(3,5-dichloro-4-(2,6-dioxopiperidin-3-yl)benzyl)-1-(pyridin-4-yl)cyclopentane-1-carboxamide (12.64 mg, 25.2 μmol, 9% yield) as a white solid.

$^1$H NMR (400 MHZ, DMSO-$d_6$) δ=10.95 (s, 1H), 8.51 (d, J=6.0 Hz, 2H), 8.27 (t, J=6.0 Hz, 1H), 7.33-7.31 (m, 2H), 7.08 (s, 1H), 7.04 (s, 1H), 4.53 (dd, J=5.6, 12.8 Hz, 1H), 4.19 (d, J=6.0 Hz, 2H), 2.84 (ddd, J=5.6, 14.0, 16.8 Hz, 1H), 2.57-2.54 (m, 1H), 2.30-2.25 (m, 1H), 1.95-1.79 (m, 4H), 1.71-1.54 (m, 5H). MS (ESI) m/z 460.1/462.1 $[M+H]^+$ Exemplary Compound 148

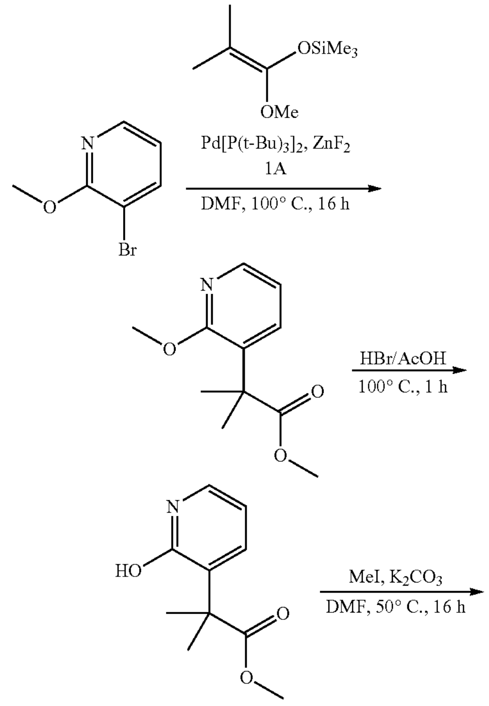

-continued

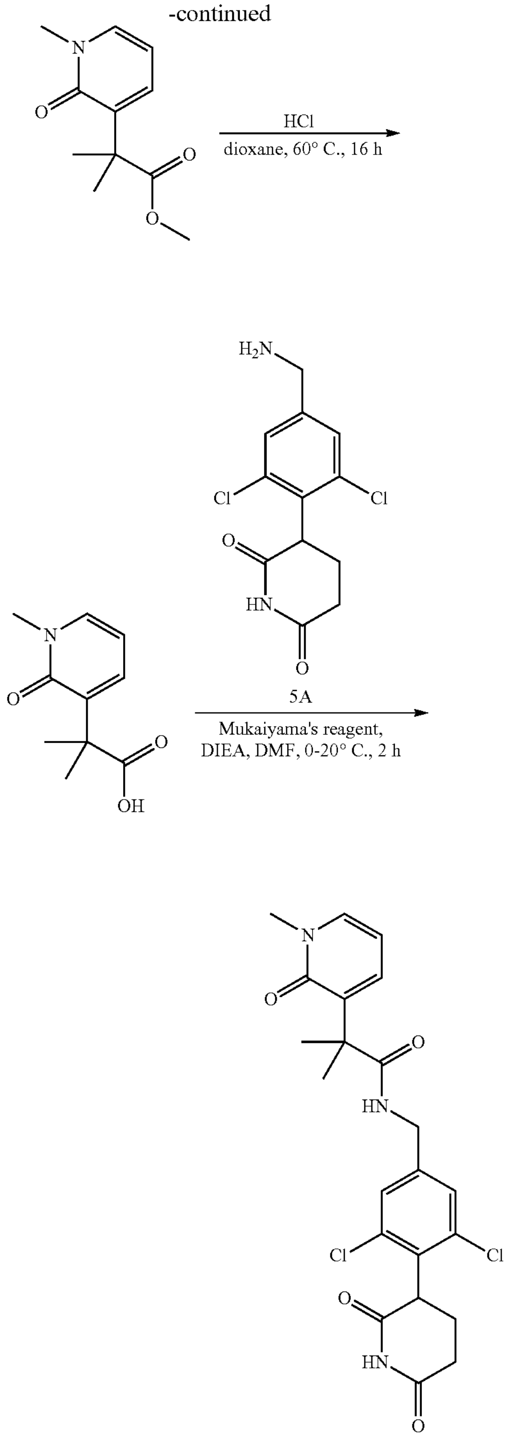

Step 1. A mixture of 3-bromo-2-methoxypyridine (2.00 g, 10.6 mmol, 1.00 eq.), ((1-methoxy-2-methylprop-1-en-1-yl) oxy)trimethylsilane (3.71 g, 21.3 mmol, 2.00 eq.), palladium tri-tert-butylphosphane (544 mg, 1.06 mmol, 0.10 eq.), and zinc (II) fluoride (2.20 g, 21.3 mmol, 2.00 eq.) in N,N-dimethylformamide (10 mL) stirred at 100° C. for 16 h under nitrogen atmosphere. The reaction mixture was cooled to room temperature and filtered through a pad of Celite. The filtrate was diluted with water (50 mL) and extracted with ethyl acetate (3×25 mL). The combined organic layers were washed with brine (25 mL), dried over anhydrous sodium sulfate, filtered, and concentrated under reduced pressure. The residue was purified via Purification Method 2 to afford methyl 2-(2-methoxypyridin-3-yl)-2-methylpropanoate (2.00 g, 9.46 mmol, 89% yield) as a colourless oil.

Step 2. A solution of methyl 2-(2-methoxypyridin-3-yl)-2-methylpropanoate (2.00 g, 9.56 mmol, 1.00 eq.) in hydrogen bromide in acetic acid (10 mL) was stirred at 100° C. for 1 h under nitrogen atmosphere. The mixture was cooled to 25° C., and concentrated under reduced pressure. The residue was diluted with water (5 mL) and the pH of the mixture was adjusted to 7~8 by addition saturated aqueous sodium bicarbonate solution (10 mL). The mixture was extracted with ethyl acetate (3×25 mL). The combined organic layers were washed with brine (20 mL), dried over anhydrous sodium sulfate, filtered, and concentrated under reduced pressure to give methyl 2-(2-hydroxypyridin-3-yl)-2-methylpropanoate (530 mg, 2.69 mmol, 28% yield) as a white solid.

Step 3. To a solution of methyl 2-(2-hydroxypyridin-3-yl)-2-methylpropanoate (900 mg, 4.61 mmol, 1.00 eq.) and potassium carbonate (3.19 g, 23.1 mmol, 5.00 eq.) in N,N-dimethylformamide (2 mL) was added iodomethane (6.54 g, 46.1 mmol, 10.0 eq.). The mixture was stirred at 50° C. for 16 h. The reaction was quenched with water (2 mL) at 25° C., then diluted with water (10 mL) and extracted with ethyl acetate (3×10 mL). The combined organic layers were washed with brine (10 mL), dried over anhydrous sodium sulfate, filtered, and concentrated under reduced pressure. The residue was purified via Purification Method 1 to afford methyl 2-methyl-2-(1-methyl-2-oxo-1,2-dihydropyridin-3-yl) propanoate (416 mg, 1.97 mmol, 43% yield) as a white solid.

Step 4. A solution of methyl 2-methyl-2-(1-methyl-2-oxo-1,2-dihydropyridin-3-yl) propanoate (400 mg, 1.91 mmol, 1.00 eq.) in hydrogen chloride (12 M, 10 mL) and dioxane (10 mL) was stirred at 60° C. for 16 h under nitrogen atmosphere. The mixture was cooled to room temperature and concentrated under reduced pressure to give 2-methyl-2-(1-methyl-2-oxo-1,2-dihydropyridin-3-yl) propanoic acid (370 mg, 1.78 mmol, 93% yield) as a white solid.

Step 5. To a solution of 2-methyl-2-(1-methyl-2-oxo-1,2-dihydropyridin-3-yl) propanoic acid (170 mg, 871 μmol, 1.00 eq.) and N-ethyl-N-isopropylpropan-2-amine (450 mg, 3.48 mmol, 4.00 eq.) in N,N-dimethylformamide (2 mL) was added 2-chloro-1-methyl-pyridin-1-ium iodide (111 mg, 435 μmol, 0.50 eq.) at 0° C. The mixture was stirred at 20° C. for 0.5 h. Then 3-(4-(aminomethyl)-2,6-dichlorophenyl) piperidine-2,6-dione hydrochloride (98.6 mg, 305 μmol, 0.35 eq.) was added. The reaction was stirred at 20° C. for 1.5 h. The mixture was quenched with water (2 mL), then diluted with water (10 mL) and extracted with ethyl acetate (3× 10 mL). The combined organic layers were washed with brine (10 mL), dried over sodium sulfate, filtered, and concentrated under reduced pressure. The residue was purified via Purification Method I to afford N-(3,5-dichloro-4-(2,6-dioxopiperidin-3-yl)benzyl)-2-methyl-2-(1-methyl-2-oxo-1,2-dihydropyridin-3-yl) propanamide (46.2 mg, 98.5 μmol, 11% yield) as a white solid.

$^1$H NMR (400 MHZ, DMSO-$d_6$) δ=10.94 (s, 1H), 7.67-7.59 (m, 2H), 7.46 (d, J=1.6 Hz, 1H), 7.42-7.36 (m, 2H), 6.24 (t, J=6.8 Hz, 1H), 4.56 (dd, J=5.6, 12.8 Hz, 1H), 4.19 (d, J=6.0 Hz, 2H), 3.47 (s, 3H), 2.93-2.79 (m, 1H), 2.59-2.52 (m, 1H), 2.41-2.31 (m, 1H), 1.96-1.85 (m, 1H), 1.39 (s, 6H). MS (ESI) m/z 464.1 $[M+H]^+$

Exemplary Compounds 152 and 153

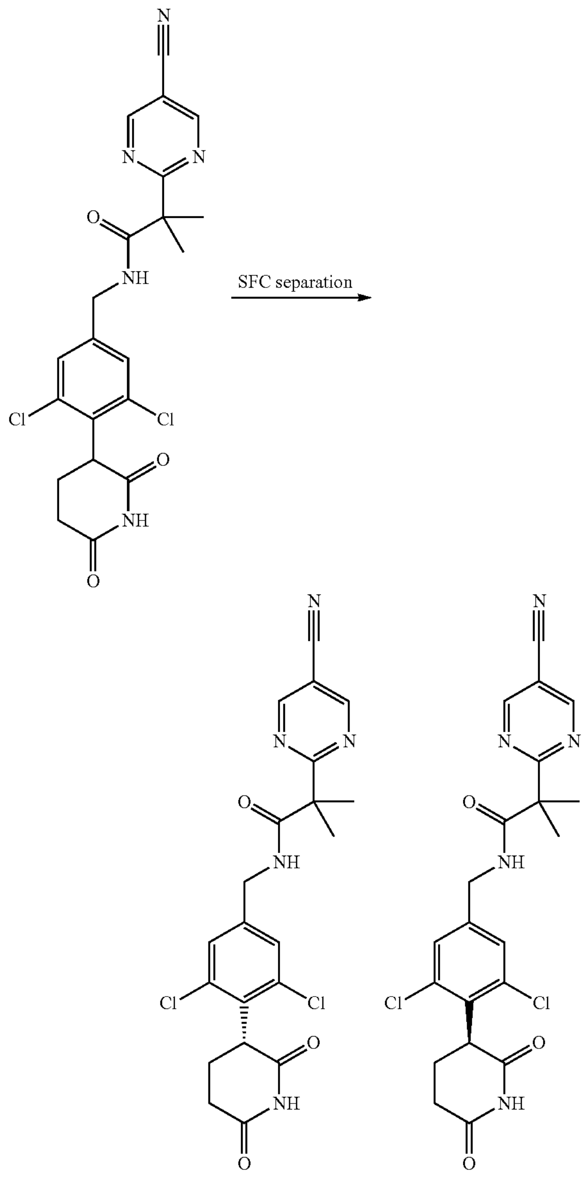

Compound 153 Compound 152

Note: for these enantiomers, their absolute configuration was not determined and was assigned arbitrarily.

2-(5-cyanopyrimidin-2-yl)-N-(3,5-dichloro-4-(2,6-dioxopiperidin-3-yl)benzyl)-2-methylpropanamide (200 mg, 434 μmol, 1.00 eq.) was separated by Chiral SFC (column: DAICEL CHIRALPAK IC (250 mm×30 mm, 10 μm); mobile phase: [carbon dioxide-propan-2-ol/acetonitrile]; B %: 40%, isocratic elution mode) to give two peaks.

Peak one was purified by Prep-HPLC (column: YMC-Actus Triart C 18 150 mm×25 mm×5 um; mobile phase: [water (ammonium bicarbonate)-acetonitrile]; gradient: 25%-55% B over 9 min) and lyophilized to give(S)-2-(5-cyanopyrimidin-2-yl)-N-(3,5-dichloro-4-(2,6-dioxopiperidin-3-yl)benzyl)-2-methylpropanamide (47.8 mg, 102 μmol, 23% yield) as a white solid.

$^{1}$H NMR (400 MHZ, DMSO-$d_6$) δ=10.96 (s, 1H), 9.30 (s, 2H), 8.14 (t, J=6.0 Hz, 1H), 7.35 (s, 1H), 7.29 (s, 1H), 4.57 (dd, J=5.6, 12.8 Hz, 1H), 4.25 (d, J=6.0 Hz, 2H), 2.86 (d, J=5.6, 14.0, 16.8 Hz, 1H), 2.62-2.52 (m, 1H), 2.36 (q, J=4.4, 13.2 Hz, 1H), 1.96-1.82 (m, 1H), 1.57 (s, 6H). MS (ESI) m/z 460.1 $[M+H]^+$

Peak two was lyophilized to give (R)-2-(5-cyanopyrimidin-2-yl)-N-(3,5-dichloro-4-(2,6-dioxopiperidin-3-yl)benzyl)-2-methylpropanamide (58.4 mg, 124 μmol, 28% yield) as a yellow solid.

$^{1}$H NMR (400 MHZ, DMSO-$d_6$) δ=10.96 (s, 1H), 9.30 (s, 2H), 8.13 (t, J=6.0 Hz, 1H), 7.35 (s, 1H), 7.29 (s, 1H), 4.57 (dd, J=5.6, 12.8 Hz, 1H), 4.25 (d, J=6.0 Hz, 2H), 2.86 (d, J=5.6, 14.0, 16.8 Hz, 1H), 2.56 (d, J=1.6 Hz, 1H), 2.36 (dq, J=4.4, 13.2 Hz, 1H), 1.97-1.83 (m, 1H), 1.57 (s, 6H). MS (ESI) m/z 460.1 $[M+H]^+$

Exemplary Compounds 154 and 155

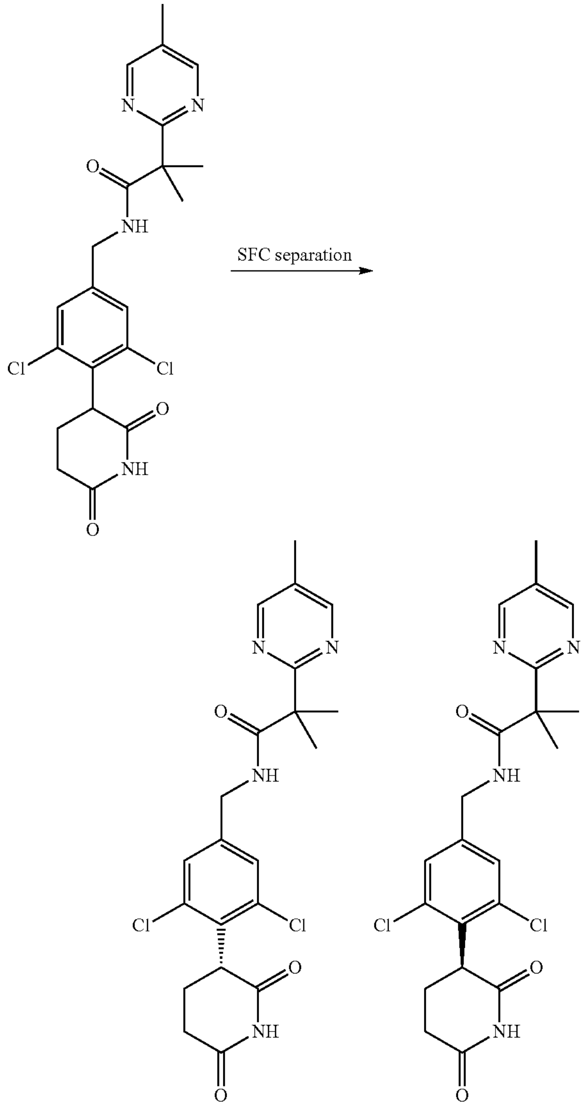

Compound 155 Compound 154

Note: for these enantiomers, their absolute configuration was not determined and was assigned arbitrarily.

N-(3,5-dichloro-4-(2,6-dioxopiperidin-3-yl)benzyl)-2-methyl-2-(5-methylpyrimidin-2-yl) propanamide (600 mg, 1.34 mmol, 1.00 eq.) was separated by Chiral SFC (column:

DAICEL CHIRALCEL OX (250 mm×30 mm, 10 μm); mobile phase: [carbon dioxide-isopropanol/acetonitrile/acetonitrile]; B %: 62.5%, isocratic elution mode) to give two peaks.

Peak one was diluted with water (10 mL) and lyophilized to give(S)—N-(3,5-dichloro-4-(2,6-dioxopiperidin-3-yl) benzyl)-2-methyl-2-(5-methylpyrimidin-2-yl) propanamide (248 mg, 546 μmol, 40% yield) as a white solid.

$^1$H NMR (400 MHZ, DMSO-$d_6$)>=10.94 (s, 1H), 8.64 (s, 2H), 8.02 (t, J=6.0 Hz, 1H), 7.40 (s, 1H), 7.34 (s, 1H), 4.56 (dd, J=5.6, 12.8 Hz, 1H), 4.25 (d, J=6.0 Hz, 2H), 2.86 (ddd, J=5.6, 14.0, 16.8 Hz, 1H), 2.60-2.52 (m, 1H), 2.44-2.31 (m, 1H), 2.27 (s, 3H), 1.95-1.84 (m, 1H), 1.53 (s, 6H). MS (ESI) m/z 449.1 $[M+H]^+$ Peak two was diluted with water (10 mL) and lyophilized to give (R)—N-(3,5-dichloro-4-(2,6-dioxopiperidin-3-yl) benzyl)-2-methyl-2-(5-methylpyrimidin-2-yl) propanamide (232 mg, 513 μmol, 38% yield) as a white solid.

$^1$H NMR (400 MHZ, DMSO-$d_6$) δ=10.95 (s, 1H), 8.64 (s, 2H), 8.03 (t, J=6.0 Hz, 1H), 7.40 (s, 1H), 7.34 (s, 1H), 4.56 (dd, J=5.6, 12.8 Hz, 1H), 4.25 (d, J=6.0 Hz, 2H), 2.94-2.78 (m, 1H), 2.56 (s, 1H), 2.45-2.32 (m, 1H), 2.27 (s, 3H), 1.96-1.82 (m, 1H), 1.53 (s, 6H). MS (ESI) m/z 449.1 $[M+H]^+$

Exemplary Compound 156

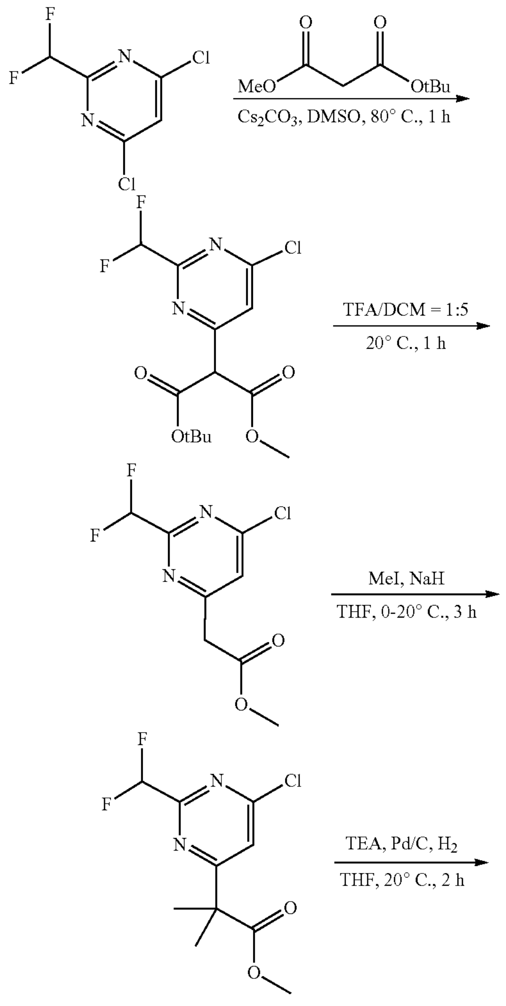

-continued

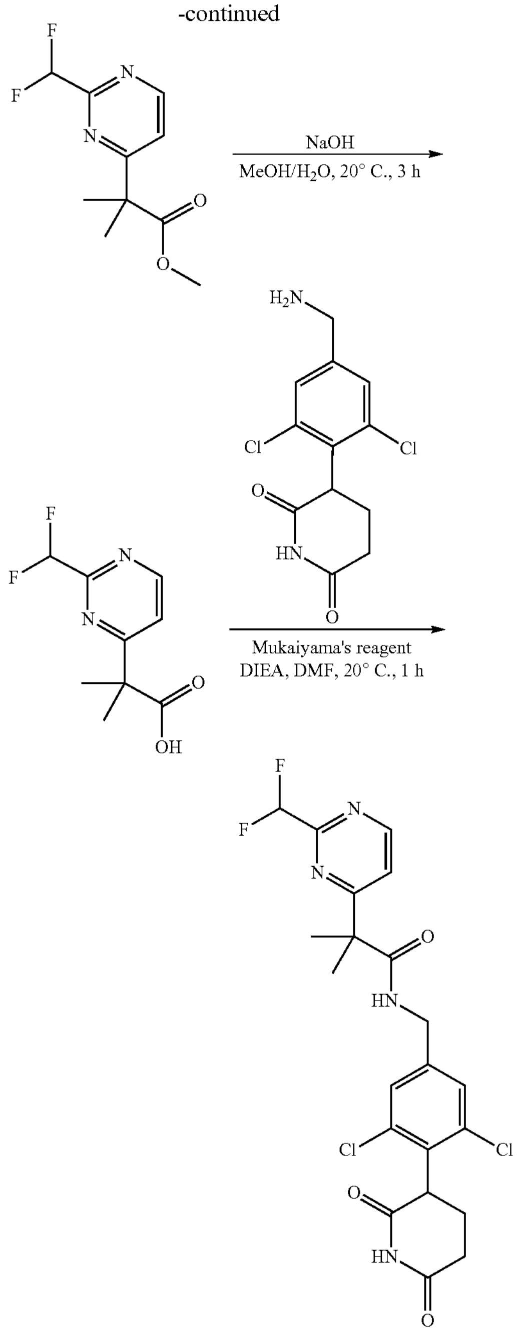

Step 1. To a solution of 4,6-dichloro-2-(difluoromethyl) pyrimidine (2.00 g, 10.0 mmol, 1.00 eq.) in dimethylsulfoxide (40 mL) was added caesium carbonate (6.50 g, 19.9 mmol, 1.98 eq.) and tert-butyl methyl malonate (2.10 g, 12.0 mmol, 1.20 eq.). The mixture was stirred at 80° C. for 1 h. The reaction mixture was diluted with water (40 mL) and extracted with ethyl acetate (2× 40 mL). The combined organic extracts were washed with brine (60 mL), dried over sodium sulfate, filtered, and concentrated under reduced pressure. The residue was purified via Purification Method 2 to afford 1-(tert-butyl) 3-methyl 2-(6-chloro-2-(difluoromethyl)pyrimidin-4-yl) malonate (2.94 g, 7.86 mmol, 78% yield) as a white solid.

Step 2. To a solution of 1-(tert-butyl) 3-methyl 2-(6-chloro-2-(difluoromethyl)pyrimidin-4-yl) malonate (2.94 g, 8.73 mmol, 1.00 eq.) in dichloromethane (50 mL) was added trifluoroacetic acid (10 mL). The mixture was stirred at 20° C. for 1 h. The mixture was concentrated under reduced pressure. The residue was purified via Purification Method 2 to afford methyl 2-(6-chloro-2-(difluoromethyl)pyrimidin-4-yl)acetate (1.74 g, 7.13 mmol, 81% yield) as a colourless oil.

Step 3. To a solution of methyl 2-(6-chloro-2-(difluoromethyl)pyrimidin-4-yl)acetate (1.64 g, 6.93 mmol, 1.00 eq.) in tetrahydrofuran (50 mL) was added sodium hydride (1.11 g, 27.7 mmol, 60% purity, 4.00 eq.) in portions at 0° C. under nitrogen atmosphere. The mixture was stirred at 20° C. for 30 min. Then iodomethane (1.50 mL, 24.1 mmol, 3.48 eq.) was added at 0° C., and the reaction was stirred at 0° C. for 2.5 h. The reaction mixture was added dropwise to water (100 mL) at 0° C.

Then the mixture was extracted with ethyl acetate (3×100 mL). The combined organic layers were washed with brine (150 mL), dried over sodium sulfate, filtered, and concentrated under reduced pressure. The residue was purified via Purification Method 2 to afford methyl 2-(6-chloro-2-(difluoromethyl)pyrimidin-4-yl)-2-methylpropanoate (1.20 g, 4.08 mmol, 59% yield) as a colourless oil.

Step 4. Palladium on carbon (600 mg, 10% purity) was added to the flask under nitrogen atmosphere. A solution of methyl 2-(6-chloro-2-(difluoromethyl)pyrimidin-4-yl)-2-methylpropanoate (1.20 g, 4.53 mmol, 1.00 eq.) and triethylamine (1.00 mL, 7.18 mmol, 1.58 eq.) in ethanol (25 mL) was added to the flask. The mixture was stirred under hydrogen atmosphere (15 psi) at 20° C. for 2 h. The reaction mixture was filtered, and the filtrate was concentrated under reduced pressure. The residue was purified via Purification Method 2 to afford methyl 2-(2-(difluoromethyl)pyrimidin-4-yl)-2-methylpropanoate (450 mg, 1.90 mmol, 42% yield) as a colourless oil.

Step 5. To a solution of methyl 2-(2-(difluoromethyl)pyrimidin-4-yl)-2-methylpropanoate (400 mg, 1.74 mmol, 1.00 eq.) in methanol (5 mL) was added sodium hydroxide (347 mg, 8.69 mmol, 5.00 eq.) in water (0.5 mL). The reaction was stirred at 20° C. for 3 h. The mixture was diluted with water (10 mL) and dichloromethane (10 mL). The aqueous phase was separated and washed with dichloromethane (10 mL). The aqueous phase was adjusted to pH ~4 with hydrochloric acid (1 M) and extracted with dichloromethane (3×10 mL). The combined organic extracts were washed with brine (30 mL) and dried over sodium sulfate, filtered, and concentrated under reduced pressure to give 2-(2-(difluoromethyl)pyrimidin-4-yl)-2-methylpropanoic acid (350 mg, 1.30 mmol, 74% yield) as a white gum.

Step 6. To a solution of 2-(2-(difluoromethyl)pyrimidin-4-yl)-2-methylpropanoic acid (120 mg, 555 μmol, 1.50 eq.) in dimethylformamide (8 mL) was added N,N-diisopropylethylamine (200 μL, 1.15 mmol, 3.10 eq.) and 2-chloro-1-methyl-pyridin-1-ium iodide (120 mg, 469 μmol, 1.27 eq.). The mixture was stirred at 20° C. for 0.5 h. Then 3-(4-(aminomethyl)-2,6-dichlorophenyl) piperidine-2,6-dione hydrochloride (120 mg, 370 μmol, 1.00 eq.) was added, and the reaction was stirred at 20° C. for 0.5 h. The reaction mixture was diluted with water (20 mL) and extracted with ethyl acetate (2×20 mL). The combined organic extracts were washed with brine (30 mL). The organic phase was dried over sodium sulfate, filtered, and concentrated under reduced pressure. The residue was purified via Purification Method 1 to afford N-(3,5-dichloro-4-(2,6-dioxopiperidin-3-yl)benzyl)-2-(2-(difluoromethyl)pyrimidin-4-yl)-2-methylpropanamide (127.36 mg, 259 μmol, 70% yield) as a white solid.

Exemplary Compound 166

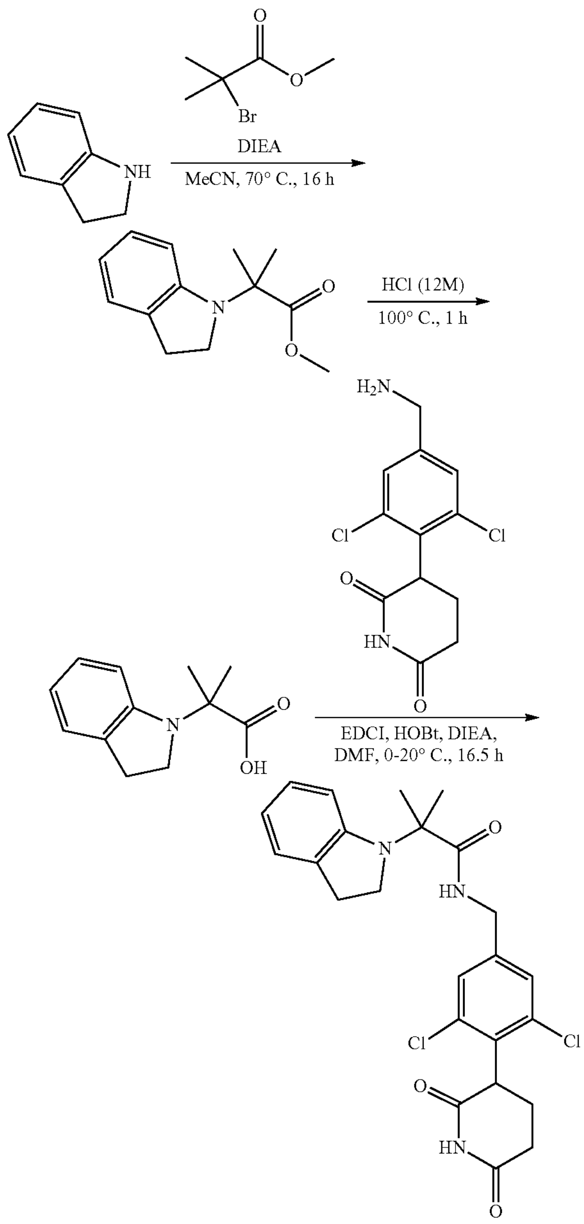

Step 1. To a solution of indoline (5.00 g, 42.0 mmol, 4.70 mL, 1.00 eq.) in acetonitrile (50 mL) was added N-ethyl-N-isopropylpropan-2-amine (13.6 g, 105 mmol, 18.3 mL, 2.50 eq.) and methyl 2-bromo-2-methyl-propanoate (9.11 g, 50.4 mmol, 6.52 mL, 1.20 eq.). The mixture was stirred at 70° C. for 16 h. The mixture was cooled to 25° C., and concentrated under reduced pressure. The residue was diluted with water (50 mL) and extracted with ethyl acetate (3×50 mL). The combined organic layers were washed with brine (50 mL), dried over sodium sulfate, filtered, and concentrated under reduced pressure to give a residue. The residue was via Purification Method 2 to afford methyl 2-(indolin-1-yl)-2-methylpropanoate (420 mg, 1.84 mmol, 4% yield) as a colourless oil.

Step 2. A solution of methyl 2-(indolin-1-yl)-2-methylpropanoate (250 mg, 1.14 mmol, 1.00 eq.) in hydrochloric acid (12.0 M, 3 mL) was stirred at 100° C. for 1 h under nitrogen atmosphere. The mixture was concentrated under reduced pressure to afford 2-indolin-1-yl-2-methyl-propanoic acid (440 mg, 943 μmol, 83% yield) as a brown oil.

Step 3. To a solution of 2-indolin-1-yl-2-methyl-propanoic acid (400 mg, 857 μmol, 1.00 eq.) in dimethyl formamide (3 mL) were added 1-(3-dimethylaminopropyl)-3-ethylcarbodiimide hydrochloride (197 mg, 1.03 mmol, 1.20 eq.), 1-hydroxybenzotriazole (139 mg, 1.03 mmol, 1.20 eq.) and N-ethyl-N-isopropylpropan-2-amine (443 mg, 3.43 mmol, 597 μL, 4.00 eq.) at 0° C. The mixture was stirred at 0° C. for 30 min. Then 3-(4-(aminomethyl)-2,6-dichlorophenyl) piperidine-2,6-dione hydrochloride (166 mg, 514 μmol, 0.600 eq.) was added, and the reaction was stirred at 20° C. for 16 h. The reaction was quenched with water (12 mL) and extracted with ethyl acetate (3× 10 mL). The combined organic layers were washed with brine (10 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-(indolin-1-yl)-2-methylpropanamide (112 mg, 234 μmol, 27% yield) as a pink solid.

Exemplary Compound 169

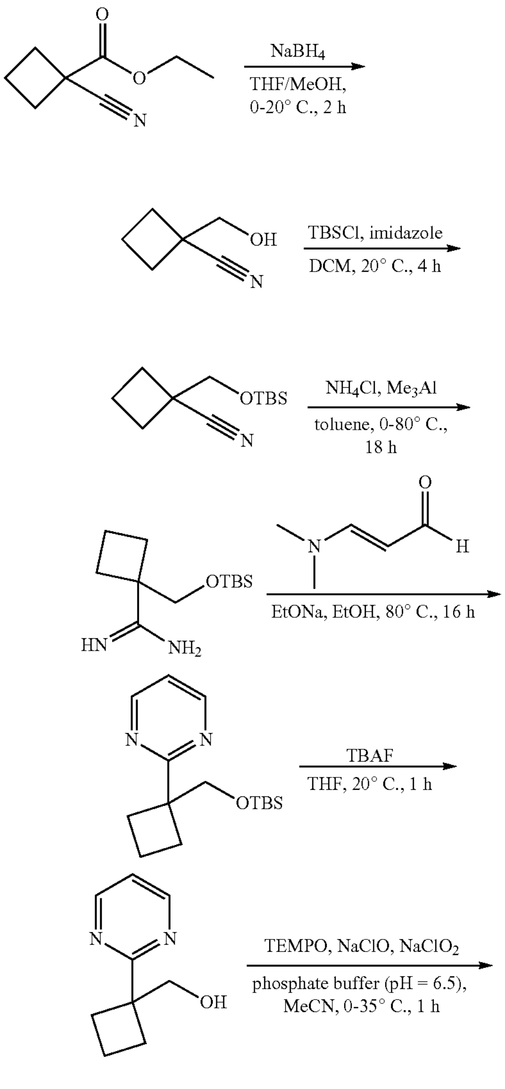

-continued

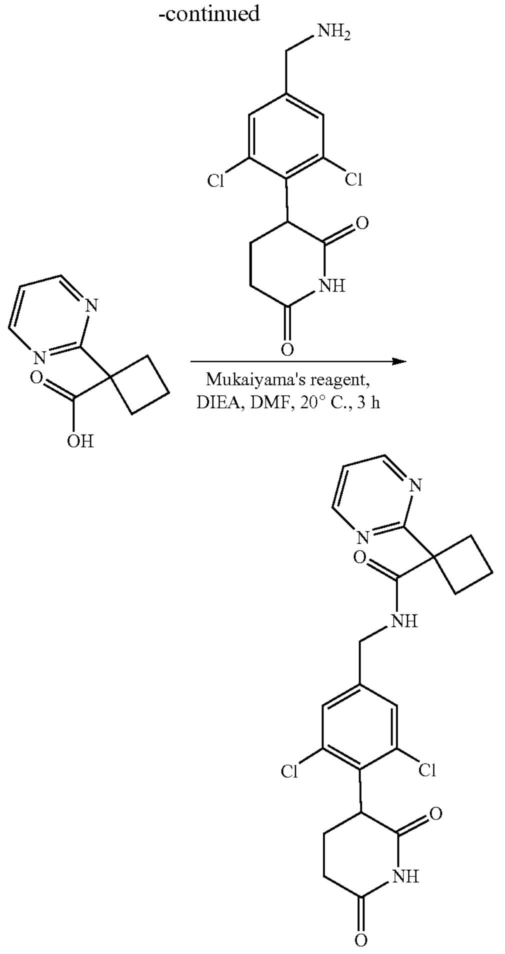

Step 1. To a solution of ethyl 1-cyanocyclobutane-1-carboxylate (5.00 g, 32.6 mmol, 1.00 eq.) in tetrahydrofuran (80 mL) and methanol (20 mL) was added sodium borohydride (2.61 g, 69.0 mmol, 2.11 eq.) at 0° C. under nitrogen atmosphere. The reaction was stirred at 20° C. for 2 h. The reaction was quenched with water (50 mL) and extracted with ethyl acetate (2× 50 mL). The combined organic extracts were washed with brine (80 mL) and dried over sodium sulfate, filtered, and concentrated under reduced pressure to give 1-(hydroxymethyl)cyclobutane-1-carbonitrile (2.7 g, 24.29 mmol, 74% yield) as a colourless oil.

Step 2. To a solution of 1-(hydroxymethyl)cyclobutane-1-carbonitrile (2.70 g, 24.3 mmol, 1.00 eq.) in dichloromethane (60 mL) was added imidazole (3.31 g, 48.6 mmol, 2.00 eq.) and tert-butylchlorodimethylsilane (4.77 g, 31.6 mmol, 1.30 eq.). The mixture was stirred at 20° C. for 4 h. The reaction mixture was diluted with water (100 mL) and extracted with ethyl acetate (2×150 mL). The combined organic extracts were washed with brine (200 mL). The organic phase was dried over sodium sulfate, filtered, and concentrated under reduced pressure. The residue was purified via Purification Method 2 to afford 1-(((tert-butyldimethylsilyl)oxy)methyl)cyclobutane-1-carbonitrile (3.70 g, 16.4 mmol, 67% yield) as a colourless oil.

Step 3. To a solution of ammonium chloride (1.58 g, 29.5 mmol, 1.80 eq.) in toluene (50 mL) was added trimethylaluminum (2 M in toluene, 14.6 mL, 1.78 eq.) dropwise at 0° C. under nitrogen. The reaction was stirred at 20 ° C. for 2 h, then 1-(((tert-butyldimethylsilyl)oxy)methyl)cyclobutane-1-carbonitrile (3.70 g, 16.4 mmol, 1.00 eq.) dissolved in toluene (10 mL) was added at 20° C. The reaction was stirred at 80° C. for 16 h under nitrogen atmosphere. The reaction mixture was added dropwise to methanol (100 mL) at 0° C. The mixture was filtered, and the filtrate was concentrated under vacuum. The residue was triturated with ethyl acetate/petroleum ether=1/1 (60 mL) for 60 min at 20° C. Then the mixture was filtered, and the filter cake was dried under vacuum to give 1-(((tert-butyldimethylsilyl) oxy)-methyl)cyclobutane-1-carboximidamide (2.00 g, 8.25 mmol, 50% yield) as a white solid.

Step 4. To a solution of 1-(((tert-butyldimethylsilyl)oxy) methyl)cyclobutane-1-carboximidamide (1.90 g, 7.84 mmol, 1.00 eq.) and (E)-3-(dimethylamino) acrylaldehyde (1.90 g, 19.1 mmol, 2.45 eq.) in ethanol (30 mL) was added sodium ethanolate (3.23 g, 47.4 mmol, 6.06 eq.). The mixture was stirred at 80° C. for 16 h. The reaction mixture was diluted with water (50 mL) and extracted with ethyl acetate (2×50 mL). The combined organic extracts were washed with brine (60 mL). The organic phase was dried over sodium sulfate, filtered, and concentrated under reduced pressure. The residue was purified by flash silica gel chromatography (eluent of 0~30% ethyl acetate/petroleum ether) to give 2-(1-(((tert-butyldimethylsilyl)oxy)methyl)-cyclobutyl)pyrimidine (480 mg, 1.55 mmol, 19% yield) as a yellow oil.

Step 5. To a solution of 2-(1-(((tert-butyldimethylsilyl) oxy)methyl)cyclobutyl)pyrimidine (400 mg, 1.44 mmol, 1.00 eq.) in tetrahydrofuran (10 mL) was added tetrabutylammonium fluoride (1 M in tetrahydrofuran, 5.00 mL, 3.48 eq.). The mixture was stirred at 20° C. for 1 h. The reaction mixture was diluted with water (20 mL) and extracted with ethyl acetate (2×20 mL). The combined organic extracts were washed with brine (40 mL). The organic phase was dried over sodium sulfate, filtered, and concentrated under reduced pressure. The residue was purified via Purification Method 2 to afford (1-(pyrimidin-2-yl)cyclobutyl) methanol (150 mg, 904 μmol, 63% yield) a colourless oil.

Step 6. To a solution of (1-pyrimidin-2-ylcyclobutyl) methanol (80.0 mg, 487 μmol, 1.00 eq.) in acetonitrile (1.5 mL) and phosphate buffer (1.5 mL) (PH=6.5) was added 2,2,6,6-tetramethylpiperidine 1-oxyl free radical (80.0 mg, 508 μmol, 1.04 eq.) followed by a solution of sodium chlorite (90.0 mg, 995 μmol, 2.04 eq.) in water (0.3 mL) and sodium hypochlorite (620 μL, 502 μmol, 5% purity, 1.03 eq.) in portions at 0° C. The mixture was stirred at 35° C. for 1 h.

The mixture was diluted with water (10 mL) and ethyl acetate (10 mL). The aqueous phase was separated and washed with ethyl acetate (10 mL). The aqueous phase was adjusted to pH 3-4 with hydrochloric acid (1 M) and extracted with ethyl acetate (3× 10 mL). The combined organic layers were dried over sodium sulfate, filtered, and concentrated under reduced pressure to give 1-(pyrimidin-2-yl)cyclobutane-1-carboxylic acid (80.0 mg, 449 μmol, 92% yield) as a yellow oil.

Step 7. To a solution of 1-(pyrimidin-2-yl)cyclobutane-1-carboxylic acid (120 mg, 673 μmol, 1.00 eq.) in dimethylformamide (4 mL) were added N,N-diisopropylethylamine (360 μL, 2.07 mmol, 3.07 eq.) and 2-chloro-1-methylpyridin-1-ium iodide (206 mg, 806 μmol, 1.20 eq.). The mixture was stirred at 20° C. for 0.5 h. Then 3-(4-(aminomethyl)-2,6-dichlorophenyl) piperidine-2,6-dione hydrochloride (150 mg, 463 μmol, 0.70 eq.) was added, and the reaction was stirred at 20° C. for 2.5 h. The reaction mixture was diluted with water (20 mL) and extracted with ethyl acetate (2×20 mL). The combined organic extracts were washed with brine (30 mL), dried over sodium sulfate, filtered, and concentrated under reduced pressure. The residue was purified via Purification Method 1 to afford N-(3,5-dichloro-4-(2,6-dioxopiperidin-3-yl)benzyl)-1-(pyrimidin-2-yl)cyclobutane-1-carboxamide (97.16 mg, 206 μmol, 30% yield) as a white solid.

Exemplary Compound 170

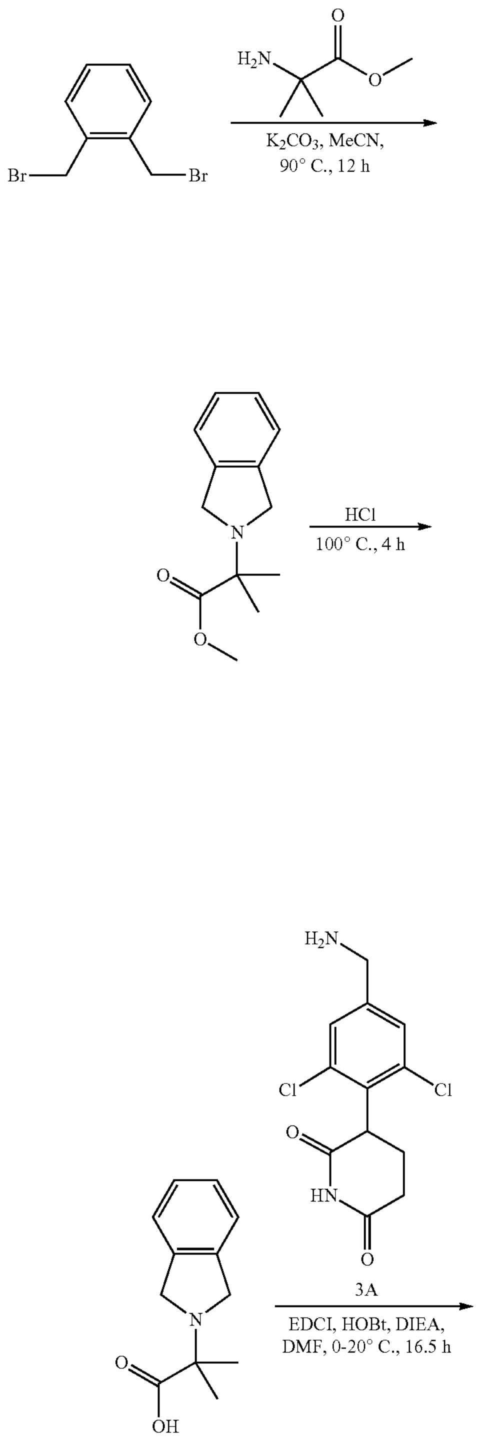

-continued

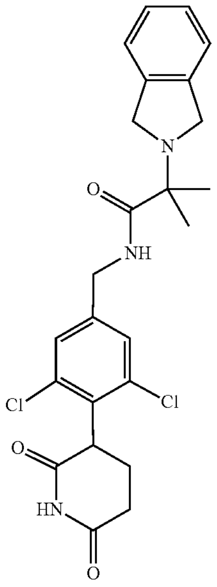

Step 1. To a solution of 1,2-bis(bromomethyl)benzene (1.00 g, 3.79 mmol, 1.00 eq.) and methyl 2-amino-2-methylpropanoate (489 mg, 4.17 mmol, 1.10 eq.) in acetonitrile (20 mL) was added potassium carbonate (1.60 g, 11.6 mmol, 3.06 eq.). The reaction was stirred at 90° C. for 12 h. The mixture was filtered, and the filtrate concentrated under reduced pressure. The crude product was purified via Purification Method 2 to afford methyl 2-(isoindolin-2-yl)-2-methylpropanoate (1.57 g, 5.94 mmol, 78% yield) as a colourless oil.

Step 2. A solution of methyl 2-(isoindolin-2-yl)-2-methylpropanoate (300 mg, 1.37 mmol, 1.00 eq.) in concentrated hydrochloric acid (6 mL, 12 M) was stirred at 100° C. for 4 h. The mixture was concentrated under reduced pressure to give 2-(isoindolin-2-yl)-2-methylpropanoic acid (390 mg, crude) as a yellow solid.

Step 3. To a solution of 2-(isoindolin-2-yl)-2-methylpropanoic acid (195 mg, 950 μmol, 1.54 eq.) in N,N-dimethylformamide (5 mL) were added 1-(3-dimethylaminopropyl)-3-ethylcarbodiimide hydrochloride (143 mg, 746 μmol, 1.21 eq.), 1-hydroxybenzotriazole (102 mg, 755 μmol, 1.22 eq.)

and N,N-diisopropylethylamine (440 μL, 2.53 mmol, 4.09 eq.) at 0° C. The mixture was stirred at 20° C. for 0.5 h. 3-(4-(aminomethyl)-2,6-dichlorophenyl) piperidine-2,6-dione hydrochloride (200 mg, 618 μmol, 1.00 eq.) was added, and the reaction was stirred at 20° C. for 16 h. The reaction mixture was diluted with water (15 mL) and extracted with ethyl acetate (2×10 mL). The combined organic layers were dried over sodium sulfate, filtered, and concentrated under reduced pressure. The residue was purified via Purification Method 1 to afford N-(3,5-dichloro-4-(2,6-dioxopiperidin-3-yl)benzyl)-2-(isoindolin-2-yl)-2-methylpropanamide (182 mg, 379 μmol, 61% yield) as a white solid.

Exemplary Compound 177

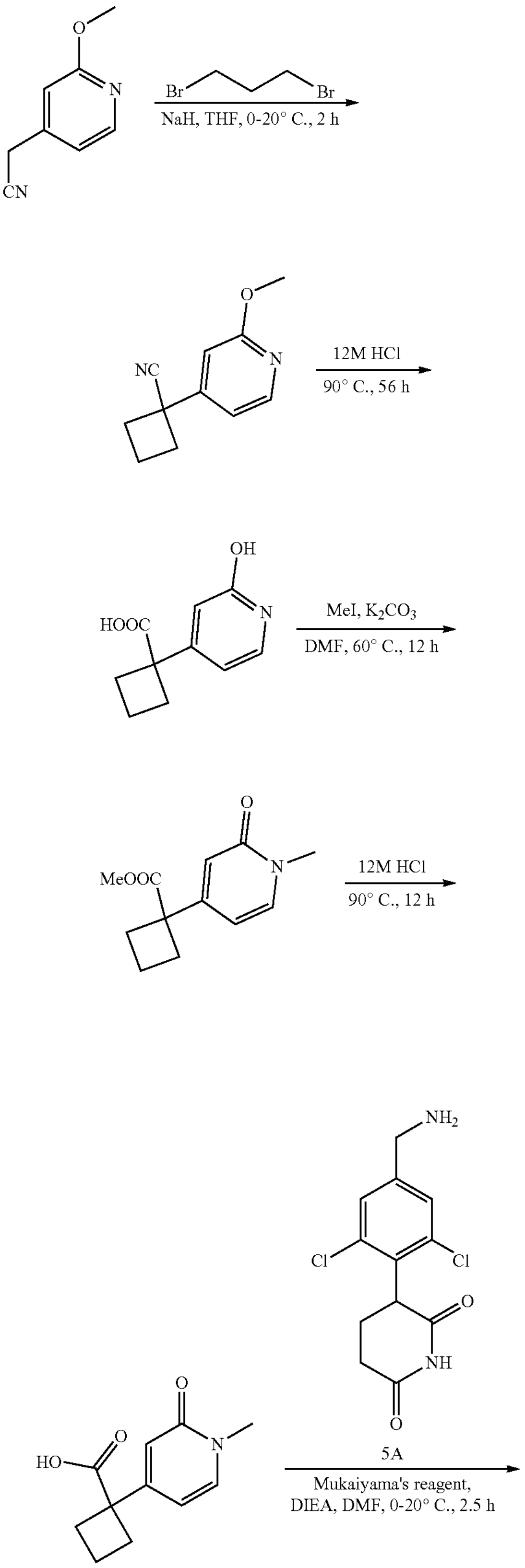

-continued

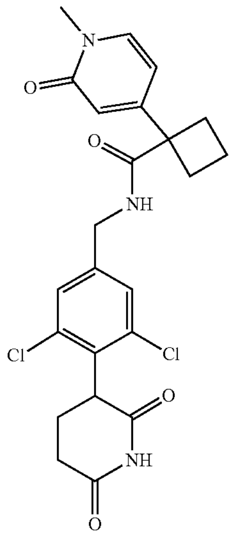

Step 1. To a solution of 2-(2-methoxypyridin-4-yl) acetonitrile (1.20 g, 8.10 mmol, 1.00 eq.) and 1,3-dibromopropane (1.46 g, 7.25 mmol, 0.90 eq.) in tetrahydrofuran (20 mL) was added sodium hydride (810 mg, 20.3 mmol, 60% purity, 2.50 eq.) at 0° C. under nitrogen atmosphere. The reaction was stirred at 0° C. for 30 min and then at 20° C. for 1.5 h. The reaction mixture was quenched with saturated ammonium chloride solution (20 mL) at 0° C. The mixture was diluted with ethyl acetate (20 mL) and water (10 mL). The layers were separated, and the aqueous phase was extracted with ethyl acetate (2×15 mL). The combined organic layers were washed with brine (30 mL) and dried over anhydrous sodium sulfate, filtered, and concentrated in vacuo. The residue was purified via Purification Method 2 to afford 1-(2-methoxypyridin-4-yl)cyclobutane-1-carbonitrile (670 mg, 3.52 mmol, 44% yield) as a colourless oil.

Step 2. A mixture of 1-(2-methoxypyridin-4-yl)cyclobutane-1-carbonitrile (200 mg, 1.06 mmol, 1.00 eq.) in concentrated hydrochloric acid (12 M, 10 mL) was stirred at 90° C. for 56 h. The reaction mixture was concentrated in vacuo. The residue was purified via Purification Method 2 to afford 1-(2-hydroxypyridin-4-yl)cyclobutane-1-carboxylic acid (120 mg, 559 μmol, 53% yield) as a white solid.

Step 3. To a solution of 1-(2-hydroxypyridin-4-yl)cyclobutane-1-carboxylic acid (110 mg, 531 μmol, 1.00 eq.) in dimethylformamide (2 mL) were added potassium carbonate (220 mg, 1.59 mmol, 3.00 eq.) and iodomethane (377 mg, 2.65 mmol, 5.00 eq.). The reaction was stirred at 60° C. for 12 h. The reaction mixture was diluted with ethyl acetate (10 mL) and water (5 mL). The layers were separated, and the aqueous phase was extracted with ethyl acetate (2× 8 mL). The combined organic layers were washed with brine (15 mL), dried over anhydrous sodium sulfate, filtered, and concentrated in vacuo. The residue was purified via Purification Method 2 to afford methyl 1-(1-methyl-2-oxo-1,2-dihydropyridin-4-yl)cyclobutane-1-carboxylate (110 mg, 492 μmol, 93% yield) as a yellow oil.

Step 4. A mixture of methyl 1-(1-methyl-2-oxo-1,2-dihydropyridin-4-yl)cyclobutane-1-carboxylate (100 mg, 452 μmol, 1.00 eq.) in hydrochloric acid (12 M, 2.00 mL) was stirred at 90° C. for 12 h. The reaction mixture was concentrated in vacuo to afford 1-(1-methyl-2-oxo-1,2-dihydropyridin-4-yl)cyclobutane-1-carboxylic acid (90 mg, crude) as a yellow oil.

Step 5. To a solution of 1-(1-methyl-2-oxo-1,2-dihydropyridin-4-yl)cyclobutane-1-carboxylic acid (90.0 mg, 434 μmol, 1.00 eq.) and N,N-diisopropylethylamine (168 mg, 1.30 mmol, 3.00 eq.) in dimethylformamide (2 mL) was added 2-chloro-1-methyl-pyridin-1-ium iodide (133 mg, 521 μmol, 1.20 eq.) at 0° C. The reaction was stirred at 15° C. for 0.5 h. Then 3-(4-(aminomethyl)-2,6-dichlorophenyl)piperidine-2,6-dione (100 mg, 348 μmol, 0.80 eq.) was added, and the reaction was stirred at 20° C. for 2 h. The reaction mixture was diluted with ethyl acetate (8 mL) and water (5 mL). The layers were separated, and the aqueous phase was extracted with ethyl acetate (2× 5 mL). The combined organic layers were washed with brine (15 mL), dried over anhydrous sodium sulfate, filtered, and concentrated in vacuo. The residue was purified via Purification Method I to afford (56.25 mg, 115 μmol, 26% yield) as a white solid.

Exemplary Compounds 179 and 180

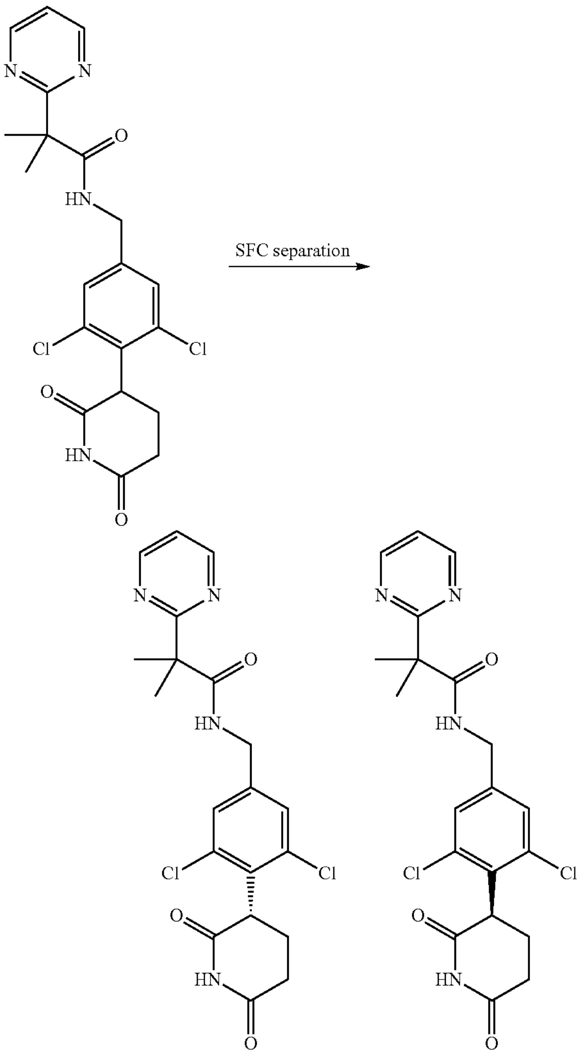

Compound 179 Compound 180

Note: for these enantiomers, their absolute configuration was not determined and was assigned arbitrarily.

N-(3,5-dichloro-4-(2,6-dioxopiperidin-3-yl)benzyl)-2-methyl-2-(pyrimidin-2-yl) propanamide (500 mg, 1.15 mmol, 1.00 eq.) was separated by Chiral SFC (column: DAICEL CHIRALCEL OX (250 mm×30 mm, 10 μm); mobile phase: [carbon dioxide-isopropanol/acetonitrile]; B %: 50%, isocratic elution mode) to give two peaks.

Peak one was further purified by Prep-HPLC (column: YMC-Actus Triart C 18 150×30 mm×7 μm; mobile phase: [water (formic acid)-acetonitrile]; gradient: 30%-60% B over 10 min) and lyophilized to give (R)—N-(3,5-dichloro-4-(2,6-dioxopiperidin-3-yl)benzyl)-2-methyl-2-(pyrimidin-2-yl) propanamide (198.35 mg, 451 μmol, 39% yield) as a white solid.

$^1$H NMR (400 MHZ, DMSO-$d_6$) δ=10.95 (s, 1H), 8.86-8.75 (m, 2H), 8.10-8.07 (t, J=6.0 Hz, 1H), 7.43-7.39 (m, 2H), 7.36 (s, 1H), 4.59-4.54 (dd, J=5.6, 12.8 Hz, 1H), 4.26 (d, J=6.0 Hz, 2H), 2.90-2.81 (ddd, J=5.6, 14.0, 16.8 Hz, 1H), 2.56 (m, 1H), 2.42-2.31 (dq, J=4.4, 13.2 Hz, 1H), 1.92-1.87 (m, 1H), 1.55 (s, 6H). MS (ESI) m/z 435.2 $[M+H]^+$ Peak two was further purified by Prep-HPLC (column: YMC-Actus Triart C 18 150×30 mm×7 μm; mobile phase: [water (formic acid)-acetonitrile]; gradient: 28%-58% B over 10 min) and lyophilized to give(S)—N-(3,5-dichloro-4-(2,6-dioxopiperidin-3-yl)benzyl)-2-methyl-2-(pyrimidin-2-yl) propanamide (211.63 mg, 481 μmol, 42% yield) as a white solid.

$^1$H NMR (400 MHZ, DMSO-$d_6$) δ=10.96 (s, 1H), 8.92-8.70 (m, 2H), 8.11-8.08 (t, J=6.0 Hz, 1H), 7.43-7.39 (m, 2H), 7.37 (s, 1H), 4.59-4.54 (dd, J=5.6, 12.8 Hz, 1H), 4.26 (d, J=6.0 Hz, 2H), 2.90-2.81 (m, 1H), 2.56 (m, 1H), 2.42-2.31 (dq, J=4.4, 13.2 Hz, 1H), 1.92-1.87 (m, 1H), 1.55 (s, 6H). MS (ESI) m/z 435.1 $[M+H]^+$

Exemplary Compound 181

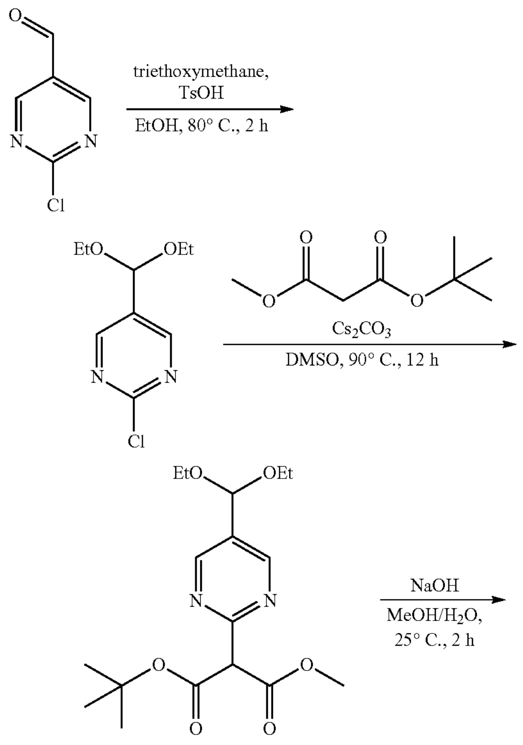

-continued

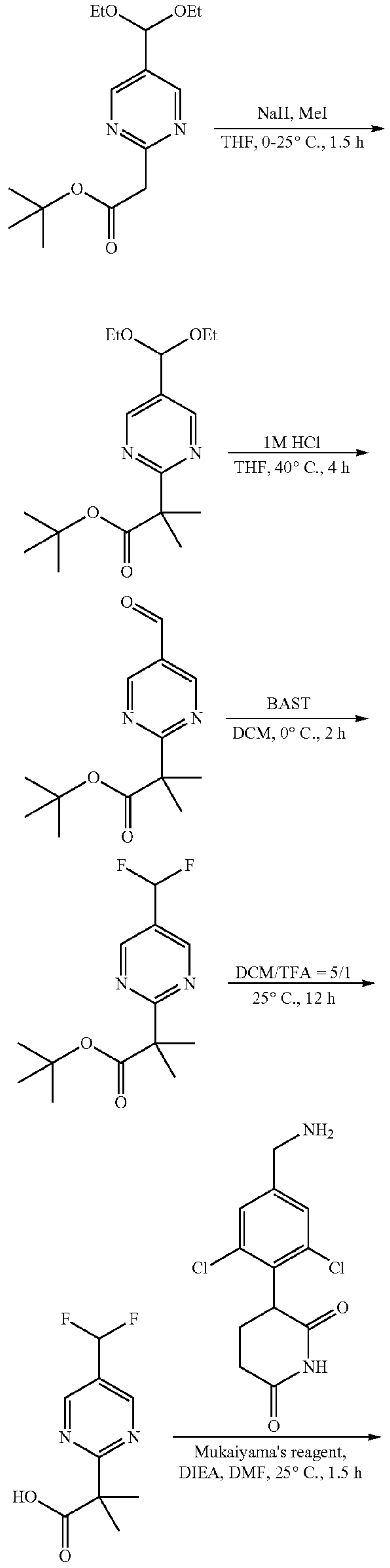

-continued

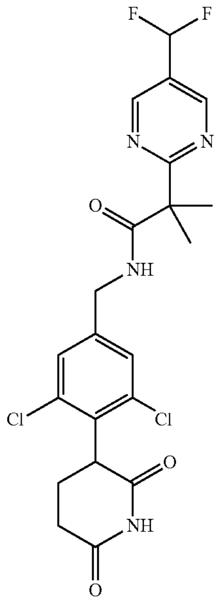

Step 1. To a solution of 2-chloropyrimidine-5-carbaldehyde (10.0 g, 70.2 mmol, 1.00 eq.) and 4-methylbenzenesulfonic acid (1.33 g, 7.02 mmol, 0.10 eq.) in ethanol (180 mL) was added triethoxymethane (40.8 mL, 246 mmol, 3.50 eq.). The mixture was stirred at 80° C. for 2 h under nitrogen atmosphere. After cooling to room temperature, the reaction mixture was added to saturated sodium bicarbonate solution (30 mL) at 0° C., and then concentrated under reduced pressure to remove ethanol. The residue was extracted with ethyl acetate (4×40 mL). The combined organic layers were dried over sodium sulfate, filtered, and concentrated under reduced pressure. The residue was via Purification Method 2 to afford 2-chloro-5-(diethoxymethyl)pyrimidine (15.3 g, 69.4 mmol, 99% yield) as a colourless oil.

Step 2. To a solution of 2-chloro-5-(diethoxymethyl) pyrimidine (15.3 g, 70.8 mmol, 1.00 eq.) in dimethyl sulfoxide (80 mL) was added caesium carbonate (57.7 g, 177 mmol, 2.50 eq.) in one portion at 25° C. Then tert-butyl methyl malonate (12.0 mL, 70.8 mmol, 1.00 eq.) was added dropwise to the mixture. The mixture was stirred at 90° C. for 12 h. The mixture was diluted with water (100 mL) and extracted with ethyl acetate (100 mL). The combined organic layers were washed with water (2×100 mL) and brine (100 mL), dried over sodium sulfate, filtered, and concentrated under reduced pressure. The residue was purified via Purification Method 2 to afford 1-(tert-butyl) 3-methyl 2-(5-(diethoxymethyl)-pyrimidin-2-yl) malonate (19.0 g, 42.9 mmol, 61% yield) as a yellow oil.

Step 3. To a solution of 1-(tert-butyl) 3-methyl 2-(5-(diethoxymethyl)pyrimidin-2-yl) malonate (19.0 g, 53.6 mmol, 1.00 eq.) in methanol (60 mL) and water (30 mL) was added sodium hydroxide (4.29 g, 107 mmol 2.00 eq.) at 25° C. The mixture was stirred at 25° C. for 2 h. The pH of the mixture was adjusted to 6 with 2M hydrochloric acid. The mixture was extracted with ethyl acetate (4× 80 mL). The combined organic layers were dried over sodium sulfate, filtered, and concentrated under reduced pressure. The residue was purified via Purification Method 2 to afford tert-butyl 2-(5-(diethoxymethyl)pyrimidin-2-yl)acetate (10.0 g, 30.4 mmol, 57% yield) as a yellow oil.

Step 4. To a solution of tert-butyl 2-(5-(diethoxymethyl) pyrimidin-2-yl)acetate (10.0 g, 33.7 mmol, 1.00 eq.) in tetrahydrofuran (100 mL) was added sodium hydride (3.70 g, 92.5 mmol, 60% purity, 2.74 eq.) at 0° C. under nitrogen atmosphere. After addition, the mixture was stirred at 25° C. for 30 min. Then methyl iodide (8.00 mL, 129 mmol, 3.81 eq.) was added dropwise at 0° C. The reaction was stirred at 25° C. for 1 h. The reaction was quenched with saturated ammonium chloride solution (100 mL) at 0° C., and diluted with ethyl acetate (100 mL). The layers were separated, and the aqueous phase was extracted with ethyl acetate (2×100 mL). The combined organic layers were washed with brine (200 mL), dried over sodium sulfate, filtered, and concentrated under reduced pressure. The residue was purified via Purification Method 2 to afford tert-butyl 2-(5-(diethoxymethyl)-pyrimidin-2-yl)-2-methylpropanoate (9.82 g, 29.4 mmol, 87% yield) as a colourless oil.

Step 5. To a solution of tert-butyl 2-(5-(diethoxymethyl) pyrimidin-2-yl)-2-methylpropanoate (9.82 g, 30.3 mmol, 1.00 eq.) in tetrahydrofuran (40 mL) was added hydrochloric acid (1 M, 40 mL). The mixture was stirred at 40° C. for 4 h. The mixture was extracted with ethyl acetate (3×50 mL). The combined organic layers were dried over sodium sulfate, filtered, and concentrated under reduced pressure. The residue was purified via Purification Method 2 to afford tert-butyl 2-(5-formylpyrimidin-2-yl)-2-methylpropanoate (7.21 g, 25.9 mmol, 86% yield) as a yellow oil.

Step 6. To a solution of tert-butyl 2-(5-formylpyrimidin-2-yl)-2-methylpropanoate (7.21 g, 28.8 mmol, 1.00 eq.) in dichloromethane (50 mL) was added 1,1,1-trifluoro-N,N-bis (2-methoxyethyl)-$\lambda^4$-sulfanamine (12.6 mL, 57.6 mmol, 2.00 eq.) at 0° C. under nitrogen atmosphere. The mixture was stirred at 0° C. for 2 h. The reaction was quenched with saturated sodium bicarbonate (40 mL) and extracted with ethyl acetate (3× 60 mL). The combined organic layers were dried over anhydrous sodium sulfate, filtered, and concentrated under reduced pressure. The residue was purified via Purification Method 2 to afford tert-butyl 2-(5-(difluoromethyl)pyrimidin-2-yl)-2-methylpropanoate (5.01 g, 17.7 mmol, 61% yield) as a colourless oil.

Step 7. To a solution of tert-butyl 2-(5-(difluoromethyl) pyrimidin-2-yl)-2-methylpropanoate (5.01 g, 18.4 mmol, 1.00 eq.) in dichloromethane (30 mL) was added trifluoroacetic acid (6 mL) at 25° C. The mixture was stirred at 25° C. for 12 h. The mixture was concentrated under reduced pressure, then diluted with dichloromethane (20 mL). The mixture was extracted with saturated sodium bicarbonate (2×20 mL). The pH of the combined aqueous phases was adjusted to 4 with 2M hydrochloric acid. Then it was extracted with dichloromethane (3×30 mL). The combined organic layers were dried over sodium sulfate, filtered, and concentrated under reduced pressure to give 2-(5-(difluoromethyl)pyrimidin-2-yl)-2-methylpropanoic acid (2.64 g, 11.0 mmol, 60% yield) as a colourless oil.

Step 8. To a solution of 2-(5-(difluoromethyl)pyrimidin-2-yl)-2-methylpropanoic acid (2.53 g, 10.5 mmol, 1.31 eq.) in N,N-dimethyl formamide (20 mL) were added N,N-diisopropylethylamine (5.60 mL, 32.1 mmol, 4.00 eq.) and 2-chloro-1-methyl-pyridin-1-ium iodide (2.46 g, 9.64 mmol, 1.20 eq.). After addition, the mixture was stirred at 25° C. for 30 min, then 3-(4-(aminomethyl)-2,6-dichlorophenyl) piperidine-2,6-dione hydrochloride (2.60 g, 8.03 mmol, 1.00 eq.) was added. The reaction was stirred at 25° C. for 1 h. The mixture was diluted with water (40 mL) and extracted with ethyl acetate (40 mL). The combined organic layers were washed with water (2×40 mL) and brine (60 mL), dried over sodium sulfate, filtered, and concentrated under reduced pressure. The residue was purified via Purification Method 2 to afford N-(3,5-dichloro-4-(2,6-dioxopiperidin- 3-yl)benzyl)-2-(5-(difluoromethyl)pyrimidin-2-yl)-2-methylpropanamide (2.83 g, 5.77 mmol, 72% yield) as a white solid.
$^1$H NMR (400 MHZ, DMSO-$d_6$) δ=10.95 (s, 1H), 9.03 (s, 2H), 8.13 (t, J=6.0 Hz, 1H), 7.39-7.10 (m, 3H), 4.59-4.54 (dd, J=5.6, 12.8 Hz, 1H), 4.27 (d, J=6.0 Hz, 2H), 2.86 (ddd, J=5.6, 14.0, 16.8 Hz, 1H), 2.56-2.55 (m, 1H), 2.36 (dq, J=4.4, 13.2 Hz, 1H), 1.92-1.87 (m, 1H), 1.58 (s, 6H). MS (ESI) m/z 485.0 [M+H]$^+$
Exemplary Compound 184
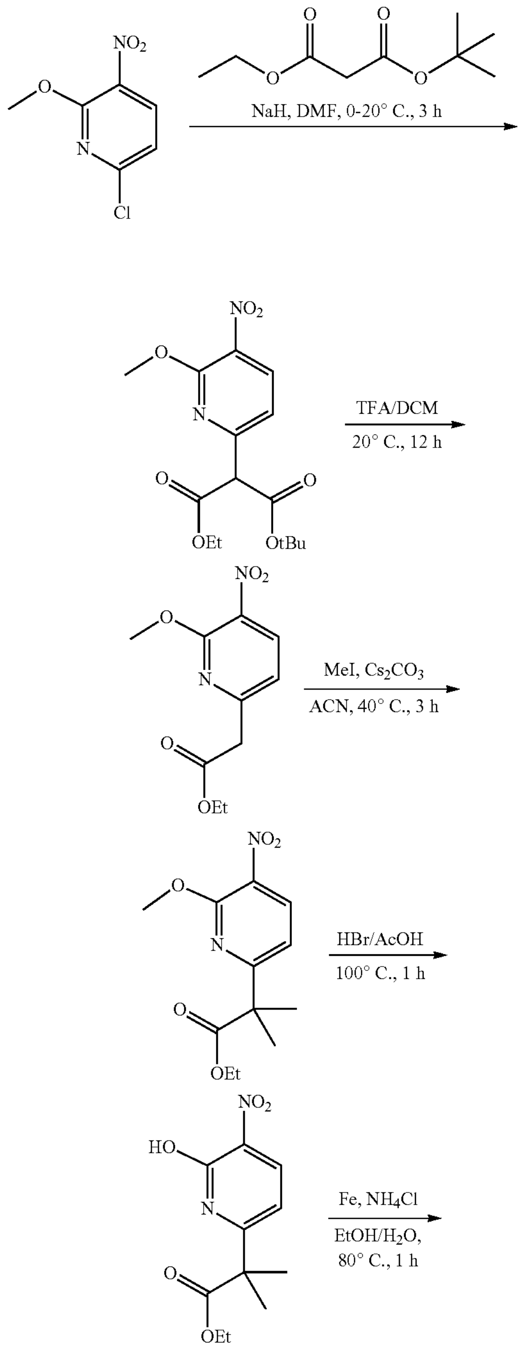
-continued
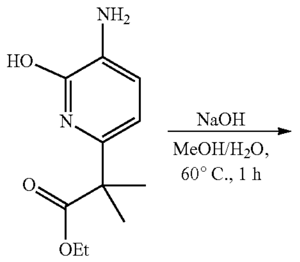
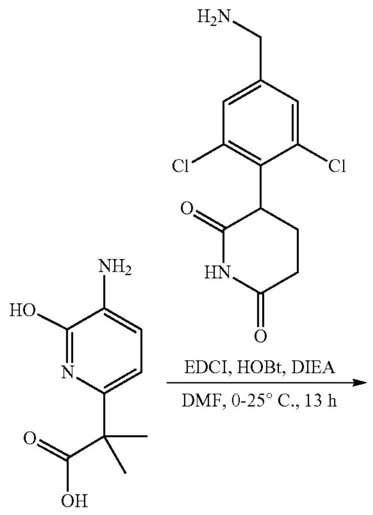
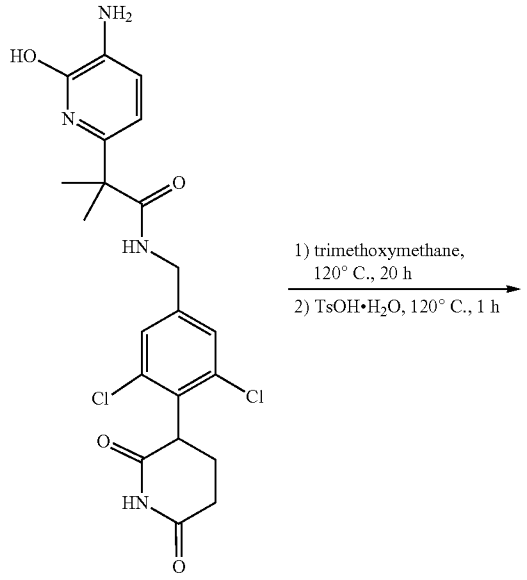

-continued

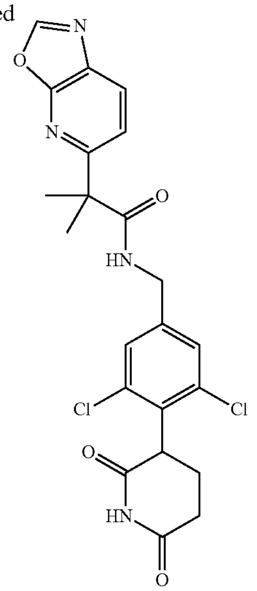

Step 1. To a suspension of sodium hydride (2.13 g, 53.3 mmol, 60% purity, 2.01 eq.) in N,N-dimethylformamide (30 mL) was added tert-butyl ethyl malonate (10.0 mL, 53.0 mmol, 2.00 eq.) at 0° C. under nitrogen atmosphere. The mixture was stirred at 20° C. for 3 h under nitrogen atmosphere. Then 6-chloro-2-methoxy-3-nitropyridine (5.00 g, 26.5 mmol, 1.00 eq.) in N,N-dimethylformamide (20 mL) was added at 20° C. under nitrogen atmosphere. The mixture was stirred at 20° C. for 3 h under nitrogen atmosphere. The mixture was quenched with saturated aqueous ammonium chloride (100 mL) at 0° C. under nitrogen atmosphere. The mixture was extracted with ethyl acetate (3×100 mL). The combined organic layers were dried over sodium sulfate and filtered. The filtrate was concentrated under reduced pressure. The residue was purified via Purification Method 2 to afford 1-(tert-butyl) 3-ethyl 2-(6-methoxy-5-nitropyridin-2-yl) malonate (7.40 g, 21.5 mmol, 81% yield) as a yellow oil.

Step 2. To a solution of 1-(tert-butyl) 3-ethyl 2-(6-methoxy-5-nitropyridin-2-yl) malonate (7.40 g, 21.7 mmol, 1.00 eq.) in dichloromethane (50 mL) was added 2,2,2-trifluoroacetic acid (10 mL). The reaction was stirred at 20° C. for 12 h. The mixture was diluted with water (80 mL) and extracted with dichloromethane (2×60 mL). The combined organic layers were washed with brine (80 mL), dried over sodium sulfate, filtered, and the filtrate was concentrated under reduced pressure. The residue was purified via Purification Method 2 to afford ethyl 2-(6-methoxy-5-nitropyridin-2-yl)acetate (5.25 g, 21.4 mmol, 98% yield) as a yellow oil.

Step 3. To a suspension of ethyl 2-(6-methoxy-5-nitropyridin-2-yl)acetate (3.20 g, 13.3 mmol, 1.00 eq.) and caesium carbonate (21.7 g, 66.6 mmol, 5.00 eq.) in acetonitrile (50 mL) was added iodomethane (7.68 mL, 123 mmol, 9.26 eq.). The reaction was stirred at 40° C. for 3 h under nitrogen atmosphere. The reaction mixture was filtered, and the filtrate was diluted with water (100 mL). The mixture was extracted with ethyl acetate (2×70 mL). The combined organic layers were washed with brine (100 mL), dried over sodium sulfate, filtered, and the filtrate was concentrated under reduced pressure to afford ethyl 2-(6-methoxy-5-nitropyridin-2-yl)-2-methylpropanoate (3.60 g, 13.0 mmol, 98% yield) as a yellow oil.

Step 4. A solution of ethyl 2-(6-methoxy-5-nitropyridin-2-yl)-2-methylpropanoate (4.90 g, 18.3 mmol, 1.00 eq.) in hydrogen bromide/acetic acid (50 mL) was stirred at 100° C. for 1 h. The reaction mixture was concentrated under reduced pressure. The mixture was diluted with water (50 mL) and adjusted to pH=6 with 1 M sodium hydroxide at 0° C. The mixture was extracted with ethyl acetate (3×100 mL). The combined organic layers were washed with brine (250 mL), dried over sodium sulfate, filtered, and the filtrate was concentrated under reduced pressure to afford ethyl 2-(6-hydroxy-5-nitropyridin-2-yl)-2-methylpropanoate (4.90 g, 17.4 mmol, 95% yield) as a yellow oil.

Step 5. To a solution of ethyl 2-(6-hydroxy-5-nitropyridin-2-yl)-2-methylpropanoate (4.90 g, 19.3 mmol, 1.00 eq.) in ethanol (50 mL) and water (50 mL) were added ammonium chloride (5.15 g, 96.2 mmol, 4.99 eq.) and ferrous powder (5.35 g, 95.8 mmol, 4.97 eq.). The mixture was stirred at 80° C. for 1 h. The reaction mixture was filtered, and the filtrate was concentrated under reduced pressure. The residue was purified via Purification Method 2 to afford ethyl 2-(5-amino-6-hydroxypyridin-2-yl)-2-methylpropanoate (2.70 g, 11.1 mmol, 58% yield) as a yellow solid.

Step 6. To a solution of ethyl 2-(5-amino-6-hydroxypyridin-2-yl)-2-methylpropanoate (1.00 g, 4.46 mmol, 1.00 eq.) in methanol (12 mL) was added sodium hydroxide (900 mg, 22.5 mmol, 5.05 eq.) in water (12 mL). The reaction was stirred at 60° C. for 1 h. The mixture was diluted with water (10 mL) and the pH was adjusted to 7 with 1 M hydrochloric acid at 0° C. Methanol was removed in vacuo and the mixture was lyophilized to afford 2-(5-amino-6-hydroxypyridin-2-yl)-2-methylpropanoic acid (1.81 g, 4.15 mmol, 93% yield, 45% purity) as a brown solid.

Step 7. To a solution of 2-(5-amino-6-hydroxypyridin-2-yl)-2-methylpropanoic acid (595 mg, 1.21 mmol, 1.01 eq.) in N,N-dimethylformamide (10 mL) were added N-ethyl-N-isopropylpropan-2-amine (1.03 mL, 5.89 mmol, 4.90 eq.), 1-(3-dimethylaminopropyl)-3-ethylcarbodiimide hydrochloride (280 mg, 1.46 mmol, 1.22 eq.) and 1H-benzo[d][1,2,3]triazol-1-ol (210 mg, 1.55 mmol, 1.29 eq.) at 0° C. The mixture was stirred at 25° C. for 1 h. Then 3-(4-(aminomethyl)-2,6-dichlorophenyl) piperidine-2,6-dione hydrochloride (350 mg, 1.08 mmol, 0.90 eq.) was added at 25° C. The mixture was stirred at 25° C. for 12 h. The reaction mixture was filtered, and the filtrate was concentrated under reduced pressure. The residue was purified via Purification Method 1 to afford 2-(5-amino-6-hydroxypyridin-2-yl)-N-(3,5-dichloro-4-(2,6-dioxopiperidin-3-yl)benzyl)-2-methylpropanamide (200 mg, 417 μmol, 35% yield) as a brown solid.

Step 8. A solution of 2-(5-amino-6-hydroxypyridin-2-yl)-N-(3,5-dichloro-4-(2,6-dioxopiperidin-3-yl)benzyl)-2-methylpropanamide (200 mg, 430 μmol, 1.00 eq.) in trimethoxymethane (20 mL) was stirred at 120° C. for 20 h. Then 4-methylbenzenesulfonic acid hydrate (8.00 mg, 42.1 μmol, 0.1 eq.) was added. The mixture was stirred at 120° C. for 1 h. The reaction mixture was concentrated under reduced pressure. The residue was purified via Purification Method I to afford N-(3,5-dichloro-4-(2,6-dioxopiperidin-3-yl)benzyl)-2-methyl-2-(oxazolo [5,4-b]pyridin-5-yl) propanamide (40.9 mg, 85.1 μmol, 20% yield) as off-white solid.

$^1$H NMR (400 MHZ, DMSO-$d_6$) δ=10.95 (s, 1H), 8.89 (s, 1H), 8.27 (d, J=8.0 Hz, 1H), 8.05 (t, J=6.0 Hz, 1H), 7.50 (d, J=8.0 Hz, 1H), 7.21 (d, J=1.2 Hz, 1H), 7.14 (d, J=1.2 Hz, 1H), 4.58-4.50 (m, 1H), 4.23 (d, J=6.0 Hz, 2H), 2.90-2.79 (m, 1H), 2.58-2.52 (m, 1H), 2.40-2.28 (m, 1H), 1.92-1.83 (m, 1H), 1.60 (s, 6H). MS (ESI) m/z 474.9 $[M+H]^+$

Exemplary Compound 186

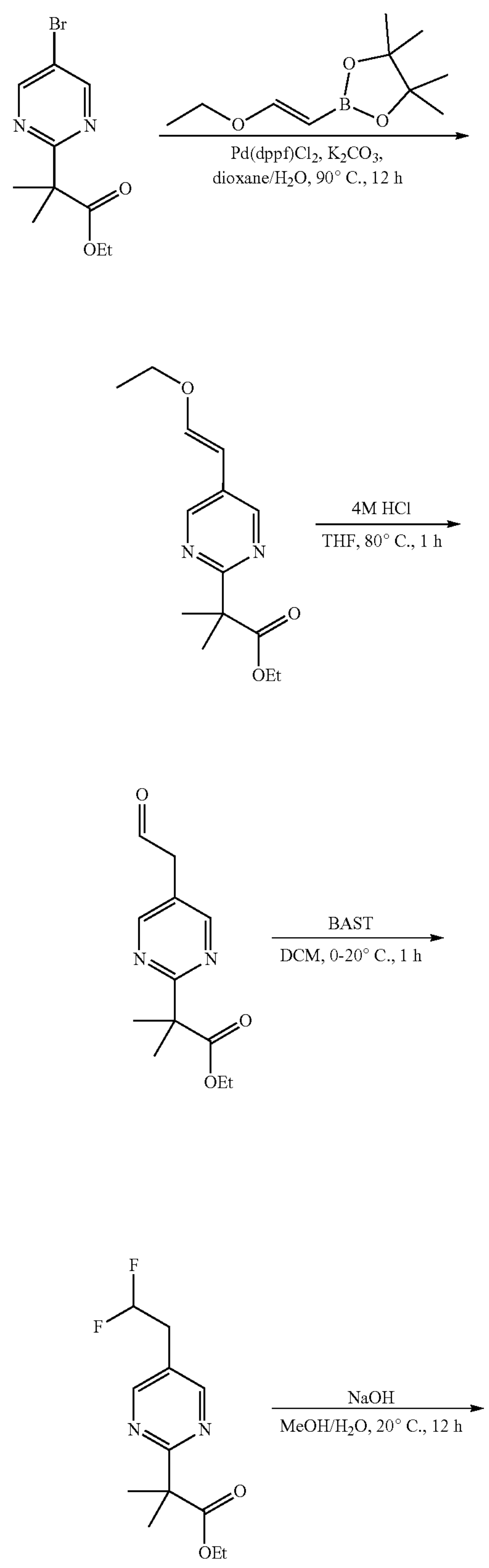

-continued

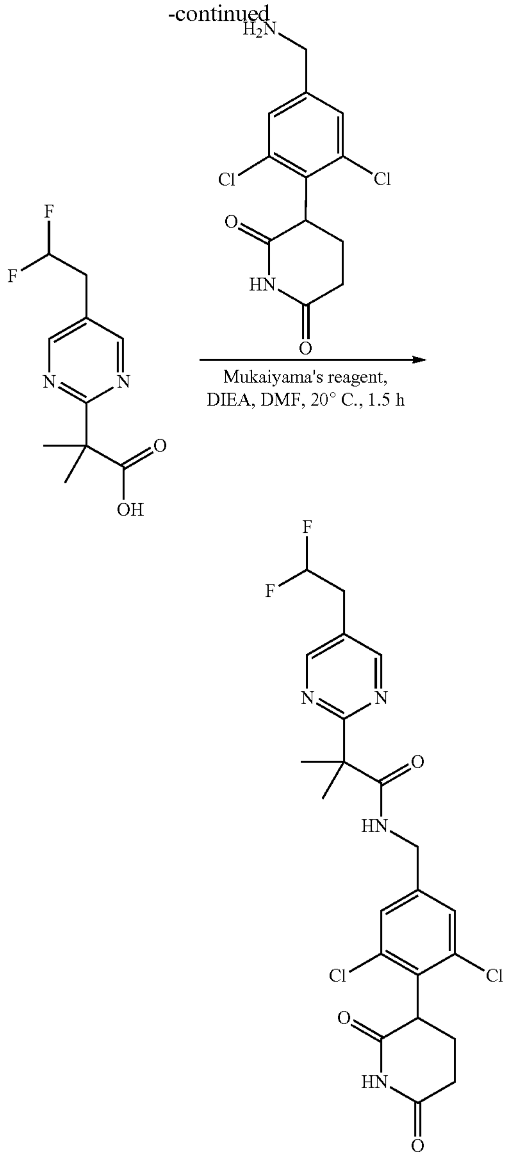

Step 1. To a mixture of ethyl 2-(5-bromopyrimidin-2-yl)-2-methyl-propanoate (2.00 g, 7.32 mmol, 1.00 eq.) and (E)-2-(2-ethoxyvinyl)-4,4,5,5-tetramethyl-1,3,2-dioxaborolane (1.60 g, 8.05 mmol, 1.10 eq.) in dioxane (40 mL) and water (10 mL) were added [1,1'-bis(diphenylphosphino) ferrocene]dichloropalladium (II) (268 mg, 366 μmol, 0.05 eq.) and potassium carbonate (3.04 g, 22.0 mmol, 3.00 eq.) in one portion. The mixture was stirred at 90° C. under nitrogen atmosphere for 12 h. The mixture was poured into water (50 mL) and extracted with ethyl acetate (3×20 mL). The combined organic layers were washed with brine (30 mL), dried over anhydrous sodium sulfate, filtered, and the filtrate was concentrated under reduced pressure. The residue was purified via Purification Method 2 to afford ethyl (E)-2-(5-(2-ethoxyvinyl)pyrimidin-2-yl)-2-methylpropanoate (2.00 g, 6.73 mmol, 91% yield) as a colourless oil.

Step 2. To a solution of ethyl(E)-2-(5-(2-ethoxyvinyl) pyrimidin-2-yl)-2-methylpropanoate (2.00 g, 7.57 mmol, 1.00 eq.) in tetrahydrofuran (120 mL) was added hydrochloric acid (4 M, 40 mL) dropwise at 20° C. The mixture was stirred at 80° C. for 1 h. The mixture was poured into saturated aqueous sodium bicarbonate (50 mL) and extracted with ethyl acetate (5×50 mL). The combined organic layers were washed with brine (50 mL), dried over anhydrous sodium sulfate, filtered, and the filtrate was concentrated under reduced pressure. The residue was purified via Purification Method 2 to afford ethyl 2-methyl-2-(5-(2-oxoethyl)pyrimidin-2-yl) propanoate (700 mg, 2.96 mmol, 39% yield) as a light-yellow oil.

Step 3. To a solution of ethyl 2-methyl-2-(5-(2-oxoethyl) pyrimidin-2-yl) propanoate (650 mg, 2.75 mmol, 1.00 eq.) in dichloromethane (20 mL) was added 1,1,1-trifluoro-N,N-bis (2-methoxyethyl)-$2^4$-sulfanamine (1.22 g, 5.50 mmol, 2.00 eq.) dropwise at 0° C. The mixture was stirred at 20° C. for 1 h. The mixture was poured into saturated sodium bicarbonate solution (50 mL) and sodium bicarbonate solid was added to adjust the pH to 7, then the mixture was filtered. The filtrate was extracted with ethyl acetate (3×20 mL). The combined organic layers were washed with brine (30 mL), dried over anhydrous sodium sulfate, filtered, and the filtrate was concentrated under reduced pressure. The residue was purified via Purification Method 2 to afford ethyl 2-(5-(2,2-difluoroethyl)pyrimidin-2-yl)-2-methylpropanoate (360 mg, 1.39 mmol, 50% yield) as a light-yellow oil.

Step 4. To a solution of ethyl 2-(5-(2,2-difluoroethyl) pyrimidin-2-yl)-2-methylpropanoate (310 mg, 1.20 mmol, 1.00 eq.) in methanol (3 mL) and water (3 mL) was added sodium hydroxide (2 M, 3.00 mL, 5.00 eq.) in one portion at 20° C. The reaction was stirred at 20° C. for 12 h. The mixture was poured into water (20 mL) and washed with ethyl acetate (3× 20 mL). The aqueous layer was collected and adjusted to pH 2-3 with 2 N hydrochloric acid. The mixture was extracted with ethyl acetate (3× 20 mL). The combined organic layers were washed with brine (30 mL), dried over anhydrous sodium sulfate, filtered, and the filtrate was concentrated under reduced pressure. The residue was purified via Purification Method 1 to afford 2-(5-(2,2-difluoroethyl)pyrimidin-2-yl)-2-methylpropanoic acid (60.0 mg, 242 μmol, 20% yield) as a white solid.

Step 5. To a solution of 2-(5-(2,2-difluoroethyl)pyrimidin-2-yl)-2-methylpropanoic acid (50.0 mg, 217 μmol, 1.00 eq.) and 2-chloro-1-methyl-pyridin-1-ium iodide (61.0 mg, 239 μmol, 1.10 eq.) in dimethyl formamide (0.5 mL) was added diisopropylethylamine (112 mg, 869 μmol, 4.00 eq.) dropwise at 20° C. The reaction was stirred at 20° C. for 0.5 h, then 3-(4-(aminomethyl)-2,6-dichlorophenyl) piperidine-2,6-dione hydrochloride (70.3 mg, 217 μmol, 1.00 eq.) was added. The reaction was stirred at 20° C. for 1 h. The mixture was poured into water (20 mL) and extracted with ethyl acetate (3×20 mL). The combined organic layers were washed with brine (30 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-(5-(2,2-difluoroethyl)pyrimidin-2-yl)-2-methylpropanamide (35.4 mg, 69.5 μmol, 32% yield) as a white solid.

$^1$H NMR (400 MHZ, DMSO-$d_6$) δ=10.97 (br s, 1H), 8.75 (s, 2H), 8.16 (t, J=6.0 Hz, 1H), 7.44 (d, J=1.6 Hz, 1H), 7.38 (d, J=1.6 Hz, 1H), 6.51-6.14 (m, 1H), 4.57 (dd, J=5.6, 12.8 Hz, 1H), 4.27 (d, J=6.0 Hz, 2H), 3.29-3.22 (m, 2H), 2.87 (ddd, J=6.0, 13.6, 17.2 Hz, 1H), 2.59-2.55 (m, 1H), 2.42-2.35 (m, 1H), 1.95-1.85 (m, 1H), 1.55 (s, 6H). MS (ESI) m/z 499.1 [M+H]$^+$ Exemplary Compound 187

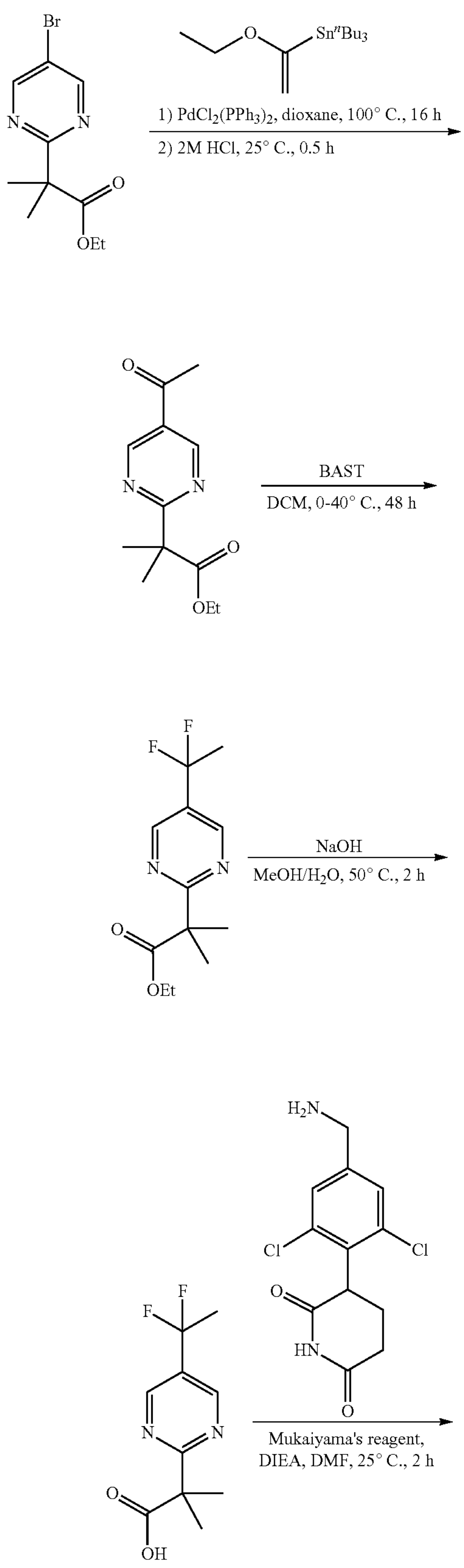

-continued

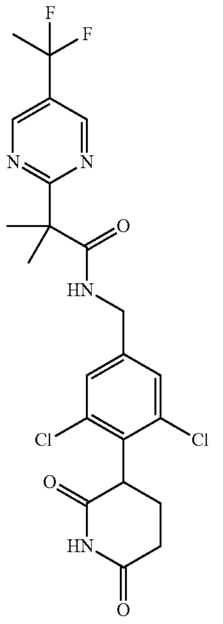

Step 1. To a solution of ethyl 2-(5-bromopyrimidin-2-yl)-2-methylpropanoate (2.00 g, 7.32 mmol, 1.00 eq.) in dioxane (20 mL) was added tributyl (1-ethoxyvinyl) stannane (3.17 g, 8.79 mmol, 2.97 mL, 1.20 eq.) and bis (triphenylphosphine) palladium (II) chloride (514 mg, 732 μmol, 0.100 eq.).

The mixture stirred at 100° C. for 16 h under nitrogen atmosphere. The mixture was cooled to room temperature and acidified to pH 3 with hydrochloric acid (2 M), and stirred for 0.5 h at 25° C. The mixture was poured into potassium fluoride (50 mL) and diluted with water (50 mL) and extracted with ethyl acetate (3×100 mL). The combined organic layers were dried over anhydrous sodium sulfate, filtered, and concentrated under reduced pressure to give a residue, which was purified via Purification Method 2 to afford ethyl 2-(5-acetylpyrimidin-2-yl)-2-methylpropanoate (1.40 g, 5.81 mmol, 79% yield) as a yellow oil.

Step 2. To a solution of ethyl 2-(5-acetylpyrimidin-2-yl)-2-methylpropanoate (1.14 g, 4.83 mmol, 1.00 eq.) in dichloromethane (20 mL) was added 1,1,1-trifluoro-N,N-bis (2-methoxyethyl)-14-sulfanamine (5.34 g, 24.1 mmol, 5.28 mL, 5.00 eq.) at 0° C. under nitrogen atmosphere. The mixture was stirred at 40° C. for 48 h. The reaction was quenched with ice water (60 mL) and extracted with dichloromethane (3×60 mL). The combined organic layers were washed with brine (80 mL), dried over anhydrous sodium sulfate, filtered, and concentrated under reduced pressure to give a residue, which was purified via Purification Method 2 to afford ethyl 2-(5-(1,1-difluoroethyl)pyrimidin-2-yl)-2-methylpropanoate (940 mg, 3.60 mmol, 75% yield) as a yellow oil Step 3. To a solution of ethyl 2-(5-(1,1-difluoroethyl) pyrimidin-2-yl)-2-methylpropanoate (400 mg, 1.55 mmol, 1.00 eq.) in methanol (3 mL) was added a solution of sodium hydroxide (310 mg, 7.74 mmol, 5.00 eq.) in water (3 mL). The reaction was stirred at 50° C. for 2 h. The reaction mixture was washed with water (30 mL) and ethyl acetate (2×30 mL). The aqueous phase was adjusted to pH 6 with 1M hydrochloric acid, and then it was extracted with ethyl acetate (3×30 mL). The combined organic layers were washed with brine (50 mL), dried over anhydrous sodium sulfate, filtered, and concentrated under reduced pressure to give 2-(5-(1,1-difluoroethyl)pyrimidin-2-yl)-2-methylpropanoic acid (300 mg, 1.07 mmol, 69% yield) as a white solid.

Step 4. To a solution of 2-(5-(1,1-difluoroethyl)pyrimidin-2-yl)-2-methylpropanoic acid (130 mg, 463 μmol, 1.00 eq.) in N,N-dimethylformamide (6 mL) was added 2-chloro-1-methyl-pyridin-1-ium;iodide (142 mg, 556 μmol, 1.20 eq.) and N-ethyl-N-isopropylpropan-2-amine (239 mg, 1.85 mmol, 323 μL, 4.00 eq.) at 0° C. The mixture was stirred at 25° C. for 0.5 h. Then 3-[4-(aminomethyl)-2,6-dichloro-phenyl]piperidine-2,6-dione hydrochloride (120 mg, 370 μmol, 0.800 eq.) was added. After addition, the mixture was stirred at 25° C. for 1.5 h. The reaction mixture was diluted with water (20 mL) and extracted with ethyl acetate (3× 20 mL). The combined organic layers were washed with brine (30 mL), dried over anhydrous sodium sulfate, filtered, and concentrated under reduced pressure. The residue was purified via Purification Method I to afford N-(3,5-dichloro-4-(2,6-dioxopiperidin-3-yl)benzyl)-2-(5-(1,1-difluoroethyl) pyrimidin-2-yl)-2-methylpropanamide (114 mg, 218 μmol, 47% yield) as a white solid.

$^1$H NMR (400 MHZ, DMSO-$d_6$)>=10.96 (s, 1H), 9.03 (s, 2H), 8.13 (t, J=6.0 Hz, 1H), 7.38 (d, J=1.2 Hz, 1H), 7.32 (s, 1H), 4.56 (dd, J=5.6, 12.8 Hz, 1H), 4.26 (d, J=6.0 Hz, 2H), 2.89-2.80 (m, 1H), 2.60-2.53 (m, 1H), 2.41-2.30 (m, 1H), 2.07 (t, J=19.2 Hz, 3H), 1.94-1.84 (m, 1H), 1.57 (s, 6H). MS (ESI) m/z 499.2 [M+H]$^+$

Exemplary Compound 188

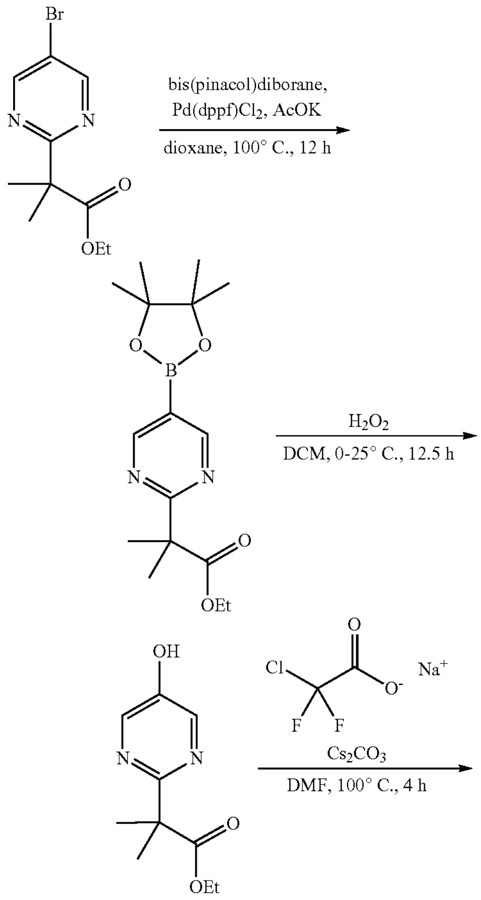

-continued

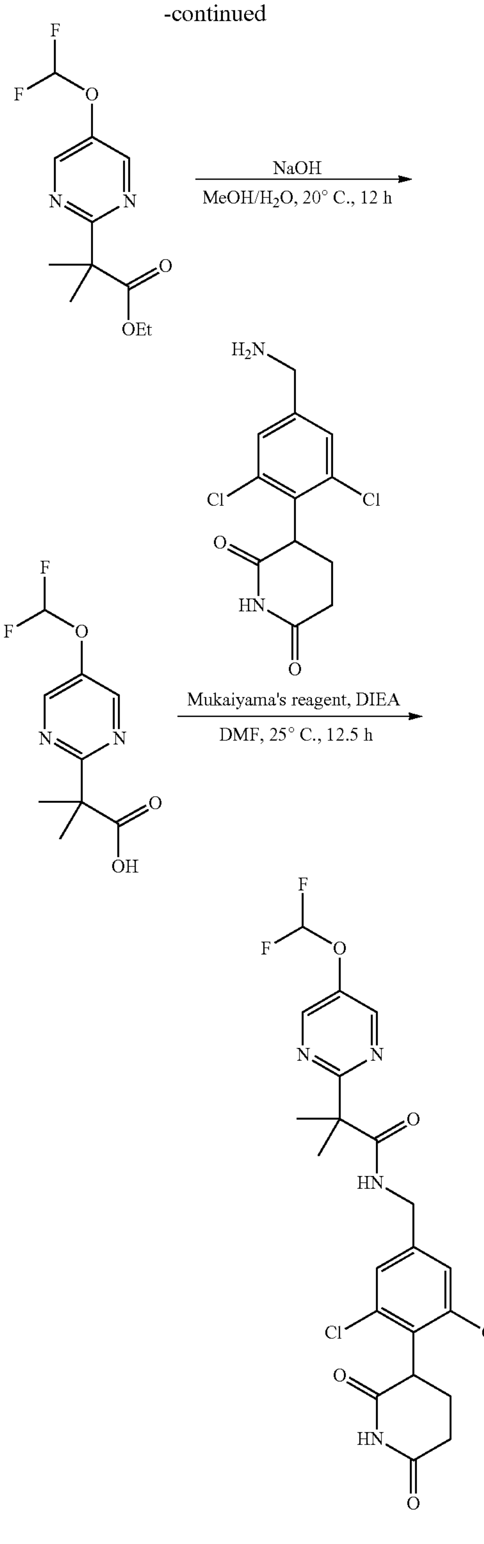

Step 1. To a mixture of ethyl 2-(5-bromopyrimidin-2-yl)-2-methylpropanoate (2.00 g, 7.32 mmol, 1.00 eq.), 4,4,5,5-tetramethyl-2-(4,4,5,5-tetramethyl-1,3,2-dioxaborolan-2-yl)-1,3,2-dioxaborolane (2.79 g, 10.9 mmol, 1.50 eq.), potassium acetate (2.16 g, 21.9 mmol, 3.00 eq.) in dioxane (32 mL) was added [1,1'-bis(diphenylphosphino)-ferrocene] dichloropalladium (II) (535 mg, 732 μmol, 0.10 eq.) in one portion at 25° C. The mixture was stirred at 100° C. under nitrogen atmosphere for 12 h. The reaction was cooled to 25° C. then poured into water (50 mL). The mixture was extracted with ethyl acetate (3× 50 mL). The combined organic layers were washed with brine (50 mL), dried over anhydrous sodium sulfate, filtered, and the filtrate was concentrated under reduced pressure. The residue was purified via Purification Method 2 to afford ethyl 2-methyl-2-(5-(4,4,5,5-tetramethyl-1,3,2-dioxaborolan-2-yl)pyrimidin-2-yl) propanoate (2.20 g, 6.60 mmol, 90% yield) as a white solid.

Step 2. To a solution of ethyl 2-methyl-2-(5-(4,4,5,5-tetramethyl-1,3,2-dioxaborolan-2-yl)pyrimidin-2-yl) propanoate (2.20 g, 6.87 mmol, 1.00 eq.) in dichloromethane (30 mL) was added hydrogen peroxide (4.91 g, 43.3 mmol, 30% purity, 6.30 eq.) dropwise at 0° C. over 0.5 h. The mixture was stirred at 25° C. for 12 h. A saturated sodium sulfite solution (100 mL) was added to the reaction, and the mixture extracted with dichloromethane (3×100 mL). The combined organic layers were washed with brine (100 mL), dried over anhydrous sodium sulfate, filtered, and the filtrate was concentrated under reduced pressure. The residue was purified via Purification Method 2 to afford ethyl 2-(5-hydroxypyrimidin-2-yl)-2-methyl-propanoate (1.40 g, 6.53 mmol, 94% yield) as a white solid.

Step 3. To a solution of ethyl 2-(5-hydroxypyrimidin-2-yl)-2-methylpropanoate (300 mg, 1.43 mmol, 1.00 eq.) in dimethyl formamide (5 mL) were added caesium carbonate (1.39 g, 4.28 mmol, 3.00 eq.) and sodium 2-chloro-2,2-difluoroacetate (435 mg, 2.85 mmol, 2.00 eq.) in portions at 20° C. The reaction was stirred at 100° C. for 4 h. The mixture was cooled to 25° C. then poured into water (10 mL). The mixture was extracted with ethyl acetate (3×10 mL). The combined organic layers were washed with brine (10 mL), dried over anhydrous sodium sulfate, filtered, and the filtrate was concentrated under reduced pressure. The residue was purified via Purification Method 2 to afford ethyl 2-(5-(difluoromethoxy)pyrimidin-2-yl)-2-methylpropanoate (190 mg, 722 μmol, 50% yield) as a colourless oil.

Step 4. To a mixture of ethyl 2-(5-(difluoromethoxy) pyrimidin-2-yl)-2-methylpropanoate (190 mg, 730 μmol, 1.00 eq.) in methanol (1 mL) and water (1 mL) was added sodium hydroxide (146 mg, 3.65 mmol, 5.00 eq.) in portions at 20° C. The mixture was stirred at 20° C. for 12 h. The mixture was poured into water (20 mL) and adjusted to pH 2 with 36% aqueous hydrochloric acid. The mixture was extracted with ethyl acetate (3×20 mL). The combined organic extracts were washed with brine (20 mL) and dried over anhydrous sodium sulfate, filtered, and concentrated under reduced pressure to give 2-(5-(difluoromethoxy)pyrimidin-2-yl)-2-methylpropanoic acid (160 mg, 675 μmol, 92% yield) as a yellow solid.

Step 5. To a mixture of 2-(5-(difluoromethoxy)pyrimidin-2-yl)-2-methylpropanoic acid (80.0 mg, 344 μmol, 1.00 eq.) and 2-chloro-1-methyl-pyridin-1-ium iodide (105 mg, 413 μmol, 1.20 eq.) in dimethyl formamide (1.5 mL) was added diisopropylethylamine (178 mg, 1.38 mmol, 4.00 eq.) dropwise at 25° C. The mixture was stirred at 25° C. for 0.5 h then 3-(4-(aminomethyl)-2,6-dichlorophenyl) piperidine-2,6-dione hydrochloride (111 mg, 344 μmol, 1.00 eq.) was added. The reaction was stirred at 25° C. for 12 h. The mixture was poured into water (20 mL) and extracted with ethyl acetate (3×20 mL). The combined organic layers were washed with brine (20 mL), dried over anhydrous sodium sulfate, filtered, and the filtrate was concentrated under reduced pressure. The residue was purified via Purification Method 1 to afford N-(3,5-dichloro-4-(2,6-dioxopiperidin- 3-yl)benzyl)-2-(5-(difluoromethoxy)-pyrimidin-2-yl)-2-methylpropanamide (79.8 mg, 156 μmol, 45% yield) as a white solid.

$^1$H NMR (400 MHZ, DMSO-$d_6$) δ=10.96 (br s, 1H), 8.76 (s, 2H), 8.12 (t, J=6.0 Hz, 1H), 7.58-7.19 (m, 3H), 4.57 (dd, J=5.6, 12.8 Hz, 1H), 4.26 (d, J=6.0 Hz, 2H), 2.86 (ddd, J=6.0, 14.0, 16.8 Hz, 1H), 2.59-2.51 (m, 1H), 2.36 (q, J=4.4, 13.2 Hz, 1H), 1.94-1.83 (m, 1H), 1.56 (s, 6H). MS (ESI) m/z 501.0 [M+H]$^+$ Exemplary Compound 192

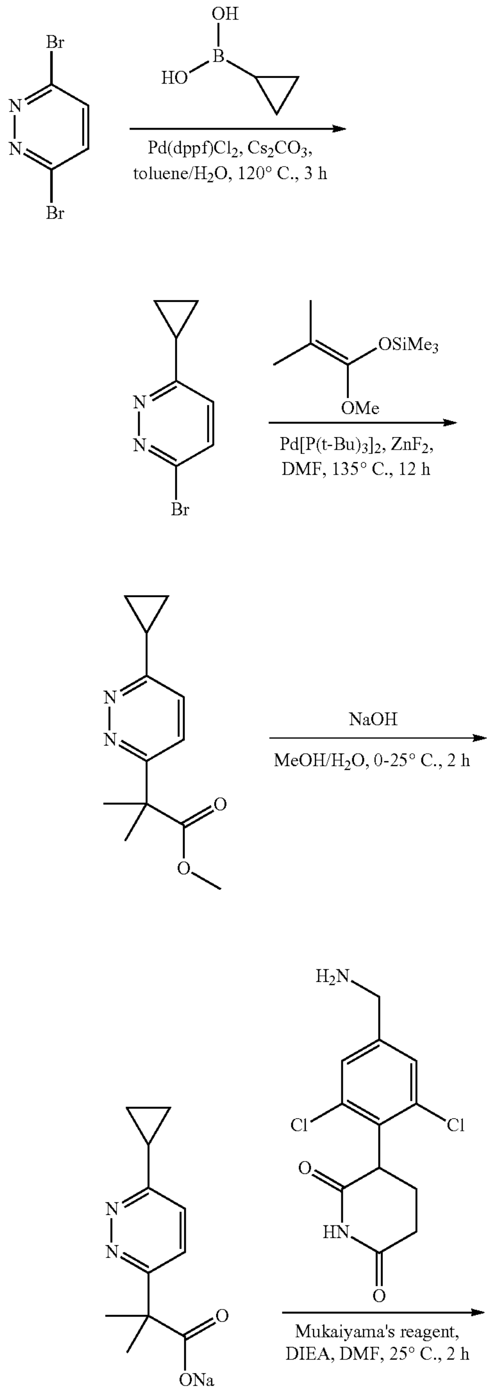

-continued

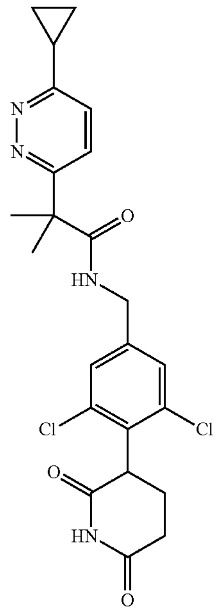

Step 1. To a solution of 3,6-dibromopyridazine (4.98 g, 20.9 mmol, 1.20 eq.), cyclopropylboronic acid (1.50 g, 17.5 mmol, 1.00 eq.) in toluene (20 mL) and water (2 mL) were added caesium carbonate (17.0 g, 52.4 mmol, 3.00 eq.) and [1,1'-bis(diphenylphosphino)ferrocene]dichloropalladium (II) (713 mg, 873 μmol, 0.05 eq.) under nitrogen atmosphere. The reaction was stirred at 120° C. for 3 h under nitrogen. The mixture was diluted with water (30 mL) and ethyl acetate (40 mL). The layers were separated, and the organic phase was washed with brine (30 mL), dried over sodium sulfate, filtered, and concentrated under vacuum. The residue was purified via Purification Method 2 to afford 3-bromo-6-cyclopropylpyridazine (1.60 g, 7.56 mmol, 43% yield) as a yellow solid.

Step 2. To a solution of 3-bromo-6-cyclopropylpyridazine (1.50 g, 7.54 mmol, 1.00 eq.) and ((1-methoxy-2-methyl-prop-1-en-1-yl)oxy)trimethylsilane (2.63 g, 15.0 mmol, 2.00 eq.) in dimethyl formamide (10 mL) was added zinc (II) fluoride (779 mg, 7.54 mmol, 1.00 eq.) and bis (tri-t-butylphosphine) palladium (0) (192 mg, 376 μmol, 0.05 eq.) under nitrogen atmosphere. The reaction was stirred at 135° C. for 12 h under nitrogen atmosphere. The mixture was diluted with water (10 mL) and ethyl acetate (20 mL). The layers were separated, and the organic phase was washed with water (3× 20 mL), dried over sodium sulfate, filtered, and concentrated under vacuum. The residue was purified via Purification Method 2 to afford methyl 2-(6-cyclopropylpyridazin-3-yl)-2-methylpropanoate (150 mg, 674 μmol, 8% yield) as a yellow oil.

Step 3. To a solution of methyl 2-(6-cyclopropylpyridazin-3-yl)-2-methylpropanoate (120 mg, 544 μmol, 1.00 eq.) in methanol (2 mL) and water (2 mL) was added sodium hydroxide (54.0 mg, 1.36 mmol, 2.50 eq.) at 0° C. The reaction was stirred at 25° C. for 2 h. The pH of mixture was adjusted to 7 with hydrochloric acid (2 M, 2 mL) at 0° C. The mixture was concentrated under vacuum. The residue was diluted with water and lyophilized to give sodium 2-(6-cyclopropylpyridazin-3-yl)-2-methylpropanoate (120 mg, crude) as a yellow solid.

Step 4. To a solution of sodium 2-(6-cyclopropylpyridazin-3-yl)-2-methylpropanoate (120 mg, crude) in dimethyl formamide (5 mL) were added N,N-diisopropylethylamine (157 mg, 1.22 mmol, 3.00 eq.) and 2-chloro-1-methyl-pyridin-1-ium iodide (124 mg, 488 μmol, 1.20 eq.). The reaction was stirred at 25° C. for 1 h. Then 3-(4-(aminomethyl)-2,6-dichlorophenyl) piperidine-2,6-dione hydrochloride (105 mg, 325 μmol, 0.80 eq.) was added and stirred at 25° C. for 1 h. The mixture was diluted with water (10 mL) and ethyl acetate (20 mL). The layers were separated, and the organic phase was washed with brine (20 mL), dried over sodium sulfate, filtered, and concentrated under vacuum. The residue was purified via Purification Method 2 then Purification Method 1 to afford 2-(6-cyclopropylpyridazin-3-yl)-N-(3,5-dichloro-4-(2,6-dioxopiperidin-3-yl)benzyl)-2-methylpropanamide (74.18 mg, 154 μmol, 37% yield) as a white solid.

$^1$H NMR (400 MHZ, DMSO-$d_6$) δ=10.96 (s, 1H), 8.15 (t, J=6.0 Hz, 1H), 7.51-7.41 (m, 2H), 7.23 (d, J=1.2 Hz, 1H), 7.17 (d, J=1.2 Hz, 1H), 4.55 (dd, J=5.6, 12.8 Hz, 1H), 4.22 (d, J=6.0 Hz, 2H), 2.91-2.77 (m, 1H), 2.59-2.52 (m, 1H), 2.37-2.31 (m, 1H), 2.23 (tt, J=5.2, 8.0 Hz, 1H), 1.94-1.81 (m, 1H), 1.57 (s, 6H), 1.12-1.00 (m, 4H). MS (ESI) m/z 475.1 [M+H]$^+$

Exemplary Compound 195

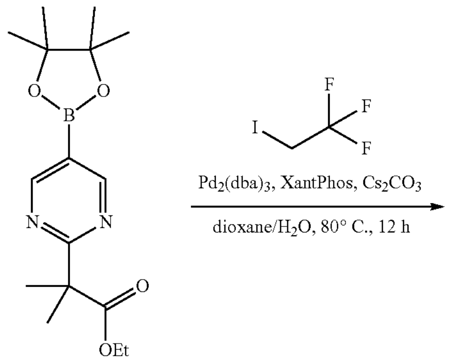

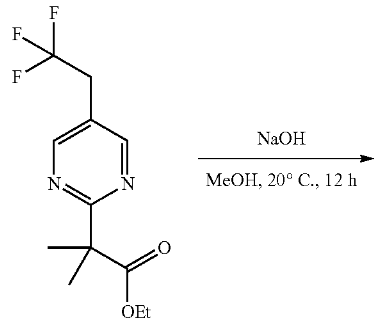

-continued

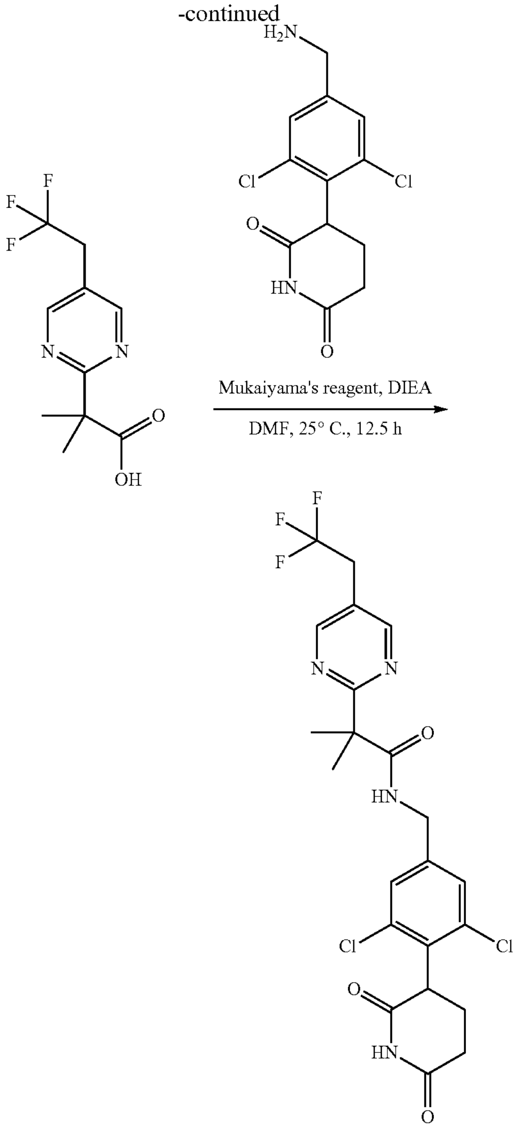

Step 1. To a mixture of ethyl 2-methyl-2-(5-(4,4,5,5-tetramethyl-1,3,2-dioxaborolan-2-yl)pyrimidin-2-yl) propanoate (400 mg, 1.25 mmol, 1.00 eq.), tris(dibenzylideneacetone) dipalladium (0) (114 mg, 124 μmol, 0.10 eq.), 4,5-bis(diphenylphosphino)-9,9-dimethylxanthene (144 mg, 249 μmol, 0.20 eq.) and caesium carbonate (1.63 g, 5.00 mmol, 4.00 eq.) in dioxane (8 mL) and water (1.6 mL) was added 1,1,1-trifluoro-2-iodoethane (524 mg, 2.50 mmol, 2.00 eq.) dropwise at 25° C. The mixture was stirred at 80° C. under nitrogen atmosphere for 12 h. The mixture was cooled to 25° C., then poured into water (30 mL). The mixture was extracted with ethyl acetate (3×30 mL). The combined organic layers were washed with brine (30 mL), dried over anhydrous sodium sulfate, filtered, and the filtrate was concentrated under reduced pressure. The residue was purified via Purification Method 2 to afford ethyl 2-methyl-2-(5-(2,2,2-trifluoroethyl)pyrimidin-2-yl) propanoate (200 mg, 723 μmol, 57% yield) as a yellow oil.

Step 2. To a mixture of ethyl 2-methyl-2-(5-(2,2,2-trifluoroethyl)pyrimidin-2-yl) propanoate (200 mg, 723 μmol, 1.00 eq.) in methanol (1 mL) and water (1 mL) was added sodium hydroxide (144 mg, 3.62 mmol, 5.00 eq.) in portions at 20° C. The reaction was stirred at 20° C. for 12 h. The mixture was poured into water (20 mL) and adjusted to pH 2 with 36% aqueous hydrochloric acid, and then extracted with ethyl acetate (3×20 mL). The combined organic extracts were washed with brine (20 mL) and dried over anhydrous sodium sulfate, filtered, and concentrated under reduced pressure to give 2-methyl-2-(5-(2,2,2-trifluoroethyl)pyrimidin-2-yl) propanoic acid (150 mg, 604 μmol, 83% yield) as a white solid.

Step 3. To a mixture of 2-methyl-2-(5-(2,2,2-trifluoroethyl)pyrimidin-2-yl) propanoic acid (76.7 mg, 309 μmol, 1.00 eq.) and 2-chloro-1-methyl-pyridin-1-ium;iodide (94.7 mg, 370 μmol, 1.20 eq.) in dimethyl formamide (2 mL) was added diisopropylethylamine (159 mg, 1.24 mmol, 4.00 eq.) dropwise at 25° C. The mixture was stirred at 25° C. for 0.5 h, then 3-(4-(aminomethyl)-2,6-dichlorophenyl) piperidine-2,6-dione (100 mg, 309 μmol, 1.00 eq., hydrochloride) was added, and the mixture was stirred at 25° C. for 12 h. The mixture was poured into water (20 mL) and extracted with ethyl acetate (3× 20 mL). The combined organic layers were washed with brine (20 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-methyl-2-(5-(2,2,2-trifluoroethyl)pyrimidin-2-yl) propanamide (30.4 mg, 52.9 μmol, 17% yield) as a white solid.

$^1$H NMR (400 MHZ, DMSO-$d_6$) δ=10.96 (s, 1H), 8.82 (s, 2H), 8.17 (t, J=5.6 Hz, 1H), 7.47-7.41 (m, 1H), 7.41-7.35 (m, 1H), 4.56 (dd, J=5.6, 12.8 Hz, 1H), 4.27 (d, J=6.0 Hz, 2H), 3.81 (q, J=11.6 Hz, 2H), 2.92-2.78 (m, 1H), 2.56 (d, J=2.0 Hz, 1H), 2.45-2.29 (m, 1H), 1.95-1.83 (m, 1H), 1.55 (s, 6H). MS (ESI) m/z 517.2 [M+H]$^+$

Exemplary Compound 196

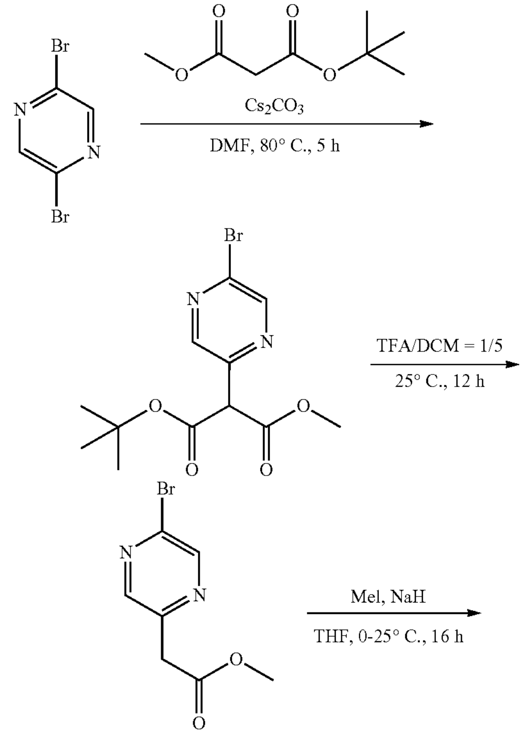

-continued

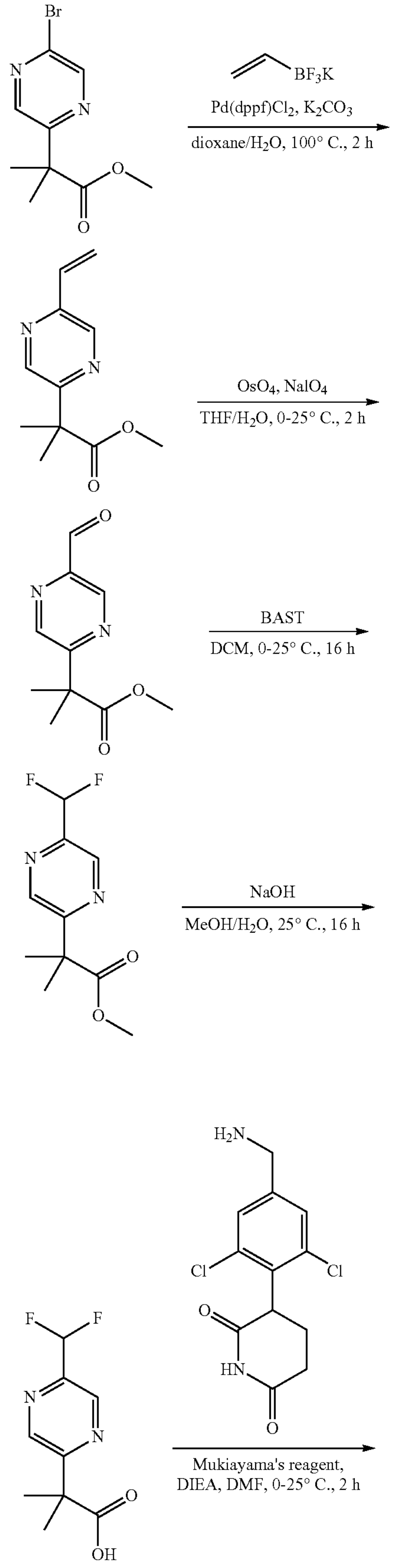

-continued

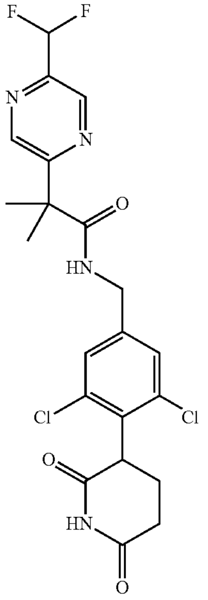

Step 1. A mixture of 2,5-dibromopyrazine (5.50 g, 23.1 mmol, 1.00 eq.), tert-butyl methyl malonate (6.44 g, 37.0 mmol, 6.26 mL, 1.60 eq.), and caesium carbonate (22.6 g, 69.4 mmol, 3.00 eq.) in N,N-dimethylformamide (100 mL) was stirred at 80° C. for 5 h under nitrogen atmosphere. The reaction mixture was filtered and concentrated under reduced pressure to give a residue. The residue was purified via Purification Method 2 to afford 1-(tert-butyl) 3-methyl 2-(5-bromopyrazin-2-yl) malonate (6.50 g, 18.8 mmol, 82% yield) as a yellow oil.

Step 2. To a solution of 1-(tert-butyl) 3-methyl 2-(5-bromopyrazin-2-yl) malonate (6.50 g, 19.6 mmol, 1.00 eq.) in dichloromethane (100 mL) was added 2,2,2-trifluoro-acetic acid (20 mL). The mixture was stirred at 25° C. for 16 h. The reaction mixture was concentrated under reduced pressure to give a residue. The residue was diluted with dichloromethane (100 mL), and the mixture was added slowly to saturated aqueous sodium bicarbonate solution (200 mL). The mixture was extracted with dichloromethane (3×200 mL). The combined organic layers were dried over anhydrous sodium sulfate, filtered, and concentrated in vacuo to give a residue. The residue was purified via Purification Method 2 to afford methyl 2-(5-bromopyrazin-2-yl)acetate (4.00 g, 16.3 mmol, 83% yield) as a yellow oil.

Step 3. To a solution of methyl 2-(5-bromopyrazin-2-yl) acetate (3.00 g, 13.0 mmol, 1.00 eq.) in tetrahydrofuran (30 mL) was added sodium hydride (1.30 g, 32.5 mmol, 60% purity, 2.50 eq.) at 0° C. under nitrogen atmosphere. The mixture was stirred at 0° C. for 1 h, followed by the addition of iodomethane (18.4 g, 130 mmol, 8.08 mL, 10.0 eq.). The reaction was stirred at 25° C. for 15 h. The reaction was quenched by addition of aqueous ammonium chloride solution (2 mL) at 0° C., and then diluted with water (20 mL) and extracted with ethyl acetate (3×50 mL). The combined organic layers were washed with brine (50 mL), dried over anhydrous sodium sulfate, filtered, and concentrated under reduced pressure. The residue was purified via Purification Method 2 to afford methyl 2-(5-bromopyrazin-2-yl)-2-methylpropanoate (1.60 g, 5.62 mmol, 43% yield) as a colourless oil.

Step 4. A mixture of methyl 2-(5-bromopyrazin-2-yl)-2-methylpropanoate (1.5 g, 5.79 mmol, 1.00 eq.), potassium trifluoro (vinyl) borate (1.55 g, 11.6 mmol, 2.00 eq.), dichloro[1,1-bis(diphenylphosphino)ferrocene]palladium (II) (424 mg, 579.0 μmol, 0.100 eq.), and caesium carbonate (3.77 g, 11.6 mmol, 2.00 eq.) in dioxane (15 mL) and water (15 mL) was stirred at 100° C. for 2 h under nitrogen atmosphere. The reaction was cooled to room temperature and filtered through a plug of Celite. The filtrate was diluted with water (50 mL) and extracted with ethyl acetate (3×50 mL). The combined organic layers were washed with brine (50 mL), dried over anhydrous sodium sulfate, filtered, and concentrated under reduced pressure. The residue was purified via Purification Method 2 to afford methyl 2-methyl-2-(5-vinylpyrazin-2-yl) propanoate (1.08 g, 4.87 mmol, 84% yield) as a light-yellow oil.

Step 5. To a solution of methyl 2-methyl-2-(5-vinylpyrazin-2-yl) propanoate (1.08 g, 5.24 mmol, 1.00 eq.) in tetrahydrofuran (15 mL) and water (5 mL) was added osmium (VIII) oxide (200 mg, 785 μmol, 40.8 μL, 0.150 eq.) at 0° C. Then a solution of sodium periodate (2.80 g, 13.1 mmol, 725 μL, 2.50 eq.) in water (10 mL) was added to the mixture. The mixture was stirred at 25° C. for 2 h. Then the reaction mixture was diluted with water (20 mL) at 0° C., and extracted with ethyl acetate (3× 30 mL). The combined organic layers were washed with brine (20 mL), dried over anhydrous sodium sulfate, filtered, and concentrated under reduced pressure. The residue was purified via Purification Method 2 to afford methyl 2-(5-formylpyrazin-2-yl)-2-methylpropanoate (935 mg, 4.40 mmol, 84% yield) as a light-yellow oil.

Step 6. To a solution of methyl 2-(5-formylpyrazin-2-yl)-2-methylpropanoate (460 mg, 2.21 mmol, 1.00 eq.) in dichloromethane (5 mL) was added bis(2-methoxyethyl) aminosulfurtrifluoride (1.47 g, 6.63 mmol, 1.45 mL, 3.00 eq.) at 0° C. The mixture was stirred at 25° C. for 16 h. The reaction mixture was quenched with saturated aqueous sodium bicarbonate solution (10 mL) at 0° C., then diluted with water (50 mL) and extracted with dichloromethane (3×30 mL). The combined organic layers were washed with brine (30 mL), dried over anhydrous sodium sulfate, filtered, and concentrated under reduced pressure. The residue was purified via Purification Method 2 to afford methyl 2-(5-(difluoromethyl) pyrazin-2-yl)-2-methylpropanoate (390 mg, 1.49 mmol, 67% yield) as a light-yellow oil.

Step 7. To a solution of methyl 2-(5-(difluoromethyl) pyrazin-2-yl)-2-methylpropanoate (390 mg, 1.69 mmol, 1.00 eq.) in methanol (10 mL) and water (5 mL) was added sodium hydroxide (136 mg, 3.39 mmol, 2.00 eq.). The mixture was stirred at 25° C. for 16 h. The reaction mixture was diluted with water (20 mL) and adjusted to pH 6 by addition of 1M hydrochloric acid. The mixture was extracted with ethyl acetate (3× 20 mL). The combined organic layers were washed with brine (30 mL), dried over anhydrous sodium sulfate, filtered, and concentrated under reduced pressure to afford 2-(5-(difluoromethyl) pyrazin-2-yl)-2-methylpropanoic acid (260 mg, 722 μmol, 43% yield, 60% purity) as a light-yellow oil.

Step 8. To a solution of 2-[5-(difluoromethyl) pyrazin-2-yl]-2-methyl-propanoic acid (120 mg, 333 μmol, 1.00 eq.) in N,N-dimethylformamide (2 mL) were added 2-chloro-1-methyl-pyridin-1-ium iodide (102 mg, 400 μmol, 1.20 eq.) and N-ethyl-N-isopropylpropan-2-amine (172 mg, 1.33 mmol, 232 μL, 4.00 eq.) at 0° C. The reaction was stirred at 25° C. for 1 h. Then 3-(4-(aminomethyl)-2,6-dichlorophenyl) piperidine-2,6-dione hydrochloride (86.2 mg, 266 μmol, 0.800 eq.) was added. The reaction was stirred at 25° C. for another 1 h. The reaction was quenched with water (2 mL), and then diluted with water (20 mL) and extracted with ethyl acetate (3x20 mL). The combined organic layers were washed with brine (30 mL), dried over anhydrous sodium sulfate, filtered, and concentrated under reduced pressure. The residue was via Purification Method I to afford N-(3, 5-dichloro-4-(2,6-dioxopiperidin-3-yl)benzyl)-2-(5-(difluoromethyl) pyrazin-2-yl)-2-methylpropanamide (49.5 mg, 101 μmol, 30% yield) as a white solid.

$^1$H NMR (400 MHZ, DMSO-$d_6$)>=10.97 (s, 1H), 8.92 (s, 1H), 8.86 (s, 1H), 8.20 (t, J=6.0 Hz, 1H), 7.32-7.00 (m, 3H), 4.57 (dd, J=5.6, 12.4 Hz, 1H), 4.25 (d, J=6.0 Hz, 2H), 2.92-2.79 (m, 1H), 2.59-2.52 (m, 1H), 2.40-2.29 (m, 1H), 1.95-1.84 (m, 1H), 1.62 (s, 6H). MS (ESI) m/z 485.2 [M+H]$^+$

Exemplary Compound 198

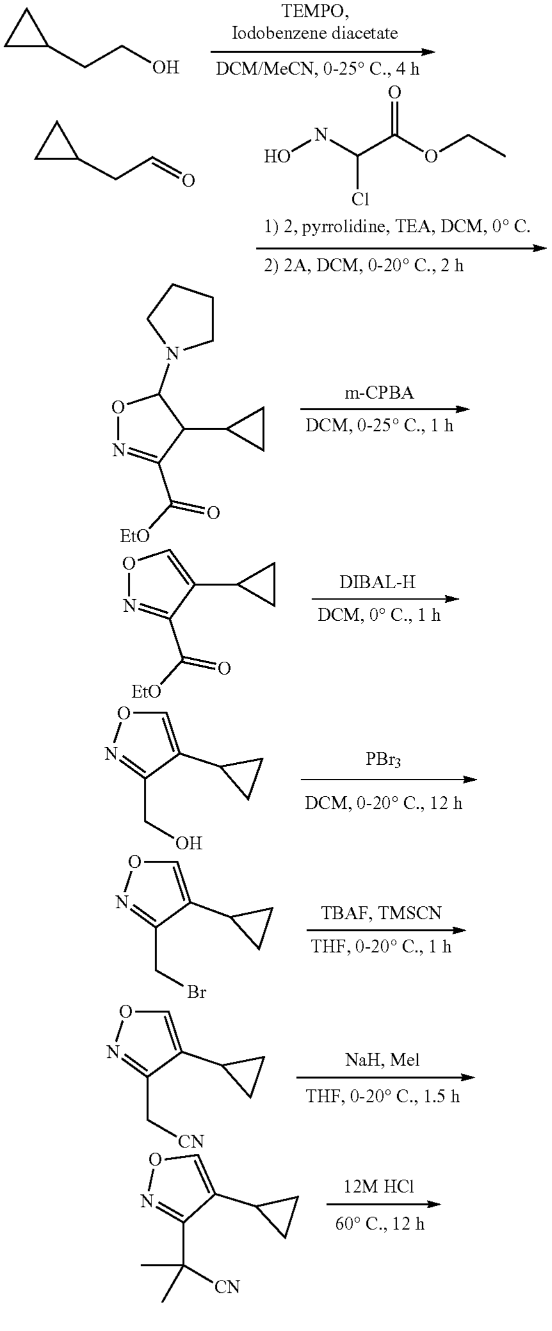

-continued

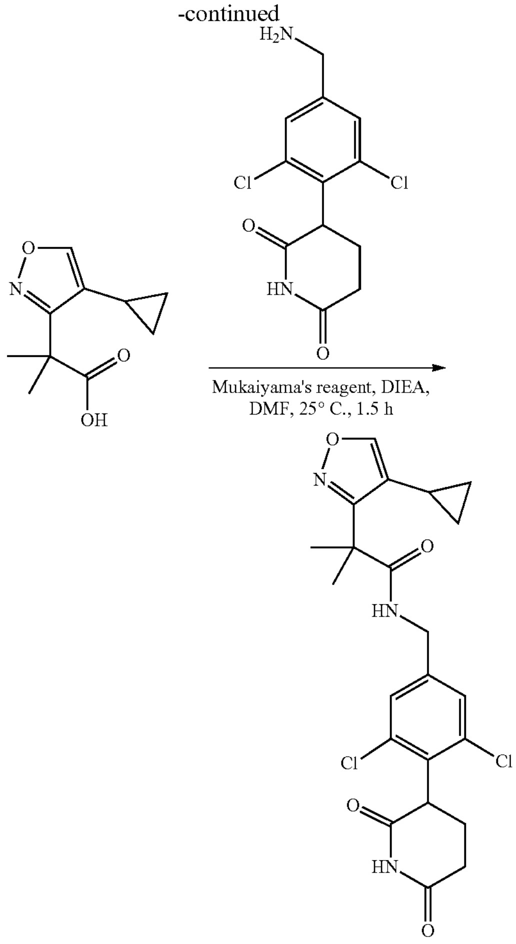

Step 1. To a solution of 2-cyclopropylethan-1-ol (5.00 g, 58.1 mmol, 1.00 eq.) and 2,2,6,6-tetramethylpiperidine 1-oxyl (456 mg, 2.90 mmol, 0.05 eq.) in dichloromethane (10 mL) and acetonitrile (50 mL) was added iodobenzene diacetate (19.6 g, 61.0 mmol, 1.05 eq.) at 0° C. The mixture was stirred at 25° C. for 4 h. The reaction was quenched with saturated sodium bicarbonate (100 mL) and extracted with dichloromethane (2x50 mL). The organic layers were washed with brine (50 mL), dried over sodium sulfate, filtered, and concentrated to remove some solvent to give a solution of 2-cyclopropylacetaldehyde (100 mL, 0.58 M in dichloromethane/acetonitrile). It was used directly without purification.

Step 2. To a solution of 2-cyclopropylacetaldehyde (0.58 M in dichloromethane/acetonitrile, 100 mL) in dichloromethane were added pyrrolidine (4.33 g, 60.9 mmol, 1.05 eq.) and triethylamine (2.94 g, 29.0 mmol, 0.50 eq.) at 0° C. A solution of ethyl 2-chloro-2-(hydroxyimino)acetate (4.40 g, 29.0 mmol, 0.50 eq.) in dichloromethane (50 mL) was added in 5 portions over 20 min. The mixture was stirred at 0° C. for 10 min, then at 20° C. for 1.5 h. The mixture was concentrated, and the residue was purified via Purification Method 2 to afford ethyl 4-cyclopropyl-5-(pyrrolidin-1-yl)-4,5-dihydroisoxazole-3-carboxylate (3.88 g, 14.4 mmol, 25% yield) as a yellow oil.

Step 3. To a solution of ethyl 4-cyclopropyl-5-(pyrrolidin-1-yl)-4,5-dihydroisoxazole-3-carboxylate (3.88 g, 15.4 mmol, 1.00 eq.) in dichloromethane (30 mL) was added 3-chlorobenzoperoxoic acid (5.00 g, 24.6 mmol, 85% purity, 1.60 eq.) at 0° C. Then the reaction was stirred at 25° C. for 1 h. The mixture was diluted with saturated sodium bicarbonate solution (150 mL) and extracted with ethyl acetate (3×50 mL). The combined organic layers were washed with saturated sodium bicarbonate solution (50 mL), dried over sodium sulfate, filtered, and concentrated in vacuo. The residue was purified via Purification Method 2 to afford ethyl 4-cyclopropylisoxazole-3-carboxylate (2.56 g, 12.4 mmol, 81% yield) as a yellow oil.

Step 4. To a solution of ethyl 4-cyclopropylisoxazole-3-carboxylate (2.66 g, 14.7 mmol, 1.00 eq.) in dichloromethane (50 mL) was added diisobutylaluminum hydride (1 M in toluene, 44.0 mL, 3.00 eq.) dropwise under nitrogen atmosphere at 0° C. The mixture was stirred at 0° C. for 1 h. The mixture was poured into saturated ammonium chloride solution (200 mL) and extracted with ethyl acetate (3×50 mL). The combined organic layers were washed with brine (50 mL), dried over sodium sulfate, filtered, and concentrated in vacuo. The residue was purified via Purification Method 2 to afford (4-cyclopropylisoxazol-3-yl) methanol (1.56 g, 11.1 mmol, 76% yield) as a yellow oil.

Step 5. To a solution of (4-cyclopropylisoxazol-3-yl) methanol (1.46 g, 10.5 mmol, 1.00 eq.) in dichloromethane (50 mL) was added phosphorus tribromide (8.52 g, 31.5 mmol, 3.00 eq.) at 0° C. The mixture was stirred at 20° C. for 12 h. The reaction was quenched by ice water (150 mL) and extracted with ethyl acetate (3×50 mL). The organic layers were washed with brine (50 mL), dried over sodium sulfate, filtered, and concentrated. The residue was purified via Purification Method 2 to afford the 3-(bromomethyl)-4-cyclopropylisoxazole (1.42 g, 6.92 mmol, 66% yield) as a colourless oil.

Step 6. To a solution of 3-(bromomethyl)-4-cyclopropylisoxazole (1.42 g, 7.03 mmol, 1.00 eq.) and trimethylsilyl cyanide (1.05 g, 10.5 mmol, 1.50 eq.) in tetrahydrofuran (20 mL) was added a solution of tetrabutylammonium fluoride (1 M in tetrahydrofuran, 10.5 mL, 1.50 eq.) dropwise at 0° C. The reaction was stirred at 20° C. for 1 h. The mixture was diluted with water (50 mL) and extracted with ethyl acetate (3× 20 mL). The combined organic layers were washed with brine (30 mL), dried over sodium sulfate, filtered, and concentrated in vacuo. The residue was purified via Purification Method 2 to afford the 2-(4-cyclopropylisoxazol-3-yl) acetonitrile (976 mg, 6.32 mmol, 90% yield) as a colourless oil.

Step 7. To a solution of 2-(4-cyclopropylisoxazol-3-yl) acetonitrile (500 mg, 3.37 mmol, 1.00 eq.) in tetrahydrofuran (10 mL) was added sodium hydride (405 mg, 10.1 mmol, 60% purity, 3.00 eq.) at 0° C. under nitrogen atmosphere. The mixture was stirred at 0° C. for 30 min, then methyl iodide (1.44 g, 10.1 mmol, 3.00 eq.) was added. The reaction was stirred at 20° C. for 1 h under nitrogen atmosphere. The reaction was quenched with saturated ammonium chloride solution (50 mL) at 0° C., and extracted with ethyl acetate (3×20 mL). The combined organic extracts were washed with brine (30 mL), dried over sodium sulfate, filtered, and concentrated under reduced pressure. The residue was purified via Purification Method 2 to afford 2-(4-cyclopropylisoxazol-3-yl)-2-methylpropanenitrile (531 mg, 2.98 mmol, 88% yield) as a colourless oil.

Step 8. A solution of 2-(4-cyclopropylisoxazol-3-yl)-2-methyl-propanenitrile (200 mg, 1.13 mmol, 1.00 eq.) in hydrochloric acid (12 M, 5 mL) was stirred at 60° C. for 12 h. The mixture was diluted with water (30 mL) and extracted with ethyl acetate (3×15 mL). The combined organic layers were washed with brine (20 mL), dried over sodium sulfate, filtered, and concentrated in vacuo. The residue was purified via Purification Method 1 to afford 2-(4-cyclopropylisoxazol-3-yl)-2-methylpropanoic acid (81.0 mg, 411 μmol, 36% yield) as a white solid.

Step 9. To a solution of 2-(4-cyclopropylisoxazol-3-yl)-2-methylpropanoic acid (70.0 mg, 359 μmol, 1.10 eq.) in N,N-dimethylformamide (5 mL) were added 2-chloro-1-methyl-pyridin-1-ium iodide (125 mg, 489 μmol, 1.50 eq.) and N,N-diisopropylethylamine (127 mg, 978 μmol, 3.00 eq.). The mixture was stirred at 25° C. for 30 min. Then 3-(4-(aminomethyl)-2,6-dichlorophenyl) piperidine-2,6-dione hydrochloride (106 mg, 326 μmol, 1.00 eq.) was added. The reaction was stirred at 25° C. for 1 h. The mixture was diluted with water (30 mL) and extracted with ethyl acetate (3×15 mL). The combined organic layers were washed with water (20 mL) and brine (20 mL), dried over sodium sulfate, filtered, and concentrated in vacuo. The residue was purified via Purification Method 1 to afford 2-(4-cyclopropylisoxazol-3-yl)-N-(3,5-dichloro-4-(2,6-dioxopiperidin-3-yl)benzyl)-2-methylpropanamide (89.6 mg, 191 μmol, 59% yield) as a white solid.

$^1H$ NMR (400 MHZ, DMSO-$d_6$) δ=10.95 (s, 1H), 8.49 (s, 1H), 8.25 (t, J=6.0 Hz, 1H), 7.33 (d, J=1.2 Hz, 1H), 7.26 (d, J=1.2 Hz, 1H), 4.63-4.49 (m, 1H), 4.22 (d, J=6.0 Hz, 2H), 2.93-2.76 (m, 1H), 2.61-2.51 (m, 1H), 2.43-2.27 (m, 1H), 1.95-1.81 (m, 1H), 1.56 (s, 6H), 1.27-1.12 (m, 1H), 0.79-0.69 (m, 2H), 0.55-0.44 (m, 2H). MS (ESI) m/z 464.1 $[M+H]^+$

Exemplary Compound 200

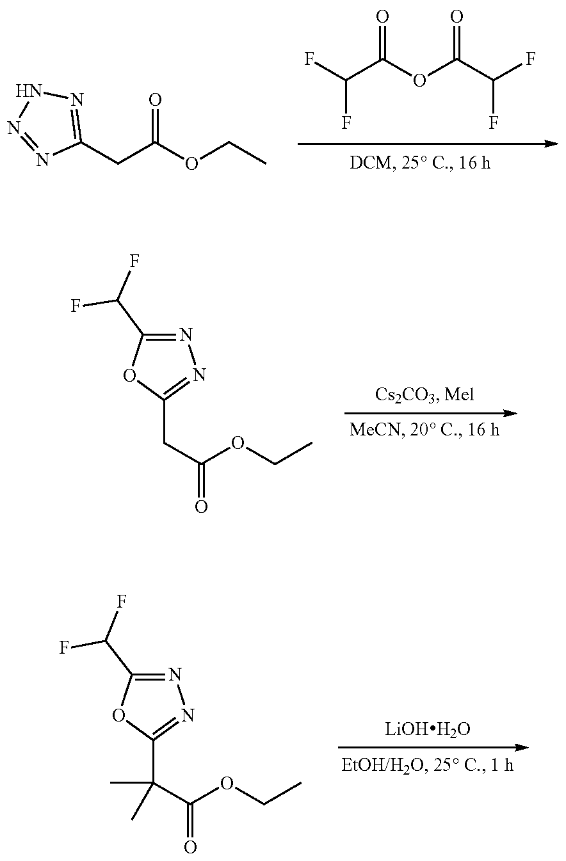

-continued

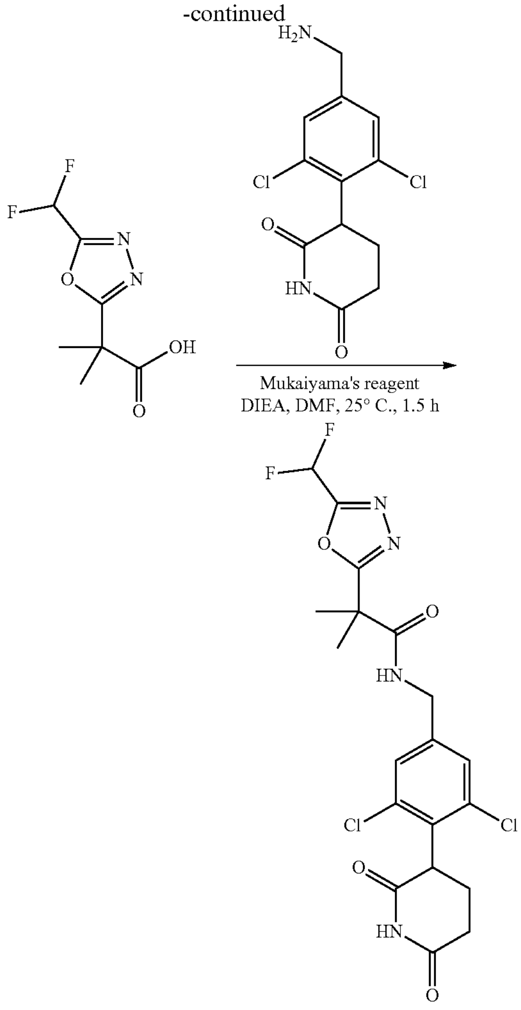

Step 1. To a solution of ethyl 2-(2H-tetrazol-5-yl)acetate (2.00 g, 12.8 mmol, 1.00 eq.) in dichloromethane (40 mL) was added 2,2-difluoroacetic anhydride (2.90 g, 16.7 mmol, 1.30 eq.). The mixture was stirred at 25° C. for 16 h. The reaction mixture was diluted with dichloromethane (100 mL) and slowly added to aqueous saturated sodium bicarbonate solution (100 mL). The layers were separated, and the organic layer was washed with water (2×100 mL), dried over sodium sulfate, filtered, and concentrated under reduced pressure. The residue was purified via Purification Method 2 to afford ethyl 2-(5-(difluoromethyl)-1,3,4-oxadiazol-2-yl)acetate (930 mg, 4.29 mmol, 33% yield) as a colourless oil.

Step 2. To a solution of ethyl 2-(5-(difluoromethyl)-1,3,4-oxadiazol-2-yl)acetate (500 mg, 2.43 mmol, 1.00 eq.) in acetonitrile (10 mL) were added caesium carbonate (2.37 g, 7.28 mmol, 3.00 eq.) and methyl iodide (24.3 mmol, 1.51 mL, 10.0 eq.). The mixture was stirred at 20° C. for 16 h.

The mixture was diluted with water (20 mL) and extracted with ethyl acetate (20 mL). The combined organic layers were washed with water (2×20 mL), dried over sodium sulfate, filtered, and concentrated under reduced pressure. The residue was purified via Purification Method 2 to afford ethyl 2-(5-(difluoromethyl)-1,3,4-oxadiazol-2-yl)-2-methylpropanoate (460 mg, 1.87 mmol, 77% yield) as a colourless oil.

Step 3. To a solution of ethyl 2-(5-(difluoromethyl)-1,3,4-oxadiazol-2-yl)-2-methylpropanoate (460 mg, 1.96 mmol, 1.00 eq.) in water (2 mL) and methanol (2 mL) was added lithium hydroxide monohydrate (90.7 mg, 2.16 mmol, 1.10 eq.). The reaction was stirred at 25° C. for 1 h. The mixture was diluted with ice water 10 mL and acidified with aqueous hydrochloric acid (1 M) to pH 5.

Then the mixture was extracted with dichloromethane (2×10 mL). The combined extracts were dried over sodium sulfate, filtered, and concentrated under vacuum to give 2-(5-(difluoromethyl)-1,3,4-oxadiazol-2-yl)-2-methylpropanoic acid (230 mg, crude) as a yellow oil, and it was used directly in the next step.

Step 4. To a solution of 2-(5-(difluoromethyl)-1,3,4-oxadiazol-2-yl)-2-methylpropanoic acid (230 mg, crude) in N,N-dimethylformamide (3 mL) were added 2-chloro-1-methyl-pyridin-1-ium iodide (314 mg, 1.23 mmol, 1.10 eq.) and N,N-diisopropylethylamine (3.35 mmol, 580 μL, 3.00 eq.). The mixture was stirred at 25° C. for 0.5 h. Then 3-(4-(aminomethyl)-2,6-dichlorophenyl) piperidine-2,6-dione hydrochloride (150 mg, 464 μmol, 0.40 eq.) was added, and the reaction was stirred at 25° C. for 1 h. The mixture was diluted with water (10 mL) and extracted with ethyl acetate (10 mL). The combined organic layers were washed with water (2×10 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-(5-(difluoromethyl)-1,3,4-oxadiazol-2-yl)-2-methylpropanamide (199.9 mg, 416 μmol, 37% yield) as a white solid.

$^1$H NMR (400 MHZ, DMSO-$d_6$) δ=10.96 (s, 1H), 8.58 (t, J=5.6 Hz, 1H), 7.49 (t, J=51.2 Hz, 1H), 7.34 (s, 1H), 7.27 (s, 1H), 4.58 (dd, J=5.6, 12.8 Hz, 1H), 4.27 (d, J=5.6 Hz, 2H), 2.86 (ddd, J=5.6, 14.0, 16.8 Hz, 1H), 2.56 (m, 1H), 2.36 (dq, J=4.4, 13.2 Hz, 1H), 1.97-1.83 (m, 1H), 1.65 (s, 6H). MS (ESI) m/z 475.1 $[M+H]^+$ Exemplary Compound 202

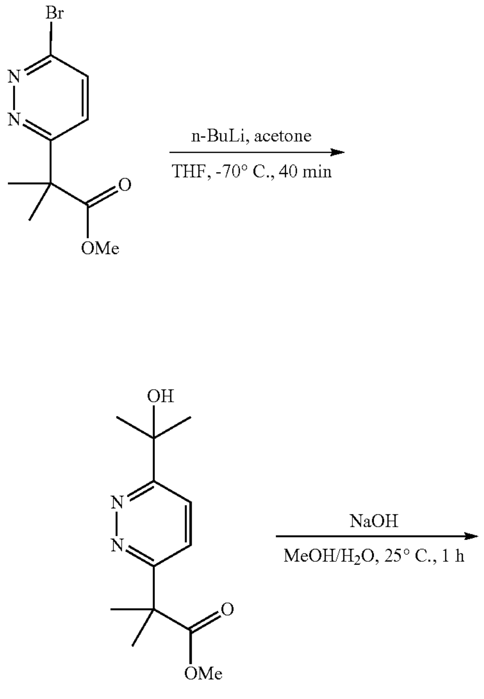

-continued

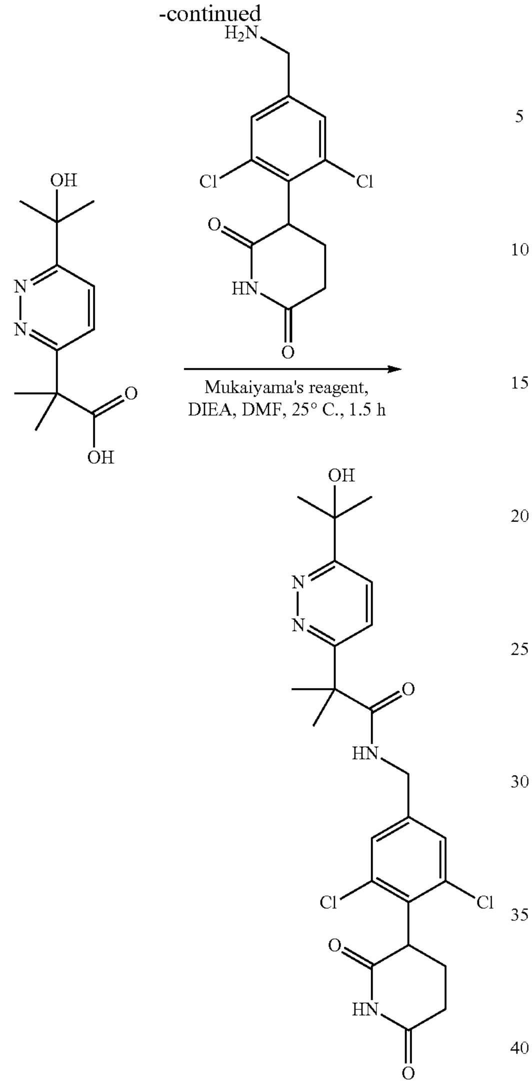

Step 1. To a solution of methyl 2-(6-bromopyridazin-3-yl)-2-methylpropanoate (1.00 g, 3.86 mmol, 1.00 eq.) and acetone (448 mg, 7.72 mmol, 2.00 eq.) in tetrahydrofuran (20 mL) was added n-butyllithium (2.5 M in hexane, 2.32 mL, 1.50 eq.) dropwise at −70° C. over 10 min under nitrogen. The reaction was stirred at −70° C. for 30 min under nitrogen. Water (30 mL) was added to the reaction at −70° C. The mixture was extracted with ethyl acetate (3×15 mL). The combined organic layers were washed with brine (30 mL), dried over sodium sulfate, filtered, and concentrated under reduced pressure. The residue was purified via Purification Method 2 to afford methyl 2-(6-(2-hydroxypropan-2-yl)pyridazin-3-yl)-2-methylpropanoate (92.0 mg, 232 μmol, 6% yield) as a colourless oil.

Step 2. To a solution of methyl 2-(6-(2-hydroxypropan-2-yl)pyridazin-3-yl)-2-methylpropanoate (125 mg, 525 μmol, 1.00 eq.) in methanol (2 mL) and water (2 mL) was added sodium hydroxide (105 mg, 2.62 mmol, 5.00 eq.). The reaction was stirred at 25° C. for 1 h. The mixture was diluted with water (30 mL) and the pH was adjusted to 9-10 with hydrochloric acid (2 M). The mixture was extracted with ethyl acetate (2×15 mL). Then the pH of the mixture was adjusted to 7-8 with hydrochloric acid (2 M in water). It was lyophilized to give the 2-(6-(2-hydroxypropan-2-yl)pyridazin-3-yl)-2-methylpropanoic acid (283 mg, crude) as a white solid.

Step 3. To a solution of 2-(6-(2-hydroxypropan-2-yl)pyridazin-3-yl)-2-methylpropanoic acid (283 mg, crude) in N, N-dimethylformamide (5 mL) were added 2-chloro-1-methyl-pyridin-1-ium iodide (116 mg, 454 μmol, 1.50 eq.) and N,N-diisopropylethylamine (117 mg, 909 μmol, 3.00 eq.). The mixture was stirred at 25° C. for 30 min. Then 3-(4-(aminomethyl)-2,6-dichlorophenyl) piperidine-2,6-dione hydrochloride (87.0 mg, 269 μmol, 0.89 eq.) was added, and the reaction was stirred at 25° C. for 1 h. The mixture was diluted with water (30 mL) and extracted with ethyl acetate (3×15 mL). The combined organic layers were washed with water (20 mL) and brine (20 mL), dried over sodium sulfate, filtered, and concentrated in vacuo. The residue was purified via Purification Method 1 to afford N-(3,5-dichloro-4-(2,6-dioxopiperidin-3-yl)benzyl)-2-(6-(2-hydroxypropan-2-yl)pyridazin-3-yl)-2-methylpropanamide (42.7 mg, 85.7 μmol, 28% yield) as a white solid.

$^1$H NMR (400 MHZ, DMSO-$d_6$) δ=10.95 (s, 1H), 8.24 (t, J=6.0 Hz, 1H), 7.84 (d, J=8.8 Hz, 1H), 7.63 (d, J=8.8 Hz, 1H), 7.28 (s, 1H), 7.21 (s, 1H), 5.46 (br s, 1H) 4.63-4.46 (m, 1H), 4.25 (d, J=6.0 Hz, 2H), 2.94-2.77 (m, 1H), 2.55-2.53 (m, 1H), 2.41-2.27 (m, 1H), 1.94-1.83 (m, 1H), 1.60 (s, 6H), 1.53 (s, 6H). MS (ESI) m/z 493.1 $[M+H]^+$

Exemplary Compound 204

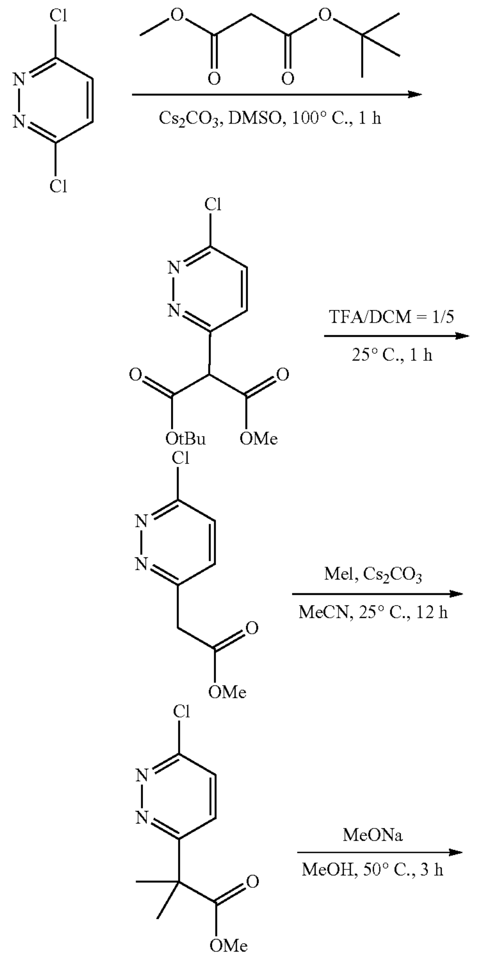

-continued

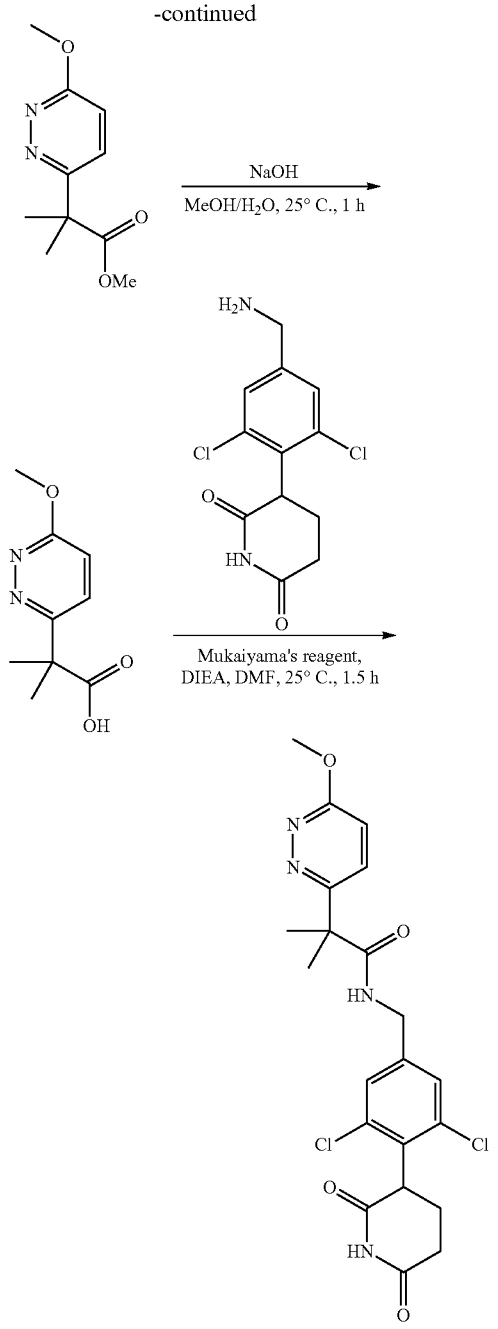

Step 1. To a solution of 3,6-dichloropyridazine (5.00 g, 33.6 mmol, 1.00 eq.) in dimethyl sulfoxide (30 mL) were added caesium carbonate (32.8 g, 101 mmol, 3.00 eq.) and tert-butyl methyl malonate (8.77 g, 50.3 mmol, 1.50 eq.). The mixture was stirred at 100° C. for 1 h. The mixture was diluted with water (100 mL) and extracted with ethyl acetate (100 mL). The combined organic layers were washed with water (2×100 mL) and brine (100 mL), dried over sodium sulfate, filtered, and concentrated under reduced pressure. The residue was purified via Purification Method 2 to afford 1-(tert-butyl) 3-methyl 2-(6-chloropyridazin-3-yl) malonate (7.93 g, 26.0 mmol, 77% yield) as a yellow solid.

Step 2. To a solution of 1-(tert-butyl) 3-methyl 2-(6-chloropyridazin-3-yl) malonate (7.70 g, 26.9 mmol, 1.00 eq.) in dichloromethane (30 mL) was added trifluoroacetic acid (6 mL) in one portion at 25° C. The mixture was stirred at 25° C. for 1 h. The mixture was concentrated under reduced pressure, then diluted with dichloromethane (20 mL). The mixture was washed with saturated sodium bicarbonate (2×20 mL). The combined organic layers were dried over sodium sulfate, filtered, and concentrated under reduced pressure to give methyl 2-(6-chloropyridazin-3-yl) acetate (5.16 g, 26.0 mmol, 97% yield) as a yellow solid.

Step 3. To a solution of methyl 2-(6-chloropyridazin-3-yl)acetate (4.95 g, 26.5 mmol, 1.00 eq.) in acetonitrile (20 mL) were added caesium carbonate (25.9 g, 79.6 mmol, 3.00 eq.) and methyl iodide (16.5 mL, 265 mmol, 10.0 eq.) at 25° C. under nitrogen atmosphere. The mixture was stirred at 25° C. under nitrogen atmosphere for 12 h. The mixture was diluted with water (40 mL) and extracted with ethyl acetate (40 mL). The combined organic layers were washed with water (2×30 mL) and brine (30 mL), dried over sodium sulfate, filtered, and concentrated under reduced pressure. The residue was purified via Purification Method 2 to afford methyl 2-(6-chloropyridazin-3-yl)-2-methylpropanoate (3.63 g, 16.2 mmol, 61% yield) as a yellow solid.

Step 4. To a solution of methyl 2-(6-chloropyridazin-3-yl)-2-methylpropanoate (1.00 g, 4.66 mmol, 1.00 eq.) in methanol (8 mL) were added sodium methoxide (755 mg, 14.0 mmol, 3.00 eq.) at 20° C. under nitrogen atmosphere. The reaction was stirred at 50° C. for 3 h under nitrogen atmosphere. The mixture was concentrated under reduced pressure. The residue was purified via Purification Method 2 to afford methyl 2-(6-methoxypyridazin-3-yl)-2-methylpropanoate (530 mg, 1.51 mmol, 32% yield, 60% purity) as a yellow oil.

Step 5. To a solution of methyl 2-(6-methoxypyridazin-3-yl)-2-methylpropanoate (180 mg, 856 μmol, 1.00 eq.) in methanol (3 mL) were added water (1.5 mL) and sodium hydroxide (171 mg, 4.28 mmol, 5.00 eq.) at 25° C. The mixture was stirred at 25° C. for 1 h. The reaction mixture was diluted with water (10 mL) and extracted with dichloromethane (3×10 mL). The aqueous phase was adjusted to 6 with 2M hydrochloric acid, then lyophilized to give 2-(6-methoxypyridazin-3-yl)-2-methylpropanoic acid (330 mg, crude) as a white solid.

Step 6. To a solution of 2-(6-methoxypyridazin-3-yl)-2-methylpropanoic acid (318 mg, crude) in dimethyl formamide (4 mL) were added N,N-diisopropylethylamine (254 μL, 1.46 mmol, 3.0 eq.) and 2-chloro-1-methyl-pyridin-1-ium iodide (149 mg, 583 μmol, 1.20 eq.). After addition, the mixture was stirred at 25° C. for 30 min. Then 3-(4-(aminomethyl)-2,6-dichlorophenyl) piperidine-2,6-dione hydrochloride (110 mg, 340 μmol, 0.70 eq.) was added. The reaction was stirred at 25° C. for 1 h. The mixture was diluted with water (10 mL) and extracted with ethyl acetate (10 mL). The combined organic layers were washed with water (2×10 mL) and brine (10 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-(6-methoxypyridazin-3-yl)-2-methylpropanamide (31.48 mg, 67.0 μmol, 14% yield) as a white solid.

$^1H$ NMR (400 MHZ, DMSO-$d_6$) δ=10.95 (s, 1H), 8.16 (t, J=6.0 Hz, 1H), 7.56 (d, J=9.2 Hz, 1H), 7.24 (d, J=1.6 Hz, 1H), 7.18-7.15 (m, 2H), 4.55 (dd, J=5.6, 12.8 Hz, 1H), 4.22 (d, J=6.0 Hz, 2H), 4.02 (s, 3H), 2.89-2.80 (m, 1H), 2.55-2.54 (m, 1H), 2.40-2.29 (m, 1H), 1.91-1.85 (m, 1H), 1.57 (s, 6H). MS (ESI) m/z 465.1 $[M+H]^+$

Exemplary Compound 206

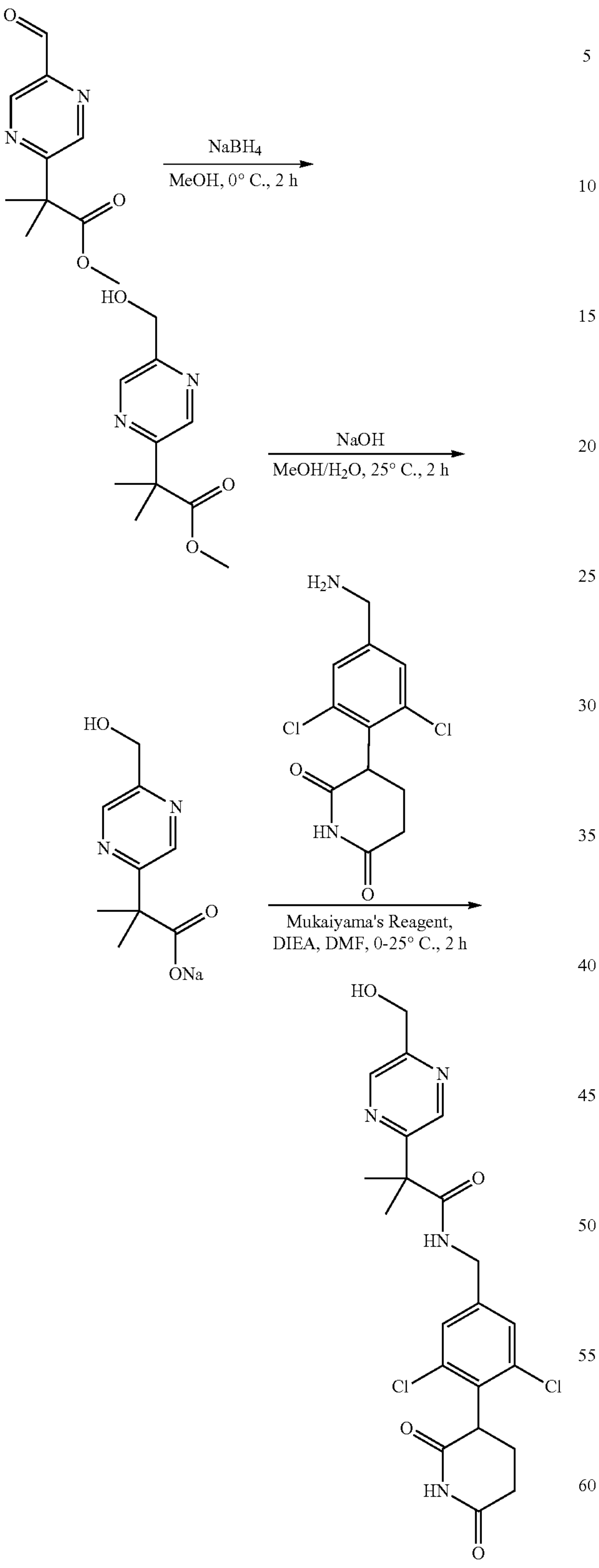

Step 1. To a solution of methyl 2-(5-formylpyrazin-2-yl)-2-methylpropanoate (350 mg, 1.68 mmol, 1.00 eq.) in methanol (2 mL) was added sodium borohydride (159 mg, 4.20 mmol, 2.50 eq.) at 0° C. The mixture was stirred at 0° C. for 2 h. The reaction was quenched by addition saturated ammonium chloride solution (2 mL) at 0° C., then diluted with water (25 mL) and extracted with ethyl acetate (3×20 mL). The combined organic layers were washed with brine (30 mL), dried over anhydrous sodium sulfate, filtered, and concentrated under reduced pressure. The residue was purified via Purification Method 2 to afford methyl 2-(5-(hydroxymethyl) pyrazin-2-yl)-2-methylpropanoate (220 mg, 963 μmol, 57% yield) as a light-yellow oil.

Step 2. To a solution of methyl 2-(5-(hydroxymethyl) pyrazin-2-yl)-2-methylpropanoate (270 mg, 1.28 mmol, 1.00 eq.) in methanol (2 mL) and water (1 mL) was added sodium hydroxide (257 mg, 6.42 mmol, 5.00 eq.). The mixture was stirred at 25° C. for 2 h. The mixture was diluted with water (10 mL) and adjusted to pH 8 by addition of saturated aqueous sodium bicarbonate solution. Then the mixture was concentrated under reduced pressure to remove methanol, followed by lyophilization to afford sodium 2-(5-(hydroxymethyl) pyrazin-2-yl)-2-methylpropanoate (620 mg, 1.27 mmol, 99% yield, 45% purity) as a white solid. The crude product was used to the next step without purification.

Step 3. To a solution of sodium 2-(5-(hydroxymethyl) pyrazin-2-yl)-2-methylpropanoate (250 mg, 573 μmol, 1.00 eq., 45% purity) in N,N-dimethylformamide (2 mL) was added 2-chloro-1-methyl-pyridin-1-ium iodide (176 mg, 688 μmol, 1.20 eq.) and N,N-diisopropylethylamine (296 mg, 2.29 mmol, 4.00 eq.) at 0° C. The mixture was stirred at 25° C. for 1 h. Then 3-(4-(aminomethyl)-2,6-dichlorophenyl) piperidine-2,6-dione hydrochloride (130 mg, 401 μmol, 0.70 eq.) was added to the mixture. The mixture was stirred at 25° C. for another 1 h. The reaction was quenched with water (2 mL) at 0° C., and then diluted with water (20 mL) and extracted with ethyl acetate (3× 20 mL). The combined organic layers were washed with brine (10 mL), dried over anhydrous sodium sulfate, filtered, and concentrated under reduced pressure. The residue was purified via Purification Method 1 to afford N-(3,5-dichloro-4-(2,6-dioxopiperidin-3-yl)benzyl)-2-(5-(hydroxymethyl) pyrazin-2-yl)-2-methylpropanamide (58.8 mg, 125 μmol, 22% yield) as a white solid.

$^1H$ NMR (400 MHZ, DMSO-$d_6$) δ=10.95 (s, 1H), 8.66 (s, 1H), 8.60 (s, 1H), 8.12 (t, J=6.0 Hz, 1H), 7.32 (d, J=1.6 Hz, 1H), 7.25 (d, J=1.2 Hz, 1H), 5.59 (t, J=4.8 Hz, 1H), 4.62 (d, J=4.0 Hz, 2H), 4.56 (dd, J=5.6, 12.8 Hz, 1H), 4.24 (d, J=6.0 Hz, 2H), 2.89-2.79 (m, 1H), 2.57-2.52 (m, 1H), 2.40-2.30 (m, 1H), 1.94-1.83 (m, 1H), 1.57 (s, 6H). MS (ESI) m/z 465.1 $[M+H]^+$

Exemplary Compound 207

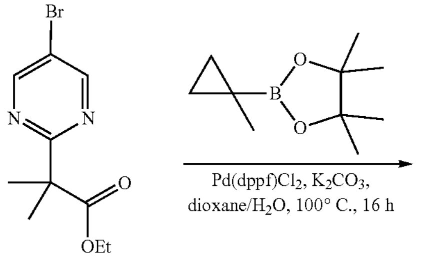

-continued

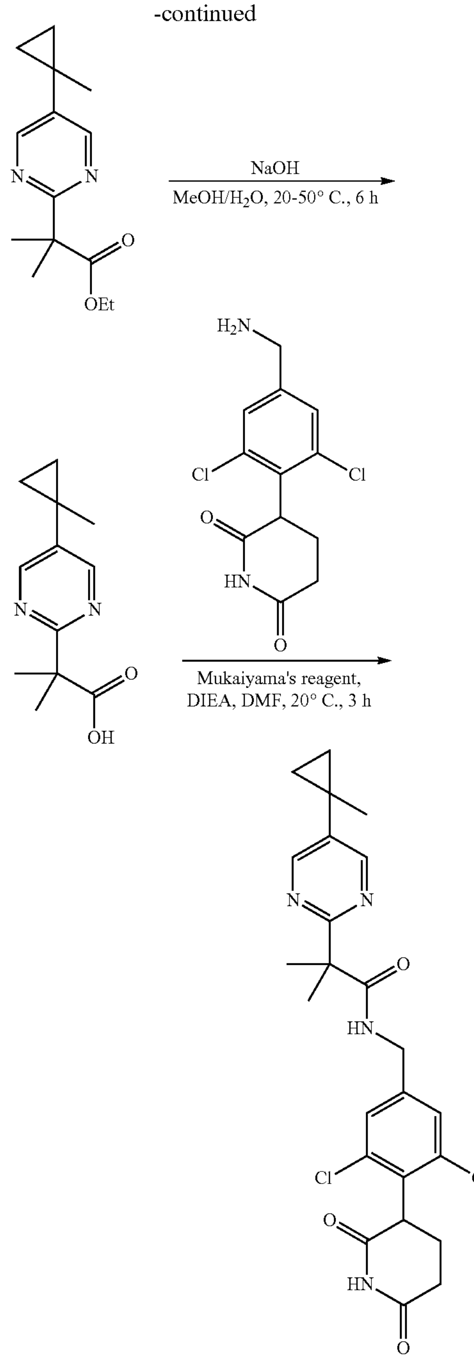

Step 1. To a solution of ethyl 2-(5-bromopyrimidin-2-yl)-2-methylpropanoate (720 mg, 2.64 mmol, 1.20 eq.) and 4,4,5,5-tetramethyl-2-(1-methylcyclopropyl)-1,3,2-dioxaborolane (400 mg, 2.20 mmol, 1.00 eq.) in dioxane (10 mL) was added [1,1-bis(diphenylphosphino)ferrocene]dichloropalladium (II) (320 mg, 437 μmol, 0.20 eq.), potassium carbonate (600 mg, 4.34 mmol, 1.98 eq.) and water (1 mL). The mixture was stirred at 100° C. under nitrogen for 16 h. The mixture was filtered, and the filtrate was diluted with water (30 mL) and extracted with ethyl acetate (2×30 mL). The combined organic extracts were washed with brine (50 mL), dried over sodium sulfate, filtered, and concentrated under reduced pressure. The residue was purified via Purification Method 2 to afford ethyl 2-methyl-2-(5-(1-methylcyclopropyl)pyrimidin-2-yl) propanoate (100 mg, 322 μmol, 14% yield) as a colourless oil.

Step 2. To a solution of ethyl 2-methyl-2-(5-(1-methylcyclopropyl)pyrimidin-2-yl) propanoate (100 mg, 402 μmol, 1.00 eq.) in methanol (3 mL) was added a solution of sodium hydroxide (80.0 mg, 2.00 mmol, 4.97 eq.) in water (0.5 mL). The mixture was stirred at 20° C. for 3 h and stirred at 50° C. for 3 h. The mixture was diluted with water (10 mL) and dichloromethane (10 mL). The aqueous phase was separated and washed with dichloromethane (10 mL). The aqueous phase was adjusted to pH~6 with hydrochloric acid (1 M) and lyophilized to afford 2-methyl-2-(5-(1-methylcyclopropyl)pyrimidin-2-yl) propanoic acid (400 mg, crude) as a white solid.

Step 3. To a solution of 2-methyl-2-(5-(1-methylcyclopropyl)pyrimidin-2-yl) propanoic acid (350 mg, 238 μmol, 1.00 eq.) in dimethylformamide (5 mL) was added N,N-diisopropylethylamine (113 mg, 878 μmol, 3.69 eq.) and 2-chloro-1-methyl-pyridin-1-ium iodide (85 mg, 332 μmol, 1.40 eq.).

The mixture was stirred at 20° C. for 0.5 h. Then 3-(4-(aminomethyl)-2,6-dichlorophenyl) piperidine-2,6-dione hydrochloride (80 mg, 247 μmol, 1.04 eq.) was added to the mixture and the mixture was stirred at 20° C. for 2.5 h. The reaction mixture was diluted with water (20 mL) and extracted with ethyl acetate (2×20 mL). The combined organic extracts were washed with brine (30 mL). The organic phase was dried over sodium sulfate, filtered, and concentrated under reduced pressure. The residue was purified via Purification Method 1 to afford N-(3,5-dichloro-4-(2,6-dioxopiperidin-3-yl)benzyl)-2-methyl-2-(5-(1-methylcyclopropyl)pyrimidin-2-yl) propanamide (27.16 mg, 54.4 μmol, 20% yield) as a white solid.

$^1$H NMR (400 MHZ, DMSO-$d_6$) δ=10.96 (s, 1H), 8.66 (s, 2H), 8.03 (t, J=6.0 Hz, 1H), 7.39 (d, J=1.2 Hz, 1H), 7.33 (d, J=1.2 Hz, 1H), 4.61-4.51 (m, 1H), 4.25 (d, J=6.0 Hz, 2H), 2.92-2.79 (m, 1H), 2.58-2.53 (m, 1H), 2.42-2.31 (m, 1H), 1.94-1.84 (m, 1H), 1.53 (s, 6H), 1.41 (s, 3H), 1.00-0.93 (m, 2H), 0.87-0.81 (m, 2H). MS (ESI) m/z 489.1 $[M+H]^+$

Exemplary Compound 208

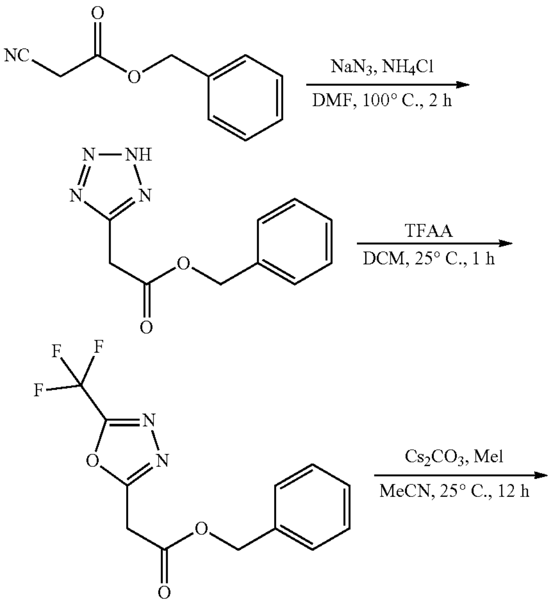

-continued

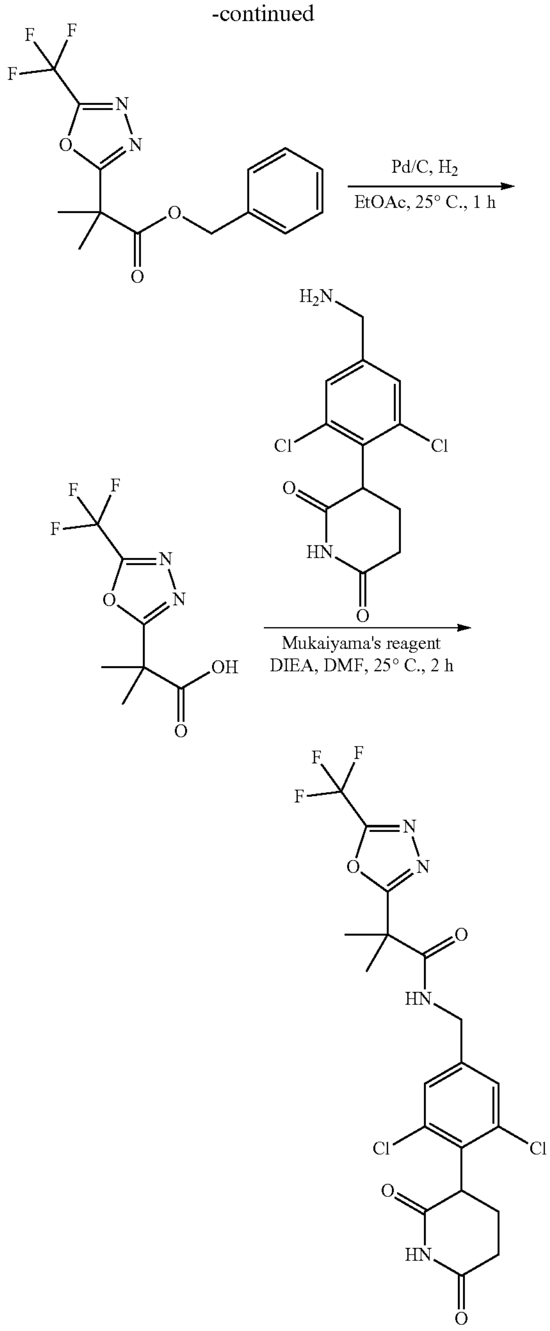

Step 1. To a solution of benzyl 2-cyanoacetate (1.00 g, 5.71 mmol, 1.00 eq.) in dimethyl formamide (15 mL) were added ammonium chloride (320 mg, 5.99 mmol, 1.05 eq.) and sodium azide (410 mg, 6.31 mmol, 1.10 eq.). The reaction was stirred at 100° C. for 2 h. The mixture was diluted with water (20 mL) and ethyl acetate (20 mL). The layers were separated, and the aqueous phase was adjusted to pH 6 with hydrochloric acid (2 M, 0.5 mL). Then it was extracted with ethyl acetate (30 mL). The organic phase was washed with brine (10 mL), dried over sodium sulfate, filtered, and concentrated under vacuum. The residue was purified via Purification Method 2 to afford benzyl 2-(2H-tetrazol-5-yl)acetate (320 mg, 1.44 mmol, 25% yield) as a white solid.

Step 2. To a solution of benzyl 2-(2H-tetrazol-5-yl)acetate (320 mg, 1.47 mmol, 1.00 eq.) in dichloromethane (5 mL) was added (2,2,2-trifluoroacetyl) 2,2,2-trifluoroacetate (244 μL, 1.76 mmol, 1.20 eq.). The reaction was stirred at 25° C. for 1 h. The mixture was diluted with water (10 mL) and dichloromethane (20 mL). The layers were separated, and the organic phase was washed with saturated sodium bicarbonate (10 mL), dried over sodium sulfate, filtered, and concentrated under vacuum. The residue was purified via Purification Method 2 to afford benzyl 2-(5-(trifluoromethyl)-1,3,4-oxadiazol-2-yl)acetate (410 mg, 1.36 mmol, 92% yield) as a colourless oil.

Step 3. To a solution of benzyl 2-(5-(trifluoromethyl)-1,3,4-oxadiazol-2-yl)acetate (360 mg, 1.26 mmol, 1.00 eq.) in acetonitrile (8 mL) were added caesium carbonate (1.23 g, 3.77 mmol, 3.00 eq.) and methyl iodide (1.79 g, 12.6 mmol, 10.0 eq.). The reaction was stirred at 25° C. for 12 h.

The mixture was diluted with water (10 mL) and ethyl acetate (20 mL). The layers were separated.

Then the organic phase was washed with brine (10 mL), dried over sodium sulfate, filtered, and concentrated under vacuum. The residue was purified via Purification Method 2 to afford benzyl 2-methyl-2-(5-(trifluoromethyl)-1,3,4-oxadiazol-2-yl) propanoate (320 mg, 1.01 mmol, 80% yield) as a yellow oil.

Step 4. A solution of palladium on carbon (100 mg, 10% purity) in ethyl acetate (15 mL) was degassed with nitrogen. Then a solution of benzyl 2-methyl-2-(5-(trifluoromethyl)-1,3,4-oxadiazol-2-yl) propanoate (300 mg, 954 μmol, 1.00 eq.) in ethyl acetate (2 mL) was added under nitrogen, and the reaction was stirred at 25° C. for 1 h under hydrogen (15 psi). The mixture was filtered concentrated under vacuum. The residue was diluted with water (10 mL) and ethyl acetate (20 mL). The layers were separated. Then the organic phase was washed with brine (10 mL), dried over sodium sulfate, filtered, and concentrated under vacuum to give 2-methyl-2-(5-(trifluoromethyl)-1,3,4-oxadiazol-2-yl) propanoic acid (95.0 mg, 398 μmol, 41% yield) as a yellow oil.

Step 5. To a solution of 2-methyl-2-(5-(trifluoromethyl)-1,3,4-oxadiazol-2-yl) propanoic acid (75.0 mg, 334 μmol, 1.00 eq.) in N,N-dimethylformamide (3 mL) was added N,N-diisopropylethylamine (129 mg, 1.00 mmol, 3.00 eq.) and 2-chloro-1-methyl-pyridin-1-ium iodide (102 mg, 401 μmol, 1.20 eq.). The reaction was stirred at 25° C. for 1 h. Then 3-(4-(aminomethyl)-2,6-dichlorophenyl) piperidine-2,6-dione hydrochloride (87.0 mg, 267 μmol, 0.80 eq.) was added and stirred at 25° C. for 1 h. The mixture was diluted with water (10 mL) and ethyl acetate (20 mL).

The layers were separated. Then the organic phase was washed with brine (20 mL), dried over sodium sulfate, filtered, and concentrated under vacuum. The residue was purified via Purification Method 1 to afford N-(3,5-dichloro-4-(2,6-dioxopiperidin-3-yl)benzyl)-2-methyl-2-(5-(trifluoromethyl)-1,3,4-oxadiazol-2-yl) propanamide (26.25 mg, 52.0 μmol, 15% yield) as a white solid.

$^1H$ NMR (400 MHZ, DMSO-$d_6$) δ=10.96 (s, 1H), 8.59 (t, J=5.6 Hz, 1H), 7.34 (d, J=1.2 Hz, 1H), 7.27 (d, J=1.2 Hz, 1H), 4.58 (dd, J=5.6, 12.4 Hz, 1H), 4.27 (d, J=5.6 Hz, 2H), 2.85 (ddd, J=5.6, 14.0, 16.8 Hz, 1H), 2.61-2.53 (m, 1H), 2.43-2.32 (m, 1H), 1.94-1.85 (m, 1H), 1.66 (s, 6H). MS (ESI) m/z 493.0 $[M+H]^+$ Exemplary Compound 211

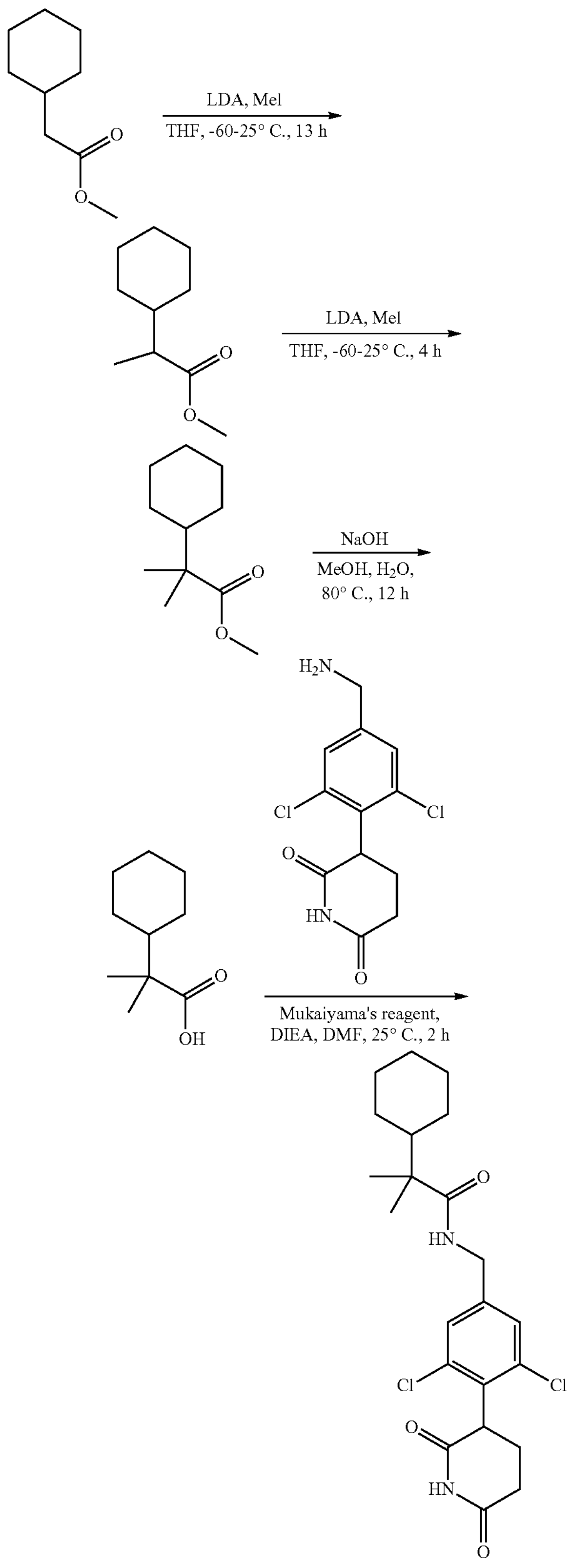

Step 1. To a solution of methyl 2-cyclohexylacetate (1.05 mL, 6.40 mmol, 1.00 eq.) in tetrahydrofuran (20 mL) under nitrogen was added lithium diisopropyl amide (2 M in tetrahydrofuran, 8.00 mL, 2.50 eq.) at −60° C., and stirred at −60° C. for 1 h under nitrogen atmosphere. Then methyl iodide (1.99 mL, 32.0 mmol, 5.00 eq.) was added at −60° C., and stirred at 25° C. for 12 h. The reaction was quenched with saturated ammonium chloride solution (10 mL) at 0° C. The mixture was diluted water (20 mL) and ethyl acetate (30 mL). The layers were separated. Then the organic phase was washed with brine (10 mL), dried over sodium sulfate, filtered, and concentrated under vacuum. The residue was purified via Purification Method 2 to afford methyl 2-cyclohexylpropanoate (740 mg, 2.61 mmol, 40% yield, 60% purity) as a colourless oil.

Step 2. To a solution of methyl 2-cyclohexylacetate (740 mg, 4.35 mmol, 1.00 eq.) in tetrahydrofuran (10 mL) under nitrogen was added lithium diisopropyl amide (2 M in tetrahydrofuran, 6.52 mL, 3.00 eq.) at −60° C., and stirred at −60° C. for 1 h under nitrogen atmosphere. Then methyl iodide (1.35 mL, 21.7 mmol, 5.00 eq.) was added at −60° C., and stirred at 25° C. for 3 h. The reaction was quenched with saturated ammonium chloride solution (10 mL) at 0° C. The mixture was diluted with water (20 mL) and ethyl acetate (30 mL). The layers were separated. Then the organic phase was washed with brine (10 mL), dried over sodium sulfate, filtered, and concentrated under vacuum. The residue was purified via Purification Method 2 to afford methyl 2-cyclohexyl-2-methylpropanoate (440 mg, 2.10 mmol, 48% yield, 88% purity) as a colourless oil.

Step 3. To a solution of methyl 2-cyclohexyl-2-methylpropanoate (220 mg, 1.19 mmol, 1.00 eq.) in methanol (3 mL) and water (3 mL) was added sodium hydroxide (143 mg, 3.58 mmol, 3.00 eq.).

The reaction was stirred at 80° C. for 12 h. The reaction mixture was diluted with water (10 mL) and ethyl acetate (20 mL). The layers were separated, and the organic phase was discarded. The pH of the aqueous phase was adjusted to 6 with hydrochloric acid (2 M), and then extracted with ethyl acetate (20 mL). The organic phase was washed with brine (10 mL), dried over sodium sulfate, filtered, and concentrated under vacuum. The residue was purified via Purification Method 2 to afford 2-cyclohexyl-2-methylpropanoic acid (90.0 mg, 422 μmol, 35% yield, 80% purity) as a yellow oil.

Step 4. To a solution of 2-cyclohexyl-2-methylpropanoic acid (70.0 mg, 328 μmol, 1.00 eq.) in N,N-dimethylformamide (3 mL) was added N,N-diisopropylethylamine (172 μL, 986 μmol, 3.00 eq.) and 2-chloro-1-methyl-pyridin-1-ium iodide (100 mg, 394 μmol, 1.20 eq.). The reaction was stirred at 25° C. for 1 h. Then 3-(4-(aminomethyl)-2,6-dichlorophenyl) piperidine-2,6-dione hydrochloride (95.0 mg, 296 μmol, 0.90 eq.) was added and stirred at 25° C. for 1 h. The mixture was diluted with water (10 mL) and extracted with ethyl acetate (20 mL). The organic phase was washed with brine (20 mL), dried over sodium sulfate, filtered, and concentrated under vacuum.

The residue was purified via Purification Method 1 to afford 2-cyclohexyl-N-(3,5-dichloro-4-(2,6-dioxopiperidin-3-yl)benzyl)-2-methylpropanamide (51.68 mg, 116 μmol, 35% yield) as a white solid.

$^1$H NMR (400 MHZ, DMSO-$d_6$) δ=10.95 (s, 1H), 8.10 (t, J=6.0 Hz, 1H), 7.34 (s, 1H), 7.28 (s, 1H), 4.56 (dd, J=5.6, 12.8 Hz, 1H), 4.23 (d, J=5.6 Hz, 2H), 2.85 (ddd, J=5.6, 14.0, 16.8 Hz, 1H), 2.59-2.53 (m, 1H), 2.40-2.32 (m, 1H), 1.96-1.83 (m, 1H), 1.70 (d, J=12.4 Hz, 2H), 1.65-1.53 (m, 2H), 1.50 (d, J=14.0 Hz, 2H), 1.24-1.07 (m, 3H), 1.01 (s, 6H), 0.96-0.85 (m, 2H). MS (ESI) m/z 439.1 $[M+H]^+$ Exemplary Compound 212

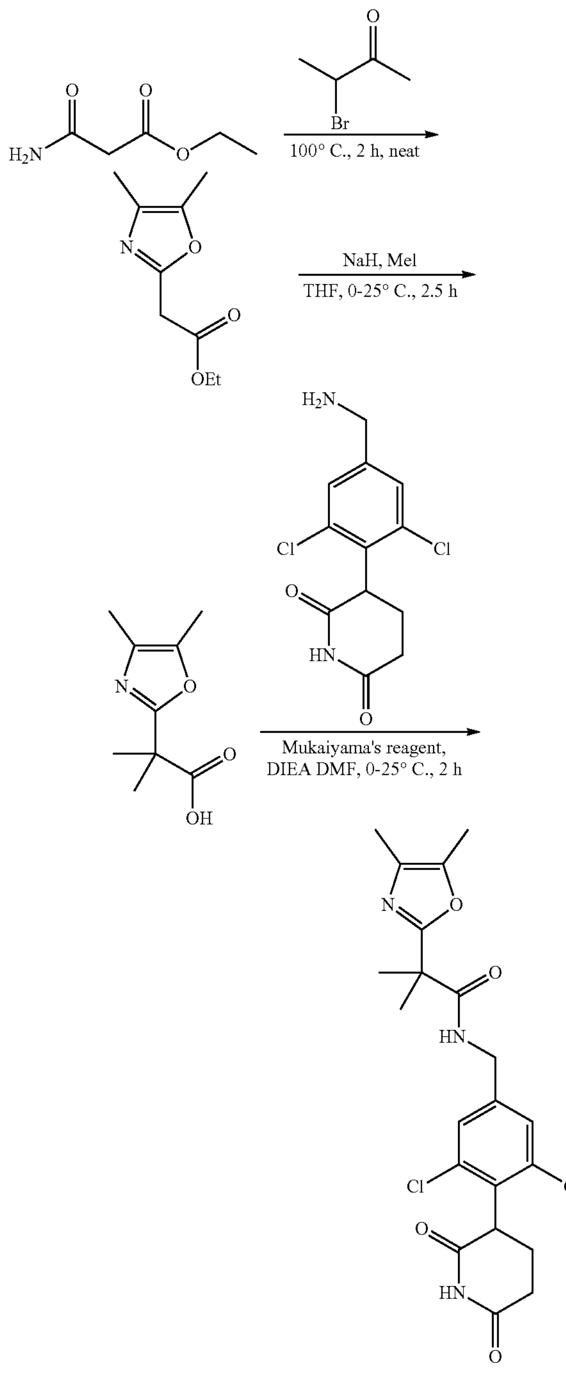

Step 1. A mixture of ethyl 3-amino-3-oxopropanoate (5.00 g, 38.1 mmol, 1.00 eq.) and 3-bromobutan-2-one (6.40 g, 38.1 mmol, 1.00 eq.) was stirred at 100° C. for 2 h. The mixture was concentrated under reduced pressure. The residue was purified via Purification Method 2 to afford ethyl 2-(4,5-dimethyloxazol-2-yl)acetate (460 mg, 2.26 mmol, 6% yield) as orange oil.

Step 2. To a solution of ethyl 2-(4,5-dimethyloxazol-2-yl)acetate (510 mg, 2.78 mmol, 1.00 eq.) in tetrahydrofuran (10 mL) was added sodium hydride (357 mg, 8.92 mmol, 60% purity, 3.21 eq.) at 0° C. under nitrogen atmosphere. The mixture was stirred at 25° C. for 0.5 h under nitrogen atmosphere. Then iodomethane (8.35 mmol, 520 μL, 3.00 eq.) was added, and the reaction was stirred at 25° C. for 12 h under nitrogen atmosphere. The mixture was quenched with water (20 mL) at 0° C., and washed with dichloromethane (2×10 mL). The aqueous layer was adjusted to pH 5 with 1 M hydrochloric acid, and then extracted with 5% methanol in dichloromethane (2×10 mL). The combined organic layers were dried over sodium sulfate, filtered, and concentrated under reduced pressure to give 2-(4,5-dimethyloxazol-2-yl)-2-methylpropanoic acid (80.0 mg, 349 μmol, 13% yield, 80% purity) as a light brown solid.

Step 3. To a solution of 2-(4,5-dimethyloxazol-2-yl)-2-methylpropanoic acid (45.0 mg, 197 μmol, 80% purity, 1.00 eq.) in N,N-dimethylformamide (1 mL) were added N-ethyl-N-isopropylpropan-2-amine (804 μmol, 140 μL, 4.09 eq.) and 2-chloro-1-methyl-pyridin-1-ium iodide (61.0 mg, 239 μmol, 1.22 eq.) at 0° C. The mixture was stirred at 25° C. for 0.5 h. Then 3-(4-(aminomethyl)-2,6-dichlorophenyl) piperidine-2,6-dione hydrochloride (60.0 mg, 185 μmol, 0.940 eq.) was added. The reaction was stirred at 25° C. for 1 h. Then the mixture was diluted with water (20 mL) and extracted with dichloromethane (3×20 mL). The combined organic layers were dried over sodium sulfate, filtered, and concentrated under reduced pressure. The residue was purified via Purification Method 1 to afford N-(3,5-dichloro-4-(2,6-dioxopiperidin-3-yl)benzyl)-2-(4,5-dimethyloxazol-2-yl)-2-methylpropanamide (66.0 mg, 145 μmol, 74% yield) as an off-white solid.

$^1$H NMR (400 MHZ, DMSO-$d_6$) δ=10.94 (s, 1H), 8.25 (t, J=6.0 Hz, 1H), 7.31 (s, 1H), 7.23 (s, 1H), 4.56 (dd, J=5.6, 12.8 Hz, 1H), 4.24 (d, J=6.0 Hz, 2H), 2.90-2.80 (m, 1H), 2.59-2.51 (m, 1H), 2.41-2.31 (m, 1H), 2.20 (s, 3H), 2.01 (s, 3H), 1.94-1.84 (m, 1H), 1.50 (s, 6H). MS (ESI) m/z 452.0 $[M+H]^+$

Exemplary Compound 213

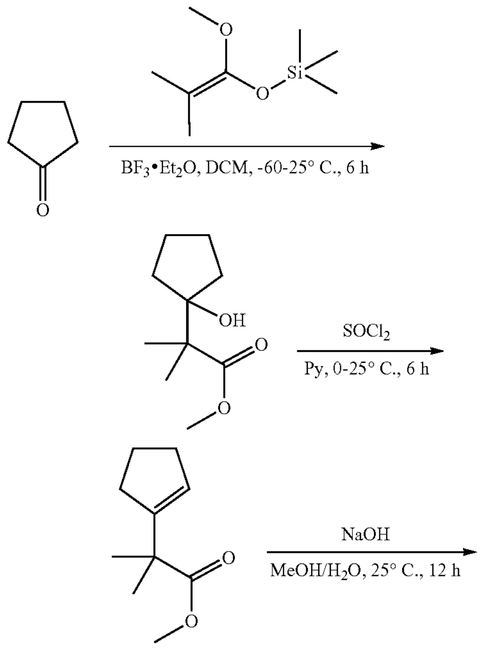

-continued

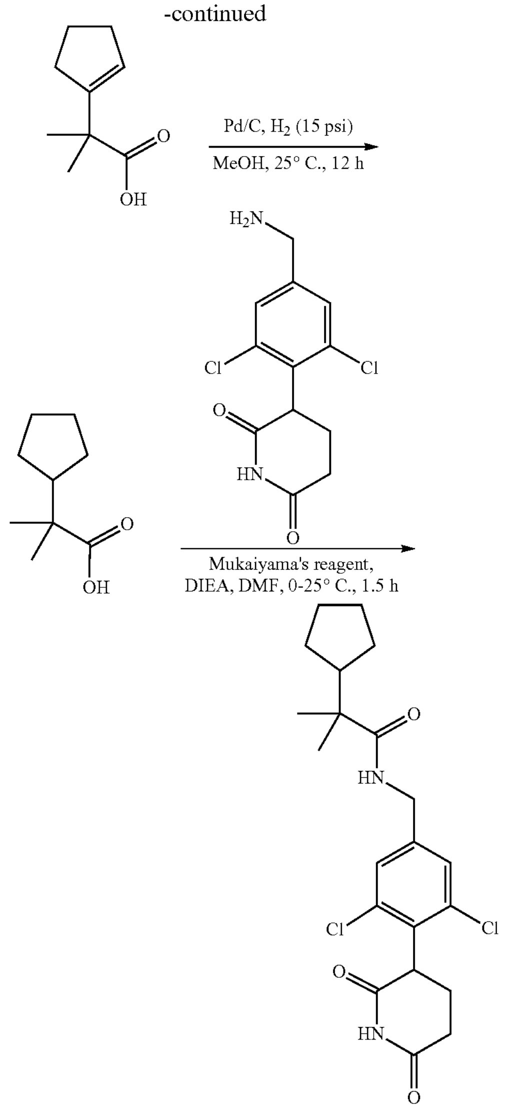

Step 1. To a solution of cyclopentanone (5.00 g, 59.4 mmol, 1.00 eq.) and ((1-methoxy-2-methylprop-1-en-1-yl) oxy)trimethylsilane (20.7 g, 119 mmol, 2.00 eq.) in dichloromethane (150 mL) was added dropwise boron trifluoride ethyl ether complex (95.1 mmol, 11.7 mL, 1.60 eq.) at −60° C. under nitrogen atmosphere. The mixture was stirred at 25° C. for 6 h under nitrogen atmosphere. The reaction was quenched with saturated aqueous sodium bicarbonate solution (200 mL) at 0° C. The layers were separated, and the aqueous layer was extracted with dichloromethane (100 mL). The combined organic layers were dried over sodium sulfate, filtered, and concentrated under reduced pressure. The residue was purified via Purification Method 2 to afford methyl 2-(1-hydroxycyclopentyl)-2-methylpropanoate (10.3 g, 54.6 mmol, 92% yield) as a light-yellow liquid.

Step 2. To a solution of methyl 2-(1-hydroxycyclopentyl)-2-methylpropanoate (1.00 g, 5.37 mmol, 1.00 eq.) in pyridine (10 mL) was added sulfurous dichloride (6.20 mmol, 450 μL, 1.15 eq.) dropwise at 0° C. under nitrogen atmosphere. The mixture was stirred at 25° C. for 6 h under nitrogen atmosphere. The mixture was poured onto ice (10.0 g). Then the mixture was adjusted to pH 2 with cold 6 M hydrochloric acid. The mixture was extracted with ethyl acetate (3× 20 mL). The combined organic layers were washed with ice-water (3×50 mL), dried over sodium sulfate, filtered, and concentrated under reduced pressure to give methyl 2-(cyclopent-1-en-1-yl)-2-methylpropanoate (710 mg, 4.18 mmol, 78% yield) as a light-yellow liquid.

Step 3. To a solution of methyl 2-(cyclopent-1-en-1-yl)-2-methylpropanoate (660 mg, 3.92 mmol, 1.00 eq.) in methanol (10 mL) was added a solution of sodium hydroxide (792 mg, 19.8 mmol, 5.05 eq.) in water (10 mL). The mixture was stirred at 25° C. for 12 h. Then the mixture was diluted with water (30 mL) and extracted with dichloromethane (2×20 mL). The combined organic layers were discarded, and the aqueous layer was adjusted to pH 2 with 2 M hydrochloric acid. The mixture was extracted with a mixed solvent dichloromethane/methanol=20/1 (3×20 mL). The combined organic layers were dried over sodium sulfate, filtered, and concentrated under reduced pressure to give 2-(cyclopent-1-en-1-yl)-2-methylpropanoic acid (540 mg, 3.47 mmol, 88% yield) as a colourless oil.

Step 4. To a suspension of palladium on carbon (540 mg, 10% purity) in methanol (15 mL) was added 2-(cyclopent-1-en-1-yl)-2-methylpropanoic acid (540 mg, 3.50 mmol, 1.00 eq.). The mixture was stirred at 25° C. for 12 h under hydrogen atmosphere (15 psi). The mixture was filtered through a pad of Celite and washed with methanol (50 mL). The filtrate was concentrated under reduced pressure to give 2-cyclopentyl-2-methylpropanoic acid (590 mg, 3.40 mmol, 97% yield) as a light-yellow oil.

Step 5. To a solution of 2-cyclopentyl-2-methylpropanoic acid (70.0 mg, 403 μmol, 1.00 eq.) in N,N-dimethylformamide (1 mL) were added N-ethyl-N-isopropylpropan-2-amine (1.72 mmol, 300 μL, 4.27 eq.) and 2-chloro-1-methylpyridin-1-ium iodide (124 mg, 485 μmol, 1.20 eq.) at 0° C. The mixture was stirred at 25° C. for 0.5 h. Then 3-(4-(aminomethyl)-2,6-dichlorophenyl) piperidine-2,6-dione hydrochloride (92.0 mg, 284 μmol, 0.70 eq.) was added, and the reaction was stirred at 25° C. for 1 h. The mixture was diluted with water (20 mL) and extracted with dichloromethane (3×20 mL). The combined organic layers were dried over sodium sulfate, filtered, and concentrated under reduced pressure. The residue was purified via Purification Method 1 to afford 2-cyclopentyl-N-(3,5-dichloro-4-(2,6-dioxopiperidin-3-yl)benzyl)-2-methylpropanamide (39.8 mg, 92.7 μmol, 23% yield) as a white solid.

$^1$H NMR (400 MHZ, DMSO-$d_6$) δ=10.95 (s, 1H), 8.08 (t, J=6.0 Hz, 1H), 7.34 (s, 1H), 7.27 (s, 1H), 4.56 (dd, J=5.6, 12.8 Hz, 1H), 4.23 (d, J=6.0 Hz, 2H), 2.91-2.78 (m, 1H), 2.58-2.51 (m, 1H), 2.41-2.32 (m, 1H), 2.17-2.06 (m, 1H), 1.96-1.84 (m, 1H), 1.56-1.40 (m, 6H), 1.31-1.14 (m, 2H), 1.06 (s, 6H). MS (ESI) m/z 425.1 $[M+H]^+$

Exemplary Compound 214

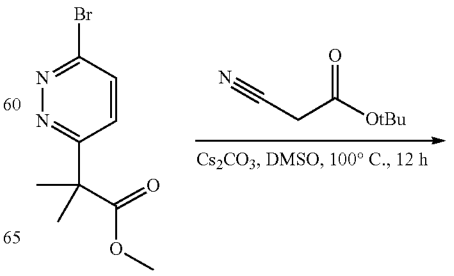

-continued

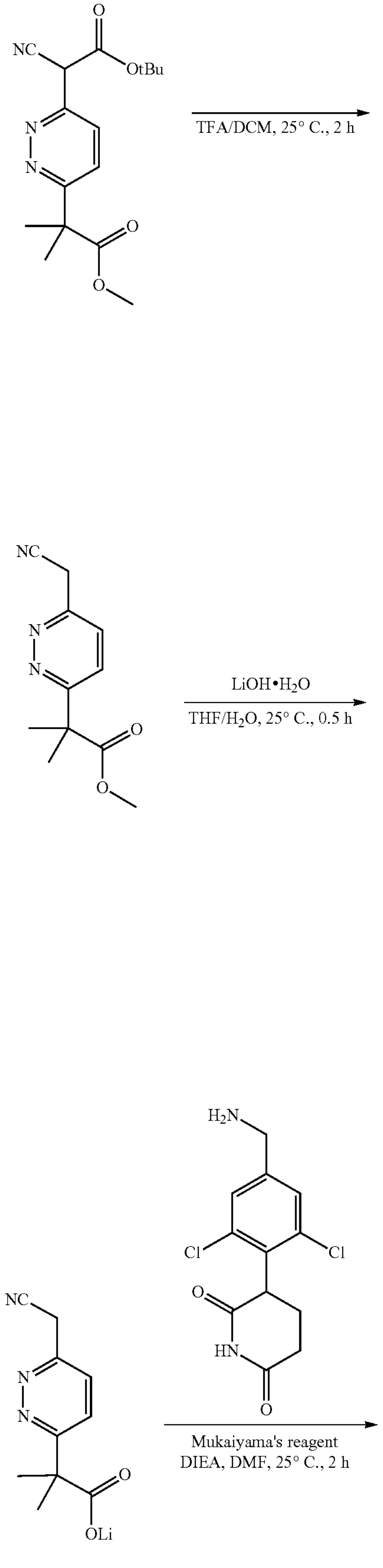

-continued

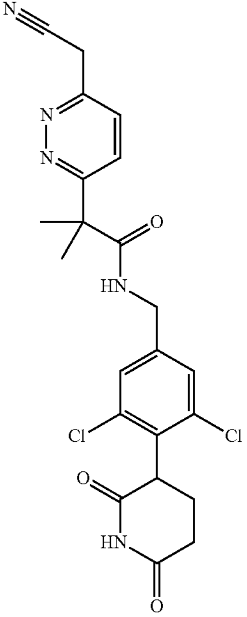 [SMILES: CC(C)(C(=O)NCc1cc(Cl)c(C2CCC(=O)NC2=O)c(Cl)c1)c1ccc(CC#N)nn1]

Step 1. To a solution of methyl 2-(6-bromopyridazin-3-yl)-2-methylpropanoate (700 mg, 2.70 mmol, 1.00 eq.) in (methylsulfinyl) methane (6 mL) was added tert-butyl 2-cyanoacetate (763 mg, 5.40 mmol, 773 μL, 2.00 eq.) and caesium carbonate (2.64 g, 8.10 mmol, 3.00 eq.). The mixture was stirred at 100° C. for 12 h. After cooling to room temperature, the reaction mixture was diluted with water (50 mL) and extracted with ethyl acetate (3×50 mL). The combined organic layers were washed with brine (80 mL), dried over anhydrous sodium sulfate, filtered, and concentrated under reduced pressure. The residue was purified via Purification Method 2 to afford methyl 2-(6-(2-(tert-butoxy)-1-cyano-2-oxoethyl)pyridazin-3-yl)-2-methylpropanoate (1 g, crude) as a yellow solid.

Step 2. To a solution of methyl 2-(6-(2-(tert-butoxy)-1-cyano-2-oxoethyl)pyridazin-3-yl)-2-methylpropanoate (1.00 g, 3.13 mmol, 1.00 eq.) in dichloromethane (10 mL) was added trifluoroacetic acid (2.0 mL). The mixture was stirred at 25° C. for 2 h. The reaction mixture was diluted with water (50 mL) and extracted with dichloromethane (3×50 mL). The combined organic layers were washed with brine (80 mL), dried over anhydrous sodium sulfate, filtered, and concentrated under reduced pressure. The residue was purified via Purification Method 2 to afford methyl 2-(6-(cyanomethyl)pyridazin-3-yl)-2-methylpropanoate (530 mg, 2.39 mmol, 76% yield) as a yellow solid.

Step 3. To a solution of methyl 2-(6-(cyanomethyl) pyridazin-3-yl)-2-methylpropanoate (300 mg, 1.37 mmol, 1.00 eq.) in tetrahydrofuran (3 mL) was added a solution of lithium hydroxide hydrate (287 mg, 6.84 mmol, 5.00 eq.) in water (3 mL). The mixture was stirred at 25° C. for 0.5 h. The reaction mixture was adjusted to pH 8 with 1M hydrochloric acid and lyophilized to afford lithium 2-(6-(cyanomethyl)pyridazin-3-yl)-2-methylpropanoate (500 mg, crude) as a yellow solid.

Step 4. To a solution of lithium 2-(6-(cyanomethyl) pyridazin-3-yl)-2-methylpropanoate (480 mg, crude) in N,N-dimethylformamide (8 mL) was added 2-chloro-1-methyl-pyridin-1-ium iodide (319 mg, 1.25 mmol, 1.20 eq.) and N-ethyl-N-isopropylpropan-2-amine (538 mg, 4.16 mmol, 725 μL, 4.00 eq.). The mixture was stirred at 25° C.

for 0.5 h. Then 3-(4-(aminomethyl)-2,6-dichlorophenyl) piperidine-2,6-dione hydrochloride (168 mg, 520 μmol, 0.500 eq.) was added, and the reaction was stirred at 25° C. for another 1.5 h. The reaction mixture was diluted with water (20 mL) and extracted with ethyl acetate (2× 20 mL). The combined organic extracts were washed with brine (30 mL), dried over sodium sulfate, filtered, and concentrated under reduced pressure. The residue was purified via Purification Method 1 to afford 2-(6-(cyanomethyl)pyridazin-3-yl)-N-(3,5-dichloro-4-(2,6-dioxopiperidin-3-yl)benzyl)-2-methylpropanamide (3.36 mg, 6.94 μmol, 1% yield) as a white solid.

$^1$H NMR (400 MHZ, DMSO-$d_6$) δ=10.96 (s, 1H), 8.24 (t, J=6.0 Hz, 1H), 7.70 (q, J=8.8 Hz, 2H), 7.25 (d, J=1.2 Hz, 1H), 7.18 (s, 1H), 4.55 (dd, J=5.6, 12.8 Hz, 1H), 4.42 (s, 2H), 4.23 (d, J=6.0 Hz, 2H), 2.89-2.80 (m, 1H), 2.59-2.52 (m, 1H), 2.40-2.29 (m, 1H), 1.93-1.83 (m, 1H), 1.61 (s, 6H). MS (ESI) m/z 474.1 $[M+H]^+$

Exemplary Compound 215

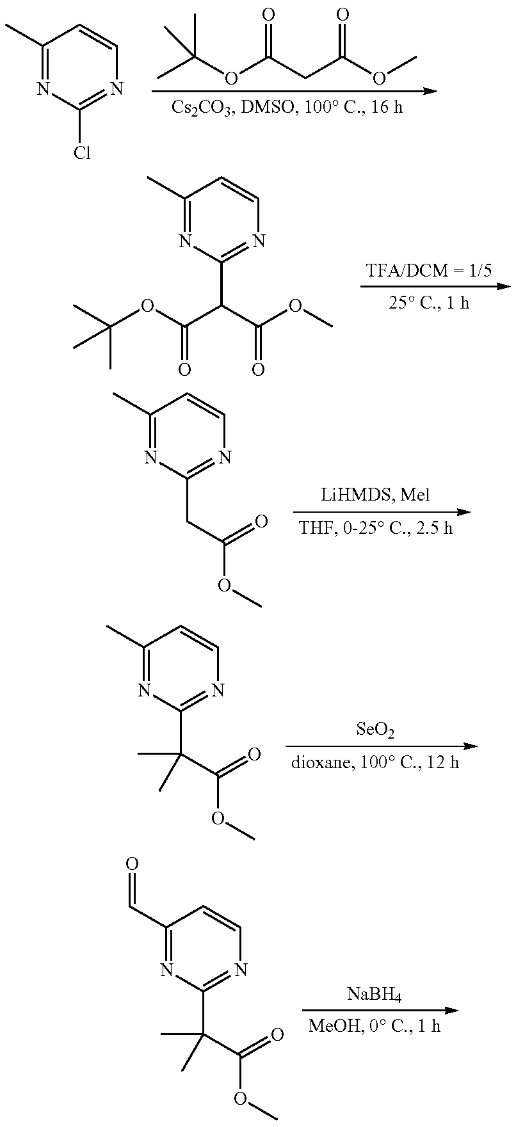

-continued

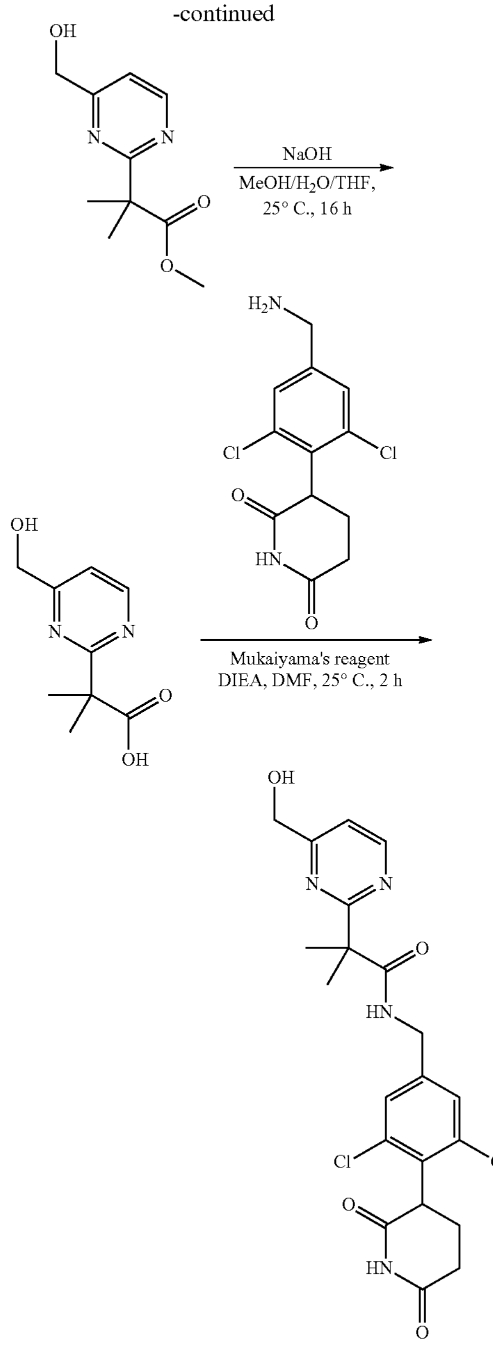

Step 1. To a solution of 2-chloro-4-methylpyrimidine (10.0 g, 77.8 mmol, 1.00 eq.) in dimethylsulfoxide (100 mL) were added tert-butyl methyl malonate (26.0 mL, 15.0 mmol, 2.00 eq.) and caesium carbonate (50.7 g, 155 mmol, 2.00 eq.). The mixture was stirred at 100° C. for 16 h. The mixture was diluted with water (500 mL) and extracted with ethyl acetate (500 mL). The combined organic layers were washed with water (2×500 mL), dried over sodium sulfate, filtered, and concentrated under reduced pressure. The residue was purified via Purification Method 2 to afford 1-(tert-butyl) 3-methyl 2-(4-methylpyrimidin-2-yl) malonate (15.0 g, 50.8 mmol, 65% yield) as a yellow oil.

Step 2. To a solution of 1-(tert-butyl) 3-methyl 2-(4-methylpyrimidin-2-yl) malonate (15.0 g, 56.3 mmol, 1.00 eq.) in dichloromethane (100 mL) was added trifluoroacetic acid (20 mL). The mixture was stirred at 25° C. for 1 h. The mixture was concentrated, and the residue was diluted with ethyl acetate (200 mL) and washed with saturated sodium bicarbonate (2×200 mL). The combined organic layers were dried over sodium sulfate, filtered, and concentrated under reduced pressure. The residue was purified via Purification Method 2 to afford methyl 2-(4-methylpyrimidin-2-yl)acetate (9.00 g, 43.3 mmol, 76% yield) as a yellow oil.

Step 3. To a solution of methyl 2-(4-methylpyrimidin-2-yl)acetate (2.00 g, 12.0 mmol, 1.00 eq.) in tetrahydrofuran (20 mL) was added lithium bis(trimethylsilyl)amide (1 M in tetrahydrofuran, 36.0 mL, 3.00 eq.) at 0° C. under nitrogen. The mixture was stirred at 0° C. for 0.5 h. Then methyl iodide (8.54 g, 60.2 mmol, 5.00 eq.) was added to the mixture at 0° C. The mixture was stirred at 25° C. under nitrogen for 2 h. The reaction was quenched with saturated ammonium chloride (20 mL) and extracted with ethyl acetate (3x30 mL). The combined organic extracts were washed with saturated ammonium chloride (20 mL) and brine (20 mL), dried over sodium sulfate, filtered, and concentrated under reduced pressure. The residue was purified via Purification Method 2 to afford methyl 2-methyl-2-(4-methylpyrimidin-2-yl) propanoate (1.50 g, 6.95 mmol, 57% yield) as a yellow oil.

Step 4. To a solution of methyl 2-methyl-2-(4-methylpyrimidin-2-yl) propanoate (1.50 g, 7.72 mmol, 1.00 eq.) in dioxane (20 mL) was added selenium dioxide (15.5 mmol, 1.68 mL, 2.00 eq.). The mixture was stirred at 100° C. for 12 h. The mixture was filtered and concentrated under reduced pressure. The residue was purified via Purification Method 2 to afford methyl 2-(4-formylpyrimidin-2-yl)-2-methylpropanoate (1.00 g, 4.56 mmol, 59% yield) as a yellow oil.

Step 5. To a solution of methyl 2-(4-formylpyrimidin-2-yl)-2-methylpropanoate (1.00 g, 4.80 mmol, 1.00 eq.) in methanol (10 mL) was added sodium borohydride (400 mg, 10.6 mmol, 2.20 eq.) at 0° C. under nitrogen. The mixture was stirred at 0° C. for 1 h. The reaction was quenched with saturated ammonium chloride (20 mL) and extracted with ethyl acetate (3x 20 mL). The combined organic extracts were washed with saturated ammonium chloride (20 mL) and brine (20 mL), then dried over sodium sulfate, filtered, and concentrated under vacuum. The residue was purified via Purification Method 2 to afford methyl 2-(4-(hydroxymethyl)pyrimidin-2-yl)-2-methylpropanoate (670 mg, 2.87 mmol, 59% yield) as a yellow oil.

Step 6. To a solution of methyl 2-(4-(hydroxymethyl) pyrimidin-2-yl)-2-methylpropanoate (100 mg, 475 μmol, 1.00 eq.) in methanol (1 mL) and water (1 mL) was added sodium hydroxide (76.0 mg, 1.90 mmol, 4.00 eq.). The reaction was stirred at 25° C. for 16 h. The pH was adjusted to 6 with hydrochloric acid (2 M) at 0° C. The mixture was diluted with water (10 mL) and dichloromethane (10 mL). The layers were separated, and the water phase was collected and lyophilized to give 2-(4-(hydroxymethyl)pyrimidin-2-yl)-2-methylpropanoic acid (165 mg, crude) as a white solid.

Step 7. To a solution of 2-(4-(hydroxymethyl)pyrimidin-2-yl)-2-methylpropanoic acid (165 mg, crude) in N,N-dimethylformamide (5 mL) were added N,N-diisopropylethylamine (114 mg, 883 μmol, 3.00 eq.) and 2-chloro-1-methylpyridin-1-ium iodide (90.0 mg, 353 μmol, 1.20 eq.). The reaction was stirred at 25° C. for 1 h. Then 3-(4-(aminomethyl)-2,6-dichlorophenyl) piperidine-2,6-dione hydrochloride (95.3 mg, 294 μmol, 1.00 eq.) was added and stirred at 25° C. for 1 h. The mixture was diluted with water (10 mL) and ethyl acetate (20 mL). The layers were separated, and the organic phase was washed with brine (20 mL), dried over sodium sulfate, filtered, and concentrated under vacuum. The residue was purified via Purification Method 1 to afford N-(3,5-dichloro-4-(2,6-dioxopiperidin-3-yl)benzyl)-2-(4-(hydroxymethyl)pyrimidin-2-yl)-2-methylpropanamide (75.28 mg, 158 μmol, 53% yield) as a white solid.

$^1$H NMR (400 MHZ, DMSO-$d_6$) δ=10.96 (s, 1H), 8.77 (d, J=5.2 Hz, 1H), 8.03 (t, J=6.0 Hz, 1H), 7.44 (d, J=5.2 Hz, 1H), 7.38 (s, 1H), 7.31 (d, J=1.2 Hz, 1H), 5.63 (s, 1H), 4.64-4.46 (m, 3H), 4.25 (d, J=5.8 Hz, 2H), 2.93-2.79 (m, 1H), 2.60-2.52 (m, 1H), 2.43-2.31 (m, 1H), 1.96-1.84 (m, 1H), 1.52 (s, 6H). MS (ESI) m/z 465.1 [M+H]$^+$

Exemplary Compound 216

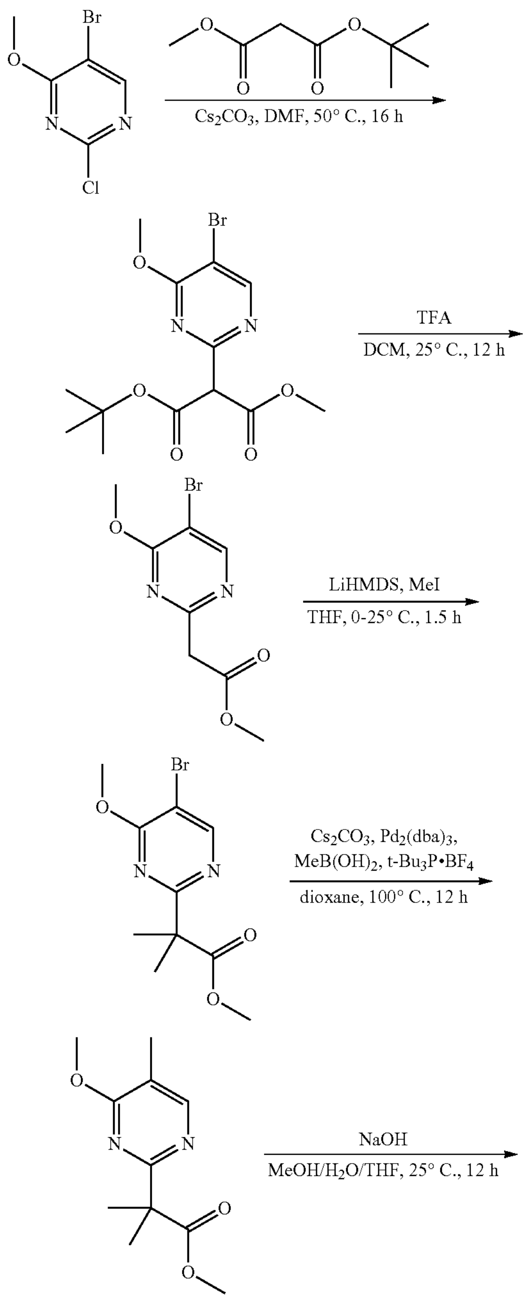

-continued

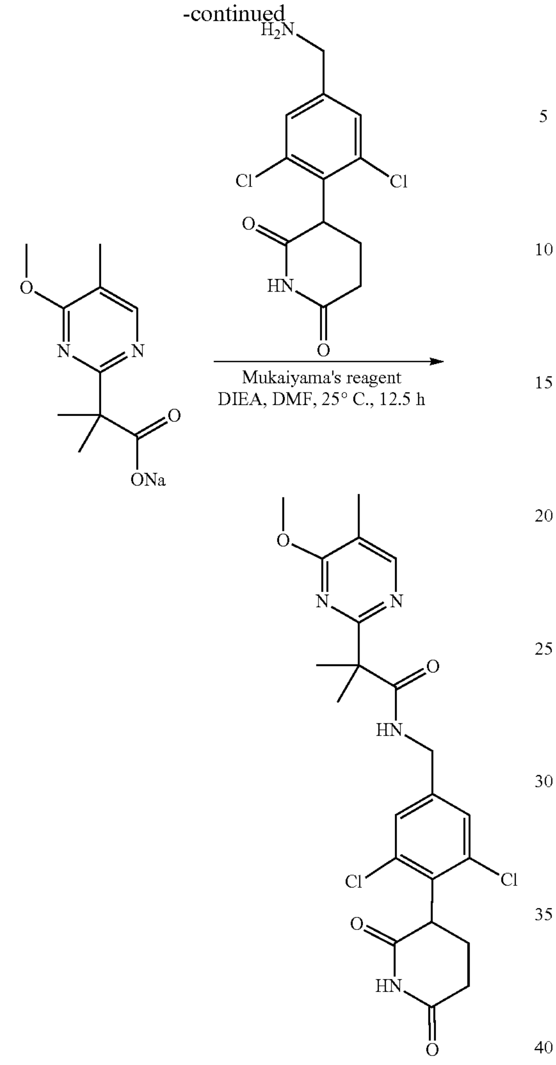

Step 1. To a mixture of 5-bromo-2-chloro-4-methoxypyrimidine (9.80 g, 43.8 mmol, 1.00 eq.) and caesium carbonate (21.4 g, 65.7 mmol, 1.50 eq.) in dimethyl formamide (40 mL) was added tert-butyl methyl malonate (11.4 g, 65.7 mmol, 1.50 eq.) dropwise at 25° C. The mixture was stirred at 50° C. for 16 h. The mixture was cooled to 25° C., and poured into water (40 mL). The mixture was extracted with ethyl acetate (3×50 mL). The combined organic layers were washed with brine (40 mL), dried over anhydrous sodium sulfate, filtered, and the filtrate was concentrated under reduced pressure. The residue was purified via Purification Method 2 to afford 1-(tert-butyl) 3-methyl 2-(5-bromo-4-methoxypyrimidin-2-yl) malonate (10.8 g, 29.0 mmol, 66% yield) as a yellow oil.

Step 2. To a mixture of 1-(tert-butyl) 3-methyl 2-(5-bromo-4-methoxypyrimidin-2-yl) malonate (10.8 g, 29.9 mmol, 1.00 eq.) in dichloromethane (50 mL) was added trifluoroacetic acid (10.8 mL) dropwise at 25° C. The mixture was stirred at 25° C. for 12 h. The mixture was concentrated under reduced pressure and poured into saturated aqueous sodium bicarbonate (40 mL). The mixture was extracted with ethyl acetate (3×50 mL). The combined organic layers were washed with brine (40 mL), dried over anhydrous sodium sulfate, filtered, and the filtrate was concentrated under reduced pressure. The residue was purified via Purification Method 2 to afford methyl 2-(5-bromo-4-methoxypyrimidin-2-yl)acetate (7.20 g, 27.3 mmol, 91% yield) as a yellow oil.

Step 3. To a mixture of methyl 2-(5-bromo-4-methoxypyrimidin-2-yl)acetate (2.00 g, 7.66 mmol, 1.00 eq.) in tetrahydrofuran (20 mL) was added lithium bis(trimethylsilyl)amide (1 M in tetrahydrofuran, 22.9 mL, 3.00 eq.) dropwise at 0° C. The mixture was stirred at 0° C. for 0.5 h then iodomethane (5.44 g, 38.3 mmol, 5.00 eq.) was added dropwise. The mixture was stirred at 25° C. for 1 h under nitrogen atmosphere. The mixture was poured into saturated aqueous ammonium chloride (20 mL). The mixture was extracted with ethyl acetate (3×30 mL). The combined organic layers were washed with brine (20 mL), dried over anhydrous sodium sulfate, filtered, and the filtrate was concentrated under reduced pressure. The residue was purified via Purification Method 2 afford methyl 2-(5-bromo-4-methoxypyrimidin-2-yl)-2-methylpropanoate (1.60 g, 5.42 mmol, 70% yield) as a yellow oil.

Step 4. To a mixture of methyl 2-(5-bromo-4-methoxypyrimidin-2-yl)-2-methylpropanoate (1.60 g, 5.53 mmol, 1.00 eq.) and methylboronic acid (1.66 g, 27.6 mmol, 5.00 eq.) in dioxane (16 mL) were added tris(dibenzylideneacetone) dipalladium (0) (253 mg, 276 μmol, 0.05 eq.), tri-tert-butylphosphonium tetrafluoroborate (160 mg, 553 μmol, 0.10 eq.) and caesium carbonate (5.41 g, 16.6 mmol, 3.00 eq.) in one portion at 25° C. The mixture was stirred at 100° C. for 12 h under nitrogen atmosphere. The mixture was cooled to 25° C., and poured into water (30 mL). The mixture was extracted with ethyl acetate (3×50 mL). The combined organic layers were washed with brine (30 mL), dried over anhydrous sodium sulfate, filtered, and the filtrate was concentrated under reduced pressure. The residue was purified via Purification Method 2 to afford methyl 2-(4-methoxy-5-methylpyrimidin-2-yl)-2-methylpropanoate (1.30 g, 4.64 mmol, 83% yield) as a yellow oil.

Step 5. To a mixture of methyl 2-(4-methoxy-5-methylpyrimidin-2-yl)-2-methylpropanoate (200 mg, 892 μmol, 1.00 eq.) in tetrahydrofuran (1 mL), water (1 mL) and methanol (1 mL) was added sodium hydroxide (178 mg, 4.46 mmol, 5.00 eq.) in one portion at 25° C. The mixture was stirred at 25° C. for 12 h. The mixture was poured into water (20 mL). The aqueous layer was adjusted to pH 8-9 with 2 M aqueous hydrochloric acid then lyophilized to give sodium 2-(4-methoxy-5-methylpyrimidin-2-yl)-2-methylpropanoate (530 mg, crude) as a white solid.

Step 6. To a solution of sodium 2-(4-methoxy-5-methylpyrimidin-2-yl)-2-methylpropanoate (287 mg, 370 μmol, 1.20 eq.) and 2-chloro-1-methyl-pyridin-1-ium iodide (94.7 mg, 370 μmol, 1.20 eq.) in dimethyl formamide (3 mL) was added diisopropylethylamine (119 mg, 927 μmol, 3.00 eq.) dropwise at 25° C. The mixture was stirred at 25° C. for 0.5 h then 3-(4-(aminomethyl)-2,6-dichlorophenyl) piperidine-2,6-dione hydrochloride (100 mg, 309 μmol, 1.00 eq.) was added. The mixture was stirred at 25° C. for 12 h. The mixture was poured into water (20 mL). The mixture was extracted with ethyl acetate (3× 20 mL). The combined organic layers were washed with brine (10 mL), dried over anhydrous sodium sulfate, filtered, and the filtrate was concentrated under reduced pressure. The residue was purified via Purification Method I to afford N-(3,5-dichloro-4-(2,6-dioxopiperidin-3-yl)benzyl)-2-(4-methoxy-5-methylpyrimidin-2-yl)-2-methylpropanamide (64.9 mg, 132 μmol, 42% yield) as a white solid.

$^1H$ NMR (400 MHZ, DMSO-$d_6$) δ=10.95 (s, 1H), 8.33 (d, J=0.8 Hz, 1H), 7.95 (t, J=6.0 Hz, 1H), 7.34 (d, J=1.2 Hz, 1H), 7.27 (d, J=1.2 Hz, 1H), 4.56 (dd, J=5.6, 12.8 Hz, 1H), 4.23 (d, J=6.0 Hz, 2H), 3.90 (s, 3H), 2.93-2.78 (m, 1H), 2.59-2.53 (m, 1H), 2.38-2.31 (m, 1H), 2.08 (s, 3H), 1.95-1.83 (m, 1H), 1.52 (s, 6H). MS (ESI) m/z 479.1 $[M+H]^+$

Exemplary Compound 217

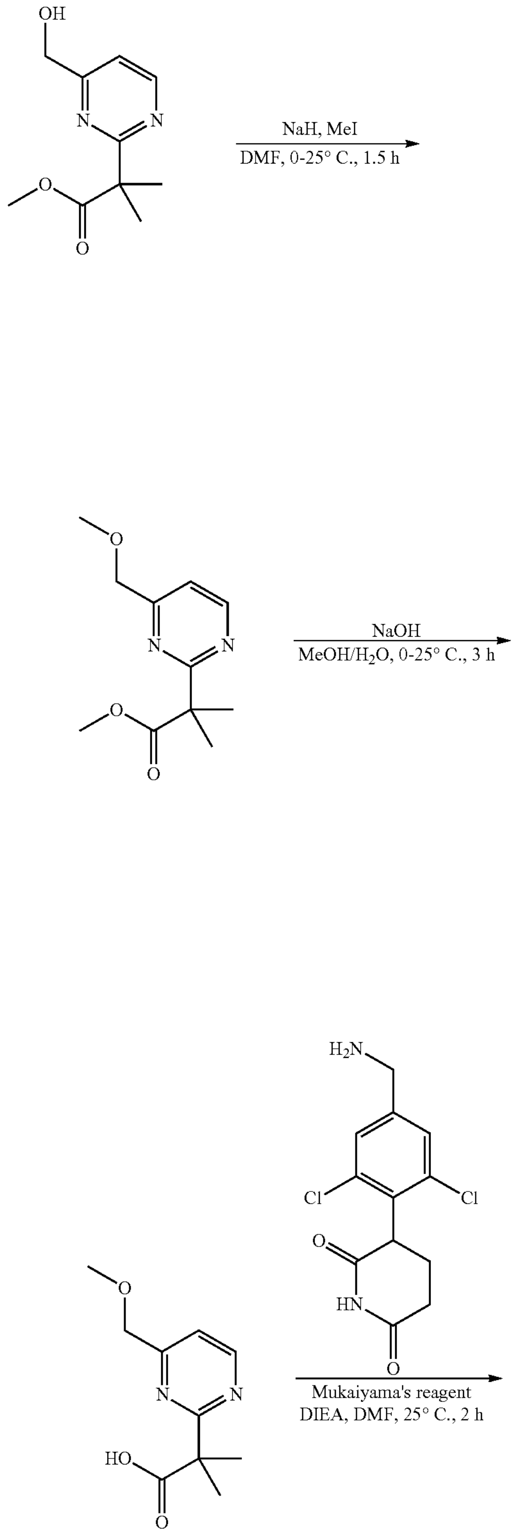

-continued

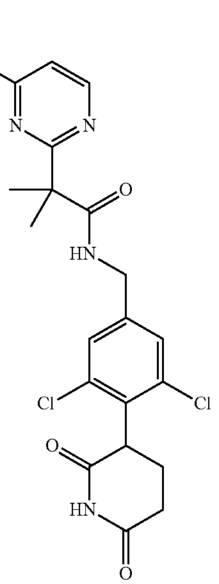

Step 1. Sodium hydride (125 mg, 3.14 mmol, 60% purity, 1.50 eq.) was suspended in N,N-dimethylformamide (10 mL) under nitrogen. The reaction mixture was cooled to 0° C. Then a solution of methyl 2-(4-(hydroxymethyl)pyrimidin-2-yl)-2-methylpropanoate (440 mg, 2.09 mmol, 1.00 eq.) in N,N-dimethylformamide (2 mL) was added. The reaction was stirred at 25° C. for 30 min. Then methyl iodide (891 mg, 6.28 mmol, 3.00 eq.) was added and stirred at 25° C. for 1 h. The reaction mixture was added to ammonium chloride (10 mL) at 0° C. Then the mixture was added water (20 mL) and extracted with ethyl acetate (30 mL). The organic phase was washed with brine (20 mL), dried over sodium sulfate, filtered, and concentrated under vacuum. The residue was purified via Purification Method 2 to afford methyl 2-(4-(methoxymethyl)pyrimidin-2-yl)-2-methylpropanoate (150 mg, 642 μmol, 30% yield) as a yellow oil.

Step 2. To a solution of methyl 2-(4-(methoxymethyl) pyrimidin-2-yl)-2-methylpropanoate (115 mg, 512 μmol, 1.00 eq.) in methanol (1.5 mL) and water (1.5 mL) was added sodium hydroxide (82.0 mg, 2.05 mmol, 4.00 eq.) at 0° C. The reaction was stirred at 25° C. for 3 h. The pH of the mixture was adjusted to 6 with hydrochloric acid (2 M) at 0° C. The mixture was added water (10 mL) and dichloromethane (10 mL). The layers were separated. Then the water phase was collected and lyophilized to give 2-(4-(methoxymethyl)pyrimidin-2-yl)-2-methylpropanoic acid (200 mg, crude) as a white solid.

Step 3. To a solution of 2-(4-(methoxymethyl)pyrimidin-2-yl)-2-methylpropanoic acid (245 mg, crude) in N,N-dimethylformamide (5 mL) were added N,N-diisopropylethylamine (180 mg, 1.40 mmol, 3.00 eq.), 2-chloro-1-methylpyridin-1-ium iodide (142 mg, 559 μmol, 1.20 eq.). The reaction was stirred at 25° C. for 1 h. Then 3-(4-(aminomethyl)-2,6-dichlorophenyl) piperidine-2,6-dione hydrochloride (110 mg, 339 μmol, 0.70 eq.) was added and stirred at 25° C. for 1 h. The mixture was added water (20 mL) and ethyl acetate (30 mL). The layers were separated. Then the organic phase was washed with brine (20 mL), dried over sodium sulfate, filtered, and concentrated under vacuum. The residue was purified via Purification Method 1 to afford N-(3,5-dichloro-4-(2,6-dioxopiperidin-3-yl)benzyl)-2-(4-

(methoxymethyl)pyrimidin-2-yl)-2-methylpropanamide (94.47 mg, 195 μmol, 41% yield) as a white solid.

$^1H$ NMR (400 MHZ, DMSO-$d_6$) δ=10.95 (s, 1H), 8.79 (d, J=5.2 Hz, 1H), 8.03 (t, J=6.0 Hz, 1H), 7.38 (s, 1H), 7.37 (d, J=5.2 Hz, 1H), 7.31 (s, 1H), 4.57 (dd, J=5.6, 12.8 Hz, 1H), 4.51 (s, 2H), 4.25 (d, J=6.0 Hz, 2H), 3.41 (s, 3H), 2.86 (ddd, J=6.0, 14.2, 16.9 Hz, 1H), 2.60-2.54 (m, 1H), 2.40-2.31 (m, 1H), 1.96-1.84 (m, 1H), 1.53 (s, 6H). MS (ESI) m/z 479.1 $[M+H]^+$ Exemplary Compound 218

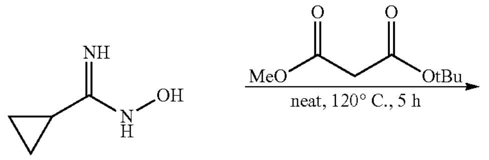

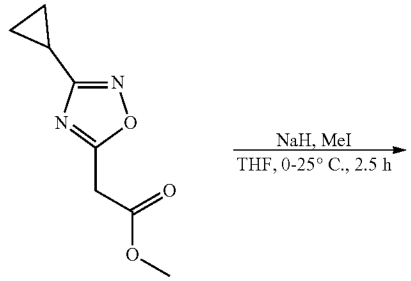

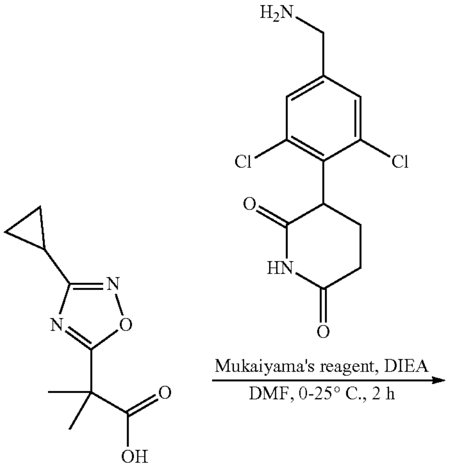

-continued

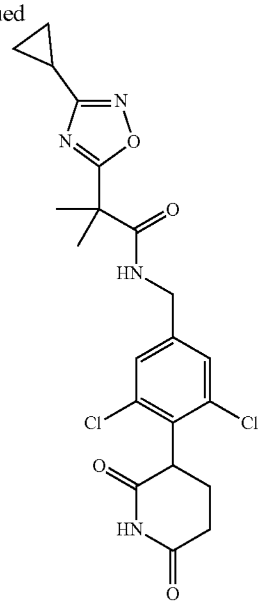

Step 1. A solution of N-hydroxycyclopropane carboximidamide (3.00 g, 30.0 mmol, 1.00 eq.) in tert-butyl methyl malonate (10.1 mL, 59.9 mmol, 2.00 eq.) was stirred at 120° C. for 5 h under nitrogen atmosphere. After the reaction was completed, the reaction mixture was concentrated under reduced pressure. The residue was purified via Purification Method 2 to afford methyl 2-(3-cyclopropyl-1,2,4-oxadiazol-5-yl)acetate (550 mg, 2.99 mmol, 10% yield) as a light-yellow oil Step 2. To a solution of methyl 2-(3-cyclopropyl-1,2,4-oxadiazol-5-yl)acetate (550 mg, 2.87 mmol, 1.00 eq.) in tetrahydrofuran (10 mL) was added sodium hydride (340 mg, 8.50 mmol, 60% purity, 2.96 eq.) under nitrogen atmosphere at 0° C. After addition, the mixture was stirred at this temperature for 0.5 h, and then methyl iodide (1.80 mL, 28.9 mmol, 10.0 eq.) was added dropwise. The reaction was stirred at 25° C. for 2 h under nitrogen atmosphere. The reaction mixture was quenched by addition saturated ammonium chloride solution (10 mL) at 0° C., and then concentrated under reduced pressure to remove tetrahydrofuran. The mixture was adjusted to pH 7 by addition of hydrochloric acid (2M). Then the mixture was lyophilized to afford the product as a white solid (contained sodium chloride). The product was dissolved in dimethyl formamide and then filtered. The filtrate was concentrated in vacuo. The residue was purified via Purification Method 1 to afford 2-(3-cyclopropyl-1,2,4-oxadiazol-5-yl)-2-methylpropanoic acid (65.0 mg, 305 μmol, 11% yield) as a white solid.

Step 3. To a solution of 2-(3-cyclopropyl-1,2,4-oxadiazol-5-yl)-2-methylpropanoic acid (65.0 mg, 305 μmol, 1.00 eq.) in dimethyl formamide (1 mL) was added 2-chloro-1-methyl-pyridin-1-ium iodide (93.4 mg, 366 μmol, 1.20 eq.) and N-ethyl-N-isopropylpropan-2-amine (158 mg, 1.22 mmol, 4.00 eq.) at 0° C. After addition, the mixture was stirred at 25° C. for 0.5 h, and then 3-(4-(aminomethyl)-2,6-dichlorophenyl) piperidine-2,6-dione hydrochloride (98.6 mg, 305 μmol, 1.00 eq.) in dimethyl formamide (1 mL) was added dropwise. The reaction was stirred at 25° C. for 1.5 h. The reaction mixture was diluted with water (10 mL) and extracted with dichloromethane (5×20 mL). The combined organic layers were dried over anhydrous sodium sulfate, filtered, and concentrated under reduced pressure. The residue was purified via Purification Method I to afford 2-(3-cyclopropyl-1,2,4-oxadiazol-5-yl)-N-(3,5-dichloro-4-(2,6-dioxopiperidin-3-yl)benzyl)-2-methylpropanamide (115 mg, 244 μmol, 80% yield) as a white solid.

$^1$H NMR (400 MHZ, DMSO-$d_6$) δ=10.96 (s, 1H), 8.50 (t, J=6.0 Hz, 1H), 7.37-7.30 (m, 1H), 7.29-7.22 (m, 1H), 4.58 (dd, J=5.6, 12.4 Hz, 1H), 4.26 (d, J=6.0 Hz, 2H), 2.94-2.78 (m, 1H), 2.59-2.52 (m, 1H), 2.42-2.30 (m, 1H), 2.15-2.06 (m, 1H), 1.96-1.84 (m, 1H), 1.57 (s, 6H), 1.09-1.02 (m, 2H), 0.92-0.85 (m, 2H). MS (ESI) m/z 465.2 [M+H]$^+$

Exemplary Compound 221

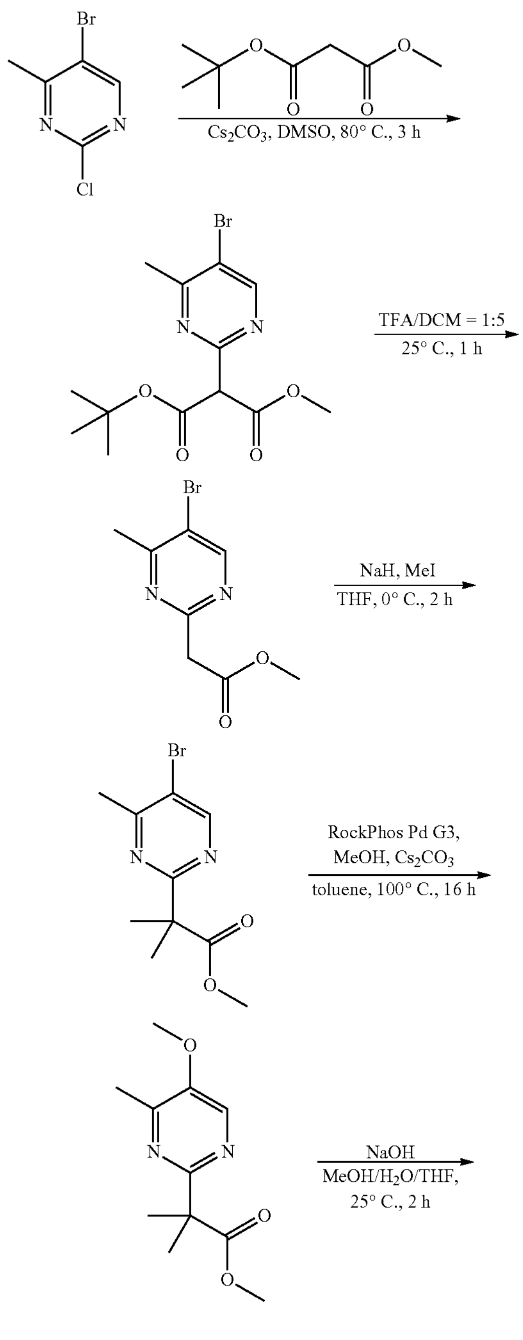

-continued

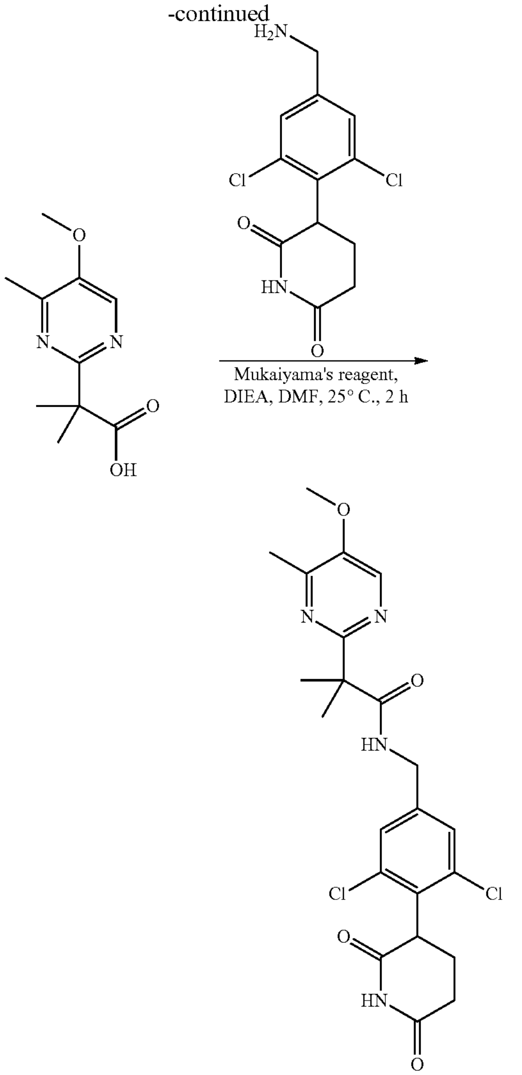

Step 1. To a solution of 5-bromo-2-chloro-4-methylpyrimidine (5.00 g, 24.1 mmol, 1.00 eq.) in dimethylsulfoxide (150 mL) were added caesium carbonate (15.0 g, 46.0 mmol, 1.91 eq.) and tert-butyl methyl malonate (6.25 mL, 36.9 mmol, 1.53 eq.). The mixture was stirred at 80° C. for 3 h. The reaction mixture was diluted with water (200 mL) and extracted with ethyl acetate (2×200 mL). The combined organic extracts were washed with brine (400 mL). The organic phase was dried over sodium sulfate, filtered, and concentrated under reduced pressure. The residue was purified via Purification Method 2 to afford 1-(tert-butyl) 3-methyl 2-(5-bromo-4-methylpyrimidin-2-yl) malonate (4.00 g, 5.79 mmol, 24% yield) as a yellow oil.

Step 2. A solution of 1-(tert-butyl) 3-methyl 2-(5-bromo-4-methylpyrimidin-2-yl) malonate (3.50 g, 5.07 mmol, 1.00 eq.) in dichloromethane (30 mL) and trifluoroacetic acid (6 mL) was stirred at 25° C. for 1 h. The reaction mixture was diluted with water (50 mL) and extracted with ethyl acetate (2×50 mL). The combined organic extracts were washed with brine (80 mL). The organic phase was dried over sodium sulfate, filtered, and concentrated under reduced pressure. The residue was purified via Purification Method 2 to afford methyl 2-(5-bromo-4-methylpyrimidin-2-yl)acetate (1.20 g, 4.41 mmol, 87% yield) as a yellow oil.

Step 3. To a solution of methyl 2-(5-bromo-4-methylpyrimidin-2-yl)acetate (1.00 g, 4.08 mmol, 1.00 eq.) in tetrahydrofuran (10 mL) was added sodium hydride (650 mg, 16.2 mmol, 60% purity, 3.98 eq.) in portions at 0° C. under nitrogen atmosphere. The mixture was stirred at 0° C. for 30 min. Then iodomethane (1.00 mL, 16.0 mmol, 3.94 eq.) was added to the mixture at 0° C., and the mixture was stirred at 0° C. for 1.5 h. The reaction mixture was poured into saturated ammonium chloride solution (30 mL) at 0° C. Then the mixture was diluted with ethyl acetate (30 mL). The layers were separated, and the aqueous phase was extracted with ethyl acetate (2×30 mL). The combined organic layers were washed with brine (50 mL), dried over sodium sulfate, filtered, and concentrated under reduced pressure. The residue was purified via Purification Method 2 to afford methyl 2-(5-bromo-4-methylpyrimidin-2-yl)-2-methylpropanoate (1.00 g, 3.62 mmol, 88% yield) as a yellow oil.

Step 4. To a solution of methyl 2-(5-bromo-4-methylpyrimidin-2-yl)-2-methylpropanoate (1.00 g, 3.66 mmol, 1.00 eq.) in toluene (20 mL) were added caesium carbonate (2.50 g, 7.67 mmol, 2.10 eq.), methanol (400 μL, 9.88 mmol, 2.70 eq.) and methanesulfonato (2-(di-t-butylphosphino) 3-methoxy-6-methyl-2',4',6'-tri-i-propyl-1,1'-biphenyl) (2'-amino-1,1'-biphenyl-2-yl) palladium (II) (130 mg, 155 μmol, 0.04 eq.) under nitrogen atmosphere. The mixture was stirred at 100° C. for 16 h. The mixture was filtered, and the filtrate was diluted with water (50 mL) and extracted with ethyl acetate (2×50 mL). The combined organic extracts were washed with brine (100 mL). The organic phase was dried over sodium sulfate, filtered, and concentrated under reduced pressure.

The residue was purified via Purification Method 1 to afford methyl 2-(5-methoxy-4-methylpyrimidin-2-yl)-2-methylpropanoate (250 mg, 1.10 mmol, 30% yield) as a yellow oil.

Step 5. To a solution of methyl 2-(5-methoxy-4-methylpyrimidin-2-yl)-2-methylpropanoate (200 mg, 891 μmol, 1.00 eq.) in methanol (2 mL) and tetrahydrofuran (2 mL) was added sodium hydroxide (200 mg, 5.00 mmol, 5.61 eq.) in water (400 μL). The mixture was stirred at 25° C. for 2 h. The mixture was diluted with water (10 mL) and dichloromethane (10 mL). The aqueous phase was separated and washed with dichloromethane (10 mL). The pH of the aqueous phase was adjusted to 7 with hydrochloric acid (1 M) and lyophilized to afford 2-(5-methoxy-4-methylpyrimidin-2-yl)-2-methylpropanoic acid (700 mg, crude) as a white solid.

Step 6. To a solution of 2-(5-methoxy-4-methylpyrimidin-2-yl)-2-methylpropanoic acid (350 mg, 416 μmol, 1.35 eq.) in dimethylformamide (5 mL) was added N,N-diisopropylethylamine (200 μL, 1.15 mmol, 3.72 eq.) and 2-chloro-1-methyl-pyridin-1-ium iodide (120 mg, 470 μmol, 1.52 eq.). The mixture was stirred at 25° C. for 0.5 h. Then 3-(4-(aminomethyl)-2,6-dichlorophenyl) piperidine-2,6-dione hydrochloride (100 mg, 309 μmol, 1.00 eq.) was added and the reaction was stirred at 25° C. for 1.5 h. The reaction mixture was diluted with water (20 mL) and extracted with ethyl acetate (2×20 mL). The combined organic extracts were washed with brine (30 mL). The organic phase was dried over sodium sulfate, filtered, and concentrated under reduced pressure. The residue was purified via Purification Method 1 to afford N-(3,5-dichloro-4-(2,6-dioxopiperidin-3-yl)benzyl)-2-(5-methoxy-4-methylpyrimidin-2-yl)-2-methylpropanamide (43.63 mg, 90.1 μmol, 29% yield) as a white solid.

$^1$H NMR (400 MHZ, DMSO-$d_6$)>=10.96 (s, 1H), 8.38 (s, 1H), 7.91 (t, J=6.0 Hz, 1H), 7.35 (s, 1H), 7.28 (s, 1H), 4.66-4.47 (m, 1H), 4.24 (d, J=6.0 Hz, 2H), 3.91 (s, 3H), 2.95-2.77 (m, 1H), 2.61-2.53 (m, 1H), 2.38 (s, 3H), 2.37-2.29 (m, 1H), 1.96-1.83 (m, 1H), 1.52 (s, 6H). MS (ESI) m/z 479.1 [M+H]$^+$

Exemplary Compound 222

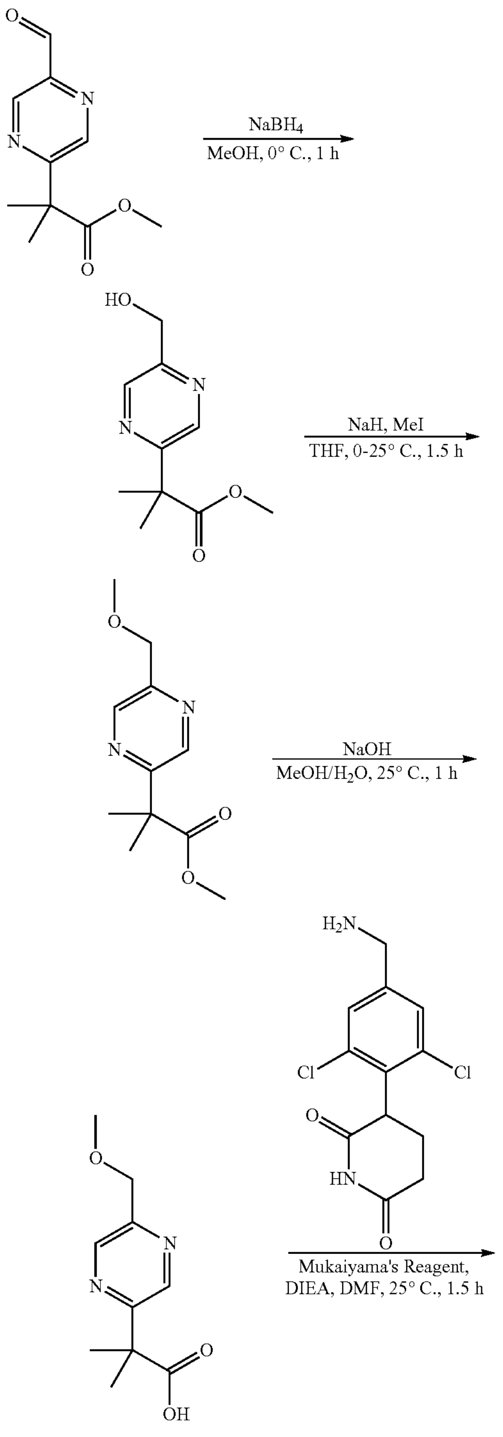

-continued

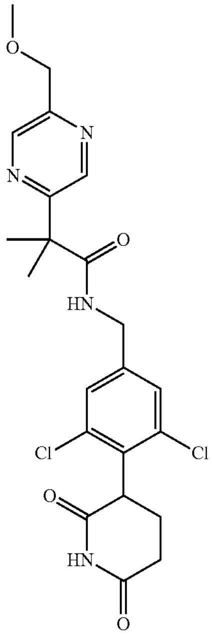 [SMILES: COCc1cnc(C(C)(C)C(=O)NCc2cc(Cl)c(C3CCC(=O)NC3=O)c(Cl)c2)cn1]

Step 1. To a solution of methyl 2-(5-formylpyrazin-2-yl)-2-methylpropanoate (3.15 g, 15.1 mmol, 1.00 eq.) in methanol (30 mL) was added sodium borohydride (920 mg, 24.3 mmol, 1.61 eq.) at 0° C. under nitrogen atmosphere. The mixture was stirred at 0° C. under nitrogen atmosphere for 1 h. The reaction mixture was quenched with saturated ammonium chloride solution (50 mL) at 0° C. under nitrogen atmosphere and diluted with ethyl acetate (60 mL). The layers were separated, and the aqueous phase was extracted with ethyl acetate (2×60 mL). The combined organic layers were washed with brine (100 mL), dried over sodium sulfate, filtered, and concentrated under reduced pressure to give methyl 2-(5-(hydroxymethyl) pyrazin-2-yl)-2-methylpropanoate (2.82 g, 12.1 mmol, 80% yield) as a yellow oil.

Step 2. To a solution of methyl 2-(5-(hydroxymethyl) pyrazin-2-yl)-2-methylpropanoate (500 mg, 2.38 mmol, 1.00 eq.) in tetrahydrofuran (10 mL) was added sodium hydride (143 mg, 3.57 mmol, 60% purity, 1.51 eq.) at 0° C. under nitrogen atmosphere. After addition, the mixture was stirred at 25° C. for 30 min under nitrogen atmosphere, and then methyl iodide (296 μL, 4.76 mmol, 2.00 eq.) was added dropwise at 0° C. The reaction was stirred at 25° C. for 1 h. The reaction mixture was quenched with saturated ammonium chloride solution (20 mL) at 0° C., and diluted with ethyl acetate (20 mL). The layers were separated, and the aqueous phase was extracted with ethyl acetate (2× 20 mL). The combined organic layers were dried over sodium sulfate, filtered, and concentrated under reduced pressure. The residue was purified via Purification Method 2 to afford methyl 2-(5-(methoxymethyl)-pyrazin-2-yl)-2-methylpropanoate (177 mg, 710 μmol, 30% yield) as a colourless oil.

Step 3. To a solution of methyl 2-(5-(methoxymethyl) pyrazin-2-yl)-2-methylpropanoate (170 mg, 758 μmol, 1.00 eq.) in methanol (1.5 mL) was added sodium hydroxide (152 mg, 3.79 mmol, 5.00 eq.) in water (1.5 mL) at 0° C. The mixture was stirred at 25° C. for 1 h. The reaction mixture was adjusted to 6 with 2 M hydrochloric acid and lyophilized to give 2-(5-(methoxymethyl) pyrazin-2-yl)-2-methylpropanoic acid (325 mg, crude) as a white solid.

Step 4. To a solution of 2-(5-(methoxymethyl) pyrazin-2-yl)-2-methylpropanoic acid (325 mg, crude) in N,N-dimethyl formamide (5 mL) were added N,N-diisopropylethylamine (242 μL, 1.39 mmol, 3.00 eq.) and 2-chloro-1-methylpyridin-1-ium iodide (142 mg, 556 μmol, 1.20 eq.). After addition, the mixture was stirred at 25° C. for 30 min, and then 3-(4-(aminomethyl)-2,6-dichlorophenyl) piperidine-2,6-dione hydrochloride (150 mg, 464 μmol, 1.00 eq.) was added. The reaction was stirred at 25° C. for 1 h. The mixture was diluted with water (20 mL), extracted with ethyl acetate (20 mL). The combined organic layers were washed with water (2×20 mL) and brine (20 mL) dried over sodium sulfate, filtered, and concentrated under reduced pressure. The residue was purified via Purification Method 1 to afford N-(3,5-dichloro-4-(2,6-dioxopiperidin-3-yl)benzyl)-2-(5-(methoxymethyl) pyrazin-2-yl)-2-methylpropanamide (140.88 mg, 291 μmol, 63% yield) as a white solid.

$^1$H NMR (400 MHZ, DMSO-$d_6$) δ=10.97 (s, 1H), 8.68 (d, J=1.2 Hz, 1H), 8.65 (s, 1H), 8.15 (t, J=6.0 Hz, 1H), 7.33 (s, 1H), 7.26 (s, 1H), 4.60-4.56 (m, 3H), 4.26 (d, J=6.0 Hz, 2H), 3.40 (s, 3H), 2.87 (ddd, J=5.6, 14.0, 16.8 Hz, 1H), 2.64-2.53 (m, 1H), 2.37 (dq, J=4.0, 13.2 Hz, 1H), 1.94-1.88 (m, 1H), 1.59 (s, 6H).

Exemplary Compound 223

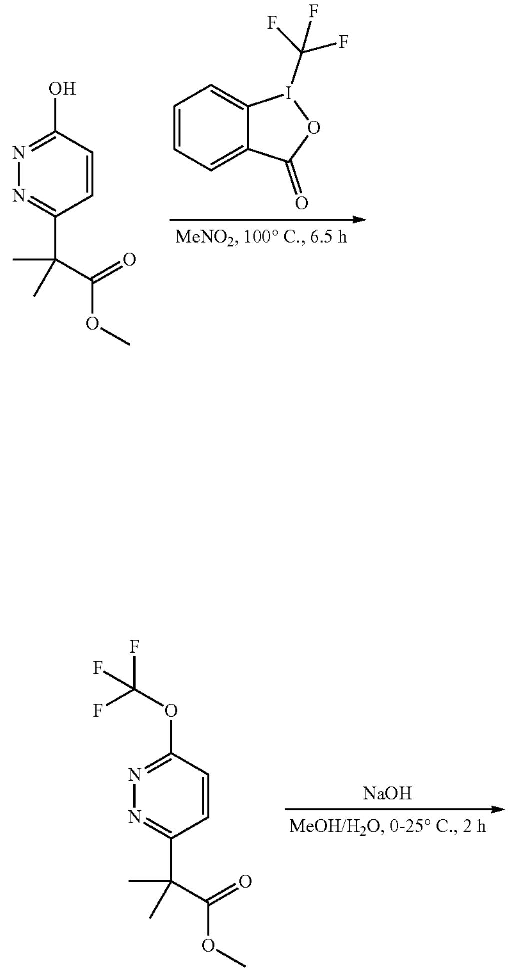

-continued

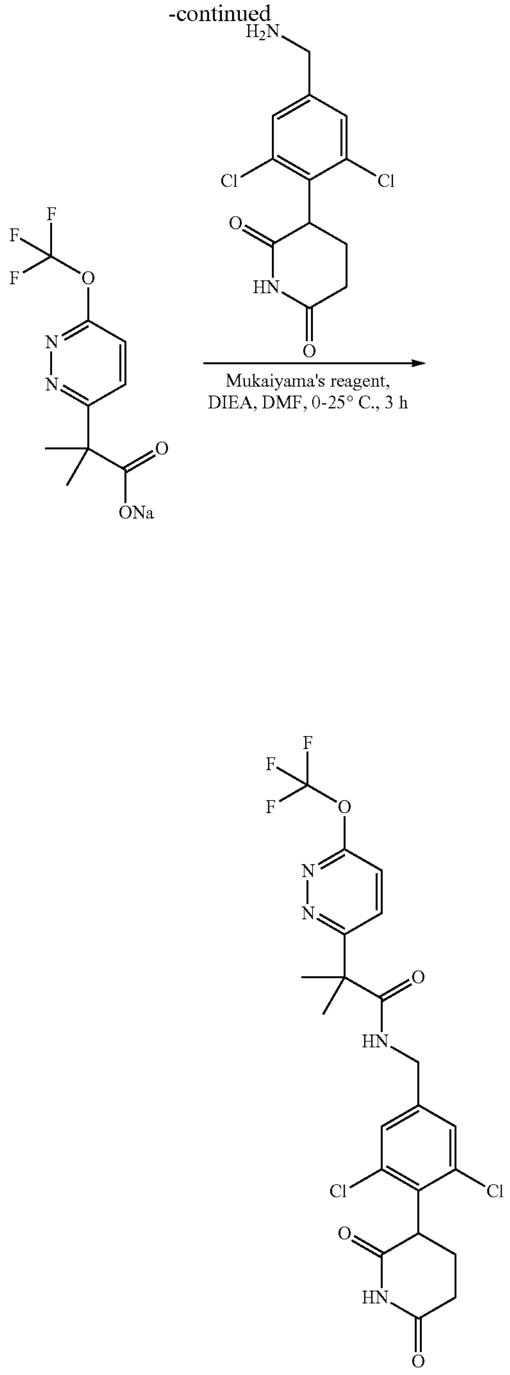

Step 1. To a solution of methyl 2-(6-hydroxypyridazin-3-yl)-2-methylpropanoate (500 mg, 2.55 mmol, 1.00 eq.) in nitromethane (15 mL) was added d 1-(trifluoromethyl)-123-benzo[d][1,2]iodaoxol-3 (1H)-one (1.60 g, 5.06 mmol, 1.99 eq.) under nitrogen atmosphere. The mixture was stirred at 100° C. for 1.5 h under nitrogen atmosphere. Then another 1-(trifluoromethyl)-123-benzo[d][1,2]iodaoxol-3 (1H)-one (1.00 g, 3.16 mmol, 1.24 eq.) was added at 100° C. under nitrogen atmosphere. The mixture was stirred at 100° C. for another 5 h under nitrogen atmosphere. The reaction mixture was cooled to 25° C. The reaction was diluted with ethanol (30 mL) at 25° C. under nitrogen. The mixture was concentrated under reduced pressure. The residue was purified via Purification Method 2 to afford methyl 2-methyl-2-(6-(trifluoromethoxy)pyridazin-3-yl) propanoate (220 mg, 783 μmol, 15% yield) as a yellow oil.

Step 2. To a solution of methyl 2-methyl-2-(6-(trifluoromethoxy)pyridazin-3-yl) propanoate (180 mg, 681 μmol, 1.00 eq.) in methanol (5 mL) was added a solution of sodium hydroxide (144 mg, 3.60 mmol, 5.28 eq.) in water (1 mL) at 0° C. The mixture was stirred at 25° C. for 2 h. The mixture was diluted with water (30 mL). The mixture was adjusted to pH 7 with 2 M hydrochloric acid at 0° C. The mixture was concentrated under reduced pressure to remove methanol. The mixture was lyophilized to give sodium 2-methyl-2-(6-(trifluoromethoxy)pyridazin-3-yl) propanoate (340 mg, 373 μmol, 55% yield, 30% purity) as a white solid.

Step 3. To a suspension of sodium 2-methyl-2-(6-(trifluoromethoxy)pyridazin-3-yl) propanoate (340 mg, 373 μmol, 30% purity, 1.00 eq.) in N,N-dimethylformamide (4 mL) were added 2-chloro-1-methylpyridin-1-ium iodide (123 mg, 481 μmol, 1.29 eq.) and N,N-diisopropylethylamine (280 μL, 1.61 mmol, 4.31 eq.) at 0° C. The mixture was stirred at 25° C. for 1 h. Then 3-(4-(aminomethyl)-2,6-dichlorophenyl) piperidine-2,6-dione hydrochloride (90.0 mg, 278 μmol, 0.75 eq.) was added at 25° C. The mixture was stirred at 25° C. for 2 h. The mixture was diluted with water (15 mL), the mixture was extracted with ethyl acetate (3× 20 mL). The combined organic layers were dried over sodium sulfate, filtered, and concentrated under reduced pressure. The residue was purified via Purification Method 1 to afford N-(3,5-dichloro-4-(2,6-dioxopiperidin-3-yl)benzyl)-2-methyl-2-(6-(trifluoromethoxy)pyridazin-3-yl) propanamide (13.6 mg, 25.9 μmol, 7% yield) as an off-white solid.

$^1$H NMR (400 MHZ, DMSO-$d_6$)>=10.95 (s, 1H), 8.27 (t, J=6.0 Hz, 1H), 7.94 (d, J=9.2 Hz, 1H), 7.70 (d, J=9.2 Hz, 1H), 7.26 (d, J=1.2 Hz, 1H), 7.20 (d, J=1.2 Hz, 1H), 4.59-4.52 (m, 1H), 4.24 (d, J=6.0 Hz, 2H), 2.91-2.79 (m, 1H), 2.57-2.53 (m, 1H), 2.38-2.31 (m, 1H), 1.93-1.84 (m, 1H), 1.62 (s, 6H). MS (ESI) m/z 519.1 $[M+H]^+$

Exemplary Compounds 224 and 225

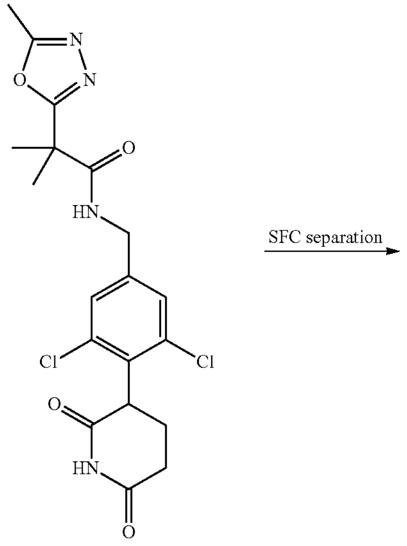

-continued

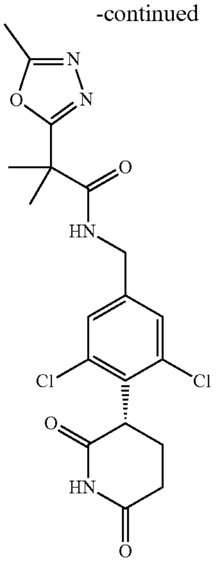

Compound 224

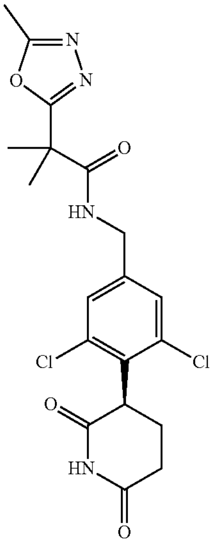

Compound 225

Note: for these enantiomers, their absolute configuration was not determined and was assigned arbitrarily.

N-(3,5-dichloro-4-(2,6-dioxopiperidin-3-yl)benzyl)-2-methyl-2-(5-methyl-1,3,4-oxadiazol-2-yl) propanamide (1.00 g, 2.28 mmol) was separated by SFC (column: DAICEL CHIRALPAK IC (250 mm×30 mm, 10 μm); mobile phase: [carbon dioxide-isopropanol/acetonitrile]; B %: 50%, isocratic elution mode) to give two peaks.

Peak one was further purified by Prep-HPLC (column: Phenomenex luna C18 150×40 mm×15 μm; mobile phase: [water (formic acid)-acetonitrile]; gradient: 18%-48% B over 15 min) and lyophilized to give(S)—N-(3,5-dichloro-4-(2,6-dioxopiperidin-3-yl)benzyl)-2-methyl-2-(5-methyl-1,3,4-oxadiazol-2-yl) propanamide (436.83 mg, 975 μmol, 43% yield) as a white solid.

$^1$H NMR (400 MHZ, DMSO-$d_6$) δ=10.96 (s, 1H), 8.45 (t, J=6.0 Hz, 1H), 7.32 (d, J=1.2 Hz, 1H), 7.25 (s, 1H), 4.57 (dd, J=5.6, 12.8 Hz, 1H), 4.25 (d, J=5.9 Hz, 2H), 2.85 (ddd, J=5.6, 14.0, 16.8 Hz, 1H), 2.59-2.52 (m, 1H), 2.48 (s, 3H), 2.36 (dq, J=4.0, 13.2 Hz, 1H), 1.95-1.83 (m, 1H), 1.58 (s, 6H). MS (ESI) m/z 439.1 $[M+H]^+$ Peak two was further purified by Prep-HPLC (column: Phenomenex luna C18 150×40 mm×15 μm; mobile phase: [water (formic acid)-acetonitrile]; gradient: 18%-48% B over 15 min) and lyophilized to give (R)—N-(3,5-dichloro-4-(2,6-dioxopiperidin-3-yl)benzyl)-2-methyl-2-(5-methyl-1,3,4-oxadiazol-2-yl) propanamide (315.64 mg, 711 μmol, 31% yield) as a white solid.

$^1$H NMR (400 MHZ, DMSO-$d_6$) δ=10.96 (s, 1H), 8.45 (t, J=6.0 Hz, 1H), 7.32 (s, 1H), 7.25 (s, 1H), 4.57 (dd, J=5.6, 12.8 Hz, 1H), 4.25 (d, J=6.0 Hz, 2H), 2.93-2.79 (m, 1H), 2.58-2.51 (m, 1H), 2.48 (s, 3H), 2.36 (dq, J=4.0, 13.2 Hz, 1H), 1.97-1.82 (m, 1H), 1.58 (s, 6H). MS (ESI) m/z 439.1 $[M+H]^+$

Exemplary Compound 226

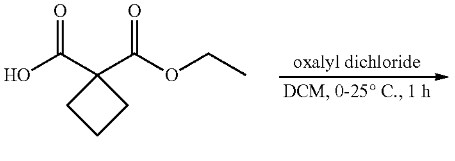

-continued

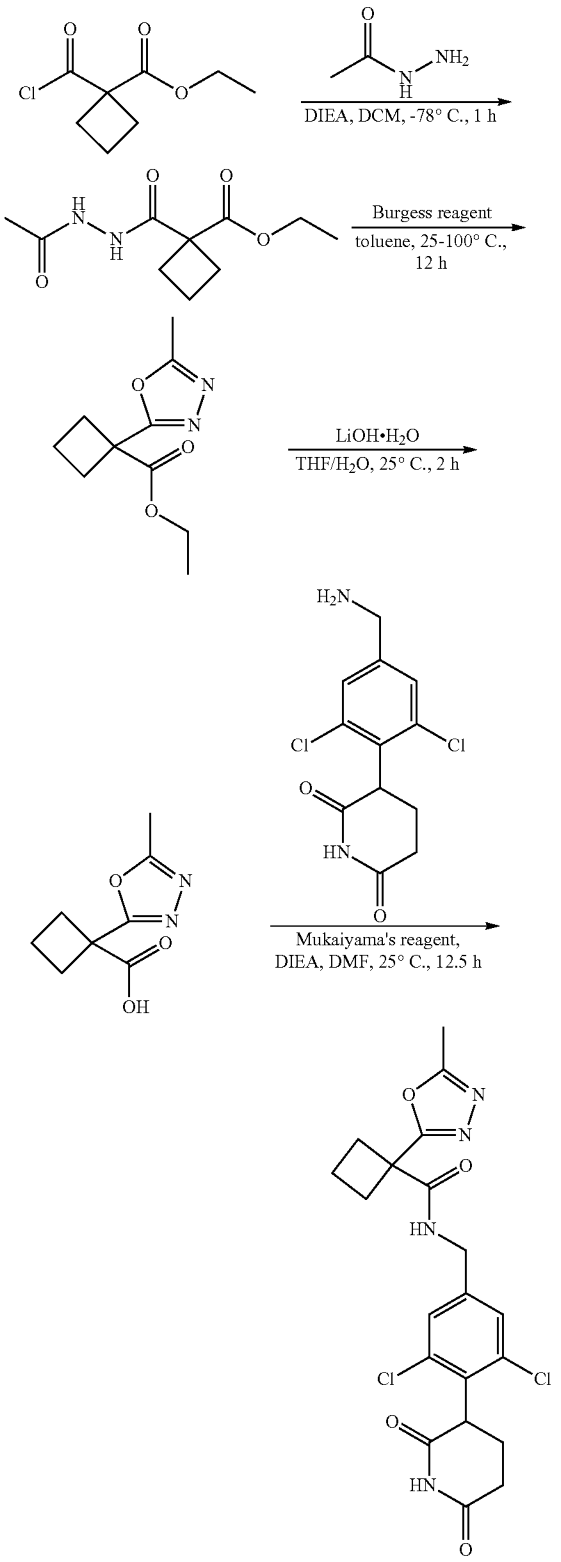

Step 1. To a mixture of 1-(ethoxycarbonyl)cyclobutane-1-carboxylic acid (500 mg, 2.90 mmol, 1.00 eq.) in dichloromethane (5 mL) was oxalyl dichloride (737 mg, 5.81 mmol, 2.00 eq.) dropwise at 0° C. The mixture was stirred at 25° C. for 1 h. The mixture was concentrated under reduced pressure to give ethyl 1-(chlorocarbonyl)cyclobutane-1-carboxylate (500 mg, 2.62 mmol, 90% yield) as a colourless oil.

Step 2. To a mixture of ethyl 1-(chlorocarbonyl)cyclobutane-1-carboxylate (500 mg, 2.62 mmol, 1.00 eq.) in dichloromethane (2 mL) was added a solution of acetohydrazide (233 mg, 3.15 mmol, 1.20 eq.) and diisopropylethylamine (677 mg, 5.25 mmol, 2.00 eq.) in dichloromethane (2 mL) dropwise at −78° C. The mixture was stirred at −78° C. for 1 h. The mixture was warmed to 25° C. and concentrated under reduced pressure. The residue was purified via Purification Method 2 to afford ethyl 1-(2-acetylhydrazine-1-carbonyl)cyclobutane-1-carboxylate (220 mg, 954 μmol, 36% yield) as a white solid.

Step 3. To a mixture of ethyl 1-(2-acetylhydrazine-1-carbonyl)cyclobutane-1-carboxylate (220 mg, 963 μmol, 1.00 eq.) in toluene (3 mL) was added Burgess reagent (689 mg, 2.89 mmol, 3.00 eq.) in portions at 25° C. The mixture was stirred at 100° C. for 12 h. The mixture was cooled to 25° C. then poured into water (10 mL) and extracted with ethyl acetate (3× 20 mL). The combined organic layers were washed with brine (10 mL), dried over anhydrous sodium sulfate, filtered, and the filtrate was concentrated under reduced pressure. The residue was purified via Purification Method 2 to afford ethyl 1-(5-methyl-1,3,4-oxadiazol-2-yl)-cyclobutane-1-carboxylate (150 mg, 635 μmol, 65% yield) as a colourless oil.

Step 4. To a solution of ethyl 1-(5-methyl-1,3,4-oxadiazol-2-yl)cyclobutane-1-carboxylate (190 mg, 903 μmol, 1.00 eq.) in tetrahydrofuran (1 mL) and water (1 mL) was added lithium hydroxide monohydrate (189 mg, 4.52 mmol, 5.00 eq.) in one portion at 25° C. The mixture was stirred at 25° C. for 2 h. The mixture was poured into water (10 mL). The aqueous layer was adjusted pH 8-9 with 6% aqueous hydrochloric acid then lyophilized. The residue was purified via Purification Method 1 to afford 1-(5-methyl-1,3,4-oxadiazol-2-yl)cyclobutane-1-carboxylic acid (115 mg, 618 μmol, 68% yield) as a colourless oil.

Step 5. To a solution of 1-(5-methyl-1,3,4-oxadiazol-2-yl)cyclobutane-1-carboxylic acid (90.0 mg, 494 μmol, 1.00 eq.) and 2-chloro-1-methyl-pyridin-1-ium iodide (151 mg, 592 μmol, 1.20 eq.) in dimethyl formamide (1 mL) was added diisopropylethylamine (191 mg, 1.48 mmol, 3.00 eq.) dropwise at 25° C. The mixture was stirred at 25° C. for 0.5 h then 3-(4-(aminomethyl)-2,6-dichlorophenyl) piperidine-2,6-dione hydrochloride (159 mg, 494 μmol, 1.00 eq.) was added. The mixture was stirred at 25° C. for 12 h. The mixture was poured into water (20 mL). The mixture was extracted with ethyl acetate (3×20 mL). The combined organic layers were washed with brine (10 mL), dried over anhydrous sodium sulfate, filtered, and the filtrate was concentrated under reduced pressure. The residue was purified via Purification Method I to afford N-(3,5-dichloro-4-(2,6-dioxopiperidin-3-yl)benzyl)-1-(5-methyl-1,3,4-oxadiazol-2-yl)-cyclobutane-1-carboxamide (49.5 mg, 108 μmol, 22% yield) as an off-white solid.

$^1$H NMR (400 MHZ, DMSO-$d_6$) δ=10.95 (s, 1H), 8.54 (t, J=6.0 Hz, 1H), 7.34 (s, 1H), 7.27 (d, J=1.2 Hz, 1H), 4.57 (dd, J=5.6, 12.8 Hz, 1H), 4.28 (d, J=6.0 Hz, 2H), 2.85 (ddd, J=6.0, 14.4, 16.8 Hz, 1H), 2.75-2.66 (m, 2H), 2.64-2.53 (m, 3H), 2.52-2.51 (m, 3H), 2.39-2.30 (m, 1H), 2.06-1.83 (m, 3H). MS (ESI) m/z 451.0 [M+H]$^+$ Exemplary Compound 227

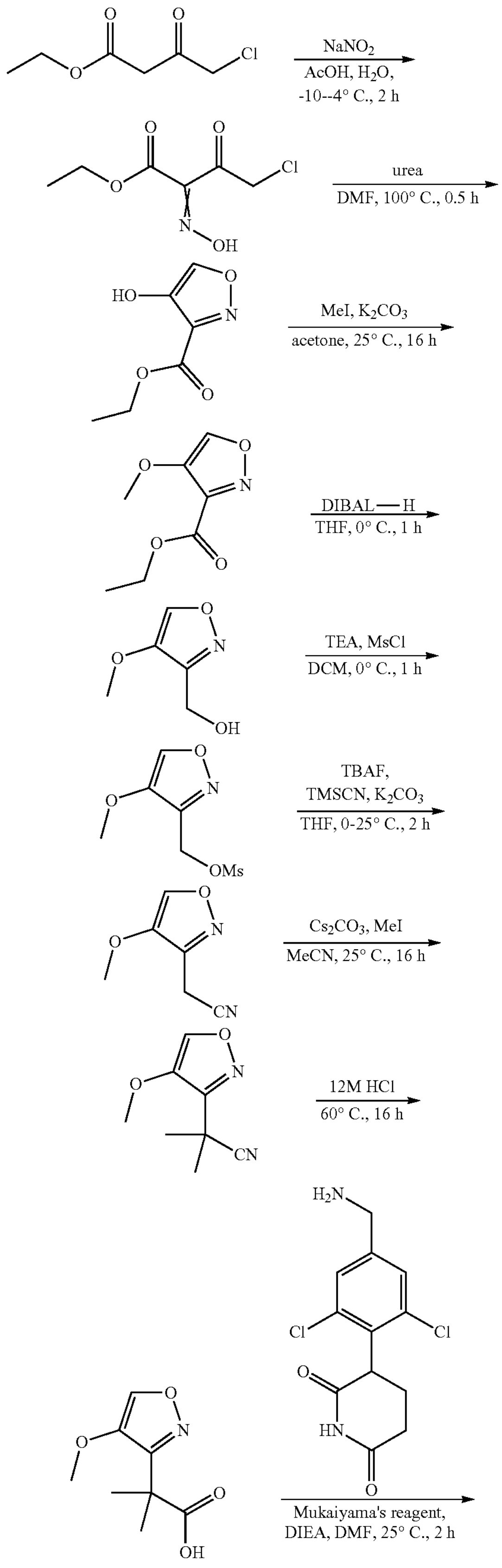

-continued

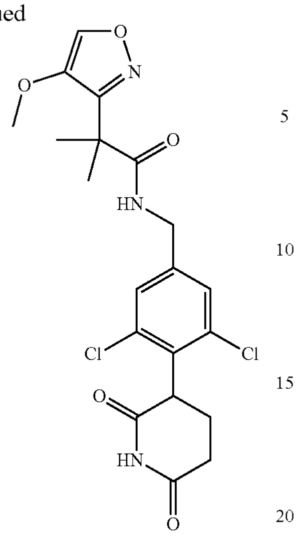

Step 1. Ethyl 4-chloro-3-oxobutanoate (5.00 g, 30.4 mmol, 1.00 eq.) was dissolved in acetic acid (10 mL) and a solution of sodium nitrite (2.72 g, 39.5 mmol, 1.30 eq.) in water (10 mL) was added dropwise at −10° C. The reaction was stirred at −4° C. for 2 h. The mixture was diluted with water (20 mL) and extracted with ethyl acetate (2× 40 mL). The organic layers were combined and washed with water (2×30 mL), dried over sodium sulfate, filtered, and concentrated under reduced pressure. The residue was purified via Purification Method 2 to afford ethyl 4-chloro-2-(hydroxyimino)-3-oxobutanoate (4.35 g, 20.0 mmol, 66% yield) as a yellow solid.

Step 2. To a solution of ethyl 4-chloro-2-(hydroxyimino)-3-oxobutanoate (3.35 g, 17.3 mmol, 1.00 eq.) in N,N-dimethylformamide (20 mL) was added urea (8.31 g, 138 mmol, 8.00 eq.). The mixture was stirred at 100° C. for 0.5 h. The mixture was diluted with water (30 mL), extracted with dichloromethane (2×40 mL). The organic layers were combined, washed with water (2×50 mL), dried over sodium sulfate, filtered, and concentrated under reduced pressure. The residue was purified via Purification Method 2 to afford ethyl 4-hydroxyisoxazole-3-carboxylate (3.39 g, 10.8 mmol, 62% yield, 50% purity) as a colourless oil.

Step 3. To a solution of ethyl 4-hydroxyisoxazole-3-carboxylate (2.70 g, 10.3 mmol, 1.00 eq.) and potassium carbonate (4.27 g, 30.9 mmol, 3.00 eq.) in acetone (15 mL) was added methyl iodide (4.38 g, 30.8 mmol, 2.99 eq.). The mixture was stirred at 25° C. for 16 h. The mixture was diluted with water (30 mL), extracted with ethyl acetate (2×30 mL). The combined organic layers were washed with water (2×20 mL), dried over sodium sulfate, filtered, and concentrated under reduced pressure to give ethyl 4-methoxyisoxazole-3-carboxylate (1.75 g, 9.20 mmol, 89% yield) as a white solid.

Step 4. To a solution of ethyl 4-methoxyisoxazole-3-carboxylate (2.28 g, 6.66 mmol, 1.00 eq.) in dichloromethane (15 mL) was added diisobutylaluminum hydride (1 M in toluene, 20.0 mL, 3.05 eq.). The mixture was stirred at 0° C. under nitrogen atmosphere for 1 h. The mixture was poured into saturated aqueous ammonium chloride (40 mL) and extracted with ethyl acetate (2×50 mL). The combined organic layers were washed with brine (60 mL), dried over sodium sulfate, filtered, and the filtrate was concentrated under reduced pressure. The residue was purified via Purification Method 2 to afford (4-methoxyisoxazol-3-yl) methanol (590 mg, 4.34 mmol, 65% yield) as a purple oil.

Step 5. To a mixture of (4-methoxyisoxazol-3-yl) methanol (240 mg, 1.86 mmol, 1.00 eq.) in dichloromethane (10 mL) were added triethylamine (376 mg, 3.72 mmol, 2.00 eq.) and methanesulfonyl chloride (650 mg, 5.67 mmol, 3.05 eq.) dropwise at 0° C. The mixture was stirred at 0° C. for 1 h under nitrogen atmosphere. The mixture was poured into ice water (15 mL). The mixture was extracted with dichloromethane (30 mL). The combined organic layers were washed with brine (20 mL), dried over sodium sulfate, filtered, and concentrated under reduced pressure.

The residue was purified via Purification Method 2 to afford (4-methoxyisoxazol-3-yl)methyl methanesulfonate (330 mg, 1.58 mmol, 84% yield) as a colourless oil.

Step 6. To a solution of (4-methoxyisoxazol-3-yl)methyl methanesulfonate (420 mg, 2.03 mmol, 1.00 eq.) in tetrahydrofuran (10 mL) were added potassium carbonate (700 mg, 5.07 mmol, 2.50 eq.), trimethylsilyl-formonitrile (241 mg, 2.43 mmol, 1.20 eq.). Then tetrabutylammonium fluoride (1M in tetrahydrofuran, 4.00 mL, 2.00 eq.) was added at 0° C. under nitrogen atmosphere. The reaction was stirred at 25° C. for 2 h. The mixture was added water (10 mL) and ethyl acetate (20 mL). The layers were separated. Then the organic phase was washed with brine (10 mL), dried over sodium sulfate, filtered, and concentrated under vacuum. The residue was purified via Purification Method 2 to afford 2-(4-methoxyisoxazol-3-yl) acetonitrile (250 mg, 1.79 mmol, 88% yield) as a colourless oil.

Step 7. To a solution of 2-(4-methoxyisoxazol-3-yl) acetonitrile (240 mg, 1.74 mmol, 1.00 eq.) in acetonitrile (10 mL) were added caesium carbonate (1.70 g, 5.21 mmol, 3.00 eq.) and methyl iodide (2.47 g, 17.4 mmol, 10.0 eq.). The reaction was stirred at 25° C. for 16 h. The reaction mixture was filtered and washed with ethyl acetate (20 mL). Then the filtrate was washed with water (20 mL), dried over sodium sulfate, filtered, and concentrated under vacuum. The residue was purified via Purification Method 2 to afford 2-(4-methoxyisoxazol-3-yl)-2-methylpropanenitrile (200 mg, 1.13 mmol, 65% yield) as a colourless oil.

Step 8. A solution of 2-(4-methoxyisoxazol-3-yl)-2-methylpropanenitrile (100 mg, 601 μmol, 1.00 eq.) in hydrochloric acid (12 M, 3 mL) was stirred at 60° C. for 16 h. The mixture was added water (10 mL) and ethyl acetate (20 mL). The layers were separated. Then the organic phase was washed with brine (10 mL), dried over sodium sulfate, filtered, and concentrated under vacuum to give 2-(4-methoxyisoxazol-3-yl)-2-methylpropanoic acid (110 mg, 534 μmol, 88% yield) as a white solid.

Step 9. To a solution of 2-(4-methoxyisoxazol-3-yl)-2-methylpropanoic acid (100 mg, 540 μmol, 1.00 eq.) in N,N-dimethylformamide (3 mL) were added N,N-diisopropylethylamine (348 mg, 2.70 mmol, 5.00 eq.) and 2-chloro-1-methyl-pyridin-1-ium iodide (165 mg, 648 μmol, 1.20 eq.). The reaction was stirred at 25° C. for 1 h. Then 3-(4-(aminomethyl)-2,6-dichlorophenyl) piperidine-2,6-dione hydrochloride (130 mg, 401 μmol, 0.74 eq.) was added and stirred at 25° C. for 1 h. The mixture was added water (10 mL) and ethyl acetate (20 mL). The layers were separated. Then the organic phase was washed with brine (20 mL), dried over sodium sulfate, filtered, and concentrated under vacuum. The residue was purified via Purification Method 1 to afford N-(3,5-dichloro-4-(2,6-dioxopiperidin-3-yl)benzyl)-2-(4-methoxyisoxazol-3-yl)-2-methylpropanamide (117.7 mg, 256 μmol, 47% yield) as a white solid.

$^1$H NMR (400 MHZ, DMSO-$d_6$) δ=10.95 (s, 1H), 8.67 (s, 1H), 8.11 (t, J=6.0 Hz, 1H), 7.32 (s, 1H), 7.25 (s, 1H), 4.57

(dd, J=5.6, 12.8 Hz, 1H), 4.22 (d, J=6.0 Hz, 2H), 3.68 (s, 3H), 2.85 (ddd, J=5.6, 14.0, 16.8 Hz, 1H), 2.58-2.52 (m, 1H), 2.36 (dq, J=4.4, 13.2 Hz, 1H), 1.97-1.83 (m, 1H), 1.48 (s, 6H). MS (ESI) m/z 454.1 $[M+H]^+$ Exemplary Compound 229

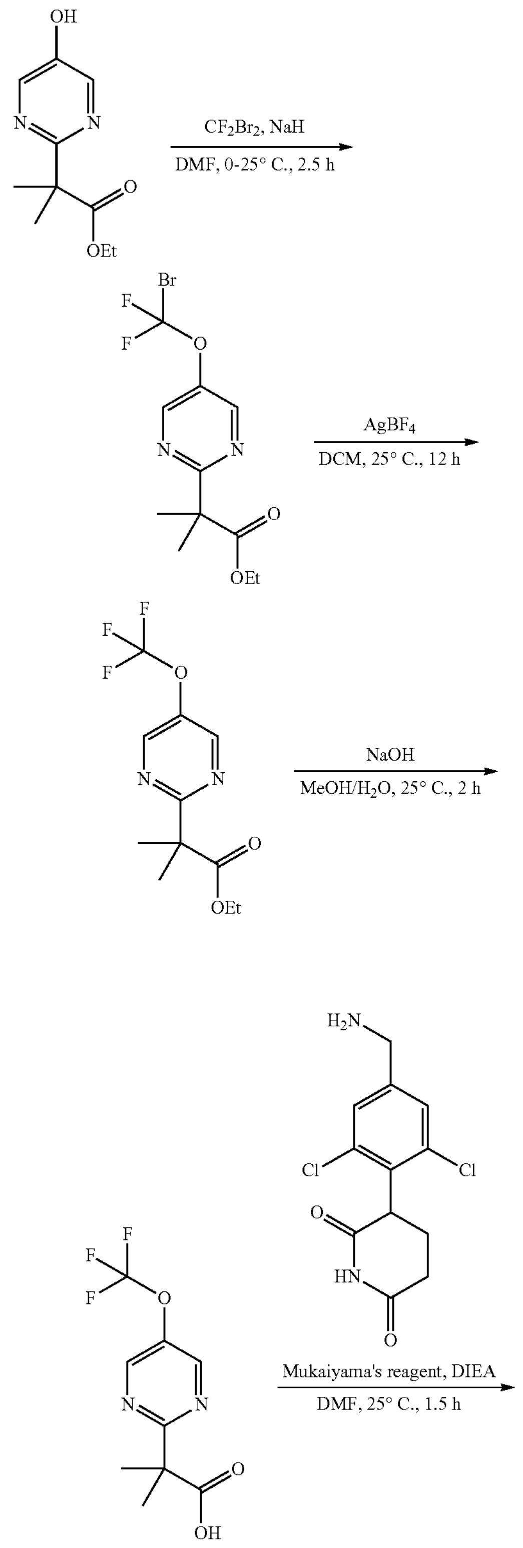

-continued

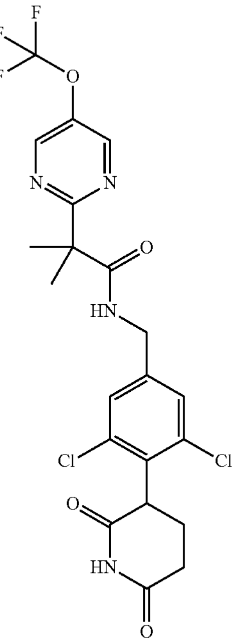

Step 1. To a mixture of ethyl 2-(5-hydroxypyrimidin-2-yl)-2-methylpropanoate (0.78 g, 3.71 mmol, 1.00 eq.) in dimethylformamide (8 mL) was added sodium hydride (296 mg, 7.42 mmol, 60% purity, 2.00 eq.) in portions at 0° C. The mixture was stirred at 0° C. for 0.5 h. Then dibromodifluoromethane (2.07 g, 7.42 mmol, 2.00 eq.) was added and the mixture was stirred at 25° C. for 2 h. The reaction was quenched with saturated aqueous ammonium chloride (30 mL) and extracted with ethyl acetate (3×30 mL). The combined organic layers were washed with brine (30 mL), dried over anhydrous sodium sulfate, filtered, and the filtrate was concentrated under reduced pressure. The residue was purified via Purification Method 2 to afford ethyl 2-(5-(bromodifluoromethoxy)pyrimidin-2-yl)-2-methylpropanoate (100 mg, 262 μmol, 7% yield) as a colourless oil.

Step 2. To a solution of ethyl 2-(5-(bromodifluoromethoxy)pyrimidin-2-yl)-2-methylpropanoate (100 mg, 294 μmol, 1.00 eq.) in dichloromethane (2 mL) was added silver (I) tetrafluoroborate (172 mg, 884 μmol, 3.00 eq.) in portions. The mixture was stirred at 25° C. for 12 h. The mixture was filtered, and the filtrate was concentrated under reduced pressure to give ethyl 2-methyl-2-(5-(trifluoromethoxy)pyrimidin-2-yl) propanoate (80.0 mg, crude) as a yellow oil.

Step 3. To a mixture of ethyl 2-methyl-2-(5-(trifluoromethoxy)pyrimidin-2-yl) propanoate (80.0 mg, 287 μmol, 1.00 eq.) in methanol (1 mL) and water (1 mL) was added sodium hydroxide (57.5 mg, 1.44 mmol, 5.00 eq.) in portions at 25° C. The mixture was stirred at 25° C. for 2 h. The mixture was poured into water (10 mL) and adjusted to pH 2-3 by using of 6% aqueous hydrochloric acid then extracted with ethyl acetate (3×10 mL). The combined organic extracts were washed with brine (10 mL) and dried over anhydrous sodium sulfate, filtered, and concentrated under reduced pressure to give 2-methyl-2-(5-(trifluoromethoxy) pyrimidin-2-yl) propanoic acid (45.0 mg, 140 μmol, 48% yield) as a brown solid.

Step 4. To a mixture of 2-methyl-2-(5-(trifluoromethoxy) pyrimidin-2-yl) propanoic acid (40.0 mg, 159 μmol, 1.00 eq.) and 2-chloro-1-methyl-pyridin-1-ium iodide (40.8 mg, 159 μmol, 1.00 eq.) in dimethylformamide (2 mL) was added diisopropylethylamine (82.6 mg, 639 μmol, 4.00 eq.) dropwise at 25° C. The mixture was stirred at 25° C. for 0.5 h then 3-(4-(aminomethyl)-2,6-dichlorophenyl) piperidine-2,6-dione hydrochloride (41.3 mg, 127 μmol, 0.80 eq.) was added and the mixture was stirred at 25° C. for 1 h. The mixture was poured into water (10 mL). The mixture was extracted with ethyl acetate (3×10 mL). The combined organic layers were washed with brine (10 mL), dried over anhydrous sodium sulfate, filtered, and the filtrate was concentrated under reduced pressure. The residue was purified via Purification Method I to afford N-(3,5-dichloro-4-(2,6-dioxopiperidin-3-yl)benzyl)-2-methyl-2-(5-(trifluoromethoxy)-pyrimidin-2-yl) propanamide (16.4 mg, 31.4 μmol, 19% yield) as a white solid.

$^1$H NMR (400 MHZ, DMSO-$d_6$) δ=10.95 (br s, 1H), 8.98 (s, 2H), 8.14 (t, J=6.0 Hz, 1H), 7.36 (s, 1H), 7.30 (s, 1H), 4.56 (dd, J=5.6, 12.8 Hz, 1H), 4.26 (d, J=6.0 Hz, 2H), 2.85 (ddd, J=5.6, 14.0, 16.8 Hz, 1H), 2.60-2.52 (m, 1H), 2.41-2.30 (m, 1H), 1.96-1.83 (m, 1H), 1.57 (s, 6H). MS (ESI) m/z 519.0 $[M+H]^+$ Exemplary Compound 230

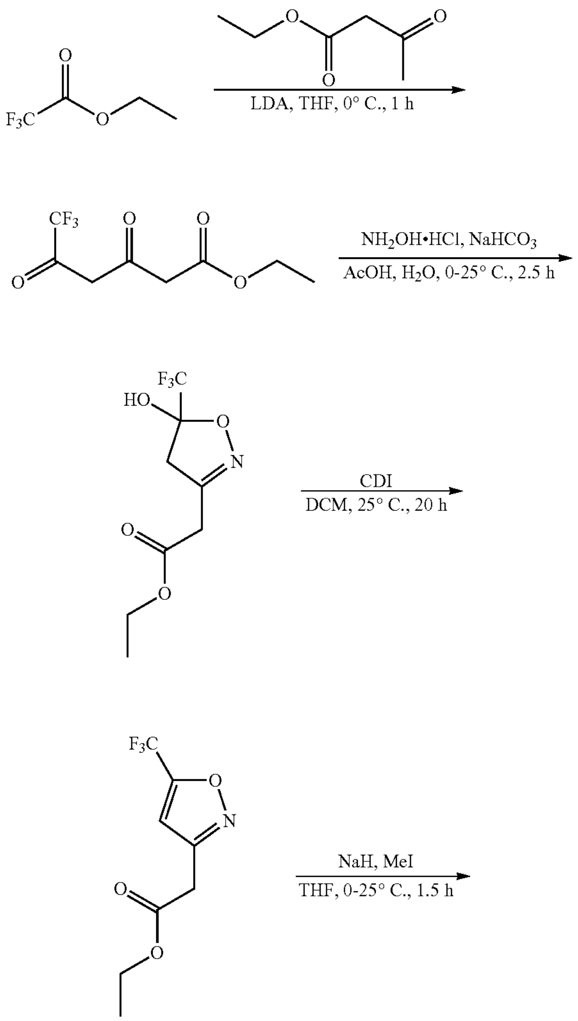

-continued

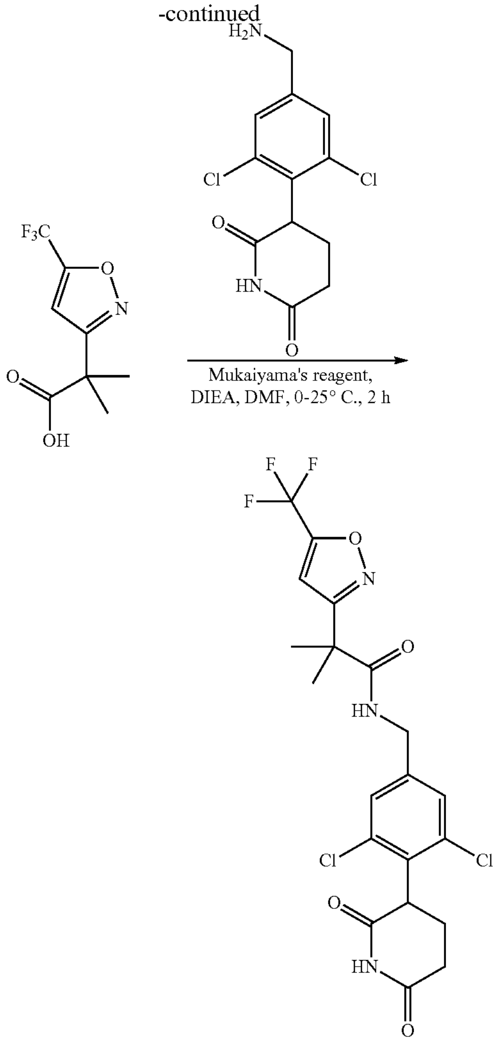

Step 1. To a solution of lithium diisopropylamide (2 M, 21.1 mL, 3.00 eq.) in tetrahydrofuran (20 mL) was added dropwise ethyl 3-oxobutanoate (1.83 g, 14.1 mmol, 1.78 mL, 1.00 eq.) at 0° C. under nitrogen atmosphere. After addition, the mixture was stirred at this temperature for 1 h, and then ethyl 2,2,2-trifluoroacetate (2.00 g, 14.1 mmol, 1.93 mL, 1.00 eq.) was added dropwise at −70° C. The reaction was stirred at 25° C. for 12 h under nitrogen atmosphere. The reaction mixture was quenched by addition of hydrochloric acid (1M, 20 mL) at 0° C., and then extracted with dichloromethane (4×40 mL). The combined organic layers were washed with brine (2×30 mL), dried over sodium sulfate, filtered, and concentrated under reduced pressure to afford the crude product of ethyl 6,6,6-trifluoro-3,5-dioxohexanoate.

Step 2. Then to a solution of sodium bicarbonate (1.42 g, 16.9 mmol, 657 μL, 1.20 eq.) in water (10 mL) was added hydroxylamine hydrochloride (1.17 g, 16.9 mmol, 1.20 eq.) at 0° C. The mixture was stirred at 0° C. for 0.5 h. This solution was added to the crude product of ethyl 6,6,6-trifluoro-3,5-dioxohexanoate in acetic acid (30 mL) at 0° C. The reaction was stirred at 25° C. for 2 h. The reaction mixture was concentrated under reduced pressure to give a residue. The residue was purified via Purification Method 2 to afford ethyl 2-(5-hydroxy-5-(trifluoromethyl)-4,5-dihydroisoxazol-3-yl)acetate (2.78 g, 10.7 mmol, 76% yield) as brown oil.

Step 3. To a solution of ethyl 2-(5-hydroxy-5-(trifluoromethyl)-4,5-dihydroisoxazol-3-yl)acetate (2.50 g, 9.64 mmol, 1.00 eq.) in dichloromethane (25 mL) was added di (1H-imidazol-1-yl) methanone (1.95 g, 12.1 mmol, 1.25 eq.). The mixture was stirred at 25° C. for 20 h. The reaction mixture was diluted with dichloromethane (20 mL) and then washed with saturated sodium hydrogen sulfate solution (2×20 mL) and brine (2×20 mL). The organic phase was dried over sodium sulfate, filtered, and concentrated in vacuo to afford ethyl 2-(5-(trifluoromethyl) isoxazol-3-yl)acetate (2 g, crude) as a brown oil Step 4. To a solution of ethyl 2-(5-(trifluoromethyl) isoxazol-3-yl)acetate (650 mg, 2.91 mmol, 1 00 eq.) in tetrahydrofuran (10 mL) was added sodium hydride (350 mg, 8.74 mmol, 60% purity, 3.00 eq.) at 0° C. under nitrogen atmosphere. After addition, the mixture was stirred at this temperature for 0.5 h. Then iodomethane (4.13 g, 29.1 mmol, 1.81 mL, 10.0 eq.) was added dropwise to the mixture at 0° C. The reaction was stirred at 25° C. for 1 h under nitrogen atmosphere. The reaction mixture was quenched by addition of saturated ammonium chloride solution (10 mL) at 0° C. Then the pH of the mixture was adjusted to 10 by addition of sodium hydroxide solution and the mixture was washed with dichloromethane (2×15 mL). The aqueous phase was adjusted to pH 3 by addition of hydrochloric acid (2M). The mixture was extracted with ethyl acetate (4×30 mL). The combined organic layers were washed with brine (2×15 mL), dried over sodium sulfate, filtered, and concentrated under reduced pressure to afford 2-methyl-2-(5-(trifluoromethyl) isoxazol-3-yl) propanoic acid (425 mg, 1.71 mmol, 59% yield) as brown oil.

Step 5. To a solution of 2-methyl-2-(5-(trifluoromethyl) isoxazol-3-yl) propanoic acid (150 mg, 605 μmol, 1.00 eq.) in dimethylformamide (2 mL) was added 2-chloro-1-methyl-pyridin-1-ium iodide (185 mg, 726 μmol, 1.20 eq.) and N-ethyl-N-isopropylpropan-2-amine (313 mg, 2.42 mmol, 422 μL, 4.00 eq.) at 0° C. After addition, the mixture was stirred at 25° C. for 0.5 h, and then 3-(4-(aminomethyl)-2,6-dichlorophenyl) piperidine-2,6-dione hydrochloride (137 mg, 423 μmol, 0.700 eq., hydrochloric acid) in dimethylformamide (2 mL) was added dropwise to the mixture. The reaction was stirred at 25° C. for another 1.5 h. The reaction mixture was diluted with water (10 mL) and extracted with ethyl acetate (5×10 mL). The combined organic layers were washed with brine (3×5 mL), dried over sodium sulfate, filtered, and concentrated under reduced pressure to give a residue. The residue was purified via Purification Method 1 to afford N-(3,5-dichloro-4-(2,6-dioxopiperidin-3-yl)benzyl)-2-methyl-2-(5-(trifluoromethyl) isoxazol-3-yl) propanamide (56.3 mg, 113 μmol, 19% yield) as a white solid.

$^1H$ NMR (400 MHz, DMSO-$d_6$) δ=10.96 (s, 1H), 8.38 (t, J=6.0 Hz, 1H), 7.53 (s, 1H), 7.34-7.27 (m, 1H), 7.26-7.17 (m, 1H), 4.56 (dd, J=5.6, 12.8 Hz, 1H), 4.25 (d, J=6.0 Hz, 2H), 2.91-2.80 (m, 1H), 2.60-2.53 (m, 1H), 2.40-2.29 (m, 1H), 1.94-1.84 (m, 1H), 1.57 (s, 6H). MS (ESI) m/z 509.1 $[M+H2O]^+$

Exemplary Compound 231

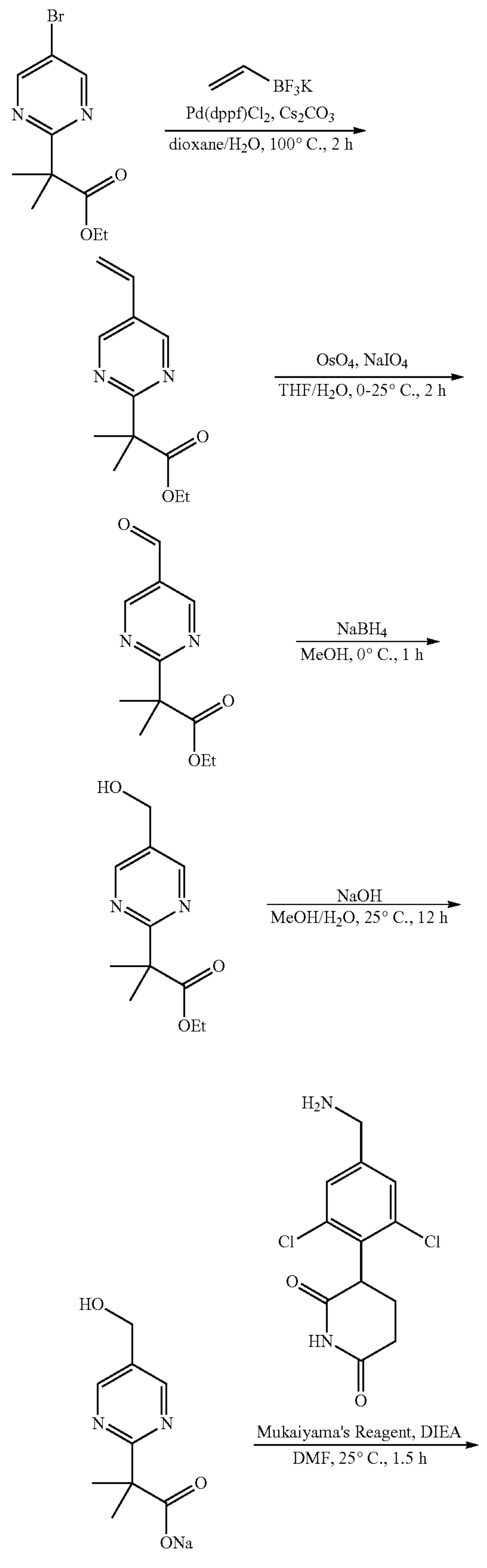

-continued

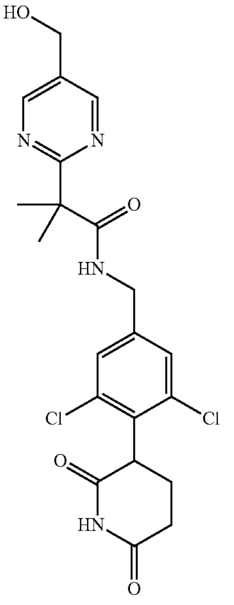 [SMILES: CC(C)(C(=O)NCc1cc(Cl)c(C2CCC(=O)NC2=O)c(Cl)c1)c1ncc(CO)cn1]

Step 1. To a mixture of ethyl 2-(5-bromopyrimidin-2-yl)-2-methylpropanoate (5.50 g, 20.1 mmol, 1.00 eq.), trifluoro (vinyl)-14-borane, potassium salt (5.39 g, 40.2 mmol, 2.00 eq.) and caesium carbonate (13.1 g, 40.2 mmol, 2.00 eq.) in dioxane (20 mL) and water (20 mL) was added [1,1'-bis (diphenylphosphino)ferrocene]dichloropalladium (II) (736 mg, 1.01 mmol, 0.05 eq.) in portions at 25° C. The mixture was stirred at 100° C. under nitrogen atmosphere for 2 h. The mixture was cooled to 25° C. then poured into water (50 mL). The mixture was extracted with ethyl acetate (3× 50 mL). The combined organic layers were washed with brine (50 mL), dried over anhydrous sodium sulfate, filtered, and the filtrate was concentrated under reduced pressure. The residue was purified by via Purification Method 2 and 1 to afford ethyl 2-methyl-2-(5-vinylpyrimidin-2-yl) propanoate (3.30 g, 14.3 mmol, 71% yield) as a colourless oil.

Step 2. To a solution of ethyl 2-methyl-2-(5-vinylpyrimidin-2-yl) propanoate (1.50 g, 6.81 mmol, 1.00 eq.) in tetrahydrofuran (15 mL) and water (5 mL) was added a solution of osmium (VIII) oxide (242 mg, 953 μmol, 0.14 eq.) in tetrahydrofuran (5 mL) dropwise at 0° C. Then a solution of sodium periodate (3.64 g, 17.0 mmol, 2.50 eq.) in water (10 mL) was added and the mixture was stirred at 25° C. under nitrogen atmosphere for 2 h. The mixture was poured into water (30 mL). The mixture was extracted with ethyl acetate (3x30 mL). The combined organic layers were washed with brine (30 mL), dried over anhydrous sodium sulfate, filtered, and the filtrate was concentrated under reduced pressure. The residue was purified via Purification Method 2 to afford ethyl 2-(5-formylpyrimidin-2-yl)-2-methylpropanoate (1.30 g, 5.79 mmol, 85% yield) as a colourless oil.

Step 3. To a solution of ethyl 2-(5-formylpyrimidin-2-yl)-2-methylpropanoate (500 mg, 2.25 mmol, 1.00 eq.) in methanol (10 mL) was added sodium borohydride (220 mg, 5.82 mmol, 2.58 eq.) in portions at 0° C. The mixture was stirred at 0° C. under nitrogen atmosphere for 1 h. The reaction was quenched with saturated aqueous ammonium chloride (30 mL) at 0° C. under nitrogen atmosphere and extracted with ethyl acetate (3x30 mL). The combined organic layers were washed with brine (30 mL), dried over anhydrous sodium sulfate, filtered, and the filtrate was concentrated under reduced pressure to give ethyl 2-(5-(hydroxymethyl)pyrimidin-2-yl)-2-methylpropanoate (500 mg, 2.21 mmol, 98% yield) as a colourless oil.

Step 4. To a mixture of ethyl 2-(5-(hydroxymethyl)pyrimidin-2-yl)-2-methylpropanoate (580 mg, 2.59 mmol, 1.00 eq.) in methanol (5 mL) and water (5 mL) was added sodium hydroxide (517 mg, 12.9 mmol, 5.00 eq.) in portions at 25° C. The mixture was stirred at 25° C. for 12 h. The mixture was poured into water (10 mL) and adjusted to pH 7-8 by with 6% aqueous hydrochloric acid.

Then the mixture was concentrated under reduced pressure to remove methanol and lyophilized to give sodium 2-(5-(hydroxymethyl)pyrimidin-2-yl)-2-methylpropanoate (1.20 g, crude) as a white solid.

Step 5. To a mixture of sodium 2-(5-(hydroxymethyl) pyrimidin-2-yl)-2-methylpropanoate (404 mg, 1.85 mmol, 2.00 eq.) and 2-chloro-1-methyl-pyridin-1-ium;iodide (236 mg, 927 μmol, 1.00 eq.) in dimethyl formamide (5 mL) was added diisopropylethylamine (359 mg, 2.78 mmol, 3.00 eq.) dropwise at 25° C. The mixture was stirred at 25° C. for 0.5 h then 3-(4-(aminomethyl)-2,6-dichlorophenyl) piperidine-2,6-dione (300 mg, 927 μmol, 1.00 eq., hydrochloride) was added and the mixture was stirred at 25° C. for 1 h. The mixture was poured into water (30 mL). The mixture was extracted with ethyl acetate (3x30 mL). The combined organic layers were washed with brine (20 mL), dried over anhydrous sodium sulfate, filtered, and the filtrate was concentrated under reduced pressure. The residue was purified via Purification Method 2 to afford N-(3,5-dichloro-4-(2,6-dioxopiperidin-3-yl)benzyl)-2-(5-(hydroxymethyl)pyrimidin-2-yl)-2-methylpropanamide (127 mg, 271 μmol, 29% yield) as a white solid.

$^1$H NMR (400 MHZ, DMSO-$d_6$) δ=10.95 (s, 1H), 8.73 (s, 2H), 8.08 (t, J=6.0 Hz, 1H), 7.44 (s, 1H), 7.37 (s, 1H), 5.43 (t, J=5.6 Hz, 1H), 4.61-4.50 (m, 3H), 4.26 (d, J=6.0 Hz, 2H), 2.94-2.76 (m, 1H), 2.56 (br s, 1H), 2.36 (q, J=4.4, 13.2 Hz, 1H), 1.96-1.82 (m, 1H), 1.54 (s, 6H). MS (ESI) m/z 465.1 $[M+H]^+$

Exemplary Compound 233

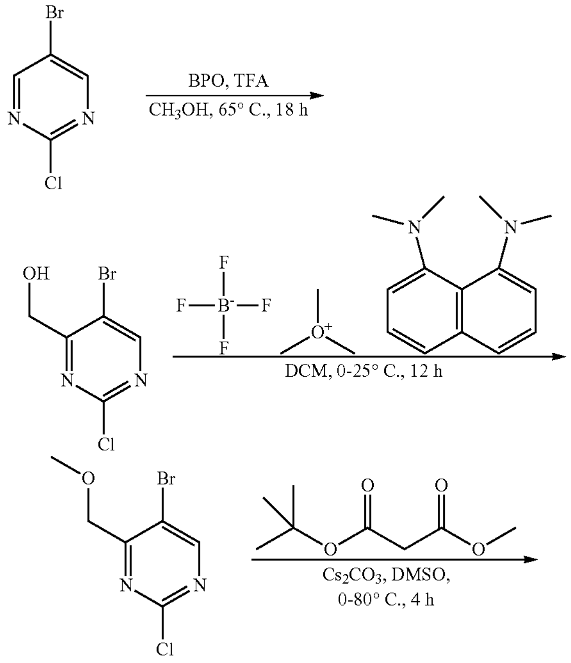

-continued

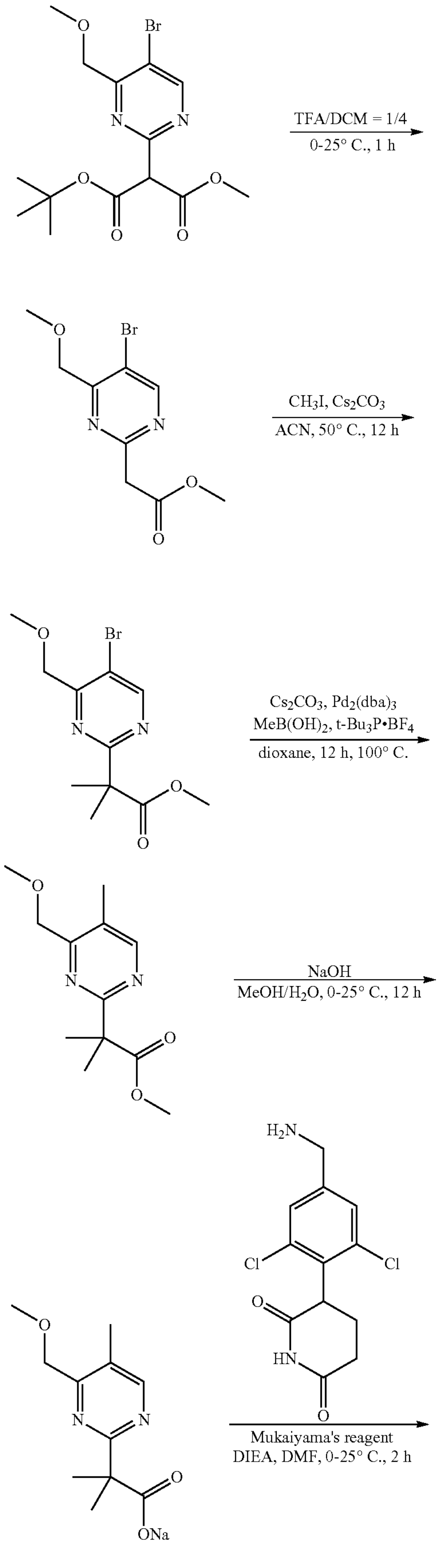

-continued

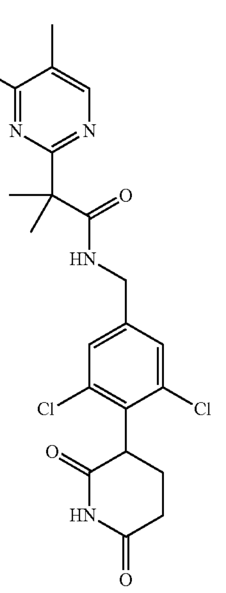

Step 1. To a solution of 5-bromo-2-chloro-pyrimidine (20.0 g, 103 mmol, 1.00 eq.) in methanol (200 mL) was added benzoic peroxyanhydride (30.0 g, 124 mmol, 1.20 eq.) and 2,2,2-trifluoroacetic acid (14.0 g, 123 mmol, 9.12 mL, 1.19 eq.) at 25° C. The mixture was stirred at 65° C. for 18 h. After cooling to room temperature, the reaction mixture was concentrated under reduced pressure to remove 2,2,2-trifluoroacetic acid and methanol. The residue was diluted with ethyl acetate (100 mL), and then saturated aqueous sodium bicarbonate solution (100 mL) was added to the mixture. The combined organic layers were separated, and the aqueous layer was extracted with ethyl acetate (3×100 mL). The combined organic layers were washed with brine (100 mL), dried over anhydrous sodium sulfate, filtered, and concentrated under reduced pressure. The residue was purified via Purification Method 2 to afford (5-bromo-2-chloropyrimidin-4-yl) methanol (5.00 g, 22.2 mmol, 21% yield) as a white solid.

Step 2. To a solution of (5-bromo-2-chloro-pyrimidin-4-yl) methanol (5.00 g, 22.2 mmol, 1.00 eq.) in dichloromethane (100 mL) was added trimethyloxonium tetrafluoroborate (4.91 g, 33.2 mmol, 1.50 eq.) and $N^1,N^1,N^8,N^8$-tetramethylnaphthalene-1,8-diamine (7.12 g, 33.2 mmol, 1.50 eq.) at 0° C. The mixture was stirred at 25° C. for 12 h. The reaction mixture was quenched with water (70 mL) at 0° C., and then extracted with dichloromethane (3×50 mL). The combined organic layers were washed with brine (50 mL), dried over anhydrous sodium sulfate, filtered, and concentrated under reduced pressure. The residue was purified via Purification Method 2 to afford 5-bromo-2-chloro-4-(methoxymethyl) pyrimidine (1.70 g, 7.09 mmol, 32% yield) as a light-yellow solid.

Step 3. A mixture of 5-bromo-2-chloro-4-(methoxymethyl)pyrimidine (1.70 g, 7.16 mmol, 1.00 eq.), tert-butyl methyl malonate (2.49 g, 14.3 mmol, 2.42 mL, 2.00 eq.) and caesium carbonate (5.83 g, 17.9 mmol, 2.50 eq.) in dimethyl sulfoxide (10 mL) was stirred at 80° C. for 4 h under nitrogen atmosphere. The reaction mixture was quenched with water (220 mL) and extracted with ethyl acetate (3×100 mL). The combined organic layers were washed with brine (50 mL), dried over anhydrous sodium sulfate, filtered, and concentrated under reduced pressure. The residue was purified via Purification Method 2 to afford 1-(tert-butyl) 3-methyl 2-(5-bromo-4-(methoxymethyl)pyrimidin-2-yl) malonate (1.48 g, 3.89 mmol, 54% yield) as a light-yellow oil.

Step 4. To a solution of 1-(tert-butyl) 3-methyl 2-(5-bromo-4-(methoxymethyl)pyrimidin-2-yl) malonate (1.45 g, 3.86 mmol, 1.00 eq.) in dichloromethane (8 mL) was added 2,2,2-trifluoroacetic acid (2 mL) at 0° C. The mixture was stirred at 25° C. for 1 h. The mixture was added dropwise to a saturated sodium bicarbonate solution (50 mL) at 0° C. The aqueous layer was extracted with dichloromethane (3x50 mL). The combined organic layers were washed with brine (30 mL), dried over anhydrous sodium sulfate, filtered, and concentrated under reduced. The residue was purified via Purification Method 2 to afford methyl 2-(5-bromo-4-(methoxymethyl)pyrimidin-2-yl)acetate (610 mg, 2.20 mmol, 57% yield) as a light-yellow oil.

Step 5. To a solution of methyl 2-(5-bromo-4-(methoxymethyl)pyrimidin-2-yl)acetate (650 mg, 2.36 mmol, 1.00 eq.) in acetonitrile (10 mL) was added caesium carbonate (2.31 g, 7.09 mmol, 3.00 eq.) and iodomethane (1.68 g, 11.8 mmol, 735 μL, 5.00 eq.) under nitrogen atmosphere. The mixture was stirred at 50° C. for 12 h. The mixture was cooled to room temperature, and then diluted with ethyl acetate (50 mL). The mixture was filtered, and the filtrate was concentrated under reduced pressure. The residue was purified via Purification Method 2 to afford methyl 2-(5-bromo-4-(methoxymethyl)pyrimidin-2-yl)-2-methylpropanoate (500 mg, 1.63 mmol, 69% yield) as a colourless oil.

Step 6. A mixture of methyl 2-(5-bromo-4-(methoxymethyl)pyrimidin-2-yl)-2-methylpropanoate (390 mg, 1.29 mmol, 1.00 eq.), methylboronic acid (385 mg, 6.43 mmol, 5.00 eq.), caesium carbonate (1.26 g, 3.86 mmol, 3.00 eq.), tri-tert-butylphosphonium tetrafluoroborate (74.7 mg, 257 μmol, 0.200 eq.) and tris(dibenzylideneacetone) dipalladium (118 mg, 129 μmol, 0.100 eq.) in dioxane (10 mL) stirred at 100° C. for 12 h under nitrogen atmosphere. The mixture was cooled to room temperature and then filtered through a plug of Celite. The filter cake was washed with ethyl acetate (60 mL). The filtrate was concentrated under reduced pressure to give a residue. The residue was purified via Purification Method 2 to afford methyl 2-(4-(methoxymethyl)-5-methylpyrimidin-2-yl)-2-methylpropanoate (277 mg, 1.15 mmol, 89% yield) as a colourless oil.

Step 7. To a solution of methyl 2-(4-(methoxymethyl)-5-methylpyrimidin-2-yl)-2-methylpropanoate (277 mg, 1.16 mmol, 1.00 eq.) in methanol (4 mL) and water (2 mL) was added sodium hydroxide (232 mg, 5.81 mmol, 5.00 eq.) at 0° C. The mixture was stirred at 25° C. for 12 h. The reaction mixture was diluted with water (20 mL) and the aqueous phase was adjusted to pH 7 by addition of 1M hydrochloric acid, followed by lyophilization to afford sodium 2-(4-(methoxymethyl)-5-methylpyrimidin-2-yl)-2-methylpropanoate (540 mg, crude) as a white solid.

Step 8. To a solution of sodium 2-(4-(methoxymethyl)-5-methylpyrimidin-2-yl)-2-methylpropanoate (250 mg, 538 μmol, 1.00 eq.) in dimethyl formamide (2 mL) was added N-ethyl-N-isopropylpropan-2-amine (278 mg, 2.15 mmol, 375 μL, 4.00 eq.) and 2-chloro-1-methyl-pyridin-1-ium iodide (165 mg, 646 μmol, 1.20 eq.) at 0° C. The mixture was stirred at 25° C. for 1 h. Then 3-(4-(aminomethyl)-2,6-dichlorophenyl) piperidine-2,6-dione hydrochloride (87.1 mg, 269 μmol, 0.500 eq.) was added to the mixture. The mixture was stirred at 25° C. for 1 h. The reaction was quenched with water (22 mL) at 0° C., and then extracted with ethyl acetate (3x20 mL). The combined organic layers were washed with brine (10 mL), dried over sodium sulfate, filtered, and concentrated under reduced pressure. The residue was purified via Purification Method 2 to afford N-(3,5-dichloro-4-(2,6-dioxopiperidin-3-yl)benzyl)-2-(4-(methoxymethyl)-5-methylpyrimidin-2-yl)-2-methylpropanamide (69.7 mg, 140 μmol, 26% yield) as a white solid.

$^1$H NMR (400 MHz, DMSO-$d_6$) δ=10.94 (s, 1H), 8.57 (s, 1H), 8.00 (t, J=6.0 Hz, 1H), 7.37 (s, 1H), 7.30 (s, 1H), 4.56 (dd, J=5.6, 12.4 Hz, 1H), 4.51 (s, 2H), 4.24 (d, J=6.0 Hz, 2H), 3.31-3.31 (m, 3H), 2.90-2.80 (m, 1H), 2.61-2.52 (m, 1H), 2.40-2.30 (m, 1H), 2.28 (s, 3H), 1.94-1.84 (m, 1H), 1.53 (s, 6H). MS (ESI) m/z 493.2 [M+H]$^+$

Exemplary Compound 234

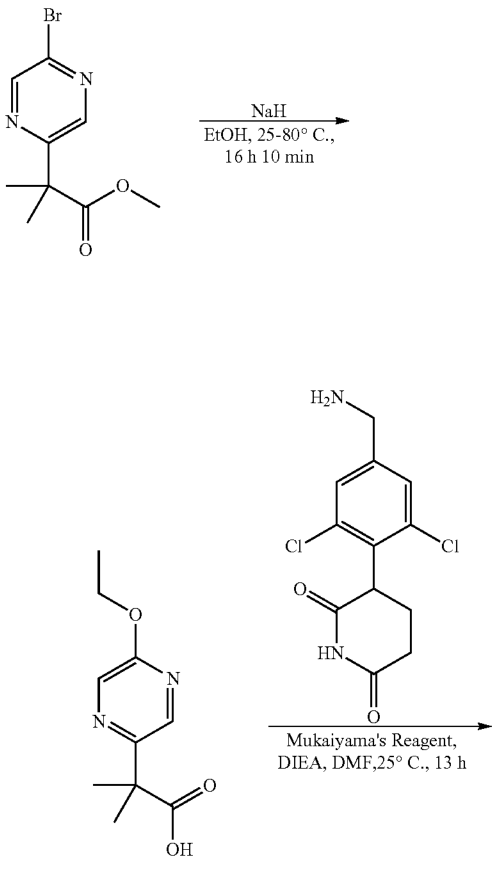

-continued

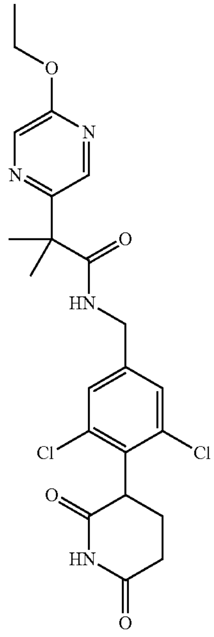

Step 1. Sodium hydride (390 mg, 9.75 mmol, 60% purity, 5.00 eq.) was added to ethyl alcohol (4 mL) at 0° C. under nitrogen atmosphere. It was stirred at 25° C. for 10 min. When the solution clears, a solution of methyl 2-(5-bromopyrazin-2-yl)-2-methylpropanoate (500 mg, 1.93 mmol, 1.00 eq.) in ethyl alcohol (30 mL) was added to the mixture. It was stirred at 80° C. for 16 h under nitrogen atmosphere. The reaction mixture was concentrated in vacuo. The residue was poured into water (30 mL) and washed with dichloromethane (30 mL). The pH of the aqueous phase was adjusted to 3 using 1 N hydrochloric acid. The aqueous phase was extracted with dichloromethane (2×30 mL). Combined extracts were washed with brine (20 mL), dried over anhydrous sodium sulfate, filtered, and concentrated to give 2-(5-ethoxypyrazin-2-yl)-2-methylpropanoic acid (380 mg, 1.45 mmol, 75% yield, 80% purity) as a brown solid.

Step 2. To a solution of 2-(5-ethoxypyrazin-2-yl)-2-methylpropanoic acid (100 mg, 475 μmol, 1.00 eq.) in N,N-dimethylformamide (3 mL) were added N,N-diisopropylethylamine (2.40 mmol, 420 μL, 500 eq.) and 2-chloro-1-methyl-pyridinium iodide (145 mg, 570 μmol, 1.20 eq.). It was stirred at 25° C. for 1 h. Then 3-(4-(aminomethyl)-2,6-dichlorophenyl) piperidine-2,6-dione hydrochloride (92.0 mg, 285 μmol, 0.60 eq.,) was added to the mixture. It was stirred at 25° C. for 12 h. The mixture was diluted with ethyl acetate (15 mL) and water (15 mL). The layers were separated, and the aqueous phase was extracted with ethyl acetate (2×15 mL). The combined organic layers were washed with brine (15 mL), dried over anhydrous sodium sulfate, filtered, and concentrated in vacuo. The residue was purified via Purification Method 1 to afford N-(3,5-dichloro-4-(2,6-dioxopiperidin-3-yl)benzyl)-2-(5-ethoxypyrazin-2-yl)-2-methylpropanamide (55.06 mg, 115 μmol, 24% yield) as an off-white solid.

$^1$H NMR (400 MHZ, DMSO-$d_6$) δ=10.95 (s, 1H), 8.22 (dd, J=1.2, 4.8 Hz, 2H), 7.99 (t, J=6.0 Hz, 1H), 7.26 (s, 1H), 7.20 (d, J=1.2 Hz, 1H), 4.55 (dd, J=5.6, 12.8 Hz, 1H), 4.34 (q, J=7.2 Hz, 2H), 4.21 (d, J=5.8 Hz, 2H), 2.85 (ddd, J=5.6, 14.0, 16.8 Hz, 1H), 2.55 (m, 1H), 2.34 (dq, J=4.4, 13.2 Hz, 1H), 1.93-1.83 (m, 1H), 1.53 (s, 6H), 1.34 (t, J=7.2 Hz, 3H). MS (ESI) m/z 479.1 $[M+H]^+$ Exemplary Compound 235

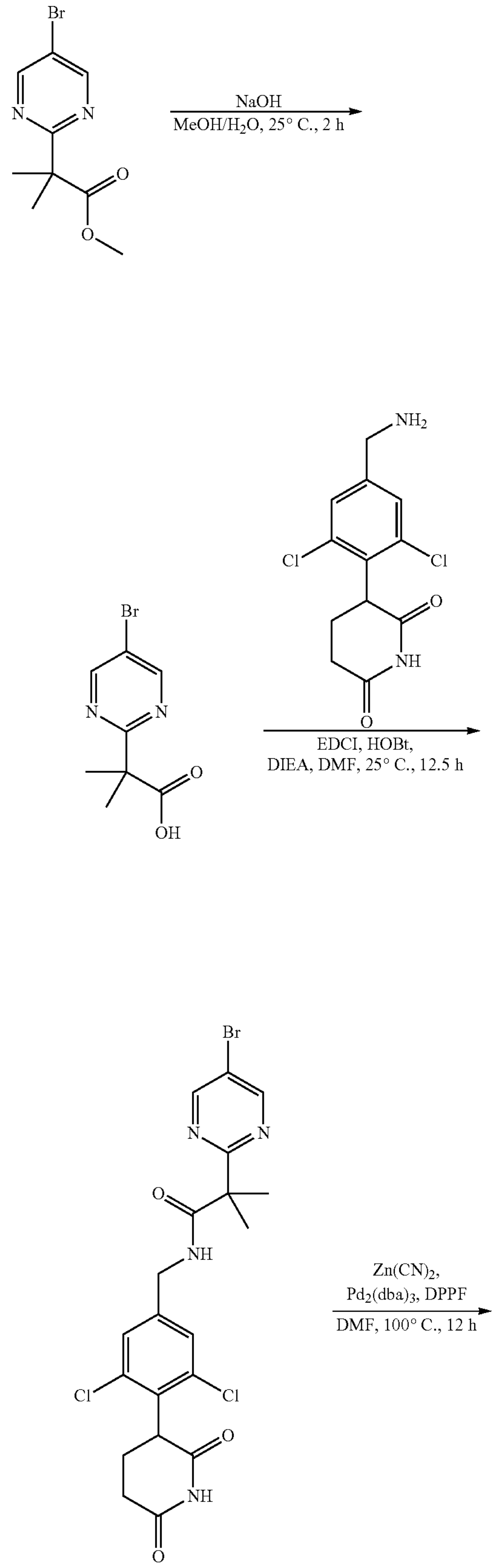

-continued

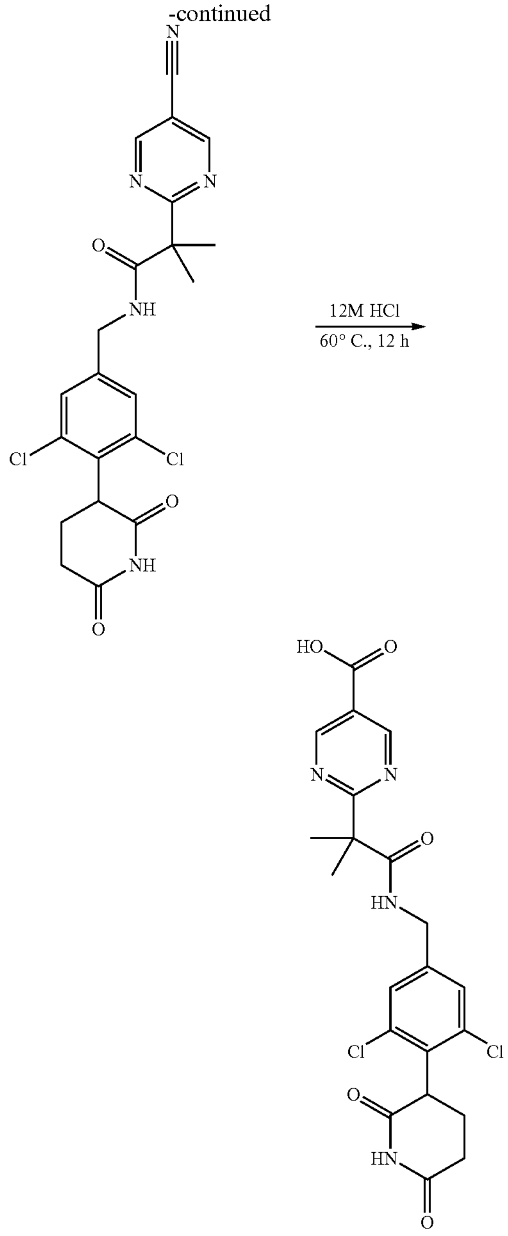

Step 1. To a mixture of methyl 2-(5-bromopyrimidin-2-yl)-2-methylpropanoate (15.0 g, 57.8 mmol, 1.00 eq.) in methanol (50 mL) and water (50 mL) was added sodium hydroxide (11.5 g, 289 mmol, 5.00 eq.) in portions at 25° C. The mixture was stirred at 25° C. for 2 h. The mixture was adjusted to pH 2 with 36% aqueous hydrochloric acid, and then extracted with dichloromethane (3×80 mL). The combined organic extracts were washed with brine (50 mL), dried over anhydrous sodium sulfate, filtered, and concentrated under reduced pressure to give 2-(5-bromopyrimidin-2-yl)-2-methylpropanoic acid (13.4 g, 53.0 mmol, 91% yield) as a white solid.

Step 2. To a mixture of 2-(5-bromopyrimidin-2-yl)-2-methylpropanoic acid (13.4 g, 54.6 mmol, 1.10 eq.), 1H-benzo[d][1,2,3]triazol-1-ol (8.06 g, 59.6 mmol, 1.20 eq.) and $N^1$-((ethylimino)methylene)-$N^3$,$N^3$-dimethylpropane-1,3-diamine hydrochloride (11.4 g, 59.6 mmol, 1.20 eq.) in dimethyl formamide (130 mL) was added diisopropylethylamine (19.2 g, 149 mmol, 3.00 eq.) dropwise at 25° C. The mixture was stirred at 25° C. for 0.5 h, and then 3-(4-(aminomethyl)-2,6-dichlorophenyl) piperidine-2,6-dione (16.0 g, 49.7 mmol, 1.00 eq., hydrochloride) was added. The mixture was stirred at 25° C. for 12 h. The mixture was poured into water (200 mL) and filtered. The filter cake was triturated with water (150 mL), and then filtered, the filter cake was collected and dried under reduced pressure to give 2-(5-bromopyrimidin-2-yl)-N-(3,5-dichloro-4-(2,6-dioxopiperidin-3-yl)benzyl)-2-methylpropanamide (22.1 g, 41.6 mmol, 83% yield) as a white solid.

Step 3. To a mixture of 2-(5-bromopyrimidin-2-yl)-N-(3,5-dichloro-4-(2,6-dioxopiperidin-3-yl)benzyl)-2-methylpropanamide (15.0 g, 29.1 mmol, 1.00 eq.), tris(dibenzylideneacetone) dipalladium (0) (2.67 g, 2.92 mmol, 0.10 eq.) and 1,1'-bis(diphenylphosphino)ferrocene (1.62 g, 2.92 mmol, 0.10 eq.) in dimethyl formamide (120 mL) was added zinc cyanide (4.90 g, 41.7 mmol, 1.43 eq.) in portions at 25° C. The mixture was stirred at 100° C. under nitrogen atmosphere for 12 h. The mixture was cooled to 25° C., and then diluted with ethyl acetate (100 mL) and filtered. The filtrate was quenched with water (150 mL) and extracted with ethyl acetate (3×100 mL). The combined organic layers were washed with brine (200 mL), dried over anhydrous sodium sulfate, filtered, and the filtrate was concentrated under reduced pressure. The residue was purified via Purification Method 2 to afford a crude product. The crude product was dissolved in ethyl acetate (100 mL). After that petroleum ether (100 mL) was added dropwise to the solution, a large amount of white solid separated out. The mixture was filtered, the filter cake was collected and dried under reduced pressure to give 2-(5-cyanopyrimidin-2-yl)-N-(3,5-dichloro-4-(2,6-dioxopiperidin-3-yl)benzyl)-2-methylpropanamide (12.5 g, 27.0 mmol, 92% yield) as a white solid.

Step 4. A solution of 2-(5-cyanopyrimidin-2-yl)-N-(3,5-dichloro-4-(2,6-dioxopiperidin-3-yl)benzyl)-2-methylpropanamide (140 mg, 304 μmol, 1.00 eq.) in hydrochloric acid (12 M, 5 mL) was stirred at 60° C. for 12 h. The mixture was cooled to 25° C. then poured into water (20 mL). The mixture was extracted with dichloromethane (3×20 mL). The combined organic layers were washed with brine (10 mL), dried over anhydrous sodium sulfate, filtered, and the filtrate was concentrated under reduced pressure. The residue was purified via Purification Method I to afford 2-(1-((3,5-dichloro-4-(2,6-dioxopiperidin-3-yl)benzyl)amino)-2-methyl-1-oxopropan-2-yl)pyrimidine-5-carboxylic acid (42.4 mg, 87.7 μmol, 28% yield) as a white solid.

$^1$H NMR (400 MHZ, DMSO-$d_6$) δ=10.95 (s, 1H), 9.21 (s, 2H), 8.09 (t, J=6.0 Hz, 1H), 7.39 (s, 1H), 7.32 (s, 1H), 4.56 (dd, J=5.6, 12.8 Hz, 1H), 4.26 (d, J=5.6 Hz, 2H), 2.85 (d, J=5.6, 14.4, 16.8 Hz, 1H), 2.56 (br s, 1H), 2.36 (q, J=4.4, 13.2 Hz, 1H), 1.96-1.81 (m, 1H), 1.58 (s, 6H). MS (ESI) m/z 479.1 [M+H]$^+$

Exemplary Compound 238

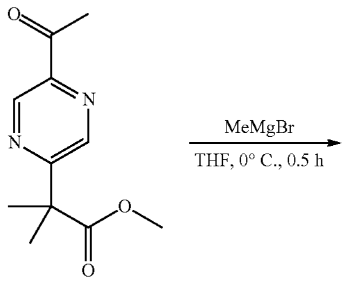

-continued

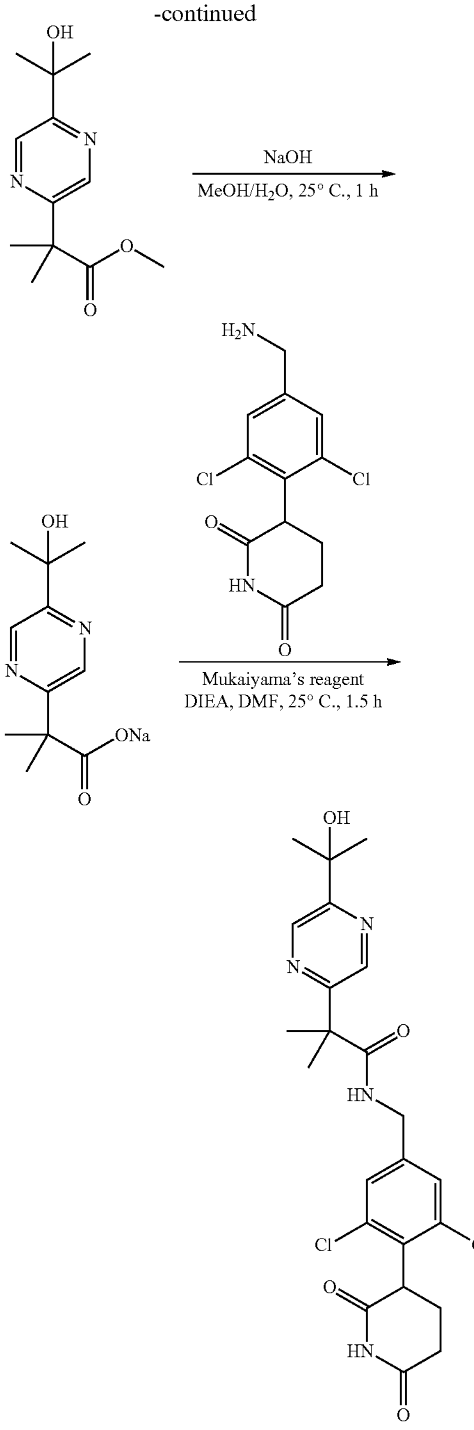

Step 1. To a solution of methyl 2-(5-acetylpyrazin-2-yl)-2-methylpropanoate (500 mg, 2.25 mmol, 1.00 eq.) in tetrahydrofuran (25 mL) was added methylmagnesium bromide (3 M in tetrahydrofuran, 900 μL, 1.20 eq.) dropwise at 0° C. The solution was stirred at 0° C. under nitrogen atmosphere for 0.5 h. The mixture was poured into saturated aqueous ammonium chloride (30 mL) and extracted with ethyl acetate (3×30 mL). The combined organic layers were washed with brine (30 mL), dried over anhydrous sodium sulfate, filtered, and the filtrate was concentrated under reduced pressure. The residue was purified via Purification Method 2 to afford methyl 2-(5-(2-hydroxypropan-2-yl) pyrazin-2-yl)-2-methylpropanoate (400 mg, 1.24 mmol, 55% yield) as a light-yellow oil.

Step 2. To a solution of methyl 2-(5-(2-hydroxypropan-2-yl) pyrazin-2-yl)-2-methylpropanoate (460 mg, 1.93 mmol, 1.00 eq.) in methanol (4 mL) and water (4 mL) was added sodium hydroxide (386 mg, 9.65 mmol, 5.00 eq.) in portions at 25° C. The solution was stirred at 25° C. for 1 h. The mixture was poured into water (10 mL) and adjusted to pH 7-8 with 2N hydrochloric acid. The mixture was extracted with ethyl acetate (2× 10 mL). The aqueous layer was collected and lyophilized to give sodium 2-(5-(2-hydroxypropan-2-yl) pyrazin-2-yl)-2-methylpropanoate (800 mg, 1.62 mmol, 84% yield, 50% purity) as a red solid.

Step 3. To a mixture of sodium 2-(5-(2-hydroxypropan-2-yl) pyrazin-2-yl)-2-methylpropanoate (250 mg, 508 μmol, 1.00 eq.) and 2-chloro-1-methyl-pyridin-1-ium;iodide (143 mg, 558 μmol, 1.10 eq.) in dimethyl formamide (3 mL) was added diisopropylethylamine (262 mg, 2.03 mmol, 4.00 eq.) dropwise at 25° C. The mixture was stirred at 25° C. for 0.5 h then 3-(4-(aminomethyl)-2,6-dichlorophenyl) piperidine-2,6-dione (115 mg, 355 μmol, 0.70 eq., hydrochloride) was added. The mixture was stirred at 25° C. for 1 h. The mixture was poured into water (20 mL) and extracted with ethyl acetate (3×20 mL). The combined organic layers were washed with brine (30 mL), dried over anhydrous sodium sulfate, filtered, and the filtrate was concentrated under reduced pressure. The residue was purified via Purification Method 1 to afford N-(3,5-dichloro-4-(2,6-dioxopiperidin-3-yl)benzyl)-2-(5-(2-hydroxypropan-2-yl) pyrazin-2-yl)-2-methylpropanamide (159 mg, 318 μmol, 62% yield) as a white solid.

$^1H$ NMR (400 MHZ, DMSO-$d_6$) δ=10.96 (s, 1H), 8.87 (d, J=1.6 Hz, 1H), 8.59 (d, J=1.6 Hz, 1H), 8.17 (t, J=6.0 Hz, 1H), 7.33 (d, J=1.2 Hz, 1H), 7.26 (d, J=1.2 Hz, 1H), 5.43 (s, 1H), 4.56 (dd, J=5.6, 12.8 Hz, 1H), 4.25 (d, J=6.0 Hz, 2H), 2.92-2.79 (m, 1H), 2.57-2.54 (m, 1H), 2.38-2.30 (m, 1H), 1.94-1.82 (m, 1H), 1.56 (s, 6H), 1.46 (s, 6H). MS (ESI) m/z 493.2 $[M+H]^+$

Exemplary Compound 239

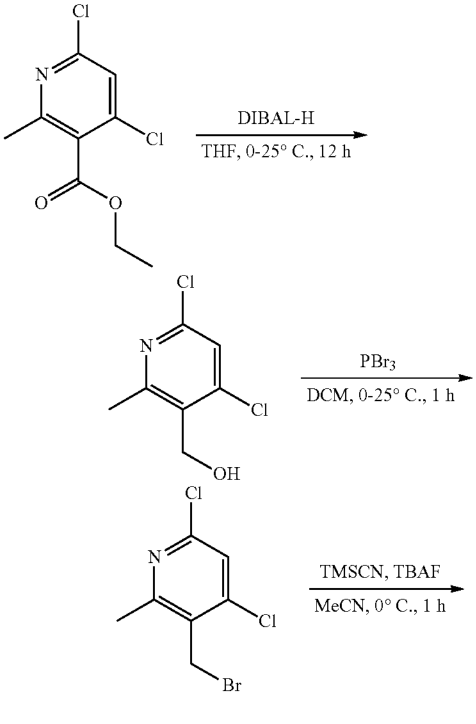

-continued

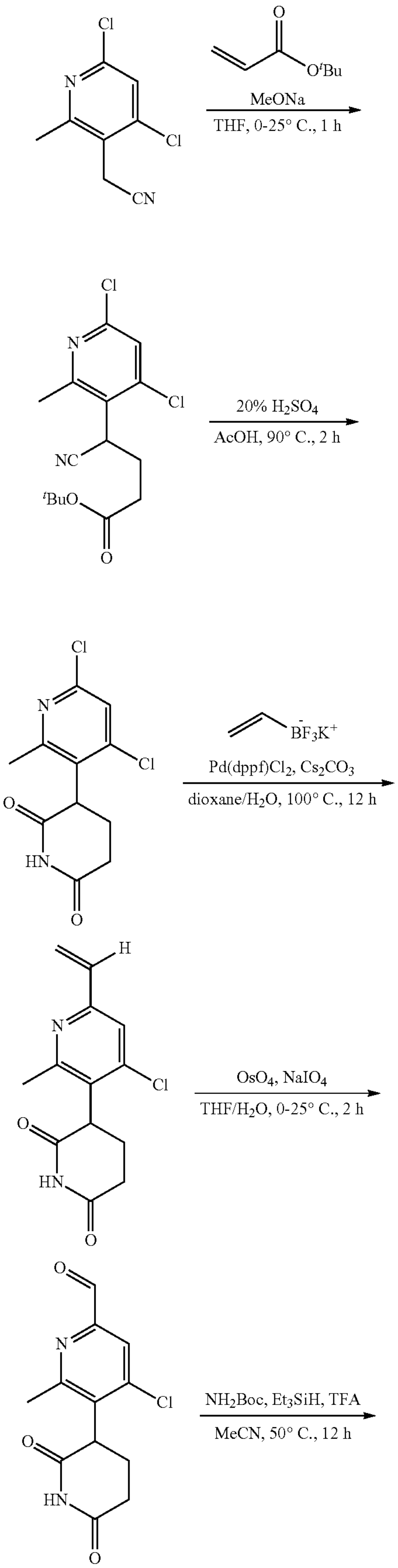

-continued

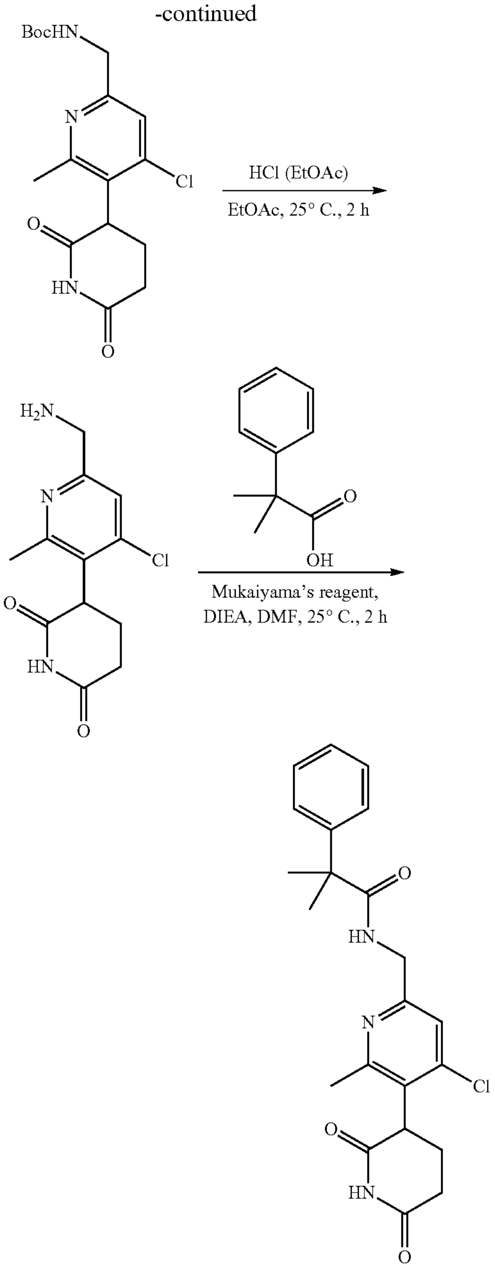

Step 1: To a solution of ethyl 4,6-dichloro-2-methylnicotinate (7.20 g, 30.8 mmol, 1.00 eq.) in THF (50 mL) was added DIBAL-H (1 M, 68.0 mL, 2.21 eq.) at 0° C. over 30 min under nitrogen.

The reaction was stirred at 25° C. for 12 h. The reaction was quenched by transferring into 1M hydrochloric acid (60 mL) at 0° C. The mixture was diluted with ethyl acetate (80 mL) and water (20 mL). The layers were separated, and the aqueous layer was extracted with ethyl acetate (2×70 mL). The combined organic layers were washed with brine (100 mL), dried over anhydrous sodium sulfate, filtered, and concentrated under reduced pressure to give a residue. The residue was purified via Purification Method 2 to afford (4,6-dichloro-2-methylpyridin-3-yl) methanol (5.70 g, 29.4 mmol, 96% yield) as a colourless oil.

Step 2: To a solution of (4,6-dichloro-2-methylpyridin-3-yl) methanol (5.70 g, 29.7 mmol, 1.00 eq.) in DCM (50 mL)

was added PBr3 (20.0 g, 73.9 mmol, 2.49 eq.) at 0° C. under nitrogen. The reaction was stirred at 25° C. for 1 h, then it was quenched by transferring the mixture into water (100 mL). The aqueous layer was extracted with dichloromethane (2×50 mL). The combined organic layers were washed with brine (60 mL), dried over anhydrous sodium sulfate, filtered, and concentrated under reduced pressure to afford 3-(bromomethyl)-4,6-dichloro-2-methylpyridine (7 g, crude) as a colourless oil.

Step 3: To a solution of 3-(bromomethyl)-4,6-dichloro-2-methylpyridine (7.00 g, 27.5 mmol, 1.00 eq.) and TMSCN (5.25 mL, 42.0 mmol, 1.53 eq.) in MeCN(50 mL) was added TBAF (1 M in THF, 41.3 mL, 1.50 eq.) at 0° C. under nitrogen. The reaction was stirred at 0° C. for 1 h, then it was diluted with ethyl acetate (50 mL) and water (40 mL). The layers were separated, and the aqueous layer was extracted with ethyl acetate (40 mL). The combined organic layers were washed with brine (40 mL), dried over anhydrous sodium sulfate, filtered, and concentrated under reduced pressure to give a residue. The residue was purified via Purification Method 2 to afford 2-(4,6-dichloro-2-methylpyridin-3-yl) acetonitrile (5.10 g, 24.9 mmol, 91% yield) as a yellow solid.

Step 4: To a solution of 2-(4,6-dichloro-2-methyl-3-pyridyl) acetonitrile (3.00 g, 14.9 mmol, 1.00 eq.) in THF (30 mL) were added tert-butyl acrylate (1.91 g, 14.9 mmol, 1.00 eq.) and sodium methylate (80.0 mg, 1.48 mmol, 0.10 eq.) at 0° C. under nitrogen. The reaction was stirred at 25° C. for 1 h. The mixture was diluted with ethyl acetate (40 mL) and water (30 mL). The layers were separated, and the aqueous layer was extracted with ethyl acetate (30 mL). The combined organic layers were washed with brine (40 mL), dried over anhydrous sodium sulfate, filtered, and concentrated under reduced pressure to afford tert-butyl 4-cyano-4-(4,6-dichloro-2-methylpyridin-3-yl) butanoate (3.78 g, 11.3 mmol, 75% yield) as a yellow solid.

Step 5: A mixture of tert-butyl 4-cyano-4-(4,6-dichloro-2-methylpyridin-3-yl) butanoate (5.70 g, 17.3 mmol, 1.00 eq.) in sulfuric acid (10 mL) and acetic acid (50 mL) was stirred at 90° C. for 2 h.

The reaction mixture was quenched by pouring the mixture into ice water. The mixture was diluted with dichloromethane (80 mL) and water (30 mL). The layers were separated, and the aqueous layer was extracted with dichloromethane (2×40 mL). The combined organic layers were washed with brine (80 mL), dried over anhydrous sodium sulfate, filtered, and concentrated under reduced pressure to afford 3-(4,6-dichloro-2-methylpyridin-3-yl) piperidine-2,6-dione (2.80 g, 10.2 mmol, 59% yield) as a white solid.

Step 6: To a solution of 3-(4,6-dichloro-2-methyl-3-pyridyl) piperidine-2,6-dione (3.63 g, 13.29 mmol, 1.00 eq.) and potassium trifluoro (vinyl) borate (1.96 g, 14.6 mmol, 1.10 eq.) in dioxane (30 mL) and water (3 mL) were added Pd(dppf) $Cl_2$ (944 mg, 1.29 mmol, 0.10 eq.) and caesium carbonate (8.71 g, 26.7 mmol, 2.01 eq.) under nitrogen. The reaction was stirred at 100° C. for 12 h. The mixture was filtered over a pad of celite, and the filtrate was diluted with ethyl acetate (50 mL) and water (50 mL). The layers were separated, and the aqueous layer was extracted with ethyl acetate (2×30 mL). The combined organic layers were washed with brine (50 mL) and dried over anhydrous sodium sulfate, filtered, and concentrated under reduced pressure to give a residue. The residue was purified via Purification Method 2 to afford 3-(4-chloro-2-methyl-6-vinylpyridin-3-yl) piperidine-2,6-dione (1.40 g, 4.76 mmol, 36% yield) as a white solid.

Step 7: To a solution of 3-(4-chloro-2-methyl-6-vinylpyridin-3-yl) piperidine-2,6-dione (1.30 g, 4.91 mmol, 1.00 eq.) in THF (15 mL) was added osmium tetroxide (200 mg, 787 μmol, 0.16 eq.) in THF (4 mL) at 0° C. under nitrogen. Then a solution of sodium periodate (2.60 g, 12.2 mmol, 2.48 eq.) in water (20 mL) was added dropwise over 30 min at 0° C. The reaction was stirred at 25° C. for 2 h. The mixture was diluted with ethyl acetate (25 mL) and water (25 mL). The layers were separated, and the aqueous layer was extracted with ethyl acetate (20 mL). The combined organic layers were washed with brine (25 mL) and dried over anhydrous sodium sulfate, filtered, and concentrated under reduced pressure to give a residue. The residue was purified via Purification Method 2 to afford 4-chloro-5-(2,6-dioxopiperidin-3-yl)-6-methylpicolinaldehyde (640 mg, 2.23 mmol, 45% yield) as an off-white solid.

Step 8: To a solution of 4-chloro-5-(2,6-dioxopiperidin-3-yl)-6-methylpicolinaldehyde (590 mg, 2.21 mmol, 1.00 eq.) and tert-butyl carbamate (780 mg, 6.66 mmol, 3.01 eq.) in acetonitrile (10 mL) were added triethylsilane (772 mg, 6.64 mmol, 3.00 eq.) and trifluoroacetic acid (300 μL, 4.04 mmol, 1.83 eq.). The reaction was stirred at 25° C. for 12 h under nitrogen. The mixture was adjusted to pH 8 with $NaHCO_3$sat. sol., then it was diluted with ethyl acetate (10 mL) and water (10 mL). The layers were separated, and the aqueous layer was extracted with ethyl acetate (2×10 mL). The combined organic layers were washed with brine (15 mL) and dried over anhydrous sodium sulfate, filtered, and concentrated under reduced pressure to give a residue. The residue was purified via Purification Method 2 to afford tert-butyl ((4-chloro-5-(2,6-dioxopiperidin-3-yl)-6-methylpyridin-2-yl)methyl) carbamate (200 mg, 506 μmol, 23% yield) as a colourless oil.

Step 9: A mixture of tert-butyl ((4-chloro-5-(2,6-dioxopiperidin-3-yl)-6-methylpyridin-2-yl)methyl) carbamate (200 mg, 544 μmol, 1.00 eq.) in ethyl acetate (5 mL) and hydrogen chloride in ethyl acetate (2 M, 10 mL) was stirred at 25° C. for 2 h. The mixture was concentrated under reduced pressure to afford 3-(6-(aminomethyl)-4-chloro-2-methylpyridin-3-yl) piperidine-2,6-dione hydrochloride (150 mg, 468 μmol, 86% yield) as a yellow solid.

$^1$H NMR (400 MHZ, DMSO-$d_6$) δ=11.00 (s, 1H), 8.49 (br d, J=12.0 Hz, 3H), 7.56 (s, 1H), 4.70-4.46 (m, 1H), 4.15-4.11 (m, 2H), 2.97-2.80 (m, 1H), 2.65 (s, 3H), 2.38 (s, 2H), 2.06-1.96 (m, 1H). MS (ESI) m/z 268.0 $[M+H]^+$

Step 10: To a solution of 2-methyl-2-phenylpropanoic acid (150 mg, 914 μmol, 1.50 eq.) and N,N-diisopropylethylamine (236 mg, 1.83 mmol, 3.00 eq.) in dimethylformamide (5 mL) was added 2-chloro-1-methyl-pyridin-1-ium iodide (165 mg, 646 μmol, 1.06 eq.) at 0° C. The reaction was stirred at 25° C. for 0.5 h. Then 3-(6-(aminomethyl)-4-chloro-2-methylpyridin-3-yl) piperidine-2,6-dione hydrochloride (150 mg, 493 μmol, 0.81 eq.) was added to the mixture. The reaction was stirred at 25° C. for 1.5 h. The reaction mixture was diluted with ethyl acetate (15 mL) and water (10 mL). The layers were separated, and the aqueous phase was extracted with ethyl acetate (2×10 mL). The combined organic layers were washed with brine (20 mL) and dried over anhydrous sodium sulfate, filtered, and concentrated in vacuo. The residue was triturated with dimethylformamide (1.5 mL) and acetonitrile (3 mL) at 25° C. for 10 min. The mixture was filtered, and the filter cake was dried under vacuum. It was purified via Purification Method I to afford N-((4-chloro-5-(2,6-dioxopiperidin-3-yl)-6-methylpyridin-2-yl)methyl)-2-methyl-2-phenylpropanamide (54.94 mg, 131 μmol, 22% yield) as a white solid.

$^{1}$H NMR (400 MHZ, DMSO-$d_6$) δ=10.94 (s, 1H), 8.03 (br d, J=5.6 Hz, 1H), 7.45-7.31 (m, 4H), 7.30-7.20 (m, 1H), 6.81 (s, 1H), 4.61-4.28 (m, 1H), 4.28-4.17 (m, 2H), 2.89-2.75 (m, 1H), 2.55 (s, 4H), 2.28 (s, 1H), 1.99-1.82 (m, 1H), 1.51 (s, 6H). MS (ESI) m/z 414.3/436.3 [M+H/M+Na]$^+$
Exemplary Compound 240
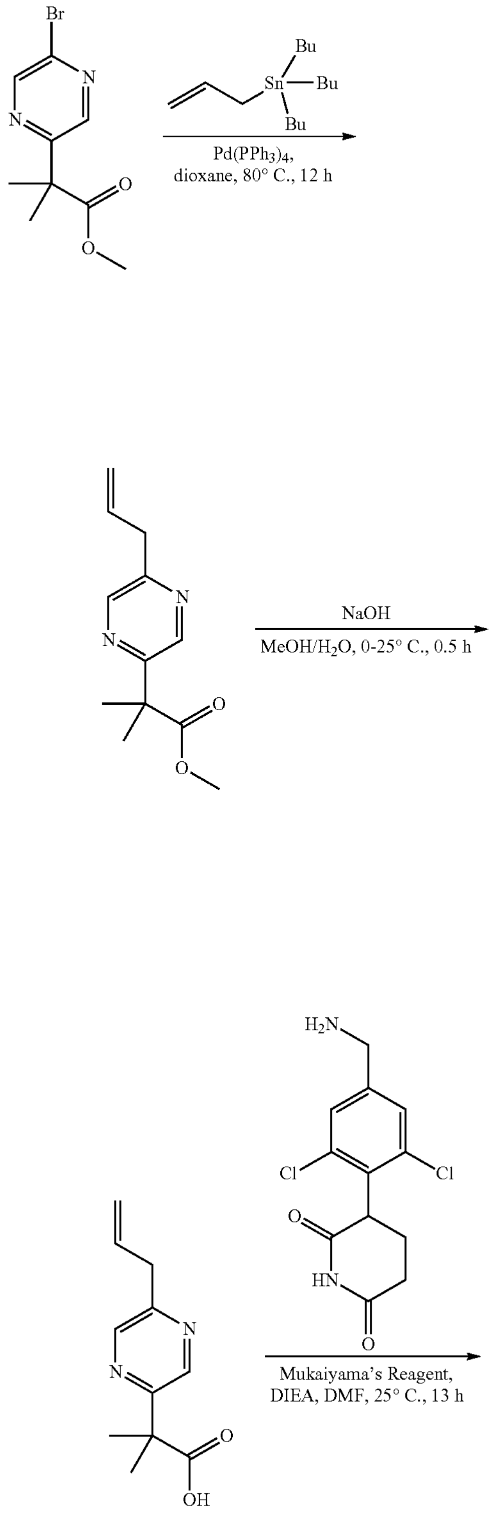
-continued
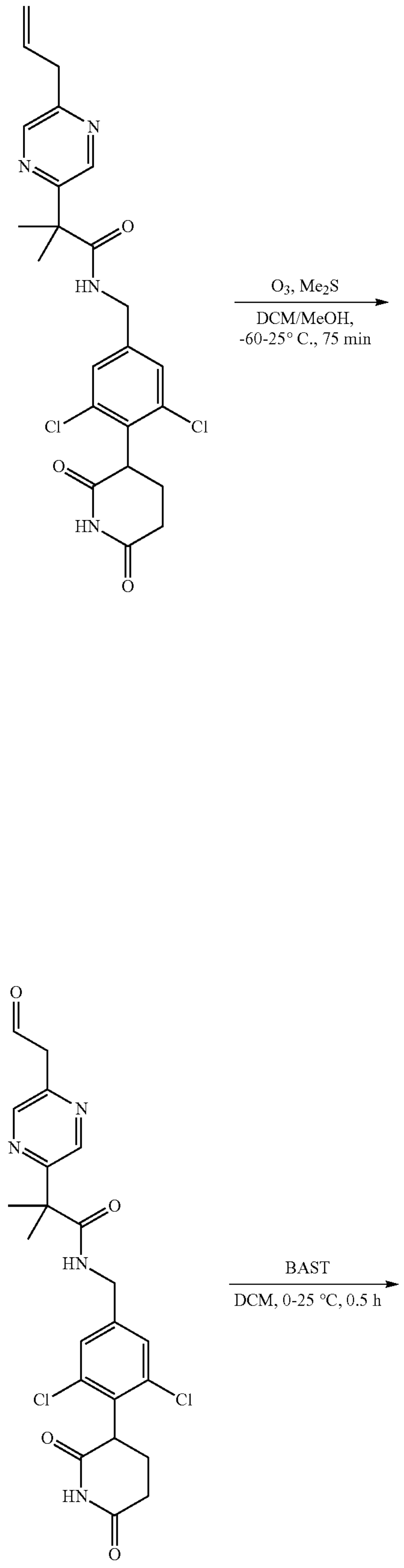

-continued

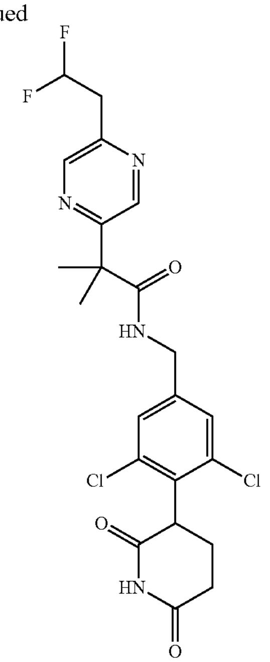

Step 1. To a solution of methyl 2-(5-bromopyrazin-2-yl)-2-methylpropanoate (2.00 g, 7.72 mmol, 1.00 eq.) in dioxane (35 mL) was added allyltributylstannane (9.57 mmol, 2.94 mL, 1.24 eq.) and tetrakis (triphenylphosphine) palladium (0) (445 mg, 385 μmol, 0.05 eq.) under nitrogen atmosphere. The reaction was stirred at 80° C. for 12 h under nitrogen atmosphere. The mixture was cooled to room temperature. The mixture was poured into potassium fluoride solution (50 mL) and diluted with water (30 mL) and extracted with ethyl acetate (2×50 mL). The combined organic layers were dried over anhydrous sodium sulfate, filtered, and concentrated under reduced pressure. The residue was purified via Purification Method 2 to afford methyl 2-(5-allylpyrazin-2-yl)-2-methylpropanoate (1.35 g, 5.95 mmol, 77% yield) as a yellow oil.

Step 2. To a solution of methyl 2-(5-allylpyrazin-2-yl)-2-methylpropanoate (1.38 g, 6.27 mmol, 1.00 eq.) in methanol (10 mL) and water (10 mL) was added sodium hydroxide (751 mg, 18.8 mmol, 3.00 eq.) at 0° C. The reaction was stirred at 25° C. for 0.5 h. The pH of the mixture was adjusted to 2 with hydrochloric acid (2M) at 0° C. The mixture was added water (15 mL) and ethyl acetate (20 mL). The layers were separated. Then the organic phase was washed with brine (10 mL), dried over sodium sulfate, filtered, and concentrated under vacuum. Then it was via Purification Method 1 to afford 2-(5-allylpyrazin-2-yl)-2-methylpropanoic acid (0.86 g, 4.00 mmol, 63% yield) as a yellow oil.

Step 3. To a solution of 2-(5-allylpyrazin-2-yl)-2-methylpropanoic acid (860 mg, 4.17 mmol, 1.00 eq.) in N,N-dimethylformamide (5 mL) were added N,N-diisopropylethylamine (12.5 mmol, 2.18 mL, 3.00 eq.) and 2-chloro-1-methyl-pyridin-1-ium iodide (1.28 g, 5.00 mmol, 1.20 eq.). The reaction was stirred at 25° C. for 1 h. Then 3-(4-(aminomethyl)-2,6-dichlorophenyl) piperidine-2,6-dione hydrochloride (1.08 g, 3.34 mmol, 0.80 eq.) was added and stirred at 25° C. for 12 h. The mixture was added water (20 mL) and ethyl acetate (30 mL). The layers were separated. Then the organic phase was washed with water (2×20 mL), dried over sodium sulfate, filtered, and concentrated under vacuum. The crude product was triturated with ethyl acetate:petroleum ether =1:1 at 25° C. for 5 min. The solid was filtered and washed with petroleum and concentrated under vacuum to give 2-(5-allylpyrazin-2-yl)-N-(3,5-dichloro-4-(2,6-dioxopiperidin-3-yl)benzyl)-2-methylpropanamide (0.98 g, 2.04 mmol, 49% yield) as a yellow solid.

Step 4. Ozone was bubbled into a solution of 2-(5-allylpyrazin-2-yl)-N-(3,5-dichloro-4-(2,6-dioxopiperidin-3-yl)benzyl)-2-methylpropanamide (380 mg, 799 μmol, 1.00 eq.) in dichloromethane (30 mL) and methanol (6 mL) at −60° C. for 15 minutes. After the excess ozone was purged by nitrogen, dimethylsulfane (2.89 g, 46.5 mmol, 58.2 eq.) was added at −60° C., and stirred at 25° C. for 1 h. The mixture was concentrated under vacuum to give N-(3,5-dichloro-4-(2,6-dioxopiperidin-3-yl)benzyl)-2-methyl-2-(5-(2-oxoethyl) pyrazin-2-yl) propanamide (500 mg, 523 μmol, 65% yield, 50% purity) as a yellow solid.

Step 5. To a solution of N-(3,5-dichloro-4-(2,6-dioxopiperidin-3-yl)benzyl)-2-methyl-2-(5-(2-oxoethyl) pyrazin-2-yl) propanamide (500 mg, 837 μmol 1.00 eq.) in dichloromethane (16 mL) was added bis(2-methoxyethyl) aminosulfur trifluoride (2.65 mmol, 0.58 mL, 3.16 eq.) at 0° C. under nitrogen. The reaction was stirred at 25° C. for 0.5 h. The mixture was added to ice water (10 mL) and extracted with dichloromethane (10 mL). The layers were separated. Then the organic phase was washed with brine (10 mL), dried over sodium sulfate, filtered, and concentrated under vacuum. The residue was purified via Purification Method 1 to afford N-(3,5-dichloro-4-(2,6-dioxopiperidin-3-yl)benzyl)-2-methyl-2-(5-(2-oxoethyl) pyrazin-2-yl) propanamide (33.53 mg, 65.1 μmol, 7% yield) as a white solid.

$^1$H NMR (400 MHZ, DMSO-$d_6$) δ=10.97 (s, 1H), 8.68 (d, J=1.6 Hz, 1H), 8.61 (d, J=1.2 Hz, 1H), 8.19 (t, J=6.0 Hz, 1H), 7.32 (d, J=1.6 Hz, 1H), 7.25 (d, J=1.2 Hz, 1H), 6.62-6.27 (m, 1H), 4.56 (dd, J=5.6, 12.8 Hz, 1H), 4.24 (d, J=6.0 Hz, 2H), 3.45 (m, J=4.4 Hz, 2H), 2.85 (ddd, J=5.6, 14.0, 16.8 Hz, 1H), 2.55 (d, J=2.4 Hz, 1H), 2.40-2.29 (m, 1H), 1.94-1.84 (m, 1H), 1.57 (s, 6H). MS (ESI) m/z 499.2 [M+H]$^+$ Exemplary Compound 241

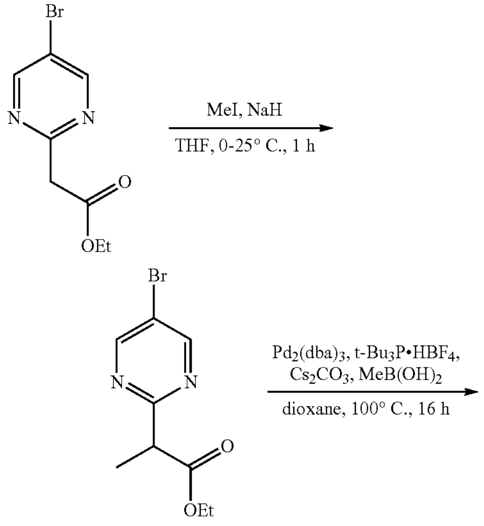

-continued

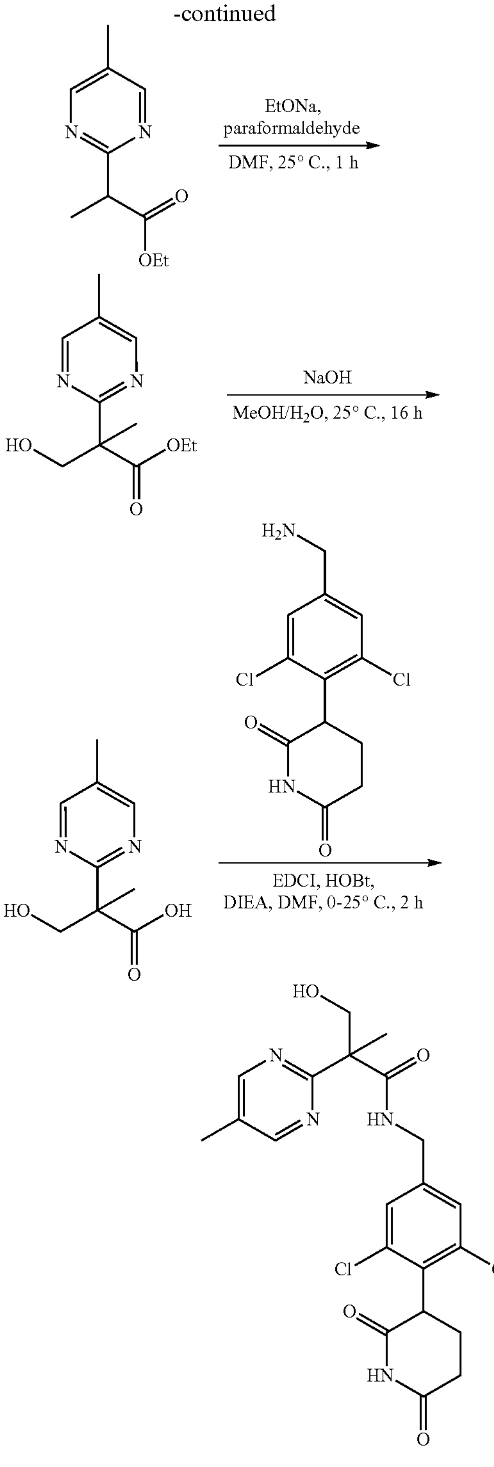

Step 1. To a solution of ethyl 2-(5-bromopyrimidin-2-yl) acetate (3.00 g, 12.2 mmol, 1.00 eq.) in tetrahydrofuran (30 mL) was added dropwise sodium hydride (600 mg, 15.0 mmol, 60% purity, 1.23 eq.) at 0° C. under nitrogen atmosphere. The mixture was stirred at 0° C. for 30 min. Then the solution of iodomethane (1.80 g, 12.7 mmol, 1.04 eq.) dissolved in tetrahydrofuran (5 mL) was added to the mixture and the mixture was stirred at 25° C. for 30 min. The reaction mixture was added dropwise to saturated ammonium chloride solution (50 mL) under nitrogen atmosphere at 0° C. Then the mixture was diluted with ethyl acetate (50 mL). The layers were separated, and the aqueous phase was extracted with ethyl acetate (2× 50 mL). The combined organic layers were washed with brine (80 mL), dried over sodium sulfate, filtered, and concentrated under reduced pressure. The residue was purified via Purification Method 2 to afford ethyl 2-(5-bromopyrimidin-2-yl) propanoate (2.00 g, 7.56 mmol, 61% yield) as a colourless oil.

Step 2. To a solution of ethyl 2-(5-bromopyrimidin-2-yl) propanoate (2.00 g, 7.72 mmol, 1.00 eq.) in dioxane (20 mL) were added caesium carbonate (7.60 g, 23.3 mmol, 3.02 eq.), methylboronic acid (2.40 g, 40.0 mmol, 5.19 eq.), tri-tert-butylphosphonium tetrafluoroborate (500 mg, 1.72 mmol, 0.22 eq.) and tris(dibenzylideneacetone)-dipalladium (0) (750 mg, 819 μmol, 0.10 eq.). The mixture was stirred at 100° C. under nitrogen atmosphere for 16 h. The reaction mixture was diluted with water (30 mL). Then the mixture was extracted with ethyl acetate (2×30 mL). The combined organic extracts were washed with brine (50 mL) and dried over anhydrous sodium sulfate, filtered, and concentrated under vacuum. The residue was purified via Purification Method 2 to afford ethyl 2-(5-methylpyrimidin-2-yl) propanoate (1.22 g, 5.02 mmol, 65% yield) as a yellow oil.

Step 3. To a solution of ethyl 2-(5-methylpyrimidin-2-yl) propanoate (1.22 g, 6.28 mmol, 1.00 eq.) in dimethylformamide (10 mL) was added paraformaldehyde (600 mg, 12.5 mmol, 2.00 eq.) and sodium ethanolate (854 mg, 12.5 mmol, 2.00 eq.). The mixture was stirred at 25° C. for 1 h. The reaction mixture was added dropwise to hydrochloric acid (0.5M in water, 20 mL) at 0° C. Then the mixture was diluted with ethyl acetate (20 mL). The layers were separated, and the aqueous phase was extracted with ethyl acetate (2×20 mL). The combined organic layers were washed with brine (30 mL), dried over sodium sulfate, filtered, and concentrated under reduced pressure. The residue was purified via Purification Method 2 to afford ethyl 3-hydroxy-2-methyl-2-(5-methylpyrimidin-2-yl) propanoate (420 mg, 1.82 mmol, 28% yield) as a yellow oil.

Step 4. To a solution of ethyl 3-hydroxy-2-methyl-2-(5-methylpyrimidin-2-yl) propanoate (400 mg, 1.78 mmol, 1.00 eq.) in methanol (5 mL) and water (1 mL) was added sodium hydroxide (400 mg, 10.0 mmol, 5.61 eq.). The mixture was stirred at 25° C. for 16 h. The mixture was diluted with water (10 mL) and dichloromethane (10 mL). The aqueous phase was separated and washed with dichloromethane (10 mL). The pH of the aqueous phase was adjusted to 7 with hydrochloric acid (1 M) and lyophilized to afford 3-hydroxy-2-methyl-2-(5-methylpyrimidin-2-yl) propanoic acid (1.10 g, crude) as a white solid.

Step 5. To a solution of 3-hydroxy-2-methyl-2-(5-methylpyrimidin-2-yl) propanoic acid (500 mg, crude) in dimethylformamide (5 mL) were added N,N-diisopropylethylamine (200 μL, 1.15 mmol, 3.10 eq.), 1-(3-dimethylaminopropyl)-3-ethylcarbodiimide hydrochloride (180 mg, 938 μmol, 2.53 eq.) and 1H-benzo[d][1,2,3]triazol-1-ol (125 mg, 930 μmol, 2.51 eq.) at 0° C. The mixture was stirred at 25° C. for 0.5 h. Then 3-(4-(aminomethyl)-2,6-dichlorophenyl) piperidine-2,6-dione hydrochloride (120 mg, 370 μmol, 1.00 eq.) was added to the mixture and the mixture was stirred at 25° C. for 1.5 h. Then the reaction mixture was diluted with water (10 mL) and extracted with ethyl acetate (2×10 mL). The combined organic extracts were washed with brine (20 mL) and dried over anhydrous sodium sulfate, filtered, and concentrated under reduced pressure. The residue was purified via Purification Method I to afford N-(3,5-dichloro-4-(2,6-dioxopiperidin-3-yl)benzyl)-3-hydroxy-2-methyl-2-(5-methylpyrimidin-2-yl) propanamide (83.3 mg, 177 μmol, 47% yield) as a white solid.

$^1$H NMR (400 MHZ, DMSO-$d_6$) δ=10.97 (s, 1H), 8.63 (s, 2H), 8.09 (t, J=6.0 Hz, 1H), 7.44 (s, 1H), 7.38 (s, 1H), 4.87 (t, J=5.2 Hz, 1H), 4.61-4.49 (m, 1H), 4.27 (d, J=6.0 Hz, 2H), 4.12-4.02 (m, 1H), 3.97-3.84 (m, 1H), 2.92-2.78 (m, 1H), 2.58-2.53 (m, 1H), 2.43-2.29 (m, 1H), 2.26 (s, 3H), 1.96-1.78 (m, 1H), 1.52 (s, 3H). MS (ESI) m/z 465.1 [M+H]$^+$
Exemplary Compound 242
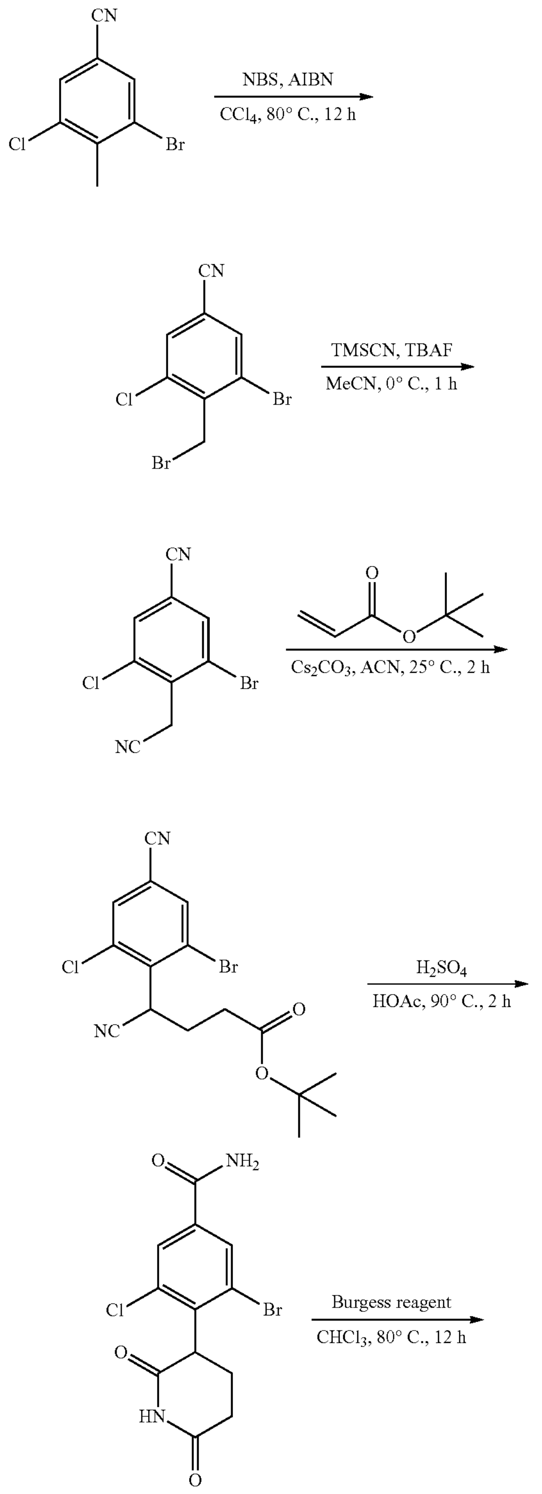
-continued
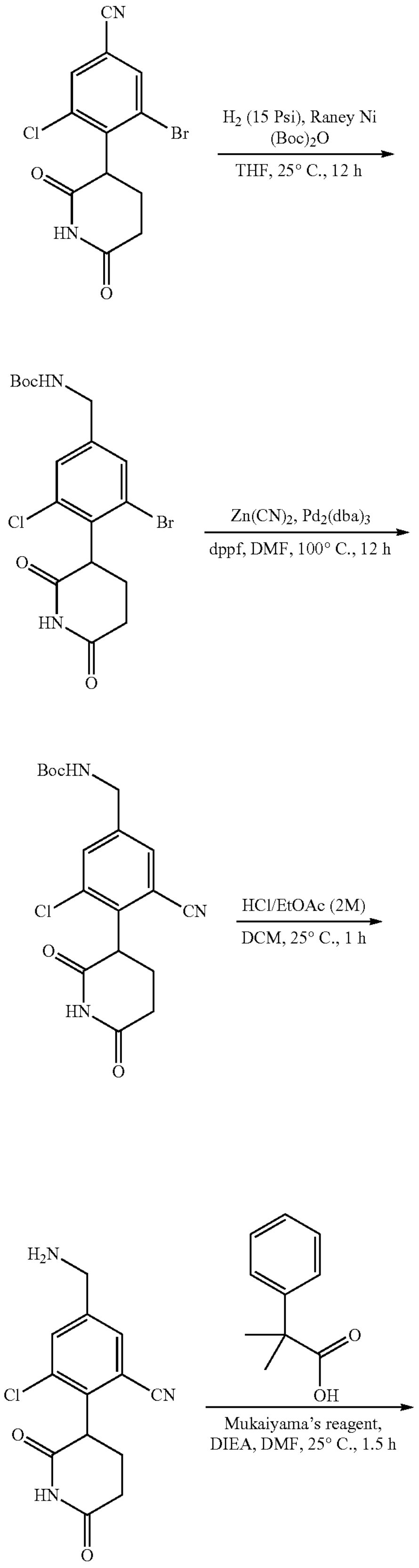

-continued

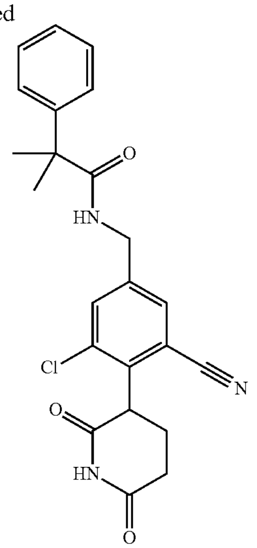

Step 1: To a solution of 3-bromo-5-chloro-4-methylbenzonitrile (4.50 g, 19.5 mmol, 1.00 eq.) in $CCl_4$ (45 mL) were added AIBN(321 mg, 1.95 mmol, 0.10 eq.) and NBS (4.17 g, 23.4 mmol, 1.20 eq.) in portions at 25° C. The reaction was stirred at 80° C. under nitrogen for 12 h. The mixture was poured into water (20 mL) and extracted with ethyl acetate (3× 20 mL). The combined organic layers were washed with brine (30 mL), dried over anhydrous sodium sulfate, filtered, and concentrated under reduced pressure to give a residue. The residue was purified via Purification Method 2 to afford 3-bromo-4-(bromomethyl)-5-chlorobenzonitrile (5.84 g, 18.9 mmol, 96% yield) as a white solid.

Step 2: To a solution of 3-bromo-4-(bromomethyl)-5-chlorobenzonitrile (5.84 g, 18.9 mmol, 1.00 eq.) and TMSCN(2.81 g, 28.3 mmol, 1.50 eq.) in MeCN(58 mL) was added TBAF (1 M in THF, 28.3 mL, 1.50 eq.) dropwise at 0° C. The reaction was stirred at 0° C. under nitrogen for 1 h. The mixture was poured into water (50 mL) and extracted with ethyl acetate (3×50 mL). The combined organic layers were washed with brine (30 mL), dried over anhydrous sodium sulfate, filtered, and concentrated under reduced pressure to give a residue. The residue was purified via Purification Method 2 to afford 3-bromo-5-chloro-4-(cyanomethyl)benzonitrile (3.94 g, 15.4 mmol, 81% yield) as a white solid.

Step 3: To a solution of 3-bromo-5-chloro-4-(cyanomethyl)benzonitrile (2.60 g, 10.2 mmol, 1.00 eq.) and tert-butyl prop-2-enoate (1.57 g, 12.2 mmol, 1.20 eq.) in MeCN (26 mL) was added caesium carbonate (3.65 g, 11.2 mmol, 1.10 eq.) in portions at 25° C. The reaction was stirred at 25° C. for 2 h, then it was filtered, and the filtrate was concentrated under reduced pressure to give a residue. The residue was purified via Purification Method 2 to afford tert-butyl 4-(2-bromo-6-chloro-4-cyanophenyl)-4-cyanobutanoate (3.52 g, 7.98 mmol, 78% yield) as a light-yellow oil.

Step 4: To a solution of tert-butyl 4-(2-bromo-6-chloro-4-cyano-phenyl)-4-cyano-butanoate (3.52 g, 9.17 mmol, 1.00 eq.) in acetic acid (35 mL) was added sulfuric acid (2.45 mL, 45.9 mmol, 5.00 eq.) dropwise at 25° C. The reaction was stirred at 90° C. for 2 h, then it was cooled to 20° C., and poured into water (20 mL). The aqueous layer was extracted with ethyl acetate (3× 20 mL). The combined organic layers were washed with brine (30 mL), dried over anhydrous sodium sulfate, filtered, and concentrated under reduced pressure to give a residue. The residue was triturated with ethyl acetate (10 mL), filtered, and washed with ethyl acetate (2×5 mL). The solid was dried under vacuum to afford 3-bromo-5-chloro-4-(2,6-dioxopiperidin-3-yl)benzamide (2.75 g, 7.32 mmol, 79% yield) as a white solid.

Step 5: To a solution of 3-bromo-5-chloro-4-(2,6-dioxopiperidin-3-yl)benzamide (2.75 g, 7.96 mmol, 1.00 eq.) in chloroform (27 mL) was added Burgess reagent (2.84 g, 11.9 mmol, 1.50 eq.) in portions at 25° C. The reaction was stirred at 80° C. for 12 h. The mixture was poured into water (30 mL) and extracted with ethyl acetate (3× 50 mL). The combined organic layers were washed with brine (30 mL), dried over anhydrous sodium sulfate, filtered, and concentrated under reduced pressure to give a residue. The residue was purified via Purification Method 2 then Purification Method 1 to afford 3-bromo-5-chloro-4-(2,6-dioxopiperidin-3-yl)benzonitrile (1.00 g, 2.84 mmol, 35% yield) as a white solid.

Step 6: To a mixture of Raney-nickel (0.5 g, 5.84 mmol, 2.39 eq.) in THF (8 mL) was added a solution of 3-bromo-5-chloro-4-(2,6-dioxopiperidin-3-yl)benzonitrile (0.80 g, 2.44 mmol, 1.00 eq.), TEA (371 mg, 3.66 mmol, 1.50 eq.) and $Boc_2O$(1.07 g, 4.88 mmol, 2.00 eq.) in THF (50 mL) dropwise at 25° C. The reaction was stirred under hydrogen atmosphere (15 psi) at 25° C. for 12 h. The mixture was filtered, and the filtrate was concentrated under reduced pressure to give a residue. The residue was purified via Purification Method 2 to afford tert-butyl (3-bromo-5-chloro-4-(2,6-dioxopiperidin-3-yl)benzyl) carbamate (375 mg, 704 μmol, 28% yield) a light-yellow solid.

Step 7: To a solution of tert-butyl (3-bromo-5-chloro-4-(2,6-dioxopiperidin-3-yl)benzyl) carbamate (325 mg, 753 μmol, 1.00 eq.) in DMF (6 mL) were added zinc cyanide (190 mg, 1.62 mmol, 2.15 eq.), $Pd_2$ (dba) 3 (68.9 mg, 75.3 μmol, 0.10 eq.) and dppf (42.5 mg, 75.3 μmol, 0.10 eq.) in one portion at 25° C. The reaction was stirred at 100° C. under nitrogen for 12 h. The mixture was cooled to 25° C., diluted with ethyl acetate (10 mL) and filtered. The filtrate was concentrated under reduced pressure to give a residue, which was purified via Purification Method 2 to afford tert-butyl (3-chloro-5-cyano-4-(2,6-dioxopiperidin-3-yl) benzyl) carbamate (320 mg, crude) as a light-yellow solid.

Step 8: To a solution of tert-butyl (3-chloro-5-cyano-4-(2,6-dioxopiperidin-3-yl)benzyl) carbamate (320 mg, 847 μmol, 1.00 eq.) in DCM (6 mL) was added hydrogen chloride/ethyl acetate (2 M, 6 mL) dropwise at 25° C. The mixture was stirred at 25° C. for 1 h. the resulting precipitate was filtered and washed with ethyl acetate (2×5 mL). The solid was dried under vacuum to afford 5-(aminomethyl)-3-chloro-2-(2,6-dioxopiperidin-3-yl)benzonitrile (200 mg, 541 μmol, 63% yield) as a light-yellow solid.

$^1H$ NMR (400 MHZ, DMSO-$d_6$) δ=11.24-11.04 (m, 1H), 8.49 (br s, 3H), 8.11-7.94 (m, 2H), 4.80-4.30 (m, 1H), 4.19-4.03 (m, 2H), 2.98-2.85 (m, 1H), 2.68-2.56 (m, 1H), 2.45-2.18 (m, 1H), 2.07-2.00 (m, 1H). MS (ESI) m/z 278.1 $[M+H]^+$

Step 9: To a mixture of 2-methyl-2-phenyl-propanoic acid (100 mg, 609 μmol, 1.00 eq.) and 2-chloro-1-methyl-pyridin-1-ium;iodide (171 mg, 670 μmol, 1.10 eq.) in dimethyl formamide (2 mL) was added diisopropylethylamine (315 mg, 2.44 mmol, 4.00 eq.) dropwise at 25° C. The mixture was stirred at 25° C. for 0.5 h, then 5-(aminomethyl)-3-chloro-2-(2,6-dioxopiperidin-3-yl)benzonitrile (153 mg, 487 μmol, 0.80 eq., hydrochloride) was added. The mixture was stirred at 25° C. for 1 h. The mixture was poured into water (20 mL) and extracted with ethyl acetate (3×20 mL). The combined organic layers were washed with brine (30 mL), dried over anhydrous sodium sulfate, filtered, and the filtrate was concentrated under reduced pressure. The residue was purified via Purification Method 1 to afford N-(3-chloro-5-cyano-4-(2,6-dioxopiperidin-3-yl)benzyl)-2-methyl-2-phenylpropanamide (85.8 mg, 200 μmol, 32% yield) as a white solid.

$^1H$ NMR (400 MHZ, DMSO-$d_6$) δ=11.21-10.97 (m, 1H), 8.05 (t, J=6.4 Hz, 1H), 7.55-7.42 (m, 2H), 7.36-7.28 (m, 4H), 7.27-7.22 (m, 1H), 4.70-4.28 (m, 1H), 4.25 (d, J=6.0 Hz, 2H), 2.89 (ddd, J=5.6, 13.6, 16.8 Hz, 1H), 2.60 (d, J=20.0 Hz, 1H), 2.41-2.16 (m, 1H), 2.05-1.95 (m, 1H), 1.49 (s, 6H). MS (ESI) m/z 424.2 $[M+H]^+$ Exemplary Compounds 243 and 244

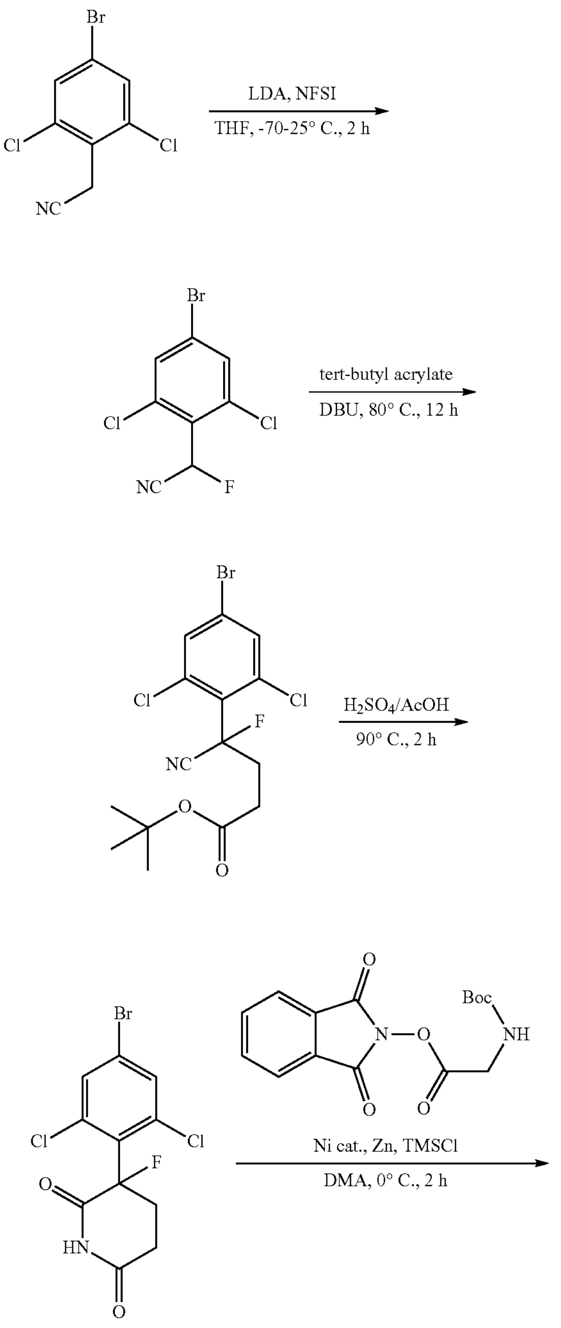

-continued

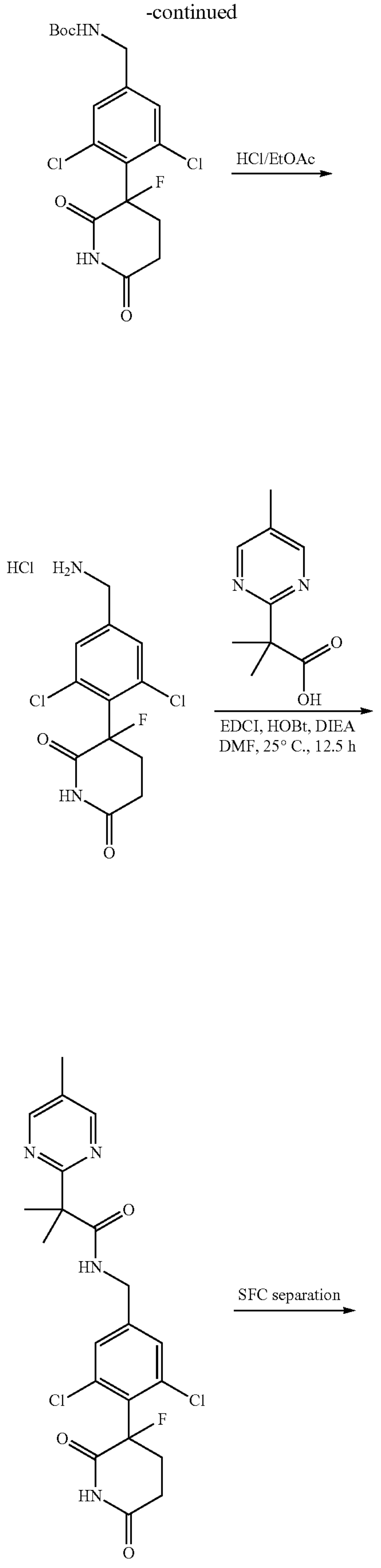

-continued

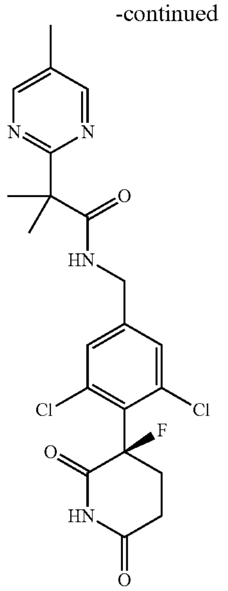

Compound 243

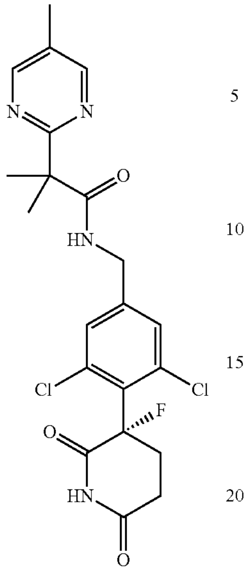

Compound 244

Note: for these enantiomers, their absolute configuration was not determined and was assigned arbitrarily.

Step 1: To a solution of 2-(4-bromo-2,6-dichlorophenyl) acetonitrile (5.40 g, 20.4 mmol, 1.00 eq.) in THF (50 mL) was added LDA (2 M in THF, 11.2 mL, 1.10 eq.) at −70° C. The reaction was stirred at −70° C. for 1 h under nitrogen, then a solution of NFSI (7.07 g, 22.4 mmol, 1.10 eq.) in THF (25 mL) was added. The reaction was stirred at 25° C. for 1 h under nitrogen, then it was quenched with $NH_4Cl$ sat. sol. (150 mL) at 0° C. The aqueous layer was extracted with ethyl acetate (3×50 mL). The combined organic layers were washed with brine (70 mL), dried over sodium sulfate, filtered, and concentrated under reduced pressure to give a residue. The residue was purified via Purification Method 2 to afford 2-(4-bromo-2,6-dichlorophenyl)-2-fluoroacetonitrile (5.32 g, 17.9 mmol, 88% yield) as a yellow oil.

Step 2: To a solution of 2-(4-bromo-2,6-dichlorophenyl)-2-fluoroacetonitrile (5.32 g, 18.8 mmol, 1.00 eq.) in DMSO (50 mL) were added tert-butyl acrylate (4.82 g, 37.6 mmol, 2.00 eq.) and DBU (859 mg, 5.64 mmol, 0.30 eq.). The reaction was stirred at 80° C. for 12 h, then it was quenched with water (150 mL) and the aqueous layer was extracted with ethyl acetate (3× 50 mL). The combined organic layers were washed with water (50 mL) and brine (50 mL), dried over sodium sulfate, filtered, and concentrated under reduced pressure to give a residue. The residue was purified via Purification Method 2 to afford tert-butyl 4-(4-bromo-2,6-dichlorophenyl)-4-cyano-4-fluorobutanoate (5.34 g, 12.0 mmol, 64% yield) as a yellow oil.

Step 3: To a solution of tert-butyl 4-(4-bromo-2,6-dichlorophenyl)-4-cyano-4-fluorobutanoate (5.34 g, 13.0 mmol, 1.00 eq.) in acetic acid (50 mL) was added sulfuric acid (5 mL). The reaction was stirred at 90° C. for 2 h. The mixture was cooled to room temperature and poured into ice water (150 mL). The resulting precipitate was filtered, washed with water (100 mL), and dried under vacuum to afford the 3-(4-bromo-2,6-dichlorophenyl)-3-fluoropiperidine-2,6-dione (4.60 g, 12.3 mmol, 95% yield) as a white solid.

Step 4: To a solution of 3-(4-bromo-2,6-dichlorophenyl)-3-fluoropiperidine-2,6-dione (1.00 g, 2.82 mmol, 1.00 eq.), 1,3-dioxoisoindolin-2-yl (tert-butoxycarbonyl)glycinate (1.00 g, 3.13 mmol, 1.11 eq.), Nickel cat. (100 mg, 165 μmol, eq.) and zinc powder (1.50 g, 22.9 mmol, 8.14 eq.) in DMAC (15 mL) was added TMSCl (918 mg, 8.45 mmol, 3.00 eq.) at 0° C. under nitrogen. The reaction was stirred at 0° C. for 2 h, then it was quenched by $NaHCO_3$sat. sol. (75 mL) at 0° C., and filtered over a pad of Celite. The filtrate was diluted with ethyl acetate (25 mL) and water (20 mL). The layers were separated, and the aqueous layer was extracted with ethyl acetate (2×25 mL). The combined organic layers were washed with brine (25 mL), dried over anhydrous sodium sulfate, filtered, and concentrated under reduced pressure to give a residue. The residue was purified via Purification Method 2 to afford tert-butyl (3,5-dichloro-4-(3-fluoro-2,6-dioxopiperidin-3-yl)benzyl) carbamate (324 mg, 664 μmol, 24% yield) as a white solid.

Step 5: A solution of tert-butyl (3,5-dichloro-4-(3-fluoro-2,6-dioxopiperidin-3-yl)benzyl) carbamate (570 mg, 1.41 mmol, 1.00 eq.) in hydrogen chloride (2 M in ethyl acetate, 5 mL) was stirred at 25° C. for 1 h. It was concentrated under reduced pressure to afford 3-(4-(aminomethyl)-2,6-dichlorophenyl)-3-fluoropiperidine-2,6-dione hydrochloride (420 mg, 1.11 mmol, 79% yield) as a white solid.

$^1H$ NMR (400 MHZ, DMSO-$d_6$) δ=11.58 (s, 1H), 8.58 (s, 3H), 7.74 (s, 2H), 4.06 (s, 2H), 2.90-2.60 (m, 3H), 2.49-2.41 (m, 1H). MS (ESI) m/z 305.0 $[M+H]^+$

Step 6: To a solution of 2-methyl-2-(5-methylpyrimidin-2-yl) propanoic acid (190 mg, 1.05 mmol, 1.20 eq.) in DMF (3 mL) were added EDCI (202 mg, 1.05 mmol, 1.20 eq.), HOBt (142 mg, 1.05 mmol, 1.20 eq.) and DIPEA (341 mg, 2.63 mmol, 3.00 eq.). The reaction was stirred at 25° C. for 30 min. Then 3-(4-(aminomethyl)-2,6-dichlorophenyl)-3-fluoropiperidine-2,6-dione hydrochloride (300 mg, 878 μmol, 1.00 eq.) was added. The reaction was stirred at 25° C. for 12, then it was diluted with water (75 mL) and extracted with ethyl acetate (3× 25 mL). The combined organic layers were washed with water (35 mL) and brine (35 mL), dried over anhydrous sodium sulfate, filtered, and concentrated under reduced pressure. The residue was purified Purification Method 1 to afford N-(3,5-dichloro-4-(3-fluoro-2,6-dioxopiperidin-3-yl)benzyl)-2-methyl-2-(5-methyl-pyrimidin-2-yl) propenamide (374 mg, 792 μmol, 90% yield) as a white solid.

Compound N-(3,5-dichloro-4-(3-fluoro-2,6-dioxopiperidin-3-yl)benzyl)-2-methyl-2-(5-methylpyrimidin-2-yl) propenamide (374 mg, 792 μmol) was separated by SFC (column: DAICEL CHIRALCEL OJ (250 mm*30 mm, 10 μm); mobile phase: [carbon dioxide-propan-2-ol]; B %: 30%, isocratic elution mode) to give two peaks.

Peak 1: (R)—N-(3,5-dichloro-4-(3-fluoro-2,6-dioxopiperidin-3-yl)benzyl)-2-methyl-2-(5-methyl-pyrimidin-2-yl) propenamide (135.73 mg, 288 μmol, 36% yield) was obtained as a white solid.

$^1H$ NMR (400 MHz, DMSO-$d_6$) δ=11.51 (s, 1H), 8.64 (s, 2H), 8.06 (t, J=6.0 Hz, 1H), 7.43 (s, 2H), 4.27 (d, J=6.0 Hz, 2H), 2.88-2.57 (m, 3H), 2.49-2.39 (m, 1H), 2.27 (s, 3H), 1.53 (s, 6H). MS (ESI) m/z 467.1 $[M+H]^+$

Peak 2: (S)—N-(3,5-dichloro-4-(3-fluoro-2,6-dioxopiperidin-3-yl)benzyl)-2-methyl-2-(5-methyl-pyrimidin-2-yl) propenamide (136.07 mg, 288 μmol, 36% yield) was obtained as a white solid.

$^1H$ NMR (400 MHZ, DMSO-$d_6$) δ=11.51 (s, 1H), 8.64 (s, 2H), 8.06 (t, J=6.0 Hz, 1H), 7.43 (s, 2H), 4.27 (d, J=6.0 Hz, 2H), 2.90-2.57 (m, 3H), 2.49-2.38 (m, 1H), 2.27 (s, 3H), 1.53 (s, 6H). MS (ESI) m/z 467.1 $[M+H]^+$

Exemplary Compound 245

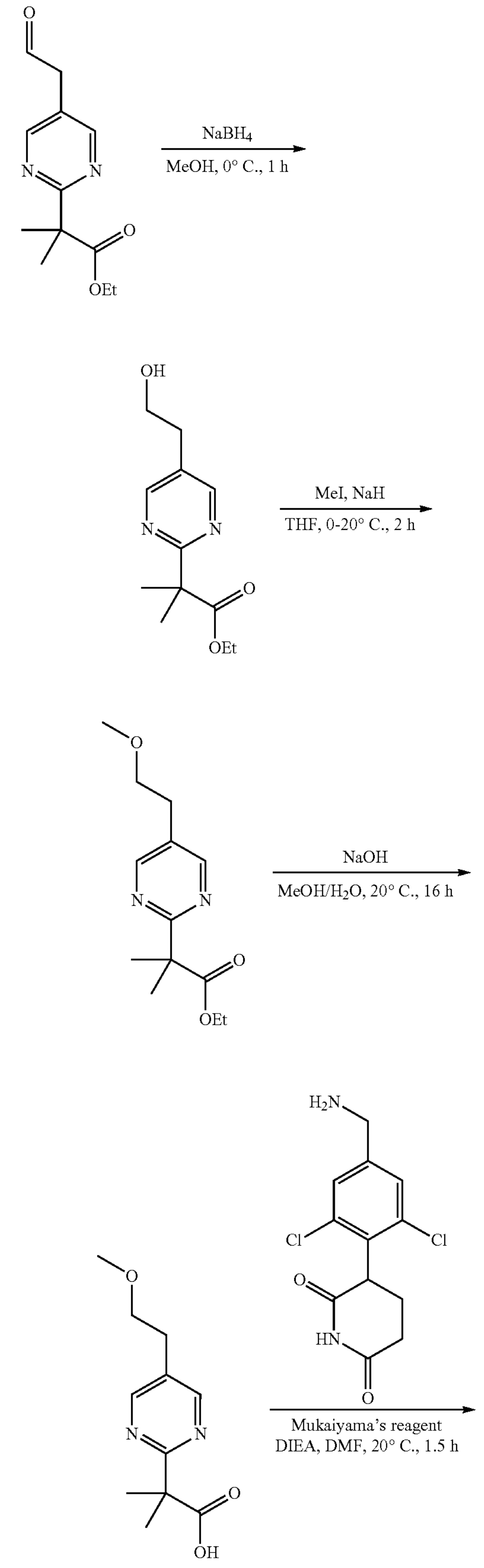

-continued

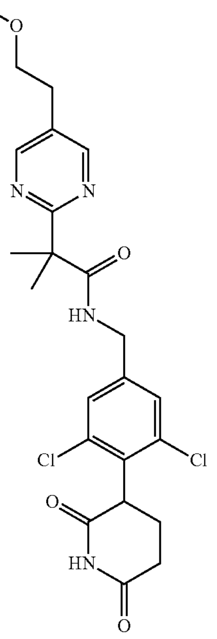

Step 1. To a solution of ethyl 2-methyl-2-(5-(2-oxoethyl) pyrimidin-2-yl) propanoate (920 mg, 3.89 mmol, 1.00 eq.) in methanol (10 mL) was added sodium borohydride (260 mg, 6.87 mmol, 1.76 eq.) at 0° C. under nitrogen. The mixture was stirred at 0° C. for 1 h. The mixture was quenched with saturated ammonium chloride (20 mL) at 0° C. under nitrogen, extracted with ethyl acetate (20 mL). The combined organic layers were washed with water (2×20 mL), dried over sodium sulfate, filtered, and concentrated under reduced pressure. The residue was purified via Purification Method 2 to afford ethyl 2-(5-(2-hydroxyethyl) pyrimidin-2-yl)-2-methylpropanoate (550 mg, 2.19 mmol, 56% yield) as a yellow oil.

Step 2. To a solution of ethyl 2-(5-(2-hydroxyethyl) pyrimidin-2-yl)-2-methylpropanoate (400 mg, 1.68 mmol, 1.00 eq.) in tetrahydrofuran (20 mL) was added sodium hydride (101 mg, 2.52 mmol, 60% purity, 1.50 eq.) at 0° C. under nitrogen. The mixture was stirred at 0° C. for 0.5 h. Then methyl iodide (209 μL, 3.36 mmol, 2.00 eq.) was added to the mixture. The mixture was stirred at 20° C. for 1.5 h. The mixture was pure into saturated ammonium chloride (20 mL) at 0° C. under nitrogen.

Then the mixture was extracted with ethyl acetate (20 mL). The combined organic layers were washed with water (2×20 mL), dried over sodium sulfate, filtered, and concentrated under reduced pressure. The residue was purified via Purification Method 2 to afford ethyl 2-(5-(2-methoxyethyl) pyrimidin-2-yl)-2-methylpropanoate (260 mg, 927 μmol, 55% yield) as a yellow oil.

Step 3. To a solution of ethyl 2-(5-(2-methoxyethyl) pyrimidin-2-yl)-2-methylpropanoate (240 mg, 951 μmol, 1.00 eq.) in methanol (2 mL) and water (2 mL) was added sodium hydroxide (190 mg, 4.76 mmol, 5.00 eq.). The mixture was stirred at 20° C. for 16 h. The mixture was acidified with aqueous hydrochloric acid (1M) till pH=5 at 0° C., then it was extracted with dichloromethane (3× 20 mL). Combined extracts were washed with brine (20 mL), dried over sodium sulfate, filtered, and concentrated under vacuum to give 2-(5-(2-methoxyethyl)pyrimidin-2-yl)-2-methylpropanoic acid (220 mg, crude) as a white solid. It was used directly in the next step.

Step 4. To a solution of 2-(5-(2-methoxyethyl)pyrimidin-2-yl)-2-methylpropanoic acid (100 mg, crude) in N,N-dimethylformamide (4 mL) were added 2-chloro-1-methyl-pyridin-1-ium iodide (137 mg, 535 μmol, 1.20 eq.) and N,N-diisopropylethylamine (233 μL, 11.3 mmol, 3.00 eq.). The mixture was stirred at 20° C. for 0.5 h. Then 3-(4-(aminomethyl)-2,6-dichlorophenyl) piperidine-2,6-dione hydrochloride (120 mg, 371 μmol, 0.70 eq.) was added to the mixture. The mixture was stirred at 20° C. for 1 h. The mixture was diluted with water (20 mL), extracted with ethyl acetate (20 mL). The combined organic layers were washed with water (2×20 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-(5-(2-methoxyethyl)pyrimidin-2-yl)-2-methylpropanamide (114.21 mg, 229 μmol, 51% yield) as a white solid.

$^1H$ NMR (400 MHZ, DMSO-$d_6$) δ=10.96 (s, 1H), 8.67 (s, 2H), 8.10 (t, J=6.0 Hz, 1H), 7.43 (s, 1H), 7.37 (s, 1H), 4.56 (dd, J=5.6, 12.8 Hz, 1H), 4.26 (d, J=6.0 Hz, 2H), 3.57 (t, J=6.4 Hz, 2H), 3.24 (s, 3H), 2.91-2.78 (m, 3H), 2.55 (m, 1H), 2.42-2.28 (m, 1H), 1.89 (td, J=5.6, 11.2 Hz, 1H), 1.53 (s, 6H). MS (ESI) m/z 493.2 $[M+H]^+$

Exemplary Compound 246

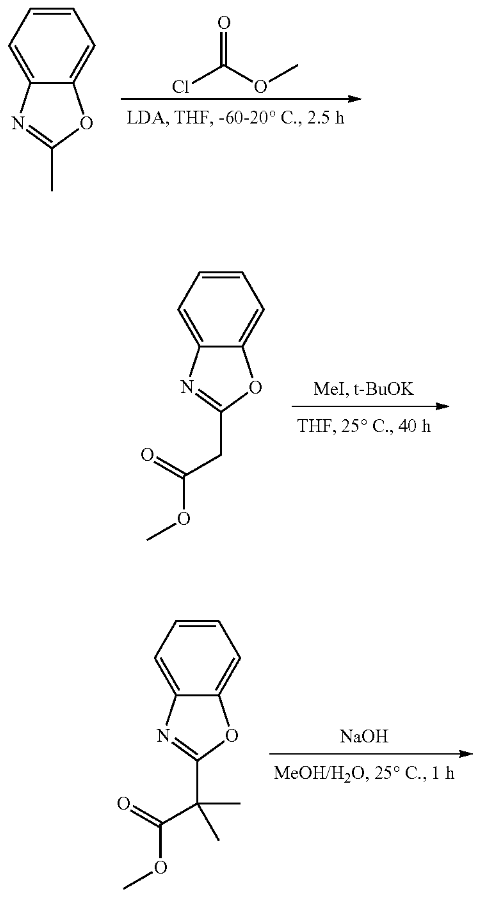

-continued

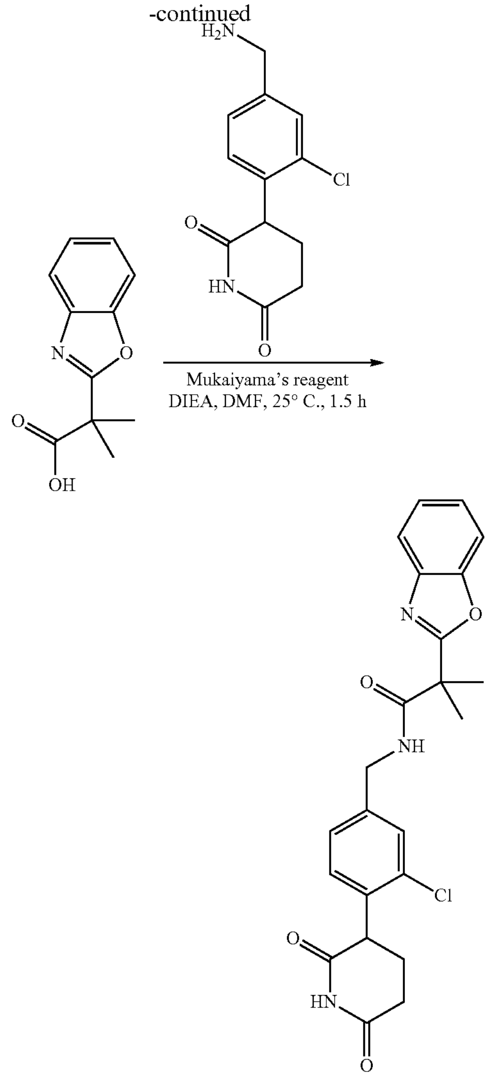

Step 1. To a solution of 2-methylbenzo[d]oxazole (2.00 g, 15.0 mmol, 1.79 mL, 1.00 eq.) in tetrahydrofuran (30 mL) was added dropwise lithium diisopropylamide (2.0 M in tetrahydrofuran and n-heptane, 11.27 mL, 1.50 eq.) at −60° C. under nitrogen atmosphere. The mixture was stirred at −60° C. for 0.5 h under nitrogen atmosphere. Then methyl carbonochloridate (26.0 mmol, 2.01 mL, 1.73 eq.) was added at −60° C. under nitrogen atmosphere. The mixture was stirred at 20° C. for 2 h under nitrogen atmosphere. The mixture was quenched with saturated ammonium chloride (50 mL) at 0° C. under nitrogen atmosphere. The mixture was extracted with ethyl acetate (3×30 mL). The combined organic layers were washed with brine (2×50 mL), dried over sodium sulfate, filtered, and concentrated under reduced pressure. The crude product was purified via Purification Method 2 to afford methyl 2-(benzo[d]oxazol-2-yl) acetate (650 mg, 3.23 mmol, 22% yield) as a yellow oil.

Step 2. To a solution of methyl 2-(benzo[d]oxazol-2-yl) acetate (450 mg, 2.35 mmol, 1.00 eq.) in tetrahydrofuran (10 mL) were added potassium 2-methylpropan-2-olate (1.32 g, 11.8 mmol, 5.01 eq.) and iodomethane (23.5 mmol, 1.47 mL, 10.0 eq.). The mixture was stirred at 25° C. for 40 h. The mixture was filtered, and the filter cake was washed with dichloromethane (15 mL). The filtrate was concentrated under reduced pressure. The crude product was purified via Purification Method 2 to afford methyl 2-(benzo[d]oxazol-2-yl)-2-methylpropanoate (280 mg, 1.26 mmol, 54% yield) as a light-yellow oil.

Step 3. To a solution of methyl 2-(benzo[d]oxazol-2-yl)-2-methylpropanoate (280 mg, 1.28 mmol, 1.00 eq.) in methanol (2 mL) were added a solution of sodium hydroxide (511 mg, 12.8 mmol, 10.0 eq.) in water (2 mL). The mixture was stirred at 25° C. for 1 h. The mixture was diluted with water (20 mL). The mixture was adjusted to pH 8 with 2 M hydrochloric acid. The mixture was concentrated under reduced pressure to remove methanol. Then the mixture was lyophilized to give 2-(benzo[d]oxazol-2-yl)-2-methylpropanoic acid (900 mg, 1.27 mmol, 99% yield, 29% purity, contains sodium chloride) as a light-yellow solid.

Step 4. To a solution of 2-(benzo[d]oxazol-2-yl)-2-methylpropanoic acid (180 mg, 380 μmol, 48% purity, 1.00 eq.) in N,N-dimethyl formamide (3 mL) were added 2-chloro-1-methylpyridin-1-ium iodide (146 mg, 571 μmol, 1.50 eq.) and N,N-diisopropylethylamine (148 mg, 1.14 mmol, 3.00 eq.). The mixture was stirred at 25° C. for 30 min. Then 3-(4-(aminomethyl)-2-chlorophenyl) piperidine-2,6-dione hydrochloride (110 mg, 380 μmol, 1.00 eq.) was added to the mixture. The mixture was stirred at 25° C. for 1 h. The mixture was diluted with water (25 mL) and extracted with ethyl acetate (3×10 mL). The combined organic layers were washed with water (20 mL) and brine (20 mL), dried over anhydrous sodium sulfate, filtered, and concentrated under reduced pressure to give a residue. The residue was purified via Purification Method 1 to afford 2-(benzo[d]oxazol-2-yl)-N-(3-chloro-4-(2,6-dioxopiperidin-3-yl)benzyl)-2-methylpropanamide (128.04 mg, 288 μmol, 76% yield) as a white solid.

$^1$H NMR (400 MHZ, DMSO-$d_6$) δ=10.89 (s, 1H), 8.44 (t, J=5.6 Hz, 1H), 7.76-7.69 (m, 2H), 7.41-7.35 (m, 2H), 7.28-7.25 (m, 2H), 7.15 (d, J=7.6 Hz, 1H), 4.27 (d, J=6.0 Hz, 2H), 4.19-4.13 (m 1H), 2.85-2.67 (m, 1H), 2.55-2.52 (m, 1H), 2.33-2.21 (m, 1H), 2.04-1.89 (m, 1H), 1.67 (s, 6H). MS (ESI) m/z 440.3 $[M+H]^+$

Exemplary Compound 247

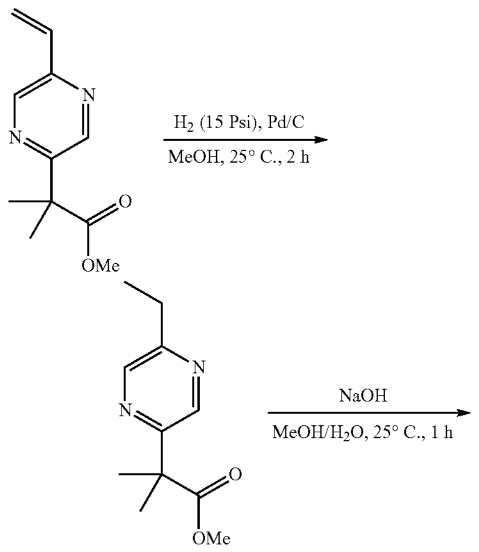

-continued

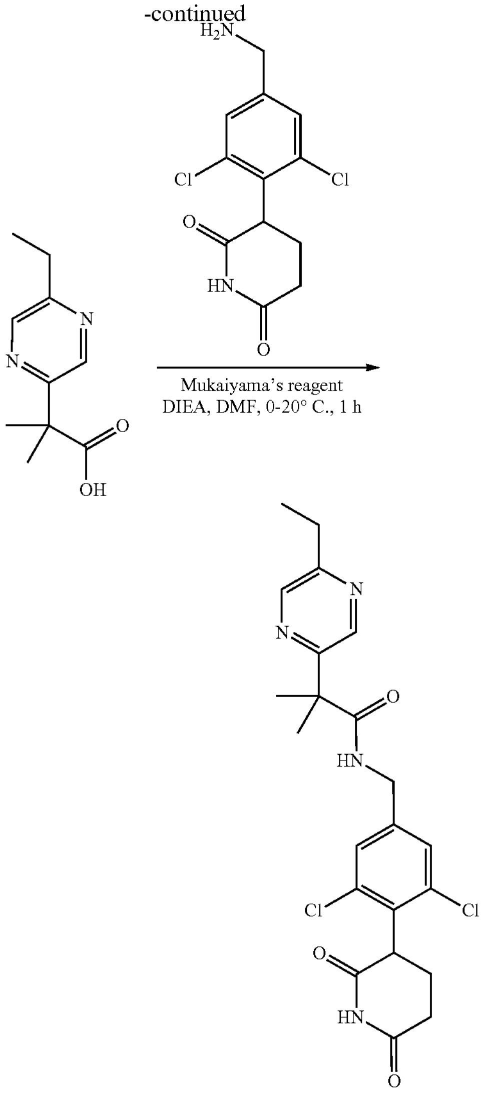

Step 1. To a solution of methyl 2-methyl-2-(5-vinylpyrazin-2-yl) propanoate (200 mg, 970 μmol, 1.00 eq.) in methanol (5 mL) was added Palladium on Carbon (20 mg, 10% purity). The mixture was stirred at 25° C. under hydrogen (15 Psi) for 2 h. The mixture was filtered. The filtrate was concentrated to give methyl 2-(5-ethylpyrazin-2-yl)-2-methylpropanoate (210 mg, crude) as a colourless oil. It was used directly in the next step.

Step 2. To a solution of methyl 2-(5-ethylpyrazin-2-yl)-2-methylpropanoate (210 mg, crude) in methanol (2 mL) and water (2 mL) was added sodium hydroxide (202 mg, 5.04 mmol, 5.00 eq.). The mixture was stirred at 25° C. for 1 h. The mixture was acidified with aqueous hydrochloric acid (2 M) until pH 6 at 0° C. The mixture was extracted with dichloromethane (3× 10 mL), dried over sodium sulfate, filtered, and concentrated under reduced pressure to give 2-(5-ethylpyrazin-2-yl)-2-methylpropanoic acid (100 mg, 489 μmol, 49% yield, 95% purity) as a yellow solid. It was used directly in the next step.

Step 3. To a solution of 2-(5-ethylpyrazin-2-yl)-2-methylpropanoic acid (200 mg, 1.03 mmol, 2.22 eq.) in N,N-dimethylformamide (3 mL) were added N,N-diisopropylethylamine (2.32 mmol, 400 μL, 5.00 eq.) and 2-chloro-1-methyl-pyridinium iodide (142 mg, 556 μmol, 1.20 eq.) at 0°

C. It was stirred at 20° C. for 0.5 h. Then 3-(4-(aminomethyl)-2,6-dichlorophenyl) piperidine-2,6-dione hydrochloride (150 mg, 463 μmol, 1.00 eq.) was added to the mixture. It was stirred at 20° C. for 0.5 h. The mixture was diluted with ethyl acetate (20 mL) and water (20 mL). The layers were separated, and the aqueous phase was extracted with ethyl acetate (2×20 mL). Combined extracts were washed with brine (15 mL), dried over anhydrous sodium sulfate, filtered, and concentrated in vacuo. The residue was purified via Purification Method I to afford N-[[3,5-dichloro-4-(2,6-dioxo-3-piperidyl)phenyl]methyl]-2-(5-ethylpyrazin-2-yl)-2-methyl-propanamide (88.09 mg, 188 μmol, 40% yield, 99% purity) as a white solid.

$^1H$ NMR (400 MHZ, DMSO-$d_6$) δ=10.97 (s, 1H), 8.61 (s, 1H), 8.52 (s, 1H), 8.11 (t, J=5.6 Hz, 1H), 7.30 (s, 1H), 7.23 (s, 1H), 4.56 (dd, J=5.2, 12.8 Hz, 1H), 4.24 (d, J=5.6 Hz, 2H), 2.91-2.74 (m, 3H), 2.60-2.52 (m, 1H), 2.42-2.27 (m, 1H), 1.95-1.81 (m, 1H), 1.56 (s, 6H), 1.25 (t, J=7.6 Hz, 3H). MS (ESI) m/z 463.1 $[M+H]^+$

Exemplary Compound 260

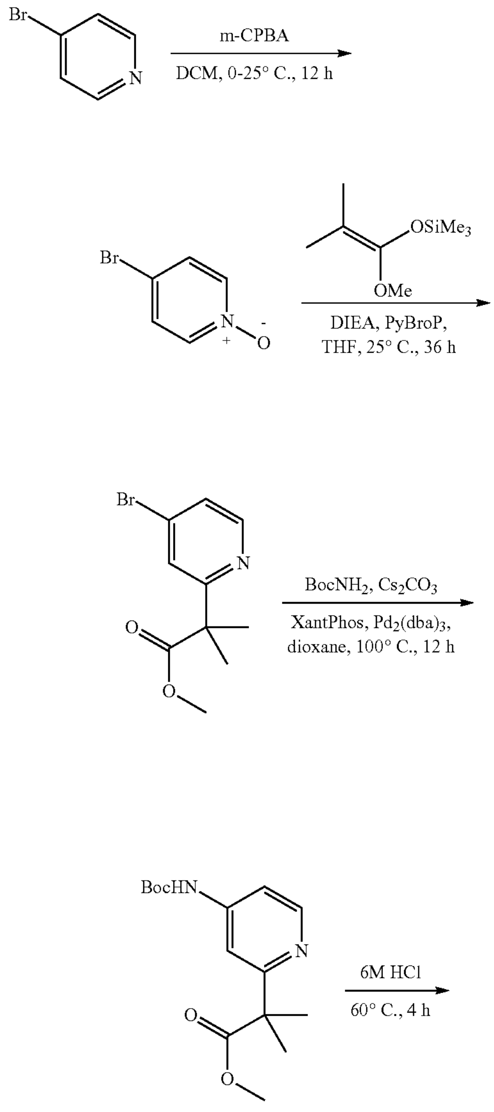

-continued

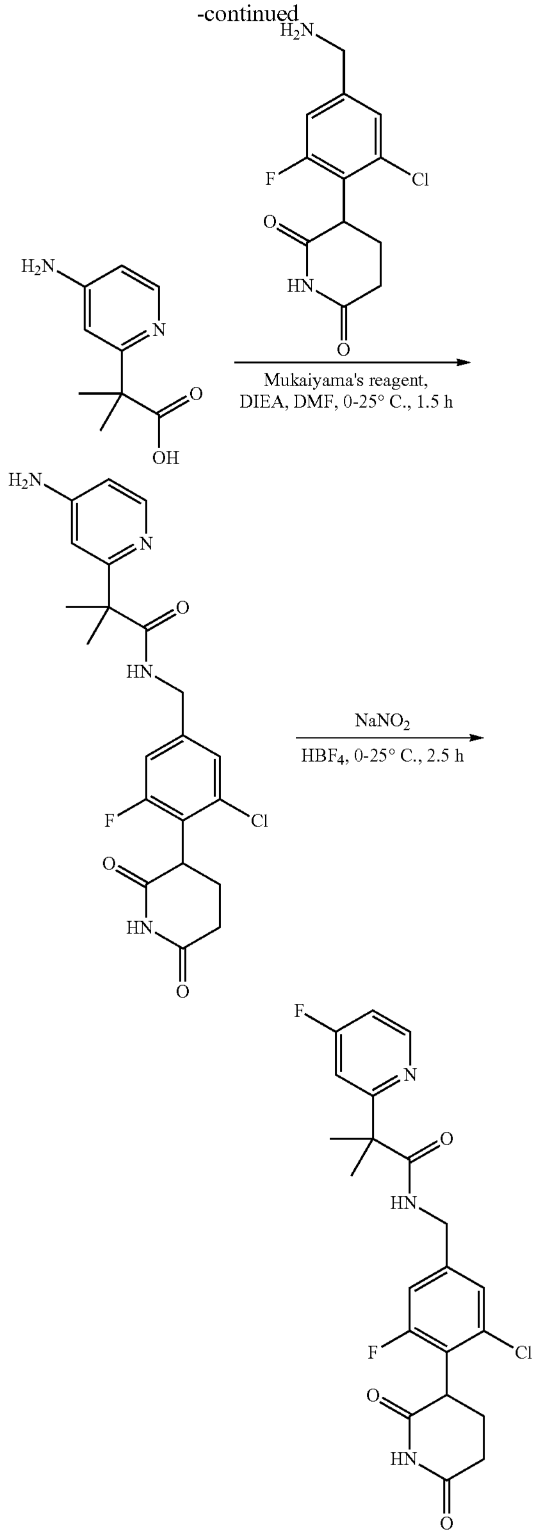

Step 1. To a solution of 4-bromopyridine (5.00 g, 31.7 mmol, 1.00 eq.) in dichloromethane (50 mL) was added 3-chlorobenzoperoxoic acid (10.9 g, 53.8 mmol, 85% purity, 1.70 eq.) at 0° C. The mixture was stirred at 25° C. for 12 h. The mixture was concentrated in vacuo. The crude product was purified via Purification Method 2 to afford a crude product. The crude product was triturated with ethyl acetate (40 mL) at 25° C. for 30 min. The mixture was filtered, and the filter cake was collected and dried in vacuo to give 4-bromopyridine 1-oxide (3.80 g, 20.8 mmol, 65% yield) as a white solid.

Step 2. To a solution of 4-bromopyridine 1-oxide (1.00 g, 5.75 mmol, 1.00 eq.) in tetrahydrofuran (10 mL) was added N,N-diisopropylethylamine (3.00 mL, 17.2 mmol, 3.00 eq.), ((1-methoxy-2-methylprop-1-en-1-yl)oxy)trimethylsilane (3.01 g, 17.3 mmol, 3.00 eq.) and bromo-tris-pyrrolidino-phosphonium hexafluorophosphate (2.95 g, 6.33 mmol, 1.10 eq.). The mixture was stirred at 25° C. for 36 h under nitrogen atmosphere. (The reaction was carried out in 4 batches.) The reaction mixture was diluted with water (40 mL) then the mixture was extracted with ethyl acetate (3×100 mL). The combined organic layers were dried over sodium sulfate, filtered, and concentrated under reduced pressure. The crude product was purified via Purification Method 2 to afford methyl 2-(4-bromopyridin-2-yl)-2-methylpropanoate (4.13 g, 15.2 mmol, 66% yield) as a yellow oil.

Step 3. To a solution of methyl 2-(4-bromopyridin-2-yl)-2-methylpropanoate (4.13 g, 16.0 mmol, 1.00 eq.) in dioxane (50 mL) were added caesium carbonate (11.0 g, 33.8 mmol, 2.11 eq.), tert-butyl carbamate (2.30 g, 19.6 mmol, 1.23 eq.) and (9,9-dimethyl-9H-xanthene-4,5-diyl) bis(di-tert-butylphosphine) (1.85 g, 3.20 mmol, 0.20 eq.). Then tris(dibenzylideneacetone) dipalladium (1.47 g, 1.60 mmol, 0.10 eq.) was added under nitrogen atmosphere. The mixture was stirred at 100° C. for 12 h under nitrogen atmosphere. The resulting mixture was filtered, and the filtrate was diluted with water (50 mL), then the mixture was extracted with ethyl acetate (3×30 mL). The combined organic layer was dried over sodium sulfate, filtered, and concentrated under reduced pressure. The crude product was purified via Purification Method 2 to afford methyl 2-(4-((tert-butoxycarbonyl)amino)pyridin-2-yl)-2-methylpropanoate (3.49 g, 10.6 mmol, 66% yield, 89% purity) as a brown oil.

Step 4. A mixture of methyl 2-(4-((tert-butoxycarbonyl) amino)pyridin-2-yl)-2-methylpropanoate (500 mg, 1.70 mmol, 1.00 eq.) in hydrochloric acid (10 mL, 6 M) was stirred at 60° C. for 4 h. The mixture was concentrated under reduced pressure to give 2-(4-aminopyridin-2-yl)-2-methylpropanoic acid hydrochloride (345 mg, 1.54 mmol, 90% yield) as a yellow solid.

Step 5. To a solution of 2-(4-aminopyridin-2-yl)-2-methylpropanoic acid hydrochloride (200 mg, 840 μmol, 1.00 eq.) in N,N-dimethylformamide (4 mL) were added 2-chloro-1-methylpyridin-1-ium iodide (258 mg, 1.01 mmol, 1.20 eq.) and N,N-diisopropylethylamine (590 μL, 3.39 mmol, 4.03 eq.) at 0° C. The mixture was stirred at 25° C. for 0.5 h. Then 3-(4-(aminomethyl)-2-chloro-6-fluorophenyl) piperidine-2,6-dione hydrochloride (233 mg, 759 μmol, 0.90 eq.) was added, the reaction was stirred at 25° C. for 1 h. The reaction mixture was diluted with water (35 mL), then the mixture was extracted with ethyl acetate (2×20 mL) followed by dichloromethane (3×20 mL). The combined organic layers were dried over sodium sulfate, filtered, and concentrated under reduced pressure. The residue was purified via Purification Method 1 to afford 2-(4-aminopyridin-2-yl)-N-(3-chloro-4-(2,6-dioxopiperidin-3-yl)-5-fluorobenzyl)-2-methylpropanamide (110 mg, 244 μmol, 29% yield) as a white solid.

Step 6. A mixture of 2-(4-aminopyridin-2-yl)-N-(3-chloro-4-(2,6-dioxopiperidin-3-yl)-5-fluorobenzyl)-2-methylpropanamide (100 mg, 231 μmol, 1.00 eq.) in trifluoroborane hydrofluoride (2 mL) was stirred at 0° C. for 0.5 h. Then sodium nitrite (32.0 mg, 464 μmol, 2.01 eq.) was added, and the reaction was stirred at 25° C. for 2 h. The reaction mixture was quenched by adding it to water (20 mL) at 0° C. The mixture was adjusted to pH 5 with saturated sodium bicarbonate. The mixture was extracted with dichloromethane (3×20 mL). The combined organic layers were dried over sodium sulfate, filtered, and concentrated under reduced pressure. The residue was purified via Purification Method 1 to afford N-(3-chloro-4-(2,6-dioxopiperidin-3-yl)-5-fluorobenzyl)-2-(4-fluoropyridin-2-yl)-2-methylpropanamide (33.5 mg, 74.6 μmol, 32% yield) as a white solid.

$^1$H NMR (400 MHZ, DMSO-$d_6$) δ=10.95 (s, 1H), 8.60 (dd, J=5.6, 9.2 Hz, 1H), 8.06 (t, J=6.0 Hz, 1H), 7.32 (dd, J=2.4, 10.8 Hz, 1H), 7.25 (ddd, J=2.4, 6.0, 8.8 Hz, 1H), 7.17 (s, 1H), 7.04 (d, J=11.2 Hz, 1H), 4.33 (dd, J=5.6, 12.8 Hz, 1H), 4.24 (d, J=6.0 Hz, 2H), 2.82 (ddd, J=5.6, 13.6, 17.2 Hz, 1H), 2.62-2.53 (m, 1H), 2.00-1.85 (m, 1H), 1.53 (s, 6H). MS (ESI) m/z 436.1 $[M+H]^+$ Exemplary Compound 265

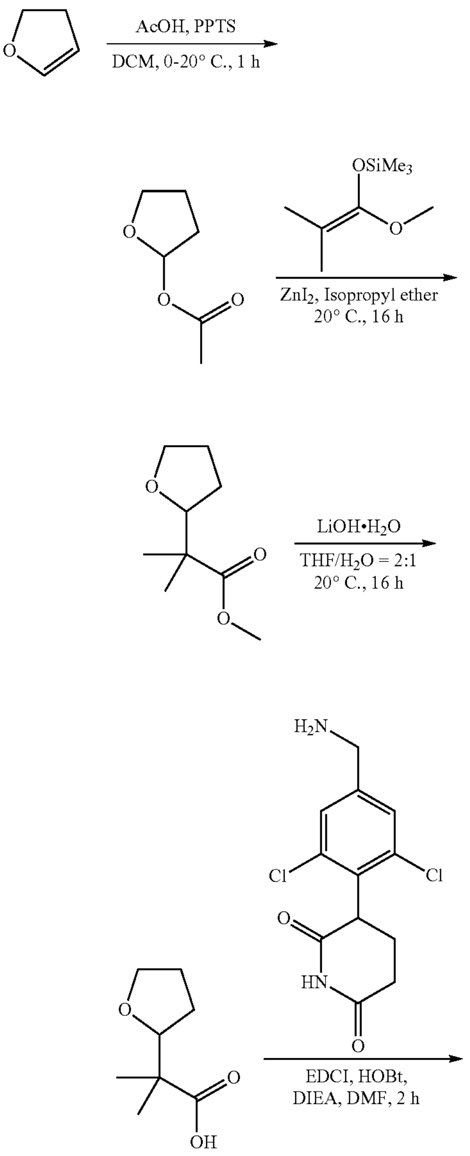

-continued

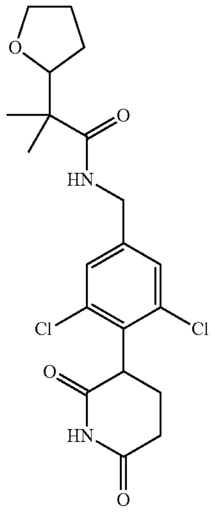 [SMILES: CC(C)(C(=O)NCc1cc(Cl)c(C2CCC(=O)NC2=O)c(Cl)c1)C1CCCO1]

Step 1. To a solution of 2,3-dihydrofuran (3.00 g, 42.8 mmol, 1.00 eq.) in dichloromethane (20 mL) was added pyridin-1-ium 4-methylbenzenesulfonate (1.08 g, 4.28 mmol, 0.10 eq.) and acetic acid (2.45 mL, 42.8 mmol, 1.00 eq.) at 0° C. The mixture was stirred at 20° C. for 1 h. The reaction mixture was diluted with water (30 mL) and extracted with ethyl acetate (2× 30 mL). The combined organic extracts were washed with brine (50 mL). The organic phase was dried over sodium sulfate, filtered, and concentrated under reduced pressure to afford tetrahydrofuran-2-yl acetate (3.70 g, 28.4 mmol, 66% yield) as a colourless oil.

Step 2. To a solution of tetrahydrofuran-2-yl acetate (1.00 g, 7.68 mmol, 1.00 eq.) and ((1-methoxy-2-methylprop-1-en-1-yl)oxy)trimethylsilane (1.34 g, 7.68 mmol, 1.00 eq.) in isopropyl ether (20 mL) was added zinc (II) iodide (1.23 g, 3.84 mmol, 0.50 eq.). The mixture was stirred at 20° C. for 16 h. The reaction mixture was diluted with water (20 mL) and extracted with ethyl acetate (2×20 mL). The combined organic extracts were washed with brine (30 mL). The organic phase was dried over sodium sulfate, filtered, and concentrated under reduced pressure. The residue was purified via Purification Method 2 to afford methyl 2-methyl-2-(tetrahydrofuran-2-yl) propanoate (200 mg, 1.16 mmol, 15% yield) as a colourless oil.

Step 3. To a solution of methyl 2-methyl-2-(tetrahydrofuran-2-yl) propanoate (200 mg, 1.16 mmol, 1.00 eq.) in tetrahydrofuran (2 mL) and water (1 mL) was added lithium hydroxide monohydrate (150 mg, 3.58 mmol, 3.08 eq.). The mixture was stirred at 20° C. for 16 h. The mixture was diluted with water (10 mL) and dichloromethane (10 mL). The aqueous phase was separated and washed with dichloromethane (10 mL). The pH of the aqueous phase was adjusted to 6 with hydrochloric acid (1 M) and extracted with dichloromethane (3×10 mL). The combined organic extracts were washed with brine (20 mL) dried over sodium sulfate, filtered, and concentrated under reduced pressure to afford 2-methyl-2-(tetrahydrofuran-2-yl) propanoic acid (100 mg, 632 μmol, 54% yield) as a colourless oil.

Step 4. To a solution of 2-methyl-2-(tetrahydrofuran-2-yl) propanoic acid (100 mg, 632 μmol, 1.70 eq.) in dimethylformamide (5 mL) was added N,N-diisopropylethylamine (194 μL, 1.12 mmol, 3.02 eq.), 1H-benzo[d][1,2,3]triazol-1-ol (75.1 mg, 556 μmol, 1.50 eq.) and 1-(3-dimethylaminopropyl)-3-ethylcarbodiimide hydrochloride (106 mg, 556 μmol, 1.50 eq.). The mixture was stirred at 25° C. for 0.5 h. Then 3-(4-(aminomethyl)-2,6-dichlorophenyl) piperidine-2,6-dione hydrochloride (120 mg, 371 μmol, 1.00 eq.) was added to the mixture and the mixture was stirred at 25° C. for 1.5 h. The reaction mixture was diluted with water (10 mL) and extracted with ethyl acetate (2×10 mL). The combined organic extracts were washed with brine (20 mL), dried over sodium sulfate, filtered, and concentrated under reduced pressure. The residue was purified via Purification Method 1 to afford N-(3,5-dichloro-4-(2,6-dioxopiperidin-3-yl)benzyl)-2-methyl-2-(tetrahydrofuran-2-yl) propanamide (128.3 mg, 297 μmol, 80% yield) as a white solid.

$^1$H NMR (400 MHZ, DMSO-$d_6$) δ=10.95 (s, 1H), 8.03 (t, J=6.0 Hz, 1H), 7.38 (d, J=1.2 Hz, 1H), 7.31 (d, J=1.2 Hz, 1H), 4.63-4.48 (m, 1H), 4.33-4.16 (m, 2H), 3.90-3.82 (m, 1H), 3.80-3.71 (m, 1H), 3.68-3.60 (m, 1H), 2.91-2.79 (m, 1H), 2.61-2.52 (m, 1H), 2.43-2.29 (m, 1H), 1.95-1.85 (m, 1H), 1.83-1.68 (m, 3H), 1.62-1.48 (m, 1H), 1.07 (d, J=3.2 Hz, 6H). MS (ESI) m/z 427.1 $[M+H]^+$

Exemplary Compound 266

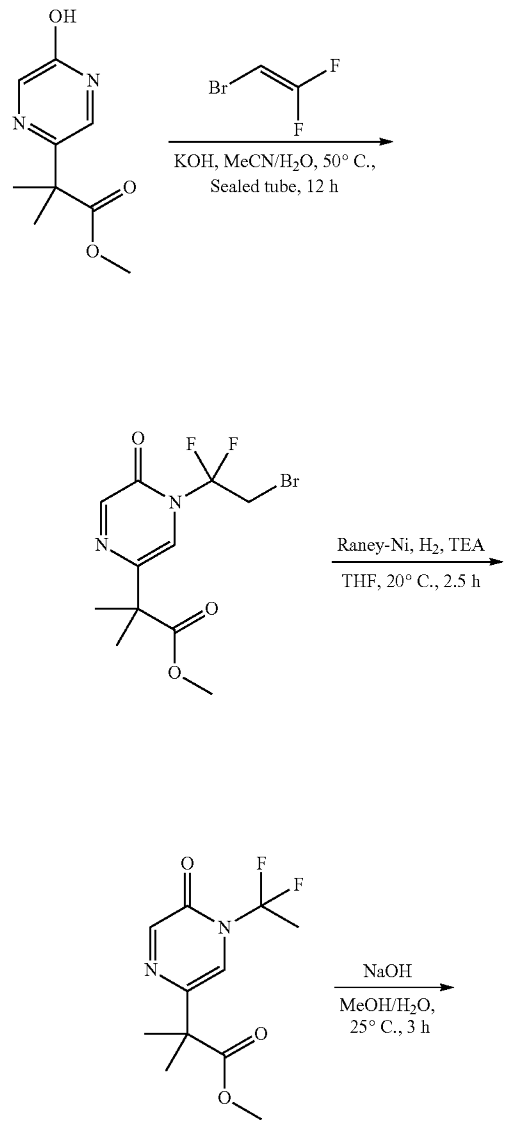

-continued

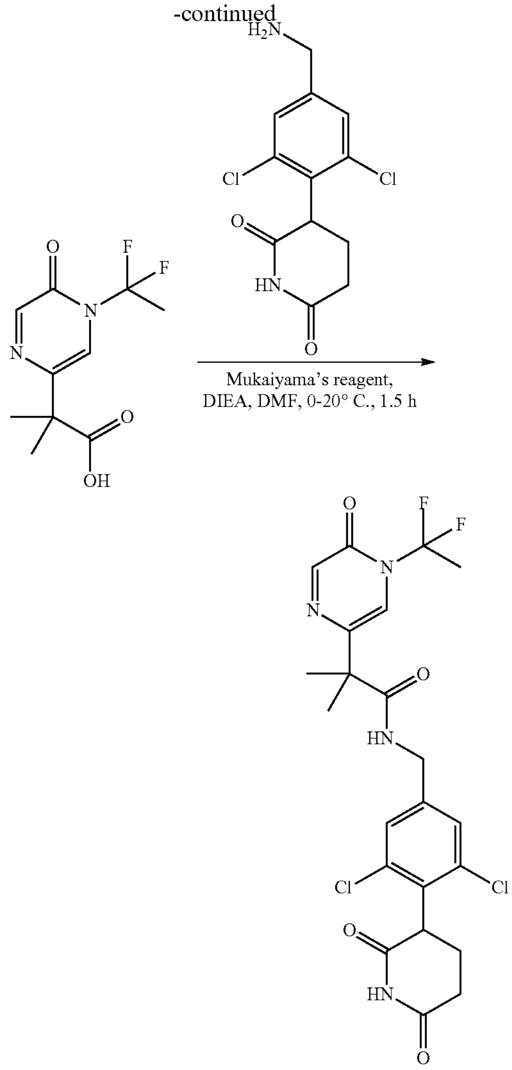

Step 1. 2-bromo-1,1-difluoroethene (5.40 g, 37.7 mmol, 7.41 eq.) was bubbled into acetonitrile (10 mL) at 0° C. to achieve a concentration of ~540 mg/mL (~3.6 M) solution. A separate flask is charged with methyl 2-(5-hydroxy-pyrazin-2-yl)-2-methylpropanoate (1.00 g, 5.10 mmol, 1.00 eq.), acetonitrile (5 mL), water (0.8 mL) and potassium hydroxide (286 mg, 5.10 mmol, 1.00 eq.). The 2-bromo-1,1-difluoroethene solution was added to the mixture. The resultant mixture was heated to 50° C. with stirring for 12 h. The mixture was diluted with water (20 mL) and extracted with ethyl acetate (2× 40 mL). Combined extracts were washed with brine (30 mL), dried over anhydrous sodium sulfate, filtered, and concentrated in vacuo. The residue was purified via Purification Method 2 to afford methyl 2-(4-(2-bromo-1,1-difluoroethyl)-5-oxo-4,5-dihydropyrazin-2-yl)-2-methylpropanoate (600 mg, 1.59 mmol, 31% yield, 90% purity) as a white solid.

Step 2. Raney-Ni (1.00 g) was added to a flask (100 mL) under nitrogen atmosphere followed by tetrahydrofuran (6 mL). Then a solution of methyl 2-(4-(2-bromo-1,1-difluoroethyl)-5-oxo-4,5-dihydropyrazin-2-yl)-2-methylpropanoate (470 mg, 1.39 mmol, 1.00 eq.) and triethylamine (701 mg, 6.93 mmol, 5.00 eq.) in tetrahydrofuran (6 mL) was added to the mixture. It was stirred at 20° C. for 2.5 h under hydrogen atmosphere (15 psi). The reaction mixture was filtered, and the filtrate was concentrated under reduced pressure. The residue was purified via Purification Method 2 to afford methyl 2-(4-(1,1-difluoroethyl)-5-oxo-4,5-dihydropyrazin-2-yl)-2-methylpropanoate (200 mg, 615 μmol, 44% yield) as a yellow oil.

Step 3. To a solution of methyl 2-(4-(1,1-difluoroethyl)-5-oxo-4,5-dihydropyrazin-2-yl)-2-methylpropanoate (260 mg, 999 μmol, 1.00 eq.) in methanol (10 mL) and water (10 mL) was added sodium hydroxide (200 mg, 5.00 mmol, 5.00 eq.). It was stirred at 25° C. for 3 h. The reaction mixture was diluted water (10 mL). Then the pH of the mixture was adjusted to 3 using 2N hydrochloric acid at 0° C. It was extracted with ethyl acetate (2×30 mL). The combined organic phases were dried over sodium sulfate, filtered, and concentrated in vacuo to give 2-(4-(1,1-difluoroethyl)-5-oxo-4,5-dihydropyrazin-2-yl)-2-methylpropanoic acid (140 mg, 455 μmol, 45% yield) as a colourless oil.

Step 4. To a solution of 2-(4-(1,1-difluoroethyl)-5-oxo-4,5-dihydropyrazin-2-yl)-2-methylpropanoic acid (120 mg, 341 μmol, 1.00 eq.) in N,N-dimethylformamide (4 mL) were added N,N-diisopropylethylamine (1.71 mmol, 300 μL, 5.00 eq.) and 2-chloro-1-methyl-pyridinium iodide (105 mg, 411 μmol, 1.20 eq.) at 0° C. It was stirred at 20° C. for 1 h. Then 3-(4-(aminomethyl)-2,6-dichlorophenyl) piperidine-2,6-dione hydrochloride (110 mg, 341 μmol, 1.00 eq.) was added to the mixture. It was stirred at 20° C. for 30 min. The mixture was diluted with water (20 mL) and extracted with ethyl acetate (2×20 mL). Combined extracts were washed with brine (15 mL), dried over anhydrous sodium sulfate, filtered, and concentrated in vacuo. The residue was purified via Purification Method 1 to afford N-(3,5-dichloro-4-(2,6-dioxopiperidin-3-yl)benzyl)-2-(4-(1,1-difluoroethyl)-5-oxo-4,5-dihydropyrazin-2-yl)-2-methylpropanamide (55.62 mg, 97.1 μmol, 28% yield) as an off-white solid.

$^1$H NMR (400 MHZ, DMSO-$d_6$)>=10.96 (s, 1H), 8.12 (s, 1H), 7.91 (t, J=5.6 Hz, 1H), 7.34 (s, 1H), 7.30 (s, 1H), 7.24 (s, 1H), 4.56 (dd, J=5.6, 12.4 Hz, 1H), 4.22 (d, J=5.6 Hz, 2H), 2.90-2.80 (m, 1H), 2.55 (m, 1H), 2.38-2.23 (m, 4H), 1.94-1.83 (m, 1H), 1.44 (s, 6H). MS (ESI) m/z 537.1 [M+Na]$^+$

Exemplary Compound 269

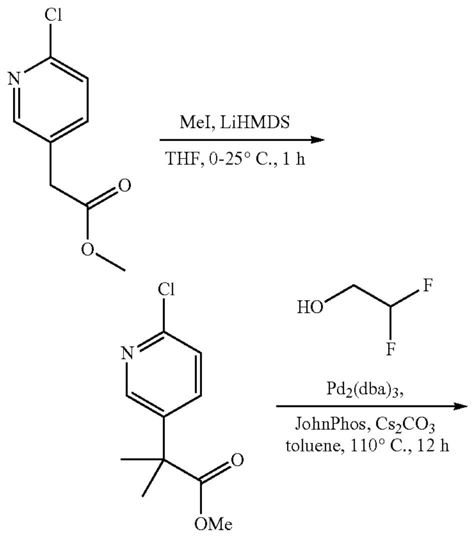

-continued

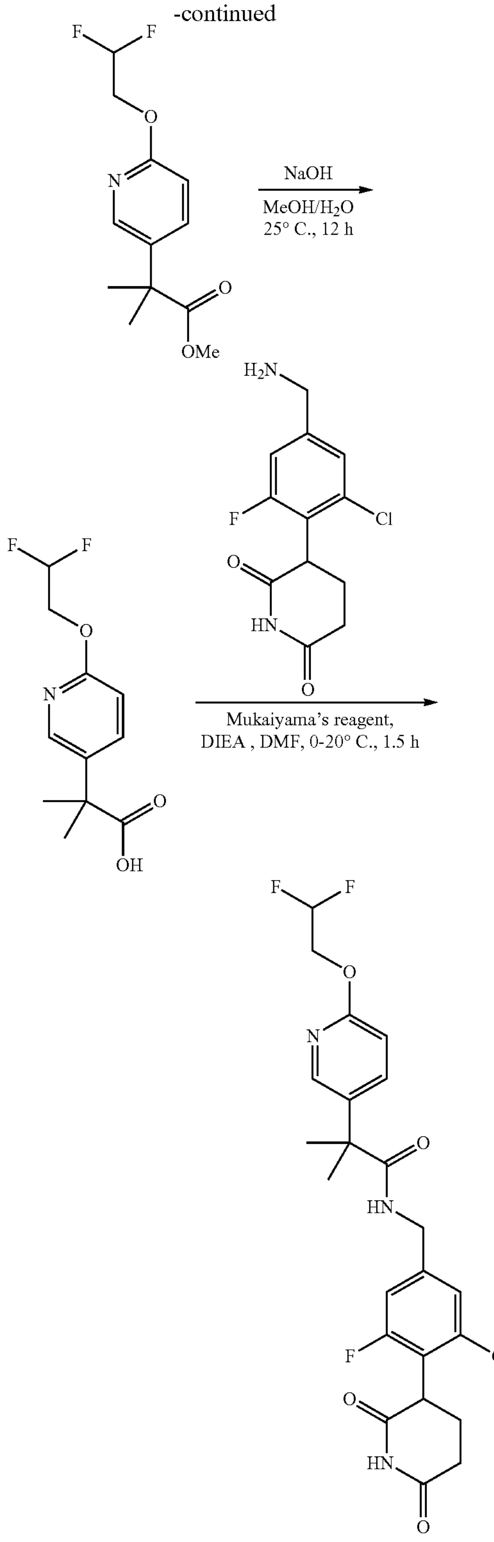

Step 1. To a solution of methyl 2-(6-chloropyridin-3-yl) acetate (2.00 g, 10.8 mmol, 1.0 eq.) in tetrahydrofuran (30 mL) was added lithium bis(trimethylsilyl)amide (1 M in tetrahydrofuran, 32 mL, 3.00 eq.) at 0° C. under nitrogen atmosphere. It was stirred at 0° C. for 30 min. Then methyl iodide (43.1 mmol, 2.7 mL, 4.00 eq.) was added to the mixture. It was stirred at 25° C. for 30 min. The reaction mixture was poured into saturated ammonium chloride (30 mL) at 0° C. The mixture was extracted with ethyl acetate (30 mL). The layers were separated, and the aqueous phase was extracted with ethyl acetate (3×30 mL). Combined extracts were washed with brine (20 mL), dried over anhydrous sodium sulfate, filtered, and concentrated in vacuo. The residue was purified via Purification Method 2 to afford methyl 2-(6-chloropyridin-3-yl)-2-methylpropanoate (2.10 g, 8.85 mmol, 82% yield, 90% purity) as a colourless oil.

Step 2. To a solution of methyl 2-(6-chloropyridin-3-yl)-2-methylpropanoate (250 mg, 1.17 mmol, 1.00 eq.) and 2,2-difluoroethan-1-ol (195 mg, 2.38 mmol, 2.03 eq.) in toluene (4 mL) were added caesium carbonate (1.15 g, 3.51 mmol, 3.00 eq.), [1,1'-biphenyl]-2-yldi-tert-butylphosphine (70.0 mg, 235 μmol, 0.200 eq.) and tris(dibenzylideneacetone) dipalladium (110 mg, 120 μmol, 0.100 eq.). The system was purged with nitrogen for three times. The mixture was stirred at 110° C. for 12 h under nitrogen atmosphere. After cooling to 25° C., the mixture was filtered, and the filter cake was washed with dichloromethane (20 mL). The filtrate was concentrated under reduced pressure to give a residue. The residue was purified via Purification Method 2 to afford methyl 2-(6-(2,2-difluoroethoxy)pyridin-3-yl)-2-methylpropanoate (150 mg, 550 μmol, 47% yield) as a colourless oil.

Step 3. To a solution of methyl 2-(6-(2,2-difluoroethoxy)pyridin-3-yl)-2-methylpropanoate (130 mg, 501 μmol, 1.00 eq.) in methanol (2 mL) was added a solution of sodium hydroxide (101 mg, 2.53 mmol, 5.04 eq.) in water (2 mL). The mixture was stirred at 25° C. for 12 h. The mixture was adjusted to pH 3 with 2 M hydrochloric acid. The mixture was extracted with dichloromethane (3× 20 mL). The combined organic layers were dried over sodium sulfate, filtered, and concentrated under reduced pressure to give 2-(6-(2,2-difluoroethoxy)pyridin-3-yl)-2-methylpropanoic acid (110 mg, 426 μmol, 85% yield) as a light-yellow oil.

Step 4. To a solution of 2-(6-(2,2-difluoroethoxy)pyridin-3-yl)-2-methylpropanoic acid (81.0 mg, 330 μmol, 1.10 eq.) in N,N-dimethylformamide (2 mL) were added 2-chloro-1-methyl-pyridin-1-ium iodide (115 mg, 450 μmol, 1.50 eq.) and N,N-diisopropylethylamine (116 mg, 901 μmol, 3.00 eq.). The mixture was stirred at 20° C. for 30 min. Then 3-(4-(aminomethyl)-2-chloro-6-fluorophenyl) piperidine-2,6-dione hydrochloride (92.2 mg, 300 μmol, 1.00 eq.) was added to the mixture. The mixture was stirred at 20° C. for 1 h. The mixture was diluted with water (25 mL) and extracted with ethyl acetate (3×10 mL). The combined organic layers were washed with water (15 mL) and brine (15 mL), dried over sodium sulfate, filtered, and concentrated under reduced pressure to give a residue. The residue was purified via Purification Method 1 to afford N-(3-chloro-4-(2,6-dioxopiperidin-3-yl)-5-fluorobenzyl)-2-(6-(2,2-difluoroethoxy)pyridin-3-yl)-2-methylpropanamide (71.3 mg, 140 μmol, 47% yield) as a white solid.

$^1H$ NMR (400 MHZ, DMSO-$d_6$) δ=10.91 (s, 1H), 8.14 (d, J=2.8 Hz, 1H), 8.06 (t, J=6.0 Hz, 1H), 7.62-7.63 (m, 1H), 7.01 (s, 1H), 6.93 (d, J=11.2 Hz, 1H), 6.88 (d, J=8.4 Hz, 1H), 6.56-6.20 (m, 1H), 4.62-4.48 (m, 2H), 4.37-4.27 (m, 1H), 4.21 (d, J=6.0 Hz, 2H), 2.92-2.72 (m, 1H), 2.58-2.51 (m, 1H), 2.26-2.03 (m, 1H), 2.00-1.88 (m, 1H), 1.51 (s, 6H). MS (ESI) m/z 498.1 $[M+H]^+$

Exemplary Compound 270

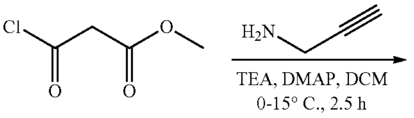

-continued

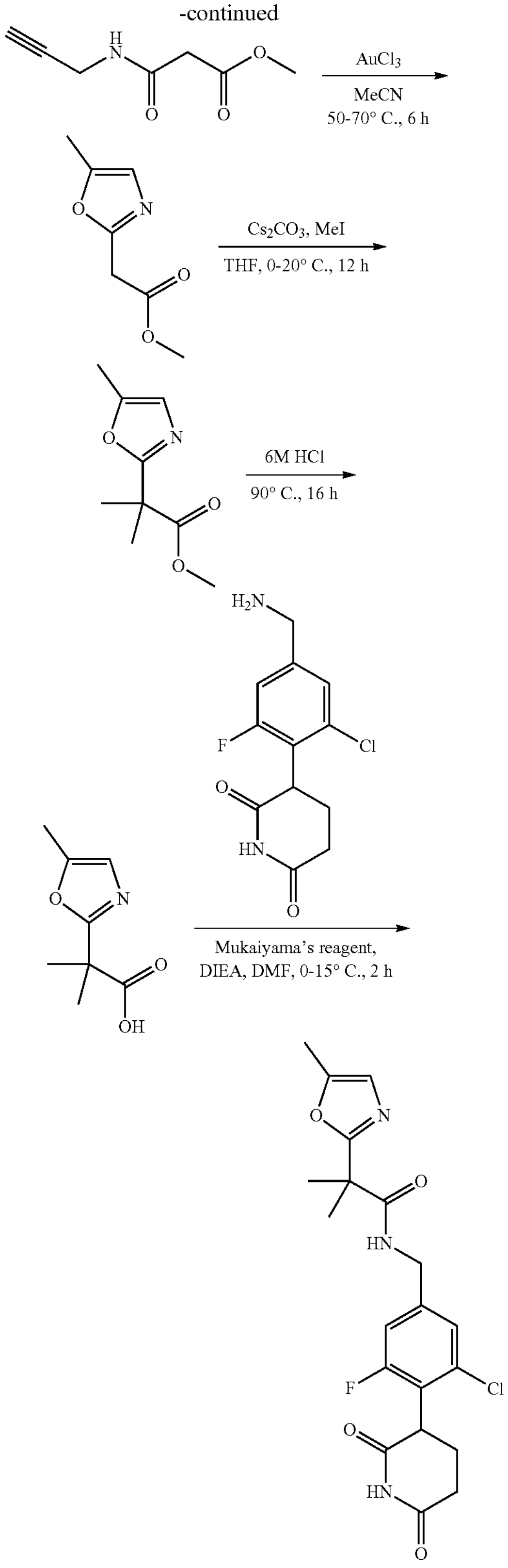

Step 1. To a solution of prop-2-yn-1-amine (2.00 g, 36.3 mmol, 1.00 eq.), triethylamine (3.71 g, 36.6 mmol, 1.01 eq.) and 4-dimethylaminopyridine (50.0 mg, 409 μmol, 0.01 eq.) in dichloromethane (50 mL) was added dropwise methyl 3-chloro-3-oxopropanoate (4.96 g, 36.3 mmol, 1.00 eq.) at 0° C. under nitrogen atmosphere. The reaction was stirred at 0° C. for 0.5 h and then stirred at 15° C. for 2 h. The reaction mixture was diluted with ethyl acetate (30 mL) and water (30 mL). The layers were separated, and the aqueous phase was extracted with ethyl acetate (2×30 mL). The combined organic layers were washed with brine (35 mL) and dried over anhydrous sodium sulfate, filtered, and concentrated in vacuo to afford crude product methyl 3-oxo-3-(prop-2-yn-1-ylamino) propanoate (3.80 g, crude) as a brown oil. The crude product was used to the next step without purification.

Step 2. A mixture of methyl 3-oxo-3-(prop-2-yn-1-ylamino) propanoate (1.90 g, 7.35 mmol, 1.00 eq.) and gold trichloride (80.0 mg, 344 μmol, 0.05 eq.) in acetonitrile (10 mL) was stirred at 50° C. for 2 h. gold trichloride (80.0 mg, 344 μmol, 0.05 eq.) was added to the mixture and the reaction was stirred at 70° C. for 4 h (the reaction was carried out with two batches in parallels). The reaction mixture was filtered, and the filtrate was concentrated on vacuo. The residue was purified via Purification Method 2 to afford methyl 2-(5-methyloxazol-2-yl)acetate (330 mg, 2.06 mmol, 14% yield) as a yellow oil.

Step 3. To a solution of methyl 2-(5-methyloxazol-2-yl) acetate (400 mg, 2.58 mmol, 1.00 eq.) and caesium carbonate (2.52 g, 7.73 mmol, 3.00 eq.) in acetonitrile (5 mL) was added methyl iodide (1.60 mL, 25.8 mmol, 10.0 eq.) at 0° C. The reaction was stirred at 20° C. for 12 h. The reaction mixture was diluted with ethyl acetate (10 mL) and water (10 mL). The layers were separated, and the aqueous phase was extracted with ethyl acetate (10 mL). The combined organic layers were washed with brine (20 mL) and dried over anhydrous sodium sulfate, filtered, and concentrated in vacuo. The residue was purified via Purification Method 2 to afford methyl 2-methyl-2-(5-methyloxazol-2-yl) propanoate (180 mg, 963 μmol, 37% yield) as a colourless oil.

Step 4. A mixture of methyl 2-methyl-2-(5-methyloxazol-2-yl) propanoate (170 mg, 928 μmol, 1.00 eq.) in hydrochloric acid (6 M, 4 mL) was stirred at 90° C. for 16 h. The reaction mixture was concentrated in vacuo. The residue was purified via Purification Method 1 to afford 2-methyl-2-(5-methyloxazol-2-yl) propanoic acid (70.0 mg, 410 μmol, 44% yield) as a white solid.

Step 5. To a solution of 2-methyl-2-(5-methyloxazol-2-yl) propanoic acid (95.0 mg, 562 μmol, 1.00 eq.) and N,N-diisopropylethylamine (228 mg, 1.76 mmol, 3.14 eq.) in dimethylformamide (4 mL) was added 2-chloro-1-methyl-pyridin-1-ium iodide (171 mg, 669 μmol, 1.19 eq.) at 0° C. The reaction was stirred at 15° C. for 0.5 h. Then 3-(4-(aminomethyl)-2-chloro-6-fluorophenyl) piperidine-2,6-dione hydrochloride (170 mg, 553 μmol, 1.00 eq.) was added to the mixture. The reaction mixture was stirred at 15° C. for 1.5 h. The reaction mixture was diluted with ethyl acetate (15 mL) and water (15 mL). The layers were separated, and the aqueous phase was extracted with ethyl acetate (15 mL). The combined organic layers were washed with brine (20 mL) and dried over anhydrous sodium sulfate, filtered, and concentrated in vacuo. The residue was purified via Purification Method 1 to afford N-(3-chloro-4-(2,6-dioxopiperidin-3-yl)-5-fluorobenzyl)-2-methyl-2-(5-methyloxazol-2-yl) propanamide (59.97 mg, 139 μmol, 25% yield) as a white solid.

$^1$H NMR (400 MHZ, DMSO-$d_6$)>=10.95 (s, 1H), 8.27 (t, J=6.0 Hz, 1H), 7.15 (s, 1H), 7.00 (d, J=11.2 Hz, 1H), 6.77 (s, 1H), 4.34 (dd, J=5.2, 12.4 Hz, 1H), 4.25 (d, J=6.0 Hz, 2H), 2.91-2.76 (m, 1H), 2.54 (d, J=3.2 Hz, 1H), 2.27 (s, 3H), 2.24-2.02 (m, 1H), 2.01-1.88 (m, 1H), 1.52 (s, 6H). MS (ESI) m/z 422.2 $[M+H]^+$

Exemplary Compounds 273 and 274

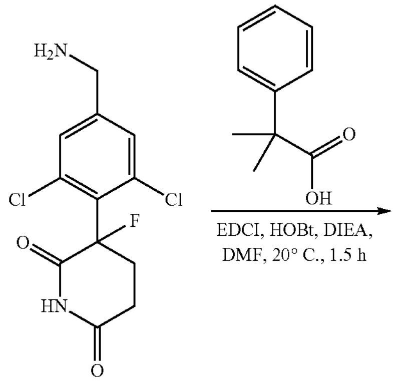

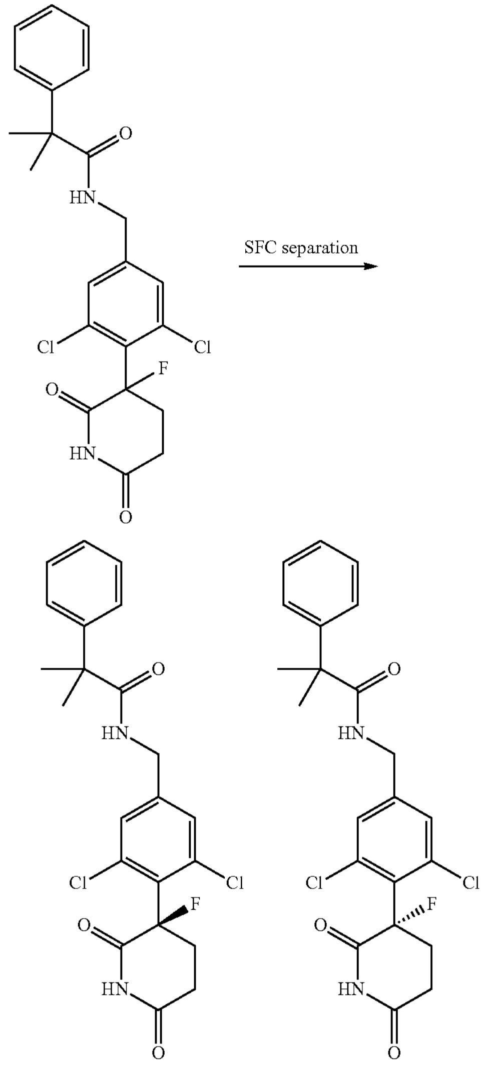

Compound 273 Compound 274

Note: for these enantiomers, their absolute configuration was not determined and was assigned arbitrarily.

Step 1. To a solution of 2-methyl-2-phenylpropanoic acid (173 mg, 1.05 mmol, 1.20 eq.), 1-(3-dimethylaminopropyl)-3-ethylcarbodiimide hydrochloride (202 mg, 1.05 mmol, 1.20 eq.) and N,N-diisopropylethylamine (341 mg, 2.63 mmol, 3.00 eq.) in N,N-dimethylformamide (3 mL) was added 1-hydroxybenzotriazole (142 mg, 1.05 mmol, 1.20 eq.). The mixture was stirred at 20° C. for 30 min. Then 3-(4-(aminomethyl)-2,6-dichlorophenyl)-3-fluoropiperidine-2,6-dione hydrochloride (300 mg, 878 μmol, 1.00 eq.) was added. The reaction was stirred at 20° C. for 1 h.

The mixture was diluted with water (25 mL) and extracted with ethyl acetate (3×10 mL). The combined organic layers were washed with water (15 mL) and brine (15 mL), dried over sodium sulfate, filtered, and concentrated under reduced pressure. The residue was purified via Purification Method 1 to afford N-(3,5-dichloro-4-(3-fluoro-2,6-dioxopiperidin-3-yl)benzyl)-2-methyl-2-phenylpropanamide (310 mg, 680 μmol, 77% yield) as a yellow solid.

N-(3,5-dichloro-4-(3-fluoro-2,6-dioxopiperidin-3-yl)benzyl)-2-methyl-2-phenylpropanamide (310 mg, 687 μmol) was separated by SFC (column: DAICEL CHIRALPAK IC (250 mm*30 mm, 10 μm); mobile phase: [carbon dioxide-propan-2-ol and formic acid]; B %: 35%, isocratic elution mode) to give peak 1 and peak 2.

Peak 1 was purified by Prep-HPLC (column: Welch Xtimate C18 150*25 mm*5 μm; mobile phase: [water (formic acid)-acetonitrile]; gradient: 40%-60% B over 10 min) and lyophilized to give (R)—N-(3,5-dichloro-4-(3-fluoro-2,6-dioxopiperidin-3-yl)benzyl)-2-methyl-2-phenylpropanamide (90.04 mg, 197.51 μmol, 29% yield) as a white solid.

$^1$H NMR (400 MHZ, DMSO-$d_6$) δ=11.53 (s, 1H), 8.04 (t, J=6.0 Hz, 1H), 7.38-7.29 (m, 4H), 7.28-7.23 (m, 1H), 7.21 (s, 2H), 4.23 (d, J=6.0 Hz, 2H), 2.91-2.57 (m, 3H), 2.49-2.40 (m, 1H), 1.49 (s, 6H). MS (ESI) m/z 451.1 $[M+H]^+$

Peak 2 was purified by Prep-HPLC (column: Welch Xtimate C18 150*25 mm*5 μm; mobile phase: [water (formic acid)-acetonitrile]; gradient: 40%-60% B over 10 min) and lyophilized to give(S)—N-(3,5-dichloro-4-(3-fluoro-2,6-dioxopiperidin-3-yl)benzyl)-2-methyl-2-phenylpropanamide (85.94 mg, 188.52 μmol, 27% yield) as a white solid.

$^1$H NMR (400 MHZ, DMSO-$d_6$) δ=11.52 (s, 1H), 8.03 (t, J=6.0 Hz, 1H), 7.36-7.29 (m, 4H), 7.27-7.22 (m, 1H), 7.20 (s, 2H), 4.22 (d, J=6.0 Hz, 2H), 2.89-2.57 (m, 3H), 2.48-2.38 (m, 1H), 1.48 (s, 6H). MS (ESI) m/z 451.1 $[M+H]^+$

TABLE 2

Exemplary compounds - additional examples

| Compound ID | Synthesis | Characterization |
|---|---|---|
| Compound 3 | Synthesized in analogy to compound 5 | $^1$H NMR (400 MHz, DMSO-$d_6$) δ = 10.96 (s, 1H), 8.74 (d, J = 1.6 Hz, 2H), 8.19 (t, J = 5.6 Hz, 1H), 7.26 (d, J = 8.0 Hz, 1H), 7.18 (s, 1H), 7.15 − 7.08 (m, 1H), 4.23 (d, J = 6.0 Hz, 2H), 4.16 (dd, J = 5.2, 12.4 Hz, 1H), 2.82 − 2.68 (m, 1H), 2.53 (m, 1H), 2.32 − 2.20 (m, 1H), 2.03 − 1.87 (m, 1H), 1.58 (s, 6H). MS (ESI) m/z 419.2 $[M + H]^+$ |
| Compound 8 | Synthesized in analogy to compound 6 | $^1$H NMR (400 MHz, DMSO-$d_6$) δ = 10.96 (s, 1H), 9.04 (d, J = 3.2 Hz, 1H), 8.78 (d, J = 3.2 Hz, 1H), 8.31 (t, J = 6.0 Hz, 1H), 7.34 (d, J = 1.6 Hz, 1H), 7.27 (d, J = 1.2 Hz, 1H), 4.57 (dd, J = 5.6, 12.4 Hz, 1H), 4.26 (d, J = 6.0 Hz, 2H), 2.93 − 2.78 (m, 1H), 2.61 − 2.52 (m, 1H), 2.42 − 2.33 (m, 1H), 1.95 − 1.82 (m, 1H), 1.54 (s, 6H). MS (ESI) m/z 453.1 $[M + H]^+$ |
| Compound 11 | Synthesized in analogy to compound 6 | $^1$H NMR (400 MHz, DMSO-$d_6$) δ = 10.96 (s, 1H), 8.87 (s, 2H), 8.06 (t, J = 6.0 Hz, 1H), 7.36 (s, 1H), 7.30 (d, J = 1.2 Hz, 1H), 4.56 (dd, J = 5.6, 12.8 Hz, 1H), 4.24 (d, J = 6.0 Hz, 2H), 2.92 − 2.79 (m, 1H), 2.55 (d, J = 1.6 Hz, 1H), 2.40 − 2.29 (m, 1H), 1.95 − 1.84 (m, 1H), 1.56 (s, 6H). MS (ESI) m/z 453.1 $[M + H]^+$ |
| Compound 12 | Synthesized in analogy to compound 10 | $^1$H NMR (400 MHz, DMSO-$d_6$) δ = 10.94 (s, 1H), 8.14 (t, J = 6.0 Hz, 1H), 7.54 − 7.49 (m, 2H), 7.23 (d, J = 1.2 Hz, 1H), 7.16 (d, J = 1.2 Hz, 1H), 4.57 − 4.53 (m, 1H), 4.22 (d, J = 6.0 Hz, 2H), 2.89 − 2.80 (m, 1H), 2.60 (s, 3H), 2.56 − 2.55 (m, 1H), 2.40 − 2.29 (m, 1H), 1.91 − 1.86 (m, 1H), 1.59 (s, 6H). MS (ESI) m/z 449.1 $[M + H]^+$ |
| Compound 13 | Synthesized in analogy to compound 10 | $^1$H NMR (400 MHz, DMSO-$d_6$) δ = 10.97 (br s, 1H), 9.00 (s, 2H), 8.28 − 8.25 (t, J = 5.6 Hz, 1H), 7.24 (s, 1H), 7.19 (d, J = 1.2 Hz, 1H), 4.59 − 4.54 (dd, J = 5.6, 12.8 Hz, 1H), 4.23 (d, J = 5.6 Hz, 2H), 2.90 − 2.81 (ddd, J = 5.6, 14.0, 16.8 Hz, 1H), 2.55 − 2.54 (m, 1H), 2.40 − 2.29 (dq, J = 4.4, 13.2 Hz, 1H), 1.91 − 1.86 (m, 1H), 1.61 (s, 6H). MS (ESI) m/z 460.3 $[M + H]^+$ |
| Compound 17 | Synthesized in analogy to compound 10 | $^1$H NMR (400 MHz, DMSO-$d_6$) δ = 10.94 (s, 1H), 8.73 (s, 1H), 8.01 (t, J = 6.0 Hz, 1H), 7.78 (d, J = 1.6 Hz, 1H), 7.70 (d, J = 8.4 Hz, 1H), 7.35 (dd, J = 2.0, 8.4 Hz, 1H), 7.09 (d, J = 1.6 Hz, 1H), 7.01 (d, J = 1.6 Hz, 1H), 4.52 (dd, J = 5.6, 12.8 Hz, 1H), 4.19 (d, J = 6.0 Hz, 2H), 2.91 − 2.76 (m, 1H), 2.58 − 2.52 (m, 1H), 2.41 − 2.25 (m, 1H), 1.90 − 1.81 (m, 1H), 1.57 (s, 6H). MS (ESI) m/z 474.1 $[M + H]^+$ |
| Compound 18 | Synthesized in analogy to compound 21 | $^1$H NMR (400 MHz, DMSO-$d_6$) δ = 10.88 (s, 1H), 8.08 (t, J = 6.0 Hz, 1H), 7.77 − 7.68 (m, 2H), 7.66 − 7.60 (m, 1H), 7.58 − 7.50 (m, 1H), 7.23 (d, J = 8.0 Hz, 1H), 7.11 − 7.02 (m, 2H), 4.22 (d, J = 6.0 Hz, 2H), 4.19 − 4.09 (m, 1H), 2.82 − 2.68 (m, 1H), 2.58 − 2.51 (m, 1H), 2.34 − 2.18 (m, 1H), 2.01 − 1.87 (m, 1H), 1.52 (s, 6H). MS (ESI) m/z 424.2 $[M + H]^+$ |
| Compound 20 | Synthesized in analogy to compound 7 | $^1$H NMR (400 MHz, DMSO-$d_6$) δ = 10.95 (s, 1H), 8.57 (dd, J = 0.8, 4.8 Hz, 1H), 8.02 (t, J = 6.0 Hz, 1H), 7.85 −7.70 (m, 1H), 7.39 (d, J = 8.0 Hz, 1H), 7.33 (s, 1H), 7.31 − 7.22 (m, 2H), 4.55 (dd, J = 5.6, 12.4 Hz, 1H), 4.24 (d, J = 6.0 Hz, 2H), 2.95 − 2.74 (m, 1H), 2.59 − 2.51 (m, 1H), 2.44 − 2.25 (m, 1H), 1.98 − 1.81 (m, 1H), 1.52 (s, 6H). MS (ESI) m/z 434.1 $[M + H]^+$ |
| Compound 22 | Synthesized in analogy to Compound 21 | $^1$H NMR (400 MHz, DMSO-$d_6$) δ = 10.96 (s, 1H), 8.53 (d, J = 3.2 Hz, 1H), 8.04 − 8.01 (t, J = 6.0 Hz, 1H), 7.73 − 7.68 (dt, J = 3.2, 8.8 Hz, 1H), 7.49 − 7.46 (dd, J = 4.4, 8.8 Hz, 1H), 7.28 (s, 1H), 7.22 (d, J = 1.2 Hz, 1H), 4.59 − 4.54 (dd, J = 5.6, 12.8 Hz, 1H), 4.24 − 4.23 (d, J = 6.0 Hz, 2H), 2.91 − 2.81 (m, 1H), 2.57 − 2.56 (m, 1H), 2.41 − 2.30 (dq, J = 4.4, 13.2 Hz, 1H), 1.92 − 1.87 (m, 1H), 1.53 (s, 6H). MS (ESI) m/z 452.1 $[M + H]^+$ |
| Compound 23 | Synthesized in analogy to Compound 9, with 2,2,2-trifluoroethyl trifluoro-methanesulfonate as the | $^1$H NMR (400 MHz, DMSO-$d_6$) δ = 10.95 (s, 1H), 8.21 (t, J = 6.0 Hz, 1H), 7.60 (d, J = 7.2 Hz, 1H), 7.24 (s, 1H), 7.17 (s, 1H), 6.41 (d, J = 2.0 Hz, 1H), 6.16 (dd, J = 2.0, 7.2 Hz, 1H), 4.82 (q, J = 9.2 Hz, 2H), 4.56 (dd, J = 5.6, 12.8 Hz, 1H), 4.22 (d, J = 6.0 Hz, 2H), 2.97 − 2.76 (m, 1H), 2.55 (d, J = 2.0 Hz, 1H), 2.39 − 2.30 (m, 1H), 1.96 − 1.81 (m, 1H), 1.41 (s, 6H). MS (ESI) m/z 532.2 $[M + H]^+$ |

TABLE 2-continued

Exemplary compounds - additional examples

| Compound ID | Synthesis | Characterization |
| --- | --- | --- |
| | alkylating agent | |
| Compound 24 | Synthesized in analogy to compound 26 | $^1H$ NMR (400 MHz, DMSO-$d_6$) δ = 10.90 (s, 1H), 7.89 (t, J = 5.6 Hz, 1H), 7.43 (t, J = 7.6 Hz, 1H), 7.36 − 7.29 (m, 1H), 7.28 − 7.17 (m, 3H), 7.17 − 7.07 (m, 2H), 4.28 − 4.08 (m, 3H), 2.84 − 2.71 (m, 1H), 2.54 (d, J = 3.2 Hz, 1H), 2.27 (d, J = 3.6, 12.8 Hz, 1H), 2.01 − 1.89 (m, 1H), 1.48 (s, 6H). MS (ESI) m/z 417.3 $[M + H]^+$ |
| Compound 27 | Synthesized in analogy to compound 25 | H NMR (400 MHz, DMSO-$d_6$) δ = 10.96 (s, 1H), 8.08 (t, J = 6.0 Hz, 1H), 7.46 − 7.32 (m, 1H), 7.18 (s, 1H), 7.16 − 7.00 (m, 4H), 4.55 (dd, J = 5.6, 12.8 Hz, 1H), 4.21 (d, J = 6.0 Hz, 2H), 2.85 (ddd, J = 5.2, 13.6, 16.4 Hz, 1H), 2.55 (s, 1H), 2.34 (dq, J = 4.4, 13.2 Hz, 1H), 1.97 − 1.80 (m, 1H), 1.49 (s, 6H). MS (ESI) m/z 451.2$[M + H]^+$ |
| Compound 26 | Synthesized in analogy to compound 130 | $^1H$ NMR (400 MHz, DMSO-$d_6$) δ = 10.97 (s, 1H), 7.92 (t, J = 6.0 Hz, 1H), 7.44 (d, J = 1.6, 8.0 Hz, 1H), 7.37 − 7.28 (m, 2H), 7.26 − 7.18 (m, 2H), 7.16 − 7.11 (m, 1H), 4.56 (dd, J = 5.6, 12.8 Hz, 1H), 4.20 (d, J = 6.0 Hz, 2H), 2.90 − 2.81 (m, 1H), 2.60 − 2.53 (m, 1H), 2.35 (d, J = 4.4, 13.2 Hz, 1H), 1.94 − 1.84 (m, 1H), 1.47 (s, 6H). MS (ESI) m/z 451.3 $[M + H]^+$ |
| Compound 28 | Synthesized in analogy to compound 130 | $^1H$ NMR (400 MHz, DMSO-$d_6$) δ = 10.90 (s, 1H), 8.10 (t, J = 6.0 Hz, 1H), 7.80 (d, J = 8.4 Hz, 2H), 7.50 (d, J = 8.4 Hz, 2H), 7.24 (d, J = 8.0 Hz, 1H), 7.12 − 7.00 (m, 2H), 4.22 (d, J = 6.0 Hz, 2H), 4.16 (dd, J = 4.8, 12.4 Hz, 1H), 2.82 − 2.69 (m, 1H), 2.54 (d, J = 3.6 Hz, 1H), 2.27 (dq, J = 4.4, 12.8 Hz, 1H), 1.99 − 1.90 (m, 1H), 1.51 (s, 6H). MS (ESI) m/z 424.3$[M + H]^+$ |
| Compound 29 | Synthesized in analogy to compound 130 | $^1H$ NMR (400 MHz, DMSO-$d_6$) δ = 10.97 (s, 1H), 8.13 (t, J = 5.6 Hz, 1H), 7.87 − 7.72 (m, 2H), 7.55 − 7.43 (m, 2H), 7.13 (s, 1H), 7.07 (s, 1H), 4.55 (dd, J = 5.6, 12.4 Hz, 1H), 4.21 (d, J = 5.6 Hz, 2H), 2.93 − 2.77 (m, 1H), 2.55 (s, 1H), 2.34 (dq, J = 4.4, 13.2 Hz, 1H), 1.93 − 1.82 (m, 1H), 1.51 (s, 6H). MS (ESI) m/z 458.2$[M + H]^+$ |
| Compound 30 | Synthesized in analogy to compound 96 | $^1H$ NMR (400 MHz, DMSO-$d_6$) δ = 10.86 (s, 1H), 7.97 (t, J = 6.0 Hz, 1H), 7.39 − 7.29 (m, 2H), 7.23 (d, J = 8.0 Hz, 1H), 7.18 − 7.03 (m, 4H), 4.21 (d, J = 6.0 Hz, 2H), 4.15 (dd, J = 5.2, 12.4 Hz, 1H), 2.81 − 2.70 (m, 1H), 2.56 − 2.52 (m, 1H), 2.36 − 2.18 (m, 1H), 2.04 − 1.86 (m, 1H), 1.48 (s, 6H). MS (ESI) m/z 417.0 $[M + H]^+$ |
| Compound 31 | Synthesized in analogy to compound 37 | $^1H$ NMR (400 MHz, DMSO-$d_6$) δ = 10.95 (s, 1H), 8.01 (t, J = 6.0 Hz, 1H), 7.44 − 7.29 (m, 4H), 7.28 − 7.20 (m, 1H), 7.04 (s, 1H), 6.90 (d, J = 11.2 Hz, 1H), 4.32 (dd, J = 5.2, 12.4 Hz, 1H), 4.21 (d, J = 5.6 Hz, 2H), 2.91 − 2.75 (m, 1H), 2.59 − 2.51 (m, 1H), 2.27 − 2.01 (m, 1H), 2.00 − 1.85 (m, 1H), 1.49 (s, 6H). MS (ESI) m/z 417.1 $[M + H]^+$ |
| Compound 33 | Synthesized in analogy to compound 6 | $^1H$ NMR (400 MHz, DMSO-$d_6$) δ = 10.95 (s, 1H), 9.62 (s, 1H), 9.28 (s, 1H), 8.12 − 8.09 (m, 2H), 8.00 − 7.95 (m, 2H), 7.12 (d, J = 1.2 Hz, 1H), 7.06 (d, J = 1.2 Hz, 1H), 4.54 − 4.50 (dd, J = 5.6, 12.6 Hz, 1H), 4.22 − 4.20 (d, J = 6.0 Hz, 2H), 2.85 − 2.80 (ddd, J = 5.6, 14.0, 16.8 Hz, 1H), 2.53 − 2.53 (m, 1H), 2.33 − 2.29 (m, 1H), 1.87 − 1.84 (m, 1H), 1.63 (s, 6H). MS (ESI) m/z 485.1 $[M + H]^+$ |
| Compound 34 | Synthesized in analogy to compound 7 | $^1H$ NMR (400 MHz, DMSO-$d_6$) δ = 10.96 (s, 1H), 8.81 (d, J = 4.8 Hz, 2H), 8.11 − 8.08 (t, J = 6.0 Hz, 1H), 7.43 − 7.39 (m, 2H), 7.36 (d, J = 1.2 Hz, 1H), 4.59 − 4.54 (dd, J = 5.6, 12.8 Hz, 1H), 4.26 (d, J = 5.6 Hz, 2H), 2.90 − 2.81 (ddd, J = 5.6, 14.0, 16.8 Hz, 1H), 2.57 − 2.52 (m, 1H), 2.41 − 2.30 (dq, J = 4.4, 13.2 Hz, 1H), 1.92 − 1.86 (m, 1H), 1.55 (s, 6H). MS (ESI) m/z 435.2 $[M + H]^+$ |
| Compound 40 | Synthesized in analogy to compound 32 | $^1H$ NMR (400 MHz, DMSO-$d_6$) δ = 10.96 (s, 1H), 8.19 − 8.09 (m, 1H), 7.79 (s, 1H), 7.76 (d, J = 8.8 Hz, 1H), 7.53 − 7.45 (m, 2H), 7.17 (s, 1H), 7.09 (s, 1H), 4.55 (dd, J = 5.6, 12.8 Hz, 1H), 4.37 (s, 2H), 4.21 (d, J = 5.6 Hz, 2H), 2.91 − 2.78 (m, 1H), 2.55 (s, 1H), 2.34 (dd, J = 3.2, 13.2 Hz, 1H), 1.93 − 1.82 (m, 1H), 1.52 (s, 6H). MS (ESI) m/z 524.1 $[M + H]^+$ |

TABLE 2-continued

| Exemplary compounds - additional examples | | |
|---|---|---|
| Compound ID | Synthesis | Characterization |
| Compound 41 | Synthesized in analogy to compound 10 | $^1$H NMR (400 MHz, DMSO-$d_6$) δ = 10.95 (s, 1H), 9.36 (d, J = 5.6 Hz, 1H), 8.41 (d, J = 9.2 Hz, 1H), 8.22 (d, J = 6.0 Hz, 1H), 8.12 (t, J = 6.0 Hz, 1H), 8.00 (d, J = 1.6 Hz, 1H), 7.85 (dd, J = 2.0, 9.2 Hz, 1H), 7.15 (s, 1H), 7.08 (s, 1H), 4.53 (dd, J = 5.6, 12.8 Hz, 1H), 4.22 (d, J = 6.0 Hz, 2H), 2.84 (ddd, J = 5.6, 14.0, 16.8 Hz, 1H), 2.57 − 2.51 (m, 1H), 2.39 − 2.25 (m, 1H), 1.93 − 1.81 (m, 1H), 1.63 (s, 6H). MS (ESI) m/z 485.2. $[M + H]^+$ |
| Compound 45 | Synthesized in analogy to compound 9 | $^1$H NMR (400 MHz, DMSO-$d_6$) δ = 10.96 (s, 1H), 8.14 (t, J = 6.0 Hz, 1H), 7.61 (d, J = 6.8 Hz, 1H), 7.22 (s, 1H), 7.15 (s, 1H), 6.32 (d, J = 2.0 Hz, 1H), 6.04 (dd, J = 2.0, 7.2 Hz, 1H), 4.55 (dd, J = 5.6, 12.8 Hz, 1H), 4.21 (d, J = 6.0 Hz, 2H), 3.86 (q, J = 7.2 Hz, 2H), 2.85 (ddd, J = 6.0, 14.0, 16.8 Hz, 1H), 2.54 (d, J = 2.8 Hz, 1H), 2.37 − 2.28 (m, 1H), 1.94 − 1.82 (m, 1H), 1.39 (s, 6H), 1.19 (t, J = 6.8 Hz, 3H). MS (ESI) m/z 478.2, 480.2 $[M + H]^+$ |
| Compound 46 | Synthesized in analogy to compound 10 | $^1$H NMR (400 MHz, DMSO-$d_6$) δ = 10.96 (s, 1H), 8.55 (d, J = 5.2 Hz, 1H), 8.09 (t, J = 6.0 Hz, 1H), 7.27 (d, J = 1.6 Hz, 1H), 7.21 (d, J = 1.6 Hz, 1H), 7.09 (d, J = 5.2 Hz, 1H), 4.56 (dd, J = 5.2, 12.4 Hz, 1H), 4.23 (d, J = 6.0 Hz, 2H), 3.88 (s, 3H), 2.93 − 2.78 (m, 1H), 2.59 − 2.51 (m, 1H), 2.35 (dq, J = 4.4, 13.2 Hz, 1H), 1.94 − 1.82 (m, 1H), 1.49 (s, 6H). MS (ESI) m/z 465.1, 467.1 $[M + H]^+$ |
| Compound 49 | Synthesized in analogy to compound 7 | $^1$H NMR (400 MHz, DMSO-$d_6$) δ = 10.95 (s, 1H), 8.94 (dd, J = 2.0, 10.0 Hz, 2H), 8.13 (t, J = 6.0 Hz, 1H), 8.09 − 8.01 (m, 2H), 7.77 (dd, J = 2.0, 8.8 Hz, 1H), 7.11 (d, J = 1.6 Hz, 1H), 7.04 (d, J = 1.2 Hz, 1H), 4.51 (dd, J = 5.6, 12.8 Hz, 1H), 4.21 (d, J = 6.0 Hz, 2H), 2.83 (ddd, J = 6.0, 14.0, 16.8 Hz, 1H), 2.57 − 2.52 (m, 1H), 2.30 (dq, J = 4.4, 13.2 Hz, 1H), 1.89 − 1.79 (m, 1H), 1.64 (s, 6H). MS (ESI) m/z 485.1$[M + H]^+$ |
| Compound 53 | Synthesized in analogy to compound 9 | $^1$H NMR (400 MHz, DMSO-$d_6$) δ = 10.95 (s, 1H), 8.09 (t, J = 6.0 Hz, 1H), 7.22 (d, J = 1.2 Hz, 1H), 7.13 (d, J = 1.2 Hz, 1H), 6.24 (d, J = 1.6 Hz, 1H), 5.95 (d, J = 1.2 Hz, 1H), 4.55 (dd, J = 5.6, 12.8 Hz, 1H), 4.20 (d, J = 6.0 Hz, 2H), 3.38 (s, 3H), 2.85 (ddd, J = 5.6, 14.0, 16.8 Hz, 1H), 2.62 − 2.52 (m, 1H), 2.34 (dd, J = 4.0, 13.6 Hz, 1H), 2.30 (s, 3H), 1.92 − 1.84 (m, 1H), 1.38 (s, 6H). MS (ESI) m/z 478.1 $[M + H]^+$ |
| Compound 54 | Synthesized in analogy to compound 50 | $^1$H NMR (400 MHz, DMSO-$d_6$) δ = 10.95 (s, 1H), 9.71 (s, 1H), 8.00 (t, J = 5.6 Hz, 1H), 7.33 − 7.25 (m, 1H), 7.21 (d, J = 6.8 Hz, 2H), 7.14 − 7.07 (m, 2H), 7.04 (d, J = 7.6 Hz, 1H), 4.59 − 4.50 (m, 1H), 4.20 (d, J = 5.6 Hz, 2H), 2.95 (s, 3H), 2.91 − 2.79 (m, 1H), 2.59 − 2.52 (m, 1H), 2.42 − 2.26 (m, 1H), 1.93 − 1.82 (m, 1H), 1.46 (s, 6H). MS (ESI) m/z 526.2 $[M + H]^+$ |
| Compound 55 | Synthesized in analogy to compound 35 | $^1$H NMR (400 MHz, DMSO-$d_6$) δ = 10.94 (s, 1H), 8.70 (d, J = 7.2 Hz, 1H), 8.16 (d, J = 1.2 Hz, 1H), 8.14 − 8.10 (m, 1H), 7.92 (d, J = 1.6 Hz, 1H), 7.67 (s, 1H), 7.17 (d, J = 1.2 Hz, 1H), 7.14 (dd, J = 1.6, 7.2 Hz, 1H), 7.08 (d, J = 1.2 Hz, 1H), 4.53 (dd, J = 5.6, 12.8 Hz, 1H), 4.22 (d, J = 6.0 Hz, 2H), 2.90 − 2.76 (m, 1H), 2.57 − 2.52 (m, 1H), 2.32 (dq, J = 4.0, 13.2 Hz, 1H), 1.92 − 1.81 (m, 1H), 1.58 (s, 6H). MS (ESI) m/z 473.2 $[M + H]^+$ |
| Compound 57 | Synthesized in analogy to compound 51 | $^1$H NMR (400 MHz, DMSO-$d_6$) δ = 10.95 (s, 1H), 8.12 (t, J = 6.0 Hz, 1H), 7.65 (t, J = 8.0 Hz, 1H), 7.59 (br s, 2H), 7.22 − 7.14 (m, 3H), 7.12 (d, J = 1.6 Hz, 1H), 4.55 (dd, J = 5.6, 12.8 Hz, 1H), 4.21 (d, J = 6.0 Hz, 2H), 2.85 (ddd, J = 5.6, 14.0, 17.0 Hz, 1H), 2.59 − 2.51 (m, 1H), 2.34 (dq, J = 4.8, 13.2 Hz, 1H), 1.97 − 1.79 (m, 1H), 1.50 (s, 6H). MS (ESI) m/z 494.2 $[M + H]^+$ |
| Compound 58 | Synthesized in analogy to compound 10 | $^1$H NMR (400 MHz, DMSO-$d_6$) δ = 10.95 (s, 1H), 8.14 (t, J = 5.6 Hz, 1H), 7.72 (d, J = 8.4 Hz, 2H), 7.58 (d, J = 8.4 Hz, 2H), 7.16 (s, 1H), 7.11 (d, J = 1.6 Hz, 1H), 4.59 − 4.47 (m, 1H), 4.22 (d, J = 5.6 Hz, 2H), 2.93 − 2.77 (m, 1H), 2.61 (s, 6H), 2.54 (d, J = 2.0 Hz, 1H), 2.37 − 2.30 (m, 1H), 1.92 − 1.83 (m, 1H), 1.53 (s, 6H). MS (ESI) m/z 540.0 $[M + H]^+$ |

TABLE 2-continued

| Exemplary compounds - additional examples | | |
|---|---|---|
| Compound ID | Synthesis | Characterization |
| Compound 60 | Synthesized in analogy to compound 43 | $^1$H NMR (400 MHz, DMSO-$d_6$) δ = 10.96 (s, 1H), 8.18 (t, J = 6.0 Hz, 1H), 7.83 (s, 1H), 7.74 − 7.69 (m, 1H), 7.56 − 7.46 (m, 2H), 7.35 (s, 2H), 7.24 (s, 1H), 7.17 (s, 1H), 4.55 (dd, J = 5.6, 12.6 Hz, 1H), 4.22 (d, J = 6.0 Hz, 2H), 2.92 − 2.77 (m, 1H), 2.61 − 2.54 (m, 1H), 2.43 − 2.27 (m, 1H), 1.94 − 1.83 (m, 1H), 1.53 (s, 6H). MS (ESI) m/z 512.4 $[M + H]^+$ |
| Compound 61 | Synthesized in analogy to compound 10 | $^1$H NMR (400 MHz, DMSO-$d_6$) δ = 10.96 (s, 1H), 8.15 (t, J = 6.0 Hz, 1H), 7.76 (d, J = 8.4 Hz, 2H), 7.54 (d, J = 8.4 Hz, 2H), 7.41 (q, J = 4.8 Hz, 1H), 7.18 (d, J = 1.2 Hz, 1H), 7.12 (s, 1H), 4.55 (dd, J = 5.6, 12.8 Hz, 1H), 4.22 (d, J = 6.0 Hz, 2H), 2.89 − 2.79 (m, 1H), 2.57 − 2.54 (m, 1H), 2.41 (d, J = 4.8 Hz, 3H), 2.38 − 2.31 (m, 1H), 1.93 − 1.85 (m, 1H), 1.53 (s, 6H). MS (ESI) m/z 526.2 $[M + H]^+$ |
| Compound 62 | Synthesized in analogy to compound 7 | $^1$H NMR (400 MHz, DMSO-$d_6$) δ = 10.95 (s, 1H), 8.17 (t, J = 6.0 Hz, 1H), 7.87 − 7.80 (m, 2H), 7.65 − 7.59 (m, 2H), 7.19 (s, 1H), 7.12 (s, 1H), 4.55 (dd, J = 5.6, 12.4 Hz, 1H), 4.22 (d, J = 6.0 Hz, 2H), 3.19 (s, 3H), 2.92 − 2.77 (m, 1H), 2.54 ( d, J = 2.0 Hz, 1H), 2.33 (dd, J = 4.0, 13.2 Hz, 1H), 1.93 − 1.82 (m, 1H), 1.55 (s, 6H). MS (ESI) m/z = 511.2 $[M + H]^+$ |
| Compound 63 | Synthesized in analogy to compound 10 | $^1$H NMR (400 MHz, DMSO-$d_6$) δ = 10.97 (s, 1 H), 8.91 (d, J = 4.8 Hz, 1 H), 8.05 (d, J = 8.4 Hz, 1 H), 7.93 (t, J = 5.6 Hz, 1 H), 7.81 (d, J = 8.4 Hz, 1 H), 7.70 (t, J = 7.2 Hz, 1 H), 7.60 (d, J = 4.8 Hz, 1 H), 7.49 − 7.39 (m, 1 H), 7.09 (s, 1 H), 7.02 (s, 1 H), 4.54 (dd, J = 5.2, 12.8 Hz, 1 H), 4.13 (d, J = 5.2 Hz, 2 H), 2.91 − 2.79 (m, 1 H), 2.56 (s, 1 H), 2.35 − 2.31 (m, 1 H), 1.93 − 1.83 (m, 1 H), 1.64 (s, 6 H). MS (ESI) m/z 484.0 $[M + H]^+$ |
| Compound 66 | Synthesized in analogy to compound 7 | $^1$H NMR (400 MHz, DMSO-$d_6$) δ = 10.96 (s, 1H), 8.15 (t, J = 6.0 Hz, 1H), 7.90 (d, J = 8.4 Hz, 2H), 7.58 (d, J = 8.4 Hz, 2H), 7.17 (s, 1H), 7.12 (s, 1H), 4.55 (dd, J = 5.6, 12.8 Hz, 1H), 4.22 (d, J = 6.0 Hz, 2H), 3.19 (s, 3H), 2.92 − 2.78 (m, 1H), 2.54 (d, J = 1.6 Hz, 1H), 2.37 − 2.27 (m, 1H), 1.93 − 1.82 (m, 1H), 1.53 (s, 6H). MS (ESI) m/z 511.2 $[M + H]^+$ |
| Compound 72 | Synthesized in analogy to compound 10 | $^1$H NMR (400 MHz, DMSO-$d_6$) δ = 10.94 (s, 1H), 10.76 (s, 1H), 7.89 (t, J = 6.0 Hz, 1H), 7.06 − 6.93 (m, 5H), 4.52 (dd, J = 5.2, 12.4 Hz, 1H), 4.18 (d, J = 6.0 Hz, 2H), 3.25 (s, 3H), 2.84 (ddd, J = 6.0, 14.0, 16.8 Hz, 1H), 2.54 (s, 1H), 2.34 − 2.24 (m, 1H), 1.92 − 1.80 (m, 1H), 1.50 (s, 6H). MS (ESI) m/z 503.1 $[M + H]^+$ |
| Compound 73 | Synthesized in analogy to compound 21 | $^1$H NMR (400 MHz, DMSO-$d_6$) δ = 10.96 (s, 1 H), 8.19 (t, J = 6.0 Hz, 1 H), 7.22 (d, J = 1.2 Hz, 1 H), 7.16 (d, J = 1.2 Hz, 1 H), 7.08 (s, 2 H), 4.56 (dd, J = 5.6, 12.8 Hz, 1 H), 4.22 (d, J = 5.6 Hz, 2 H), 2.85 (ddd, J = 20.0, 14.0, 6 Hz, 1 H), 2.59 − 2.51 (m, 1 H), 2.40 − 2.29 (m, 1 H), 1.92 − 1.84 (m, 1 H), 1.52 (s, 6 H). MS (ESI) m/z 470.0 $[M + H]^+$ |
| Compound 74 | Synthesized in analogy to compound 10 | $^1$H NMR (400 MHz, DMSO-$d_6$) δ = 10.95 (s, 1H), 9.36 (s, 1H), 8.14 (d, J = 1.6 Hz, 1H), 8.06 − 8.02 (m, 2H), 7.46 (dd, J = 8.8, 2.0 Hz, 1H), 7.13 (s, 1H), 7.06 (d, J = 1.2 Hz, 1H), 4.52 (dd, J = 12.8, 5.6 Hz, 1H), 4.21 (d, J = 5.6 Hz, 2H), 2.89 − 2.78 (m, 1H), 2.58 − 2.52 (m, 1H), 2.32 (qd, J = 4.4, 13.2 Hz, 1H), 1.90 − 1.82 (m, 1H), 1.58 (s, 6H). MS (ESI) m/z 490.2 $[M + H]^+$ |
| Compound 75 | Synthesized in analogy to compound 9 | $^1$H NMR (400 MHz, DMSO-$d_6$) δ = 10.96 (s, 1H), 8.11 (t, J = 5.6 Hz, 1H), 7.60 (d, J = 7.2 Hz, 1H), 7.21 (s, 1H), 7.14 (s, 1H), 6.33 (d, J = 2.0 Hz, 1H), 6.03 (dd, J = 2.0, 7.2 Hz, 1H), 4.55 (dd, J = 5.6, 12.8 Hz, 1H), 4.20 (d, J = 6.0 Hz, 2H), 3.38 (s, 3H), 2.92 − 2.77 (m, 1H), 2.55 (d, J = 2.0 Hz, 1H), 2.33 (d, J = 4.0 Hz, 1H), 1.96 − 1.81 (m, 1H), 1.40 (s, 6H). MS (ESI) m/z 464.2 $[M + H]^+$ |
| Compound 76 | Synthesized in analogy to compound 128 | $^1$H NMR (400 MHz, DMSO-$d_6$) δ = 10.97 (s, 1H), 8.13 (t, J = 6.0 Hz, 1H), 7.78 (d, J = 8.4 Hz, 2H), 7.49 (d, J = 8.4 Hz, 2H), 7.33 (s, 2H), 7.21 (d, J = 1.2 Hz, 1H), 7.15 (s, 1H), 4.55 (dd, J = 5.6, 12.8 Hz, 1H), 4.21 (d, J = 5.6 Hz, 2H), 2.92 − 2.78 (m, 1H), 2.54 (d, J = 2.4 Hz, 1H), 2.38 − 2.27 (m, 1H), 1.93 − 1.82 (m, 1H), 1.51 (s, 6H). MS (ESI) m/z 512.2 $[M + H]^+$ |

TABLE 2-continued

| Exemplary compounds - additional examples | | |
|---|---|---|
| Compound ID | Synthesis | Characterization |
| Compound 77 | Synthesized in analogy to compound 10 | $^1$H NMR (400 MHz, DMSO-$d_6$) δ = 11.60 (br s, 1H), 10.95 (s, 1H), 7.98 (s, 1H), 7.25 (d, J = 1.6 Hz, 1H), 7.12 – 7.02 (m, 3H), 7.00 (d, J = 1.2 Hz, 1H), 4.53 (dd, J = 5.6, 12.8 Hz, 1H), 4.19 (d, J = 6.0 Hz, 2H), 2.84 (ddd, J = 5.6, 14.0, 16.8 Hz, 1H), 2.57 – 2.51 (m, 1H), 2.32 (qd, J = 4.0, 13.2 Hz, 1H), 1.92 – 1.79 (m, 1H), 1.50 (d, J = 1.6 Hz, 6H). MS (ESI) m/z 490.0 $[M + H]^+$ |
| Compound 78 | Synthesized in analogy to compound 10 | $^1$H NMR (400 MHz, DMSO-$d_6$) δ = 10.94 (s, 1H), 7.99 (s, 1H), 7.94 (t, J = 6.0 Hz, 1H), 7.68 (d, J = 8.4 Hz, 1H), 7.54 (s, 1H), 7.16 (s, 1H), 7.09 (s, 1H), 7.05 (dd, J = 1.2, 8.4 Hz, 1H), 4.53 (dd, J = 5.6, 12.4 Hz, 1H), 4.19 (d, J = 6.0 Hz, 2H), 4.03 (s, 3H), 2.92 – 2.76 (m, 1H), 2.52 (br s, 1H), 2.36 – 2.29 (m, 1H), 1.94 – 1.78 (m, 1H), 1.57 (s, 6H). MS (ESI) m/z 487.0 $[M + H]^+$ |
| Compound 81 | Synthesized in analogy to compound 10 | $^1$H NMR (400 MHz, DMSO-$d_6$) δ = 10.94 (s, 1H), 8.13 (t, J = 6.0 Hz, 1H), 7.99 – 7.92 (m, 2H), 7.42 (dd, J = 1.6, 9.6 Hz, 1H), 7.18 (s, 1H), 7.12 (s, 1H), 4.54 (dd, J = 5.2, 12.8 Hz, 1H), 4.21 (d, J = 6.0 Hz, 2H), 2.90 – 2.77 (m, 1H), 2.58 – 2.51 (m, 1H), 2.33 (qd, J = 4.4, 13.2 Hz, 1H), 1.93 – 1.81 (m, 1H), 1.56 (s, 6H). MS (ESI) m/z 475.0 $[M + H]^+$ |
| Compound 82 | Synthesized in analogy to compound 35 | $^1$H NMR (400 MHz, DMSO-$d_6$) δ = 10.96 (s, 1H), 8.58 (d, J = 7.2 Hz, 1H), 8.10 (t, J = 8.0 Hz, 1H), 7.96 (d, J = 4.0 Hz, 1H), 7.59 (s, 1H), 7.18 (s, 1H), 7.11 (s, 1H), 6.71 (d, J = 8.0 Hz, 1H), 6.58 (s, 1H), 4.53 (dd, J = 8.0, 12.0 Hz, 1H), 4.21 (d, J = 8.0 Hz, 2H), 2.93 – 2.76 (m, 1H), 2.59 (s, 1H), 2.32 (qd, J = 4.0, 12.0 Hz, 1H), 1.93 – 1.81 (m, 1H), 1.52 (s, 6H). MS (ESI) m/z 495.0 $[M + Na]^+$ |
| Compound 83 | Synthesized in analogy to compound 10 | $^1$H NMR (400 MHz, DMSO-$d_6$) δ = 10.95 (s, 1H), 8.05 (t, J = 5.6 Hz, 1H), 7.93 (s, 1H), 7.85 (d, J = 8.4 Hz, 2H), 7.38 (d, J = 8.4 Hz, 2H), 7.30 (s, 1H), 7.16 (s, 1H), 7.09 (s, 1H), 4.54 (dd, J = 5.6, 12.8 Hz, 1H) 4.20 (d, J = 5.6 Hz, 2H), 2.84 (ddd, J = 6.0, 14.0, 16.8 Hz, 1H), 2.52 – 2.61 (m, 1H), 2.24 – 2.41 (m, 1H), 1.79 – 1.95 (m, 1H), 1.50 (s, 6H). MS (ESI) m/z 476.0 $[M + H]^+$ |
| Compound 84 | Synthesized in analogy to compound 79 | $^1$H NMR (400 MHz, DMSO-$d_6$) δ = 11.44 (s, 1H), 10.97 (s, 1H), 8.14 (t, J = 6.0 Hz, 1H), 7.27 (d, J = 6.8 Hz, 1H), 7.22 (d, J = 1.2 Hz, 1H), 7.16 (s, 1H), 6.26 (d, J = 1.6 Hz, 1H), 5.99 (dd, J = 7.2, 1.6 Hz, 1H), 4.55 (dd, J = 12.8, 5.6 Hz, 1H), 4.20 (d, J = 6.0 Hz, 2H), 2.55 –3 .35 (m, 1H), 2.54 (d, J = 2.4 Hz, 1H), 2.34 (qd, J = 13.2, 4.4 Hz, 1H), 1.84 – 1.95 (m, 1H), 1.39 (s, 6H). MS (ESI) m/z 450.0 $[M + H]^+$ |
| Compound 85 | Synthesized in analogy to compound 10 | $^1$H NMR (400 MHz, DMSO-$d_6$) δ = 10.96 (s, 1 H), 8.49 (d, J = 2.8 Hz, 1 H), 8.43 (t, J = 1.6 Hz, 1 H), 8.20 (t, J = 6.0 Hz, 1 H), 7.63 (dt, J = 10.4, 2.4 Hz, 1 H), 7.21 (d, J = 1.2 Hz, 1 H), 7.15 (d, J = 1.2 Hz, 1 H), 4.56 (dd, J = 12.8, 5.6 Hz, 1 H), 4.23 (d, J = 6.0 Hz, 2 H), 2.85 (ddd, J = 16.8, 14.0, 5.6 Hz, 1 H), 2.53 – 2.58 (m, 1 H), 2.35 (dd, J = 13.6, 4.0 Hz, 1 H), 1.81 – 1.96 (m, 1 H), 1.55 (s, 6 H). MS (ESI) m/z 474.0 $[M + Na]^+$ |
| Compound 86 | Synthesized in analogy to compound 10 | $^1$H NMR (400 MHz, DMSO-$d_6$) δ = 10.97 (s, 1 H), 8.10 (t, J = 4.4 Hz, 1 H), 7.24 (s, 1 H), 7.17 (s, 1 H), 6.99 (s, 2 H), 4.57 (dd, J = 12.4, 4.8 Hz, 1 H), 4.22 (d, J = 6.0 Hz, 2 H), 2.77 – 2.96 (m, 1 H), 2.61 – 2.71 (m, 1 H), 2.42 (s, 6 H), 2.30 – 2.37 (m, 1 H), 1.81 – 1.97 (m, 1 H), 1.46 (s, 6 H). MS (ESI) m/z 462.1 $[M + H]^+$ |
| Compound 88 | Synthesized in analogy to compound 19 | $^1$H NMR (400 MHz, DMSO-$d_6$) δ = 10.95 (s, 1H), 8.55 – 8.35 (m, 2H), 8.12 (t, J = 6.0 Hz, 1H), 7.48 (dd, J = 5.2, 6.8 Hz, 1H), 7.30 (s, 1H), 7.24 (s, 1H), 4.57 (dd, J = 5.6, 12.8 Hz, 1H), 4.23 (d, J = 6.0 Hz, 2H), 2.86 (ddd, J = 5.6, 14.0, 16.8 Hz, 1H), 2.59 – 2.51 (m, 1H), 2.36 (dq, J = 4.4, 13.2 Hz, 1H), 1.97 – 1.82 (m, 1H), 1.50 (s, 6H). MS (ESI) m/z 452.1 $[M + H]^+$ |
| Compound 92 | Synthesized in analogy to compound 7 | $^1$H NMR (400 MHz, DMSO-$d_6$) δ = 10.96 (s, 1H), 8.69 (d, J = 5.2 Hz, 1H), 8.20 (t, J = 6.0 Hz, 1H), 7.98 (d, J = 1.2 Hz, 1H), 7.63 (dd, J = 2.0, 5.6 Hz, 1H), 7.19 (d, J = 1.2 Hz, 1H), 7.14 (d, J = 1.2 Hz, 1H), 4.56 (dd, J = 5.6, 12.8 Hz, 1H), 4.22 (d, J = 6.0 |

TABLE 2-continued

| Exemplary compounds - additional examples | | |
|---|---|---|
| Compound ID | Synthesis | Characterization |
| | | Hz, 2H), 2.92 - 2.77 (m, 1H), 2.58 - 2.52 (m, 1H), 2.41 - 2.32 (m, 1H), 1.94 - 1.81 (m, 1H), 1.53 (s, 6H). MS (ESI) m/z 459.1, 461.1 $[M + H]^+$ |
| Compound 93 | Synthesized in analogy to compound 19 | $^1$H NMR (400 MHz, DMSO-$d_6$) δ = 10.96 (s, 1H), 8.23 - 8.14 (m, 2H), 7.23 (td, J = 1.6, 5.2 Hz, 1H), 7.21 (s, 1H), 7.15 (s, 1H), 7.07 (s, 1H), 4.56 (dd, J = 5.6, 12.8 Hz, 1H), 4.22 (d, J = 5.6 Hz, 2H), 2.94 - 2.77 (m, 1H), 2.58 - 2.53 (m, 1H), 2.34 (dq, J = 4.4, 13.2 Hz, 1H), 1.94 - 1.83 (m, 1H), 1.51 (s, 6H). MS (ESI) m/z 452.1 $[M + H]^+$ |
| Compound 95 | Synthesized in analogy to compound 94 | $^1$H NMR (400 MHz, DMSO-$d_6$) δ = 10.96 (s, 1H), 8.38 (d, J = 5.2 Hz, 1H), 8.12 (t, J = 6.0 Hz, 1H), 7.22 (s, 1H), 7.16 (s, 1H), 7.12 (s, 1H), 7.09 (d, J = 5.2 Hz, 1H), 4.56 (dd, J = 5.6, 12.4 Hz, 1H), 4.21 (d, J = 6.0 Hz, 2H), 2.85 (ddd, J = 6.0, 14.0, 16.8 Hz, 1H), 2.57 - 2.52 (m, 1H), 2.44 (s, 3H), 2.35 (dq, J = 4.4, 13.2 Hz, 1H), 1.93 - 1.81 (m, 1H), 1.47 (s, 6H). MS (ESI) m/z 448.0 $[M + H]^+$ |
| Compound 96 | Synthesized in analogy to compound 94 | $^1$H NMR (400 MHz, DMSO-$d_6$) δ = 10.95 (s, 1H), 8.02 (t, J = 6.0 Hz, 1H), 7.41 - 7.27 (m, 2H), 7.20 - 7.11 (m, 3H), 7.10 (s, 1H), 4.55 (dd, J = 5.6, 12.8 Hz, 1H), 4.27 - 4.12 (m, 2H), 2.90 - 2.79 (m, 1H), 2.60 - 2.53 (m, 1H), 2.40 - 2.26 (m, 1H), 1.95 - 1.82 (m, 1H), 1.49 (s, 6H). MS (ESI) m/z 451.0 $[M + H]^+$ |
| Compound 97 | Synthesized in analogy to compound 6 | $^1$H NMR (400 MHz, DMSO-$d_6$) δ = 10.95 (s, 1H), 8.72 (d, J = 5.2 Hz, 1H), 8.25 (t, J = 5.6 Hz, 1H), 7.70 (s, 1H), 7.63 (d, J = 4.8 Hz, 1H), 7.21 (s, 1H), 7.16 (s, 1H), 4.56 (dd, J = 5.6, 12.4 Hz, 1H), 4.23 (d, J = 5.6 Hz, 2H), 2.91 - 2.79 (m, 1H), 2.55 (d, J = 2.4 Hz, 1H), 2.36 (d, J = 3.6 Hz, 1H), 1.93 - 1.82 (m, 1H), 1.55 (s, 6H). MS (ESI) m/z 502.1 $[M + H]^+$ |
| Compound 98 | Synthesized in analogy to compound 7 | $^1$H NMR (400 MHz, DMSO-$d_6$) δ = 10.96 (s, 1H), 8.14 - 8.09 (m, 2H), 7.21 (s, 1H), 7.14 (s, 1H), 6.87 (dd, J = 1.6, 5.4 Hz, 1H), 6.72 (s, 1H), 4.56 (dd, J = 5.6, 12.8 Hz, 1H), 4.21 (d, J = 5.6 Hz, 2H), 3.84 (s, 3H), 2.86 (ddd, J = 5.6, 14.0, 16.8 Hz, 2H), 2.37 - 2.33 (m, 1H), 1.93 - 1.85 (m, 1H), 1.47 (s, 6H). MS (ESI) m/z 464.1 $[M + H]^+$ |
| Compound 100 | Synthesized according to General Scheme 1 | MS (ESI) m/z 483.2 $[M + H]^+$ |
| Compound 101 | Synthesized according to General Scheme 1 | MS (ESI) m/z 433 $[M + H]^+$ |
| Compound 102 | Synthesized according to General Scheme 1 | MS (ESI) m/z 425 $[M + H]^+$ |
| Compound 103 | Synthesized in analogy to compound 37 | $^1$H NMR (400 MHz, DMSO-$d_6$) δ = 10.88 (s, 1H), 7.97 (t, J = 6.0 Hz, 1H), 7.38 - 7.32 (m, 2H), 7.32 (s, 2H), 7.26 - 7.19 (m, 2H), 7.14 (s, 1H), 7.07 (d, J = 8.0 Hz, 1H), 4.21 (d, J = 6.0 Hz, 2H), 4.15 (dd, J = 5.2, 12.4 Hz, 1H), 2.81 - 2.70 (m, 1H), 2.53 (m, 1H), 2.26 (dq, J = 4.4, 12.8 Hz, 1H), 1.99 - 1.90 (m, 1H), 1.48 (s, 6H). MS (ESI) m/z 399.1 $[M + H]^+$ |
| Compound 104 | according to General Scheme 1 | MS (ESI) m/z 468 $[M + H]^+$. |
| Compound 105 | Synthesized according to General Scheme 1 | MS (ESI) m/z 434 $[M + H]^+$ |
| Compound 108 | Synthesized in analogy to compound 94 | $^1$H NMR (400 MHz, DMSO-$d_6$) δ = 10.96 (s, 1H), 8.52 (d, J = 5.6 Hz, 2H), 8.17 - 8.12 (m, 1H), 7.29 (d, J = 6.0 Hz, 2H), 7.21 (d, J = 1.2 Hz, 1H), 7.16 (s, 1H), 4.56 (dd, J = 5.6, 12.8 Hz, 1H), 4.22 (d, J = 6.0 Hz, 2H), 2.95 - 2.76 (m, 1H), 2.55 (d, J = 1.6 Hz, 1H), 2.35 (dq, J = 4.4, 13.2 Hz, 1H), 1.95 - 1.81 (m, 1H), 1.49 (s, 6H). MS (ESI) m/z 434.0 $[M + H]^+$ |
| Compound 109 | Synthesized in analogy to compound 106 | $^1$H NMR (400 MHz, DMSO-$d_6$) δ = 10.88 (s, 1H), 8.67 - 8.39 (m, 2H), 8.11 (t, J = 6.0 Hz, 1H), 7.32 - 7.27 (m, 2H), 7.24 (d, J = 8.0 Hz, 1H), 7.15 (s, 1H), 7.09 (dd, J = 1.2, 8.0 Hz, 1H), 4.22 (d, J = 6.0 Hz, 2H), 4.16 (dd, J = 5.2, 12.4 Hz, 1H), 2.81 - 2.70 (m, |

TABLE 2-continued

| Exemplary compounds - additional examples | | |
|---|---|---|
| Compound ID | Synthesis | Characterization |
| | | 1H), 2.53 (d, J = 3.6 Hz, 1H), 2.34 – 2.19 (m, 1H), 1.99 – 1.88 (m, 1H), 1.49 (s, 6H). MS (ESI) m/z 400.1 $[M + H]^+$ |
| Compound 110 | Synthesized in analogy to compound 7 | $^1$H NMR (400 MHz, DMSO-$d_6$) δ = 10.97 (s, 1H), 8.46 (t, J = 6.0 Hz, 1H), 7.32 (s, 1H), 7.25 (d, J = 1.2 Hz, 1H), 4.57 (dd, J = 5.6, 12.8 Hz, 1H), 4.25 (d, J = 6.0 Hz, 2H), 2.92 – 2.79 (m, 1H), 2.58 – 2.51 (m, 1H), 2.48 (s, 3H), 2.36 (dq, J = 4.4, 13.2 Hz, 1H), 1.94 – 1.84 (m, 1H), 1.58 (s, 6H). MS (ESI) m/z 439.2 $[M + H]^+$ |
| Compound 111 | Synthesized according to General Scheme 1 | MS (ESI) m/z 489.2 $[M + H]^+$ |
| Compound 112 | Synthesized according to General Scheme 1 | MS (ESI) m/z 452.2 $[M + H]^+$ |
| Compound 113 | Synthesized according to General Scheme 1 | MS (ESI) m/z 440 $[M + H]^+$ |
| Compound 114 | Synthesized according to General Scheme 1 | |
| Compound 115 | Synthesized according to General Scheme 1 | MS (ESI) m/z 423 $[M + H]^+$ |
| Compound 116 | Synthesized according to General Scheme 1 | MS (ESI) m/z 451.2 $[M + H]^+$ |
| Compound 117 | Synthesized according to General Scheme 1 | MS (ESI) m/z 437 $[M + H]^+$ |
| Compound 118 | Synthesized according to General Scheme 1 | MS (ESI) m/z 423.2 $[M + H]^+$ |
| Compound 119 | Synthesized according to General Scheme 1 | MS (ESI) m/z 438 $[M + H]^+$ |
| Compound 121 | Synthesized in analogy to compound 120 | $^1$H NMR (400 MHz, DMSO-$d_6$) δ = 10.96 (s, 1H), 8.85 (d, J = 1.6 Hz, 1H), 8.23 (t, J = 6.0 Hz, 1H), 7.29 (s, 1H), 7.22 (d, J = 1.2 Hz, 1H), 6.56 (d, J = 1.6 Hz, 1H), 4.56 (dd, J = 5.6, 12.8 Hz, 1H), 4.23 (d, J = 6.0 Hz, 2H), 2.85 (ddd, J = 5.6, 14.0, 16.8 Hz, 1H), 2.60 – 2.51 (m, 1H), 2.35 (q, J = 4.4, 13.2 Hz, 1H), 1.94 – 1.85 (m, 1H), 1.52 (s, 6H). MS (ESI) m/z 424.1 $[M + H]^+$ |
| Compound 122 | Synthesized in analogy to compound 120 | $^1$H NMR (400 MHz, DMSO-$d_6$) δ = 10.97 (s, 1H), 8.30 (s, 1H), 8.15 (t, J = 6.0 Hz, 1H), 7.25 (d, J = 1.2 Hz, 1H), 7.19 (d, J = 1.2 Hz, 1H), 7.06 (s, 1H), 4.56 (dd, J = 5.6, 12.4 Hz, 1H), 4.21 (d, J = 6.0 Hz, 2H), 2.95 – 2.77 (m, 1H), 2.58 – 2.51 (m, 1H), 2.35 (dq, J = 4.4, 13.2 Hz, 1H), 1.95 – 1.82 (m, 1H), 1.48 (s, 6H). MS (ESI) m/z 424.0 $[M + H]^+$ |
| Compound 123 | Synthesized in analogy to compound 120 | $^1$H NMR (400 MHz, DMSO-$d_6$) δ = 10.97 (s, 1H), 8.02 (t, J = 6.0 Hz, 1H), 7.55 (s, 1H), 7.27 (s, 1H), 7.20 (s, 1H), 6.84 (s, 1H), 4.59 – 4.54 (m, 1H), 4.19 (d, J = 6.0 Hz, 2H), 2.85 – 2.81 (m, 1H), 2.56 – 2.55 (m, 1H), 2.37 – 2.32 (m, 1H), 1.91 – 1.87 (m, 1H), 1.46 (s, 6H). MS (ESI) m/z 437.1 $[M + H]^+$ |
| Compound 124 | Synthesized in analogy to compound 120 | $^1$H NMR (400 MHz, DMSO-$d_6$) δ = 10.96 (s, 1H), 8.33 (t, J = 6.0 Hz, 1H), 8.05 (s, 1H), 7.30 (s, 1H), 7.24 (s, 1H), 7.17 (s, 1H), 4.56 (dd, J = 5.6, 12.8 Hz, 1H), 4.24 (d, J = 6.0 Hz, 2H), 2.77 – 2.91 (m, 1H), 2.55 (s, 1H), 2.35 (qd, J = 4.4, 13.2 Hz, 1H), 1.82 – 1.95 (m, 1H), 1.55 (s, 6H). MS (ESI) m/z 424.1 $[M + H]^+$ |
| Compound 125 | Synthesized in analogy to | $^1$H NMR (400 MHz, DMSO-$d_6$) δ = 10.95 (s, 1H), 8.49 – 8.42 (m, 2H), 7.31 (d, J = 1.6 Hz, 1H), 7.28 |

TABLE 2-continued

| Exemplary compounds - additional examples | | |
|---|---|---|
| Compound ID | Synthesis | Characterization |
| | compound 120 | (s, 1H), 7.22 (s, 1H), 4.56 (dd, J = 5.6, 12.8 Hz, 1H), 4.27 (d, J = 5.6 Hz, 2H), 2.85 (ddd, J = 5.6, 14.0, 16.8 Hz, 1H), 2.59 − 2.52 (m, 1H), 2.35 (dq, J = 4.4, 13.2 Hz, 1H), 1.94 − 1.84 (m, 1H), 1.62 (s, 6H). MS (ESI) m/z 440.1/442.1 $[M + H]^+$ |
| Compound 129 | Synthesized in analogy to compound 130 | $^1$H NMR (400 MHz, DMSO-$d_6$) δ = 10.96 (s, 1H), 8.62 (t, J = 6.0 Hz, 1H), 7.43 − 7.30 (m, 5H), 7.15 (d, J = 1.6 Hz, 1H), 7.07 (d, J = 1.6 Hz, 1H), 5.10 (d, J = 6.4 Hz, 2H), 4.85 (d, J = 6.4 Hz, 2H), 4.53 (dd, J = 5.6, 12.8 Hz, 1H), 4.28 (d, J = 6.0 Hz, 2H), 2.95 − 2.76 (m, 1H), 2.58 − 2.52 (m, 1H), 2.32 (q, J = 4.4, 13.2 Hz, 1H), 1.91 − 1.81 (m, 1H). MS (ESI) m/z 447.1 $[M + 1]^+$ |
| Compound 133 | Synthesized in analogy to compound 131 | $^1$H NMR (400 MHz, CHLOROFORM-d) δ d = 7.85 (d, J = 0.8 Hz, 1H), 7.59 (dd, J = 0.8, 8.4 Hz, 1H), 7.27 (s, 1H), 7.13 (dd, J = 1.6, 8.4 Hz, 1H), 4.06 − 4.01 (m, 2H), 3.99 (s, 3H), 3.90 (td, J = 3.6, 12.0 Hz, 2H), 3.53 (dt, J = 2.0, 11.6 Hz, 2H), 2.54 (dd, J = 2.0, 13.6 Hz, 2H), 2.02 − 1.96 (m, 2H), 1.10 (t, J = 7.2 Hz, 3H). MS (ESI) m/z 289.1 $[M + H]^+$ |
| Compound 138 | Synthesized in analogy to compound 48 | $^1$H NMR (400 MHz, DMSO-$d_6$) δ = 10.86 (s, 1H), 8.26 (t, J = 6.0 Hz, 1H), 7.47 − 7.33 (m, 2H), 7.24 − 7.12 (m, 3H), 6.97 (dd, J = 1.2, 8.0 Hz, 1H), 6.88 (d, J = 1.2 Hz, 1H), 4.23 (d, J = 6.0 Hz, 2H), 4.12 (dd, J = 5.2, 12.4 Hz, 1H), 3.81 − 3.70 (m, 2H), 3.47 (t, J = 10.4 Hz, 2H), 2.81 − 2.69 (m, 1H), 2.57 − 2.51 (m, 1H), 2.47 (s, 2H), 2.30 − 2.17 (m, 1H), 1.98 − 1.79 (m, 3H). MS (ESI) m/z 459.1 $[M + H]^+$ |
| Compound 140 | Synthesized in analogy to compound 48 | $^1$H NMR (400 MHz, DMSO-$d_6$) δ = 10.94 (s, 1H), 8.68 (s, 1H), 7.41 (m, 2H), 7.24 (m, 2H), 7.10 (s, 1H), 7.03 (s, 1H), 5.11 (d, J = 6.0 Hz, 2H), 4.85 (d, J = 5.6 Hz, 2H), 4.54 (dd, J = 4.8, 12.0 Hz, 1H), 4.29 (d, J = 4.4 Hz, 2H), 2.92 − 2.75 (m, 1H), 2.59 − 2.54 (m, 1H), 2.40 − 2.25 (m, 1H), 1.96 − 1.81 (m, 1H). MS (ESI) m/z 465.0 $[M + H]^+$ |
| Compound 141 | Synthesized in analogy to compound 127 | $^1$H NMR (400 MHz, DMSO-$d_6$) δ = 10.94 (s, 1H), 8.43 (t, J = 6.0 Hz, 1H), 7.41 − 7.30 (m, 2H), 7.23 − 7.15 (m, 2H), 7.05 (s, 1H), 6.98 (s, 1H), 4.62 − 4.49 (m, 2H), 4.23 (d, J = 6.0 Hz, 2H), 3.89 − 3.82 (m, 1H), 3.82 − 3.74 (m, 2H), 2.97 − 2.78 (m, 2H), 2.58 − 2.53 (m, 1H), 2.38 − 2.29 (m, 1H), 2.25 − 2.16 (m, 1H), 1.92 − 1.81 (m, 1H). MS (ESI) m/z 479.1 $[M + H]^+$ |
| Compound 142 | Synthesized in analogy to compound 48 | $^1$H NMR (400 MHz, DMSO-$d_6$) δ = 10.94 (s, 1H), 8.30 (t, J = 6.0 Hz, 1H), 7.40 (dd, J = 5.2, 8.8 Hz, 2H), 7.18 (t, J = 8.8 Hz, 2H), 6.96 (s, 1H), 6.89 (s, 1H), 4.52 (dd, J = 5.6, 12.8 Hz, 1H), 4.22 (d, J = 6.0 Hz, 2H), 3.85 − 3.71 (m, 2H), 3.47 (t, J = 10.8 Hz, 2H), 2.83 (ddd, J = 5.6, 14.0, 16.8 Hz, 1H), 2.58 − 2.51 (m, 1H), 2.47 (s, 2H), 2.31 (dq, J = 4.4, 13.2 Hz, 1H), 1.94 − 1.77 (m, 3H). MS (ESI) m/z 493.0 $[M + H]^+$ |
| Compound 144 | Synthesized in analogy to compound 94 | $^1$H NMR (400 MHz, DMSO-$d_6$) δ = 10.95 (s, 1H), 8.54 (d, J = 5.2 Hz, 2H), 8.40 (t, J = 6.0 Hz, 1H), 7.43 − 7.29 (m, 2H), 7.09 (s, 1H), 7.04 (s, 1H), 4.53 (dd, J = 5.6, 12.8 Hz, 1H), 4.22 (d, J = 6.0 Hz, 2H), 2.88 − 2.70 (m, 3H), 2.53 (d, J = 2.0 Hz, 1H), 2.46 − 2.26 (m, 3H), 1.97 − 1.70 (m, 3H). MS (ESI) m/z 446.2 $[M + H]^+$ |
| Compound 145 | Synthesized in analogy to compound 120 | $^1$H NMR (400 MHz, DMSO-$d_6$) δ = 10.95 (s, 1H), 8.20 (t, J = 6.0 Hz, 1H), 7.27 (s, 1H), 7.20 (s, 1H), 6.17 (s, 1H), 4.56 (dd, J = 5.6, 12.8 Hz, 1H), 4.22 (d, J = 6.0 Hz, 2H), 2.91 − 2.78 (m, 1H), 2.60 − 2.52 (m, 1H), 2.42 − 2.29 (m, 4H), 1.95 − 1.81 (m, 1H), 1.48 (s, 6H). MS (ESI) m/z 438.1 $[M + H]^+$ |
| Compound 146 | Synthesized in analogy to compound 184 | $^1$H NMR (400 MHz, DMSO-$d_6$) δ = 10.96 (s, 1H), 9.08 (s, 1H), 8.89 (s, 1H), 7.98 − 7.87 (m, 2H), 7.28 (s, 1H), 7.20 (s, 1H), 4.54 (dd, J = 5.6, 12.8 Hz, 1H), 4.22 (d, J = 6.0 Hz, 2H), 2.92 − 2.78 (m, 1H), 2.54 (d, J = 2.0 Hz, 1H), 2.35-2.31 (m, 1H), 1.93 − 1.82 (m, 1H), 1.59 (s, 6H). MS (ESI) m/z 475.1 $[M + H]^+$ |
| Compound 147 | Synthesized in analogy to compound 202 | $^1$H NMR (400 MHz, DMSO-$d_6$) δ = 10.94 (br s, 1H), 8.86 (s, 2H), 8.11 (t, J = 6.0 Hz, 1H), 7.44 (s, 1H), 7.37 (s, 1H), 5.37 (s, 1H), 4.56 (dd, J = 5.6, 12.8 Hz, 1H), 4.27 (d, J = 6.0 Hz, 2H), 2.94 − 2.76 (m, 1H), 2.56 (br s, 1H), 2.36 (q, J = 4.4, 13.2 Hz, |

TABLE 2-continued

| Exemplary compounds - additional examples | | |
|---|---|---|
| Compound ID | Synthesis | Characterization |
| | | 1H), 1.97 – 1.82 (m, 1H), 1.54 (s, 6H), 1.48 (s, 6H). MS (ESI) m/z 493.1 $[M + H]^+$ |
| Compound 149 | Synthesized in analogy to compound 260 | $^1H$ NMR (400 MHz, DMSO-$d_6$) δ = 10.95 (s, 1H), 8.60 (dd, J = 5.6, 9.2 Hz, 1H), 8.03 (t, J = 6.0 Hz, 1H), 7.33 (d, J = 1.2 Hz, 1H), 7.30 (dd, J = 2.4, 11.2 Hz, 1H), 7.26 (s, 1H), 7.25 – 7.19 (m, 1H), 4.55 (dd, J = 5.6, 12.8 Hz, 1H), 4.23 (d, J = 6.0 Hz, 2H), 2.92 – 2.79 (m, 1H), 2.60 – 2.52 (m, 1H), 2.39 – 2.28 (m, 1H), 1.94 – 1.84 (m, 1H), 1.52 (s, 6H). MS (ESI) m/z 452.1 $[M + H]^+$ |
| Compound 150 | Synthesized in analogy to compound 6 | $^1H$ NMR (400 MHz, DMSO-$d_6$) δ = 10.96 (s, 1H), 8.65 – 8.64 (d, J = 5.6 Hz, 1H), 8.08 – 8.05 (t, J = 6.0 Hz, 1H), 7.32 – 7.25 (m, 2H), 7.22 (s, 1H), 4.59 – 4.54 (dd, J = 5.6, 12.8 Hz, 1H), 4.24 – 4.22 (d, J = 6.0 Hz, 2H), 2.90 – 2.81 (ddd, J = 6.0, 14.4, 16.8 Hz, 1H), 2.61 (s, 3H), 2.55 (m, 1H), 2.41 – 2.29 (dq, J = 4.8, 13.2 Hz, 1H), 1.92 – 1.85 (m, 1H), 1.49 (s, 6H). MS (ESI) m/z 449.1 $[M + H]^+$ |
| Compound 151 | Synthesized in analogy to compound 6 | $^1H$ NMR (400 MHz, DMSO-$d_6$) δ = 10.95 (s, 1H), 8.91 (d, J = 1.2 Hz, 1H), 8.09 (t, J = 6.0 Hz, 1H), 7.43 (d, J = 1.2 Hz, 1H), 7.35 (d, J = 1.6 Hz, 1H), 7.28 (d, J = 1.2 Hz, 1H), 4.56 (dd, J = 5.6, 12.8 Hz, 1H), 4.24 (d, J = 6.0 Hz, 2H), 2.85 (ddd, J = 5.6, 14.0, 16.8 Hz, 1H), 2.60 – 2.52 (m, 1H), 2.35 (dq, J = 4.4, 13.2 Hz, 1H), 2.16 – 2.07 (m, 1H), 1.93 – 1.82 (m, 1H), 1.50 (s, 6H), 1.09 – 0.99 (m, 4H). MS (ESI) m/z 475.2 $[M + H]^+$ |
| Compound 157 | Synthesized in analogy to compound 7 | $^1H$ NMR (400 MHz, DMSO-$d_6$) δ = 10.97 (s, 1H), 8.83 – 8.79 (m, 1H), 8.05 (t, J = 6.0 Hz, 1H), 7.89 (s, 1H), 7.81 – 7.75 (m, 1H), 7.30 (d, J = 1.6 Hz, 1H), 7.23 (d, J = 1.6 Hz, 1H), 4.62 – 4.51 (m, 1H), 4.23 (d, J = 6.0 Hz, 2H), 2.93 – 2.79 (m, 1H), 2.58 – 2.52 (m, 1H), 2.40 – 2.29 (m, 1H), 1.95 – 1.82 (m, 1H), 1.54 (s, 6H). MS (ESI) m/z 459.1 $[M + H]^+$ |
| Compound 158 | Synthesized in analogy to compound 6 | $^1H$ NMR (400 MHz, DMSO-$d_6$) δ = 10.97 (s, 1H), 9.00 (s, 1H), 8.50 (s, 1H), 8.18 (t, J = 6.0 Hz, 1H), 7.33 (d, J = 1.6 Hz, 1H), 7.26 (d, J = 1.6 Hz, 1H), 4.57 (dd, J = 5.6, 12.8 Hz, 1H), 4.23 (d, J = 6.0 Hz, 2H), 2.92 – 2.79 (m, 1H), 2.61 – 2.52 (m, 1H), 2.42 – 2.29 (m, 1H), 2.08 (s, 3H), 1.94 – 1.85 (m, 1H), 1.48 (s, 6H). MS (ESI) m/z 449.2 $[M + H]^+$ |
| Compound 159 | Synthesized in analogy to compound 6 | $^1H$ NMR (400 MHz, DMSO-$d_6$) δ = 10.98 (s, 1H), 9.31 (s, 1H), 8.23 (t, J = 6.0 Hz, 1H), 7.76 (s, 1H), 7.34 (d, J = 1.2 Hz, 1H), 7.27 (d, J = 1.2 Hz, 1H), 7.18 – 6.86 (t, 1H), 4.57 (dd, J = 5.6, 12.8 Hz, 1H), 4.25 (d, J = 6.0 Hz, 2H), 2.85 (m, J = 5.6, 14.0, 16.8 Hz, 1H), 2.59 – 2.51 (m, 1H), 2.40 – 2.29 (m, 1H), 1.94 – 1.83 (m, 1H), 1.56 (s, 6H). MS (ESI) m/z 485.1 $[M + H]^+$ |
| Compound 160 | Synthesized in analogy to compound 6 | $^1H$ NMR (400 MHz, DMSO-$d_6$) δ = 10.95 (s, 1H), 8.63 (d, J = 5.2 Hz, 1H), 8.02 (t, J = 6.0 Hz, 1H), 7.39 (d, J = 1.2 Hz, 1H), 7.31 (s, 1H), 7.26 (d, J = 5.2 Hz, 1H), 4.56 (dd, J = 5.6, 12.8 Hz, 1H), 4.25 (d, J = 6.0 Hz, 2H), 2.85 (ddd, J = 5.6, 14.0, 16.8 Hz, 1H), 2.58 – 2.52 (m, 1H), 2.47 (s, 3H), 2.36 (dq, J = 4.0, 13.2 Hz, 1H), 1.95 – 1.84 (m, 1H), 1.52 (s, 6H). MS (ESI) m/z 449.1 $[M + H]^+$ |
| Compound 161 | Synthesized in analogy to compound 7 | $^1H$ NMR (400 MHz, DMSO-$d_6$) δ = 10.95 (s, 1H), 8.72 (d, J = 1.6 Hz, 1H), 8.63 – 8.59 (m, 1H), 8.55 (d, J = 2.4 Hz, 1H), 8.15 (t, J = 6.0 Hz, 1H), 7.35 – 7.28 (m, 1H), 7.27 – 719 (m, 1H), 4.56 (dd, J = 5.6, 12.8 Hz, 1H), 4.24 (d, J = 6.0 Hz, 2H), 2.92 – 2.78 (m, 1H), 2.59 – 2.51 (m, 1H), 2.41 – 2.28 (m, 1H), 1.93 – 1.84 (m, 1H), 1.57 (s, 6H). MS (ESI) m/z 435.2 $[M + H]^+$ |
| Compound 162 | Synthesized in analogy to compound 19 | $^1H$ NMR (400 MHz, DMSO-$d_6$) δ = 10.98 (s, 1H), 8.57 (d, J = 1.6 Hz, 1H), 8.51 (s, 1H), 8.09 (t, J = 6.0 Hz, 1H), 7.30 (d, J = 1.6 Hz, 1H), 7.23 (d, J = 1.2 Hz, 1H), 4.57 (dd, J = 5.6, 12.8 Hz, 1H), 4.23 (d, J = 6.0 Hz, 2H), 2.93 – 2.79 (m, 1H), 2.59 – 2.52 (m, 1H), 2.49 (s, 3H), 2.40 – 2.28 (m, 1H), 1.95 – 1.84 (m, 1H), 1.56 (s, 6H). MS (ESI) m/z 449.1 $[M + H]^+$ |
| Compound 163 | Synthesized in analogy to compound 270 | $^1H$ NMR (400 MHz, DMSO-$d_6$) δ = 10.98 (s, 1H), 8.29 (s, 1H), 7.31 (d, J = 1.6 Hz, 1H), 7.24 (d, J = 1.2 Hz, 1H), 6.78 (d, J = 1.2 Hz, 1H), 4.58 (dd, J = |

TABLE 2-continued

| Exemplary compounds - additional examples | | |
|---|---|---|
| Compound ID | Synthesis | Characterization |
| | | 5.6, 12.8 Hz, 1H), 4.25 (d, J = 5.6 Hz, 2H), 2.94 – 2.79 (m, 1H), 2.61 – 2.52 (m, 1H), 2.43 – 2.32 (m, 1H), 2.28 (d, J = 1.2 Hz, 3H), 1.97 – 1.83 (m, 1H), 1.53 (s, 6H). MS (ESI) m/z 438.1 $[M + H]^+$ |
| Compound 164 | Synthesized in analogy to compound 7 | $^1H$ NMR (400 MHz, DMSO-$d_6$) δ = 10.95 (br s, 1H), 8.53 (t, J = 6.0 Hz, 1H), 7.35 (d, J = 1.2 Hz, 1H), 7.28 (s, 1H), 4.57 (dd, J = 5.6, 12.8 Hz, 1H), 4.27 (d, J = 6.0 Hz, 2H), 2.85 (d, J = 6.0, 14.0, 16.8 Hz, 1H), 2.61 – 2.51 (m, 1H), 2.44 – 2.29 (m, 4H), 1.97 – 1.83 (m, 1H), 1.61 (s, 6H). MS (ESI) m/z 440.8 $[M + H]^+$ |
| Compound 165 | Synthesized in analogy to compound 1 with cyclobutyl-amine as the coupling partner | $^1H$ NMR (400 MHz, DMSO-$d_6$) δ = 10.97 (s, 1H), 8.01 (s, 2H), 7.94 (t, J = 6.0 Hz, 1H), 7.38 (s, 1H), 7.32 (s, 1H), 4.56 (dd, J = 5.6, 12.8 Hz, 1H), 4.23 (d, J = 5.6 Hz, 2H), 3.92 (t, J = 7.2 Hz, 4H), 2.94 – 2.74 (m, 1H), 2.63 – 2.52 (m, 1H), 2.44 – 2.31 (m, 3H), 1.95 – 1.83 (m, 1H), 1.49 (s, 6H). MS (ESI) m/z 490.1 $[M + H]^+$ |
| Compound 167 | Synthesized in analogy to compound 246 | $^1H$ NMR (400 MHz, DMSO-$d_6$) δ = 10.96 (s, 1H), 8.48 (t, J = 6.0 Hz, 1H), 7.78 – 7.73 (m, 1H), 7.73 – 7.67 (m, 1H), 7.42 – 7.36 (m, 2H), 7.35 (d, J = 1.2 Hz, 1H), 7.28 (d, J = 1.2 Hz, 1H), 4.56 (dd, J = 5.6, 12.8 Hz, 1H), 4.28 (d, J = 6.0 Hz, 2H), 2.85 (ddd, J = 6.0, 14.0, 16.8 Hz, 1H), 2.58 – 2.52 (m, 1H), 2.34 (dq, J = 4.4, 13.2 Hz, 1H), 1.93 – 1.84 (m, 1H), 1.67 (s, 6H). MS (ESI) m/z 474.1 $[M + H]^+$ |
| Compound 168 | Synthesized in analogy to compound 6 | $^1H$ NMR (400 MHz, DMSO-$d_6$) δ = 10.95 (s, 1H), 8.53 (d, J = 5.2 Hz, 1H), 7.98 (t, J = 6.0 Hz, 1H), 7.37 (d, J = 1.2 Hz, 1H), 7.30 (s, 1H), 7.23 (d, J = 5.2 Hz, 1H), 4.56 (dd, J = 5.6, 12.4 Hz, 1H), 4.24 (d, J = 6.0 Hz, 2H), 2.85 (d, J = 5.6, 14.0, 16.8 Hz, 1H), 2.62 – 2.52 (m, 1H), 2.36 (dq, J = 4.4, 13.2 Hz, 1H), 2.14 – 2.03 (m, 1H), 1.97 – 1.79 (m, 1H), 1.49 (s, 6H), 1.18 – 0.88 (m, 4H). MS (ESI) m/z 475.2 $[M + H]^+$ |
| Compound 171 | Synthesized in analogy to compound 10 | $^1H$ NMR (400 MHz, DMSO-$d_6$) δ = 10.94 (s, 1H), 8.68 (s, 1H), 7.77 (t, J = 6.0 Hz, 1H), 7.70 – 7.66 (m, 1H), 7.45 – 7.39 (m, 1H), 7.36 – 7.31 (m, 1H), 7.31 – 7.28 (m, 1H), 7.26 – 7.22 (s, 1H), 4.55 (dd, J = 5.6, 12.8 Hz, 1H), 4.19 (d, J = 6.0 Hz, 2H), 2.91 – 2.78 (m, 1H), 2.59 – 2.53 (m, 1H), 2.39 – 2.27 (m, 1H), 1.93 – 1.83 (m, 1H), 1.64 (s, 6H). MS (ESI) m/z 474.0 $[M + H]^+$ |
| Compound 172 | Synthesized in analogy to compound 59 | $^1H$ NMR (400 MHz, DMSO-$d_6$) δ = 10.95 (s, 1H), 8.16 (t, J = 6.0 Hz, 1H), 7.22 (s, 1H), 7.15 (s, 1H), 6.25 (d, J = 1.6 Hz, 1H), 5.94 (dd, J = 1.6, 6.8 Hz, 1H), 4.55 (dd, J = 5.6, 12.8 Hz, 1H), 4.21 (d, J = 6.0 Hz, 2H), 3.36 (s, 3H), 2.89 – 2.77 (m, 1H), 2.56 – 2.51 (m, 1H), 2.38 – 2.28 (m, 1H), 1.93 – 1.83 (m, 1H), 1.41 (s, 6H). MS (ESI) m/z 482.1 $[M + H]^+$ |
| Compound 173 | Synthesized in analogy to compound 19 | $^1H$ NMR (400 MHz, DMSO-$d_6$) δ = 10.95 (s, 1H), 9.00 (s, 1H), 8.11 (t, J = 5.6 Hz, 1H), 7.38 (s, 1H), 7.34 (d, J = 1.6 Hz, 1H), 7.28 (s, 1H), 4.56 (dd, J = 5.6, 12.8 Hz, 1H), 4.24 (d, J = 6.0 Hz, 2H), 2.93 – 2.78 (m, 1H), 2.55 (d, J = 2.4 Hz, 1H), 2.46 (s, 3H), 2.39 – 2.30 (m, 1H), 1.96 – 1.83 (m, 1H), 1.50 (s, 6H). MS (ESI) m/z 449.1 $[M + H]^+$ |
| Compound 174 | Synthesized in analogy to compound 6 | $^1H$ NMR (400 MHz, DMSO-$d_6$) δ = 10.95 (s, 1H), 9.18 (d, J = 4.8 Hz, 1H), 8.14 (t, J = 6.0 Hz, 1H), 7.93 (d, J = 4.8 Hz, 1H), 7.36 (s, 1H), 7.29 (s, 1H), 4.57 (dd, J = 5.6, 12.8 Hz, 1H), 4.25 (d, J = 5.6 Hz, 2H), 2.86 (ddd, J = 5.6, 14.0, 16.8 Hz, 1H), 2.56 (d, J = 2.0 Hz, 1H), 2.36 (dq, J = 4.4, 13.2 Hz, 1H), 1.96 – 1.81 (m, 1H), 1.58 (s, 6H). MS (ESI) m/z 503.1 $[M + H]^+$ |
| Compound 175 | Synthesized in analogy to compound 6 | $^1H$ NMR (400 MHz, DMSO-$d_6$) δ = 10.95 (s, 1H), 9.26 (s, 2H), 8.12 (t, J = 6.0 Hz, 1H), 7.35 (s, 1H), 7.29 (s, 1H), 4.62 – 4.52 (m, 1H), 4.26 (d, J = 5.6 Hz, 2H), 2.92 – 2.79 (m, 1H), 2.60 – 2.53 (m, 1H), 2.43 – 2.28 (m, 1H), 1.96 – 1.84 (m, 1H), 1.60 (s, 6H). MS (ESI) m/z 503.1 $[M + H]^+$ |
| Compound 176 | Synthesized in analogy to compound 19 | $^1H$ NMR (400 MHz, DMSO-$d_6$) δ = 10.96 (s, 1H), 8.49 (s, 1H), 8.43 (s, 1H), 8.08 – 8.05 (t, J = 6.0 Hz, 1H), 7.27 (d, J = 1.2 Hz, 1H), 7.20 (d, J = 1.2 Hz, 1H), 4.59 – 4.54 (dd, J = 5.6, 12.8 Hz, 1H), 4.23 (d, |

TABLE 2-continued

| Compound ID | Synthesis | Characterization |
|---|---|---|
| | | J = 6.0 Hz, 2H), 2.90 - 2.81 (ddd, J = 5.6, 14.0, 16.8 Hz, 1H), 2.56 (m, 1H), 2.50 (s, 3H), 2.41 - 2.30 (dq, J = 4.4, 13.2 Hz, 1H), 1.92 - 1.86 (m, 1H), 1.55 (s, 6H). MS (ESI) m/z 449.0 $[M + H]^+$ |
| Compound 178 | Synthesized in analogy to compound 1 with 3-bromooxetane as the coupling partner | $^1$H NMR (400 MHz, DMSO-$d_6$) δ = 10.96 (s, 1H), 8.87 (s, 2H), 8.07 (t, J = 6.0 Hz, 1H), 7.40 (s, 1H), 7.34 (s, 1H), 4.95 (dd, J = 6.0, 8.4 Hz, 2H), 4.68 (t, J = 6.4 Hz, 2H), 4.56 (dd, J = 5.6, 12.8 Hz, 1H), 4.36 - 4.29 (m, 1H), 4.26 (d, J = 6.0 Hz, 2H), 2.92 - 2.79 (m, 1H), 2.58 - 2.52 (m, 1H), 2.42 - 2.29 (m, 1H), 1.94 - 1.84 (m, 1H), 1.56 (s, 6H). MS (ESI) m/z 491.1 $[M + H]^+$ |
| Compound 182 | Synthesized in analogy to Compound 181 | $^1$H NMR (400 MHz, DMSO-$d_6$) δ = 10.96 (s, 1H), 9.05 (d, J = 4.8 Hz, 1H), 8.14 (t, J = 6.0 Hz, 1H), 7.69 (d, J = 5.2 Hz, 1H), 7.38 (d, J = 1.2 Hz, 1H), 7.31 (s, 1H), 7.14 - 6.78 (m, 1H), 4.57 (dd, J = 5.6, 12.8 Hz, 1H), 4.25 (d, J = 6.0 Hz, 2H), 2.92 - 2.79 (m, 1H), 2.57 - 2.52 (m, 1H), 2.43 - 2.30 (m, 1H), 1.95 - 1.85 (m, 1H), 1.57 (s, 6H). MS (ESI) m/z 484.9 $[M + H]^+$ |
| Compound 183 | Synthesized in analogy to Compound 14 | $^1$H NMR (400 MHz, DMSO-$d_6$) δ = 10.96 (s, 1H), 8.75 (s, 2H), 8.09 (t, J = 6.0 Hz, 1H), 7.42 (s, 1H), 7.35 (s, 1H), 4.61 - 4.51 (m, 1H), 4.47 (s, 2H), 4.25 (d, J = 6.0 Hz, 2H), 3.32 (s, 3H), 2.92 - 2.78 (m, 1H), 2.62 - 2.53 (m, 1H), 2.42 - 2.29 (m, 1H), 1.96 - 1.82 (m, 1H), 1.55 (s, 6H). MS (ESI) m/z 479.2 $[M + H]^+$ |
| Compound 185 | Synthesized in analogy to Compound 120 | $^1$H NMR (400 MHz, DMSO-$d_6$) δ = 10.96 (s, 1H), 8.18 (t, 1H), 7.27 (d, J = 1.6 Hz, 1H), 7.20 (d, J = 1.2 Hz, 1H), 6.14 (s, 1H), 4.56 (dd, J = 5.6, 12.8 Hz, 1H), 4.22 (d, J = 6.0 Hz, 2H), 2.94 - 2.77 (m, 1H), 2.58 - 2.52 (m, 1H), 2.38 - 2.27 (m, 1H), 2.09 (s, 1H), 1.94 - 1.84 (m, 1H), 1.47 (s, 6H), 1.07 - 0.98 (m, 2H), 0.89 - 0.80 (m, 2H). MS (ESI) m/z 464.1 $[M + H]^+$ |
| Compound 189 | Synthesized in analogy to Compound 188 | $^1$H NMR (400 MHz, DMSO-$d_6$) δ = 10.96 (br s, 1H), 8.52 (s, 2H), 7.99 (t, J = 6.0 Hz, 1H), 7.38 (d, J = 1.6 Hz, 1H), 7.31 (d, J = 1.2 Hz, 1H), 4.56 (dd, J = 5.6, 12.8 Hz, 1H), 4.24 (d, J = 6.0 Hz, 2H), 3.90 (s, 3H), 2.91 - 2.80 (m, 1H), 2.61 - 2.51 (m, 1H), 2.40 - 2.30 (m, 1H), 1.94 - 1.84 (m, 1H), 1.53 (s, 6H). MS (ESI) m/z 465.0 $[M + H]^+$ |
| Compound 190 | Synthesized in analogy to Compound 35 | $^1$H NMR (400 MHz, DMSO-$d_6$) δ = 10.95 (s, 1H), 9.41 (s, 1H), 9.03 (dd, J = 1.6, 4.0 Hz, 1H), 8.45 (d, J = 7.6 Hz, 1H), 8.04 - 7.84 (m, 2H), 7.78 (dd, J = 4.0, 8.4 Hz, 1H), 7.31 (d, J = 1.2 Hz, 1H), 7.24 (d, J = 1.6 Hz, 1H), 4.54 (dd, J = 5.6, 12.8 Hz, 1H), 4.23 (d, J = 6.0 Hz, 2H), 2.92 - 2.77 (m, 1H), 2.60 - 2.51 (m, 1H), 2.33 (dq, J = 4.4, 13.2 Hz, 1H), 1.92 - 1.81 (m, 1H), 1.64 (s, 6H). MS (ESI) m/z 485.0 $[M + H]^+$ |
| Compound 191 | Synthesized in analogy to Compound 6 | $^1$H NMR (400 MHz, DMSO-$d_6$) δ = 10.96 (s, 1H), 8.29 - 8.26 (t, J = 6.0 Hz, 1H), 8.24 - 8.22 (d, J = 9.2 Hz, 1H), 8.02 - 8.00 (d, J = 8.8 Hz, 1H), 7.26 - 7.25 (d, J = 1.6 Hz, 1H), 7.19 (d, J = 1.6 Hz, 1H), 4.58 - 4.53 (dd, J = 5.6, 12.8 Hz, 1H), 4.26 - 4.24 (d, J = 6.0 Hz, 2H), 2.90 - 2.80 (m, 1H), 2.55 - 2.54 (m, 1H), 2.40 - 2.29 (dq, J = 4.4, 13.2 Hz, 1H), 1.91 - 1.85 (m, 1H), 1.66 (s, 6H). MS (ESI) m/z 503.2 $[M + H]^+$ |
| Compound 193 | Synthesized in analogy to Compound 120 | $^1$H NMR (400 MHz, DMSO-$d_6$) δ = 10.96 (s, 1H), 8.28 (t, J = 6.0 Hz, 1H), 7.76 (s, 1H), 7.30 (d, J = 1.2 Hz, 1H), 7.23 (d, J = 1.2 Hz, 1H), 4.57 (dd, J = 5.6, 12.8 Hz, 1H), 4.24 (d, J = 6.0 Hz, 2H), 2.92 - 2.79 (m, 1H), 2.59 - 2.52 (m, 1H), 2.36 (dq, J = 4.4, 13.2 Hz, 1H), 1.95 - 1.84 (m, 1H), 1.83 - 1.74 (m, 1H), 1.51 (s, 6H), 0.86 - 0.76 (m, 2H), 0.70 - 0.59 (m, 2H). MS (ESI) m/z 464.1 $[M + H]^+$ |
| Compound 194 | Synthesized in analogy to Compound 6 | $^1$H NMR (400 MHz, DMSO-$d_6$) δ = 10.95 (s, 1H), 8.91 (s, 2H), 8.06 (t, J = 6.0 Hz, 1H), 7.35 (s, 1H), 7.28 (s, 1H), 4.61 - 4.51 (m, 1H), 4.24 (d, J = 6.0 Hz, 2H), 2.94 - 2.77 (m, 1H), 2.59 - 2.51 (m, 1H), 2.43 - 2.29 (m, 1H), 1.96 - 1.84 (m, 1H), 1.55 (s, 6H). MS (ESI) m/z 469.0 $[M + H]^+$ |
| Compound 197 | Synthesized in analogy to | $^1$H NMR (400 MHz, DMSO-$d_6$) δ = 10.96 (s, 1H), 8.31 (t, J = 6.0 Hz, 1H), 7.73 (s, 1H), 7.32 (s, 1H), |

TABLE 2-continued

| Exemplary compounds - additional examples | | |
|---|---|---|
| Compound ID | Synthesis | Characterization |
| | Compound 120 | 7.25 (s, 1H), 4.56 (dd, J = 5.2, 12.4 Hz, 1H), 4.24 (d, J = 6.0 Hz, 2H), 2.92 − 2.78 (m, 1H), 2.59 − 2.51 (m, 1H), 2.35 (dq, J = 4.4, 13.2 Hz, 1H), 2.09 (s, 3H), 1.95 − 1.84 (m, 1H), 1.53 (s, 6H). MS (ESI) m/z 438.0 $[M + H]^+$ |
| Compound 199 | Synthesized in analogy to Compound 120 | $^1H$ NMR (400 MHz, DMSO-$d_6$) δ = 10.95 (br s, 1H), 8.68 (s, 1H), 8.19 (t, J = 6.0 Hz, 1H), 7.34 (d, J = 1.2 Hz, 1H), 7.27 (s, 1H), 4.57 (dd, J = 5.6, 12.8 Hz, 1H), 4.22 (d, J = 6.0 Hz, 2H), 2.94 − 2.77 (m, 1H), 2.60 − 2.52 (m, 1H), 2.39 − 2.29 (m, 1H), 1.95 − 1.81 (m, 1H), 1.49 (s, 6H). MS (ESI) m/z 492.0 $[M + H]^+$ |
| Compound 201 | Synthesized in analogy to Compound 120 | $^1H$ NMR (400 MHz, DMSO-$d_6$) δ = 10.95 (s, 1H), 8.59 (s, 1H), 8.25 (t, J = 6.0 Hz, 1H), 7.30 (d, J = 1.6 Hz, 1H), 7.23 (d, J = 1.6 Hz, 1H), 4.56 (dd, J = 5.6, 12.8 Hz, 1H), 4.22 (d, J = 6.0 Hz, 2H), 2.93 − 2.78 (m, 1H), 2.59 − 2.52 (m, 1H), 2.35 (dq, J = 4.4, 13.2 Hz, 1H), 1.94 − 1.85 (m, 1H), 1.79 (d, J = 0.8 Hz, 3H), 1.50 (s, 6H). MS (ESI) m/z 438.1 $[M + H]^+$ |
| Compound 203 | Synthesized in analogy to Compound 187 | $^1H$ NMR (400 MHz, DMSO-$d_6$) δ = 10.95 (s, 1H), 8.27 (t, J = 6.0 Hz, 1H), 7.99 (d, J = 8.8 Hz, 1H), 7.87 (d, J = 8.8 Hz, 1H), 7.27 (s, 1H), 7.21 (s, 1H), 4.56 (dd, J = 5.6, 12.8 Hz, 1H), 4.25 (d, J = 6.0 Hz, 2H), 2.92 − 2.77 (m, 1H), 2.60 − 2.52 (m, 1H), 2.40 − 2.29 (m, 1H), 2.15 (t, J = 19.2 Hz, 3H), 1.93 − 1.83 (m, 1H), 1.64 (s, 6H). MS (ESI) m/z 499.2 $[M + H]^+$ |
| Compound 205 | Synthesized in analogy to Compound 7 | $^1H$ NMR (400 MHz, DMSO-$d_6$) δ = 10.95 (s, 1H), 8.42 (d, J = 2.0 Hz, 1H), 8.09 (t, J = 6.0 Hz, 1H), 7.56 (dd, J = 2.4, 8.0 Hz, 1H), 7.24 − 7.15 (m, 2H), 7.10 (s, 1H), 4.55 (dd, J = 5.6, 12.8 Hz, 1H), 4.20 (d, J = 6.0 Hz, 2H), 2.91 − 2.76 (m, 1H), 2.59 − 2.52 (m, 1H), 2.44 (s, 3H), 2.34 (q, J = 4.0, 13.2 Hz, 1H), 1.94 − 1.82 (m, 1H), 1.50 (s, 6H). MS (ESI) m/z 448.2 $[M + H]^+$ |
| Compound 209 | Synthesized in analogy to Compound 6 | $^1H$ NMR (400 MHz, DMSO-$d_6$) δ = 10.95 (s, 1H), 8.37 − 8.15 (m, 2H), 7.98 (t, J = 6.0 Hz, 1H), 7.27 (s, 1H), 7.20 (s, 1H), 4.55 (dd, J = 5.6, 12.8 Hz, 1H), 4.21 (d, J = 6.0 Hz, 2H), 3.91 (s, 3H), 2.93 − 2.77 (m, 1H), 2.62 − 2.52 (m, 1H), 2.35 (dq, J = 4.0, 13.2 Hz, 1H), 1.94 − 1.82 (m, 1H), 1.53 (s, 6H). MS (ESI) m/z 465.1 $[M + H]^+$ |
| Compound 210 | Synthesized in analogy to Compound 188 | $^1H$ NMR (400 MHz, DMSO-$d_6$) δ = 10.96 (s, 1H), 8.24 (t, J = 6.0 Hz, 1H), 8.10 − 7.70 (m, 2H), 7.49 (d, J = 9.2 Hz, 1H), 7.27 (d, J = 1.6 Hz, 1H), 7.21 (s, 1H), 4.56 (dd, J = 5.6, 12.4 Hz, 1H), 4.24 (d, J = 6.0 Hz, 2H), 2.91 − 2.82 (m, 1H), 2.60 − 2.52 (m, 1H), 2.41 − 2.31 (m, 1H), 1.94 − 1.85 (m, 1H), 1.61 (s, 6H). MS (ESI) m/z 501.1 $[M + H]^+$ |
| Compound 219 | Synthesized in analogy to Compound 120 | $^1H$ NMR (400 MHz, DMSO-$d_6$) δ = 10.95 (br s, 1H), 8.66 ( t, J = 5.6 Hz, 1H), 7.54 − 7.20 (m, 3H), 4.58 (dd, J = 5.6, 12.8 Hz, 1H), 4.28 (d, J = 5.6 Hz, 2H), 2.94 − 2.76 (m, 1H), 2.57 − 2.51 (m, 1H), 2.36 (q, J = 4.4, 13.2 Hz, 1H), 1.97 − 1.85 (m, 1H), 1.68 (s, 6H). MS (ESI) m/z 497.1 $[M + H]^+$ |
| Compound 220 | Synthesized in analogy to Compound 198 | $^1H$ NMR (400 MHz, DMSO-$d_6$) δ = 10.96 (s, 1H), 9.74 (s, 1H), 8.30 (t, J = 6.0 Hz, 1H), 7.34 (d, J = 1.2 Hz, 1H), 7.27 (s, 1H), 4.66 − 4.52 (m, 1H), 4.23 (d, J = 6.0 Hz, 2H), 2.93 − 2.78 (m, 1H), 2.61 − 2.54 (m, 1H), 2.43 − 2.28 (m, 1H), 1.96 − 1.83 (m, 1H), 1.57 (s, 6H). MS (ESI) m/z 492.0 $[M + H]^+$ |
| Compound 228 | Synthesized in analogy to Compound 222 | $^1H$ NMR (400 MHz, DMSO-$d_6$) δ = 10.94 (s, 1H), 8.20 (t, J = 6.0 Hz, 1H), 7.70 − 7.59 (m, 2H), 7.25 (d, J = 1.6 Hz, 1H), 7.18 (d, J = 1.6 Hz, 1H), 4.70 (s, 2H), 4.55 (dd, J = 5.6, 12.8 Hz, 1H), 4.23 (d, J = 6.0 Hz, 2H), 3.37 (s, 3H), 2.85 (ddd, J = 5.6, 14.0, 16.8 Hz, 1H), 2.60 − 2.52 (m, 1H), 2.34 (dq, J = 4.4, 13.2 Hz, 1H), 1.94 − 1.82 (m, 1H), 1.61 (s, 6H). MS (ESI) m/z 479.1 $[M + H]^+$ |
| Compound 232 | Synthesized in analogy to Compound 207 | $^1H$ NMR (400 MHz, DMSO-$d_6$) δ = 10.95 (s, 1H), 8.56 (d, J = 1.2 Hz, 1H), 8.50 (s, 1H), 8.05 (t, J = 6.0 Hz, 1H), 7.27 (s, 1H), 7.21 (s, 1H), 4.56 (dd, J = 5.6, 12.8 Hz, 1H), 4.22 (d, J = 6.0 Hz, 2H), 2.85 (ddd, J = 5.6, 14.0, 16.8 Hz, 1H), 2.55 (m, 1H), 2.35 (dq, J = 4.0, 13.2 Hz, 1H), 2.25 − 2.14 (m, 1H), 1.89 (td, J = 5.6, 11.6 Hz, 1H), 1.53 (s, 6H), 1.08 − 0.98 |

TABLE 2-continued

| Exemplary compounds - additional examples | | |
|---|---|---|
| Compound ID | Synthesis | Characterization |
| | | (m, 2H), 0.98 – 0.90 (m, 2H). MS (ESI) m/z 475.1 $[M + H]^+$ |
| Compound 236 | Synthesized in analogy to Compound 120 | $^1$H NMR (400 MHz, DMSO-$d_6$) δ = 10.94 (s, 1H), 8.12 (s, 1H), 7.98 (s, 1H), 7.32 (s, 1H), 7.25 (s, 1H), 4.56 (dd, J = 5.6, 12.8 Hz, 1H), 4.22 (d, J = 6.0 Hz, 2H), 2.93 – 2.78 (m, 1H), 2.55 (d, J = 2.1 Hz, 1H), 2.39 – 2.28 (m, 1H), 2.24 (s, 3H), 1.95 – 1.83 (m, 1H), 1.44 (s, 6H). MS (ESI) m/z 438.0 $[M + H]^+$ |
| Compound 237 | Synthesized in analogy to Compound 14 | $^1$H NMR (400 MHz, DMSO-$d_6$) δ = 10.96 (s, 1H), 8.64 (s, 2H), 8.03 (t, J = 6.0 Hz, 1H), 7.40 (d, J = 1.6 Hz, 1H), 7.34 (d, J = 1.6 Hz, 1H), 4.56 (dd, J = 5.6, 12.8 Hz, 1H), 4.25 (d, J = 6.0 Hz, 2H), 2.95 – 2.79 (m, 1H), 2.61 – 2.53 (m, 1H), 2.39 – 2.32 (m, 1H), 2.27 (s, 3H), 1.98 – 1.82 (m, 1H). MS (ESI) m/z 455.1/477.1 $[M + H/M + Na]^+$ |
| Compound 248 | Synthesized in analogy to Compound 6 | $^1$H NMR (400 MHz, DMSO-$d_6$) δ = 10.95 (s, 1H), 8.74 (s, 1H), 8.58 (s, 1H), 8.09 (t, J = 5.6 Hz, 1H), 7.27 (s, 1H), 7.20 (s, 1H), 4.56 (dd, J = 5.6, 12.8 Hz, 1H), 4.22 (d, J = 5.6 Hz, 2H), 2.92 – 2.77 (m, 1H), 2.55 (s, 1H), 2.41 – 2.30 (m, 1H), 1.95 – 1.82 (m, 1H), 1.57 (s, 6H). MS (ESI) m/z 469.1 $[M + H]^+$ |
| Compound 249 | Synthesized in analogy to Compound 246 | $^1$H NMR (400 MHz, DMSO-$d_6$) δ = 10.96 (s, 1H), 8.48 (t, J = 6.0 Hz, 1H), 7.82 – 7.65 (m, 2H), 7.47 – 7.31 (m, 2H), 7.19 (s, 1H), 7.07 (d, J = 11.2 Hz, 1H), 4.45 – 4.16 (m, 3H), 2.94 – 2.72 (m, 1H), 2.60 – 2.52 (m, 1H), 2.33 – 2.02 (m, 1H), 2.00 – 1.87 (m, 1H), 1.67 (s, 6H). MS (ESI) m/z 458.1 $[M + H]^+$ |
| Compound 250 | Synthesized in analogy to Compound 27 | $^1$H NMR (400 MHz, DMSO-$d_6$) δ = 10.94 (s, 1H), 8.14 (d, J = 2.4 Hz, 1H), 8.05 (t, J = 6.0 Hz, 1H), 7.67 – 7.54 (m, 1H), 7.00 (s, 1H), 6.92 (d, J = 11.2 Hz, 1H), 6.77 (d, J = 8.4 Hz, 1H), 4.39 – 4.27 (m, 1H), 4.21 (d, J = 6.0 Hz, 2H), 3.83 (s, 3H), 2.89 – 2.75 (m, 1H), 2.58 – 2.52 (m, 1H), 2.28 – 2.02 (m, 1H), 2.00 – 1.84 (m, 1H), 1.50 (s, 6H). MS (ESI) m/z 448.2 $[M + H]^+$ |
| Compound 251 | Synthesized in analogy to Compound 209 | $^1$H NMR (400 MHz, DMSO-$d_6$) δ = 10.94 (s, 1H), 8.25 (dd, J = 1.2, 8.8 Hz, 2H), 7.97 (t, J = 6.0 Hz, 1H), 7.11 (s, 1H), 7.00 (d, J = 10.8 Hz, 1H), 4.33 (dd, J = 5.2, 12.4 Hz, 1H), 4.22 (d, J = 6.0 Hz, 2H), 3.91 (s, 3H), 2.82 (ddd, J = 5.6, 13.6, 17.2 Hz, 1H), 2.54 (d, J = 3.2 Hz, 1H), 2.29 – 2.00 (m, 1H), 1.99 – 1.86 (m, 1H), 1.54 (s, 6H). MS (ESI) m/z 449.1 $[M + H]^+$ |
| Compound 252 | Synthesized in analogy to Compound 234 | $^1$H NMR (400 MHz, DMSO-$d_6$) δ = 10.95 (s, 1H), 8.29 – 8.16 (m, 2H), 7.98 (t, J = 6.0 Hz, 1H), 7.11 (s, 1H), 7.00 (d, J = 11.2 Hz, 1H), 4.39 – 4.29 (m, 3H), 4.22 (d, J = 6.0 Hz, 2H), 2.93 – 2.74 (m, 1H), 2.55 – 2.51 (m, 1H), 2.33 – 2.01 (m, 1H), 2.00 – 1.88 (m, 1H), 1.53 (s, 6H), 1.34 (t, J = 7.2 Hz, 3H). MS (ESI) m/z 463.1 $[M + H]^+$ |
| Compound 253 | Synthesized in analogy to Compound 14 | $^1$H NMR (400 MHz, DMSO-$d_6$) δ = 10.95 (s, 1H), 8.63 (s, 2H), 8.03 (t, J = 6.0 Hz, 1H), 7.25 (s, 1H), 7.11 (d, J = 11.2 Hz, 1H), 4.33 (m, 1H), 4.25 (d, J = 6.0 Hz, 2H), 2.84 – 2.78 (m, 1H), 2.61 – 2.51 (m, 1H), 2.27 (s, 3H), 2.25 – 2.01 (m, 1H), 2.00 – 1.87 (m, 1H), 1.53 (s, 6H). MS (ESI) m/z 433.3 $[M + H]^+$ |
| Compound 254 | Synthesized in analogy to Compound 197 | $^1$H NMR (400 MHz, DMSO-$d_6$) δ = 10.95 (s, 1H), 8.30 (t, J = 6.0 Hz, 1H), 7.73 (d, J = 1.2 Hz, 1H), 7.16 (s, 1H), 7.04 (d, J = 11.2 Hz, 1H), 4.34 (dd, J = 5.2, 12.4 Hz, 1H), 4.25 (d, J = 6.0 Hz, 2H), 2.88 – 2.76 (m, 1H), 2.59 – 2.52 (m, 1H), 2.29 – 2.01 (m, 4H), 2.00 – 1.89 (m, 1H), 1.53 (s, 6H). MS (ESI) m/z 422.2 $[M + H]^+$ |
| Compound 255 | Synthesized in analogy to Compound 187 | $^1$H NMR (400 MHz, DMSO-$d_6$) δ = 10.96 (s, 1H), 8.92 (d, J = 1.2 Hz, 1H), 8.82 (s, 1H), 8.20 (t, J = 6.0 Hz, 1H), 7.14 (s, 1H), 7.03 (d, J = 10.8 Hz, 1H), 4.34 (dd, J = 5.2, 12.8 Hz, 1H), 4.25 (d, J = 6.0 Hz, 2H), 2.93 – 2.73 (m, 1H), 2.54 (d, J = 3.2 Hz, 1H), 2.09 – 1.99 (m, 4H), 1.95 (d, J = 5.6 Hz, 1H), 1.61 (s, 6H). MS (ESI) m/z 483.2 $[M + H]^+$ |
| Compound 256 | Synthesized in analogy to Compound 188 | $^1$H NMR (400 MHz, DMSO-$d_6$) δ = 10.96 (s, 1H), 8.52 (s, 2H), 7.99 (t, J = 6.0 Hz, 1H), 7.22 (s, 1H), 7.08 (d, J = 11.2 Hz, 1H), 4.33 (dd, J = 5.2, 12.4 Hz, 1H), 4.24 (d, J = 6.0 Hz, 2H), 3.90 (s, 3H), 2.89 – 2.75 (m, 1H), 2.54 (d, J = 3.2 Hz, 1H), |

TABLE 2-continued

| Exemplary compounds - additional examples | | |
|---|---|---|
| Compound ID | Synthesis | Characterization |
| | | 2.12 (s, 1H), 2.00 – 1.91 (m, 1H), 1.53 (s, 6H). MS (ESI) m/z 449.1 $[M + H]^+$ |
| Compound 257 | Synthesized in analogy to Compound 188 | $^1H$ NMR (400 MHz, DMSO-$d_6$) δ = 10.96 (s, 1H), 8.52 (d, J = 1.6 Hz, 1H), 8.39 (d, J = 1.6 Hz, 1H), 8.07 (t, J = 6.0 Hz, 1H), 7.71 (t, J = 72.0 Hz, 1H), 7.27 (d, J = 1.6 Hz, 1H), 7.21 (d, J = 1.2 Hz, 1H), 4.56 (dd, J = 5.6, 12.8 Hz, 1H), 4.22 (d, J = 6.0 Hz, 2H), 2.85 (ddd, J = 5.6, 14.0, 16.8 Hz, 1H), 2.58 – 2.51 (m, 1H), 2.35 (dq, J = 4.4, 13.2 Hz, 1H), 1.97 – 1.84 (m, 1H), 1.57 (s, 6H). MS (ESI) m/z 501.0 $[M + H]^+$ |
| Compound 258 | Synthesized in analogy to Compound 234 | $^1H$ NMR (400 MHz, DMSO-$d_6$) δ = 10.96 (s, 1H), 8.16 (t, J = 6.0 Hz, 1H), 7.57 (d, J = 9.2 Hz, 1H), 7.14 (d, J = 9.2 Hz, 1H), 7.09 (s, 1H), 7.00 (d, J = 11.2 Hz, 1H), 4.48 (q, J = 7.2 Hz, 2H), 4.33 (dd, J = 5.2, 12.4 Hz, 1H), 4.24 (d, J = 6.0 Hz, 2H), 2.83 (ddd, J = 5.6, 13.2, 17.2 Hz, 1H), 2.60 – 2.52 (m, 1H), 2.13 (s, 1H), 1.99 – 1.85 (m, 1H), 1.57 (s, 6H), 1.39 (t, J = 7.2 Hz, 3H). MS (ESI) m/z 463.1 $[M + H]^+$ |
| Compound 259 | Synthesized in analogy to Compound 229 | $^1H$ NMR (400 MHz, DMSO-$d_6$) δ = 10.96 (s, 1H), 8.69 (d, J = 1.2 Hz, 1H), 8.54 (d, J = 1.2 Hz, 1H), 8.11 (t, J = 6.0 Hz, 1H), 7.27 (d, J = 1.6 Hz, 1H), 7.21 (d, J = 1.2 Hz, 1H), 4.56 (dd, J = 5.6, 12.8 Hz, 1H), 4.23 (d, J = 6.0 Hz, 2H), 2.85 (ddd, J = 5.6, 14.0, 16.8 Hz, 1H), 2.58 – 2.52 (m, 1H), 2.35 (dq, J = 4.4, 13.2 Hz, 1H), 1.97 – 1.83 (m, 1H), 1.59 (s, 6H). MS (ESI) m/z 519.1 $[M + H]^+$ |
| Compound 261 | Synthesized in analogy to Compound 27 | $^1H$ NMR (400 MHz, DMSO-$d_6$) δ = 10.95 (s, 1H), 8.25 (d, J = 2.8 Hz, 1H), 7.93 (t, J = 6.0 Hz, 1H), 7.42 – 7.28 (m, 2H), 7.12 (s, 1H), 7.01 (d, J = 11.2 Hz, 1H), 4.32 (dd, J = 5.2, 12.4 Hz, 1H), 4.22 (d, J = 6.0 Hz, 2H), 3.81 (s, 3H), 2.82 (ddd, J = 5.6, 13.2, 17.2 Hz, 1H), 2.54 (d, J = 3.2 Hz, 1H), 2.30 – 2.01 (m, 1H), 1.99 – 1.88 (m, 1H), 1.50 (s, 6H). MS (ESI) m/z 448.2 $[M + H]^+$ |
| Compound 262 | Synthesized in analogy to Compound 204 | $^1H$ NMR (400 MHz, DMSO-$d_6$) δ = 10.95 (s, 1H), 8.16 (t, J = 6.0 Hz, 1H), 7.58 (d, J = 9.2 Hz, 1H), 7.18 (d, J = 9.2 Hz, 1H), 7.09 (s, 1H), 7.00 (d, J = 11.2 Hz, 1H), 4.38 – 4.30 (m, 1H), 4.24 (d, J = 6.0 Hz, 2H), 2.88 – 2.78 (m, 1H), 2.56 – 2.50 (m, 1H), 2.27 – 2.01 (m, 1H), 2.01 – 1.89 (m, 1H), 1.58 (s, 6H). MS (ESI) m/z 449.1 $[M + H]^+$. |
| Compound 263 | Synthesized in analogy to Compound 187 | $^1H$ NMR (400 MHz, DMSO-$d_6$) δ = 10.96 (s, 1H), 8.92 (d, J = 1.2 Hz, 1H), 8.82 (s, 1H), 8.19 (t, J = 6.0 Hz, 1H), 7.30 (d, J = 1.2 Hz, 1H), 7.23 (s, 1H), 4.56 (dd, J = 5.2, 12.8 Hz, 1H), 4.25 (d, J = 6.0 Hz, 2H), 2.85 (ddd, J = 6.0, 14.0, 16.8 Hz, 1H), 2.59 – 2.53 (m, 1H), 2.39 – 2.29 (m, 1H), 2.04 (t, J = 19.2 Hz, 3H), 1.93 – 1.85 (m, 1H), 1.61 (s, 6H). MS (ESI) m/z 499.2 $[M + H]^+$ |
| Compound 264 | Synthesized in analogy to Compound 259 | $^1H$ NMR (400 MHz, DMSO-$d_6$) δ = 10.95 (s, 1H), 8.69 (d, J = 0.8 Hz, 1H), 8.53 (d, J = 0.8 Hz, 1H), 8.11 (t, J = 6.0 Hz, 1H), 7.11 (s, 1H), 7.00 (d, J = 11.2 Hz, 1H), 4.33 (dd, J = 5.2, 12.4 Hz, 1H), 4.24 (d, J = 6.0 Hz, 2H), 2.90 – 2.75 (m, 1H), 2.54 (m, 1H), 2.29 – 2.01 (m, 1H), 2.00 – 1.86 (m, 1H), 1.59 (s, 6H). MS (ESI) m/z 503.1 $[M + H]^+$ |
| Compound 267 | Synthesized in analogy to Compound 35 | $^1H$ NMR (400 MHz, DMSO-$d_6$) δ = 10.95 (s, 1H), 8.22 (d, J = 2.4 Hz, 1H), 8.14 (t, J = 6.0 Hz, 1H), 7.90 – 7.48 (m, 2H), 7.05 (d, J = 8.8 Hz, 1H), 7.01 (s, 1H), 6.94 (d, J = 11.2 Hz, 1H), 4.35 – 4.20 (m, 1H), 4.22 (d, J = 6.0 Hz, 2H), 2.88 – 2.76 (m, 1H), 2.55 – 2.51 (m, 1H), 2.30 – 2.00 (m, 1H), 1.97 – 1.85 (m, 1H), 1.53 (s, 6H). MS (ESI) m/z 484.1 $[M + H]^+$ |
| Compound 268 | Synthesized in analogy to Compound 227 | $^1H$ NMR (400 MHz, DMSO-$d_6$) δ = 10.97 (s, 1H), 8.68 (s, 1H), 8.13 (t, J = 6.0 Hz, 1H), 7.17 (s, 1H), 7.03 (d, J = 11.2 Hz, 1H), 4.35 (dd, J = 5.2, 12.4 Hz, 1H), 4.23 (d, J = 6.0 Hz, 2H), 3.68 (s, 3H), 2.83 (ddd, J = 5.6, 13.6, 17.2 Hz, 1H), 2.54 (d, J = 3.2 Hz, 1H), 2.31 – 2.02 (m, 1H), 2.00 – 1.89 (m, 1H), 1.49 (s, 6H). MS (ESI) m/z 438.1 $[M + H]^+$ |
| Compound 271 | Synthesized in analogy to Compound 14 | $^1H$ NMR (400 MHz, DMSO-$d_6$) δ = 10.98 – 10.78 (m, 1H), 8.64 (s, 2H), 7.94 (t, J = 6.0 Hz, 1H), 7.23 – 7.09 (m, 1H), 7.06 – 6.94 (m, 1H), 4.58 – 4.13 (m, 3H), 2.95 – 2.66 (m, 1H), 2.55 (m, 1H), |

TABLE 2-continued

| Exemplary compounds - additional examples | | |
|---|---|---|
| Compound ID | Synthesis | Characterization |
| | | 2.41 – 2.30 (m, 3H), 2.27 (s, 3H), 2.12 (s, 1H), 1.94 – 1.81 (m, 1H), 1.54 (s, 6H). MS (ESI) [m/z 429.1 M + H]$^+$ |
| Compound 272 | Synthesized in analogy to Compound 223 | $^1$H NMR (400 MHz, DMSO-$d_6$) δ = 10.96 (s, 1H), 8.27 (t, J = 6.0 Hz, 1H), 7.96 (d, J = 9.2 Hz, 1H), 7.72 (d, J = 9.2 Hz, 1H), 7.11 (s, 1H), 7.02 (d, J = 10.8 Hz, 1H), 4.34 (dd, J = 5.2, 12.4 Hz, 1H), 4.26 (d, J = 6.0 Hz, 2H), 2.83 (ddd, J = 5.6, 13.2, 17.2 Hz, 1H), 2.57 – 2.53 (m, 1H), 2.27 – 2.03 (m, 1H), 1.99 – 1.86 (m, 1H), 1.63 (s, 6H). MS (ESI) m/z 503.1 [M + H]$^+$ |
| Compound 275 | Synthesized in analogy to Compound 12 | $^1$H NMR (400 MHz, DMSO-$d_6$) δ = 10.96 (s, 1H), 8.16 (t, J = 6.0 Hz, 1H), 7.56 – 7.53 (m, 1H), 7.53 – 7.49 (m, 1H), 7.08 (s, 1H), 7.00 (d, J = 11.2 Hz, 1H), 4.33 (dd, J = 5.6, 12.4 Hz, 1H), 4.23 (d, J = 6.0 Hz, 2H), 2.90 – 2.74 (m, 1H), 2.60 (s, 3H), 2.54 (d, J = 2.8 Hz, 1H), 2.27 – 2.02 (m, 1H), 2.01 – 1.87 (m, 1H), 1.58 (s, 6H). MS (ESI) m/z 433.1 [M + H]$^+$ |
| Compound 276 | Synthesized in analogy to Compound 210 | $^1$H NMR (400 MHz, DMSO-$d_6$) δ = 10.96 (s, 1H), 8.23 (t, J = 5.2 Hz, 1H), 8.11 – 7.69 (m, 2H), 7.53 – 7.44 (m, 1H), 7.11 (s, 1H), 7.02 (d, J = 11.2 Hz, 1H), 4.33 (dd, J = 5.2, 12.4 Hz, 1H), 4.24 (d, J = 5.6 Hz, 2H), 2.91 – 2.76 (m, 1H), 2.59 – 2.51 (m, 1H), 2.30 – 2.00 (m, 1H), 1.99 – 1.88 (m, 1H), 1.60 (s, 6H). MS (ESI) m/z 485.2 [M + H]$^+$ |
| Compound 277 | Synthesized in analogy to Compound 203 | $^1$H NMR (400 MHz, DMSO-$d_6$) δ = 10.97 (s, 1H), 8.28 (t, J = 6.0 Hz, 1H), 8.00 (d, J = 8.8 Hz,, 1H), 7.89 (d, J = 8.8 Hz, 1H), 7.12 (s, 1H), 7.02 (d, J = 11.2 Hz, 1H), 4.34 (dd, J = 5.2, 12.4 Hz, 1H), 4.27 (d, J = 6.0 Hz, 2H), 2.83 (ddd, J = 5.6, 13.6, 17.2 Hz, 1H), 2.54 (d, J = 3.2 Hz, 1H), 2.20 – 2.10 (m, 4H), 2.00 – 1.87 (m, 1H), 1.65 (s, 6H). MS (ESI) m/z 483.1 [M + H]$^+$ |
| Compound 278 | Synthesized in analogy to Compound 220 | $^1$H NMR (400 MHz, DMSO-$d_6$) δ = 10.95 (s, 1H), 9.73 (s, 1H), 8.30 (t, J = 6.0 Hz, 1H), 7.17 (s, 1H), 7.03 (d, J = 10.8 Hz, 1H), 4.42 – 4.29 (m, 1H), 4.23 (d, J = 5.4 Hz, 2H), 2.94 – 2.73 (m, 1H), 2.58 –2.52 (d, J = 2.8 Hz, 1H), 2.28 – 2.01 (m, 1H), 2.01 – 1.85 (m, 1H), 1.57 (s, 6H). MS (ESI) m/z 476.2 [M + H]$^+$ |
| Compound 279 | Synthesized in analogy to Compound 201 | $^1$H NMR (400 MHz, DMSO-$d_6$) δ = 10.96 (s, 1H), 8.59 (d, J = 0.8 Hz, 1H), 8.26 (t, J = 6.0 Hz, 1H), 7.14 (s, 1H), 7.02 (d, J = 11.2 Hz, 1H), 4.41 – 4.31 (m, 1H), 4.23 (d, J = 5.6 Hz, 2H), 2.91 – 2.76 (m, 1H), 2.55 (m, 1H), 2.21 – 2.03 (m, 1H), 1.96 – 1.93 (m, 1H), 1.79 (s, 3H), 1.50 (s, 6H). MS (ESI) m/z 422.3 [M + H]$^+$ |
| Compound 280 | Synthesized in analogy to Compound 6 | $^1$H NMR (400 MHz, DMSO-$d_6$) δ = 10.95 (s, 1H), 8.26 (t, J = 6.0 Hz, 1H), 8.05 – 7.95 (m, 1H), 7.94 – 7.86 (m, 1H), 7.28 (t, J = 54.4 Hz, 1H), 7.10 (s, 1H), 7.02 (d, J = 10.8 Hz, 1H), 4.33 (dd, J = 5.2, 12.4 Hz, 1H), 4.26 (d, J = 6.0 Hz, 2H), 2.92 – 2.74 (m, 1H), 2.54 (d, J = 3.2 Hz, 1H), 2.31 – 2.01 (m, 1H), 2.00 – 1.89 (m, 1H), 1.64 (s, 6H). MS (ESI) m/z 491.0 [M + H]$^+$ |
| Compound 281 | Synthesized in analogy to Compound 282 | $^1$H NMR (400 MHz, DMSO-$d_6$) δ = 10.95 (s, 1H), 8.10 (t, J = 6.0 Hz, 1H), 7.10 (s, 1H), 6.96 (d, J = 11.2 Hz, 1H), 6.88 (s, 1H), 4.34 (dd, J = 5.2, 12.4 Hz, 1H), 4.22 (d, J = 6.0 Hz, 2H), 2.83 (s, 1H), 2.58 – 2.51 (m, 1H), 2.36 (s, 3H), 2.31 – 2.01 (m, 1H), 2.00 – 1.88 (m, 1H), 1.45 (s, 6H). MS (ESI) m/z 422.2 [M + H]$^+$ |
| Compound 282 | Synthesized in analogy to Compound 120 | $^1$H NMR (400 MHz, DMSO-$d_6$) δ = 10.95 (s, 1H), 8.09 (t, J = 6.0 Hz, 1H), 7.26 (s, 1H), 7.19 (s, 1H), 6.87 (s, 1H), 4.56 (dd, J = 5.6, 12.8 Hz, 1H), 4.21 (d, J = 6.0 Hz, 2H), 2.91 – 2.79 (m, 1H), 2.58 – 2.52 (m, 1H), 2.42 – 2.29 (m, 4H), 1.94 – 1.84 (m, 1H), 1.44 (s, 6H). MS (ESI) m/z 438.1 [M + H]$^+$ |

Example 2. Compound Binding to CRBN by HTRF Assay

Compound activity was monitored in a Homogenous Time-Resolved Fluorescence (HTRF) assay using 1-[5-({2-[2-(2-{[2-(2,6-dioxopiperidin-3-yl)-1,3-dioxo-2,3-dihydro-1H-isoindol-4-yl]oxy}acetamido) ethoxy]ethyl}carbamoyl) pentyl]-3,3-dimethyl-2-[(1E,3E)-5-[(2E)-1,3,3-trimethyl-5-sulfo-2,3-dihydro-1H-indol-2-ylidene]penta-1,3-dien-1-yl]-3H-indol-1-ium-5-sulfonate as a fluorescent probe. Biochemical assays were conducted in Greiner white 384 well HiBase plates (Cat. No 784075-25) in 20 μL total volume.

A one pot detection solution of CRBN-DDB1 (2.5 nM), Anti-His Terbium Cryptate Gold (1X, PerkinElmer Cat. #: 61HI2TLB), and Cy5-Thalidomide (100 nM, Tenova Cat.: T52461) was prepared in 20 mM HEPES, 20 mM NaCl, 0.2 mM TCEP, 0.2 mM EDTA, and 0.005% Tween[20] was dispensed to each assay plate. Compounds were stored in dry, ambient temperatures at 10 mM. An 11-point, 1:3 dilution series was prepared from 10 mM stock concentrations in Echo-compatible LDV plates. 10 nL of each compound dilution series was dispensed into assays wells using an Echo 650 (Labcyte inc. USA). 20 nL of 10 mM Lenalidomide was transferred into the active-control wells for the assay and 20 nL of DMSO was transferred into the neutral-control wells. The assay was then allowed to incubate for 30 min at ambient temperature after transferring compound. Plate measurements were taken on a Pherastar FSX (BMG Labtech, Germany) using the HTRF Red filter (Ex. 337 nm, em1: 620 nm, em2: 665 nm) (Flashes: 50, Integration time: 60-400 μs, Z-height: 10 mm, Ratio-multipler: 10,000). The HTRF signal was then subsequently normalized to the neutral and active controls. Analysis and EC50 values were derived using KNIME analytics (KNIME Zurich) transformation and fitting within Collaborative Drug Discovery (Collaborative Drug Discovery USA). Ki was derived from the geometric mean of the EC50 values using the Cheng-Prustoff transformation.

Example 3. Experimental for NanoBIT

Cal51 NEK7 NanoBiT cell line was generated via CRISPR Knock-In of the HiBiT tag in NEK7 gene and stable infection with a lentivirus carrying LgBiT protein. The cell line was generated in house. For the experiment, cells were plated in 384-well white flat bottom plates (Corning, 3570BC) at 2500 cells per well using Multiflo (BioTek/Agilent) and in 25 μl volume in DMEM experimental medium: DMEM (DMEM, high glucose, HEPES, no phenol red (ThermoFisher 35-075-CV), 1% Scientific, 21063029) supplemented with 10% FBS (Corning, Penicillin/Streptomycin ((ThermoFisher Scientific, 15140-122), and 1% Endurazine (Nano-Glo Endurazine Live Cell Substrate (Promega, N2571)). Cells were incubated for 16 hours at 37° C., 5% $CO_2$ before compound addition. For dose response determination, 2.5 nL of a compound at different concentrations (stock compound concentration range: 10 mM to 0.5 μM, final concentration range inside cell plate: 1 μM to 0.05 nM) were dispensed into the plate using an Echo® 650 liquid handling device (Backman Coulter/Labcyte). Cells were incubated at 37° C., 5% $CO_2$ for 24 hours and then signal was read on a Pherastar FSX using "LUM plus" optic module with 4095 gain and measurement interval time 0.2 seconds.

Analysis was performed in Genedata Screener (Genedata, Basel, CH). Luminescence response (R) was calculated by the formula: response=100*(S−N)/(P−N) where S is the signal of the well, N and P the mean negative and positive control values respectively of the same plate. The luminescence response was then fitted in Genedata using a 4-parameter antagonist logistic fit (hill slope unconstrained, EC50 >0, top/bottom unconstrained).

The results are included in Table 3 and 4.

TABLE 3

HTRF Binding of compounds to CRBN and Activity for NEK7 degradation.

| No. | HTRF CRBN $EC_{50}$ uM | NEK7 NanoBIT $DC_{50}$ nM | NEK7 NanoBiT $D_{max}$ % |
|---|---|---|---|
| 1 | 0.15 | 9 | 89 |
| 2 | 0.11 | 3 | 94 |
| 3 | 0.50 | 242 | 65 |
| 4 | 0.12 | 3 | 94 |
| 5 | 0.12 | 133 | 63 |
| 6 | 0.21 | 7 | 91 |
| 7 | 0.15 | 61 | 72 |
| 8 | 0.21 | 6 | 93 |
| 9 | 0.21 | 22 | 85 |
| 10 | 0.06 | 1 | 97 |
| 11 | 0.19 | 9 | 90 |
| 12 | 0.17 | 8 | 91 |
| 13 | 0.20 | 56 | 73 |
| 14 | 0.11 | 9 | 89 |
| 15 | 0.12 | 4 | 95 |
| 16 | 0.12 | 4 | 95 |
| 17 | 0.02 | 0.1 | 98 |
| 18 | 0.54 | 206 | 61 |
| 19 | 0.14 | 23 | 84 |
| 20 | 0.07 | 13 | 86 |
| 21 | 0.09 | 3 | 94 |
| 22 | 0.12 | 4 | 93 |
| 23 | 0.22 | 22 | 88 |
| 24 | 0.32 | 76 | 74 |
| 25 | 0.29 | 23 | 87 |
| 26 | 0.07 | 2 | 96 |
| 27 | 0.05 | 1 | 96 |
| 28 | 0.47 | 17 | 91 |
| 29 | 0.08 | 0.4 | 97 |
| 30 | 0.35 | 12 | 92 |
| 31 | 0.13 | 6 | 93 |
| 32 | 0.11 | 4 | 95 |
| 33 | 0.12 | 2 | 96 |
| 34 | 0.14 | 28 | 78 |
| 35 | 0.13 | 19 | 77 |
| 36 | 0.08 | 5 | 95 |
| 37 | 0.03 | 1 | 97 |
| 38 | 0.04 | 6 | 90 |
| 39 | 0.05 | 2 | 97 |
| 40 | 0.10 | 8 | 93 |
| 41 | 0.06 | 0.4 | 98 |
| 42 | 0.18 | 20 | 93 |
| 43 | 0.04 | 1 | 97 |
| 44 | 0.23 | 38 | 88 |
| 45 | 0.53 | 13 | 91 |
| 46 | 0.05 | 61 | 71 |
| 47 | 0.03 | 4 | 85 |
| 48 | 0.13 | 54 | 66 |
| 49 | 0.07 | 0.1 | 99 |
| 50 | 0.15 | 18 | 88 |
| 51 | 0.07 | 1 | 96 |
| 52 | 0.09 | 59 | 67 |
| 53 | 0.19 | 11 | 92 |
| 54 | 0.06 | 1 | 97 |
| 55 | 0.10 | 1 | 97 |
| 56 | 0.47 | 244 | 67 |
| 57 | 0.13 | 3 | 94 |
| 58 | 0.13 | 6 | 92 |
| 59 | 0.14 | 28 | 87 |
| 60 | 0.06 | 2 | 96 |
| 61 | 0.06 | 2 | 97 |
| 62 | 0.05 | 2 | 96 |
| 63 | 0.14 | 91 | 62 |
| 64 | 0.49 | 43 | 86 |
| 65 | 0.14 | 1 | 98 |
| 66 | 0.09 | 3 | 96 |
| 67 | 0.22 | 95 | 74 |
| 68 | 0.09 | 1 | 97 |
| 69 | 0.06 | 1 | 97 |
| 70 | 0.06 | 0.5 | 97 |
| 71 | 0.14 | 9 | 90 |
| 72 | 0.47 | 11 | 90 |

TABLE 3-continued

HTRF Binding of compounds to CRBN and Activity for NEK7 degradation.

| No. | HTRF CRBN $EC_{50}$ uM | NEK7 NanoBIT $DC_{50}$ nM | NEK7 NanoBiT $D_{max}$ % |
|---|---|---|---|
| 73 | 0.17 | 4 | 93 |
| 74 | 0.03 | 1 | 97 |
| 75 | 0.30 | 14 | 92 |
| 76 | 0.07 | 2 | 97 |
| 77 | 0.07 | 3 | 95 |
| 78 | 0.06 | 0.4 | 97 |
| 79 | 0.25 | 92 | 83 |
| 80 | 0.03 | 1 | 97 |
| 81 | 0.07 | 0.4 | 98 |
| 82 | 0.09 | 1 | 96 |
| 83 | 0.14 | 7 | 94 |
| 84 | 0.18 | 22 | 93 |
| 85 | 0.04 | 11 | 81 |
| 86 | 0.16 | 21 | 85 |
| 87 | 0.03 | 0.1 | 97 |
| 88 | 0.11 | 4 | 93 |
| 89 | 0.12 | 6 | 92 |
| 90 | 0.05 | 4 | 94 |
| 91 | 0.04 | 0.4 | 97 |
| 92 | 0.18 | 65 | 71 |
| 93 | 0.07 | 4 | 92 |
| 94 | 0.07 | 1 | 98 |
| 95 | 0.10 | 6 | 92 |
| 96 | 0.08 | 1 | 97 |
| 97 | 0.17 | 50 | 76 |
| 98 | 0.11 | 3 | 95 |
| 99 | 0.08 | 8 | 87 |
| 100 | nd | 45 | 91 |
| 101 | nd | 5 | 95 |
| 102 | nd | 51 | 86 |
| 103 | 0.18 | 20 | 89 |
| 104 | nd | 122 | 80 |
| 105 | nd | 58 | 84 |
| 106 | 0.24 | 26 | 80 |
| 107 | 0.44 | 28 | 82 |
| 108 | 0.08 | 3 | 92 |
| 109 | 0.48 | 250 | 69 |
| 110 | 0.32 | 50 | 76 |
| 111 | nd | 3 | 85 |
| 112 | nd | 1000 | 40 |
| 113 | nd | 151 | 61 |
| 114 | nd | 52 | 69 |
| 115 | nd | 43 | 76 |
| 116 | nd | 20 | 80 |
| 117 | nd | 51 | 74 |
| 118 | nd | 760 | 48 |
| 119 | nd | 1000 | 45 |
| 120 | 0.10 | 61 | 68 |
| 121 | 0.29 | 30 | 80 |
| 122 | 0.23 | 56 | 73 |
| 123 | 0.61 | 100 | 70 |
| 124 | 0.4 | 78 | 73 |
| 125 | 0.07 | 54 | 71 |
| 126 | 0.05 | 3 | 94 |
| 127 | 0.04 | 5 | 90 |
| 128 | 0.04 | 8 | 95 |
| 129 | 0.09 | 22 | 90 |
| 130 | 0.04 | 2 | 96 |
| 131 | 0.02 | 1 | 96 |
| 132 | 0.05 | 5 | 92 |
| 133 | 0.03 | 2 | 94 |
| 134 | 0.07 | 2 | 93 |
| 135 | 0.02 | 16 | 71 |
| 136 | 0.06 | 63 | 65 |
| 137 | 0.05 | 1 | 97 |
| 138 | 0.18 | 26 | 88 |
| 139 | 0.04 | 8 | 90 |
| 140 | 0.09 | 14 | 89 |
| 141 | 0.02 | 6 | 91 |
| 142 | 0.05 | 3 | 94 |
| 143 | 0.04 | 3 | 92 |
| 144 | 0.05 | 6 | 78 |

TABLE 3-continued

HTRF Binding of compounds to CRBN and Activity for NEK7 degradation.

| No. | HTRF CRBN $EC_{50}$ uM | NEK7 NanoBIT $DC_{50}$ nM | NEK7 NanoBiT $D_{max}$ % |
|---|---|---|---|
| 145 | 0.43 | 10 | 86 |
| 146 | 0.18 | 5 | 91 |
| 147 | 0.55 | 776 | 52 |
| 148 | 0.15 | 176 | 58 |
| 149 | 0.13 | 12 | 85 |
| 150 | 0.15 | 91 | 53 |
| 151 | 0.48 | 88 | 60 |
| 152 | 0.24 | 2 | 95 |
| 153 | 10.00 | 53 | 90 |
| 154 | 0.18 | 4 | 89 |
| 155 | 10.00 | 186 | 75 |
| 156 | 0.33 | 435 | 54 |
| 157 | 0.19 | 178 | 60 |
| 158 | 0.32 | 8 | 91 |
| 159 | 0.28 | 28 | 79 |
| 160 | 0.20 | 34 | 76 |
| 161 | 0.23 | 54 | 69 |
| 162 | 0.29 | 13 | 86 |
| 163 | 0.25 | 18 | 80 |
| 164 | 0.24 | 66 | 68 |
| 165 | 0.17 | 47 | 69 |
| 166 | 0.09 | 203 | 56 |
| 167 | 0.09 | 1 | 96 |
| 168 | 0.15 | 137 | 57 |
| 169 | 0.18 | 42 | 75 |
| 170 | 0.18 | 55 | 73 |
| 171 | 0.12 | 7 | 90 |
| 172 | 0.19 | 2 | 97 |
| 173 | 0.23 | 19 | 85 |
| 174 | 0.18 | 30 | 77 |
| 175 | 0.28 | 6 | 94 |
| 176 | 0.05 | 116 | 60 |
| 177 | 0.55 | 53 | 85 |
| 178 | 0.29 | 95 | 66 |
| 179 | 4.17 | 578 | 59 |
| 180 | 0.12 | 16 | 81 |
| 181 | 0.19 | 5 | 93 |
| 182 | 0.20 | 54 | 72 |
| 183 | 0.37 | 56 | 71 |
| 184 | 0.18 | 3 | 95 |
| 185 | 0.22 | 15 | 83 |
| 186 | 0.09 | 90 | 65 |
| 187 | 0.10 | 4 | 93 |
| 188 | 0.08 | 4 | 93 |
| 189 | 0.07 | 4 | 94 |
| 190 | 0.09 | 6 | 90 |
| 191 | 0.17 | 13 | 85 |
| 192 | 0.09 | 5 | 92 |
| 193 | 0.08 | 10 | 87 |
| 194 | 0.12 | 1 | 96 |
| 195 | 0.22 | 138 | 63 |
| 196 | 0.31 | 9 | 90 |
| 197 | 0.12 | 13 | 87 |
| 198 | 0.13 | 22 | 83 |
| 199 | 0.14 | 99 | 67 |
| 200 | 0.17 | 46 | 74 |
| 201 | 0.14 | 7 | 93 |
| 202 | 0.17 | 87 | 68 |
| 203 | 0.20 | 4 | 94 |
| 204 | 0.08 | 1 | 98 |
| 205 | 0.11 | 1 | 97 |
| 206 | 0.10 | 18 | 85 |
| 207 | 0.09 | 19 | 82 |
| 208 | 0.17 | 345 | 56 |
| 209 | 0.09 | 1 | 97 |
| 210 | 0.46 | 2 | 96 |
| 211 | 0.90 | 8 | 90 |
| 212 | 0.07 | 6 | 90 |
| 213 | 0.08 | 33 | 78 |
| 214 | nd | 635 | 49 |
| 215 | 0.12 | 118 | 65 |
| 216 | 0.10 | 21 | 82 |

TABLE 3-continued

| HTRF Binding of compounds to CRBN and Activity for NEK7 degradation. | | | |
|---|---|---|---|
| No. | HTRF CRBN $EC_{50}$ uM | NEK7 NanoBIT $DC_{50}$ nM | NEK7 NanoBiT $D_{max}$ % |
| 217 | 0.15 | 327 | 56 |
| 218 | 0.08 | 49 | 71 |
| 219 | 0.08 | 47 | 72 |
| 220 | 0.15 | 8 | 91 |
| 221 | 0.08 | 19 | 83 |
| 222 | 0.16 | 54 | 73 |
| 223 | 0.09 | 8 | 91 |
| 224 | 0.09 | 32 | 77 |
| 225 | 6.56 | 1000 | 49 |
| 226 | 0.13 | 556 | 54 |
| 227 | 0.11 | 6 | 92 |
| 228 | 0.15 | 18 | 85 |
| 229 | 0.12 | 12 | 88 |
| 230 | 0.11 | 23 | 83 |
| 231 | 0.14 | 23 | 82 |
| 232 | 0.15 | 3 | 93 |
| 233 | 0.19 | 29 | 74 |
| 234 | 0.07 | 1 | 97 |
| 235 | 0.56 | 1000 | 11 |
| 236 | 0.25 | 41 | 71 |
| 237 | 0.15 | 11 | 87 |
| 238 | 0.17 | 153 | 63 |
| 239 | 0.66 | 909 | 47 |
| 240 | 0.15 | 79 | 69 |
| 241 | 0.14 | 15 | 86 |
| 242 | 0.43 | 319 | 59 |
| 243 | 10.00 | 1000 | 9 |
| 244 | 0.22 | 1000 | 19 |
| 245 | 0.16 | 672 | 48 |
| 246 | 0.18 | 27 | 82 |
| 247 | 0.12 | 20 | 83 |
| 248 | 0.07 | 2 | 95 |
| 249 | 0.07 | 7 | 87 |
| 250 | 0.07 | 2 | 96 |
| 251 | 0.08 | 4 | 92 |
| 252 | 0.05 | 3 | 93 |
| 253 | 0.14 | 778 | 45 |
| 254 | 0.12 | 278 | 55 |
| 255 | 0.09 | 464 | 54 |
| 256 | 0.08 | 11 | 85 |
| 257 | 0.05 | 1 | 95 |
| 258 | 0.07 | 4 | 91 |
| 259 | 0.09 | 6 | 91 |
| 260 | 0.11 | 480 | 47 |
| 261 | 0.09 | 12 | 87 |
| 262 | 0.08 | 12 | 88 |
| 263 | 0.10 | 7 | 90 |
| 264 | 0.13 | 100 | 68 |
| 265 | 0.09 | 474 | 56 |
| 266 | 0.12 | 15 | 82 |
| 267 | 0.11 | 3 | 94 |
| 268 | 0.12 | 11 | 88 |
| 269 | 0.10 | 1 | 95 |
| 270 | 0.19 | 73 | 72 |
| 271 | 0.52 | 213 | 68 |
| 272 | 0.23 | 312 | 57 |
| 273 | 0.25 | 136 | 70 |
| 274 | 10.00 | 1000 | 3 |
| 275 | 0.21 | 190 | 61 |
| 276 | 0.19 | 33 | 79 |
| 277 | 0.18 | 155 | 61 |
| 278 | 0.19 | 76 | 71 |
| 279 | 0.35 | 672 | 54 |
| 280 | 0.29 | 143 | 60 |
| 281 | 0.26 | 179 | 67 |
| 282 | 0.11 | 26 | 78 |

TABLE 4

| HTRF Binding of compounds to CRBN and Activity for NEK7 degradation. | | | |
|---|---|---|---|
| No | HTRF CRBN EC50 | NanoBIT DC50 | NanoBIT Dmax |
| 1 | B | A | A |
| 2 | B | A | A |
| 3 | B | B | B |
| 4 | B | A | A |
| 5 | B | B | B |
| 6 | B | A | A |
| 7 | B | A | B |
| 8 | B | A | A |
| 9 | B | A | A |
| 10 | A | A | A |
| 11 | B | A | A |
| 12 | B | A | A |
| 13 | B | A | B |
| 14 | B | A | A |
| 15 | B | A | A |
| 16 | B | A | A |
| 17 | A | A | A |
| 18 | B | B | B |
| 19 | B | A | A |
| 20 | A | A | A |
| 21 | A | A | A |
| 22 | B | A | A |
| 23 | B | A | A |
| 24 | B | A | B |
| 25 | B | A | A |
| 26 | A | A | A |
| 27 | A | A | A |
| 28 | B | A | A |
| 29 | A | A | A |
| 30 | B | A | A |
| 31 | B | A | A |
| 32 | B | A | A |
| 33 | B | A | A |
| 34 | B | A | A |
| 35 | B | A | A |
| 36 | A | A | A |
| 37 | A | A | A |
| 38 | A | A | A |
| 39 | A | A | A |
| 40 | A | A | A |
| 41 | A | A | A |
| 42 | B | A | A |
| 43 | A | A | A |
| 44 | B | A | A |
| 45 | B | A | A |
| 46 | A | A | B |
| 47 | A | A | A |
| 48 | B | A | B |
| 49 | A | A | A |
| 50 | B | A | A |
| 51 | A | A | A |
| 52 | A | A | B |
| 53 | B | A | A |
| 54 | A | A | A |
| 55 | B | A | A |
| 56 | B | B | B |
| 57 | B | A | A |
| 58 | B | A | A |
| 59 | B | A | A |
| 60 | A | A | A |
| 61 | A | A | A |
| 62 | A | A | A |
| 63 | B | A | B |
| 64 | B | A | A |
| 65 | B | A | A |
| 66 | A | A | A |
| 67 | B | A | B |
| 68 | A | A | A |
| 69 | A | A | A |
| 70 | A | A | A |
| 71 | B | A | A |
| 72 | B | A | A |
| 73 | B | A | A |

TABLE 4-continued

HTRF Binding of compounds to CRBN and Activity for NEK7 degradation.

| No | HTRF CRBN EC50 | NanoBIT DC50 | NanoBIT Dmax |
|---|---|---|---|
| 74 | A | A | A |
| 75 | B | A | A |
| 76 | A | A | A |
| 77 | A | A | A |
| 78 | A | A | A |
| 79 | B | A | A |
| 80 | A | A | A |
| 81 | A | A | A |
| 82 | A | A | A |
| 83 | B | A | A |
| 84 | B | A | A |
| 85 | A | A | A |
| 86 | B | A | A |
| 87 | A | A | A |
| 88 | B | A | A |
| 89 | B | A | A |
| 90 | A | A | A |
| 91 | A | A | A |
| 92 | B | A | B |
| 93 | A | A | A |
| 94 | A | A | A |
| 95 | A | A | A |
| 96 | A | A | A |
| 97 | B | A | A |
| 98 | B | A | A |
| 99 | A | A | A |
| 100 | nd | A | A |
| 101 | nd | A | A |
| 102 | nd | A | A |
| 103 | B | A | A |
| 104 | nd | B | A |
| 105 | nd | A | A |
| 106 | B | A | A |
| 107 | B | A | A |
| 108 | A | A | A |
| 109 | B | B | B |
| 110 | B | A | A |
| 111 | nd | A | A |
| 112 | nd | C | C |
| 113 | nd | B | B |
| 114 | nd | A | B |
| 115 | nd | A | A |
| 116 | nd | A | A |
| 117 | nd | A | B |
| 118 | nd | B | C |
| 119 | nd | C | C |
| 120 | A | A | B |
| 121 | B | A | A |
| 122 | B | A | B |
| 123 | B | B | B |
| 124 | B | A | B |
| 125 | A | A | B |
| 126 | A | A | A |
| 127 | A | A | A |
| 128 | A | A | A |
| 129 | A | A | A |
| 130 | A | A | A |
| 131 | A | A | A |
| 132 | A | A | A |
| 133 | A | A | A |
| 134 | A | A | A |
| 135 | A | A | B |
| 136 | A | A | B |
| 137 | A | A | A |
| 138 | B | A | A |
| 139 | A | A | A |
| 140 | A | A | A |
| 141 | A | A | A |
| 142 | A | A | A |
| 143 | A | A | A |
| 144 | A | A | A |
| 145 | B | A | A |
| 146 | B | A | A |
| 147 | B | B | B |
| 148 | B | B | B |
| 149 | B | A | A |
| 150 | B | A | B |
| 151 | B | A | B |
| 152 | B | A | A |
| 153 | C | A | A |
| 154 | B | A | A |
| 155 | C | B | B |
| 156 | B | B | B |
| 157 | B | B | B |
| 158 | B | A | A |
| 159 | B | A | A |
| 160 | B | A | A |
| 161 | B | A | B |
| 162 | B | A | A |
| 163 | B | A | A |
| 164 | B | A | B |
| 165 | B | A | B |
| 166 | A | B | B |
| 167 | A | A | A |
| 168 | B | B | B |
| 169 | B | A | B |
| 170 | B | A | B |
| 171 | B | A | A |
| 172 | B | A | A |
| 173 | B | A | A |
| 174 | B | A | A |
| 175 | B | A | A |
| 176 | A | B | B |
| 177 | B | A | A |
| 178 | B | A | B |
| 179 | C | B | B |
| 180 | B | A | A |
| 181 | B | A | A |
| 182 | B | A | B |
| 183 | B | A | B |
| 184 | B | A | A |
| 185 | B | A | A |
| 186 | A | A | B |
| 187 | B | A | A |
| 188 | A | A | A |
| 189 | A | A | A |
| 190 | A | A | A |
| 191 | B | A | A |
| 192 | A | A | A |
| 193 | A | A | A |
| 194 | B | A | A |
| 195 | B | B | B |
| 196 | B | A | A |
| 197 | B | A | A |
| 198 | B | A | A |
| 199 | B | A | B |
| 200 | B | A | B |
| 201 | B | A | A |
| 202 | B | A | B |
| 203 | B | A | A |
| 204 | A | A | A |
| 205 | B | A | A |
| 206 | B | A | A |
| 207 | A | A | A |
| 208 | B | B | B |
| 209 | A | A | A |
| 210 | B | A | A |
| 211 | B | A | A |
| 212 | A | A | A |
| 213 | A | A | A |
| 214 | | B | C |
| 215 | B | B | B |
| 216 | A | A | A |
| 217 | B | B | B |
| 218 | A | A | B |
| 219 | A | A | B |

TABLE 4-continued

HTRF Binding of compounds to CRBN and Activity for NEK7 degradation.

| No | HTRF CRBN EC50 | NanoBIT DC50 | NanoBIT Dmax |
|---|---|---|---|
| 220 | B | A | A |
| 221 | A | A | A |
| 222 | B | A | B |
| 223 | A | A | A |
| 224 | A | A | A |
| 225 | C | C | C |
| 226 | B | B | B |
| 227 | B | A | A |
| 228 | B | A | A |
| 229 | B | A | A |
| 230 | B | A | A |
| 231 | B | A | A |
| 232 | B | A | A |
| 233 | B | A | B |
| 234 | A | A | A |
| 235 | B | C | C |
| 236 | B | A | B |
| 237 | B | A | A |
| 238 | B | B | B |
| 239 | B | B | C |
| 240 | B | A | B |
| 241 | B | A | A |
| 242 | B | B | B |
| 243 | C | C | C |
| 244 | B | C | C |
| 245 | B | B | C |
| 246 | B | A | A |
| 247 | B | A | A |
| 248 | A | A | A |
| 249 | A | A | A |
| 250 | A | A | A |
| 251 | A | A | A |
| 252 | A | A | A |
| 253 | B | B | C |
| 254 | B | B | B |
| 255 | A | B | B |
| 256 | A | A | A |
| 257 | A | A | A |
| 258 | A | A | A |
| 259 | A | A | A |
| 260 | B | B | C |
| 261 | A | A | A |
| 262 | A | A | A |
| 263 | B | A | A |
| 264 | B | A | B |
| 265 | A | B | B |
| 266 | B | A | A |
| 267 | B | A | A |
| 268 | B | A | A |
| 269 | B | A | A |
| 270 | B | A | B |
| 271 | B | B | B |
| 272 | B | B | B |
| 273 | B | B | B |
| 274 | C | C | C |
| 275 | B | B | B |
| 276 | B | A | A |
| 277 | B | B | B |
| 278 | B | A | B |
| 279 | B | B | B |
| 280 | B | B | B |
| 281 | B | B | B |
| 282 | B | A | A |

In Table 4 each compound is assigned a class (HTRF class A, B or C) indicating the ability for Cereblon binding by means of their HTRF EC50 values. According to the code, A represents an EC50 value of ≤100 nM, B represents an EC50 value >100 nM and ≤1000 nM, C represents an EC50 value >1000 nM. NanoBiT Class assigns each compound a code indicating the ability for NEK7 degradation: A, B or C. According to the code, A represents a $DC_{50}$ value of ≤100 nM, B represents a $DC_{50}$ value >100 nM and ≤1000 nM and C represents a $DC_{50}$ value of >1000 nM. According to the code, A represents a DMAX value of >75%, B represents a DMAX value >50% and ≤75%, and C represents a DMAX value of ≤50%. Nd: no data.

Example 4. Functional assay for caspase-1 activity and IL-1B release in human monocyte-derived macrophages in response to inflammasome stimulation Human monocytes were enriched and isolated from a buffy coat of healthy donor whole blood with a RosetteSep™ Human Monocyte Enrichment Cocktail (Cat .No. 15068, StemCell) and Ficoll-Plaque PLUS (Cat.No. H8889, Sigma). Monocytes were differentiated into macrophages by treatment with 100 ng/mL M-CSF for 6 days at 37° C., 5% $CO_2$. Differentiated macrophages were seeded overnight (50,000 cells/well) in 100 μL of medium in a 96-well, white-bottom plate at 37° C., 5% $CO_2$. Cells were treated with a concentration range of MGD for 24 hours prior to stimulation with nigericin. Macrophages were primed with 1 μg/mL LPS for 3 h followed by 1 h stimulation with 10 μM nigericin. Media of stimulated macrophages were collected and assayed for caspase 1 activity directly (Promega G9951), according to manufacturer's instructions. For IL-1β release assay, media of stimulated macrophages were collected and stored at −20° C., then thawed at 4° C. before assaying for IL-1B activity (Promega $W^{6011}$), according to manufacturer's instructions. Compounds exhibited dose-dependent inhibition of caspase-1 activity and IL-1β release in this assay of NLRP3 inflammasome activation (Table 5).

TABLE 5

Functional assay for caspase-1 activity and IL-1β release in human monocyte-derived macrophages in response to inflammasome stimulation.

| Compound No. | Caspase-1 assay Caspase-1 IC50 (NIG) μM | IL-1b assay IL-1b IC50 (NIG) μM | n= |
|---|---|---|---|
| 34 | 0.00725 | 0.00736 | 3 |
| 16 | 0.00032 | 0.00056 | 1 |
| 14 | 0.00185 | 0.00195 | 3 |
| 110 | 0.01124 | 0.00987 | 1 |
| 162 | 0.00166 | 0.00203 | 1 |
| 181 | 0.00195 | 0.00196 | 1 |
| 108 | 0.00054 | 0.00041 | 1 |
| 97 | 0.00584 | 0.00523 | 2 |
| 96 | 0.00013 | 0.00020 | 2 |
| 95 | 0.00082 | 0.00121 | 2 |
| 94 | 4.90240E−10 | 0.00010 | 2 |
| 93 | 0.00045 | 0.00090 | 2 |
| 76 | 0.00049 | 0.00083 | 1 |
| 37 | 0.00014 | 0.00031 | 2 |
| 17 | 2.34742E−09 | 0.00003 | 2 |
| 192 | 0.00075 | 0.00094 | 2 |

In Table 5 $IC_{50}$ values (concentration at which inhibition of 50% is achieved) for each compound in caspase-1 and IL-1B assays are shown. n denotes the number of monocyte donors in which the compound was tested.

Example 5. Functional Assay of Inflammasome Activation in Human Monocyte-Derived Macrophages Using LPS/MSU Stimulation Human monocytes were enriched and isolated from a buffy coat of whole blood with a RosetteSep™ Human Monocyte Enrichment Cocktail (Cat.No. 15068, StemCell) and Ficoll-Plaque PLUS (Cat.No. H8889, Sigma). Monocytes were differentiated into macrophages by treatment with 100 ng/ml M-CSF for 6 days at 37° C., 5% $CO_2$. Differentiated macrophages were seeded overnight (50,000 cells/well) in 100 μL of medium in a 96-well white-bottom plate at 37° C., 5% $CO_2$. Cells were treated with a concentration range of MGD or the NLRP3 inhibitor selnoflast (Cat.No. HY-132831, MedChemExpress) for 24 h prior to stimulation with monosodium urate crystals (MSU). Macrophages were stimulated with 1 μg/mL lipopolysaccharide (LPS) and 0.2 mg/mL MSU for 6 h. Medium of stimulated macrophages were collected and assayed for caspase-1 activity directly (Promega G9951) as well as IL-1 (Promega $W^{6010}$), according to manufacturer's instructions.

Figure 1B:
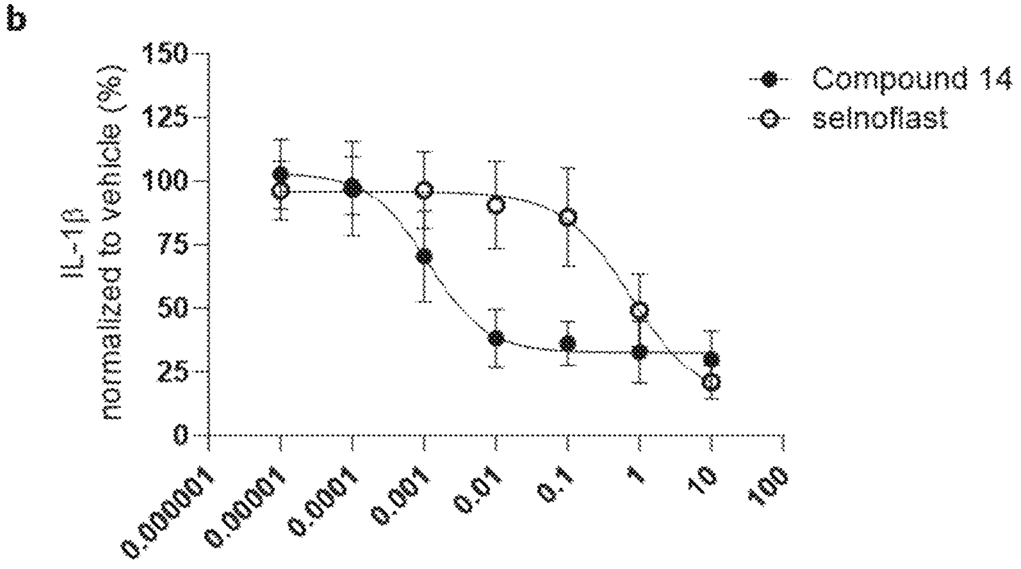
FIG. 1B depicts IL-1B activity in the supernatant following treatment of human monocyte-derived macrophages with different doses of Compound 14 or selnoflast measured as a percentage relative to mean values in DMSO.

Compound 14 exhibited dose-dependent inhibition of NLRP3-driven activation of human macrophages in this assay (FIG. 1). The MSU crystal stimulus used in this assay is relevant to the setting of gout, where MSU crystals activate NLRP3 inflammasome of joint-resident cells and consequently trigger painful flares of the disease. These data support the therapeutic application of a NEK7 MGD in gout.

As shown in FIG. 1, Compound 14 inhibits NLRP3-mediated inflammasome stimulation in primary human monocyte-derived macrophages. (a, b) Human monocyte-derived macrophages pre-treated with a dose-response of Compound 14 or selnoflast (NLRP3 inhibitor) for 24 h and stimulated with a combination of lipopolysaccharide (LPS) and monosodium urate crystals (MSU) for 6 h prior to supernatant collection. Monocytes were isolated from eight human donors. Caspase-1 (a) and IL-1B (b) in the supernatant are measured and data are expressed as percentage relative to mean values of DMSO conditions for each donor (technical triplicates).

Means of eight donors are plotted and analyzed using a four-parameter logistic regression model.

TABLE 6

Comparison of half-maximal inhibitory concentration (IC50) and maximal inhibition (Imax) for Compound 14 and selnoflast in both assays.

| | Caspase-1 activity | | IL-1β | |
|---|---|---|---|---|
| | Compound 14 | selnoflast | Compound 14 | selnoflast |
| IC50 (nM) | 1.6 | 843 | 1.1 | 746 |
| Imax (%) | 81 | 89 | 70 | 79 |

Example 6. In Vivo Rabbit Gout Model

MSU crystals were prepared by dissolving uric acid (Aladdin, cat #U105582) in boiling water (1 g in 200 mL with 6 mL of 1 N NaOH). PH value was adjusted to 7.2 by HCl. The solution was stirred and cooled to room temperature and stored at 4° C. overnight. The precipitate was filtered with filter paper and dried under low heat to obtain MSU crystals. New Zealand White rabbits received an intra-articular injection of 1 mL of MSU crystals (50 mg/mL) into both knees (MSU group) or PBS (as vehicle, control group). n=10 for MSU groups; n=6 for PBS group. Rabbits received daily prophylactic treatment of a rabbit-reactive MGD, Compound 16 (10 mg/kg), prednisolone (3 mg/kg, Aladdin, cat #P131646), selnoflast (10 mg/kg, MCE, cat #HY-132831) or vehicle (0.5% methyl cellulose, 4000 cps, in water), starting on one day prior to MSU/PBS injection.

On Day 7, tissue was harvested 2 hours post final dose. Six animals from NEK7 MGD group or vehicle were chosen based on average phenotype for the group. From these, peripheral blood mononuclear cells (PBMC) and spleens were isolated and probed for NEK7 levels using a JESS simple western. Lysates were prepared in M-PER lysis buffer and protein concentration was measured using Pierce rapid gold BCA protein Assay Kit (Thermo Fisher) according to manufacturer's protocol. The anti-NEK7(C34C3) Rabbit monoclonal antibody (mAb) (CST #3057) was used at 1:000 and anti-α-Tubulin (11H10) Rabbit mAb (CST #2125) was used at 1:2000, diluting in antibody diluent 2 (Protein Simple). The antibody diluent, capillary cartridges, 12-230 kDa pre-filled plate, ladder, buffers, and secondary antibody were derived from the 12-230 kDa Separation Module and the anti-Rabbit detection module.

The degree of joint swelling was determined by measuring knee perimeter with a digital caliper and calculated as the difference between the basal value and the test value observed at days-1,0 (6, 8, 10 and 12 h), 1, 2, 3, 4, 5, 6 and 7 after gout model establishment. For immunohistochemistry, bone sections were stained with anti-CD31 (Abcam #ab9498) diluted at 1:500. The nuclei were stained with hematoxylin. Slides were scanned using LEICA Aperio GT450 at 400× magnification. The number of positive blood vessels were counted blindly.

Figure 2A:
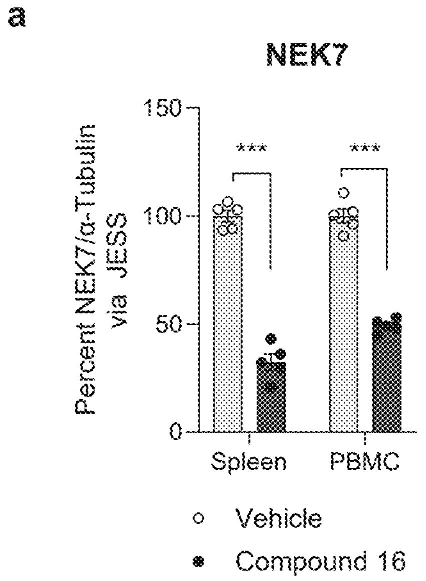
FIG. 2A depicts NEK7 degradation in spleens and peripheral blood mononuclear cells (PBMC) as analyzed by JESS and normalized to α-Tubulin.
Figure 2B:
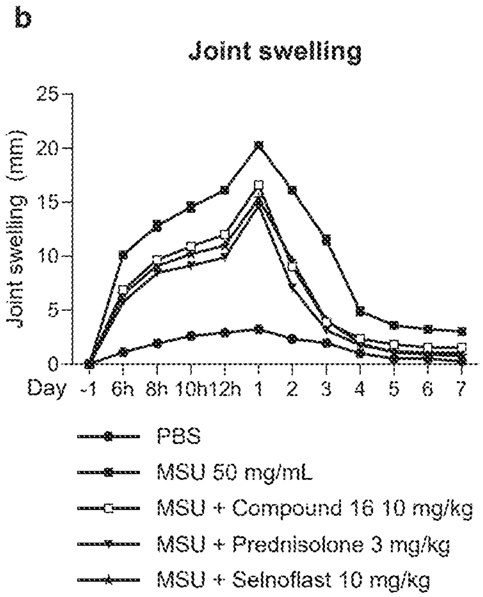
FIG. 2B depicts the degree of joint swelling in rabbits following injections of PBS, MSU crystals (50 mg/mL), Compound 16 (10 mg/kg), prednisolone (3 mg/kg) and selnoflast (10 mg/kg).
Figure 2C:
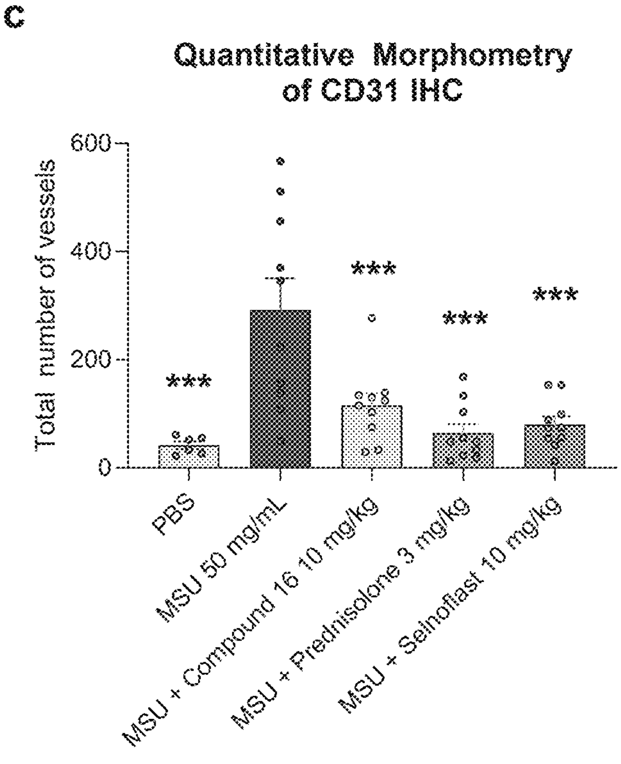
FIG. 2C depicts improvement in CD31 staining in bone tissue from rabbits treated with PBS, MSU crystals (50 mg/mL), Compound 16 (10 mg/kg), prednisolone (3 mg/kg) and selnoflast (10 mg/kg).

There was a greater than 50% degradation of NEK7 in spleen and PBMCs of rabbits dosed with Compound 16 at 10 mg/kg, QDx7, harvested 2 h after the final dose (FIG. 2*a*). There was an improvement in joint swelling induced by intra-articular MSU injection in rabbits treated prophylactically with Compound 16, prednisolone or selnoflast (FIG. 2*b*). Similarly, there was improvement in CD31 staining in bone tissue from rabbits treated prophylactically with the same test agents, suggestive of reduced inflammation (FIG. 2*c*). The therapeutic benefit observed in this in vivo, intra-articular model of gout supports the application of NEK7 MGD as a method to treat gout in human patients.

As shown in FIG. 2, NEK7 MGD reduces MSU-driven effects in rabbit gout model. (a) To determine NEK7 degradation, spleens and peripheral blood mononuclear cells (PBMC) were analyzed by JESS for NEK7 and normalized to α-Tubulin from five representative animals. (b) The degree of joint swelling was determined by caliper measurements at the indicated time points. (c) Rabbit bone tissue sections were stained and quantified for anti-CD31 immunohistochemistry. Results expressed as mean±SEM. Statistical analysis was performed using two-way ANOVA.

The difference was considered significant when $p<0.05$.

Example 7. Multiple-Dose Study with Compound 14 Induces NEK7 Degradation and Inhibits NLRP3 Inflammasome Activation In Vivo in Non-Human Primates Non-naïve male and female non-human primate (NHP) cynomolgus monkeys were orally administered with 5 consecutive daily doses of Compound 14 at 5 mg/kg, n=2 per dose group, 1 male and 1 female. Compound formulation was prepared on the day of administration in 0.5% methyl cellulose (4000 cps) in water and animals were fasted overnight. Plasma collected post dose were analyzed using a non GLP LC/MS/MS bioanalytical method to evaluate the compound concentration. Whole blood collected post dose were processed to PBMC and were analyzed using western blot method. Plasma pharmacokinetics and PMBC pharmacodynamics were assessed longitudinally throughout dosing and following dosing cessation.

Within 0.5 h of blood collection from animals that received vehicle or Compound 14 at 5 mg/kg, whole blood was aliquoted into two 0.25 mL aliquots. One aliquot was used as baseline, and the other as the ex vivo stimulated condition. For stimulation, whole blood was incubated with 100 ng/ml Lipopolysaccharide from *Escherichia coli* 0111:B4 (LPS-EB) for 3 h, followed by 10 μM nigericin for 2 h. Plasma was then isolated and concentrations of IL-1β in plasma isolated from ex vivo whole blood stimulation were measured using the IL-1B ELISA R&D Systems kit (Cat. #DY1318), with 50 μL per sample diluted with 50 μL reagent diluent/well. After reading absorbance on plate reader, standard curve and sample IL-1B levels were analyzed using 4PL method. Percent decrease in IL-1β was quantified based on IL-1β levels from whole blood of Compound 14-dosed animals relative to those from the vehicle group at each timepoint.

At 6 h after the final dose, a single oral gavage of Compound 14 at 5 mg/kg showed similar mean plasma concentration in comparison to 5 consecutive days of dosing (Table 7).

TABLE 7

Mean Plasma Concentration (ng/mL) of Compound 14 dosed orally at 5 mg/kg.

| Days of dosing (6 h post final dose) | Mean plasma concentration of Compound 14 (ng/mL) |
|---|---|
| Day 1 | 5.4 |
| Day 5 | 7.5 |

In Table 7, plasma was isolated 6 h after final dose (dosed once or over five consecutive days), n=2. Plasma collected post dose were analyzed using a non GLP LC/MS/MS bioanalytical method to evaluate the compound concentration.

PBMC NEK7 degradation showed reduction to 44% of pre-dose levels on day 1, that was further reduced to 15% by day 5 (Table 8).

TABLE 8

NEK7 level from PBMC of NHP

| Time of blood draw | Average percent NEK7/β-actin in PBMC, relative to predose |
|---|---|
| Day 1, predose | 100 |
| Day 1, 6 h | 56 |
| Day 1, 24 h | 44 |
| Day 5, 6 h | 27 |
| Day 5, 24 h | 15 |
| Day 10, 24 h | 45 |
| Day 15, 24 h | 141 |

In Table 8 compound 14 induces NEK7 degradation in vivo. NEK7 protein levels were assessed in PBMC isolated from NHP after oral administration for 5 consecutive days of Compound 14 at 5 mg/kg, n=2 per dose group. NEK7 levels were normalized to β-actin, as determined by JESS, at the indicated time points. NEK7 level at pre dose was normalized to 100%. Days 10 and 15 correspond to recovery period, 5 or 10 days after drug administration, respectively.

Commensurate with NEK7 levels, production of IL-1β was inhibited in an ex vivo whole blood stimulation assay (Table 9). The deep and sustained inhibition of IL-1β release in the ex vivo assay after oral administration over five consecutive days suggests that Compound 14 can control inflammation driven by NLRP3 inflammasome. The inhibition of IL-1β in this ex vivo stimulation assay by NEK7 MGD dosed in NHP serves as a proof-of-concept for the therapeutic use of NEK7 MGD for the treatment of multiple inflammatory diseases in which IL-1β plays a pathogenic role. Such diseases include, but are not limited to gout, pericarditis, arthritis, and Still's disease.

TABLE 9

Percent decrease in IL-1β relative to predose

| Time of blood draw for ex vivo stimulation | Percent IL-1β relative to predose |
|---|---|
| Day 1, predose | 100 |
| Day 1, 6 h | 1 |
| Day 1, 24 h | 45 |
| Day 5, 6 h | 0 |
| Day 5, 24 h | 78 |
| Day 10, 24 h | 91.5 |
| Day 15, 24 h | 141 |

In Table 9, suppression of ex vivo inflammasome activation following degradation of NEK7 in NHP is reported. Whole blood was isolated at the indicated time points from NHP dosed orally 5 mg/kg of Compound 14 over 5 days (day 1 through 5), n=2. Days 10 and 15 correspond to recovery period, 5 or 10 days after drug administration, respectively. Whole blood was stimulated ex vivo with 100 ng/mL LPS for 3 h and 10 UM nigericin for 2 h. Plasma was isolated and IL-1β was measured by ELISA. Percent decrease in IL-1β was quantified based on IL-1β levels from whole blood of Compound 14-dosed animals relative to those from the vehicle group.

Example 8. Analysis of Central Nervous System Penetrance in NHP

Naïve NHP were orally administered with 7 consecutive daily dose of Compound 14 at 30 mg/kg, n=4 per dose group, 2 male and 2 female. Compound formulation was prepared on the day of administration in 0.5% methyl cellulose (4000 cps) in water and animals were fed twice a day; water was available ad libitum. Plasma collected posted dose on Day 1 and Day 7 were analyzed using a non GLP LC/MS/MS bioanalytical method to evaluate the compound concentration. Brain samples were harvested 24 h after final dose. Lysates for different brain regions (hippocampus, frontal cortex, and cerebellum) were prepared in M-PER lysis buffer and diluted at total protein concentration of 0.4 mg/mL in 0.1X sample buffer (12-230 kDa detection module; Protein Simple). The anti-NEK7 rabbit mAb (Abcam #AB133514) was used at 1:100 and anti-β-actin rabbit mAb (CST #5125) was used at 1:500. Samples were probed for NEK7 and β-actin protein levels by JESS, and quantified relative to vehicle control.

NHPs dosed with Compound 14 at 30 mg/kg for 7 days showed oral bioavailability and favorable pharmacokinetic profile, with $C_{max}$ of 6600 ng/ml at 1.75 h after the final dose (Table 10). The brains of NHPs dosed with Compound 14 showed around 80% degradation of NEK7 across three different brain regions profiled (Table 11). These data support that certain NEK7 MGD may be suitable for applications that require exposure of CNS cells to the compound.

These include diseases of the CNS, but may also extend to other diseases, such as obesity, where some component of pathology is driven by cells within the CNS.

TABLE 10

| Plasma pharmacokinetics of Compound 14 after oral dosing for 7 days Average (male and female) | | | | |
|---|---|---|---|---|
| $C_{max}$ (ng/mL) | $t_{max}$ (hr) | $t_{last}$ (hr) | $AUC_{tlast}$ (hr*ng/ml) | $AUC_{0\text{-}24\ hr}$ (hr*ng/ml) |
| 6600 | 1.75 | 8 | 27150 | 36600 |

In Table 10, concentration of Compound 14 in NHP plasma following administration via oral gavage after 7 days post dose at 30 mg/kg is reported. NHP received daily oral administration of 30 mg/kg of Compound 14 for 7 days, n=2. $C_{max}$, $t_{max}$, $t_{last}$, $AUCt_{last}$, and $AUC_{0\text{-}24hr}$ were calculated based on the average of the group, n=4 (2 male and 2 female).

TABLE 11

NEK7 degradation in the brain of NHP.

| Brain region | Average percent NEK7/β-actin in brain, relative to vehicle |
|---|---|
| Hippocampus | 21.3 |
| Frontal Cortex | 20.3 |
| Cerebellum | 18.2 |

In Table 11, NEK7 protein degradation in brains of NHP following oral dosing of Compound 14 is reported. NHP received daily oral administration of 30 mg/kg of Compound 14 or vehicle for 7 days. For Compound 14 group, n=4 (two male and two female); for vehicle, n=2; samples taken 24 h post-final dose. Brains were harvested 24 h after final dose, sectioned by region (hippocampus, frontal cortex, cerebellum), and analyzed for NEK7 and beta-actin protein levels by JESS. The average percent of NEK7 was quantified by brain region and normalized to β-actin.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound having the structure:

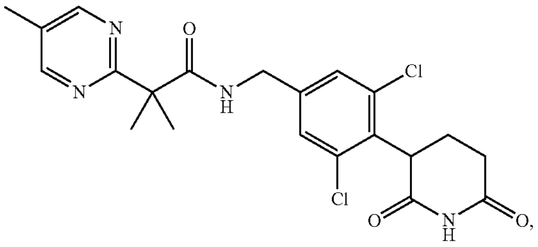 [SMILES: Cc1cnc(C(C)(C)C(=O)NCc2cc(Cl)c(C3CCC(=O)NC3=O)c(Cl)c2)nc1]

or a pharmaceutically acceptable salt thereof.

2. The compound according to claim 1 having the structure:

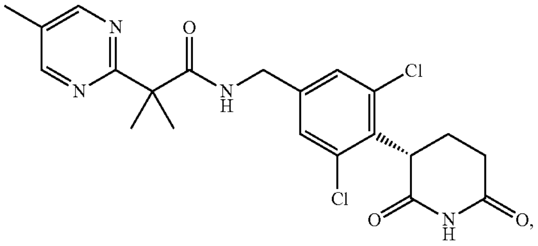 [SMILES: Cc1cnc(C(C)(C)C(=O)NCc2cc(Cl)c([C@@H]3CCC(=O)NC3=O)c(Cl)c2)nc1]

or a pharmaceutically acceptable salt thereof.

3. The compound according to claim 1 having the structure:

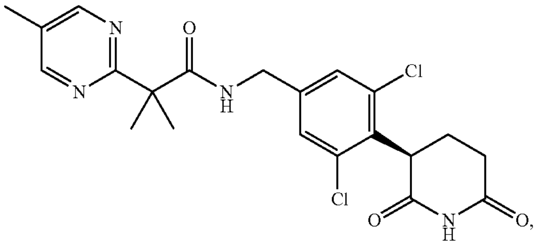 [SMILES: Cc1cnc(C(C)(C)C(=O)NCc2cc(Cl)c([C@H]3CCC(=O)NC3=O)c(Cl)c2)nc1]

or a pharmaceutically acceptable salt thereof.

4. The compound according to claim 1, or a pharmaceutically acceptable salt thereof, wherein the compound is in racemic mixture.

5. A pharmaceutical composition comprising the compound of claim 1, or a pharmaceutically acceptable salt thereof, and a pharmaceutically acceptable excipient.

* * * * *